US012404283B2

(12) United States Patent
Mandabi et al.

(10) Patent No.: US 12,404,283 B2
(45) Date of Patent: Sep. 2, 2025

(54) c-MYC mRNA TRANSLATION MODULATORS AND USES THEREOF IN THE TREATMENT OF CANCER

(71) Applicant: Anima Biotech Inc., Bernardsville, NJ (US)

(72) Inventors: Aviad Mandabi, Ramat Gan (IL); Boaz Inbal, Ramat Gan (IL); Scott Alexander Sadler, Ramat Gan (IL); Shuyu Chu, Ramat Gan (IL); David William Sheppard, Ramat Gan (IL); Jason Paul Tierney, Ramat Gan (IL); Iris Alroy, Ramat Gan (IL); Rina Wassermann, Ramat Gan (IL); Yoni Sheinberger, Ramat Gan (IL); Yaode Wang, Beijing (CN); Haitang Li, Beijing (CN); Lothar Willms, Hillscheid (DE)

(73) Assignee: Anima Biotech Inc., NJ (US)

( * ) Notice: Subject to any disclaimer, the term of this patent is extended or adjusted under 35 U.S.C. 154(b) by 0 days.

(21) Appl. No.: 18/868,756

(22) PCT Filed: Jul. 2, 2023

(86) PCT No.: PCT/US2023/026828
§ 371 (c)(1),
(2) Date: Nov. 24, 2024

(87) PCT Pub. No.: WO2024/010762
PCT Pub. Date: Jan. 11, 2024

(65) Prior Publication Data
US 2025/0129100 A1    Apr. 24, 2025

Related U.S. Application Data

(63) Continuation-in-part of application No. 17/856,998, filed on Jul. 3, 2022.

(60) Provisional application No. 63/358,134, filed on Jul. 3, 2022.

(51) Int. Cl.
| | | |
|---|---|---|
| *C07D 513/04* | (2006.01) |
| *A61K 31/429* | (2006.01) |
| *A61K 31/437* | (2006.01) |
| *A61K 31/454* | (2006.01) |
| *A61K 31/4545* | (2006.01) |
| *A61K 31/4725* | (2006.01) |
| *A61K 31/496* | (2006.01) |
| *A61K 31/5377* | (2006.01) |
| *A61K 45/06* | (2006.01) |
| *A61P 35/00* | (2006.01) |
| *C07D 513/14* | (2006.01) |

(52) U.S. Cl.
CPC .......... *C07D 513/04* (2013.01); *A61K 31/429* (2013.01); *A61K 31/437* (2013.01); *A61K 31/454* (2013.01); *A61K 31/4545* (2013.01); *A61K 31/4725* (2013.01); *A61K 31/496* (2013.01); *A61K 31/5377* (2013.01); *A61K 45/06* (2013.01); *A61P 35/00* (2018.01); *C07D 513/14* (2013.01)

(58) Field of Classification Search
CPC .. C07D 513/04; C07D 513/14; A61K 31/429; A61K 31/437; A61K 31/454; A61K 31/4545; A61K 31/4725; A61K 31/496; A61K 31/5377; A61K 45/06; A61P 35/00
See application file for complete search history.

(56) References Cited

U.S. PATENT DOCUMENTS

| | | | |
|---|---|---|---|
| 4,497,817 A | 2/1985 | Murase et al. | |
| 5,919,799 A * | 7/1999 | Tasaka | C07D 513/04 514/366 |
| 2022/0370431 A1 | 11/2022 | Sheppard et al. | |

FOREIGN PATENT DOCUMENTS

| | | |
|---|---|---|
| WO | WO 2007/109120 A2 | 9/2007 |
| WO | WO 2022/150316 A1 | 7/2022 |

OTHER PUBLICATIONS

Chao et al. "Identification of N-(5-tert-butyl-isoxazol-3-yl)-N'-{4-[7-(2-morpholin-4-yl-ethoxy) imidazo [2, 1-b][1, 3] benzothiazol-2-yl] phenyl} urea dihydrochloride (AC220), auniquely potent, selective, and efficacious FMS-like tyrosine kinase-3 (FLT3) inhibitor" Journal of medicinal chemistry. Dec. 10, 2009;52(23):7808-16; Abstract.
International Search Report for PCT Application No. PCT/US2023/026828 dated Aug. 31, 2023.
Serer et al. "A high-throughput screening for inhibitors of riboflavin synthase identifies novel antimicrobial compounds to treat brucellosis" The FEBS journal. Jul. 2019;286(13):2522-35.
Allen-Petersen et al. "Mission possible: advances in MYC therapeutic targeting in cancer" BioDrugs. Oct. 2019;33(5):539-53.
"Cancer Facts & Figures 2008" American Cancer Society, 2008.
CAS Registry No. 1053158-96-5 ,Imidazo[2,1-b]benzothiazole-7-carboxamide, N-(2,3-dimethylcyclohexyl)-2-(4-ethylphenyl)— Source of Registration: Other Sources ;Entered STN:Sep. 26, 2008.
CAS Registry No. 1053159-13-9, Imidazo[2,1-b]benzothiazole-7-carboxamide, N-(2,3-dimethylcyclohexyl)-2-phenyl—, Source of Registration: Other Sources, Entered STN: Sep. 26, 2008.
CAS Registry No. 1053159-35-5, Imidazo[2,1-b]benzothiazole-7-carboxamide, N-(2,3-dimethylcyclohexyl)-2-(4-ethoxyphenyl)—, Source of Registration: Other Sources , Entered STN: Sep. 26, 2008.

(Continued)

*Primary Examiner* — Joseph K McKane
*Assistant Examiner* — Meghan C Heasley
(74) *Attorney, Agent, or Firm* — Mark S. Cohen; PEARL COHEN ZEDEK LATZER BARATZ LLP

(57) ABSTRACT

The present invention relates to novel c-MYC mRNA translation modulators, composition and methods of preparation thereof, and uses thereof in the treatment of cancer.

38 Claims, 3 Drawing Sheets

(56) References Cited

OTHER PUBLICATIONS

CAS Registry No. 891888-55-4 Imidazo[2,1-b]benzothiazole-7-carboxamide, N-[3-(hexahydro-1H-azepin-1-yl)propyl]-2-phenyl— Entered STN: Jul. 11, 2006, Source of Registration: Chemical Library Supplier: Aurora Fine Chemicals.

CAS Registry No. 891893-91-7, Methanone, (hexahydro-1H-azepin-1-yl)[2-(4-methylphenyl)imidazo[2,1-b]benzothiazol-7-yl]—, Source of Registration: Chemical Library Supplier: Aurora Fine Chemicals, Entered STN: Jul. 11, 2006.

CAS Registry No. 891897-09-9, Methanone, [2-(4-ethoxyphenyl)imidazo[2,1-b]benzothiazol-7-yl](hexahydro-1H-azepin-1-yl)—, Source of Registration: Chemical Library Supplier: Aurora Fine Chemicals, Entered STN: Jul. 11, 2006.

CAS Registry No. 891898-68-3, Imidazo[2,1-b]benzothiazole-7-carboxamide, 2-(4-methylphenyl)-N-[2-(4-morpholinyl)ethyl]—, Source of Registration: Chemical Library Supplier: Aurora Fine Chemicals, Entered STN: Jul. 11, 2006.

CAS Registry No. 903168-07-0, Methanone, [2-(4-fluorophenyl)imidazo[2,1-b]benzothiazol-7-yl](3-methyl-1-piperidinyl)—, Source of Registration: Chemical Library Supplier: Aurora Fine Chemicals, Entered STN: Aug. 22, 2006.

Dang CV. "MYC on the path to cancer" Cell. Mar. 30, 2012;149(1):22-35.

International Search Report for PCT Application No. PCT/US2023/026827 dated Aug. 28, 2023.

Soucek et al. "Modelling Myc inhibition as a cancer therapy" Nature. Oct. 2, 2008;455(7213):679-83.

Whitfield et al. Strategies to inhibit Myc and their clinical applicability Frontiers in cell and developmental biology. Feb. 23, 2017;5:10.

* cited by examiner c-MYC mRNA TRANSLATION MODULATORS AND USES THEREOF IN THE TREATMENT OF CANCER

CROSS-REFERENCE TO RELATED APPLICATIONS

This application is a National Phase Application of PCT International Application No. PCT/US2023/026828, filed Jul. 2, 2023, which claims the benefit of U.S. Provisional Patent Application No. 63/358,134, filed Jul. 3, 2022, and which is a Continuation in Part of patent application Ser. No. 17/856,998, filed Jul. 3, 2022; all of which are hereby incorporated by reference.

FIELD OF THE INVENTION

The present invention relates to novel c-MYC mRNA translation modulators, composition and methods of preparation thereof, and uses thereof in the treatment of cancer.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (*Cancer Facts & Figures* American Cancer Society: Atlanta, GA (2008)). The rate of new cancer cases decreased by an average 0.6% per year among men between 2000 and 2009 and stayed the same for women. From 2000 through 2009, death rates from all cancers combined decreased on average 1.8% per year among men and 1.4% per year among women. This improvement in survival reflects progress in diagnosing at an earlier stage and improvements in treatment. Discovering highly effective anticancer agents with low toxicity is a primary goal of cancer research.

The Myc family includes three major members, the proto-oncogene c-Myc (cellular Myelocytomatosis, short Myc), as well as L-myc and N-myc. These three Myc homologs are involved in the early stages of carcinogenesis and metastatic spread in most human cancers. In most types of tumors Myc gene is not mutated or duplicated, but its mRNA and/or protein levels are increased, indicating that in cancer Myc overexpression is induced at the level of transcription, mRNA steady state levels and translation. Indeed, myc gene expression normally depends on growth factor signaling and both myc mRNA and Myc protein have very short half-lives (of 30 and 20 min respectively) [Dang, C. V. (2012). MYC on the path to cancer. Cell 149, 22-35]. In tumor cells however, the cellular levels of Myc become independent from such signaling and regulation, and the resulting exacerbated Myc function drives intracellular and extracellular transcription programs that allow tumors to grow and thrive. However, Myc does not necessarily need to be overexpressed in order for a cancer to be highly dependent upon its activity. A study from Soucek et al. (Nature (2008) 455 (7213):679-83) shows that tumors that express c-Myc at endogenous levels exhibit tumor regression upon Myc inhibition via a genetically engineered system. Therefore, treatment with a Myc inhibitor is not necessarily limited to cancers that overexpress Myc. Compounds according to this invention may also be used to regulate the translation of Myc mRNA, wherein the direct target for the compounds is a protein or RNA which regulate Myc mRNA translation, and as such any tumor which is Myc dependent will benefit from the therapeutic utility of these compounds.

Due to its extensive pathogenic significance, MYC is an important anticancer target. Deregulated Myc gene is found in a wide range of human hematological malignancies and solid tumors, especially in breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer and lung adenocarcinoma. Recent studies also indicate that deregulation of c-MYC is related to the occurrence of BRAF V600E thyroid cancers, choroid plexus carcinoma, and colitis-associated cancer. In addition, amplification of the MYC gene was found in a significant number of epithelial ovarian cancer cases. In TCGA datasets, the amplification of Myc occurs in several cancer types, including breast, colorectal, pancreatic, gastric, and uterine cancers.

Although Myc gene is a very important oncogene and considered as a driver in carcinogenesis and MYC protein is a key transcription factor broadly targeting various genes, rational designing a direct Myc inhibitor is still challenging. This is mainly because MYC protein lacks structural regions amenable to therapeutic inhibition by small molecules and is considered an undruggable target [BioDrugs (2019) 33:539-553].

Designing and developing MYC modulators is challenging, primarily because the MYC protein has a disordered structure which lacks a pocket or groove that can act as a binding site for modulators. Interfering with the MYC transcription, blocking the protein-protein interaction (PPI) of MYC and its cofactors, and influencing on signaling pathways related to MYC were used in the past as potential modulatory targets, but failed to be developed as drug candidates. Myc PPI inhibitors failed to show sufficinet efficacy in cell-based assays and animal models due to the requirement of high target occupancy to drive efficacy. Modulators of signaling pathways upstream to myc, for example mTOR modulators, failed due to lack of target specificity.

Nevertheless, a therapeutic approach to target c-Myc has remained elusive. The absence of a clear ligand-binding domain establishes a formidable obstacle toward direct inhibition, which is a challenging feature shared among many compelling transcriptional targets in cancer. Thus, alternative modalities that target Myc are required, as outlined herein, namely compounds which regulate Myc mRNA translation.

SUMMARY OF THE INVENTION

This invention provides a compound or its pharmaceutically acceptable salt, stereoisomer, tautomer, hydrate, N-oxide, reverse amide analog, prodrug, isotopic variants (e.g., deuterated analog), PROTAC, pharmaceutical product or any combination thereof, represented by the structure of formula I(j), I(n) and/or I(o), and by the structures listed in Table 1, as defined herein below. In various embodiments, the compound is a c-MYC mRNA translation modulator. In various embodiments, the compound is a c-MYC mRNA transcription regulator. In various embodiments, the compound is a c-MYC inhibitor. In various embodiments, the compound is any combination of a c-MYC mRNA translation modulator, c-MYC mRNA transcription regulator and c-MYC inhibitor.

This invention further provides a pharmaceutical composition comprising a compound or its pharmaceutically acceptable salt, stereoisomer, tautomer, hydrate, N-oxide, prodrug, isotopic variants (e.g., deuterated analog), PROTAC, pharmaceutical product or any combination thereof, represented by the structure of formula I(j), I(n) and/or I(o), and by the structures listed in Table 1, as defined herein below, and a pharmaceutically acceptable carrier.

This invention further provides a method of treating, suppressing, reducing the severity, reducing the risk of developing or inhibiting cancer in a subject, comprising administering a compound represented by the structure of formula I(j), I(n) and/or I(o), and by the structures listed in Table 1, as defined herein below, to a subject suffering from cancer under conditions effective to treat, suppress, reduce the severity, reduce the risk of developing, or inhibit cancer in said subject.

This invention further provides a method for suppressing, reducing or inhibiting tumor growth in a subject, comprising administering a compound represented by the structure of formula I(j), I(n) and/or I(o), and by the structures listed in Table 1, as defined herein below, to a subject, under conditions effective to suppress, reduce or inhibit tumor growth in said subject. In some embodiment, the tumor is cancerous. In some embodiment, the subject suffers from cancer.

This invention further provides a method of modulating c-MYC mRNA translation in a cell, comprising contacting a compound represented by the structure of formula I(j), I(n) and/or I(o) and by the structures listed in Table 1, as defined herein below, with a cell, thereby modulating c-MYC mRNA translation in said cell.

This invention further provides a method of regulating c-MYC mRNA transcription in a cell, comprising contacting a compound represented by the structure of formula I(j), I(n) and/or I(o) and by the structures listed in Table 1, as defined herein below, with a cell, thereby regulating c-MYC mRNA transcription in said cell.

In the upper panel, significant decrease in c-Myc protein level was observed after treatment with either actinomycin D or tested compound. Lower panel shows complete reduction in c-Myc mRNA level as well as transcription sites after treatment with actinomycin D. Treatment with tested compound although reduced c-Myc mRNA levels by 30% without affecting transcription sites. In gray, cell nuclei stained with DAPI; in red, c-Myc protein; in purple, c-Myc mRNA; in yellow, c-Myc transcription sites.

Figure 4:
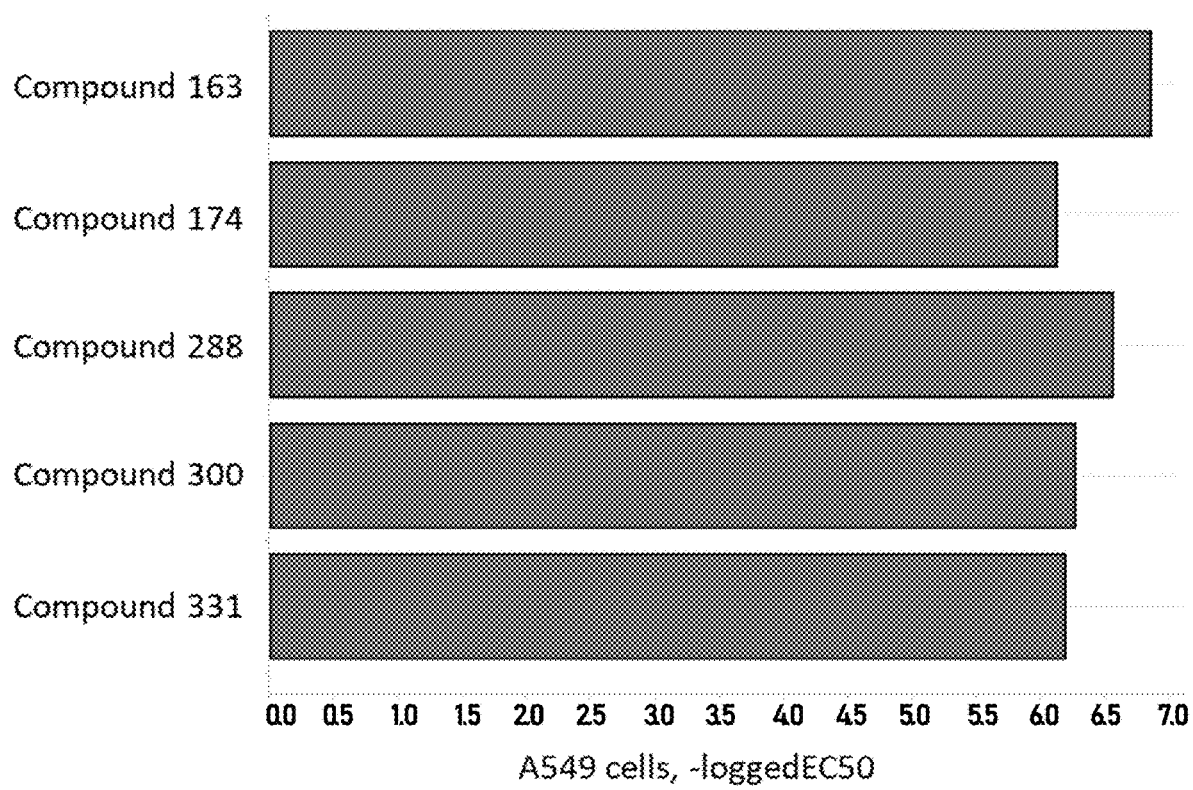

FIG. 4 demonstrates the efficacy of compounds according to this invention in A549 cells.

Figure 5:
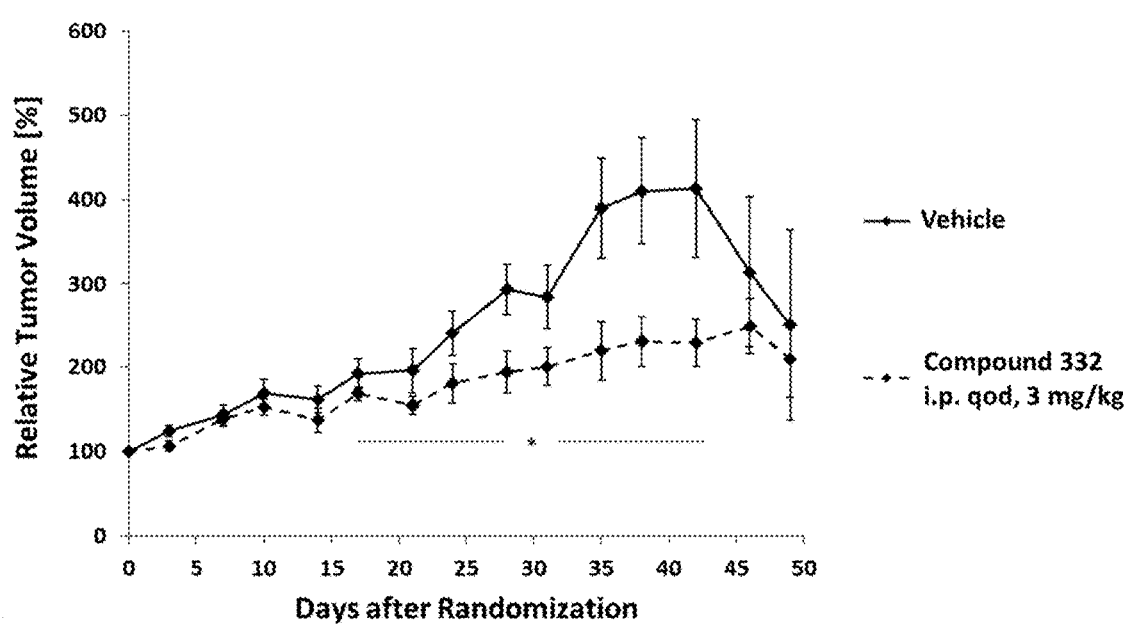

FIG. 5 demonstrates the in vivo data measured for compound 332. Compound 332 inhibited c-Myc-dependent tumor growth in-vivo. Relative tumor volumes of A549 xenografts in NMRI female nude mice after treatment with compound 3 mg/kg twice a week for 49 days. Error bars represent median±SEM, n=10 mice at each time point and analyzed by one-tailed T-TEST in Prism for *p<0.05

DETAILED DESCRIPTION OF THE INVENTION

In various embodiments, this invention is directed to a compound represented by the structure of formula (I):

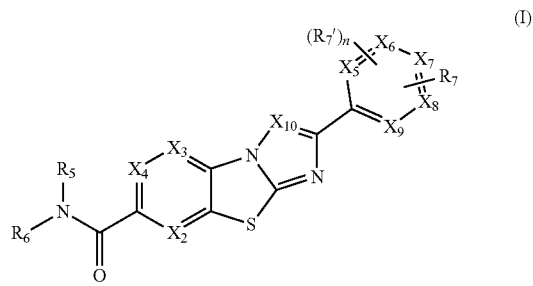

wherein
$X_2$, $X_3$, and $X_4$, are each independently nitrogen or CH;
$X_5$, $X_6$, $X_7$, $X_8$ and $X_9$ are each independently nitrogen or carbon atoms;
$X_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));
$R_5$ is H or C$_1$-C$_5$ linear or branched alkyl (e.g. methyl);
$R_6$ is H, F, Cl, Br, I, OH, SH, $R_8$—OH, $R_8$—SH, —$R_8$—O—$R_{10}$ (e.g., CH$_2$—O—CH$_3$, (CH$_2$)$_2$O—CH$_3$, (CH$_2$)$_3$O—CH$_3$, (CH$_2$)$_2$O—CH(CH$_3$)$_2$), $R_8$—S—$R_{10}$ (e.g., (CH$_2$)$_3$—S—(CH$_2$)$_2$CH$_3$), $R_8$—NHC(O)—$R_{10}$, —O—$R_8$—$R_{10}$, $R_8$-(substituted or unsubstituted C$_3$-C$_8$ cycloalkyl) (e.g., CH$_2$-cyclopropyl, CH$_2$-cyclobutanol, CH$_2$-difluorocyclopropyl, CH$_2$-methylcyclopropyl, CH$_2$-dimethylamino-cyclohexyl, (CH$_2$)$_2$-cyclopentanole, CH$_2$-cyclohexanol), $R_8$-(substituted or unsubstituted, saturated, unsaturated or aromatic, single, fused or spiro 3-10 membered heterocyclic ring) (e.g., (CH$_2$)$_3$-pyran, (CH$_2$)$_2$-pyrrazole, (CH$_2$)$_2$-imidazole, CH$_2$-tetrahydrofurane, CH$_2$-dioxane, CH$_2$-oxetane, CH$_2$-piperidine, CH$_2$-triazole, CH$_2$-1-oxa-8-azaspiro[4.5]decane, (CH$_2$)$_3$-diazabicyclo[2.2.1] heptane, CH$_2$-methyl-THF, CH$_2$-ethyl-piperidine, CH$_2$-oxa-azaspirodecane, (CH$_2$)$_3$-dimethylpyrazole, CH$_2$-2-oxo-methylpyrrolidine, CH$_2$-methyl-azetidine, CH$_2$-azaspiroheptane), CF$_3$, CD$_3$, OCD$_3$, CN, NO$_2$, —CH$_2$CN, —$R_8$CN, NH$_2$, NHR, N(R)$_2$, NH($R_{10}$), N($R_{10}$)($R_{11}$), $R_8$—N($R_{10}$)($R_{11}$) (e.g., ($CH_2$)$_3$-4-fluoro-piperidine, ($CH_2$)$_3$—N($CH_2CH_3$)$_2$, ($CH_2$)$_3$—N(CH($CH_3$)$_2$)$_2$, ($CH_2$)$_3$-piperidine, ($CH_2$)$_4$—NH($CH_3$), ($CH_2$)$_3$—NH—$CH_3$, ($CH_2$)$_3$—NH—$CH_2CH_3$, ($CH_2$)$_3$—N($CH_2CH_3$)$_2$, ($CH_2$)$_3$—$NH_2$, ($CH_2$)$_3$—N($CH_2CH_3$)($CH_2CF_3$)), $R_8$—C(O)N($R_{10}$)($R_{11}$) (e.g., ($CH_2$)$_2$—C(O)- piperidine), $R_9$—$R_8$—N($R_{10}$)($R_{11}$) (e.g., ($CH_2$)$_2$—C(O)-piperidine), B(OH)$_2$, —OC(O)$CF_3$, —$OCH_2$Ph, NHC(O)—$R_{10}$, NHCO—N($R_{10}$)($R_{11}$), COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —C(O)$NH_2$, C(O)NHR, C(O)N($R_{10}$)($R_{11}$), $SO_2$R, $SO_2$N($R_{10}$)($R_{11}$), CH($CF_3$)(NH—$R_{10}$), $C_1$-$C_5$ linear or branched, substituted or unsubstituted alkyl (e.g., CH($CH_3$)$CH_2OCH_3$, CH($CH_3$)$CH_2NH_2$, CH($CH_3$)C(O)N($CH_3$)$_2$, $CH_2$—CH(OH)Ph, ($CH_2$)$_3$N(H)$CH_2CH_3$, CH($CH_3$)($CH_2$)$_2$OH, CH($CH_2$OH)($CH_2CH_3$), ($CH_2$)$_3$—$OCH_3$, ($CH_2$)$_2$—$OCH_3$, ($CH_2$)$_2$—OCH($CH_3$)$_2$, CH($CH_2$OH)($CH_2$CH($CH_3$)$_2$), $CH_2$CH($CH_3$)($OCH_3$), $CH_2$CH(N($CH_3$)$_2$)($CH_2CH_3$), benzyl, methyl, ethyl, $CH_2$—$OCH_2$—$CH_2$—O—$CH_3$, CH($CH_3$)C(O)N($CH_3$)$_2$), $C_1$-$C_5$ linear or branched, substituted or unsubstituted alkenyl, $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy (e.g. methoxy, O—($CH_2$)$_2$O—$CH_3$), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), $R_8$-(substituted or unsubstituted $C_3$-$C_8$ cycloalkyl), substituted or unsubstituted, saturated or unsaturated, single fused, bridged or spiro 3-10 membered heterocyclic ring (e.g., piperidine, 1-methylpiperidine, 3-fluoro-1-methylpiperidine, azetidine, 1-methylazetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted $R_8$-aryl (e.g., benzyl), substituted or unsubstituted benzyl;

or $R_6$ and $R_5$ are joined to form a substituted or unsubstituted 5-8 membered heterocyclic ring (e.g., azepane, piperazine, 2-(piperazin-1-yl)acetamide);

or $R_6$ is represented by the structure of formula B or Bi:

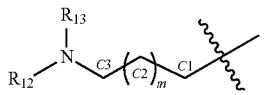

B

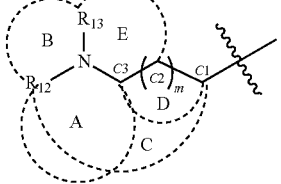

Bi wherein m is 0 or 1; and $R_{12}$ is $R_{20}$ or $C_1$-$C_5$ C(O)-alkyl, and $R_{13}$ is $R_{30}$; or $R_{12}$ and $R_{13}$ are both H;

$R_{12}$ and $R_{13}$ are each independently H or substituted or unsubstituted $C_1$-$C_5$ alkyl (e.g., ethyl, trifluoroethyl);

$R_{12}$ and C3 are joined to form ring A and $R_{13}$ is $R_{30}$; or $R_{12}$ and $R_{13}$ are joined to form ring B; or $R_{12}$ and C1 are joined to form ring C and $R_{13}$ is $R_{30}$; or C1 and C3 are joined to form ring D and $R_{12}$ and $R_{13}$ are each independently $R_{30}$; or $R_{13}$ and C2 are joined to form ring E, m is 1, and $R_{12}$ is $R_{30}$; or $R_{12}$ and $R_{13}$ are joined to form ring B and C1 and C3 are joined to form ring D;

wherein

Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine;

Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethylpyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and Ring D is a substituted or unsubstituted $C_3$-$C_8$ cycloalkyl (e.g., cyclobutane, cyclohexane);

$R_7$ is H, F, Cl, Br, I, OH, O—$R_{20}$, SH, $R_8$—OH, $R_8$—SH, $SR_{10}$, —$R_8$—O—$R_{10}$, —$R_8$—S—$R_{10}$, $R_8$—($C_3$-$C_5$ cycloalkyl), $CF_3$, $CD_3$, $OCD_3$, CN, $NO_2$, —$CH_2$CN, —$R_8$CN, $NH_2$, NHR, N(R)$_2$, NH($R_{10}$), N($R_{10}$)($R_{11}$), $R_8$—N($R_{10}$)($R_{11}$), $R_9$—$R_8$—N($R_{10}$)($R_{11}$), B(OH)$_2$, —OC(O)$CF_3$, —$OCH_2$Ph, NHC(O)—$R_{10}$, NHCO—N($R_{10}$)($R_{11}$), COOH, —C(O)Ph, C(O)O—$R_{10}$(COO—$CH_3$), $R_8$—C(O)—$R_{10}$, C(O)H, C(O)—$R_{10}$, $C_1$-$C_5$ linear or branched C(O)-haloalkyl, —C(O)$NH_2$, C(O)NHR (e.g., C(O)NH($CH_3$)), C(O)N($R_{10}$)($R_{11}$) (e.g., C(O)NH($CH_3$), C(O)NH($CH_2CH_3$), C(O)NH($CH_2CH_2OCH_3$), C(O)

NH(CH$_2$CH$_2$OH)), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., methylimidazole, methyl, ethyl), C$_1$-C$_5$ linear or branched, substituted or unsubstituted alkenyl, C$_1$-C$_5$ linear or branched, or C$_3$-C$_8$ cyclic haloalkyl (e.g., CHF$_2$), C$_1$-C$_5$ linear or branched, or C$_3$-C$_8$ cyclic alkoxy (e.g. methoxy, ethoxy), optionally wherein at least one methylene group (CH$_2$) in the alkoxy is replaced with an oxygen atom, C$_1$-C$_5$ linear or branched thioalkyl, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_5$ cycloalkyl (e.g., cyclopropyl, cyclopropanol, cyclohexyl, bicyclo[1.1.1]pentane), substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine, 4,7-diazaspiro[2.5]octane, 2,5-diazabicyclo[2.2.1]heptane, piperazine-2-one), R$_8$-(substituted or unsubstituted single, fused or spiro 3-8 membered heterocyclic ring), substituted or unsubstituted aryl, substituted or unsubstituted benzyl;

or R$_7$ is represented by the structure of formula A:

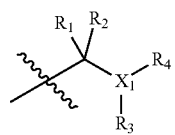

A wherein
X$_1$ is N or O;
R$_1$ and R$_2$ are each independently H, F, Cl, Br, I, OH, SH, or CF$_3$, substituted or unsubstituted C$_1$-C$_5$ alkyl (e.g., CH$_2$OH), C$_1$-C$_5$ linear or branched, or C$_3$-C$_8$ cyclic haloalkyl, substituted or unsubstituted C$_1$-C$_5$ linear or branched, or C$_3$-C$_5$ cyclic alkoxy; or R$_1$ and R$_2$ are joined to form =O or a C$_3$-C$_8$ carbocyclic or heterocyclic ring (e.g., cyclopropyl);
R$_3$ and R$_4$ are each independently H, Me, substituted or unsubstituted C$_1$-C$_5$ alkyl (e.g., methoxyethylene, methylaminoethylene, aminoethylene), —R$_8$—O—R$_{10}$ (e.g., (CH$_2$)$_2$O—CH$_3$), R$_8$—N(R$_{10}$)(R$_{11}$) (e.g., (CH$_2$)$_2$—NH(CH$_3$)), substituted or unsubstituted C$_3$-C$_8$ cycloalkyl (e.g., cyclopropyl), substituted or unsubstituted 5-7 membered heterocyclic ring (e.g., pyrrolidine, methylpyrrolidine, piperidine), or R$_{20}$;
or R$_3$ and R$_4$ are joined to form a 3-8 membered heterocyclic ring (e.g., pyrrolidine, pyrrolidone, 2-oxopyrrolidine, piperidine, morpholine, piperazine, imidazole);
or R$_2$ and R$_4$ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);
wherein if X$_1$ is O then R$_4$ is absent;
R$_7'$ is H, F, Cl, Br, I, OH, O—R$_{20}$, SH, R$_8$—OH, R$_8$—SH, —R$_8$—O—R$_{10}$, R$_8$—(C$_3$-C$_5$ cycloalkyl), R$_8$—(3-8 membered heterocyclic ring), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., isopropyl, methyl, ethyl), C$_1$-C$_5$ linear or branched, substituted or unsubstituted alkenyl, C$_1$-C$_5$ linear or branched, or C$_3$-C$_8$ cyclic haloalkyl (e.g., CHF$_2$), C$_1$-C$_5$ linear or branched, or C$_3$-C$_8$ cyclic alkoxy (e.g. methoxy), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidine-2-one, piperidin-4-ol, dioxazole, 2-oxopyrrolidine), substituted or unsubstituted aryl, substituted or unsubstituted benzyl;
or R$_7$ and R$_7'$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);
R$_{20}$ is represented by the following structure:

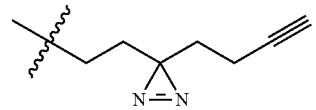 [SMILES: *CCC1(CCC#C)N=N1]

R$_{30}$ is H, R$_{20}$, F, Cl, Br, I, OH, SH, alkoxy, N(R)$_2$, NH(R$_{10}$), N(R$_{10}$)(R$_{11}$), CF$_3$, CN, NO$_2$, C$_1$-C$_5$ linear or branched, substituted or unsubstituted alkyl (e.g., methyl, ethyl, CH$_2$—CH$_2$—O—CH$_2$—CH$_2$—O—CH$_3$, CH$_2$—O—CH$_2$—CH$_2$—O—CH$_3$), C$_1$-C$_5$ linear or branched alkoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$O—CH$_3$), —R$_8$—O—R$_{10}$, —R$_8$—R$_{10}$ (e.g., (CH$_2$)$_2$—O—CH$_3$), substituted or unsubstituted aryl (e.g., phenyl), substituted or unsubstituted heteroaryl (e.g., pyridine (2, 3, and 4-pyridine);
R is H, F, Cl, Br, I, OH, SH, alkoxy, NH(R$_{10}$), NH—CH$_2$-cyclopropyl, N(R$_{10}$)(R$_{11}$), CF$_3$, CN, NO$_2$, COOH, C$_1$-C$_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2$O—$CH_3$), substituted or unsubstituted aryl (e.g., phenyl), substituted or unsubstituted heteroaryl (e.g., pyridine (2, 3, and 4-pyridine);

each $R_8$ is independently $[CH_2]p$
  wherein p is between 1 and 10;

$R_9$ is $[CH]_q$, $[C]_q$
  wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(a):

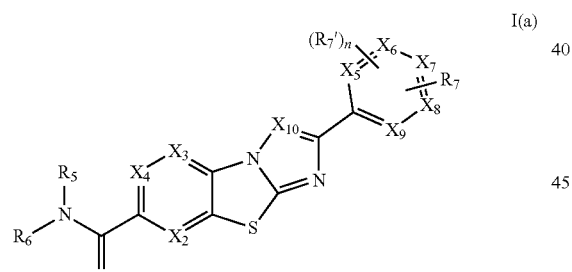

I(a)

wherein
  $X_2$, $X_3$, and $X_4$, are each independently nitrogen or CH;
  $X_5$, $X_6$, $X_7$, $X_8$ and $X_9$ are each independently nitrogen or carbon atoms;
  $X_{10}$ is N, CH, or C(R) (e.g., $C(CH_2)OH$, $C(CH_2)_2OH$, $C(NH$—$CH_2$-cyclopropyl), $C(CH_3)$, C(cyclopropyl), C(isopropoxy), C(COOH));
  $R_5$ is H or $C_1$-$C_5$ linear or branched alkyl (e.g. methyl);
  $R_6$ is H, F, Cl, Br, I, OH, SH, $R_8$—OH, $R_8$—SH, —$R_8$—O—$R_{10}$ (e.g., $CH_2$—O—$CH_3$, $(CH_2)_2O$—$CH_3$ $(CH_2)_3O$—$CH_3$, $(CH_2)_2O$—$CH(CH_3)_2)$, $R_8$—S—$R_{10}$ (e.g., $(CH_2)_3$—S—$(CH_2)_2CH_3$), $R_8$—NHC(O)—$R_{10}$, —O—$R_8$—$R_{10}$, $R_8$-(substituted or unsubstituted $C_3$-$C_8$ cycloalkyl) (e.g., $CH_2$-cyclopropyl, $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, $CH_2$-cyclohexanol), $R_8$-(substituted or unsubstituted, saturated, unsaturated or aromatic, single, fused or spiro 3-10 membered heterocyclic ring) (e.g., $(CH_2)_3$-pyran, $(CH_2)_2$-pyrrazole, $(CH_2)_2$-imidazole, $CH_2$-tetrahydrofurane, $CH_2$-dioxane, $CH_2$-oxetane, $CH_2$-piperidine, $CH_2$-triazole, $CH_2$-1-oxa-8-azaspiro[4.5]decane, $(CH_2)_3$-diazabicyclo[2.2.1]heptane, $CH_2$-methyl-THF, $CH_2$-ethyl-piperidine, $CH_2$-oxa-azaspirodecane, $(CH_2)_3$-dimethylpyrazole, $CH_2$-2-oxo-methylpyrrolidine, $CH_2$-methyl-azetidine, $CH_2$-azaspiroheptane), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$ (e.g., $(CH_2)_3$-4-fluoro-piperidine, $(CH_2)_3$—$N(CH_2CH_3)_2$, $(CH_2)_3$—$N(CH(CH_3)_2)_2$, $(CH_2)_3$-piperidine, $(CH_2)_4$—$NH(CH_3)$, $(CH_2)_3$—NH—$CH_3$, $(CH_2)_3$—NH—$CH_2CH_3$, $(CH_2)_3$—$N(CH_2CH_3)_2$, $(CH_2)_3$—$NH_2$, $(CH_2)_3$—$N(CH_2CH_3)(CH_2CF_3)$), $R_8$—C(O)N$(R_{10})(R_{11})$ (e.g., $(CH_2)_2$—C(O)- piperidine), $R_9$—$R_8$—$N(R_{10})(R_{11})$ (e.g., $(CH_2)_2$—C(O)-piperidine), $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., $CH(CH_3)CH_2OCH_3$, $CH(CH_3)CH_2NH_2$, $CH(CH_3)C(O)N(CH_3)_2$, $CH_2$—CH(OH)Ph, $(CH_2)_3N(H)CH_2CH_3$, $CH(CH_3)(CH_2)_2OH$, $CH(CH_2OH)(CH_2CH_3)$, $(CH_2)_3$—$OCH_3$, $(CH_2)_2$—$OCH_3$, $(CH_2)_2$—$OCH(CH_3)_2$, $CH(CH_2OH)(CH_2CH(CH_3)_2)$, $CH_2CH(CH_3)(OCH_3)$, $CH_2CH(N(CH_3)_2)(CH_2CH_3)$, benzyl, methyl, ethyl, $CH_2$—$OCH_2$—$CH_2$—O—$CH_3$, $CH(CH_3)C(O)N(CH_3)_2)$, $C_1$-$C_5$ linear or branched, substituted or unsubstituted alkenyl, $C_1$-$C_5$ linear or branched, or $C_3$-$C_8$ cyclic haloalkyl, substituted or unsubstituted $C_1$-$C_5$ linear or branched, or $C_3$-$C_5$ cyclic alkoxy (e.g. methoxy, O—$(CH_2)_2O$—$CH_3$), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_5$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), $R_8$-(substituted or unsubstituted $C_3$-$C_5$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyloxetane, hydroxy-tetrahydrofurane, azepan-2-one, azabicyclohexane), substituted or unsubstituted aryl, substituted or unsubstituted $R_8$-aryl (e.g., benzyl), substituted or unsubstituted benzyl;

or $R_6$ and $R_5$ are joined to form a substituted or unsubstituted 5-8 membered heterocyclic ring (e.g., azepane, piperazine, 2-(piperazin-1-yl)acetamide);

or $R_6$ is represented by the structure of formula B or Bi:

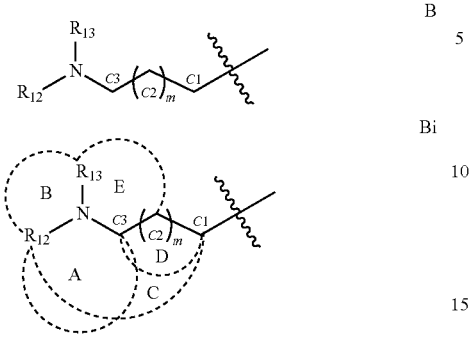

wherein
m is 0 or 1; and
$R_{12}$ is $R_{20}$ or $C_1$-$C_5$ C(O)-alkyl, and $R_{13}$ is $R_{30}$; or
$R_{12}$ and $R_{13}$ are both H;
$R_{12}$ and $R_{13}$ are each independently H or substituted or unsubstituted $C_1$-$C_5$ alkyl (e.g., ethyl, trifluoroethyl);
$R_{12}$ and C3 are joined to form ring A and $R_{13}$ is $R_{30}$; or
$R_{12}$ and $R_{13}$ are joined to form ring B; or
$R_{12}$ and C1 are joined to form ring C and $R_{13}$ is $R_{30}$; or
C1 and C3 are joined to form ring D and $R_{12}$ and $R_{13}$ are each independently $R_{30}$; or
$R_{13}$ and C2 are joined to form ring E, m is 1, and $R_{12}$ is $R_{30}$; or
$R_{12}$ and $R_{13}$ are joined to form ring B and C1 and C3 are joined to form ring D;
wherein
Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);
Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethylpyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and
Ring D is a substituted or unsubstituted $C_3$-$C_8$ cycloalkyl (e.g., cyclobutane, cyclohexane);
$R_7$ is O—$R_{20}$, SH, $R_8$—OH, $R_8$—SH, S$R_{10}$, —$R_8$—O—$R_{10}$, —$R_8$—S—$R_{10}$, $R_8$—($C_3$-$C_8$ cycloalkyl), $CD_3$, $OCD_3$, $NO_2$, —$CH_2CN$, $R_8CN$, $R_8$—$N(R_{10})(R_{11})$, $R_9$—$R_8$—$N(R_{10})(R_1)$, $B(OH)_2$, —$OC(O)CF_3$, —$OCH_2Ph$, $NHCO$—$N(R_{10})(R_{11})$, $R_8$—C(O)—$R_{10}$, $SO_2N(R_{10})(R_{11})$, $CH(CF_3)(NH$—$R_{10})$, $C_1$-$C_5$ linear or branched, substituted or unsubstituted alkenyl, $C_1$-$C_5$ linear or branched thioalkoxy, $C_1$-$C_5$ linear or branched alkoxyalkyl, substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, pyrrolidine-3-carbonitrile, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine, 4,7-diazaspiro[2.5]octane, 2,5-diazabicyclo[2.2.1]heptane, piperazine-2-one), $R_8$-(substituted or unsubstituted single, fused or spiro 3-8 membered heterocyclic ring), substituted or unsubstituted aryl, substituted or unsubstituted benzyl;
or $R_7$ is represented by the structure of formula A:

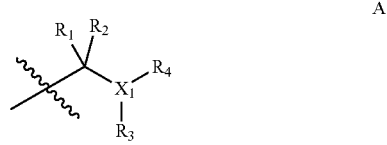

wherein
$X_1$ is N or O;
$R_1$ and $R_2$ are each independently H, F, Cl, Br, I, OH, SH, or $CF_3$, substituted or unsubstituted $C_1$-$C_5$ alkyl (e.g., $CH_2OH$), $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy;
or $R_1$ and $R_2$ are joined to form a $C_3$-$C_8$ carbocyclic or heterocyclic ring (e.g., cyclopropyl); $R_3$ and $R_4$ are each independently H, Me, substituted or unsubstituted $C_1$-$C_5$ alkyl (e.g., methoxyethylene, methylaminoethyl, aminoethyl), —$R_8$—O—$R_{10}$ (e.g., $(CH_2)_2O$—$CH_3$), $R_8$—$N(R_{10})(R_{11})$ (e.g., $(CH_2)_2$—$NH(CH_3)$), substituted or unsubstituted $C_3$-$C_8$ cycloalkyl (e.g., cyclopropyl), substituted or unsubstituted 5-7 membered heterocyclic ring (e.g., pyrrolidine, methylpyrrolidine, piperidine), or $R_{20}$;
or $R_3$ and $R_4$ are joined to form a 3-8 membered heterocyclic ring (e.g., pyrrolidine, pyrrolidone, 2-oxopyrrolidine, piperidine, morpholine, piperazine, imidazole);
or $R_2$ and $R_4$ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);
wherein if $X_1$ is O then $R_4$ is absent;
$R_7'$ is H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., isopropyl, methyl, ethyl), C$_1$-C$_5$ linear or branched, substituted or unsubstituted alkenyl, C$_1$-C$_5$ linear or branched, or C$_3$-C$_8$ cyclic haloalkyl (e.g., CHF$_2$), C$_1$-C$_5$ linear or branched, or C$_3$-C$_8$ cyclic alkoxy (e.g. methoxy), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl; or R$_7$ and R$_7$' are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine); R$_{20}$ is represented by the following structure:

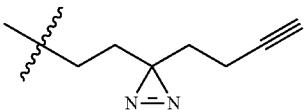 [SMILES: *CCC1(CCC#C)N=N1]

R is H, F, Cl, Br, I, OH, SH, alkoxy, NH(R$_{10}$), NH—CH$_2$-cyclopropyl, N(R$_{10}$)(R$_{11}$), CF$_3$, CN, NO$_2$, COOH, C$_1$-C$_5$ linear or branched, substituted or unsubstituted alkyl (e.g., methyl, ethyl, CH$_2$—OH, CH$_2$—CH$_2$—OH, CH$_2$—CH$_2$—O—CH$_2$—O—CH$_3$, CH$_2$—O—CH$_2$—CH$_2$—O—CH$_3$), C$_3$-C$_8$ substituted or unsubstituted cycloalkyl, cyclopropyl, C$_1$-C$_5$ linear or branched alkoxy, isopropoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$—O—CH$_3$), —R$_8$—O—R$_{10}$, —R$_8$—R$_{10}$ (e.g., (CH$_2$)$_2$O—CH$_3$), substituted or unsubstituted aryl (e.g., phenyl), substituted or unsubstituted heteroaryl (e.g., pyridine (2, 3, and 4-pyridine);

R$_{30}$ is H, R$_{20}$, F, Cl, Br, I, OH, SH, alkoxy, N(R)$_2$, NH(R$_{10}$), N(R$_{10}$)(R$_{11}$), CF$_3$, CN, NO$_2$, C$_1$-C$_5$ linear or branched, substituted or unsubstituted alkyl (e.g., methyl, ethyl, CH$_2$—CH$_2$—O—CH$_2$—CH$_2$—O—CH$_3$, CH$_2$—O—CH$_2$—CH$_2$—O—CH$_3$), C$_1$-C$_5$ linear or branched alkoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$O—CH$_3$), —R$_8$—O—R$_{10}$, —R$_8$—R$_{10}$ (e.g., (CH$_2$)$_2$—O—CH$_3$), substituted or unsubstituted aryl (e.g., phenyl), substituted or unsubstituted heteroaryl (e.g., pyridine (2, 3, and 4-pyridine);

each R$_8$ is independently [CH$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ substituted or unsubstituted linear or branched alkyl (e.g., methyl, ethyl, CH$_2$-cyclopropyl, CH$_2$—CH$_2$—O—CH$_3$), C$_1$-C$_5$ substituted or unsubstituted linear or branched haloalky (e.g., CH$_2$CF$_3$), C$_1$-C$_5$ linear or branched alkoxy (e.g., O—CH$_3$), R$_{20}$, C(O)R, or S(O)$_2$R;

or R$_{10}$ and R$_{11}$ are joined to form a substituted or unsubstituted 3-8 membered heterocyclic
ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(b):

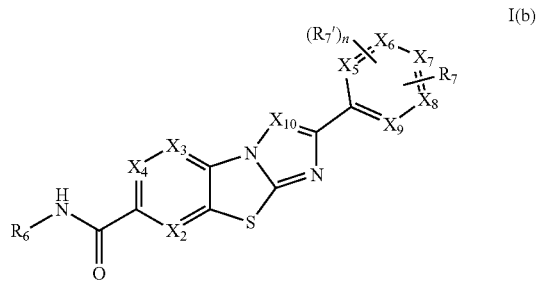

I(b)

wherein

X$_2$, X$_3$, and X$_4$, are each independently nitrogen or CH;

X$_5$, X$_6$, X$_7$, X$_8$ and X$_9$ are each independently nitrogen or carbon atoms;

X$_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));

R$_6$ is F, Cl, Br, I, OH, SH, R$_8$—OH, R$_8$—SH, —R$_8$—O—R$_{10}$ (e.g., CH$_2$—O—CH$_3$), R$_8$—S—R$_{10}$ (e.g., (CH$_2$)$_3$—S—(CH$_2$)$_2$CH$_3$), R$_8$—NHC(O)—R$_{10}$, —O—R$_8$—R$_{10}$, R$_8$-(substituted or unsubstituted C$_3$-C$_8$ cycloalkyl) (e.g., CH$_2$-cyclobutanol, CH$_2$-difluorocyclopropyl, CH$_2$-methylcyclopropyl, CH$_2$-dimethylamino-cyclohexyl, (CH$_2$)$_2$-cyclopentanole, CH$_2$-cyclohexanol), (CH$_2$)$_3$-pyran, CH$_2$-tetrahydrofurane, CH$_2$-dioxane, CH$_2$-methyl-THF, CH$_2$-oxaazaspirodecane, (CH$_2$)$_3$-dimethylpyrazole, CH$_2$-methyl-azetidine, CH$_2$-azaspiroheptane, CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., CH(CH$_3$)CH$_2$OCH$_3$, CH(CH$_3$)CH$_2$NH$_2$, CH(CH$_3$)C(O)N(CH$_3$)$_2$, CH$_2$—CH(OH)Ph, (CH$_2$)$_3$N(H)

CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$), C$_1$-C$_5$ linear or branched, substituted or unsubstituted alkenyl, C$_1$-C$_5$ linear or branched, or C$_3$-C$_8$ cyclic haloalkyl, substituted or unsubstituted C$_1$-C$_5$ linear or branched, or C$_3$-C$_8$ cyclic alkoxy (e.g. methoxy, O—(CH$_2$)$_2$O—CH$_3$), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., methoxycyclopropyl, methylcyclobutyl, cyclopropyl, aminomethyl-cyclobutyl, methoxycyclobutyl, 2,3-dihydro-1H-indenol), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyloxetane, hydroxy-tetrahydrofurane, azepan-2-one, azabicyclohexane), substituted or unsubstituted aryl, substituted or unsubstituted benzyl;

or R$_6$ and R$_5$ are joined to form a substituted or unsubstituted 5-8 membered heterocyclic ring (e.g., azepane, piperazine, 2-(piperazin-1-yl)acetamide);

or R$_6$ is represented by the structure of formula B or Bi:

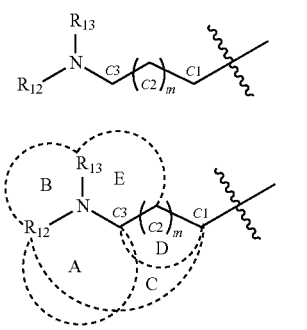

wherein
m is 0 or 1; and
R$_{12}$ is R$_{20}$ or C$_1$-C$_5$ C(O)-alkyl, and R$_{13}$ is R$_{30}$; or
R$_{12}$ and R$_{13}$ are both H; or
R$_{12}$ and C3 are joined to form ring A and R$_{13}$ is R$_{30}$; or
R$_{12}$ and R$_{13}$ are joined to form a substituted or unsubstituted pyrrolidine ring, piperazine, thiomorpholine 1,1-dioxide, 2-oxa-6-azaspiro[3.3]heptane, pyrazole, imidazole, 2,5-diazabicyclo[2.2.1]heptane or a diazabicyclo[2.2.1]heptane; or
R$_{12}$ and C1 are joined to form ring C and R$_{13}$ is R$_{30}$; or
C1 and C3 are joined to form ring D and R$_{12}$ and R$_{13}$ are each independently R$_{30}$; or
R$_{13}$ and C2 are joined to form ring E, m is 1, and R$_{12}$ is R$_{30}$; or R$_{12}$ and R$_{13}$ are joined to form ring B and C1 and C3 are joined to form ring D;
wherein
Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);
Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethylpyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and
Ring D is a substituted or unsubstituted C$_3$-C$_8$ cycloalkyl (e.g., cyclobutane, cyclohexane);
R$_7$ is H, F, Cl, Br, I, OH, O—R$_{20}$, SH, R$_8$—OH, R$_8$—SH, SR$_{10}$, —R$_8$—O—R$_{10}$, —R$_8$—S—R$_{10}$, R$_8$—(C$_3$-C$_8$ cycloalkyl), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$(COO—CH$_3$), R$_8$—C(O)—R$_{10}$, C(O)H, C(O)—R$_{10}$, C$_1$-C$_5$ linear or branched C(O)-haloalkyl, —C(O)NH$_2$, C(O)NHR (e.g., C(O)NH(CH$_3$)), C(O)N(R$_{10}$)(R$_{11}$) (e.g., C(O)NH(CH$_3$), C(O)NH(CH$_2$CH$_2$OCH$_3$), C(O)NH(CH$_2$CH$_2$OH)), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., methylimidazole, methyl, ethyl), C$_1$-C$_5$ linear or branched, substituted or unsubstituted alkenyl, C$_1$-C$_5$ linear or branched, or C$_3$-C$_8$ cyclic haloalkyl (e.g., CHF$_2$), C$_1$-C$_5$ linear or branched, or C$_3$-C$_8$ cyclic alkoxy (e.g. methoxy, ethoxy), optionally wherein at least one methylene group (CH$_2$) in the alkoxy is replaced with an oxygen atom, C$_1$-C$_5$ linear or branched thioalkyl, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclopropanol, cyclohexyl, bicyclo[1.1.1]pentane), substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, pyrrolidine-3-carbonitrile, 3-cyanopyrrolidine, 1-methylpyrrolidine, pyrrolidin-2-one, pyrrolidin-3-one, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, 2-oxopyrrolidine, 4,7-diazaspiro[2.5]octane, 2,5-diazabicyclo[2.2.1]heptane, piperazine-2-one), R$_8$-(substituted or unsubstituted single, fused or spiro 3-8 membered heterocyclic ring), substituted or unsubstituted aryl, substituted or unsubstituted benzyl;

or $R_7$ is represented by the structure of formula A:

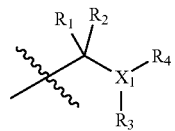

wherein $X_1$ is N or O;

$R_1$ and $R_2$ are each independently H, F, Cl, Br, I, OH, SH, or $CF_3$, substituted or unsubstituted $C_1$-$C_5$ alkyl (e.g., $CH_2OH$), $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy;

or $R_1$ and $R_2$ are joined to form =O or a $C_3$-$C_8$ carbocyclic or heterocyclic ring (e.g., cyclopropyl);

$R_3$ and $R_4$ are each independently H, Me, substituted or unsubstituted $C_1$-$C_5$ alkyl (e.g., methoxyethylene, methylaminoethylene, aminoethylene), —$R_8$—O—$R_{10}$ (e.g., $(CH_2)_2O$—$CH_3$), $R_8$—N($R_{10}$)($R_{11}$) (e.g., $(CH_2)_2$—$NH(CH_3)$), substituted or unsubstituted $C_3$-$C_8$ cycloalkyl (e.g., cyclopropyl), substituted or unsubstituted 5-7 membered heterocyclic ring (e.g., pyrrolidine, methylpyrrolidine, piperidine), or $R_{20}$;

or $R_3$ and $R_4$ are joined to form a 3-8 membered heterocyclic ring (e.g., pyrrolidine, pyrrolidone, 2-oxopyrrolidine, piperidine, morpholine, piperazine, imidazole);

or $R_2$ and $R_4$ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);

wherein if $X_1$ is O then $R_4$ is absent;

$R_7'$ is H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl; or $R_7$ and $R_7'$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

$R_{20}$ is represented by the following structure:

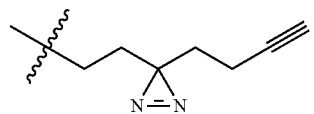 [SMILES: *CCC1(CCC#C)N=N1]

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2O$—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine);

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(c):

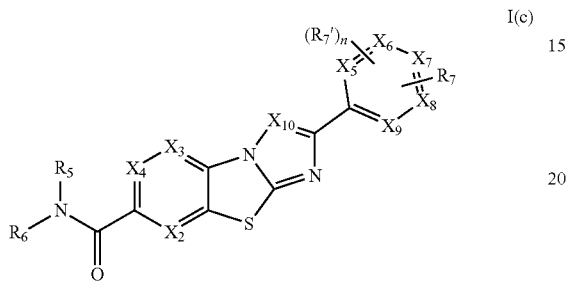

I(c)

wherein
$X_2$, $X_3$, and $X_4$, are each independently nitrogen or CH;
$X_5$, $X_6$, $X_7$, $X_8$ and $X_9$ are each independently nitrogen or carbon atoms;
$X_{10}$ is N, CH, or C(R) (e.g., $C(CH_2)OH$, $C(CH_2)_2OH$, $C(NH—CH_2$-cyclopropyl), $C(CH_3)$, C(cyclopropyl), C(isopropoxy), C(COOH));
$R_5$ is H or $C_1$-$C_5$ linear or branched alkyl (e.g. methyl);
$R_6$ is H, F, Cl, Br, I, OH, SH, $R_8$—OH, $R_8$—SH, —$R_8$—O—$R_{10}$ (e.g., $CH_2$—O—$CH_3$, $(CH_2)_2$O—$CH_3$, $(CH_2)_3$O—$CH_3$, $(CH_2)_2$O—$CH(CH_3)_2$), $R_8$—S—$R_{10}$ (e.g., $(CH_2)_3$—S—$(CH_2)_2CH_3$), $R_8$—NHC(O)—$R_{10}$, —O—$R_8$—$R_{10}$, $R_8$-(substituted or unsubstituted $C_3$-$C_8$ cycloalkyl) (e.g., $CH_2$-cyclopropyl, $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, $CH_2$-cyclohexanol), $R_8$-(substituted or unsubstituted, unsaturated or aromatic, single, fused or spiro 3-10 membered heterocyclic ring) (e.g., $(CH_2)_3$-pyran, $(CH_2)_2$-pyrrazole, $(CH_2)_2$-imidazole, $CH_2$-tetrahydrofurane, $CH_2$-dioxane, $CH_2$-oxetane, $CH_2$-piperidine, $CH_2$-triazole, $CH_2$-1-oxa-8-azaspiro[4.5]decane, $(CH_2)_3$-diazabicyclo[2.2.1]heptane, $CH_2$-methyl-THF, $CH_2$-ethyl-piperidine, $CH_2$-oxa-azaspirodecane, $(CH_2)_3$-dimethylpyrazole, $CH_2$-2-oxo-methylpyrrolidine, $CH_2$-methyl-azetidine, $CH_2$-azaspiroheptane), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$ (e.g., $(CH_2)_3$-4-fluoro-piperidine, $(CH_2)_3$—$N(CH_2CH_3)_2$, $(CH_2)_3$—$N(CH(CH_3)_2)_2$, $(CH_2)_3$-piperidine, $(CH_2)_4$—$NH(CH_3)$, $(CH_2)_3$—NH—$CH_3$, $(CH_2)_3$—NH—$CH_2CH_3$, $(CH_2)_3$—$N(CH_2CH_3)_2$, $(CH_2)_3$—$NH_2$, $(CH_2)_3$—$N(CH_2CH_3)(CH_2CF_3)$), $R_8$—$C(O)N(R_{10})(R_{11})$ (e.g., $(CH_2)_2$—C(O)- piperidine), $R_9$—$R_8$—$N(R_{10})(R_{11})$ (e.g., $(CH_2)_2$—C(O)-piperidine), $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH—R_{10})$, $C_1$-$C_5$ linear or branched, substituted or unsubstituted alkyl (e.g., $CH(CH_3)CH_2OCH_3$, $CH(CH_3)CH_2NH_2$, $CH(CH_3)C(O)N(CH_3)_2$, $CH_2$—CH(OH)Ph, $(CH_2)_3N(H)CH_2CH_3$, $CH(CH_3)(CH_2)_2OH$, $CH(CH_2OH)(CH_2CH_3)$, $(CH_2)_3$—$OCH_3$, $(CH_2)_2$—$OCH_3$, $(CH_2)_2$—$OCH(CH_3)_2$, $CH(CH_2OH)(CH_2CH(CH_3)_2)$, $CH_2CH(CH_3)(OCH_3)$, $CH_2CH(N(CH_3)_2)(CH_2CH_3)$, benzyl, methyl, ethyl, $CH_2$—$OCH_2$—$CH_2$—O—$CH_3$, $CH(CH_3)C(O)N(CH_3)_2$), $C_1$-$C_5$ linear or branched, substituted or unsubstituted alkenyl, $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy (e.g. methoxy, O—$(CH_2)_2O$—$CH_3$), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), $R_8$-(substituted or unsubstituted $C_3$-$C_5$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted $R_8$-aryl (e.g., benzyl), substituted or unsubstituted benzyl;

or $R_6$ and $R_5$ are joined to form a substituted or unsubstituted 5-8 membered heterocyclic ring (e.g., azepane, piperazine, 2-(piperazin-1-yl)acetamide);

or $R_6$ is represented by the structure of formula B or Bi:

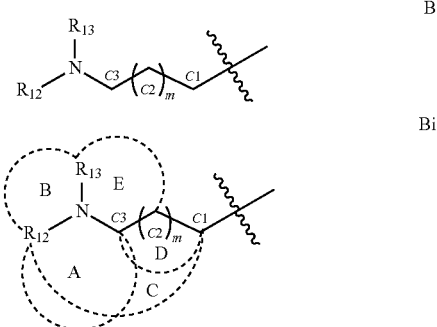

wherein
m is 0 or 1; and
$R_{12}$ is $R_{20}$ or $C_1$-$C_5$ C(O)-alkyl, and $R_{13}$ is $R_{30}$; or $R_{12}$ and $R_{13}$ are both H;
$R_{12}$ and $R_{13}$ are each independently H or substituted or unsubstituted $C_1$-$C_5$ alkyl (e.g., ethyl, trifluoroethyl);
$R_{12}$ and C3 are joined to form ring A and $R_{13}$ is $R_{30}$; or $R_{12}$ and $R_{13}$ are joined to form ring B; or $R_{12}$ and C1 are joined to form ring C and $R_{13}$ is $R_{30}$; or C1 and C3 are joined to form ring D and $R_{12}$ and $R_{13}$ are each independently $R_{30}$; or $R_{13}$ and C2 are joined to form ring E, m is 1, and $R_{12}$ is $R_{30}$; or $R_{12}$ and $R_{13}$ are joined to form ring B and C1 and C3 are joined to form ring D;

wherein

Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);

Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methyl-piperidin, fluoropiperidine, difluoropiperidine, pyrrolidine, piperazine, methylpyrrolidine, thiomorpholine 1,1-dioxide, 2-oxa-6-azaspiro [3.3]heptane, methyl-piperazine, dimethyl-pyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and Ring D is a substituted or unsubstituted $C_3$-$C_8$ cycloalkyl (e.g., cyclobutane, cyclohexane);

$R_7$ is Br, I, OH, O—$R_{20}$, SH, $R_8$—OH, $R_8$—SH, $SR_{10}$, —$R_8$—O—$R_{10}$, —$R_8$—S—$R_{10}$, $R_8$—($C_3$-$C_5$ cycloalkyl), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$(COO—$CH_3$), $R_8$—C(O)—$R_{10}$, C(O)H, C(O)—$R_{10}$, $C_1$-$C_5$ linear or branched C(O)-haloalkyl, —C(O)$NH_2$, C(O)NHR (e.g., C(O)NH(CH_3)), C(O)N($R_{10}$)($R_{11}$) (e.g., C(O)NH(CH_3), C(O)NH(CH_2CH_2OCH_3), C(O)NH(CH_2CH_2OH)), $SO_2R$, $SO_2N(R_{10})(R_{11})$, $CH(CF_3)(NH—R_{10})$, $C_1$-$C_5$ linear or branched, substituted or unsubstituted alkyl (e.g., methylimidazole, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched thioalkyl, $C_1$-$C_5$ linear or branched thioalkoxy, $C_1$-$C_5$ linear or branched alkoxyalkyl, substituted or unsubstituted $C_3$-$C_8$ cycloalkyl (e.g., cyclopropyl, cyclopropanol, cyclohexyl bicyclo[1.1.1]pentane), substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine, 4,7-diazaspiro[2.5]octane, 2,5-diazabicyclo[2.2.1]heptane, piperazine-2-one), $R_8$-(substituted or unsubstituted single, fused or spiro 3-8 membered heterocyclic ring), substituted or unsubstituted aryl, substituted or unsubstituted benzyl;

or $R_7$ is represented by the structure of formula A:

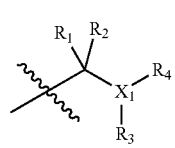

A wherein $X_1$ is N or O;

$R_1$ and $R_2$ are each independently H, F, Cl, Br, I, OH, SH, or $CF_3$, substituted or unsubstituted $C_1$-$C_5$ alkyl (e.g., $CH_2OH$), $C_1$-$C_5$ linear or branched, or $C_3$-$C_5$ cyclic haloalkyl, substituted or unsubstituted $C_1$-$C_5$ linear or branched, or $C_3$-$C_5$ cyclic alkoxy;

or $R_1$ and $R_2$ are joined to form =O or a $C_3$-$C_5$ carbocyclic or heterocyclic ring (e.g., cyclopropyl);

$R_3$ and $R_4$ are each independently H, Me, substituted or unsubstituted $C_1$-$C_5$ alkyl (e.g., methoxyethylene, methylaminoethylene, aminoethylene), —$R_8$—O—$R_{10}$ (e.g., $(CH_2)_2O$—$CH_3$), $R_8$—N($R_{10}$)($R_{11}$) (e.g., $(CH_2)_2$—$NH(CH_3)$), substituted or unsubstituted $C_3$-$C_5$ cycloalkyl (e.g., cyclopropyl), substituted or unsubstituted 5-7 membered heterocyclic ring (e.g., pyrrolidine, methylpyrrolidine, piperidine), or $R_{20}$;

or $R_3$ and $R_4$ are joined to form a 3-8 membered heterocyclic ring (e.g., pyrrolidine, pyrrolidone, 2-oxopyrrolidine, piperidine, morpholine, piperazine, imidazole);

or $R_2$ and $R_4$ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);

wherein if $X_1$ is O then $R_4$ is absent;

$R_7'$ is F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —OC(O)$CF_3$, —$OCH_2Ph$, NHC(O)—$R_{10}$, NHCO—N($R_{10}$)($R_{11}$), COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —C(O)$NH_2$, C(O)NHR, C(O)N($R_{10}$)($R_{11}$), $SO_2R$, $SO_2N(R_{10})(R_{11})$, $CH(CF_3)(NH—R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_5$ cyclic haloalkyl (e.g., CHF$_2$), C$_1$-C$_5$ linear or branched, or C$_3$-C$_5$ cyclic alkoxy (e.g. methoxy), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

wherein R$_7$' is different than R$_7$;

or R$_7$ and R$_7$' are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

R$_{20}$ is represented by the following structure:

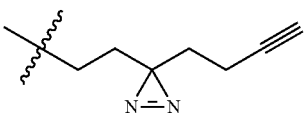 [SMILES: *CCC1(CCC#C)N=N1]

R$_{30}$ is H, R$_{20}$, F, Cl, Br, I, OH, SH, alkoxy, N(R)$_2$, NH(R$_{10}$), N(R$_{10}$)(R$_{11}$), CF$_3$, CN, NO$_2$, C$_1$-C$_5$ linear or branched, substituted or unsubstituted alkyl (e.g., methyl, ethyl, CH$_2$—CH$_2$—O—CH$_2$—CH$_2$—O—CH$_3$, CH$_2$—O—CH$_2$—CH$_2$—O—CH$_3$), C$_1$-C$_5$ linear or branched alkoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$O—CH$_3$), —R$_8$—O—R$_{10}$, —R$_8$—R$_{10}$ (e.g., (CH$_2$)$_2$—O—CH$_3$), substituted or unsubstituted aryl (e.g., phenyl), substituted or unsubstituted heteroaryl (e.g., pyridine (2, 3, and 4-pyridine);

R is H, F, Cl, Br, I, OH, SH, alkoxy, NH(R$_{10}$), NH—CH$_2$-cyclopropyl, N(R$_{10}$)(R$_{11}$), CF$_3$, CN, NO$_2$, COOH, C$_1$-C$_5$ linear or branched, substituted or unsubstituted alkyl (e.g., methyl, ethyl, CH$_2$—OH, CH$_2$—CH$_2$—OH, CH$_2$—CH$_2$—O—CH$_2$—CH$_2$—O—CH$_3$, CH$_2$—O—CH$_2$—CH$_2$—O—CH$_3$), C$_3$-C$_8$ substituted or unsubstituted cycloalkyl, cyclopropyl, C$_1$-C$_5$ linear or branched alkoxy, isopropoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$—O—CH$_3$), —R$_8$—O—R$_{10}$, —R$_8$—R$_{10}$ (e.g., (CH$_2$)$_2$O—CH$_3$), substituted or unsubstituted aryl (e.g., phenyl), substituted or unsubstituted heteroaryl (e.g., pyridine (2, 3, and 4-pyridine);

each R$_8$ is independently [CH$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ substituted or unsubstituted linear or branched alkyl (e.g., methyl, ethyl, CH$_2$-cyclopropyl, CH$_2$—CH$_2$—O—CH$_3$), C$_1$-C$_5$ substituted or unsubstituted linear or branched haloalky (e.g., CH$_2$CF$_3$), C$_1$-C$_5$ linear or branched alkoxy (e.g., O—CH$_3$), R$_{20}$, C(O)R, or S(O)$_2$R;

or R$_{10}$ and R$_{11}$ are joined to form a substituted or unsubstituted 3-8 membered heterocyclic ring (e.g., piperazine, piperidine), n is an integer between 1 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(d):

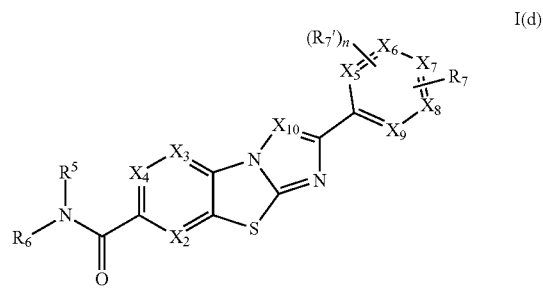

wherein

X$_2$, X$_3$, and X$_4$, are each independently nitrogen or CH;

X$_5$, X$_6$, X$_7$, X$_8$ and X$_9$ are each independently nitrogen or carbon atoms;

X$_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));

wherein at least one of X$_2$, X$_3$, X$_4$, X$_5$, X$_6$, X$_7$, X$_8$, X$_9$ or X$_{10}$ is N;

R$_5$ is H or C$_1$-C$_5$ linear or branched alkyl (e.g. methyl);

R$_6$ is H, F, Cl, Br, I, OH, SH, R$_8$—OH, R$_8$—SH, —R$_8$—O—R$_{10}$ (e.g., CH$_2$—O—CH$_3$, (CH$_2$)$_2$O—CH$_3$ (CH$_2$)$_3$O—CH$_3$, (CH$_2$)$_2$O—CH(CH$_3$)$_2$), R$_8$—S—R$_{10}$ (e.g., (CH$_2$)$_3$—S—(CH$_2$)$_2$CH$_3$), R$_8$—NHC(O)—R$_{10}$, —O—R$_8$—R$_{10}$, R$_8$-(substituted or unsubstituted C$_3$-C$_8$ cycloalkyl) (e.g., CH$_2$-cyclopropyl, CH$_2$-cyclobutanol, CH$_2$-difluorocyclopropyl, CH$_2$-methylcyclopropyl, CH$_2$-dimethylamino-cyclohexyl, (CH$_2$)$_2$-cyclopentanole, CH$_2$-cyclohexanol), R$_8$-(substituted or unsubstituted, saturated, unsaturated or aromatic, single, fused or spiro 3-10 membered heterocyclic ring) (e.g., (CH$_2$)$_3$-pyran, (CH$_2$)$_2$-pyrrazole, (CH$_2$)$_2$-imidazole, CH$_2$-tetrahydrofurane, CH$_2$-dioxane, CH$_2$-oxetane, CH$_2$-piperidine, CH$_2$-triazole, CH$_2$-1-oxa-8-azaspiro[4.5]decane, (CH$_2$)$_3$-diazabicyclo[2.2.1]heptane, CH$_2$-methyl-THF, CH$_2$-ethyl-piperidine, CH$_2$-oxa-azaspirodecane, (CH$_2$)$_3$-dimethylpyrazole, CH$_2$-2-oxo-methylpyrrolidine, CH$_2$-methyl-azetidine, CH$_2$-azaspiroheptane), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$) (e.g., (CH$_2$)$_3$-4-fluoro-piperidine, (CH$_2$)$_3$—N(CH$_2$CH$_3$)$_2$, (CH$_2$)$_3$—N(CH(CH$_3$)$_2$)$_2$, (CH$_2$)$_3$-piperidine, (CH$_2$)$_4$—NH(CH$_3$), (CH$_2$)$_3$—NH—CH$_3$, (CH$_2$)$_3$—NH—CH$_2$CH$_3$, (CH$_2$)$_3$—N(CH$_2$CH$_3$)$_2$, (CH$_2$)$_3$—

NH$_2$, (CH$_2$)$_3$—N(CH$_2$CH$_3$)(CH$_2$CF$_3$)), R$_8$—C(O)N(R$_{10}$)(R$_{11}$) (e.g., (CH$_2$)$_2$—C(O)- piperidine), R$_9$—R$_8$—N(R$_{10}$)(R$_{11}$) (e.g., (CH$_2$)$_2$—C(O)-piperidine), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., CH(CH$_3$)CH$_2$OCH$_3$, CH(CH$_3$)CH$_2$NH$_2$, CH(CH$_3$)C(O)N(CH$_3$)$_2$, CH$_2$—CH(OH)Ph, (CH$_2$)$_3$N(H)CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), C$_1$-C$_5$ linear or branched, substituted or unsubstituted alkenyl, C$_1$-C$_5$ linear or branched, or C$_3$-C$_8$ cyclic haloalkyl, substituted or unsubstituted C$_1$-C$_5$ linear or branched, or C$_3$-C$_8$ cyclic alkoxy (e.g. methoxy, O—(CH$_2$)$_2$O—CH$_3$), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), R$_8$-(substituted or unsubstituted C$_3$-C$_8$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted R$_8$-aryl (e.g., benzyl), substituted or unsubstituted benzyl;

or R$_6$ and R$_5$ are joined to form a substituted or unsubstituted 5-8 membered heterocyclic ring (e.g., azepane, piperazine, 2-(piperazin-1-yl)acetamide);

or R$_6$ is represented by the structure of formula B or Bi:

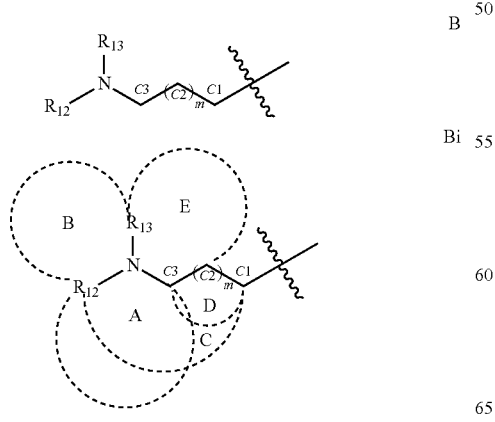

wherein m is 0 or 1; and

R$_{12}$ is R$_{20}$ or C$_1$-C$_5$ C(O)-alkyl, and R$_{13}$ is R$_{30}$; or

R$_{12}$ and R$_{13}$ are both H;

R$_{12}$ and R$_{13}$ are each independently H or substituted or unsubstituted C$_1$-C$_5$ alkyl (e.g., ethyl, trifluoroethyl);

R$_{12}$ and C3 are joined to form ring A and R$_{13}$ is R$_{30}$; or

R$_{12}$ and R$_{13}$ are joined to form ring B; or

R$_{12}$ and C1 are joined to form ring C and R$_{13}$ is R$_{30}$; or

C1 and C3 are joined to form ring D and R$_{12}$ and R$_{13}$ are each independently R$_{30}$; or R$_{13}$ and C2 are joined to form ring E, m is 1, and R$_{12}$ is R$_{30}$; or R$_{12}$ and R$_{13}$ are joined to form ring B and C1 and C3 are joined to form ring D;

wherein

Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);

Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethylpyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and Ring D is a substituted or unsubstituted C$_3$-C$_8$ cycloalkyl (e.g., cyclobutane, cyclohexane);

R$_7$ is H, F, Cl, Br, I, OH, O—R$_{20}$, SH, R$_8$—OH, R$_8$—SH, SR$_{10}$, —R$_8$—O—R$_{10}$, —R$_8$—S—R$_{10}$, R$_8$—(C$_3$-C$_5$ cycloalkyl), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$(COO—CH$_3$), R$_8$—C(O)—R$_{10}$, C(O)H, C(O)—R$_{10}$, C$_1$-C$_5$ linear or branched C(O)-haloalkyl, —C(O)NH$_2$, C(O)NHR (e.g., C(O)NH(CH$_3$)), C(O)N(R$_{10}$)(R$_{11}$) (e.g., C(O)NH(CH$_3$), C(O)NH(CH$_2$CH$_2$OCH$_3$), C(O)NH(CH$_2$CH$_2$OH)), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., methylimidazole, methyl, ethyl), C$_1$-C$_5$ linear or branched, substituted or unsubstituted alkenyl, C$_1$-C$_5$ linear or branched, or C$_3$-C$_8$ cyclic haloalkyl (e.g., CHF$_2$), C$_1$-C$_5$ linear or branched, or C$_3$-C$_8$ cyclic alkoxy (e.g. methoxy, ethoxy), optionally wherein at least one methylene group (CH$_2$) in the alkoxy is replaced with an oxygen atom, C$_1$-C$_5$ linear or branched thioalkyl, C$_1$-C$_5$ linear or branched thioalkoxy, C$_1$-C$_5$ linear or branched haloalkoxy, C$_1$-C$_5$ linear or branched alkoxyalkyl, substituted or unsubstituted C₃-C₈ cycloalkyl (e.g., cyclopropyl, cyclopropanol, cyclohexyl bicyclo[1.1.1]pentane), substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine, 4,7-diazaspiro[2.5]octane, 2,5-diazabicyclo[2.2.1]heptane, piperazine-2-one), R₈-(substituted or unsubstituted single, fused or spiro 3-8 membered heterocyclic ring), substituted or unsubstituted aryl, substituted or unsubstituted benzyl;

or R₇ is represented by the structure of formula A:

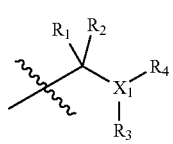

wherein
  X₁ is N or O;
  R₁ and R₂ are each independently H, F, Cl, Br, I, OH, SH, or CF₃, substituted or unsubstituted C₁-C₅ alkyl (e.g., CH₂OH), C₁-C₅ linear or branched, or C₃-C₈ cyclic haloalkyl, substituted or unsubstituted C₁-C₅ linear or branched, or C₃-C₈ cyclic alkoxy; or R₁ and R₂ are joined to form =O or a C₃-C₅ carbocyclic or heterocyclic ring (e.g., cyclopropyl);
  R₃ and R₄ are each independently H, Me, substituted or unsubstituted C₁-C₅ alkyl (e.g., methoxyethylene, methylaminoethylene, aminoethylene), —R₈—O—R₁₀ (e.g., (CH₂)₂O—CH₃), R₈—N(R₁₀)(R₁₁) (e.g., (CH₂)₂—NH(CH₃)), substituted or unsubstituted C₃-C₈ cycloalkyl (e.g., cyclopropyl), substituted or unsubstituted 5-7 membered heterocyclic ring (e.g., pyrrolidine, methylpyrrolidine), or R₂₀;
  or R₃ and R₄ are joined to form a 3-8 membered heterocyclic ring (e.g., pyrrolidine, pyrrolidone, 2-oxopyrrolidine, piperidine, morpholine, piperazine, imidazole);
  or R₂ and R₄ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);
  wherein if X₁ is O then R₄ is absent;
  R₇' is H, F, Cl, Br, I, OH, O—R₂₀, SH, R₈—OH, R₈—SH, —R₈—O—R₁₀, R₈—(C₃-C₅ cycloalkyl), R₈—(3-8 membered heterocyclic ring), CF₃, CD₃, OCD₃, CN, NO₂, —CH₂CN, —R₈CN, NH₂, NHR, N(R)₂, NH(R₁₀), N(R₁₀)(R₁₁), R₈—N(R₁₀)(R₁₁), R₉—R₈—N(R₁₀)(R₁₁), B(OH)₂, —OC(O)CF₃, —OCH₂Ph, NHC(O)—R₁₀, NHCO—N(R₁₀)(R₁₁), COOH, —C(O)Ph, C(O)O—R₁₀, R₈—C(O)—R₁₀, C(O)H, C(O)—R₁₀, C₁-C₅ linear or branched C(O)-haloalkyl, —C(O)NH₂, C(O)NHR, C(O)N(R₁₀)(R₁₁), SO₂R, SO₂N(R₁₀)(R₁₁), CH(CF₃)(NH—R₁₀), C₁-C₅ linear or branched, substituted or unsubstituted alkyl (e.g., isopropyl, methyl, ethyl), C₁-C₅ linear or branched, substituted or unsubstituted alkenyl, C₁-C₅ linear or branched, or C₃-C₈ cyclic haloalkyl (e.g., CHF₂), C₁-C₅ linear or branched, or C₃-C₈ cyclic alkoxy (e.g. methoxy), optionally wherein at least one methylene group (CH₂) in the alkoxy is replaced with an oxygen atom, C₁-C₅ linear or branched thioalkoxy, C₁-C₅ linear or branched haloalkoxy, C₁-C₅ linear or branched alkoxyalkyl, substituted or unsubstituted C₃-C₈ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or R₇ and R₇' are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

R₂₀ is represented by the following structure:

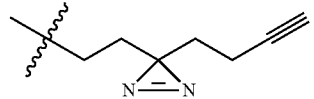 [SMILES: *CCC1(CCC#C)N=N1]

R₃₀ is H, R₂₀, F, Cl, Br, I, OH, SH, alkoxy, N(R)₂, NH(R₁₀), N(R₁₀)(R₁₁), CF₃, CN, NO₂, C₁-C₅ linear or branched, substituted or unsubstituted alkyl (e.g., methyl, ethyl, CH₂—CH₂—O—CH₂—CH₂—O—CH₃, CH₂—O—CH₂—CH₂—O—CH₃), C₁-C₅ linear or branched alkoxy, C₁-C₅ linear or branched haloalkyl (e.g., CHF₂, CF₃, CF₂CH₃, CH₂CF₃, CF₂CH₂CH₃, CH₂CH₂CF₃, CF₂CH(CH₃)₂, CF(CH₃)—CH(CH₃)₂), R₈-aryl (e.g., CH₂-Ph), —R₈—O—R₈—O—R₁₀ (e.g. (CH₂)₂—O—(CH₂)₂O—CH₃), —R₈—O—R₁₀, —R₈—R₁₀ (e.g., (CH₂)₂—O—CH₃), substituted or unsubstituted aryl (e.g., phenyl), substituted or unsubstituted heteroaryl (e.g., pyridine (2, 3, and 4-pyridine);

R is H, F, Cl, Br, I, OH, SH, alkoxy, NH(R₁₀), NH—CH₂-cyclopropyl, N(R₁₀)(R₁₁), CF₃, CN, NO₂, COOH, C₁-C₅ linear or branched, substituted or unsubstituted alkyl (e.g., methyl, ethyl, CH₂—OH, CH₂—CH₂—OH, CH₂—CH₂—O—CH₂—CH₂—O—CH₃, CH₂—O—CH₂—CH₂—O—CH₃), C₃-C₈ substituted or unsubstituted cycloalkyl, cyclopropyl, C₁-C₅ linear or branched alkoxy, isopropoxy, C₁-C₅ linear or branched haloalkyl (e.g., CHF₂, CF₃, CF₂CH₃, CH₂CF₃, CF₂CH₂CH₃, CH₂CH₂CF₃, CF₂CH(CH₃)₂, CF(CH₃)—CH(CH₃)₂), R₈-aryl (e.g., CH₂-Ph), —R₈—O—R₈—O—R₁₀ (e.g. (CH₂)₂—O—(CH₂)₂—O—CH₃), —R₈—O—R₁₀, —R₈—R₁₀ (e.g., (CH₂)₂O—CH₃), substituted or unsubstituted aryl (e.g., phenyl), substituted or unsubstituted heteroaryl (e.g., pyridine (2, 3, and 4-pyridine);

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(e):

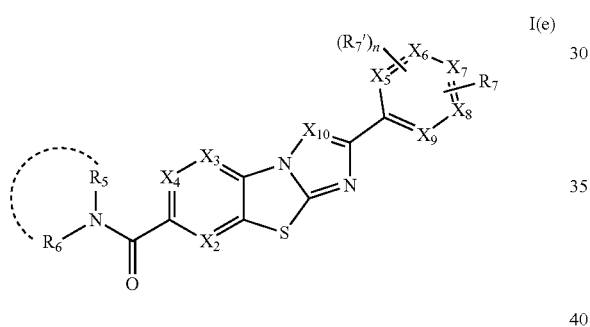

I(e)

wherein
$X_2$, $X_3$, and $X_4$, are each independently nitrogen or CH;
$X_5$, $X_6$, $X_7$, $X_8$ and $X_9$ are each independently nitrogen or carbon atoms;
$X_{10}$ is N, CH, or C(R) (e.g., $C(CH_2)OH$, $C(CH_2)_2OH$, $C(NH—CH_2$-cyclopropyl), $C(CH_3)$, C(cyclopropyl), C(isopropoxy), C(COOH));
$R_6$ and $R_5$ are joined to form a substituted or unsubstituted 5-8 membered heterocyclic ring (e.g., azepane, piperazine, 2-(piperazin-1-yl)acetamide);
$R_7$ is H, F, Cl, Br, I, OH, O—$R_{20}$, SH, $R_8$—OH, $R_8$—SH, $SR_{10}$, —$R_8$—O—$R_{10}$, —$R_8$—S—$R_{10}$, $R_8$—($C_3$-$C_5$ cycloalkyl), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$(COO—$CH_3$), $R_8$—C(O)—$R_{10}$, C(O)H, C(O)—$R_{10}$, $C_1$-$C_5$ linear or branched C(O)-haloalkyl, —$C(O)NH_2$, C(O)NHR (e.g., C(O)NH($CH_3$)), $C(O)N(R_{10})(R_{11})$ (e.g., $C(O)NH(CH_3)$, $C(O)NH(CH_2CH_2OCH_3)$, $C(O)NH(CH_2CH_2OH)$), $SO_2R$, $SO_2N(R_{10})(R_{11})$, $CH(CF_3)(NH—R_{10})$, $C_1$-$C_5$ linear or branched, substituted or unsubstituted alkyl (e.g., methylimidazole, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_5$ cyclic alkoxy (e.g. methoxy, ethoxy), optionally wherein at least one methylene group ($CH_2$) in the alkoxy is replaced with an oxygen atom, $C_1$-$C_5$ linear or branched thioalkyl, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopropanol, cyclohexyl, bicyclo[1.1.1]pentane), substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine, 4,7-diazaspiro[2.5]octane, 2,5-diazabicyclo[2.2.1]heptane, piperazine-2-one), $R_8$-(substituted or unsubstituted single, fused or spiro 3-8 membered heterocyclic ring), substituted or unsubstituted aryl, substituted or unsubstituted benzyl;

or $R_7$ is represented by the structure of formula A:

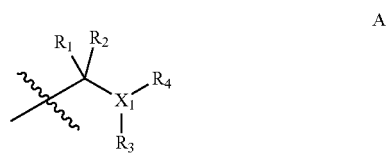

A wherein
$X_1$ is N or O;
$R_1$ and $R_2$ are each independently H, F, Cl, Br, I, OH, SH, or $CF_3$, substituted or unsubstituted $C_1$-$C_5$ alkyl (e.g., $CH_2OH$), $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy;
or $R_1$ and $R_2$ are joined to form =O or a $C_3$-$C_8$ carbocyclic or heterocyclic ring (e.g., cyclopropyl);
$R_3$ and $R_4$ are each independently H, Me, substituted or unsubstituted $C_1$-$C_5$ alkyl (e.g., methoxyethylene, methylaminoethylene, aminoethylene), —$R_8$—O—$R_{10}$ (e.g., $(CH_2)_2O$—$CH_3$), $R_8$—N$(R_{10})(R_{11})$ (e.g., $(CH_2)_2$—$NH(CH_3)$), substituted or unsubstituted $C_3$-$C_8$ cycloalkyl (e.g., cyclopropyl), substituted or unsubstituted 5-7 membered heterocyclic ring (e.g., pyrrolidine, methylpyrrolidine, piperidine), or $R_{20}$;
or $R_3$ and $R_4$ are joined to form a 3-8 membered heterocyclic ring (e.g., pyrrolidine, pyrrolidone, 2-oxopyrrolidine, piperidine, morpholine, piperazine, imidazole);
or $R_2$ and $R_4$ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);

wherein if $X_1$ is O then $R_4$ is absent;

$R_7'$ is H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(Ru)$, $B(OH)_2$, —OC(O)$CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —C(O)$NH_2$, C(O)NHR, C(O)$N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or $R_7$ and $R_7'$ are joined to form a 3-8 membered substituted or unsubstituted, saturated, unsaturated or aromatic carbocyclic or heterocyclic ring (e.g., cyclopentyl, cyclohexyl, piperidine, tetrahydrofuran, tetrahydropyran, pyrrolidine);

$R_{20}$ is represented by the following structure:

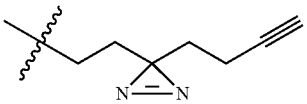 [SMILES: *CCC1(CCC#C)N=N1]

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$O—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine);

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(f):

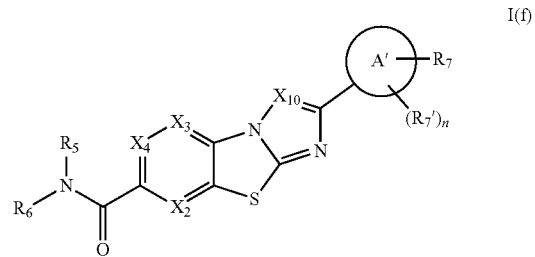

wherein
A' is a 3-8 membered single or fused, saturated, unsaturated or aromatic carbocyclic or heterocyclic ring (e.g., pyrrolidine, piperidine, piperazine, isochroman, 1,2,3,4-tetrahydroisoquinoline, indoline, isoindoline, 1,3-dihydroisobenzofuran, 2,3-dihydro-1H-indene, 1,2,3,4-tetrahydronaphthalene);

$X_2$, $X_3$, and $X_4$, are each independently nitrogen or CH;

$X_{10}$ is N, CH, or C(R) (e.g., $C(CH_2)OH$, $C(CH_2)_2OH$, $C(NH$—$CH_2$-cyclopropyl), $C(CH_3)$, $C(cyclopropyl)$, $C(isopropoxy)$, $C(COOH)$);

$R_5$ is H or $C_1$-$C_5$ linear or branched alkyl (e.g. methyl);

$R_6$ is H, F, Cl, Br, I, OH, SH, $R_8$—OH, $R_8$—SH, —$R_8$—O—$R_{10}$ (e.g., $CH_2$—O—$CH_3$, $(CH_2)_2$O—$CH_3$, $(CH_2)_3O$—$CH_3$, $(CH_2)_2O$—$CH(CH_3)_2$), $R_8$—S—$R_{10}$ (e.g., $(CH_2)_3$—S—$(CH_2)_2CH_3$), $R_8$—NHC(O)—$R_{10}$, —O—$R_8$—$R_{10}$, $R_8$-(substituted or unsubstituted $C_3$-$C_8$ cycloalkyl) (e.g., $CH_2$-cyclopropyl, $CH_2$-cyclobutanol, $CH_2$-difluorocyclopropyl, $CH_2$-methylcyclopropyl, $CH_2$- dimethylamino-cyclohexyl, (CH$_2$)$_2$-cyclopentanole, CH$_2$-cyclohexanol), R$_8$-(substituted or unsubstituted, saturated, unsaturated or aromatic, single, fused or spiro 3-10 membered heterocyclic ring) (e.g., (CH$_2$)$_3$-pyran, (CH$_2$)$_2$-pyrrazole, (CH$_2$)$_2$-imidazole, CH$_2$-tetrahydrofurane, CH$_2$-dioxane, CH$_2$-oxetane, CH$_2$-piperidine, CH$_2$-triazole, CH$_2$-1-oxa-8-azaspiro[4.5]decane, (CH$_2$)$_3$-diazabicyclo[2.2.1] heptane, CH$_2$-methyl-THF, CH$_2$-ethyl-piperidine, CH$_2$-oxa-azaspirodecane, (CH$_2$)$_3$-dimethylpyrazole, CH$_2$-2-oxo-methylpyrrolidine, CH$_2$-methyl-azetidine, CH$_2$-azaspiroheptane), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$) (e.g., (CH$_2$)$_3$-4-fluoro-piperidine, (CH$_2$)$_3$—N(CH$_2$CH$_3$)$_2$, (CH$_2$)$_3$—N(CH(CH$_3$)$_2$)$_2$, (CH$_2$)$_3$-piperidine, (CH$_2$)$_4$—NH(CH$_3$), (CH$_2$)$_3$—NH—CH$_3$, (CH$_2$)$_3$—NH—CH$_2$CH$_3$, (CH$_2$)$_3$—N(CH$_2$CH$_3$)$_2$, (CH$_2$)$_3$—NH$_2$, (CH$_2$)$_3$—N(CH$_2$CH$_3$)(CH$_2$CF$_3$)), R$_8$—C(O)N (R$_{10}$)(R$_{11}$) (e.g., (CH$_2$)$_2$—C(O)- piperidine), R$_9$—R$_8$—N(R$_{10}$)(R$_{11}$) (e.g., (CH$_2$)$_2$—C(O)-piperidine), B(OH)$_2$, —OC(O)CF$_3$, —OCH$_2$Ph, NHC (O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., CH(CH$_3$)CH$_2$OCH$_3$, CH(CH$_3$)CH$_2$NH$_2$, CH(CH$_3$)C (O)N(CH$_3$)$_2$, CH$_2$—CH(OH)Ph, (CH$_2$)$_3$N(H) CH$_2$CH$_3$, CH(CH$_3$)(CH$_2$)$_2$OH, CH(CH$_2$OH) (CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$ CH(CH$_3$)$_2$), CH$_2$CH(CH$_3$)(OCH$_3$), CH$_2$CH(N (CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), C$_1$-C$_5$ linear or branched, substituted or unsubstituted alkenyl, C$_1$-C$_5$ linear or branched, or C$_3$-C$_8$ cyclic haloalkyl, substituted or unsubstituted C$_1$-C$_5$ linear or branched, or C$_3$-C$_8$ cyclic alkoxy (e.g. methoxy, O—(CH$_2$)$_2$O—CH$_3$), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), R$_8$-(substituted or unsubstituted C$_3$-C$_5$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro [3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted R$_8$-aryl (e.g., benzyl), substituted or unsubstituted benzyl;

or R$_6$ and R$_5$ are joined to form a substituted or unsubstituted 5-8 membered heterocyclic ring (e.g., azepane, piperazine, 2-(piperazin-1-yl)acetamide;

or R$_6$ is represented by the structure of formula B or Bi:

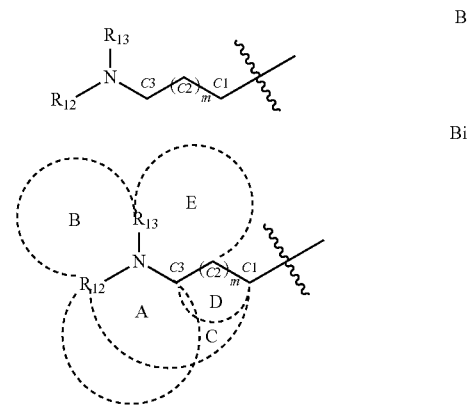

wherein
m is 0 or 1; and
R$_{12}$ is R$_{20}$ or C$_1$-C$_5$ C(O)-alkyl, and R$_{13}$ is R$_{30}$; or R$_{12}$ and R$_{13}$ are both H;
R$_{12}$ and R$_{13}$ are each independently H or substituted or unsubstituted C$_1$-C$_5$ alkyl (e.g., ethyl, trifluoroethyl);
R$_{12}$ and C3 are joined to form ring A and R$_{13}$ is R$_{30}$; or
R$_{12}$ and R$_{13}$ are joined to form ring B; or
R$_{12}$ and C1 are joined to form ring C and R$_{13}$ is R$_{30}$; or
C1 and C3 are joined to form ring D and R$_{12}$ and R$_{13}$ are each independently R$_{30}$; or
R$_{13}$ and C2 are joined to form ring E, m is 1, and R$_{12}$ is R$_{30}$; or
R$_{12}$ and R$_{13}$ are joined to form ring B and C1 and C3 are joined to form ring D;
wherein
Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);
Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro [3.3]heptane, methyl-piperazine, dimethylpyrazole, imidazole, 2-methyl-2,5-diazabicyclo [2.2.1]heptane, hydroxymethyl-pyrrolidine, diazabicyclo[2.2.1]heptane, 6-fluoro-3-azabicyclo[3.1.1]heptane; and
Ring D is a substituted or unsubstituted C$_3$-C$_8$ cycloalkyl (e.g., cyclobutane, cyclohexane);
R$_7$ is H, F, Cl, Br, I, OH, O—R$_{20}$, SH, R$_8$—OH, R$_8$—SH, SR$_{10}$, —R$_8$—O—R$_{10}$, —R$_8$—S—R$_{10}$, R$_8$—(C$_3$-C$_5$ cycloalkyl), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—

N(R₁₀)(R₁₁), B(OH)₂, —OC(O)CF₃, —OCH₂Ph, NHC(O)—R₁₀, NHCO—N(R₁₀)(R₁₁), COOH, —C(O)Ph, C(O)O—R₁₀(COO—CH₃), R₈—C(O)—R₁₀, C(O)H, C(O)—R₁₀, $C_1$-$C_5$ linear or branched C(O)-haloalkyl, —C(O)NH₂, C(O)NHR (e.g., C(O)NH(CH₃)), C(O)N(R₁₀)(R₁₁) (e.g., C(O)NH(CH₃), C(O)NH(CH₂CH₂OCH₃), C(O)NH(CH₂CH₂OH)), SO₂R, SO₂N(R₁₀)(R₁₁), CH(CF₃)(NH—R₁₀), $C_1$-$C_5$ linear or branched, substituted or unsubstituted alkyl (e.g., methylimidazole, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., CHF₂), $C_1$-$C_5$ linear or branched, or $C_3$-$C_5$ cyclic alkoxy (e.g. methoxy, ethoxy), optionally wherein at least one methylene group (CH₂) in the alkoxy is replaced with an oxygen atom, $C_1$-$C_5$ linear or branched thioalkyl, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopropanol, cyclohexyl, bicyclo[1.1.1]pentane), substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine, 4,7-diazaspiro[2.5]octane, 2,5-diazabicyclo[2.2.1]heptane, piperazine-2-one), R₈-(substituted or unsubstituted single, fused or spiro 3-8 membered heterocyclic ring), substituted or unsubstituted aryl, substituted or unsubstituted benzyl;

or R₇ is represented by the structure of formula A:

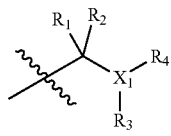

wherein
X₁ is N or O;
R₁ and R₂ are each independently H, F, Cl, Br, I, OH, SH, or CF₃, substituted or unsubstituted $C_1$-$C_5$ alkyl (e.g., CH₂OH), $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy;
or R₁ and R₂ are joined to form =O or a $C_3$-$C_8$ carbocyclic or heterocyclic ring (e.g., cyclopropyl);
R₃ and R₄ are each independently H, Me, substituted or unsubstituted $C_1$-$C_5$ alkyl (e.g., methoxyethylene, methylaminoethylene, aminoethylene), —R₈—O—R₁₀ (e.g., (CH₂)₂O—CH₃), R₈—N(R₁₀)(R₁₁) (e.g., (CH₂)₂—NH(CH₃)), substituted or unsubstituted $C_3$-$C_8$ cycloalkyl (e.g., cyclopropyl), substituted or unsubstituted 5-7 membered heterocyclic ring (e.g., pyrrolidine, methylpyrrolidine, piperidine), or R₂₀;

or R₃ and R₄ are joined to form a 3-8 membered heterocyclic ring (e.g., pyrrolidine, pyrrolidone, 2-oxopyrrolidine, piperidine, morpholine, piperazine, imidazole);

or R₂ and R₄ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);

wherein if X₁ is O then R₄ is absent;

R₇' is H, F, Cl, Br, I, OH, O—R₂₀, SH, R₈—OH, R₈—SH, —R₈—O—R₁₀, R₈—(C₃-C₈ cycloalkyl), R₈—(3-8 membered heterocyclic ring), CF₃, CD₃, OCD₃, CN, NO₂, —CH₂CN, —R₈CN, NH₂, NHR, N(R)₂, NH(R₁₀), N(R₁₀)(R₁₁), R₈—N(R₁₀)(R₁₁), R₉—R₈—N(R₁₀)(R₁₁), B(OH)₂, —OC(O)CF₃, —OCH₂Ph, NHC(O)—R₁₀, NHCO—N(R₁₀)(R₁₁), COOH, —C(O)Ph, C(O)O—R₁₀, R₈—C(O)—R₁₀, C(O)H, C(O)—R₁₀, $C_1$-$C_5$ linear or branched C(O)-haloalkyl, —C(O)NH₂, C(O)NHR, C(O)N(R₁₀)(R₁₁), SO₂R, SO₂N(R₁₀)(R₁₁), CH(CF₃)(NH—R₁₀), $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., CHF₂), $C_1$-$C_5$ linear or branched, or $C_3$-$C_8$ cyclic alkoxy (e.g. methoxy), optionally wherein at least one methylene group (CH₂) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidine-2-one, piperidin-4-ol, dioxazole, 2-oxopyrrolidine), substituted or unsubstituted aryl, substituted or unsubstituted benzyl;

or R₇ and R₇' are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

R₂₀ is represented by the following structure:

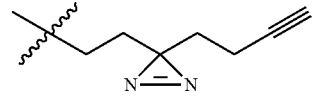 [SMILES: *CCC1(CCC#C)N=N1]

R₃₀ is H, R₂₀, F, Cl, Br, I, OH, SH, alkoxy, N(R)₂, NH(R₁₀), N(R₁₀)(R₁₁), CF₃, CN, NO₂, $C_1$-$C_5$ linear or branched, substituted or unsubstituted alkyl (e.g., methyl, ethyl, CH₂—CH₂—O—CH₂—CH₂—O—CH₃, CH₂—O—CH₂—CH₂—O—CH₃), $C_1$-$C_5$ linear or branched alkoxy, $C_1$-$C_5$ linear or branched haloalkyl (e.g., CHF₂, CF₃, CF₂CH₃, CH₂CF₃, CF₂CH₂CH₃, CH₂CH₂CF₃, CF₂CH(CH₃)₂, CF(CH₃)—CH(CH₃)₂), R₈-aryl (e.g., CH₂-Ph), —R₈—O—R₈—O—R₁₀ (e.g. (CH₂)₂—O—

(CH$_2$)$_2$O—CH$_3$), —R$_8$—O—R$_{10}$, —R$_8$—R$_{10}$ (e.g., (CH$_2$)$_2$—O—CH$_3$), substituted or unsubstituted aryl (e.g., phenyl), substituted or unsubstituted heteroaryl (e.g., pyridine (2, 3, and 4-pyridine);

R is H, F, Cl, Br, I, OH, SH, alkoxy, NH(R$_{10}$), NH—CH$_2$-cyclopropyl, N(R$_{10}$)(R$_{11}$), CF$_3$, CN, NO$_2$, COOH, C$_1$-C$_5$ linear or branched, substituted or unsubstituted alkyl (e.g., methyl, ethyl, CH$_2$—OH, CH$_2$—CH$_2$—OH, CH$_2$—CH$_2$—O—CH$_2$—CH$_2$—O—CH$_3$, CH$_2$—O—CH$_2$—CH$_2$—O—CH$_3$), C$_3$-C$_8$ substituted or unsubstituted cycloalkyl, cyclopropyl, C$_1$-C$_5$ linear or branched alkoxy, isopropoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$—O—CH$_3$), —R$_8$—O—R$_{10}$, —R$_8$—R$_{10}$ (e.g., (CH$_2$)$_2$O—CH$_3$), substituted or unsubstituted aryl (e.g., phenyl), substituted or unsubstituted heteroaryl (e.g., pyridine (2, 3, and 4-pyridine);

each R$_8$ is independently [CH$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ substituted or unsubstituted linear or branched alkyl (e.g., methyl, ethyl, CH$_2$-cyclopropyl, CH$_2$—CH$_2$—O—CH$_3$), C$_1$-C$_5$ substituted or unsubstituted linear or branched haloalky (e.g., CH$_2$CF$_3$), C$_1$-C$_5$ linear or branched alkoxy (e.g., O—CH$_3$), R$_{20}$, C(O)R, or S(O)$_2$R;

or R$_{10}$ and R$_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(g):

I(g)

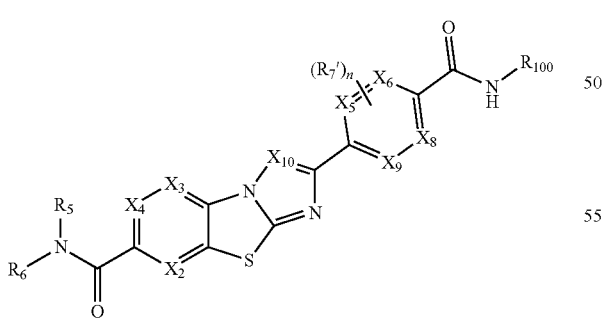

wherein
X$_2$, X$_3$, and X$_4$, are each independently nitrogen or CH;
X$_5$, X$_6$, X$_7$, X$_8$ and X$_9$ are each independently nitrogen or carbon atoms;
X$_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));

R$_{100}$ is a C$_1$-C$_5$ linear or branched, substituted or unsubstituted alkyl (e.g., methyl, ethyl), R$_8$—OH (e.g., (CH$_2$)$_2$—OH), —R$_8$—O—R$_{10}$ (e.g., (CH$_2$)$_2$O—CH$_3$), R$_8$—N(R$_{10}$)(R$_{11}$) (e.g., (e.g., (CH$_2$)$_2$—NH(CH$_3$), (CH$_2$)$_2$—NH$_2$), R$_{20}$, or a substituted or unsubstituted 3-8 membered heterocyclic ring (e.g., pyrrolidine, piperidine);

R$_5$ is H or C$_1$-C$_5$ linear or branched alkyl (e.g. methyl);

R$_6$ is H, F, Cl, Br, I, OH, SH, R$_8$—OH, R$_8$—SH, —R$_8$—O—R$_{10}$ (e.g., CH$_2$—O—CH$_3$, (CH$_2$)$_2$O—CH$_3$ (CH$_2$)$_3$O—CH$_3$, (CH$_2$)$_2$O—CH(CH$_3$)$_2$), R$_8$—S—R$_{10}$ (e.g., (CH$_2$)$_3$—S—(CH$_2$)$_2$CH$_3$), R$_8$—NHC(O)—R$_{10}$, —O—R$_8$—R$_{10}$, R$_8$-(substituted or unsubstituted C$_3$-C$_8$ cycloalkyl) (e.g., CH$_2$-cyclopropyl, CH$_2$-cyclobutanol, CH$_2$-difluorocyclopropyl, CH$_2$-methylcyclopropyl, CH$_2$-dimethylamino-cyclohexyl, (CH$_2$)$_2$-cyclopentanole, CH$_2$-cyclohexanol), R$_8$-(substituted or unsubstituted, saturated, unsaturated or aromatic, single, fused or spiro 3-10 membered heterocyclic ring) (e.g., (CH$_2$)$_3$-pyran, (CH$_2$)$_2$-pyrrazole, (CH$_2$)$_2$-imidazole, CH$_2$-tetrahydrofurane, CH$_2$-dioxane, CH$_2$-oxetane, CH$_2$-piperidine, CH$_2$-triazole, CH$_2$-1-oxa-8-azaspiro[4.5]decane, (CH$_2$)$_3$-diazabicyclo[2.2.1]heptane, CH$_2$-methyl-THF, CH$_2$-ethyl-piperidine, CH$_2$-oxa-azaspirodecane, (CH$_2$)$_3$-dimethylpyrazole, CH$_2$-2-oxo-methylpyrrolidine, CH$_2$-methyl-azetidine, CH$_2$-azaspiroheptane), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$) (e.g., (CH$_2$)$_3$-4-fluoro-piperidine, (CH$_2$)$_3$—N(CH$_2$CH$_3$)$_2$, (CH$_2$)$_3$—N(CH(CH$_3$)$_2$)$_2$, (CH$_2$)$_3$-piperidine, (CH$_2$)$_4$—NH(CH$_3$), (CH$_2$)$_3$—NH—CH$_3$, (CH$_2$)$_3$—NH—CH$_2$CH$_3$, (CH$_2$)$_3$—N(CH$_2$CH$_3$)$_2$, (CH$_2$)$_3$—NH$_2$, (CH$_2$)$_3$—N(CH$_2$CH$_3$)(CH$_2$CF$_3$)), R$_8$—C(O)N(R$_{10}$)(R$_{11}$) (e.g., (CH$_2$)$_2$—C(O)- piperidine), R$_9$—R$_8$—N(R$_{10}$)(R$_{11}$) (e.g., (CH$_2$)$_2$—C(O)-piperidine), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., CH(CH$_3$)CH$_2$OCH$_3$, CH(CH$_3$)CH$_2$NH$_2$, CH(CH$_3$)C(O)N(CH$_3$)$_2$, CH$_2$—CH(OH)Ph, (CH$_2$)$_3$N(H)CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), C$_1$-C$_5$ linear or branched, substituted or unsubstituted alkenyl, C$_1$-C$_5$ linear or branched, or C$_3$-C$_5$ cyclic haloalkyl, substituted or unsubstituted C$_1$-C$_5$ linear or branched, or C$_3$-C$_5$ cyclic alkoxy (e.g. methoxy, O—(CH$_2$)$_2$O—CH$_3$), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_5$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), R$_8$-(substituted or unsubstituted C$_3$-C$_5$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted $R_8$-aryl (e.g., benzyl), substituted or unsubstituted benzyl;

or $R_6$ and $R_5$ are joined to form a substituted or unsubstituted 5-8 membered heterocyclic ring (e.g., azepane, piperazine, 2-(piperazin-1-yl)acetamide);

or $R_6$ is represented by the structure of formula C:

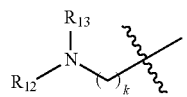

wherein
k is between 1 and 4;
$R_{12}$ and $R_{13}$ are each independently H, $C_1$-$C_5$ linear or branched, substituted or unsubstituted alkyl (e.g., ethyl, isopropyl), $R_{20}$, or
$R_{12}$ and $R_{13}$ are joined to form a substituted or unsubstituted 4-7 membered heterocyclic ring (e.g., piperidine, piperazine, pyrrolidine, oxa-6-azaspiro[3.3]heptane); or $R_6$ is represented by the structure of formula Bi:

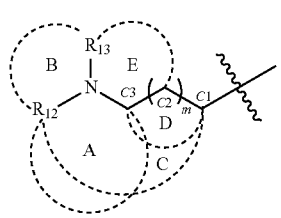

wherein
m is 0 or 1; and
$R_{12}$ is $R_{20}$ or $C_1$-$C_5$ C(O)-alkyl, and $R_{13}$ is $R_{30}$; or
$R_{12}$ and $R_{13}$ are both H;
$R_{12}$ and $R_{13}$ are each independently H or substituted or unsubstituted $C_1$-$C_5$ alkyl (e.g., ethyl, trifluoroethyl);
$R_{12}$ and C3 are joined to form ring A and $R_{13}$ is $R_{30}$; or
$R_{12}$ and $R_{13}$ are joined to form ring B; or
$R_{12}$ and C1 are joined to form ring C and $R_{13}$ is $R_{30}$; or
C1 and C3 are joined to form ring D and $R_{12}$ and $R_{13}$ are each independently $R_{30}$; or
$R_{13}$ and C2 are joined to form ring E, m is 1, and $R_{12}$ is $R_{30}$; or
$R_{12}$ and $R_{13}$ are joined to form ring B and C1 and C3 are joined to form ring D;
wherein
Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);

Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethyl-pyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and Ring D is a substituted or unsubstituted $C_3$-$C_5$ cycloalkyl (e.g., cyclobutane, cyclohexane);

$R_7'$ is H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH—R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

$R_{20}$ is represented by the following structure:

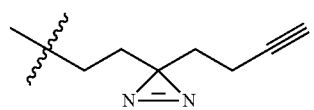 [SMILES: *CCC1(CCC#C)N=N1]

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$O—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2$O—$CH_3$), substituted or unsubstituted aryl (e.g., phenyl), substituted or unsubstituted heteroaryl (e.g., pyridine (2, 3, and 4-pyridine);

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In some embodiments, if $R_{100}$ is methyl and $R_5$ is H, then $R_{12}$ and $R_{13}$ are not both alkyls. In some embodiments, if $R_{100}$ is methyl and $R_5$ is H, then $R_{12}$ and $R_{13}$ cannot be joined to form piperidine.

In various embodiments, this invention is directed to a compound represented by the structure of formula I(h):

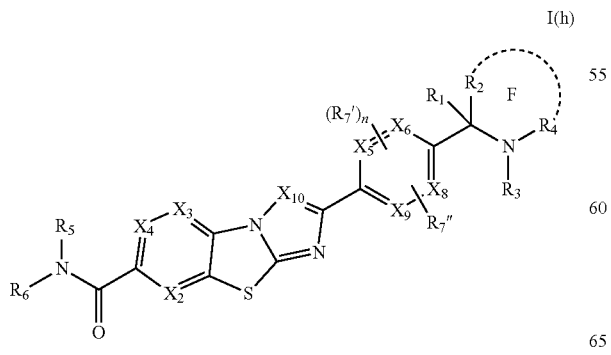

I(h)

wherein $X_2$, $X_3$, and $X_4$, are each independently nitrogen or CH;

$X_5$, $X_6$, $X_7$, $X_8$ and $X_9$ are each independently nitrogen or carbon atoms;

$X_{10}$ is N, CH, or C(R) (e.g., $C(CH_2)OH$, $C(CH_2)_2OH$, $C(NH$—$CH_2$-cyclopropyl), $C(CH_3)$, C(cyclopropyl), C(isopropoxy), C(COOH));

Ring F is absent or is a substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);

$R_1$ and $R_2$ are each independently H, F, Cl, Br, I, OH, SH, or $CF_3$, substituted or unsubstituted $C_1$-$C_5$ alkyl (e.g., $CH_2OH$), $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy;

or $R_1$ and $R_2$ are joined to form a 3-8 membered carbocyclic or heterocyclic ring (e.g., cyclopropyl);

or $R_2$ and $R_4$ are joined to form Ring F as defined above (e.g., pyrrolidine, morpholine, 1-methylpyrrolidine, pyrrolidine-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole), wherein if Ring F is aromatic, then $R_1$ and/or $R_3$ are absent;

$R_3$ and $R_4$ are each independently H, Me, substituted or unsubstituted $C_1$-$C_5$ alkyl (e.g., methoxyethylene, methylaminoethyl, aminoethyl), —$R_8$—O—$R_{10}$ (e.g., $(CH_2)_2O$—$CH_3$), $R_8$—$N(R_{10})(R_{11})$ (e.g., $(CH_2)_2$—$NH(CH_3)$), substituted or unsubstituted $C_3$-$C_8$ cycloalkyl (e.g., cyclopropyl), substituted or unsubstituted 5-7 membered heterocyclic ring (e.g., pyrrolidine, methylpyrrolidine, piperidine), or $R_{20}$;

or $R_3$ and $R_4$ are joined to form a 3-8 membered heterocyclic ring (e.g., pyrrolidine, pyrrolidone, 2-oxopyrrolidine, piperidine, morpholine, piperazine, imidazole);

$R_5$ is H or $C_1$-$C_5$ linear or branched alkyl (e.g. methyl);

$R_6$ is H, F, Cl, Br, I, OH, SH, $R_8$—OH, $R_8$—SH, —$R_8$—O—$R_{10}$ (e.g., $CH_2$—O—$CH_3$, $(CH_2)_2O$—$CH_3$ $(CH_2)_3O$—$CH_3$, $(CH_2)_2O$—$CH(CH_3)_2$), $R_8$—S—$R_{10}$ (e.g., $(CH_2)_3$—S—$(CH_2)_2CH_3$), $R_8$—$NHC(O)$—$R_{10}$, —O—$R_8$—$R_{10}$, $R_8$-(substituted or unsubstituted $C_3$-$C_8$ cycloalkyl) (e.g., $CH_2$-cyclopropyl, $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, $CH_2$-cyclohexanol), $R_8$-(substituted or unsubstituted, saturated, unsaturated or aromatic, single, fused or spiro 3-10 membered heterocyclic ring) (e.g., $(CH_2)_3$-pyran, $(CH_2)_2$-pyrrazole, $(CH_2)_2$-imidazole, $CH_2$-tetrahydrofurane, $CH_2$-dioxane, $CH_2$-oxetane, $(CH_2)_3$-piperidine, $CH_2$-triazole, $CH_2$-1-oxa-8-azaspiro[4.5]decane, $(CH_2)_3$-diazabicyclo [2.2.1]heptane, $CH_2$-methyl-THF, $CH_2$-ethylpiperidine, $CH_2$-oxa-azaspirodecane, $(CH_2)_3$-dimethylpyrazole, $CH_2$-2-oxo-methylpyrrolidine, $CH_2$-methyl-azetidine, $CH_2$-azaspiroheptane), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$ (e.g., $(CH_2)_3$-4-fluoro-piperidine, $(CH_2)_3$—N$(CH_2CH_3)_2$, $(CH_2)_3$—$N(CH(CH_3)_2)_2$, $(CH_2)_3$-piperidine, $(CH_2)_4$—$NH(CH_3)$, $(CH_2)_3$—NH—$CH_3$, $(CH_2)_3$—NH—$CH_2CH_3$, $(CH_2)_3$—$N(CH_2CH_3)_2$, $(CH_2)_3$—$NH_2$, $(CH_2)_3$—$N(CH_2CH_3)(CH_2CF_3)$), $R_8$—$C(O)N(R_{10})(R_{11})$ (e.g., $(CH_2)_2$—C(O)- piperidine), $R_9$—$R_8$—$N(R_{10})(R_{11})$ (e.g., $(CH_2)_2$—C(O)-piperidine), $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., $CH(CH_3)CH_2OCH_3$, $CH(CH_3)CH_2NH_2$, $CH(CH_3)C(O)N(CH_3)_2$, $CH_2$—CH(OH)Ph, $(CH_2)_3N(H)CH_2CH_3$, $CH(CH_3)(CH_2)_2OH$, $CH(CH_2OH)(CH_2CH_3)$, $(CH_2)_3$—$OCH_3$, $(CH_2)_2$—$OCH_3$, $(CH_2)_2$—$OCH(CH_3)_2$, $CH(CH_2OH)(CH_2CH(CH_3)_2)$, $CH_2CH(CH_3)(OCH_3)$, $CH_2CH(N(CH_3)_2)(CH_2CH_3)$, benzyl, methyl, ethyl, $CH_2$—$OCH_2$—$CH_2$—O—$CH_3$, $CH(CH_3)C(O)N(CH_3)_2$), $C_1$-$C_5$ linear or branched, substituted or unsubstituted alkenyl, $C_1$-$C_5$ linear or branched, or $C_3$-$C_5$ cyclic haloalkyl, substituted or unsubstituted $C_1$-$C_5$ linear or branched, or $C_3$-$C_5$ cyclic alkoxy (e.g. methoxy, O—$(CH_2)_2O$—$CH_3$), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_5$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), $R_8$-(substituted or unsubstituted $C_3$-$C_5$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted $R_8$-aryl (e.g., benzyl), substituted or unsubstituted benzyl;

or $R_6$ and $R_5$ are joined to form a substituted or unsubstituted 5-8 membered heterocyclic ring (e.g., azepane, piperazine, 2-(piperazin-1-yl)acetamide);

or $R_6$ is represented by the structure of formula B or Bi:

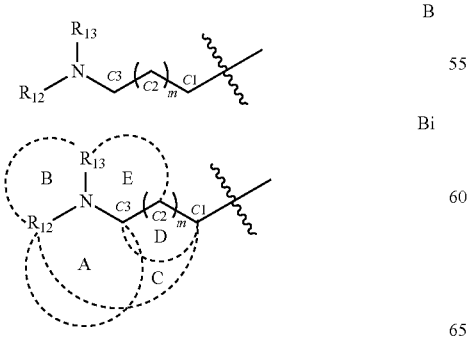

wherein
m is 0 or 1; and
$R_{12}$ is $R_{20}$ or $C_1$-$C_5$ C(O)-alkyl, and $R_{13}$ is $R_{30}$; or
$R_{12}$ and $R_{13}$ are both H;
$R_{12}$ and $R_{13}$ are each independently H or substituted or unsubstituted $C_1$-$C_5$ alkyl (e.g., ethyl, trifluoroethyl);
$R_{12}$ and C3 are joined to form ring A and $R_{13}$ is $R_{30}$; or
$R_{12}$ and $R_{13}$ are joined to form ring B; or
$R_{12}$ and C1 are joined to form ring C and $R_{13}$ is $R_{30}$; or
C1 and C3 are joined to form ring D and $R_{12}$ and $R_{13}$ are each independently $R_{30}$; or
$R_{13}$ and C2 are joined to form ring E, m is 1, and $R_{12}$ is $R_{30}$; or
$R_{12}$ and $R_{13}$ are joined to form ring B and C1 and C3 are joined to form ring D;
wherein
Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);
Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethylpyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and
Ring D is a substituted or unsubstituted $C_3$-$C_8$ cycloalkyl (e.g., cyclobutane, cyclohexane);

$R_7'$ and $R_7''$ are each independently H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or $R_7'$ and $R_7''$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

$R_{20}$ is represented by the following structure:

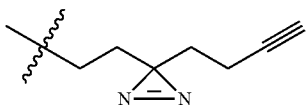 [SMILES: *CCC1(CCC#C)N=N1]

R is H, F, Cl, Br, I, OH, SH, alkoxy, $NH(R_{10})$, $NH-CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2$O—$CH_3$), substituted or unsubstituted aryl (e.g., phenyl), substituted or unsubstituted heteroaryl (e.g., pyridine (2, 3, and 4-pyridine);

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$O—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

each $R_5$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(i):

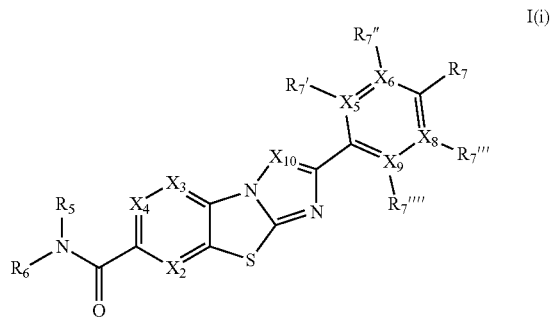

wherein $X_2$, $X_3$, and $X_4$, are each independently nitrogen or CH;

$X_5$, $X_6$, $X_7$, $X_8$ and $X_9$ are each independently nitrogen or carbon atoms;

$X_{10}$ is N, CH, or C(R) (e.g., $C(CH_2)OH$, $C(CH_2)_2OH$, $C(NH$—$CH_2$-cyclopropyl), $C(CH_3)$, $C(cyclopropyl)$, $C(isopropoxy)$, $C(COOH)$);

$R_5$ is H or $C_1$-$C_5$ linear or branched alkyl (e.g. methyl);

$R_6$ is H, F, Cl, Br, I, OH, SH, $R_8$—OH, $R_8$—SH, —$R_8$—O—$R_{10}$ (e.g., $CH_2$—O—$CH_3$, $(CH_2)_2$O—$CH_3$ $(CH_2)_3$O—$CH_3$, $(CH_2)_2$O—$CH(CH_3)_2$), $R_8$—S—$R_{10}$ (e.g., $(CH_2)_3$—S—$(CH_2)_2CH_3$), $R_8$—NHC(O)—$R_{10}$, —O—$R_8$—$R_{10}$, $R_8$-(substituted or unsubstituted $C_3$-$C_5$ cycloalkyl) (e.g., $CH_2$-cyclopropyl, $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, $CH_2$-cyclohexanol), $R_8$-(substituted or unsubstituted, saturated, unsaturated or aromatic, single, fused or spiro 3-10 membered heterocyclic ring) (e.g., $(CH_2)_3$-pyran, $(CH_2)_2$-pyrrazole, $(CH_2)_2$-imidazole, $CH_2$-tetrahydrofurane, $CH_2$-dioxane, $CH_2$-oxetane, $(CH_2)_3$-piperidine, $CH_2$-triazole, $CH_2$-1-oxa-8-azaspiro[4.5]decane, $(CH_2)_3$-diazabicyclo [2.2.1]heptane, $CH_2$-methyl-THF, $CH_2$-ethyl-piperidine, $CH_2$-oxa-azaspirodecane, $(CH_2)_3$-dimethylpyrazole, $CH_2$-2-oxo-methylpyrrolidine, $CH_2$-methyl-azetidine, $CH_2$-azaspiroheptane), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$ (e.g., $(CH_2)_3$-4-fluoro-piperidine, $(CH_2)_3$—N$(CH_2CH_3)_2$, $(CH_2)_3$—$N(CH(CH_3)_2)_2$, $(CH_2)_3$-piperidine, $(CH_2)_4$—$NH(CH_3)$, $(CH_2)_3$—NH—$CH_3$, $(CH_2)_3$—NH—$CH_2CH_3$, $(CH_2)_3$—$N(CH_2CH_3)_2$, $(CH_2)_3$—$NH_2$, $(CH_2)_3$—$N(CH_2CH_3)(CH_2CF_3)$), $R_8$—$C(O)N(R_{10})(R_{11})$ (e.g., $(CH_2)_2$—C(O)- piperidine), $R_9$—$R_8$—$N(R_{10})(R_{11})$ (e.g., $(CH_2)_2$—C(O)- piperidine), $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., $CH(CH_3)CH_2OCH_3$, $CH(CH_3)CH_2NH_2$, $CH(CH_3)C(O)N(CH_3)_2$, $CH_2$—$CH(OH)Ph$, (CH$_2$)$_3$N(H)CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), C$_1$-C$_5$ linear or branched, substituted or unsubstituted alkenyl, C$_1$-C$_5$ linear or branched, or C$_3$-C$_5$ cyclic haloalkyl, substituted or unsubstituted C$_1$-C$_5$ linear or branched, or C$_3$-C$_5$ cyclic alkoxy (e.g. methoxy, O—(CH$_2$)$_2$O—CH$_3$), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_5$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), R$_8$-(substituted or unsubstituted C$_3$-C$_5$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted R$_8$-aryl (e.g., benzyl), substituted or unsubstituted benzyl;

or R$_6$ and R$_5$ are joined to form a substituted or unsubstituted 5-8 membered heterocyclic ring (e.g., azepane, piperazine, 2-(piperazin-1-yl)acetamide);

or R$_6$ is represented by the structure of formula B or Bi:

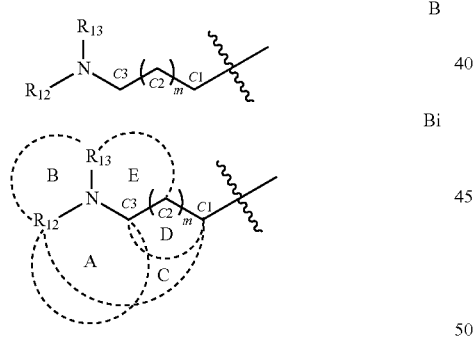

wherein
m is 0 or 1; and
R$_{12}$ is R$_{20}$ or C$_1$-C$_5$ C(O)-alkyl, and R$_{13}$ is R$_{30}$; or R$_{12}$ and R$_{13}$ are both H;
R$_{12}$ and R$_{13}$ are each independently H or substituted or unsubstituted C$_1$-C$_5$ alkyl (e.g., ethyl, trifluoroethyl);
R$_{12}$ and C3 are joined to form ring A and R$_{13}$ is R$_{30}$; or
R$_{12}$ and R$_{13}$ are joined to form ring B; or
R$_{12}$ and C1 are joined to form ring C and R$_{13}$ is R$_{30}$; or
C1 and C3 are joined to form ring D and R$_{12}$ and R$_{13}$ are each independently R$_{30}$; or
R$_{13}$ and C2 are joined to form ring E, m is 1, and R$_{12}$ is R$_{30}$; or R$_{12}$ and R$_{13}$ are joined to form ring B and C1 and C3 are joined to form ring D;
wherein
Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);
Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethylpyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and Ring D is a substituted or unsubstituted C$_3$-C$_8$ cycloalkyl (e.g., cyclobutane, cyclohexane);

R$_7$, R$_7'$, R$_7''$, R$_7'''$ and R$_7''''$ are each independently H, F, Cl, Br, I, OH, O—R$_{20}$, SH, R$_8$—OH, R$_8$—SH, —R$_8$—O—R$_{10}$, R$_8$—(C$_3$-C$_5$ cycloalkyl), R$_8$-(3-8 membered heterocyclic ring), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., isopropyl, methyl, ethyl), C$_1$-C$_5$ linear or branched, substituted or unsubstituted alkenyl, C$_1$-C$_5$ linear or branched, or C$_3$-C$_8$ cyclic haloalkyl (e.g., CHF$_2$), C$_1$-C$_5$ linear or branched, or C$_3$-C$_8$ cyclic alkoxy (e.g. methoxy), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

with the proviso that at least two of R$_7$, R$_7'$, R$_7''$, R$_7'''$ and R$_7''''$ are not H;

or R$_7'$ and R$_7''$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

or R7" and R7 are joined to form a 3-8 membered substituted or unsubstituted carbocyclic or heterocyclic ring (e.g., cyclopentyl, cyclohexyl, piperidine, tetrahydrofuran, tetrahydropyran, pyrrolidine);

or R7''' and R7"" are joined to form a 3-8 membered substituted or unsubstituted carbocyclic or heterocyclic ring (e.g., cyclopentyl, cyclohexyl, piperidine, tetrahydrofuran, tetrahydropyran, pyrrolidine);

or R7''' and R7"" are joined to form a 3-8 membered substituted or unsubstituted carbocyclic or heterocyclic ring (e.g., cyclopentyl, cyclohexyl, piperidine, tetrahydrofuran, tetrahydropyran, pyrrolidine);

$R_{20}$ is represented by the following structure:

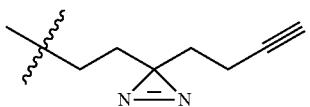 [SMILES: *CCC1(CCC#C)N=N1]

R is H, F, Cl, Br, I, OH, SH, alkoxy, NH($R_{10}$), NH—CH$_2$-cyclopropyl, N($R_{10}$)($R_{11}$), CF$_3$, CN, NO$_2$, COOH, C$_1$-C$_5$ linear or branched, substituted or unsubstituted alkyl (e.g., methyl, ethyl, CH$_2$—OH, CH$_2$—CH$_2$—OH, CH$_2$—CH$_2$—O—CH$_2$—CH$_2$—O—CH$_3$, CH$_2$—O—CH$_2$—CH$_2$—O—CH$_3$), C$_3$-C$_8$ substituted or unsubstituted cycloalkyl, cyclopropyl, C$_1$-C$_5$ linear or branched alkoxy, isopropoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), $R_8$-aryl (e.g., CH$_2$-Ph), —$R_8$—O—$R_8$—O—$R_{10}$ (e.g. (CH$_2$)$_2$—O—(CH$_2$)$_2$—O—CH$_3$), —$R_8$—O—$R_{10}$, —$R_8$—$R_{10}$ (e.g., (CH$_2$)$_2$O—CH$_3$), substituted or unsubstituted aryl (e.g., phenyl), substituted or unsubstituted heteroaryl (e.g., pyridine (2, 3, and 4-pyridine);

$R_{30}$ is H, $R_{20}$, F, Cl, Br, I, OH, SH, alkoxy, N(R)$_2$, NH($R_{10}$), N($R_{10}$)($R_{11}$), CF$_3$, CN, NO$_2$, C$_1$-C$_5$ linear or branched, substituted or unsubstituted alkyl (e.g., methyl, ethyl, CH$_2$—CH$_2$—O—CH$_2$—CH$_2$—O—CH$_3$, CH$_2$—O—CH$_2$—CH$_2$—O—CH$_3$), C$_1$-C$_5$ linear or branched alkoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), $R_8$-aryl (e.g., CH$_2$-Ph), —$R_8$—O—$R_8$—O—$R_{10}$ (e.g. (CH$_2$)$_2$—O—(CH$_2$)$_2$O—CH$_3$), —$R_8$—O—$R_{10}$, —$R_8$—$R_{10}$ (e.g., (CH$_2$)$_2$—O—CH$_3$), substituted or unsubstituted aryl (e.g., phenyl), substituted or unsubstituted heteroaryl (e.g., pyridine (2, 3, and 4-pyridine);

each $R_8$ is independently [CH$_2$]$_p$
wherein p is between 1 and 10;

$R_9$ is [CH]$_q$, [C]$_q$
wherein q is between 2 and 10;

$R_{10}$ and $R_{11}$ are each independently H, C$_1$-C$_5$ substituted or unsubstituted linear or branched alkyl (e.g., methyl, ethyl, CH$_2$-cyclopropyl, CH$_2$—CH$_2$—O—CH$_3$), C$_1$-C$_5$ substituted or unsubstituted linear or branched haloalky (e.g., CH$_2$CF$_3$), C$_1$-C$_5$ linear or branched alkoxy (e.g., O—CH$_3$), $R_{20}$, C(O)R, or S(O)$_2$R;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(j):

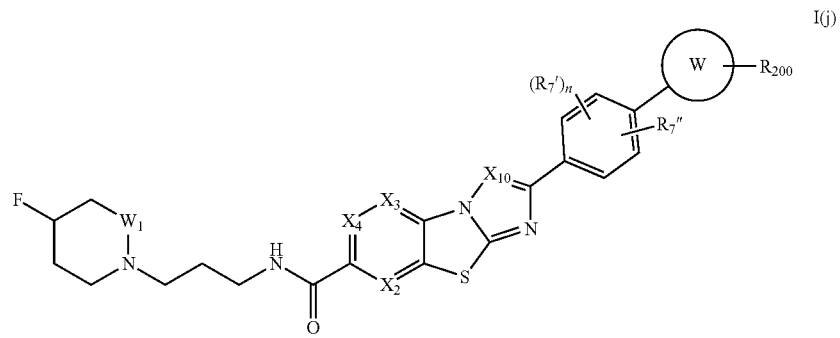

wherein
$X_2$, $X_3$, and $X_4$, are each independently nitrogen or CH;
$X_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));
Ring W is a 3-10 membered single, fused, bridged or spiro, saturated, unsaturated or aromatic, carbocyclic or heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 3-cyanopyrrolidine, 1-methylpyrrolidine, 3-(difluoromethyl)pyrrolidine, 3,3-difluoropyrrolidine, pyrrolidin-2-one, pyrrolidin-3-one, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, 2-oxopyrrolidine, cyclopropyl, 2,2-dimethylpyrrolidine, 4-azaspiro[2.4]heptane, pyrrolidin-3-one O-methyl oxime, 2-oxa-5-azaspiro[3.4]octane, 1,4-dioxa-6-azaspiro[4.4]nonane, 3,3-dimethylmorpholine, 1-methylpiperazine, 4,7-diazaspiro[2.5]octane, bicyclo[1.1.1]pentane, 2,5-diazabicyclo[2.2.1]heptane, piperazine, piperazine-2-one);
$W_1$ is CH$_2$, C═O or CH($R_{10}$) (e.g., CHCH$_3$);
$R_7$' and $R_7$" are each independently H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —C(O)$NH_2$, C(O)NHR, C(O)$N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or $R_7{}'$ and $R_7{}''$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

$R_{20}$ is represented by the following structure:

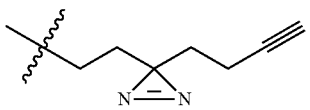 [SMILES: *CCC1(CCC#C)N=N1]

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine);

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2O$—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

$R_{200}$ is H, $R_{20}$, F, Cl, Br, I, OH, SH, alkoxy, $NH_2$, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy (e.g., methoxy), $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine); or $R_{200}$ and the carbon atom to which it is connected are C=O or $CF_2$;

each $R_8$ is independently $[CH_2]_p$ wherein p is between 1 and 10;

$R_9$ is $[CH]_q$, $[C]_q$ wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, the compound is not (R)-2-(2-fluoro-4-(pyrrolidin-2-yl)phenyl)-N-(3-(4-fluoropiperidin-1-yl)propyl) benzo[d]imidazo [2,1-b]thiazole-7-carboxamide. In various embodiments, the compound is not (S)-2-(2-fluoro-4-(pyrrolidin-2-yl)phenyl)-N-(3-(4-fluoropiperidin-1-yl)propyl)benzo[d]imidazo[2,1-b]thiazole-7-carboxamide. In various embodiments, the compound is not 2-(2-fluoro-4-(pyrrolidin-2-yl)phenyl)-N-(3-(4-fluoropiperidin-1-yl)propyl) benzo[d]imidazo[2,1-b]thiazole-7-carboxamide.

In various embodiments, this invention is directed to a compound represented by the structure of formula I(k):

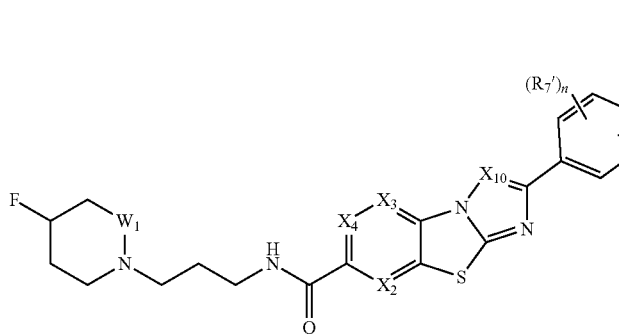
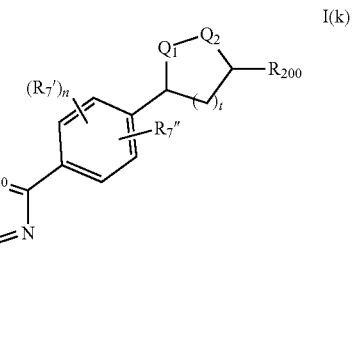

wherein
- $X_2$, $X_3$, and $X_4$, are each independently nitrogen or CH;
- $X_{10}$ is N, CH, or C(R) (e.g., $C(CH_2)OH$, $C(CH_2)_2OH$, $C(NH-CH_2\text{-cyclopropyl})$, $C(CH_3)$, $C(\text{cyclopropyl})$, $C(\text{isopropoxy})$, $C(COOH)$);
- $Q_1$ is O, NH or $CH_2$;
- $Q_2$ is C=O, NH or $CH_2$;
- $R_7$ and $R_7'$ are each independently H, F, Cl, Br, I, OH, O—$R_{20}$, SH, $R_8$—OH, $R_8$—SH, —$R_8$—O—$R_{10}$, $R_8$—($C_3$-$C_8$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH-R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;
- or $R_7$ and $R_7'$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);
- $R_{20}$ is represented by the following structure:

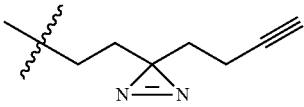 [SMILES: *CCC1(CCC#C)N=N1]

- R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine);
- $R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2O$—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);
- $R_{200}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy (e.g., methoxy), $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2O$—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);
- or $R_{200}$ and the carbon atom to which it is connected are C=O or $CF_2$;
- each $R_8$ is independently $[CH_2]_p$
  - wherein p is between 1 and 10;
- $R_9$ is $[CH]_q$, $[C]_q$
  - wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—$O$—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or S(O)$_2$R;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

t is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, the compound is not (R)-2-(2-fluoro-4-(pyrrolidin-2-yl)phenyl)-N-(3-(4-fluoropiperidin-1-yl)propyl) benzo[d]imidazo [2,1-b]thiazole-7-carboxamide. In various embodiments, the compound is not (S)-2-(2-fluoro-4-(pyrrolidin-2-yl)phenyl)-N-(3-(4-fluoropiperidin-1-yl)propyl)benzo[d]imidazo[2,1-b]thiazole-7-carboxamide. In various embodiments, the compound is not 2-(2-fluoro-4-(pyrrolidin-2-yl)phenyl)-N-(3-(4-fluoropiperidin-1-yl)propyl) benzo[d]imidazo[2,1-b]thiazole-7-carboxamide.

In various embodiments, this invention is directed to a compound represented by the structure of formula I(l):

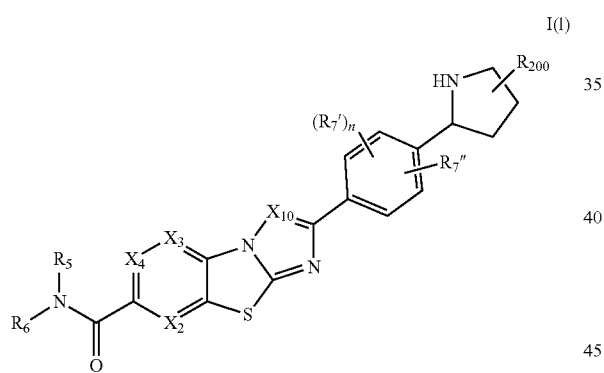

I(l)

wherein $X_2$, $X_3$, and $X_4$, are each independently nitrogen or CH;

$X_{10}$ is N, CH, or C(R) (e.g., C($CH_2$)OH, C($CH_2$)$_2$OH, C(NH—$CH_2$-cyclopropyl), C($CH_3$), C(cyclopropyl), C(isopropoxy), C(COOH));

$R_5$ is H or $C_1$-$C_5$ linear or branched alkyl (e.g. methyl);

$R_6$ is H, F, Cl, Br, I, OH, SH, $R_8$—OH, $R_8$—SH, —$R_8$—O—$R_{10}$ (e.g., $CH_2$—O—$CH_3$, ($CH_2$)$_2$O—$CH_3$ ($CH_2$)$_3$O—$CH_3$, ($CH_2$)$_2$O—$CH(CH_3)_2$), $R_8$—S—$R_{10}$ (e.g., ($CH_2$)$_3$—S—($CH_2$)$_2$$CH_3$), $R_8$—NHC(O)—$R_{10}$, —O—$R_8$—$R_{10}$, $R_8$-(substituted or unsubstituted $C_3$-$C_8$ cycloalkyl) (e.g., $CH_2$-cyclopropyl, $CH_2$-cyclobutanol, $CH_2$-difluorocyclopropyl, $CH_2$-methylcyclopropyl, $CH_2$-dimethylamino-cyclohexyl, ($CH_2$)$_2$-cyclopentanole, $CH_2$-cyclohexanol), $R_8$-(substituted or unsubstituted, saturated, unsaturated or aromatic, single, fused or spiro 3-10 membered heterocyclic ring) (e.g., ($CH_2$)$_3$-pyran, ($CH_2$)$_2$-pyrrazole, ($CH_2$)$_2$-imidazole, $CH_2$-tetrahydrofurane, $CH_2$-dioxane, $CH_2$-oxetane, $CH_2$-piperidine, $CH_2$-triazole, $CH_2$-1-oxa-8-azaspiro[4.5]decane, ($CH_2$)$_3$-diazabicyclo[2.2.1]heptane, $CH_2$-methyl-THF, $CH_2$-ethyl-piperidine, $CH_2$-oxa-azaspirodecane, ($CH_2$)$_3$-dimethylpyrazole, $CH_2$-2-oxo-methylpyrrolidine, $CH_2$-methyl-azetidine, $CH_2$-azaspiroheptane), $CF_3$, $CD_3$, $OCD_3$, CN, $NO_2$, —$CH_2CN$, —$R_8CN$, $NH_2$, NHR, N(R)$_2$, NH($R_{10}$), N($R_{10}$)($R_{11}$), $R_8$—N($R_{10}$)($R_{11}$) (e.g., ($CH_2$)$_3$-4-fluoro-piperidine, ($CH_2$)$_3$—N($CH_2CH_3$)$_2$, ($CH_2$)$_3$—N(CH($CH_3$)$_2$)$_2$, ($CH_2$)$_3$-piperidine, ($CH_2$)$_4$—NH($CH_3$), ($CH_2$)$_3$—NH—$CH_3$, ($CH_2$)$_3$—NH—$CH_2CH_3$, ($CH_2$)$_3$—N($CH_2CH_3$)$_2$, ($CH_2$)$_3$—NH$_2$, ($CH_2$)$_3$—N($CH_2CH_3$)($CH_2CF_3$)), $R_8$—C(O)N($R_{10}$)($R_{11}$) (e.g., ($CH_2$)$_2$—C(O)- piperidine), $R_9$—$R_8$—N($R_{10}$)($R_{11}$) (e.g., ($CH_2$)$_2$—C(O)-piperidine), B(OH)$_2$, —OC(O)$CF_3$, —O$CH_2$Ph, NHC(O)—$R_{10}$, NHCO—N($R_{10}$)($R_{11}$), COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —C(O)NH$_2$, C(O)NHR, C(O)N($R_{10}$)($R_{11}$), SO$_2$R, SO$_2$N($R_{10}$)($R_{11}$), CH(CF$_3$)(NH—$R_{10}$), $C_1$-$C_5$ linear or branched, substituted or unsubstituted alkyl (e.g., CH(CH$_3$)CH$_2$OCH$_3$, CH(CH$_3$)CH$_2$NH$_2$, CH(CH$_3$)C(O)N(CH$_3$)$_2$, CH$_2$—CH(OH)Ph, (CH$_2$)$_3$N(H)CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), $C_1$-$C_5$ linear or branched, substituted or unsubstituted alkenyl, $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy (e.g. methoxy, O—(CH$_2$)$_2$O—CH$_3$), optionally wherein at least one methylene group (CH$_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), $R_8$-(substituted or unsubstituted $C_3$-$C_8$ cycloalkyl), substituted or unsubstituted, saturated, unsaturated, single fused, bridged or spiro 3-10 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyloxetane, hydroxy-tetrahydrofurane, azepan-2-one, azabicyclohexane), substituted or unsubstituted aryl, substituted or unsubstituted $R_8$-aryl (e.g., benzyl), substituted or unsubstituted benzyl;

or $R_6$ and $R_5$ are joined to form a substituted or unsubstituted 5-8 membered heterocyclic ring (e.g., azepane, piperazine, 2-(piperazin-1-yl)acetamide);

$R_7'$ and $R_7''$ are each independently H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, N®$_2$, NH($R_{10}$), N($R_{10}$)($R_{11}$), $R_8$—N($R_{10}$)($R_{11}$), $R_9$—$R_8$—N($R_{10}$)($R_{11}$), B(OH)$_2$, —OC(O)$CF_3$, —OCH$_2$Ph, NHC(O)—$R_{10}$, NHCO—N($R_{10}$)($R_{11}$), COOH, —C(O)

Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., isopropyl, methyl, ethyl), C$_1$-C$_5$ linear or branched, substituted or unsubstituted alkenyl, C$_1$-C$_5$ linear or branched, or C$_3$-C$_8$ cyclic haloalkyl (e.g., CHF$_2$), C$_1$-C$_5$ linear or branched, or C$_3$-C$_8$ cyclic alkoxy (e.g. methoxy), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or R$_7$' and R$_7$" are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

R$_{20}$ is represented by the following structure:

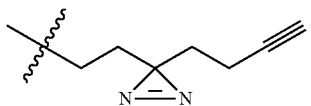 [SMILES: *CCC1(CCC#C)N=N1]

R is H, F, Cl, Br, I, OH, SH, alkoxy, NH(R$_{10}$), NH—CH$_2$-cyclopropyl, N(R$_{10}$)(R$_{11}$), CF$_3$, CN, NO$_2$, COOH, C$_1$-C$_5$ linear or branched, substituted or unsubstituted alkyl (e.g., methyl, ethyl, CH$_2$—OH, CH$_2$—CH$_2$—OH, CH$_2$—CH$_2$—O—CH$_2$—CH$_2$—O—CH$_3$, CH$_2$—O—CH$_2$—CH$_2$—O—CH$_3$), C$_3$-C$_8$ substituted or unsubstituted cycloalkyl, cyclopropyl, C$_1$-C$_5$ linear or branched alkoxy, isopropoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$—O—CH$_3$), —R$_8$—O—R$_{10}$, —R$_8$—R$_{10}$ (e.g., (CH$_2$)$_2$O—CH$_3$), substituted or unsubstituted aryl (e.g., phenyl), substituted or unsubstituted heteroaryl (e.g., pyridine (2, 3, and 4-pyridine);

R$_{30}$ is H, R$_{20}$, F, Cl, Br, I, OH, SH, alkoxy, N(R)$_2$, NH(R$_{10}$), N(R$_{10}$)(R$_{11}$), CF$_3$, CN, NO$_2$, C$_1$-C$_5$ linear or branched, substituted or unsubstituted alkyl (e.g., methyl, ethyl, CH$_2$—CH$_2$—O—CH$_2$—CH$_2$—O—CH$_3$, CH$_2$—O—CH$_2$—CH$_2$—O—CH$_3$), C$_1$-C$_5$ linear or branched alkoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$O—CH$_3$), —R$_8$—O—R$_{10}$, —R$_8$—R$_{10}$ (e.g., (CH$_2$)$_2$—O—CH$_3$), substituted or unsubstituted aryl (e.g., phenyl), substituted or unsubstituted heteroaryl (e.g., pyridine (2, 3, and 4-pyridine);

R$_{200}$ is H, R$_{20}$, F, Cl, Br, I, OH, SH, alkoxy, NH$_2$, N(R)$_2$, NH(R$_{10}$), N(R$_{10}$)(R$_{11}$), CF$_3$, CN, NO$_2$, C$_1$-C$_5$ linear or branched, substituted or unsubstituted alkyl (e.g., methyl, ethyl, CH$_2$—CH$_2$—O—CH$_2$—CH$_2$—O—CH$_3$, CH$_2$—O—CH$_2$—CH$_2$—O—CH$_3$), C$_1$-C$_5$ linear or branched alkoxy (e.g., methoxy), C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$—O—CH$_3$), —R$_8$—O—R$_{10}$, —R$_8$—R$_{10}$ (e.g., (CH$_2$)$_2$O—CH$_3$), substituted or unsubstituted aryl (e.g., phenyl), substituted or unsubstituted heteroaryl (e.g., pyridine (2, 3, and 4-pyridine); or R$_{200}$ and the carbon atom to which it is connected are C=O or CF$_2$;

each R$_8$ is independently [CH$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ substituted or unsubstituted linear or branched alkyl (e.g., methyl, ethyl, CH$_2$-cyclopropyl, CH$_2$—CH$_2$—O—CH$_3$), C$_1$-C$_5$ substituted or unsubstituted linear or branched haloalky (e.g., CH$_2$CF$_3$), C$_1$-C$_5$ linear or branched alkoxy (e.g., O—CH$_3$), R$_{20}$, C(O)R, or S(O)$_2$R;

or R$_{10}$ and R$_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, R$_6$ of compound of formula I(l) is H, C$_1$-C$_5$ linear or branched, substituted or unsubstituted alkyl (e.g., methyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane; each represents a separate embodiment according to this invention). In various embodiments, R$_6$ is H. In various embodiments, R$_6$ is C$_1$-C$_5$ linear or branched, substituted or unsubstituted alkyl. In various embodiments, R$_6$ is methyl. In various embodiments, R$_6$ is substituted or unsubstituted 3-8 membered heterocyclic ring. In various embodiments, R$_6$ is piperidine. In various embodiments, R$_6$ is 1-methylpiperidine. In various embodiments, R$_6$ is 3-fluoro-1-methylpiperidine. In various embodiments, R$_6$ is azetidine. In various embodiments, R$_6$ is 1-methyl-azetidine. In various embodiments, R$_6$ is morpholine. In various embodiments, R$_6$ is tetrahydropyran. In various embodiments, R$_6$ is tetrahydrofurane. In various embodiments, R$_6$ is 8-methyl-8-azabicyclo[3.2.1]octane. In various embodiments, R$_6$ is dioxane. In various embodiments, R$_6$ is 1,3-dioxane.

In various embodiments, this invention is directed to a compound represented by the structure of formula I(m):

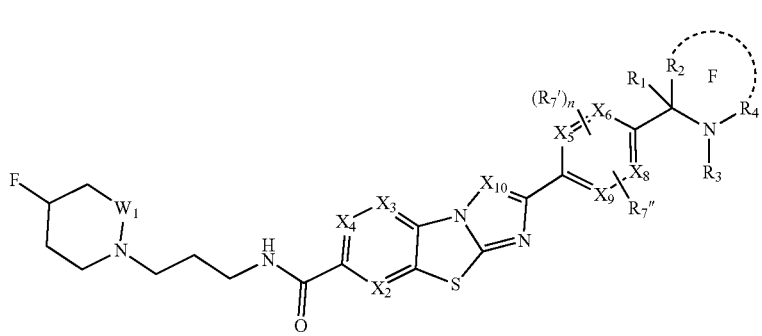

I(m)

wherein
- $X_2$, $X_3$, and $X_4$, are each independently nitrogen or CH;
- $X_5$, $X_6$, $X_7$, $X_8$ and $X_9$ are each independently nitrogen or carbon atoms;
- $X_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));
- $W_1$ is CH$_2$, C=O or CH(R$_{10}$) (e.g., CHCH$_3$);
- Ring F is absent or is a substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);
- $R_1$ and $R_2$ are each independently H, F, Cl, Br, I, OH, SH, or CF$_3$, substituted or unsubstituted C$_1$-C$_5$ alkyl (e.g., CH$_2$OH), C$_1$-C$_5$ linear or branched, or C$_3$-C$_5$ cyclic haloalkyl, substituted or unsubstituted C$_1$-C$_5$ linear or branched, or C$_3$-C$_5$ cyclic alkoxy;
- or $R_1$ and $R_2$ are joined to form a 3-8 membered carbocyclic or heterocyclic ring (e.g., cyclopropyl);
- or $R_2$ and $R_4$ are joined to form Ring F as defined above (e.g., pyrrolidine, morpholine, 1-methylpyrrolidine, pyrrolidine-2-one, pyrrolidine-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole), wherein if Ring F is aromatic, then $R_1$ and/or $R_3$ are absent;
- $R_3$ and $R_4$ are each independently H, Me, substituted or unsubstituted C$_1$-C$_5$ alkyl (e.g., methoxyethylene, methylaminoethyl, aminoethyl), —R$_8$—O—R$_{10}$ (e.g., (CH$_2$)$_2$O—CH$_3$), R$_8$—N(R$_{10}$)(R$_{11}$) (e.g., (CH$_2$)$_2$—NH(CH$_3$)), substituted or unsubstituted C$_3$-C$_5$ cycloalkyl (e.g., cyclopropyl), substituted or unsubstituted 5-7 membered heterocyclic ring (e.g., pyrrolidine, methylpyrrolidine, piperidine), or R$_{20}$; or
- $R_3$ and $R_4$ are joined to form a 3-8 membered heterocyclic ring (e.g., pyrrolidine, pyrrolidone, 2-oxopyrrolidine, piperidine, morpholine, piperazine, imidazole);
- $R_7'$ and $R_7''$ are each independently H, F, Cl, Br, I, OH, O—R$_{20}$, SH, R$_8$—OH, R$_8$—SH, —R$_8$—O—R$_{10}$, R$_8$—(C$_3$-C$_5$ cycloalkyl), R$_8$—(3-8 membered heterocyclic ring), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., isopropyl, methyl, ethyl), C$_1$-C$_5$ linear or branched, substituted or unsubstituted alkenyl, C$_1$-C$_5$ linear or branched, or C$_3$-C$_5$ cyclic haloalkyl (e.g., CHF$_2$), C$_1$-C$_5$ linear or branched, or C$_3$-C$_5$ cyclic alkoxy (e.g. methoxy), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_5$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;
- or $R_7'$ and $R_7''$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);
- $R_{20}$ is represented by the following structure:

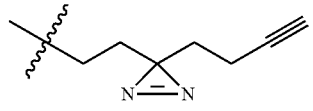 [SMILES: *CCC1(CCC#C)N=N1]

R is H, F, Cl, Br, I, OH, SH, alkoxy, NH(R$_{10}$), NH—CH$_2$-cyclopropyl, N(R$_{10}$)(R$_{11}$), CF$_3$, CN, NO$_2$, COOH, C$_1$-C$_5$ linear or branched, substituted or unsubstituted alkyl (e.g., methyl, ethyl, CH$_2$—OH, CH$_2$—CH$_2$—OH, CH$_2$—CH$_2$—O—CH$_2$—CH$_2$—O—CH$_3$, CH$_2$—O—CH$_2$—CH$_2$—O—CH$_3$), C$_3$-C$_8$ substituted or unsubstituted cycloalkyl, cyclopropyl, C$_1$-C$_5$ linear or branched alkoxy, isopropoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g.

(CH$_2$)$_2$—O—(CH$_2$)$_2$—O—CH$_3$), —R$_8$—O—R$_{10}$, —R$_8$—R$_{10}$ (e.g., (CH$_2$)$_2$O—CH$_3$), substituted or unsubstituted aryl (e.g., phenyl), substituted or unsubstituted heteroaryl (e.g., pyridine (2, 3, and 4-pyridine);

R$_{30}$ is H, R$_{20}$, F, Cl, Br, I, OH, SH, alkoxy, N(R)$_2$, NH(R$_{10}$), N(R$_{10}$)(R$_{11}$), CF$_3$, CN, NO$_2$, C$_1$-C$_5$ linear or branched, substituted or unsubstituted alkyl (e.g., methyl, ethyl, CH$_2$—CH$_2$—O—CH$_2$—CH$_2$—O—CH$_3$, CH$_2$—O—CH$_2$—CH$_2$—O—CH$_3$), C$_1$-C$_5$ linear or branched alkoxy, C$_1$-C$_5$ linear or branched haloalkyl (e.g., CHF$_2$, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), —R$_8$—O—R$_8$—O—R$_{10}$ (e.g. (CH$_2$)$_2$—O—(CH$_2$)$_2$O—CH$_3$), —R$_8$—O—R$_{10}$, —R$_8$—R$_{10}$ (e.g., (CH$_2$)$_2$—O—CH$_3$), substituted or unsubstituted aryl (e.g., phenyl), substituted or unsubstituted heteroaryl (e.g., pyridine (2, 3, and 4-pyridine);

each R$_5$ is independently [CH$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ substituted or unsubstituted linear or branched alkyl (e.g., methyl, ethyl, CH$_2$-cyclopropyl, CH$_2$—CH$_2$—O—CH$_3$), C$_1$-C$_5$ substituted or unsubstituted linear or branched haloalky (e.g., CH$_2$CF$_3$), C$_1$-C$_5$ linear or branched alkoxy (e.g., O—CH$_3$), R$_{20}$, C(O)R, or S(O)$_2$R;

or R$_{10}$ and R$_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula I(n):

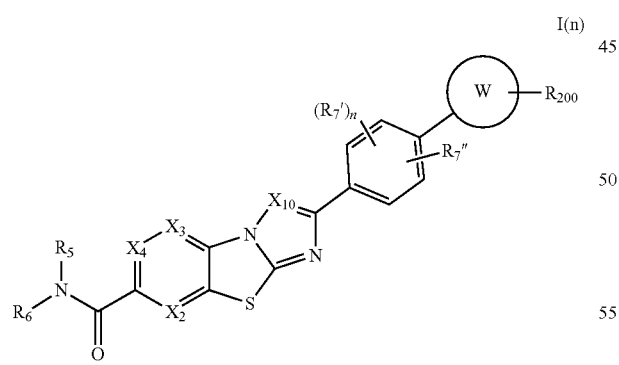

I(n)

wherein

X$_2$, X$_3$, and X$_4$, are each independently nitrogen or CH;
X$_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));

Ring W is a 3-10 membered single, fused, bridged or spiro, saturated, unsaturated or aromatic, carbocyclic or heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxy-pyrrolidine, 3-cyanopyrrolidine, 1-methylpyrrolidine, 3-(difluoromethyl)pyrrolidine, 3,3-difluoropyrrolidine, pyrrolidin-2-one, pyrrolidin-3-one, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, 2-oxopyrrolidine, cyclopropyl, 2,2-dimethylpyrrolidine, 4-azaspiro[2.4]heptane, pyrrolidin-3-one O-methyl oxime, 2-oxa-5-azaspiro[3.4]octane, 1,4-dioxa-6-azaspiro[4.4]nonane, 3,3-dimethylmorpholine, 1-methylpiperazine, 4,7-diazaspiro[2.5]octane, bicyclo[1.1.1]pentane, 2,5-diazabicyclo[2.2.1]heptane, piperazine, piperazine-2-one);

W$_1$ is CH$_2$, C=O or CH(R$_{10}$) (e.g., CHCH$_3$);

R$_5$ is H or C$_1$-C$_5$ linear or branched alkyl (e.g. methyl);

R$_6$ is H, F, Cl, Br, I, OH, SH, R$_8$—OH, R$_8$—SH, —R$_8$—O—R$_{10}$ (e.g., CH$_2$—O—CH$_3$, (CH$_2$)$_2$O—CH$_3$ (CH$_2$)$_3$O—CH$_3$, (CH$_2$)$_2$O—CH(CH$_3$)$_2$), R$_8$—S—R$_{10}$ (e.g., (CH$_2$)$_3$—S—(CH$_2$)$_2$CH$_3$), R$_8$—NHC(O)—R$_{10}$, —O—R$_8$—R$_{10}$, R$_8$-(substituted or unsubstituted C$_3$-C$_8$ cycloalkyl) (e.g., CH$_2$-cyclopropyl, CH$_2$-cyclobutanol, CH$_2$-difluorocyclopropyl, CH$_2$-methylcyclopropyl, CH$_2$-dimethylamino-cyclohexyl, (CH$_2$)$_2$-cyclopentanole, CH$_2$-cyclohexanol), R$_8$-(substituted or unsubstituted, saturated, unsaturated or aromatic, single, fused or spiro 3-10 membered heterocyclic ring) (e.g., (CH$_2$)$_3$-pyran, (CH$_2$)$_2$-pyrrazole, (CH$_2$)$_2$-imidazole, CH$_2$-tetrahydrofurane, CH$_2$-dioxane, CH$_2$-oxetane, CH$_2$-piperidine, CH$_2$-triazole, CH$_2$-1-oxa-8-azaspiro[4.5]decane, (CH$_2$)$_3$-diazabicyclo[2.2.1]heptane, CH$_2$-methyl-THF, CH$_2$-ethyl-piperidine, CH$_2$-oxa-azaspirodecane, (CH$_2$)$_3$-dimethylpyrazole, CH$_2$-2-oxo-methylpyrrolidine, CH$_2$-methyl-azetidine, CH$_2$-azaspiroheptane), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$) (e.g., (CH$_2$)$_3$-4-fluoro-piperidine, (CH$_2$)$_3$—N(CH$_2$CH$_3$)$_2$, (CH$_2$)$_3$—N(CH(CH$_3$)$_2$)$_2$, (CH$_2$)$_3$-piperidine, (CH$_2$)$_4$—NH(CH$_3$), (CH$_2$)$_3$—NH—CH$_3$, (CH$_2$)$_3$—NH—CH$_2$CH$_3$, (CH$_2$)$_3$—N(CH$_2$CH$_3$)$_2$, (CH$_2$)$_3$—NH$_2$, (CH$_2$)$_3$—N(CH$_2$CH$_3$)(CH$_2$CF$_3$)), R$_8$—C(O)N(R$_{10}$)(R$_{11}$) (e.g., (CH$_2$)$_2$—C(O)- piperidine), R$_9$—R$_8$—N(R$_{10}$)(R$_{11}$) (e.g., (CH$_2$)$_2$—C(O)-piperidine), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., CH(CH$_3$)CH$_2$OCH$_3$, CH(CH$_3$)CH$_2$NH$_2$, CH(CH$_3$)C(O)N(CH$_3$)$_2$, CH$_2$—CH(OH)Ph, (CH$_2$)$_3$N(H)CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), C$_1$-C$_5$ linear or branched, substituted or unsubstituted alkenyl, C$_1$-C$_5$ linear or branched, or C$_3$-C$_8$ cyclic haloalkyl, substituted or unsubstituted C$_1$-C$_5$ linear or branched, or C$_3$-C$_8$ cyclic alkoxy (e.g. methoxy, O—(CH$_2$)$_2$O—CH$_3$), optionally wherein at least one methylene group (CH$_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), $R_8$-(substituted or unsubstituted $C_3$-$C_8$ cycloalkyl), substituted or unsubstituted, saturated or unsaturated, single fused, bridged or spiro 3-10 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted $R_8$-aryl (e.g., benzyl), substituted or unsubstituted benzyl;

or $R_6$ and $R_5$ are joined to form a substituted or unsubstituted 5-8 membered heterocyclic ring (e.g., azepane, piperazine, 2-(piperazin-1-yl)acetamide);

$R_7'$ and $R_7''$ are each independently H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH-R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or $R_7'$ and $R_7''$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

$R_{20}$ is represented by the following structure:

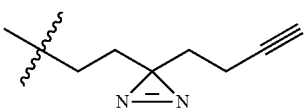 [SMILES: *CCC1(CCC#C)N=N1]

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine);

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2O$—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

$R_{200}$ is H, $R_{20}$, F, Cl, Br, I, OH, SH, alkoxy, $NH_2$, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy (e.g., methoxy), $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine); or $R_{200}$ and the carbon atom to which it is connected are C=O or $CF_2$;

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, the compound is not (R)-2-(2-fluoro-4-(pyrrolidin-2-yl)phenyl)-N-(3-(4-fluoropiperidin-1-yl)propyl) benzo[d]imidazo [2,1-b]thiazole-7-carboxamide. In various embodiments, the compound is not (S)-2-(2-fluoro-4-(pyrrolidin-2-yl)phenyl)-N-(3-(4-fluoropiperidin-1-yl)propyl)benzo[d]imidazo[2,1-b]thiazole-7-carboxamide. In various embodiments, the compound is not 2-(2-fluoro-4-(pyrrolidin-2-yl)phenyl)-N-(3-(4-fluoropiperidin-1-yl)propyl) benzo[d]imidazo[2,1-b]thiazole-7-carboxamide.

In various embodiments, this invention is directed to a compound represented by the structure of formula I(o):

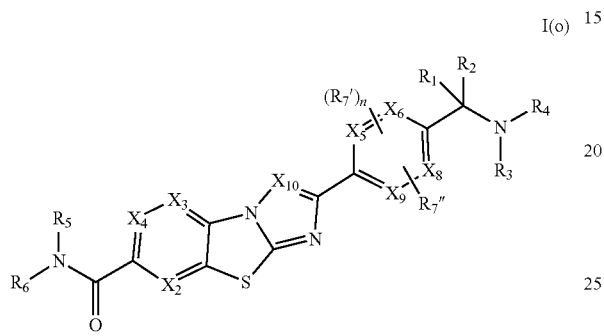

I(o)

wherein
X$_2$, X$_3$, and X$_4$ are each independently nitrogen or CH;
X$_5$, X$_6$, X$_7$, X$_8$ and X$_9$ are each independently nitrogen or carbon atoms;
X$_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));
R$_1$ is H, F, Cl, Br, I, OH, SH, or CF$_3$, substituted or unsubstituted C$_1$-C$_5$ alkyl (e.g., CH$_2$OH), C$_1$-C$_5$ linear or branched, or C$_3$-C$_8$ cyclic haloalkyl, substituted or unsubstituted C$_1$-C$_5$ linear or branched, or C$_3$-C$_8$ cyclic alkoxy;
R$_2$ is substituted or unsubstituted C$_1$-C$_5$ alkyl (e.g., CH$_2$OH, CH$_2$OCH$_3$), 3-8 membered carbocyclic or heterocyclic ring (e.g., oxetane);
or R$_1$ and R$_2$ are joined to form a 3-8 membered carbocyclic or heterocyclic ring (e.g., cyclopropyl, oxetane);
R$_3$ and R$_4$ are each independently H, Me, substituted or unsubstituted C$_1$-C$_5$ alkyl (e.g., methoxyethylene, methylaminoethyl, aminoethyl), —R$_8$—O—R$_{10}$ (e.g., (CH$_2$)$_2$O—CH$_3$), R$_8$—N(R$_{10}$)(R$_{11}$) (e.g., (CH$_2$)$_2$—NH(CH$_3$)), substituted or unsubstituted C$_3$-C$_8$ cycloalkyl (e.g., cyclopropyl), substituted or unsubstituted 5-7 membered heterocyclic ring (e.g., pyrrolidine, methylpyrrolidine, piperidine), or R$_{20}$;
or R$_3$ and R$_4$ are joined to form a 3-8 membered heterocyclic ring (e.g., pyrrolidine, pyrrolidone, 2-oxopyrrolidine, piperidine, morpholine, piperazine, imidazole);
R$_5$ is H or C$_1$-C$_5$ linear or branched alkyl (e.g. methyl);
R$_6$ is H, F, Cl, Br, I, OH, SH, R$_8$—OH, R$_8$—SH, —R$_8$—O—R$_{10}$ (e.g., CH$_2$—O—CH$_3$, (CH$_2$)$_2$O—CH$_3$, (CH$_2$)$_3$O—CH$_3$, (CH$_2$)$_2$O—CH(CH$_3$)$_2$), R$_8$—S—R$_{10}$ (e.g., (CH$_2$)$_3$—S—(CH$_2$)$_2$CH$_3$), R$_8$—NHC(O)—R$_{10}$, —O—R$_8$—R$_{10}$, R$_8$-(substituted or unsubstituted C$_3$-C$_8$ cycloalkyl) (e.g., CH$_2$-cyclopropyl, CH$_2$-cyclobutanol, CH$_2$-difluorocyclopropyl, CH$_2$-methylcyclopropyl, CH$_2$-dimethylamino-cyclohexyl, (CH$_2$)$_2$-cyclopentanole, CH$_2$-cyclohexanol), R$_8$-(substituted or unsubstituted, saturated, unsaturated or aromatic, single, fused or spiro 3-10 membered heterocyclic ring) (e.g., (CH$_2$)$_3$-pyran, (CH$_2$)$_2$-pyrrazole, (CH$_2$)$_2$-imidazole, CH$_2$-tetrahydrofurane, CH$_2$-dioxane, CH$_2$-oxetane, CH$_2$-piperidine, CH$_2$-triazole, CH$_2$-1-oxa-8-azaspiro[4.5]decane, (CH$_2$)$_3$-diazabicyclo[2.2.1]heptane, CH$_2$-methyl-THF, CH$_2$-ethyl-piperidine, CH$_2$-oxa-azaspirodecane, (CH$_2$)$_3$-dimethylpyrazole, CH$_2$-2-oxo-methylpyrrolidine, CH$_2$-methyl-azetidine, CH$_2$-azaspiroheptane), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$) (e.g., (CH$_2$)$_3$-4-fluoro-piperidine, (CH$_2$)$_3$—N(CH$_2$CH$_3$)$_2$, (CH$_2$)$_3$—N(CH(CH$_3$)$_2$)$_2$, (CH$_2$)$_3$-piperidine, (CH$_2$)$_4$—NH(CH$_3$), (CH$_2$)$_3$—NH—CH$_3$, (CH$_2$)$_3$—NH—CH$_2$CH$_3$, (CH$_2$)$_3$—N(CH$_2$CH$_3$)$_2$, (CH$_2$)$_3$—NH$_2$, (CH$_2$)$_3$—N(CH$_2$CH$_3$)(CH$_2$CF$_3$)), R$_8$—C(O)N(R$_{10}$)(R$_{11}$) (e.g., (CH$_2$)$_2$—C(O)- piperidine), R$_9$—R$_8$—N(R$_{10}$)(R$_{11}$) (e.g., (CH$_2$)$_2$—C(O)-piperidine), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., CH(CH$_3$)CH$_2$OCH$_3$, CH(CH$_3$)CH$_2$NH$_2$, CH(CH$_3$)C(O)N(CH$_3$)$_2$, CH$_2$—CH(OH)Ph, (CH$_2$)$_3$N(H)CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), C$_1$-C$_5$ linear or branched, substituted or unsubstituted alkenyl, C$_1$-C$_5$ linear or branched, or C$_3$-C$_8$ cyclic haloalkyl, substituted or unsubstituted C$_1$-C$_5$ linear or branched, or C$_3$-C$_8$ cyclic alkoxy (e.g. methoxy, O—(CH$_2$)$_2$O—CH$_3$), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), R$_8$-(substituted or unsubstituted C$_3$-C$_8$ cycloalkyl), substituted or unsubstituted, saturated or unsaturated, single fused, bridged or spiro 3-10 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted R$_8$-aryl (e.g., benzyl), substituted or unsubstituted benzyl;
or R$_6$ and R$_5$ are joined to form a substituted or unsubstituted 5-8 membered heterocyclic ring (e.g., azepane, piperazine, 2-(piperazin-1-yl)acetamide);
R$_7$' and R$_7$" are each independently H, F, Cl, Br, I, OH, O—R$_{20}$, SH, R$_8$—OH, R$_8$—SH, —R$_8$—O—R$_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —C(O)$NH_2$, C(O)NHR, C(O)$N(R_{10})(R_{11})$, $SO_2R$, $SO_2N(R_{10})(R_{11})$, $CH(CF_3)(NH—R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or $R_7'$ and $R_7''$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

$R_{20}$ is represented by the following structure:

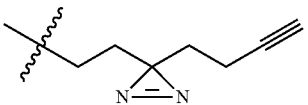 [SMILES: *CCC1(CCC#C)N=N1]

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine);

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2O$—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In various embodiments, $R_7'$ is F. In various embodiments, $R_7''$ is H. In various embodiments, $R_1$ is H. In various embodiments, $R_2$ is a substituted $C_1$-$C_5$ alkyl. In various embodiments, $R_2$ is $CH_2OH$. In various embodiments, $R_2$ is $CH_2OCH_3$. In various embodiments, $R_2$ is 3-8 membered heterocyclic ring. In various embodiments, $R_2$ is oxetane. In various embodiments, $R_2$ is 3-oxetane or 2-oxetane; each represents a separate embodiment. In various embodiments, $R_6$ is H. In various embodiments, $R_6$ is $C_1$-$C_5$ linear or branched, substituted or unsubstituted alkyl. In various embodiments, $R_6$ is methyl. In various embodiments, $R_6$ is substituted or unsubstituted, saturated or unsaturated, single fused, bridged or spiro 3-10 membered heterocyclic ring. In various embodiments, $R_6$ is substituted or unsubstituted, saturated single 3-8 membered heterocyclic ring. In various embodiments, the heterocyclic ring is tetrahydropyrane. In various embodiments, $R_7'$ is F, $R_1$ is H and $R_6$ is unsubstituted $C_1$-$C_5$ linear or branched, alkyl or substituted or unsubstituted, saturated single 3-8 membered heterocyclic ring. In various embodiments, $R_7'$ is F, $R_1$ is H and $R_6$ is methyl.

In various embodiments, this invention is directed to a compound represented by the structure of formula (II):

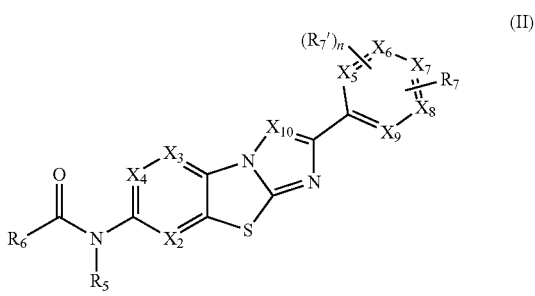

wherein
$X_2$, $X_3$, and $X_4$, are each independently nitrogen or CH;
$X_5$, $X_6$, $X_7$, $X_8$ and $X_9$ are each independently nitrogen or carbon atoms;

X$_{10}$ is N, CH, or C(R) (e.g., C(CH$_2$)OH, C(CH$_2$)$_2$OH, C(NH—CH$_2$-cyclopropyl), C(CH$_3$), C(cyclopropyl), C(isopropoxy), C(COOH));

R$_5$ is H or C$_1$-C$_5$ linear or branched alkyl (e.g. methyl);

R$_6$ is H, F, Cl, Br, I, OH, SH, R$_8$—OH, R$_8$—SH, —R$_8$—O—R$_{10}$ (e.g., CH$_2$—O—CH$_3$, (CH$_2$)$_2$O—CH$_3$ (CH$_2$)$_3$O—CH$_3$, (CH$_2$)$_2$O—CH(CH$_3$)$_2$), R$_8$—S—R$_{10}$ (e.g., (CH$_2$)$_3$—S—(CH$_2$)$_2$CH$_3$), R$_8$—NHC(O)—R$_{10}$, —O—R$_8$—R$_{10}$, R$_8$-(substituted or unsubstituted C$_3$-C$_8$ cycloalkyl) (e.g., CH$_2$-cyclopropyl, CH$_2$-cyclobutanol, CH$_2$-difluorocyclopropyl, CH$_2$-methylcyclopropyl, CH$_2$-dimethylamino-cyclohexyl, (CH$_2$)$_2$-cyclopentanole, CH$_2$-cyclohexanol), R$_8$-(substituted or unsubstituted, saturated, unsaturated or aromatic, single, fused or spiro 3-10 membered heterocyclic ring) (e.g., (CH$_2$)$_3$-pyran, (CH$_2$)$_2$-pyrrazole, (CH$_2$)$_2$-imidazole, CH$_2$-tetrahydrofurane, CH$_2$-dioxane, CH$_2$-oxetane, CH$_2$-piperidine, CH$_2$-triazole, CH$_2$-1-oxa-8-azaspiro[4.5]decane, (CH$_2$)$_3$-diazabicyclo[2.2.1]heptane, CH$_2$-methyl-THF, CH$_2$-ethyl-piperidine, CH$_2$-oxa-azaspirodecane, (CH$_2$)$_3$-dimethylpyrazole, CH$_2$-2-oxo-methylpyrrolidine, CH$_2$-methyl-azetidine, CH$_2$-azaspiroheptane), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$) (e.g., (CH$_2$)$_3$-4-fluoro-piperidine, (CH$_2$)$_3$—N(CH$_2$CH$_3$)$_2$, (CH$_2$)$_3$—N(CH(CH$_3$)$_2$)$_2$, (CH$_2$)$_3$-piperidine, (CH$_2$)$_4$—NH(CH$_3$), (CH$_2$)$_3$—NH—CH$_3$, (CH$_2$)$_3$—NH—CH$_2$CH$_3$, (CH$_2$)$_3$—N(CH$_2$CH$_3$)$_2$, (CH$_2$)$_3$—NH$_2$, (CH$_2$)$_3$—N(CH$_2$CH$_3$)(CH$_2$CF$_3$)), R$_8$—C(O)N(R$_{10}$)(R$_{11}$) (e.g., (CH$_2$)$_2$—C(O)- piperidine), R$_9$—R$_8$—N(R$_{10}$)(R$_{11}$) (e.g., (CH$_2$)$_2$—C(O)-piperidine), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl (e.g., CH(CH$_3$)CH$_2$OCH$_3$, CH(CH$_3$)CH$_2$NH$_2$, CH(CH$_3$)C(O)N(CH$_3$)$_2$, CH$_2$—CH(OH)Ph, (CH$_2$)$_3$N(H)CH$_2$CH$_3$, CH(CH$_3$)(CH$_2$)$_2$OH, CH(CH$_2$OH)(CH$_2$CH$_3$), (CH$_2$)$_3$—OCH$_3$, (CH$_2$)$_2$—OCH$_3$, (CH$_2$)$_2$—OCH(CH$_3$)$_2$, CH(CH$_2$OH)(CH$_2$CH(CH$_3$)$_2$), CH$_2$CH(CH$_3$)(OCH$_3$), CH$_2$CH(N(CH$_3$)$_2$)(CH$_2$CH$_3$), benzyl, methyl, ethyl, CH$_2$—OCH$_2$—CH$_2$—O—CH$_3$, CH(CH$_3$)C(O)N(CH$_3$)$_2$), C$_1$-C$_5$ linear or branched, substituted or unsubstituted alkenyl, C$_1$-C$_5$ linear or branched, or C$_3$-C$_8$ cyclic haloalkyl, substituted or unsubstituted C$_1$-C$_5$ linear or branched, or C$_3$-C$_8$ cyclic alkoxy (e.g. methoxy, O—(CH$_2$)$_2$O—CH$_3$), optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclobutyl, cyclohexyl, methoxycyclopropyl, methylcyclobutyl, aminomethyl-cyclobutyl, methoxycyclobutyl, 2,3-dihydro-1H-indenol), R$_8$-(substituted or unsubstituted C$_3$-C$_5$ cycloalkyl), substituted or unsubstituted 3-8 membered heterocyclic ring (e.g., piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane), substituted or unsubstituted aryl, substituted or unsubstituted R$_8$-aryl (e.g., benzyl), substituted or unsubstituted benzyl;

or R$_6$ and R$_5$ are joined to form a substituted or unsubstituted 5-8 membered heterocyclic ring (e.g., azepane, piperazine, 2-(piperazin-1-yl)acetamide);

or R$_6$ is represented by the structure of formula B or Bi:

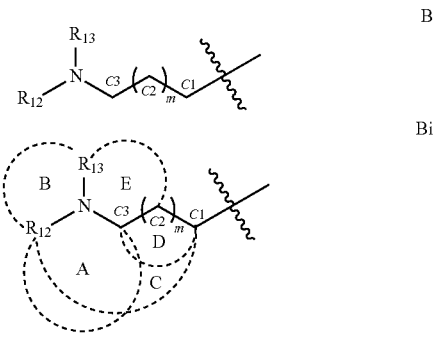

wherein m is 0 or 1; and

R$_{12}$ is R$_{20}$ or C$_1$-C$_5$ C(O)-alkyl, and R$_{13}$ is R$_{30}$; or R$_{12}$ and R$_{13}$ are both H;

R$_{12}$ and R$_{13}$ are each independently H or substituted or unsubstituted C$_1$-C$_5$ alkyl (e.g., ethyl, trifluoroethyl);

R$_{12}$ and C3 are joined to form ring A and R$_{13}$ is R$_{30}$; or

R$_{12}$ and R$_{13}$ are joined to form ring B; or

R$_{12}$ and C1 are joined to form ring C and R$_{13}$ is R$_{30}$; or

C1 and C3 are joined to form ring D and R$_{12}$ and R$_{13}$ are each independently R$_{30}$; or R$_{13}$ and C2 are joined to form ring E, m is 1, and R$_{12}$ is R$_{30}$; or R$_{12}$ and R$_{13}$ are joined to form ring B and C1 and C3 are joined to form ring D;

wherein

Ring A, C and E are each independently a substituted or unsubstituted single spiro or fused 3-8 membered heterocyclic ring (e.g., A: pyrrolidine, methylpyrrolidine, ethylpyrrolidine); C: piperidine, pyrrolidine, methyl-2-oxopyrrolidine, pyran-pyrrolidine, methyl-azetidine, azabicyclooctane, 2-azabicyclo[2.1.1]hexane, 2-azaspiro[3.3]heptane; E: pyrrolidine, azetidine, ethylpyrrolidine, oxopyrrolidine, methylpiperidine);

Ring B is a substituted or unsubstituted single, spiro or fused 3-8 membered heterocyclic ring (B: piperidine, piperidin-2-one, 4-fluoropiperidin-2-one, piperidine-4-carbonitrile, 4-fluoropiperidine, 4-fluoro-2-methylpiperidine, methylpiperidin, fluoropiperidine, difluoropiperidine, pyrrolidine, piperazine, methylpyrrolidine, thiomorpholine 1,1-dioxide, 2-oxa-6-azaspiro[3.3]heptane, methyl-piperazine, dimethylpyrazole, imidazole, 2-methyl-2,5-diazabicyclo[2.2.1]heptane, hydroxymethyl-pyrrolidine, diazabicyclo[2.2.1]heptane, 6-fluoro-3-azabicyclo[3.1.1]heptane; and Ring D is a substituted or unsubstituted $C_3$-$C_8$ cycloalkyl (e.g., cyclobutane, cyclohexane);

$R_7$ is H, F, Cl, Br, I, OH, O—$R_{20}$, SH, $R_8$—OH, $R_8$—SH, $SR_{10}$, —$R_8$—O—$R_{10}$, —$R_8$—S—$R_{10}$, $R_8$—($C_3$-$C_8$ cycloalkyl), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$(COO—$CH_3$), $R_8$—C(O)—$R_{10}$, C(O)H, C(O)—$R_{10}$, $C_1$-$C_5$ linear or branched C(O)-haloalkyl, —$C(O)NH_2$, C(O)NHR (e.g., C(O)NH($CH_3$)), $C(O)N(R_{10})(R_{11})$ (e.g., C(O)NH($CH_3$), C(O)NH($CH_2CH_3$), C(O)NH($CH_2CH_2OCH_3$), C(O)NH($CH_2CH_2OH$)), $SO_2R$, $SO_2N(R_{10})(R_{11})$, $CH(CF_3)(NH$—$R_{10})$, $C_1$-$C_5$ linear or branched, substituted or unsubstituted alkyl (e.g., methylimidazole, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy, ethoxy), optionally wherein at least one methylene group ($CH_2$) in the alkoxy is replaced with an oxygen atom, $C_1$-$C_5$ linear or branched thioalkyl, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopropanol, cyclohexyl, bicyclo[1.1.1]pentane), substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine, 4,7-diazaspiro[2.5]octane, 2,5-diazabicyclo[2.2.1]heptane, piperazine-2-one), $R_8$-(substituted or unsubstituted single, fused or spiro 3-8 membered heterocyclic ring), substituted or unsubstituted aryl, substituted or unsubstituted benzyl;

or $R_7$ is represented by the structure of formula A:

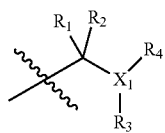

A wherein $X_1$ is N or O;

$R_1$ and $R_2$ are each independently H, F, Cl, Br, I, OH, SH, or $CF_3$, substituted or unsubstituted $C_1$-$C_5$ alkyl (e.g., $CH_2OH$), $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy;

or $R_1$ and $R_2$ are joined to form =O or a $C_3$-$C_8$ carbocyclic or heterocyclic ring (e.g., cyclopropyl);

$R_3$ and $R_4$ are each independently H, Me, substituted or unsubstituted $C_1$-$C_5$ alkyl (e.g., methoxyethylene, methylaminoethylene, aminoethylene), —$R_8$—O—$R_{10}$ (e.g., ($CH_2$)$_2$O—$CH_3$), $R_8$—N($R_{10}$)($R_{11}$) (e.g., ($CH_2$)$_2$—NH($CH_3$)), substituted or unsubstituted $C_3$-$C_8$ cycloalkyl (e.g., cyclopropyl), substituted or unsubstituted 5-7 membered heterocyclic ring (e.g., pyrrolidine, methylpyrrolidine, piperidine), or $R_{20}$;

or $R_3$ and $R_4$ are joined to form a 3-8 membered heterocyclic ring (e.g., pyrrolidine, pyrrolidone, 2-oxopyrrolidine, piperidine, morpholine, piperazine, imidazole);

or $R_2$ and $R_4$ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);

wherein if $X_1$ is O then $R_4$ is absent;

$R_7'$ is H, F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl (e.g., isopropyl, methyl, ethyl), $C_1$-$C_5$ linear or branched, substituted or unsubstituted alkenyl, $C_1$-$C_5$ linear or branched, or $C_3$-$C_8$ cyclic haloalkyl (e.g., $CHF_2$), $C_1$-$C_5$ linear or branched, or $C_3$-$C_8$ cyclic alkoxy (e.g. methoxy), optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclohexyl), substituted or unsubstituted 3-8 membered heterocyclic ring (e.g., morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine), substituted or unsubstituted aryl, substituted or unsubstituted benzyl;

or $R_7$ and $R_7'$ are joined to form a 3-8 membered substituted or unsubstituted, saturated, unsaturated or aromatic, carbocyclic or heterocyclic ring (e.g., cyclopentyl, cyclohexyl, piperidine, tetrahydrofuran, tetrahydropyran, pyrrolidine);

$R_{20}$ is represented by the following structure:

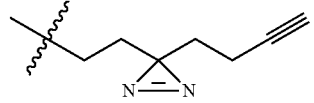 [SMILES: *CCC1(CCC#C)N=N1]

$R_{30}$ is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl (e.g., methyl, ethyl, $CH_2$—$CH_2$—O—$CH_2$—$CH_2$—O—$CH_3$, $CH_2$—O—$CH_2$—$CH_2$—O—$CH_3$), $C_1$-$C_5$ linear or branched alkoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2O$—$CH_3$), —$R_8$—O—$R_{10}$, —$R_8$—$R_{10}$ (e.g., $(CH_2)_2$—O—$CH_3$), substituted or unsubstituted aryl (e.g., phenyl), substituted or unsubstituted heteroaryl (e.g., pyridine (2, 3, and 4-pyridine);

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl (e.g., methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$), $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl (e.g., $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), —$R_8$—O—$R_8$—O—$R_{10}$ (e.g. $(CH_2)_2$—O—$(CH_2)_2$—O—$CH_3$), —$R_8$—O—$R_{10}$, —$R_8$—$R_{10}$ (e.g., $(CH_2)_2O$—$CH_3$), substituted or unsubstituted aryl (e.g., phenyl), substituted or unsubstituted heteroaryl (e.g., pyridine (2, 3, and 4-pyridine);

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl (e.g., methyl, ethyl, $CH_2$-cyclopropyl, $CH_2$—$CH_2$—O—$CH_3$), $C_1$-$C_5$ substituted or unsubstituted linear or branched haloalky (e.g., $CH_2CF_3$), $C_1$-$C_5$ linear or branched alkoxy (e.g., O—$CH_3$), $R_{20}$, C(O)R, or $S(O)_2R$;

or $R_{10}$ and $R_{11}$ are joined to form a substituted or unsubstituted 3-8 membered heterocyclic ring (e.g., piperazine, piperidine), n is an integer between 0 and 4 (e.g., 1, 2);

or its pharmaceutically acceptable salt, stereoisomer, tautomer, hydrate, N-oxide, reverse amide analog, prodrug, isotopic variant (e.g., deuterated analog), PROTAC, pharmaceutical product or any combination thereof.

In some embodiments, $X_2$ of formula I, II and/or I(a)-I(o) is a nitrogen atom. In other embodiments, $X_2$ is a CH.

In some embodiments, $X_3$ of formula I, II and/or I(a)-I(o) is a nitrogen atom. In other embodiments, $X_3$ is a CH.

In some embodiments, $X_4$ of formula I, II and/or I(a)-I(o) is a nitrogen atom. In other embodiments, $X_4$ is a CH.

In some embodiments, $X_5$ of formula I, II, I(a)-I(i), I(m) and/or I(o) is a nitrogen atom. In other embodiments, $X_5$ is a carbon atom.

In some embodiments, $X_6$ of formula I, II, I(a)-I(i), I(m) and/or I(o) is a nitrogen atom. In other embodiments, $X_6$ is a carbon atom.

In some embodiments, $X_7$ of formula I, II and/or I(a)-I(e) is a nitrogen atom. In other embodiments, $X_7$ is a carbon atom.

In some embodiments, $X_8$ of formula I, II, I(a)-I(i), I(m) and/or I(o) is a nitrogen atom. In other embodiments, $X_8$ is a carbon atom.

In some embodiments, $X_9$ of formula I, II, I(a)-I(i), I(m) and/or I(o) is a nitrogen atom. In other embodiments, $X_9$ is a carbon atom.

In some embodiments, $X_{10}$ of formula I, II and/or I(a)-I(o) is a nitrogen atom. In other embodiments, $X_{10}$ is N. In other embodiments, $X_{10}$ is CH. In other embodiments, $X_{10}$ is C(R), wherein R is as defined below. In other embodiments, $X_{10}$ is C(R), wherein R is an alkyl. In other embodiments, $X_{10}$ is C(R), wherein R is a methyl. In other embodiments, $X_{10}$ is C(R), wherein R is a cycloalkyl. In other embodiments, $X_{10}$ is C(R), wherein R is a cyclopropyl. In other embodiments, $X_{10}$ is C(R), wherein R is a COOH. In other embodiments, $X_{10}$ is C(R), wherein R is $N(H)R_{10}$; and $R_{10}$ is a substituted alkyl. In other embodiments, $X_{10}$ is C(N(H)($CH_2$-cyclopropyl)). In other embodiments, $X_{10}$ is C(R), wherein R is a substituted alkyl. In other embodiments, $X_{10}$ is C(R), wherein R is $CH_2$—OH. In other embodiments, $X_{10}$ is C(R), wherein R is $CH_2$—$CH_2$—OH. In other embodiments, $X_{10}$ is C(R), wherein R is an alkoxy. In other embodiments, $X_{10}$ is C(R), wherein R is a isopropoxy.

In some embodiments, at least one of $X_2$, $X_3$, $X_4$, $X_5$, $X_6$, $X_7$, $X_8$ and $X_9$ of formula I, II, I(a)-I(e) is a nitrogen atom. In some embodiments, at least one of $X_2$, $X_3$, $X_4$, $X_5$, $X_6$, $X_8$ and $X_9$ of formula I, II, I(a)-I(e), I(g)-I(i), I(m) and/or I(o) is a nitrogen atom. In some embodiments, at least one of $X_2$, $X_3$, $X_4$, $X_5$, $X_6$, $X_7$, $X_8$ and $X_9$ of formula I(d) is a nitrogen atom. In some embodiments, at least one of $X_2$, $X_3$, $X_4$, $X_5$, $X_6$, $X_7$, $X_8$, $X_9$ and $X_{10}$ of formula I(d) is a nitrogen atom.

In some embodiments, at least one of $X_2$, $X_3$, $X_4$, and $X_{10}$ of formula I, II and/or I(a)-I(o) is a nitrogen atom. In some embodiments, at least one of $X_2$, $X_3$, $X_4$ and $X_{10}$ of formula I(d) is a nitrogen atom. In some embodiments, at least one of $X_5$, $X_6$, $X_8$ and $X_9$ of formula I, II and/or I(a)-I(o) is a nitrogen atom.

In some embodiments, $R_5$ of formula I, II, I(a)-I(d), I(f)-I(i), I(l), I(n) and/or I(o) is H. In other embodiments, $R_5$ is $C_1$-$C_5$ linear or branched alkyl. In other embodiments, $R_5$ is methyl. In other embodiments, $R_5$ is methyl, ethyl, propyl, isopropyl, butyl, t-butyl, iso-butyl, pentyl, neopentyl; each represents a separate embodiment according to this invention.

In some embodiments, $R_5$ and $R_6$ of formula I, II, I(a)-I(i) and/or I(l) are joined to form a substituted or unsubstituted 5-8 membered heterocyclic ring. In some embodiments, $R_5$ and $R_6$ are joined to form a substituted 5-8 membered heterocyclic ring. In some embodiments, $R_5$ and $R_6$ are joined to form an unsubstituted 5-8 membered heterocyclic ring. In some embodiments, the heterocyclic ring is azepane, piperazine or 2-(piperazin-1-yl)acetamide; each represents a separate embodiment according to this invention. In some embodiments, the heterocyclic ring is substituted with at least one substitution selected from: F, Cl, Br, I, $CF_3$, $R_{20}$, $C_1$-$C_5$ linear or branched alkyl, $C_1$-$C_5$ linear or branched haloalkyl, OH, alkoxy, $R_8$—OH (e.g., $CH_2$—OH), OMe, amide, $C(O)N(R)_2$, $C(O)N(R_{10})(R_{11})$, $R_8$—$C(O)N(R_{10})(R_{11})$, C(O)-pyrrolidine, C(O)-piperidine, $N(R)_2$, $NH(R_{10})$, $N(R_{10})(R_{11})$, $N(CH_3)_2$, $NH_2$, $CF_3$, aryl, phenyl, heteroaryl, substituted or unsubstituted $C_3$-$C_8$ cycloalkyl, cyclobutanol, substituted or unsubstituted 3-8 membered heterocyclic ring, which may be saturated, unsaturated, aromatice, single fused or spiral, pyran, oxetane, piperidine, pyrazole, methyl-pyrrazole, triazole, imidazole, halophenyl, (benzyloxy)phenyl, CN, and $NO_2$; each is a separate embodiment according to this invention. In some embodiments, the heterocyclic ring of formula I(e) is not substituted with $CO_2$—R.

In some embodiments, $R_6$ of formula I, II, I(a)-I(d), I(f)-I(i), I(l), I(n), and/or I(o) is H. In other embodiments, $R_6$ is H, F, Cl, Br, I, OH, SH, $R_8$—OH, $R_8$—SH, —$R_8$—O—$R_{10}$, $CH_2$—O—$CH_3$, $(CH_2)_2O$—$CH_3$, $(CH_2)_3O$—$CH_3$, $(CH_2)_2O$—$CH(CH_3)_2$, $R_8$—S—$R_{10}$, $(CH_2)_2$—S—$(CH_2)_2CH_3$, $R_8$—NHC(O)—$R_{10}$, —O—$R_8$—$R_{10}$, $R_8$-(substituted or unsubstituted $C_3$-$C_8$ cycloalkyl), $CH_2$-cyclopropyl, $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, $CH_2$-cyclohexanol), $R_8$-(substituted or unsubstituted, saturated, unsaturated or aromatic, single, fused or spiro 3-10 membered heterocyclic ring), $(CH_2)_3$-pyran, $(CH_2)_2$-pyrrazole, $(CH_2)_2$-imidazole, $CH_2$-tetrahydrofurane, $CH_2$-dioxane, $CH_2$-oxetane, $CH_2$-piperidine, $CH_2$-triazole, $CH_2$-1-oxa-8-azaspiro[4.5]decane, $(CH_2)_3$-diazabicyclo[2.2.1]heptane, $CH_2$-methyl-THF, $CH_2$-ethyl-piperidine, $CH_2$-oxa-azaspirodecane, $(CH_2)_3$-dimethylpyrazole, $CH_2$-2-oxo-methylpyrrolidine, $CH_2$-methyl-azetidine, $CH_2$-azaspiroheptane, $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $(CH_2)_3$—$N(CH_2CH_3)_2$, $(CH_2)_3$—$N(CH(CH_3)_2)_2$, $(CH_2)_3$-piperidine, $(CH_2)_3$-4-fluoro-piperidine, $(CH_2)_3$-piperidine-2-one, $(CH_2)_3$-4-cyano-piperidine, $(CH_2)_3$-4-trifluoromethyl-piperidine, $(CH_2)_4$—$NH(CH_3)$, $(CH_2)_3$—NH—$CH_3$, $(CH_2)_3$—NH—$CH_2CH_3$, $(CH_2)_3$—$N(CH_2CH_3)_2$, $(CH_2)_3$—$NH_2$, $(CH_2)_3$—$N(CH_2CH_3)(CH_2CF_3)$, $R_8$—$C(O)N(R_{10})(R_{11})$, $(CH_2)_2$—C(O)-piperidine, $R_9$—$R_8$—$N(R_{10})(R_1)$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —C(O)$NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl, $CH(CH_3)CH_2OCH_3$, $CH(CH_3)CH_2NH_2$, $CH(CH_3)C(O)N(CH_3)_2$, $CH_2$—CH(OH)Ph, $(CH_2)_3N(H)CH_2CH_3$, $CH(CH_3)(CH_2)_2OH$, $CH(CH_2OH)(CH_2CH_3)$, $(CH_2)_3$—$OCH_3$, $(CH_2)_2$—$OCH_3$, $(CH_2)_2$—$OCH(CH_3)_2$, $CH(CH_2OH)(CH_2CH(CH_3)_2)$, $CH_2CH(CH_3)(OCH_3)$, $CH_2CH(N(CH_3)_2)(CH_2CH_3)$, benzyl, methyl, ethyl, propyl, iso-propyl, butyl, isobutyl, tert-butyl, pentyl, isopentyl, neopentyl, hexyl, $CH_2$—$OCH_2$—$CH_2$—O—$CH_3$, $CH(CH_3)C(O)N(CH_3)_2$, $C_1$-$C_5$ linear or branched, substituted or unsubstituted alkenyl, $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy methoxy, optionally wherein at least one methylene group ($CH_2$) in the alkoxy is replaced with an oxygen atom, O—$(CH_2)_2O$—$CH_3$, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, cyclopropyl, cyclobutyl, cyclohexyl, 4,4-difluorocyclohexane, methoxycyclopropyl, methylcyclobutyl, cyclopropyl, aminomethylcyclobutyl, methoxycyclobutyl, 2,3-dihydro-1H-indenol, $R_8$-(substituted or unsubstituted $C_3$-$C_8$ cycloalkyl), substituted or unsubstituted saturated or unsaturated, single fused, bridged or spiro 3-10 membered carbocyclic or heterocyclic ring, piperidine (2, 3, or 4-piperidine), 1-methylpiperidine (e.g., 1-methyl-3-piperidine, 1-methyl-4-piperidine), 3-fluoro-1-methylpiperidine, 1-(2,2,2-trifluoroethyl)piperidine, azetidine, 1-methyl-azetidine (e.g., 1-methyl-3-azetidine), morpholine, pyrrolidine, pyrrolidinone, quinuclidine, tetrahydropyran (e.g., 4 or 3-tetrahydropyrane), tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane, 4,4-difluorocyclohexane, substituted or unsubstituted aryl, substituted or unsubstituted $R_8$-aryl (e.g., benzyl), or substituted or unsubstituted benzyl; each represents a separate embodiment according to this invention. In some embodiments, $R_6$ may be further substituted with at least one substitution selected from: F, Cl, Br, I, $C_1$-$C_5$ linear or branched alkyl, OH, alkoxy, OMe, amide, $C(O)N(R)_2$, C(O)-alkyl, C(O)-pyrrolidine, C(O)-piperidine, $N(R)_2$, $NH(R_{10})$, $N(R_{10})(R_{11})$, $N(CH_3)_2$, $NH_2$, $CF_3$, aryl, phenyl, heteroaryl, substituted or unsubstituted $C_3$-$C_8$ cycloalkyl, cyclobutanol, substituted or unsubstituted 3-8 membered heterocyclic ring pyran, oxetane, piperidine, pyrazole, methyl-pyrrazole, triazole, imidazole, $C_1$-$C_5$ linear or branched haloalkyl (e.g., $CH_2CF_3$, $CHF_2$), halophenyl, (benzyloxy)phenyl, CN, and $NO_2$; each represents a separate embodiment according to this invention. In some embodiments, $R_6$ is H. In some embodiments, $R_6$ is —$R_8$—O—$R_{10}$. In some embodiments, $R_6$ is $CH_2$—O—$CH_3$. In some embodiments, $R_6$ is $R_8$—S—$R_{10}$. In some embodiments, $R_6$ is $(CH_2)_3$—S—$(CH_2)_2CH_3$. In some embodiments, $R_6$ is $R_8$—NHC(O)—$R_{10}$. In some embodiments, $R_6$ is $(CH_2)_3$—NHC(O)—$R_{10}$. In some embodiments, $R_6$ is $(CH_2)$—NHC(O)—$R_{10}$. In some embodiments, $R_6$ is $R_8$-(substituted or unsubstituted $C_3$-$C_8$ cycloalkyl). Examples of $R_8$-(substituted or unsubstituted $C_3$-$C_8$ cycloalkyl) include but not limited to: $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, and $CH_2$-cyclohexanol; each represents a separate embodiment according to this invention. In some embodiments, $R_6$ is $R_8$-(substituted or unsubstituted saturated, unsaturated or aromatic, single, fused or spiro 3-8 membered heterocyclic ring). In some embodiments, $R_6$ is $R_8$-(substituted or unsubstituted saturated, single 3-8 membered heterocyclic ring). In some embodiments, $R_6$ is $R_8$-(substituted or unsubstituted unsaturated, single 3-8 membered heterocyclic ring). In some embodiments, $R_6$ is $(CH_2)_3$-4-fluoro-piperidine. In some embodiments, $R_6$ is $R_8$-(substituted or unsubstituted aromatic, single 3-8 membered heterocyclic ring). In some embodiments, $R_6$ is $R_8$-(substituted or unsubstituted saturated, fused 3-8 membered heterocyclic ring). In some embodiments, $R_6$ is $R_8$-(substituted or unsubstituted unsaturated, fused 3-8 membered heterocyclic ring). In some embodiments, $R_6$ is $R_8$-(substituted or unsubstituted aromatic, fused 3-8 membered heterocyclic ring). In some embodiments, $R_6$ is $R_8$-(substituted or unsubstituted spiro 3-8 membered heterocyclic ring). Examples of $R_8$-(substituted or unsubstituted saturated, unsaturated or aromatic, single, fused or spiro 3-8 membered heterocyclic ring) include but not limited to: $(CH_2)_3$-4-fluoro-piperidine, $(CH_2)_3$-pyran, $(CH_2)_2$-pyrrazole, $(CH_2)_2$-imidazole, $CH_2$-tetrahydrofurane, $CH_2$-dioxane, $CH_2$-oxetane, $CH_2$-piperidine, $CH_2$-triazole, $CH_2$-1-oxa-8-azaspiro[4.5]decane, $(CH_2)_3$-diazabicyclo[2.2.1]heptane, $CH_2$-methyl-THF, $CH_2$-ethyl-piperidine, $CH_2$-oxa-azaspirodecane, $(CH_2)_3$-dimethylpyrazole, $CH_2$-2-oxo-methylpyrrolidine, $CH_2$-methyl-azetidine, and $CH_2$-azaspiroheptane. In some embodiments, $R_6$ is $NH_2$. In some embodiments, $R_6$ is NHR. In some embodiments, $R_6$ is $N(R)_2$. In some embodiments, $R_6$ is $NH(R_{10})$. In some embodiments, $R_6$ is $N(R_{10})(R_{11})$. In some embodiments, $R_6$ is $R_8$—$N(R_{10})(R_{11})$. In some embodiments, $R_8$—$N(R_{10})(R_{11})$ includes but not limited to: $(CH_2)_3$—$N(CH_2CH_3)_2$, $(CH_2)_3$—$N(CH(CH_3)_2)_2$, $(CH_2)_3$-piperidine, $(CH_2)_4$—$NH(CH_3)$, $(CH_2)_3$—NH—$CH_3$, $(CH_2)_3$—NH—$CH_2CH_3$, $(CH_2)_3$—$N(CH_2CH_3)_2$, $(CH_2)_3$—$NH_2$, and $(CH_2)_3$—$N(CH_2CH_3)(CH_2CF_3)$. In some embodiments, $R_6$ is $R_8$—$C(O)N(R_{10})(R_{11})$ such as $(CH_2)_2$—C(O)-piperidine. In some embodiments, $R_6$ is $C_1$-$C_5$ linear or branched, substituted or unsubstituted alkyl.

Examples of $C_1$-$C_5$ linear or branched, substituted or unsubstituted alkyl include but not limited to: $CH(CH_3)$ $CH_2OCH_3$, $CH_2OCH_3$, $CH(CH_3)CH_2NH_2$, $CH(CH_3)C(O)N(CH_3)_2$, $CH_2$—$CH(OH)Ph$, $(CH_2)_3N(H)CH_2CH_3$, $CH(CH_3)$ $(CH_2)_2OH$, $CH(CH_2OH)(CH_2CH_3)$, $(CH_2)_3$—$OCH_3$, $(CH_2)_2$—$OCH_3$, $(CH_2)_2$—$OCH(CH_3)_2$, $CH(CH_2OH)$ $(CH_2CH(CH_3)_2)$, $CH_2CH(CH_3)(OCH_3)$, $CH_2CH(N(CH_3)_2)$ $(CH_2CH_3)$, $CH(CH_3)C(O)N(CH_3)_2$, benzyl, methyl, ethyl, and $CH_2$—$OCH_2$—$CH_2$—$O$—$CH_3$. In some embodiments, $R_6$ is substituted or unsubstituted $C_3$-$C_8$ cycloalkyl. In some embodiments, substituted or unsubstituted $C_3$-$C_8$ cycloalkyl include: cyclopropyl, cyclobutyl, cyclohexyl, methoxycyclopropyl, methylcyclobutyl, aminomethyl-cyclobutyl, methoxycyclobutyl and 2,3-dihydro-1H-indeno. In some embodiments, $R_6$ is $R_8$-(substituted or unsubstituted $C_3$-$C_8$ cycloalkyl). In some embodiments, $R_6$ is substituted or unsubstituted saturated or unsaturated, single fused, bridged or spiro 3-10 membered carbocyclic or heterocyclic ring. In some embodiments, the ring may be further substituted with at least one substitution selected from: F, Cl, Br, I, $C_1$-$C_5$ linear or branched alkyl, OH, alkoxy, OMe, amide, $C(O)N$ $(R)_2$, $C(O)$-alkyl, $C(O)$-pyrrolidine, $C(O)$-piperidine, $N(R)_2$, $NH(R_{10})$, $N(R_{10})(R_{11})$, $N(CH_3)_2$, $NH_2$, $CF_3$, aryl, phenyl, heteroaryl, substituted or unsubstituted $C_3$-$C_8$ cycloalkyl, cyclobutanol, substituted or unsubstituted 3-8 membered heterocyclic ring pyran, oxetane, piperidine, pyrazole, methyl-pyrrazole, triazole, imidazole, $C_1$-$C_5$ linear or branched haloalkyl (e.g., $CH_2CF_3$, $CHF_2$), halophenyl, (benzyloxy)phenyl, CN, and $NO_2$; each represents a separate embodiment according to this invention.

In some embodiments, $R_6$ is substituted or unsubstituted saturated or unsaturated, single fused, bridged or spiro 3-10 membered heterocyclic ring. In some embodiments, $R_6$ is substituted or unsubstituted saturated, unsaturated or aromatic, single, fused or spiro 3-10 membered heterocyclic ring. In some embodiments, $R_6$ is substituted or unsubstituted saturated, unsaturated or aromatic, single 3-10 membered heterocyclic ring. In some embodiments, $R_6$ is substituted or unsubstituted saturated single 3-10 membered heterocyclic ring. In some embodiments, the ring is piperidine, 1-methylpiperidine, 3-fluoro-1-methylpiperidine, 1-(2,2,2-trifluoroethyl)piperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane; each represents a separate embodiment according to this invention. In some embodiments, $R_6$ is substituted or unsubstituted saturated or unsaturated, single fused, bridged or spiro 3-10 membered carbocyclic ring. In some embodiments, $R_6$ is 4,4-difluorocyclohexane. In some embodiments, $R_6$ is substituted or unsubstituted $R_8$-aryl, such as benzyl. In some embodiments, $R_6$ may be further substituted by at least one substitution selected from: F, Cl, Br, I, $CF_3$, $R_{20}$, $C_1$-$C_5$ linear or branched alkyl, $C_1$-$C_5$ linear or branched haloalkyl, OH, alkoxy, $R_8$—OH (e.g., $CH_2$—OH), OMe, amide, $C(O)N(R)_2$, $C(O)N(R_{10})(R_{11})$, $R_8$—$C(O)N(R_{10})(R_{11})$, $C(O)$-pyrrolidine, $C(O)$-piperidine, $N(R)_2$, $NH(R_{10})$, $N(R_{10})$ $(R_{11})$, $N(CH_3)_2$, $NH_2$, $CF_3$, aryl, phenyl, heteroaryl, substituted or unsubstituted $C_3$-$C_8$ cycloalkyl, cyclobutanol, substituted or unsubstituted 3-8 membered heterocyclic ring, which may be saturated, unsaturated, aromatice, single fused or spiral, pyran, oxetane, piperidine, pyrazole, methyl-pyrrazole, triazole, imidazole, $C_1$-$C_5$ linear or branched haloalkyl (e.g., $CH_2CF_3$, $CHF_2$), halophenyl, (benzyloxy)phenyl, CN, and $NO_2$; each is a separate embodiment according to this invention.

In some embodiments, $R_6$ of formula I(n) and/or I(o) is H. In some embodiments, $R_6$ is $CD_3$. In some embodiments, $R_6$ is $C_1$-$C_5$ linear or branched alkyl. In some embodiments, $R_6$ is methyl. In some embodiments, $R_6$ is ethyl. In some embodiments, $R_6$ is iso-propyl. In some embodiments, $R_6$ is substituted or unsubstituted, saturated or unsaturated, single fused, bridged or spiro 3-10 membered heterocyclic ring. In some embodiments, $R_6$ is unsubstituted single 3-8 membered heterocyclic ring. In some embodiments, $R_6$ is piperidine. In some embodiments, $R_6$ is 4-piperidine. In some embodiments, $R_6$ is azetidine. In some embodiments, $R_6$ is morpholine. In some embodiments, $R_6$ is tetrahydropyran. In some embodiments, $R_6$ is tetrahydrofurane. In some embodiments, $R_6$ is dioxane. In some embodiments, $R_6$ is 1,3-dioxane. In some embodiments, $R_6$ is pyrrolidine. In some embodiments, $R_6$ is substituted single 3-8 membered heterocyclic ring. In some embodiments, $R_6$ is 1-methylpiperidine. In some embodiments, $R_6$ is 3-fluoro-1-methylpiperidine. In some embodiments, $R_6$ is 1-methyl-azetidine. In some embodiments, $R_6$ is trifluoromethyl-oxetane. In some embodiments, $R_6$ is hydroxy-tetrahydrofurane. In some embodiments, $R_6$ is 1-(2,2,2-trifluoroethyl)piperidine. In some embodiments, $R_6$ is substituted or unsubstituted, unsaturated, single 3-8 membered heterocyclic ring. In some embodiments, $R_6$ is pyrrolidinone. In some embodiments, $R_6$ is imidazole. In some embodiments, $R_6$ is azepan-2-one. In some embodiments, $R_6$ is substituted or unsubstituted, saturated bridged 3-10 membered heterocyclic ring. In some embodiments, $R_6$ is quinuclidine. In some embodiments, $R_6$ is 8-methyl-8-azabicyclo[3.2.1]octane. In some embodiments, $R_6$ is azabicyclohexane. In some embodiments, $R_6$ is substituted or unsubstituted, saturated spiro 3-10 membered heterocyclic ring. In some embodiments, $R_6$ is azaspiro[3.3]heptane. In some embodiments, $R_6$ is substituted or unsubstituted $C_3$-$C_8$ cycloalkyl. In some embodiments, $R_6$ is cyclopropyl In some embodiments, $R_6$ is 4,4-difluorocyclohexane.

In some embodiments, $R_6$ and $R_5$ of formula I, II, I(a)-I(i), I(l), I(n) and/or I(o) are joined to form a substituted or unsubstituted saturated, unsaturated or aromatic, single, fused or spiro 5-8 membered heterocyclic ring. In some embodiments, the substituted or unsubstituted saturated, unsaturated or aromatic, single, fused or spiro 5-8 membered heterocyclic ring is azepane, piperazine, or 2-(piperazin-1-yl)acetamide; each represents a separate embodiment according to this invention. In some embodiments, the ring may be further substituted by at least one substitution selected from: F, Cl, Br, I, $C_1$-$C_5$ linear or branched alkyl, OH, alkoxy (e.g., OMe), amide (e.g., $C(O)N(R)_2$, $C(O)$-pyrrolidine, $C(O)$-piperidine, $N(R)_2$ $NH(R_{10})$, $N(R_{10})(R_{11})$, (e.g., $N(CH_3)_2$, $NH_2$), $CF_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), $C_1$-$C_5$ linear or branched haloalkyl (e.g., $CH_2CF_3$, $CHF_2$), halophenyl, (benzyloxy)phenyl, CN and $NO_2$; each represents a separate embodiment according to this invention.

In some embodiments, $R_6$ of formula I, II and/or I(a)-I(i) is represented by the structure of formula B:

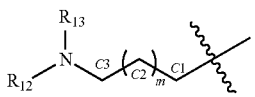

wherein
m is 0 or 1; and
R$_{12}$ is R$_{20}$ or C$_1$-C$_5$ C(O)-alkyl, and R$_{13}$ is R$_{30}$; or
R$_{12}$ and R$_{13}$ are both H; or
R$_{12}$ and R$_{13}$ are each independently H or substituted or unsubstituted C$_1$-C$_5$ alkyl (e.g., ethyl, trifluoroethyl); or
R$_{12}$ and C3 are joined to form ring A and R$_{13}$ is R$_{30}$; or
R$_{12}$ and R$_{13}$ are joined to form ring B; or
R$_{12}$ and C1 are joined to form ring C and R$_{13}$ is R$_{30}$; or
C1 and C3 are joined to form ring D and R$_{12}$ and R$_{13}$ are each independently R$_{30}$; or
R$_{13}$ and C2 are joined to form ring E, m is 1, and Rn is R$_{30}$; or
R$_2$ and R$_{13}$ are joined to form ring B and C1 and C3 are joined to form ring D;
wherein
Ring A, C and E are each independently a substituted or unsubstituted single spiro or fused 3-8 membered heterocyclic rings;
Ring B is a substituted or unsubstituted single, spiro or fused 3-8 membered heterocyclic ring; and
Ring D is a substituted or unsubstituted C$_3$-C$_5$ cycloalkyl;
In some embodiments, formula B is represented by formula Bi.
In some embodiments, R$_6$ of formula I, II and/or I(a)-I(i) is represented by the structure of formula Bi:

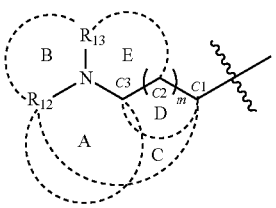

wherein
m is 0 or 1; and
R$_{12}$ is R$_{20}$ or C$_1$-C$_5$ C(O)-alkyl, and R$_{13}$ is R$_{30}$; or
R$_{12}$ and R$_{13}$ are both H; or
R$_{12}$ and R$_{13}$ are each independently H or substituted or unsubstituted C$_1$-C$_5$ alkyl (e.g., ethyl, trifluoroethyl); or
R$_{12}$ and C3 are joined to form ring A and R$_{13}$ is R$_{30}$; or
R$_{12}$ and R$_{13}$ are joined to form ring B; or
R$_{12}$ and C1 are joined to form ring C and R$_{13}$ is R$_{30}$; or
C1 and C3 are joined to form ring D and R$_{12}$ and R$_{13}$ are each independently R$_{30}$; or
R$_{13}$ and C2 are joined to form ring E, m is 1, and R$_{12}$ is R$_{30}$; or
R$_{12}$ and R$_{13}$ are joined to form ring B and C1 and C3 are joined to form ring D;
wherein
Ring A, C and E are each independently a substituted or unsubstituted single spiro or fused 3-8 membered heterocyclic rings;
Ring B is a substituted or unsubstituted single, spiro or fused 3-8 membered heterocyclic ring; and
Ring D is a substituted or unsubstituted C$_3$-C$_5$ cycloalkyl;

In some embodiments, R$_{12}$ of formula B and/or Bi is H. In some embodiments, R$_{12}$ is R$_{20}$. In other embodiments, R$_{12}$ is R$_{30}$. In some embodiments, R$_{12}$ is C$_1$-C$_5$ C(O)-alkyl. In some embodiments, R$_{12}$ is substituted or unsubstituted C$_1$-C$_5$ alkyl. In some embodiments, R$_{12}$ is unsubstituted C$_1$-C$_5$ alkyl. In some embodiments, the alkyl is ethyl. In some embodiments, R$_{12}$ is substituted C$_1$-C$_5$ alkyl. In some embodiments, the alkyl is trifluoroethyl.

In some embodiments, R$_{13}$ of formula B and/or Bi is H. In other embodiments, R$_{13}$ is R$_{30}$. In some embodiments, R$_{13}$ is substituted or unsubstituted C$_1$-C$_5$ alkyl. In some embodiments, R$_{13}$ is unsubstituted C$_1$-C$_5$ alkyl. In some embodiments, the alkyl is ethyl. In some embodiments, R$_{13}$ is substituted C$_1$-C$_5$ alkyl. In some embodiments, the alkyl is trifluoroethyl.

In some embodiments, R$_6$ of formula I, II and/or I(a)-I(i) is represented by formula B. In some embodiments, R$_{12}$ of formula B is R$_{20}$ or C$_1$-C$_5$ C(O)-alkyl, and R$_{13}$ is R$_{30}$. In some embodiments, R$_{12}$ and R$_{13}$ of formula B are both H. In some embodiments, R$_{12}$ and R$_{13}$ of formula B are each independently H or substituted or unsubstituted C$_1$-C$_5$ alkyl (e.g., ethyl, trifluoroethyl). In some embodiments, R$_{12}$ and R$_{13}$ of formula B are each independently H or trifluoroethyl. In some embodiments, R$_{12}$ and C3 of formula B are joined to form ring A and R$_{13}$ is R$_{30}$. In some embodiments, R$_{12}$ and R$_{13}$ of formula B are joined to form ring B. In some embodiments, R$_{12}$ and C$_1$ of formula B are joined to form ring C and R$_{13}$ is R$_{30}$. In some embodiments, C$_1$ and C$_3$ of formula B are joined to form ring D and R$_{12}$ and R$_{13}$ of formula B are each independently R$_{30}$. In some embodiments, R$_{13}$ and C$_2$ of formula B are joined to form ring E, m is 1, and R$_{12}$ of formula B is R$_{30}$. In some embodiments, R$_{12}$ and R$_{13}$ of formula B are joined to form ring B and C$_1$ and C$_3$ of formula B are joined to form ring D.

In some embodiments, R$_6$ of formula I, II and/or I(a)-I(h) is represented by formula Bi. in some embodiments, R$_{12}$ of formula Bi is R$_{20}$ or C$_1$-C$_5$ C(O)-alkyl, and R$_{13}$ is R$_{30}$. In some embodiments, R$_{12}$ and R$_{13}$ of formula Bi are both H. In some embodiments, R$_{12}$ and R$_{13}$ of formula Bi are each independently H or substituted or unsubstituted C$_1$-C$_5$ alkyl (e.g., ethyl, trifluoroethyl). In some embodiments, R$_{12}$ and R$_{13}$ of formula Bi are each independently H or trifluoroethyl. In some embodiments, R$_{12}$ and C3 of formula Bi are joined to form ring A and R$_{13}$ is R$_{30}$. In some embodiments, R$_{12}$ and R$_{13}$ of formula Bi are joined to form ring B. In some embodiments, R$_{12}$ and C$_1$ of formula Bi are joined to form ring C and R$_{13}$ is R$_{30}$. In some embodiments, C$_1$ and C$_3$ of formula Bi are joined to form ring D and R$_{12}$ and R$_{13}$ of formula Bi are each independently R$_{30}$. In some embodiments, R$_{13}$ and C$_2$ of formula Bi are joined to form ring E, m is 1, and R$_{12}$ of formula Bi is R$_{30}$. In some embodiments, R$_{12}$ and R$_{13}$ of formula Bi are joined to form ring B and C$_1$ and C$_3$ of formula Bi are joined to form ring D.

In some embodiments, R$_6$ of formula I(g) is represented by the structure of formula C:

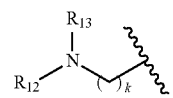

wherein
- k is an integer number between 1 and 4;
- $R_{12}$ and $R_{13}$ are each independently H, $C_1$-$C_5$ linear or branched, substituted or unsubstituted alkyl (e.g., ethyl, isopropyl), $R_{20}$, or
- $R_{12}$ and $R_{13}$ are joined to form a substituted or unsubstituted 4-7 membered heterocyclic ring (e.g., piperidine, piperazine, pyrrolidine, oxa-6-azaspiro[3.3]heptane).

In some embodiments, k of formula C is 1. In some embodiments, k is 2. In some embodiments, k is 3. In some embodiments, k is 4.

In some embodiments, $R_{12}$ and $R_{13}$ of formula C are each independently H, $C_1$-$C_5$ linear or branched, substituted or unsubstituted alkyl (e.g., ethyl, isopropyl) or $R_{20}$; each represents a separate embodiment according to this invention. In some embodiments, $R_{12}$ and $R_{13}$ of formula C are both ethyls. In some embodiments, $R_{12}$ and $R_{13}$ of formula C are both isopropyls. In some embodiments, $R_{12}$ and $R_{13}$ of formula C are both alkyls.

In some embodiments, $R_{12}$ and $R_{13}$ of formula C are joined to form a substituted or unsubstituted 4-7 membered heterocyclic ring. In some embodiments, $R_{12}$ and $R_{13}$ of formula C are joined to form a piperidine, piperazine, pyrrolidine, oxa-6-azaspiro[3.3]heptane; each represents a separate embodiment according to this invention. in some embodiments the heterocyclic ring maybe further substituted with at least one substitution as defined herein for heterocyclic rings.

In some embodiments, $R_6$ of formula I(b) is represented by formula Bi and/or B and
- $R_{12}$ of formula Bi and/or B is $R_{20}$ or $C_1$-$C_5$ C(O)-alkyl, and $R_{13}$ of formula Bi and/or B is $R_{30}$; or
- $R_{12}$ and $R_{13}$ are both H, or
- $R_{12}$ and $R_{13}$ are each independently H or trifluoroethyl; or
- $R_{12}$ and C3 are joined to form ring A and $R_{13}$ is $R_{30}$; or
- $R_{12}$ and $R_{13}$ are joined to form a substituted or unsubstituted pyrrolidine ring, piperazine, thiomorpholine 1,1-dioxide 2-oxa-6-azaspiro[3.3]heptane, pyrazole, imidazole, 2,5-diazabicyclo[2.2.1]heptane or a diazabicyclo[2.2.1]heptane; or
- $R_{12}$ and C1 are joined to form ring C and $R_{13}$ is $R_{30}$; or C1 and C3 are joined to form ring D and $R_{12}$ and $R_{13}$ are each independently $R_{30}$; or
- $R_{13}$ and C2 are joined to form ring E, m is 1, and $R_{12}$ is $R_{30}$; or
- $R_{12}$ and $R_{13}$ are joined to form ring B and C1 and C3 are joined to form ring D.

In some embodiments, $R_6$ of formula I(b) is represented by formula Bi and/or B and
- $R_{12}$ of formula Bi and/or B is $R_{20}$ or $C_1$-$C_5$ C(O)-alkyl, and $R_{13}$ of formula Bi and/or B is $R_{30}$; or
- $R_{12}$ and C3 are joined to form ring A and $R_{13}$ is $R_{30}$; or
- $R_{12}$ and $R_{13}$ are joined to form a substituted or unsubstituted pyrrolidine ring, piperazine, thiomorpholine 1,1-dioxide 2-oxa-6-azaspiro[3.3]heptane, pyrazole, imidazole, 2,5-diazabicyclo[2.2.1]heptane or a diazabicyclo[2.2.1]heptane; or
- $R_{12}$ and C1 are joined to form ring C and $R_{13}$ is $R_{30}$; or C1 and C3 are joined to form ring D and $R_{12}$ and $R_{13}$ are each independently $R_{30}$; or
- $R_{13}$ and C2 are joined to form ring E, m is 1, and $R_{12}$ is $R_{30}$; or
- $R_{12}$ and $R_{13}$ are joined to form ring B and C1 and C3 are joined to form ring D.

In some embodiments, ring A of formula Bi, is a substituted or unsubstituted single spiro or fused 3-8 membered heterocyclic ring. In some embodiments, ring A, is an unsubstituted single 3-8 membered heterocyclic ring. In some embodiments, ring A, is an unsubstituted spiro 3-8 membered heterocyclic ring. In some embodiments, ring A, is an unsubstituted fused 3-8 membered heterocyclic ring. In some embodiments, ring A, is a substituted single 3-8 membered heterocyclic ring. In some embodiments, ring A, is a substituted spiro 3-8 membered heterocyclic ring. In some embodiments, ring A, is a substituted fused 3-8 membered heterocyclic ring. In some embodiments, ring A is: pyrrolidine, methylpyrrolidine, ethylpyrrolidine, 2-oxopyrrolidine, piperidine, methylpiperidine, methyl-2-oxopyrrolidine, pyran-azetidine, methyl-azetidine, azabicyclooctane, 2-azabicyclo[2.1.1]hexane, or 2-azaspiro[3.3]heptane; each represents a separate embodiment according to this invention. In some embodiments, ring A is: pyrrolidine, methylpyrrolidine, or ethylpyrrolidine; each represents a separate embodiment according to this invention.

In some embodiments, ring B of formula Bi, is a substituted or unsubstituted single spiro or fused 3-8 membered heterocyclic ring. In some embodiments, ring B, is an unsubstituted single 3-8 membered heterocyclic ring. In some embodiments, ring B, is an unsubstituted spiro 3-8 membered heterocyclic ring. In some embodiments, ring B, is an unsubstituted fused 3-8 membered heterocyclic ring. In some embodiments, ring B, is a substituted single 3-8 membered heterocyclic ring. In some embodiments, ring B, is a substituted spiro 3-8 membered heterocyclic ring. In some embodiments, ring B, is a substituted fused 3-8 membered heterocyclic ring. In some embodiments, ring B is: pyrrolidine, methylpyrrolidine, ethylpyrrolidine, 2-oxopyrrolidine, hydroxymethyl-pyrrolidine, piperidine, piperidin-2-one, 4-fluoropiperidin-2-one, piperidine-4-carbonitrile, methylpiperidine, fluoropiperidine, 4-fluoropiperidine, 4-fluoro-2-methylpiperidine, difluoropiperidine, piperazine, methyl-piperazine, dimethyl-pyrazole, methyl-2-oxopyrrolidine, pyran-, azetidine, methyl-azetidine, imidazole, azabicyclooctane, 2-azabicyclo[2.1.1]hexane, or 2-azaspiro[3.3]heptane, diazabicyclo[2.2.1]heptane, 2-methyl-2,5-diazabicyclo[2.2.1]heptane, thiomorpholine, or 1,1-dioxide-2-oxa-6-azaspiro[3.3]heptane; each represents a separate embodiment according to this invention. In some embodiments, ring B is: piperidine, methyl-piperidin, fluoropiperidine, difluoropiperidine, pyrrolidine, piperazine, methylpyrrolidine, thiomorpholine, methyl-piperazine, dimethyl-pyrazole, imidazole, 2-methyl-2,5-diazabicyclo[2.2.1]heptane, 1,1-dioxide-2-oxa-6-azaspiro[3.3]heptane, hydroxymethyl-pyrrolidine or diazabicyclo[2.2.1]heptane, 6-fluoro-3-azabicyclo[3.1.1]heptane; each represents a separate embodiment according to this invention.

In some embodiments, ring C of formula Bi, is a substituted or unsubstituted single spiro or fused 3-8 membered heterocyclic ring. In some embodiments, ring C, is an unsubstituted single 3-8 membered heterocyclic ring. In some embodiments, ring C, is an unsubstituted spiro 3-8 membered heterocyclic ring. In some embodiments, ring C, is an unsubstituted fused 3-8 membered heterocyclic ring. In some embodiments, ring C, is a substituted single 3-8 membered heterocyclic ring. In some embodiments, ring C, is a substituted spiro 3-8 membered heterocyclic ring. In some embodiments, ring C, is a substituted fused 3-8 membered heterocyclic ring. In some embodiments, ring C is: pyrrolidine, methylpyrrolidine, ethylpyrrolidine, 2-oxopyrrolidine, piperidine, methylpiperidine, methyl-2-oxopyrrolidine, pyran-azetidine, methyl-azetidine, azabicyclooctane, 2-azabicyclo[2.1.1]hexane, or 2-azaspiro[3.3]heptane; each represents a separate embodiment according to this invention. In some embodiments, ring C is: piperidine, pyrrolidine, methyl-2-oxopyrrolidine, pyran-pyrrolidine, methyl-azetidine, azabicyclooctane, 2-azabicyclo[2.1.1]hexane, or 2-azaspiro[3.3]heptane; each represents a separate embodiment according to this invention.

In some embodiments, ring D of formula Bi, is a substituted or unsubstituted $C_3$-$C_5$ cycloalkyl.

In some embodiments, ring D, is a substituted $C_3$-$C_8$ cycloalkyl. In some embodiments, ring D, is an unsubstituted $C_3$-$C_8$ cycloalkyl. In some embodiments, ring D is cyclopropane, cyclobutane, cyclopentane, cyclohexane or cycloheptane; each represents a separate embodiment according to this invention.

In some embodiments, ring E of formula Bi, is a substituted or unsubstituted single spiro or fused 3-8 membered heterocyclic ring. In some embodiments, ring E, is an unsubstituted single 3-8 membered heterocyclic ring. In some embodiments, ring E, is an unsubstituted spiro 3-8 membered heterocyclic ring. In some embodiments, ring E, is an unsubstituted fused 3-8 membered heterocyclic ring. In some embodiments, ring E, is a substituted single 3-8 membered heterocyclic ring. In some embodiments, ring E, is a substituted spiro 3-8 membered heterocyclic ring. In some embodiments, ring E, is a substituted fused 3-8 membered heterocyclic ring. In some embodiments, ring E is: pyrrolidine, methylpyrrolidine, ethylpyrrolidine, 2-oxopyrrolidine, piperidine, methylpiperidine, methyl-2-oxopyrrolidine, pyran-azetidine, methyl-azetidine, azabicyclooctane, 2-azabicyclo[2.1.1]hexane, or 2-azaspiro[3.3]heptane; each represents a separate embodiment according to this invention. In some embodiments, ring E is: pyrrolidine, azetidine, ethylpyrrolidine, oxopyrrolidine, or methylpiperidine; each represents a separate embodiment according to this invention.

In some embodiments, $R_6$ of formula I(b) is F, Cl, Br, I, OH, SH, $R_8$—OH, $R_8$—SH, —$R_8$—O—$R_{10}$, $CH_2$—O—$CH_3$, $R_8$—S—$R_{10}$, $(CH_2)_3$—S—$(CH_2)_2CH_3$, $R_8$—NHC(O)—$R_{10}$, —O—$R_8$—$R_{10}$, $R_8$-(substituted or unsubstituted $C_3$-$C_5$ cycloalkyl), $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, $CH_2$-cyclohexanol, $(CH_2)_3$-pyran, $CH_2$-tetrahydrofurane, $CH_2$-dioxane, $CH_2$-methyl-THF, $CH_2$-oxa-azaspirodecane, $CH_2$-azaspiroheptane, $(CH_2)_3$-dimethylpyrazole, $CH_2$-methyl-azetidine, $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_9$—$R_8$—$N(R_{10})(R_{11})$, $B(OH)_2$, —$OC(O)CF_3$, —$OCH_2Ph$, $NHC(O)$—$R_{10}$, NHCO—$N(R_{10})(R_{11})$, COOH, —$C(O)Ph$, $C(O)O$—$R_{10}$, $R_8$—$C(O)$—$R_{10}$, $C(O)H$, $C(O)$—$R_{10}$, $C_1$-$C_5$ linear or branched $C(O)$-haloalkyl, —$C(O)NH_2$, $C(O)NHR$, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl, $CH(CH_3)CH_2OCH_3$, $CH(CH_3)CH_2NH_2$, $CH(CH_3)C(O)N(CH_3)_2$, $CH_2$—$CH(OH)Ph$, $(CH_2)_3N(H)CH_2CH_3$, $CH(CH_3)(CH_2)_2OH$, $CH(CH_2OH)(CH_2CH_3)$, $(CH_2)_3$—$OCH_3$, $(CH_2)_2$—$OCH_3$, $(CH_2)_2$—$OCH(CH_3)_2$, $CH(CH_2OH)(CH_2CH(CH_3)_2)$, $CH_2CH(CH_3)(OCH_3)$, $CH_2CH(N(CH_3)_2)(CH_2CH_3)$, benzyl, methyl, ethyl, iso-propyl, butyl, isobutyl, tert-butyl, pentyl, isopentyl, neopentyl, hexyl, $CH_2$—$OCH_2$—$CH_2$—O—$CH_3$, $C_1$-$C_5$ linear or branched, substituted or unsubstituted alkenyl, $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy, methoxy, O—$(CH_2)_2O$—$CH_3$), substituted or unsubstituted $C_1$-$C_5$ linear or branched, or $C_3$-$C_5$ cyclic alkoxy wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, methoxycyclopropyl, methylcyclobutyl, cyclopropyl, cyclobutyl, cyclohexyl, 4,4-difluorocyclohexane, aminomethyl-cyclobutyl, methoxycyclobutyl, 2,3-dihydro-1H-indenol, substituted or unsubstituted saturated or unsaturated, single fused, bridged or spiro 3-10 membered carbocyclic or heterocyclic ring, piperidine, 1-methylpiperidine, 3-fluoro-1-methylpiperidine, 1-(2,2,2-trifluoroethyl)piperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane, 4,4-difluorocyclohexane, substituted or unsubstituted aryl, or substituted or unsubstituted benzyl; each represents a separate embodiment according to this invention. In some embodiments, $R_6$ may be further substituted with at least one substitution selected from: F, Cl, Br, I, $C_1$-$C_5$ linear or branched alkyl, OH, alkoxy (e.g., OMe), amide (e.g., $C(O)N(R)_2$), $C(O)$-alkyl, $C(O)$-pyrrolidine, $C(O)$-piperidine, $N(R)_2$ (e.g., $N(CH_3)_2$, $NH_2$), $NH(R_{10})$, $N(R_{10})(R_{11})$, $CF_3$, aryl, phenyl, heteroaryl, substituted or unsubstituted $C_3$-$C_8$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), $C_1$-$C_5$ linear or branched haloalkyl (e.g., $CH_2CF_3$, $CHF_2$), halophenyl, (benzyloxy)phenyl, CN, and $NO_2$; each represents a separate embodiment according to this invention.

In some embodiments, $R_6$ of formula I(b) and/or I(l) is —$R_8$—O—$R_{10}$. In some embodiments, —$R_8$—O—$R_{10}$ is $CH_2$—O—$CH_3$. In some embodiments, $R_6$ is $R_8$—S—$R_{10}$. In some embodiments, $R_8$—S—$R_{10}$ is $(CH_2)_3$—S—$(CH_2)_2CH_3$. In some embodiments, $R_6$ is $R_8$—NHC(O)—$R_{10}$. In some embodiments, $R_6$ is $R_8$-(substituted or unsubstituted $C_3$-$C_8$ cycloalkyl). In some embodiments, the $R_8$-(substituted or unsubstituted $C_3$-$C_8$ cycloalkyl) is $CH_2$-cyclobutanol, $CH_2$-difluorocyclopropyl, $CH_2$-methylcyclopropyl, $CH_2$-dimethylamino-cyclohexyl, $(CH_2)_2$-cyclopentanole, $CH_2$-cyclohexanol), $(CH_2)_3$-pyran, $CH_2$-tetrahydrofurane, $CH_2$-dioxane, $CH_2$-methyl-THF, $CH_2$-oxa-azaspirodecane, $(CH_2)_3$-dimethylpyrazole, $CH_2$-methyl-azetidine, or $CH_2$-azaspiroheptane; each represents a separate embodiment according to this invention. In some embodiments, $R_6$ is $C_1$-$C_5$ linear or branched, substituted or unsubstituted alkyl. In some embodiments, $R_6$ is $C_1$-$C_5$ linear or branched, substituted alkyl. In some embodiments, the substituted alkyl is $CH(CH_3)CH_2OCH_3$, $CH(CH_3)CH_2NH_2$, $CH(CH_3)C(O)N(CH_3)_2$, $CH_2$—$CH(OH)Ph$, $(CH_2)_3N(H)CH_2CH_3$, $CH(CH_3)(CH_2)_2OH$, $CH(CH_2OH)(CH_2CH_3)$, $(CH_2)_3$—$OCH_3$, $(CH_2)_2$—$OCH_3$, $(CH_2)_2$—$OCH(CH_3)_2$, $CH(CH_2OH)(CH_2CH(CH_3)_2)$, $CH_2CH(CH_3)(OCH_3)$, $CH_2CH(N(CH_3)_2)(CH_2CH_3)$, $CH_2$—$OCH_2$—$CH_2$—O—$CH_3$ or benzyl; each represents a separate embodiment according to this invention. In some embodiments, $R_6$ is $C_1$-$C_5$ linear or branched, unsubstituted alkyl. In some embodiments, the unsubstituted alkyl is methyl, ethyl, propyl, isopropyl, butyl, isobutyl, tert-butyl, pentyl, or neopentyl; each represents a separate embodiment according to this invention. In some embodiments, $R_6$ is substituted or unsubstituted $C_3$-$C_8$ cycloalkyl. In some embodiments, $R_6$ is substituted $C_3$-$C_8$ cycloalkyl. In some embodiments, the substituted cycloalkyl is methoxycyclopropyl, methylcyclobutyl, aminomethyl-cyclobutyl, or methoxycyclobutyl, 2,3-dihydro-1H-indenol; each represents a separate embodiment according to this invention. In some embodiments, $R_6$ is unsubstituted $C_3$-$C_8$ cycloalkyl. In some embodiments, the unsubstituted cycloalkyl is cyclopropyl, cyclobutyl, cyclopentyl, cyclohexyl, cycloheptyl or cyclooctyl; each represents a separate embodiment according to this invention. In some embodiments, $R_6$ is substituted or unsubstituted saturated or unsaturated, single fused, bridged or spiro 3-10 membered carbocyclic or heterocyclic ring. In some embodiments, $R_6$ the carbocyclic or heterocyclic ring as defined in $R_6$ is further substituted with at least one substitution selected from: F, Cl, Br, I, $C_1$-$C_5$ linear or branched alkyl, OH, alkoxy (e.g., OMe), amide, C(O)N(R)$_2$, C(O)-alkyl, C(O)-pyrrolidine, C(O)-piperidine, N(R)$_2$, NH(R$_{10}$), N(R$_{10}$)(R$_{11}$), N(CH$_3$)$_2$, NH$_2$, CF$_3$, aryl, phenyl, heteroaryl, substituted or unsubstituted $C_3$-$C_8$ cycloalkyl (e.g., cyclobutanol), substituted or unsubstituted 3-8 membered heterocyclic ring (e.g., pyran, oxetane, piperidine, pyrazole, triazole, imidazole), $C_1$-$C_5$ linear or branched haloalkyl (e.g., CH$_2$CF$_3$, CHF$_2$), halophenyl, (benzyloxy)phenyl, CN, and NO$_2$. In some embodiments, $R_6$ is substituted or unsubstituted 3-10 membered heterocyclic ring. In some embodiments, the substituted heterocyclic ring is piperidine, 1-methylpiperidine, 3-fluoro-1-methylpiperidine, 1-(2,2,2-trifluoroethyl)piperidine, azetidine, 1-methyl-azetidine, morpholine, pyrrolidine, pyrrolidinone, quinuclidine, tetrahydropyran, tetrahydrofurane, azaspiro[3.3]heptane, 8-methyl-8-azabicyclo[3.2.1]octane, dioxane, 1,3-dioxane, imidazole, trifluoromethyl-oxetane, hydroxy-tetrahydrofurane, azepan-2-one, azabicyclohexane; each represents a separate embodiment according to this invention. In some embodiments, $R_6$ is piperidine. In some embodiments, $R_6$ is 1-methylpiperidine. In some embodiments, $R_6$ is 3-fluoro-1-methylpiperidine. In some embodiments, $R_6$ is 1-(2,2,2-trifluoroethyl)piperidine, In some embodiments, $R_6$ is azetidine. In some embodiments, $R_6$ is 1-methyl-azetidine. In some embodiments, $R_6$ is morpholine. In some embodiments, $R_6$ is pyrrolidine. In some embodiments, $R_6$ is pyrrolidinone. In some embodiments, $R_6$ is tetrahydropyran. In some embodiments, $R_6$ is tetrahydrofurane. In some embodiments, $R_6$ is 8-methyl-8-azabicyclo[3.2.1]octane. In some embodiments, $R_6$ is dioxane. In some embodiments, $R_6$ is 1,3-dioxane. In some embodiments, $R_6$ is substituted or unsubstituted saturated or unsaturated, single fused, bridged or spiro 3-10 membered carbocyclic ring. In some embodiments, $R_6$ is 4,4-difluorocyclohexane.

In some embodiments, $R_7$ of formula I, II, I(a)-I(f) and/or I(i) is H, F, Cl, Br, I, OH, O—R$_{20}$, SH, R$_8$—OH, R$_8$—SH, SR$_{10}$, —R$_8$—O—R$_{10}$, —R$_8$—S—R$_{10}$, R$_8$—(C$_3$-C$_8$ cycloalkyl), R$_8$—(3-8 membered heterocyclic ring), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, COO—CH$_3$, R$_8$—C(O)—R$_{10}$, C(O)H, C(O)—R$_{10}$, $C_1$-$C_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), $C_1$-$C_5$ linear or branched, substituted or unsubstituted alkyl, methylimidazole, methyl, ethyl, $C_1$-$C_5$ linear or branched, substituted or unsubstituted alkenyl, $C_1$-$C_5$ linear or branched, or $C_3$-$C_8$ cyclic haloalkyl, $C_1$-$C_5$ linear or branched, or $C_3$-$C_8$ cyclic alkoxy optionally wherein at least one methylene group (CH$_2$) in the alkoxy is replaced with an oxygen atom, $C_1$-$C_5$ linear or branched thioalkyl, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_5$ cycloalkyl, cyclopropyl-1-ol, cyclopropylamine, oxetane-3-ol, bicyclo[1.1.1]pentane, substituted or unsubstituted 4-7 membered heterocyclic ring, morpholine, 3,3-dimethylmorpholine, tetrahydrofuran, tetrahydropyran, oxetane, oxetan-3-ol, pyrrolidine, pyrrolidin-2-ol, pyrrolidin-3-ol, 3-methoxypyrrolidine, pyrrolidine-3-carbonitrile, 3-cyanopyrrolidine, 1-methylpyrrolidine, 2,2-dimethylpyrrolidine, 3,3-difluoropyrrolidine, difluoromethylpyrrolidine, pyrrolidin-3-one-O-methyloxime, pyrrolidin-2-one, pyrrolidin-3-one, pyrrolidinone, imidazole, pyrazole, isoxazolidine, piperazine, piperazine-2-one, 1-methylpiperazine, piperidine, piperidin-3-ol, piperidin-4-ol, piperidine-2-one, piperidine-4-carbonitrile, 4-fluoropiperidine, oxadiazole, triazole, 2-oxopyrrolidine, isoxazolidine, piperazine-2-one, substituted or unsubstituted 3-10 membered bridged, fused or spiro heterocyclic ring, 4-azaspiro[2.4]heptane, 2-oxa-5-azaspiro[3.4]octane, 1,4-dioxa-6-azaspiro[4.4]nonane, 4,7-diazaspiro[2.5]octane, 2,5-diazabicyclo[2.2.1]heptane, R$_8$-(substituted or unsubstituted single, fused or spiro 3-8 membered heterocyclic ring), substituted or unsubstituted aryl, or substituted or unsubstituted benzyl; each represents a separate embodiment according to this invention. In some embodiments, $R_7$ is further substituted with at least one substitution selected from: F, Cl, Br, I, $C_1$-$C_5$ linear or branched alkyl, OH, alkoxy (e.g., OMe), amide (e.g., C(O)N(R)$_2$), C(O)-alkyl, C(O)-pyrrolidine, C(O)-piperidine, N(R)$_2$ NH(R$_{10}$), N(R$_{10}$)(R$_{11}$), (e.g., N(CH$_3$)$_2$, NH$_2$), CF$_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and NO$_2$; each represents a separate embodiment according to this invention.

In some embodiments, $R_7$ of formula I, II, I(b), I(d)-I(f) and/or I(i) is H. In some embodiments, $R^7$ is F. In some embodiments, $R_7$ is Cl. In some embodiments, $R_7$ is Br. In some embodiments, $R_7$ is I. In some embodiments, $R_7$ is OH. In some embodiments, $R_7$ is O—R$_{20}$. In some embodiments, $R_7$ is CF$_3$. In some embodiments, $R_7$ is CN. In some embodiments, $R_7$ is NH$_2$. In some embodiments, $R_7$ is NHR. In some embodiments, $R_7$ is N(R)$_2$. In some embodiments, $R_7$ is NH(R$_{10}$). In some embodiments, $R_7$ is N(R$_{10}$)(R$_{11}$). In some embodiments, $R_7$ is NHC(O)—R$_{10}$. In some embodiments, $R_7$ is COOH. In some embodiments, $R_7$ is —C(O)Ph. In some embodiments, $R_7$ is C(O)O—R$_{10}$. In some embodiments, $R_7$ is COO—CH$_3$. In some embodiments, $R_7$ is C(O)H. In some embodiments, $R_7$ is C(O)—R$_{10}$. In some embodiments, $R_7$ is $C_1$-$C_5$ linear or branched C(O)-haloalkyl. In some embodiments, $R_7$ is —C(O)NH$_2$. In some embodiments, $R_7$ is C(O)NHR. In some embodiments, C(O)NHR is C(O)NH(CH$_3$). In some embodiments, $R_7$ is C(O)N(R$_{10}$)(R$_{11}$). In some embodiments, C(O)N(R$_{10}$)(R$_{11}$) is C(O)NH(CH$_3$), C(O)NH(CH$_2$CH$_2$OCH$_3$), or C(O)NH(CH$_2$CH$_2$OH); each represents a separate embodiment according to this invention. In some embodiments, $R_7$ is SO$_2$R. In some embodiments, $R_7$ is $C_1$-$C_5$ linear or branched, substituted or unsubstituted alkyl. In some embodiments, the alkyl is methylimidazole, methyl, ethyl, propyl, isopropyl, butyl, isobutyl, tert-butyl, pentyl, neopentyl or hexyl; each represents a separate embodiment according to this invention. In some embodiments, $R_7$ is $C_1$-$C_5$ linear or branched, or $C_3$-$C_8$ cyclic haloalkyl. In some embodiments, $R_7$ is $C_1$-$C_5$ linear haloalkyl. In some embodiments, the haloalkyl is CHF$_2$. In some embodiments, $R_7$ is $C_1$-$C_5$ branched haloalkyl. In some embodiments, $R_7$ is $C_3$-$C_8$ cyclic haloalkyl. In some embodiments, $R_7$ is $C_1$-$C_5$ linear or branched, or $C_3$-$C_8$ cyclic alkoxy optionally wherein at least one methylene group (CH$_2$) in the alkoxy is replaced with an oxygen atom. In some embodiments, $R_7$ is $C_1$-$C_5$ linear alkoxy. In some embodiments, the alkoxy is methoxy. In some embodiments, the alkoxy is ethoxy. In some embodiments, $R_7$ is $C_1$-$C_5$ branched alkoxy. In some embodiments, $R_7$ is $C_3$-$C_8$ cyclic alkoxy. In some embodiments, $R_7$ is $C_1$-$C_5$ linear or branched thioalkyl. In some embodiments, $R_7$ is $C_1$-$C_5$ linear or branched haloalkoxy. In some embodiments, $R_7$ is $C_1$-$C_5$ linear haloalkoxy. In some embodiments, $R_7$ is $C_1$-$C_5$ branched haloalkoxy. In some embodiments, $R_7$ is $C_1$-$C_5$ linear or branched alkoxyalkyl. In some embodiments, $R_7$ is substituted or unsubstituted $C_3$-$C_8$ cycloalkyl. In some embodiments, the cycloalkyl is cyclopropyl, cyclopropanol, cyclobutyl, cyclopentyl, bicyclo[1.1.1]pentane, cyclohexyl, cycloheptyl or cyclooctyl; each represents a separate embodiment according to this invention. In some embodiments, $R_7$ is substituted or unsubstituted 3-10 membered single, fused, bridged or spiro, saturated, unsaturated or aromatic, carbocyclic or heterocyclic ring. In some embodiments, $R_7$ is substituted or unsubstituted 3-membered single, fused, bridged or spiro, saturated, unsaturated or aromatic heterocyclic ring. In some embodiments, $R_7$ is substituted or unsubstituted 4-7 membered heterocyclic ring. In some embodiments, $R_7$ is unsubstituted 4-7 membered heterocyclic ring. In some embodiments, the heterocyclic ring is morpholine, tetrahydrofuran, tetrahydropyran, oxetane, pyrrolidine, pyrrolidin-3-one, pyrrolidin-2-one, pyrrolidinone, imidazole, pyrazole, isoxazolidine, piperazine, piperazine-2-one, piperidine, piperidine-2-one, oxadiazole, triazole, isoxazolidine, or 2-oxopyrrolidine; each represents a separate embodiment according to this invention. In some embodiments, $R_7$ is substituted 4-7 membered heterocyclic ring. In some embodiments, the heterocyclic ring is 3,3-dimethylmorpholine, oxetan-3-ol, pyrrolidin-2-ol, pyrrolidin-3-ol, 3-methoxypyrrolidine, pyrrolidine-3-carbonitrile, 3-cyanopyrrolidine, 1-methylpyrrolidine, 2,2-dimethylpyrrolidine, 3,3-difluoropyrrolidine, difluoromethylpyrrolidine, pyrrolidin-3-one-O-methyloxime, pyrrolidin-3-one O-methyl oxime, 1-methylpiperazine, 1-methylpiperazine, piperidin-3-ol, piperidin-4-ol, piperidine-4-carbonitrile, 4-fluoropiperidine; each represents a separate embodiment according to this invention. In some embodiments, $R_7$ is a substituted or unsubstituted 3-10 membered bridged, fused or spiro heterocyclic ring. In some embodiments, the ring is 4-azaspiro[2.4]heptane, 2-oxa-5-azaspiro[3.4]octane, 1,4-dioxa-6-azaspiro[4.4]nonane, 4,7-diazaspiro[2.5]octane, 2,5-diazabicyclo[2.2.1]heptane; each represents a separate embodiment according to this invention. In some embodiments, $R_7$ is $R_8$-(substituted or unsubstituted single, fused or spiro 3-8 membered heterocyclic ring). In some embodiments, $R_7$ is $R_8$-(unsubstituted single 3-8 membered heterocyclic ring). In some embodiments, $R_7$ is $R_8$-(unsubstituted fused 3-8 membered heterocyclic ring). In some embodiments, $R_7$ is $R_8$-(unsubstituted spiro 3-8 membered heterocyclic ring). In some embodiments, $R_7$ is $R_8$-(substituted single 3-8 membered heterocyclic ring). In some embodiments, $R_7$ is $R_8$-(substituted fused 3-8 membered heterocyclic ring). In some embodiments, $R_7$ is $R_8$-(substituted spiro 3-8 membered heterocyclic ring). In some embodiments, the heterocyclic ring may be saturated. In some embodiments, the heterocyclic ring may be unsaturated. In some embodiments, the hetrocyclic ring may be aromatic. In some embodiments, $R_7$ is substituted or unsubstituted aryl. In some embodiments, $R_7$ is phenyl. In some embodiments, R may be further substituted with at least one substitution selected from: F, Cl, Br, I, $C_1$-$C_5$ linear or branched alkyl, OH, alkoxy (e.g., OMe), amide (e.g., C(O)N(R)$_2$, C(O)-pyrrolidine, C(O)-piperidine, N(R)$_2$ NH(R$_{10}$), N(R$_{10}$)(R$_{11}$), (e.g., N(CH$_3$)$_2$, NH$_2$), CF$_3$, aryl, phenyl, heteroaryl, substituted or unsubstituted $C_3$-$C_8$ cycloalkyl (e.g., cyclobutanol), $C_1$-$C_5$ linear or branched haloalkyl (e.g., CH$_2$CF$_3$, CHF$_2$), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and NO$_2$; each represents a separate embodiment according to this invention.

In some embodiments, $R_7$ of formula I(a) is O—R$_{20}$. In some embodiments, $R_7$ is substituted or unsubstituted 4-7 membered heterocyclic ring. In some embodiments, R is substituted or unsubstituted 3-10 membered single, fused, bridged or spiro, saturated, unsaturated or aromatic, carbocyclic or heterocyclic ring. In some embodiments, $R_7$ is substituted or unsubstituted 3-10 membered single, fused, bridged or spiro, saturated, unsaturated or aromatic heterocyclic ring. In some embodiments, $R_7$ is substituted or unsubstituted 4-7 membered heterocyclic ring. In some embodiments, R is unsubstituted 4-7 membered heterocyclic ring. In some embodiments, the heterocyclic ring is morpholine, tetrahydrofuran, tetrahydropyran, oxetane, pyrrolidine, pyrrolidin-3-one, pyrrolidin-2-one, pyrrolidinone, imidazole, pyrazole, isoxazolidine, piperazine, piperidine, piperidine-2-one, oxadiazole, triazole, isoxazolidine, or 2-oxopyrrolidine; each represents a separate embodiment according to this invention. In some embodiments, $R_7$ is substituted 4-7 membered heterocyclic ring. In some embodiments, the heterocyclic ring is 3,3-dimethylmorpholine, oxetan-3-ol, pyrrolidin-2-ol, pyrrolidin-3-ol, 3-methoxypyrrolidine, pyrrolidine-3-carbonitrile, 3-cyanopyrrolidine, 1-methylpyrrolidine, 2,2-dimethylpyrrolidine, 3,3-difluoropyrrolidine, difluoromethylpyrrolidine, pyrrolidin-3-one-O-methyloxime, pyrrolidin-3-one O-methyl oxime, 1-methylpiperazine, 1-methylpiperazine, piperidin-3-ol, piperidin-4-ol, piperidine-4-carbonitrile, 4-fluoropiperidine; each represents a separate embodiment according to this invention. In some embodiments, $R_7$ is a substituted or unsubstituted 3-10 membered bridged, fused or spiro heterocyclic ring. In some embodiments, the ring is 4-azaspiro[2.4]heptane, 2-oxa-5-azaspiro[3.4]octane, 1,4-dioxa-6-azaspiro[4.4]nonane; each represents a separate embodiment according to this invention. In some embodiments, $R_7$ is morpholine. In some embodiments, $R_7$ is tetrahydrofuran. In some embodiments, R is tetrahydropyran. In some embodiments, $R_7$ is oxetane. In some embodiments, $R_7$ is oxetan-3-ol. In some embodiments, $R_7$ is pyrrolidine. In some embodiments, $R_7$ is pyrrolidin-2-ol. In some embodiments, $R_7$ is pyrrolidin-3-ol. In some embodiments, $R_7$ is 3-methoxypyrrolidine. In some embodiments, $R_7$ is pyrrolidine-3-carbonitrile. In some embodiments, $R_7$ is 1-methylpyrrolidine. In some embodiments, $R_7$ is pyrrolidin-2-one. In some embodiments, $R_7$ is pyrrolidin-3-one. In some embodiments, R is pyrrolidinone. In some embodiments, R is imidazole. In some embodiments, $R_7$ is pyrazole. In some embodiments, $R_7$ is isoxazolidine. In some embodiments, $R_7$ is piperazine. In some embodiments, $R_7$ is piperidine. In some embodiments, $R_7$ is piperidin-3-ol. In some embodiments, $R_7$ is piperidin-4-ol. In some embodiments, $R_7$ is piperidine-2-one. In some embodiments, $R_7$ is piperazine-2-one. In some embodiments, $R_7$ is piperidine-4-carbonitrile. In some embodiments, $R_7$ is 4-fluoropiperidine. In some embodiments, $R_7$ is 2,2-dimethylpyrrolidine. In some embodiments, $R_7$ is pyrrolidin-3-one O-methyl oxime. In some embodiments, $R_7$ is a substituted or unsubstituted 3-10 membered bridged, fused or spiro heterocyclic ring. In some embodiments, $R_7$ is 4-azaspiro[2.4]heptane. In some embodiments, $R_7$ is 2-oxa-5-azaspiro[3.4]octane. In some embodiments, $R_7$ is 1,4-dioxa-6-azaspiro[4.4]nonane. In some embodiments, $R_7$ is 4,7-diazaspiro[2.5]octane. In some embodiments, $R_7$ is 2,5-diazabicyclo[2.2.1]heptane. In some embodiments, $R_7$ is 3,3-dimethylmorpholine. In some embodiments, $R_7$ is 1-methylpiperazine. In some embodiments, $R_7$ is oxadiazole. In some embodiments, $R_7$ is triazole. In some embodiments, $R_7$ is substituted or unsubstituted aryl. In some embodiments, $R_7$ is phenyl. In some embodiments, $R_7$ may be further substituted with at least one substitution selected from F, Cl, Br, I, $C_1$-$C_5$ linear or branched alkyl, OH, alkoxy (e.g., OMe), amide (e.g., C(O)N(R)$_2$, C(O)-pyrrolidine, C(O)-piperidine, N(R)$_2$ NH(R$_{10}$), N(R$_{10}$)(R$_{11}$), (e.g., N(CH$_3$)$_2$, NH$_2$), CF$_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), $C_1$-$C_5$ linear or branched haloalkyl (e.g., CH$_2$CF$_3$, CHF$_2$), halophenyl, (benzyloxy)phenyl, CN and NO$_2$; each represents a separate embodiment according to this invention.

In some embodiments, $R_7$ of formula I(c) is not H, F, Cl, $C_1$-$C_5$ linear or branched, or $C_3$-$C_8$ cyclic alkoxy, $C_1$-$C_5$ linear or branched haloalkoxy or $C_1$-$C_5$ linear or branched, substituted or unsubstituted alkyl.

In some embodiments, $R_7$ of formula I, II, I(a)-I(f) and/or I(i) is represented by the structure of formula A:

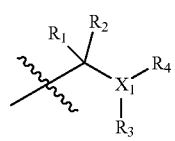

A wherein
$X_1$ is N or O;
$R_1$ and $R_2$ are each independently H, F, Cl, Br, I, OH, SH, or CF$_3$, substituted or unsubstituted $C_1$-$C_5$ alkyl (e.g., CH$_2$OH, CH$_2$OCH$_3$), $C_1$-$C_5$ linear or branched, or $C_3$-$C_5$ cyclic haloalkyl, substituted or unsubstituted $C_1$-$C_5$ linear or branched, or $C_3$-$C_5$ cyclic alkoxy, 3-8 membered carbocyclic or heterocyclic ring (e.g., oxetane);
or $R_1$ and $R_2$ are joined to form a $C_3$-$C_8$ carbocyclic or heterocyclic ring (e.g., cyclopropyl);
$R_3$ and $R_4$ are each independently H, Me, substituted or unsubstituted $C_1$-$C_5$ alkyl (e.g., methoxyethylene, methylaminoethyl, aminoethyl), —R$_8$—O—R$_{10}$ (e.g., (CH$_2$)$_2$O—CH$_3$), R$_8$—N(R$_{10}$)(R$_{11}$) (e.g., (CH$_2$)$_2$—NH(CH$_3$)), substituted or unsubstituted $C_3$-$C_8$ cycloalkyl (e.g., cyclopropyl), substituted or unsubstituted 5-7 membered heterocyclic ring (e.g., pyrrolidine, methylpyrrolidine, piperidine), or R$_{20}$;
or $R_3$ and $R_4$ are joined to form a 3-8 membered heterocyclic ring (e.g., pyrrolidine, pyrrolidone, 2-oxopyrrolidine, piperidine, morpholine, piperazine, imidazole); or $R_2$ and $R_4$ are joined to form substituted or unsubstituted, saturated or unsaturated, 4-8 membered heterocyclic ring (e.g., pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, pyrazole);
wherein if $X_1$ is O then $R_4$ is absent;

In some embodiments, $X_1$ of formula A is N. In other embodiments $X_1$ is O.

In some embodiments, $R_1$ of formula A, I(h), I(m), and/or I(o) is H. In other embodiments, $R_1$ is F. In other embodiments $R_1$ is CF$_3$. In other embodiments, $R_1$ is Cl. In other embodiments, $R_1$ is Br. In other embodiments, $R_1$ is I. In other embodiments, $R_1$ is OH. In other embodiments, $R_1$ is SH. In other embodiments, $R_1$ is substituted or unsubstituted $C_1$-$C_5$ alkyl. In other embodiments, $R_1$ is CH$_2$OH. In other embodiments, $R_1$ is CH$_2$OCH$_3$. In other embodiments, $R_1$ is $C_1$-$C_5$ linear or branched, or $C_3$-$C_8$ cyclic haloalkyl. In other embodiments, $R_1$ is substituted or unsubstituted $C_1$-$C_5$ linear or branched, or $C_3$-$C_8$ cyclic alkoxy. In other embodiments, $R_1$ is 3-8 membered carbocyclic or heterocyclic ring. In other embodiments, $R_1$ is 3-8 membered heterocyclic ring. In other embodiments, $R_1$ is oxetane. In other embodiments, $R_1$ is 3-8 membered carbocyclic ring.

In some embodiments, $R_2$ of formula A, I(h), I(m), and/or I(o) is H. In other embodiments $R_2$ is F. In other embodiments $R_2$ is CF$_3$. In other embodiments, $R_2$ is Cl. In other embodiments, $R_2$ is Br. In other embodiments, $R_2$ is I. In other embodiments, $R_2$ is OH. In other embodiments, $R_2$ is SH. In other embodiments, $R_2$ is substituted or unsubstituted $C_1$-$C_5$ alkyl. In other embodiments, $R_2$ is CH$_2$OH. In other embodiments, $R_2$ is CH$_2$OCH$_3$. In other embodiments, $R_2$ is $C_1$-$C_5$ linear or branched, or $C_3$-$C_8$ cyclic haloalkyl. In other embodiments, $R_2$ is substituted or unsubstituted $C_1$-$C_5$ linear or branched, or $C_3$-$C_8$ cyclic alkoxy. In other embodiments, $R_2$ is 3-8 membered carbocyclic or heterocyclic ring. In other embodiments, $R_2$ is 3-8 membered heterocyclic ring. In other embodiments, $R_2$ is oxetane. In other embodiments, $R_2$ is 3-8 membered carbocyclic ring.

In some embodiments, $R_1$ and $R_2$ of formula A, I(h), I(m), and/or I(o) are joined to form =O. In other embodiments, $R_1$ and $R_2$ are joined to form a 3-8 membered carbocyclic or heterocyclic ring. In other embodiments, $R_1$ and $R_2$ are joined to form a 3-8 membered carbocyclic ring. In some embodiments, the carbocyclic ring is cyclopropyl. In other embodiments, $R_1$ and $R_2$ are joined to form a 3-8 membered heterocyclic ring.

In some embodiments, $R_1$ and $R_2$ of formula A or formula I(a) and/or I(h), are not joined to form =O.

In some embodiments, $R_3$ of formula A, I(h), I(m), and/or I(o) is H. In some embodiments, $R_3$ is methyl. In some embodiments, $R_3$ is substituted or unsubstituted $C_1$-$C_5$ alkyl. In some embodiments, the alkyl is methoxyethylene, methylaminoethylene, aminoethylene; each represents a separate embodiment according to this invention. In some embodiments, $R_3$ is —R$_8$—O—R$_{10}$. In some embodiments, $R_3$ is (CH$_2$)$_2$O—CH$_3$). In some embodiments, $R_3$ is R$_8$—N(R$_{10}$)(R$_{11}$). In some embodiments, $R_3$ is (CH$_2$)$_2$—NH(CH$_3$). In some embodiments, $R_3$ is substituted or unsubstituted $C_3$-$C_8$ cycloalkyl. In some embodiments, the cycloalkyl is cyclopropyl. In some embodiments, $R_3$ is substituted or unsubstituted 5-7 membered heterocyclic ring. In some embodiments, the heterocyclic ring is pyrrolidine, methylpyrrolidine, or piperidine; each represents a separate embodiment according to this invention. In some embodiments, $R_3$ is pyrrolidine. In some embodiments, $R_3$ is methylpyrrolidine. In some embodiments, $R_3$ is piperidine. In some embodiments, $R_3$ is R$_{20}$ as defined hereinbelow.

In some embodiments, $R_4$ of formula A, I(h), I(m), and/or I(o) is H. In some embodiments, $R_4$ is methyl. In some embodiments, $R_4$ is substituted or unsubstituted $C_1$-$C_5$ alkyl. In some embodiments, the alkyl is methoxyethylene, methylaminoethylene, aminoethylene; each represents a separate embodiment according to this invention. In some embodiments, $R_4$ is $-R_8-O-R_{10}$. In some embodiments, $R_4$ is $(CH_2)_2O-CH_3$). In some embodiments, $R_4$ is $R_8-N(R_{10})(R_{11})$. In some embodiments, $R_4$ is $(CH_2)_2-NH(CH_3)$. In some embodiments, $R_4$ is substituted or unsubstituted $C_3$-$C_8$ cycloalkyl. In some embodiments, the cycloalkyl is cyclopropyl. In some embodiments, $R_4$ is substituted or unsubstituted 5-7 membered heterocyclic ring. In some embodiments, the heterocyclic ring is pyrrolidine, methylpyrrolidine, or piperidine; each represents a separate embodiment according to this invention. In some embodiments, $R_4$ is pyrrolidine. In some embodiments, $R_4$ is methylpyrrolidine. In some embodiments, $R_4$ is piperidine. In some embodiments, $R_4$ is $R_{20}$ as defined hereinbelow.

In some embodiments, $R_3$ and $R_4$ of formula A, I(h), I(m), and/or I(o) are joined to form a 3-8 membered heterocyclic ring. In some embodiments, the heterocyclic ring is imidazole, pyrrolidine, pyrrolidone, 2-oxopyrrolidine, piperidine, morpholine, or piperazine; each represents a separate embodiment according to this invention.

In some embodiments, $R_2$ and $R_4$ of formula A, I(h) and/or I(m) are joined to form Ring F. In some embodiments, Ring F is absent. In some embodiments, Ring F is a substituted or unsubstituted, saturated or unsaturated, 4-8 membered heterocyclic ring. In some embodiments, $R_2$ and $R_4$ are joined to form pyrrolidine, 1-methylpyrrolidine, pyrrolidin-2-one, pyridine, piperidine, imidazole, pyrimidine, triazole, oxadiazole, pyrazole; each represents a separate embodiment according to this invention. In some embodiments, Ring F is unsubstituted, saturated 4-8 membered heterocyclic ring. In some embodiments, Ring F is pyrrolidine, morpholine or piperidine; each represents a separate embodiment according to this invention. In some embodiments, Ring F is a substituted saturated 4-8 membered heterocyclic ring. In some embodiments, Ring F is 1-methylpyrrolidine, 3,3-difluoropyrrolidine, pyrrolidine-3-ol, 3-methoxypyrrolidine, 3-(difluoromethyl)pyrrolidine, or pyrrolidine-3-carbonitrile; each represents a separate embodiment according to this invention. In some embodiments, Ring F is a substituted or unsubstituted unsaturated, 4-8 membered heterocyclic ring. In some embodiments, Ring F is pyrrolidin-2-one, pyrrolidin-3-one, pyridine, piperidine-2-one, imidazole, pyrimidine, triazole, oxadiazole, or pyrazole; each represents a separate embodiment according to this invention. In some embodiments, if Ring F is aromatic, then $R_1$ is absent. In some embodiments, if Ring F is aromatic, then $R_3$ is absent. In some embodiments, if Ring F is aromatic, then $R_1$ and/or $R_3$ are absent.

In some embodiments, $R_2$ and $R_4$ of formula A, I(h) and/or I(m) are joined to form substituted or unsubstituted, saturated or unsaturated, 4-8 membered heterocyclic ring. In some embodiments, the heterocyclic ring is pyrrolidine, morpholine, 1-methylpyrrolidine, pyrrolidin-2-one, pyrrolidin-3-one, 3,3-difluoropyrrolidine, pyrrolidine-3-ol, 3-methoxypyrrolidine, 3-(difluoromethyl)pyrrolidine, pyrrolidine-3-carbonitrile, pyridine, piperidine, piperidine-2-one, imidazole, pyrimidine, triazole, oxadiazole, or pyrazole; each represents a separate embodiment according to this invention.

In some embodiments, if $X_1$ of formula A is O then $R_4$ is absent.

In some embodiments, $R_2$ and $R_4$ of formula I(h) and/or I(m) are joined to form Ring F. In some embodiments, Ring F is absent. In some embodiments, Ring F is a substituted or unsubstituted, saturated or unsaturated, 4-8 membered heterocyclic ring. In some embodiments, Ring F is unsubstituted, saturated 4-8 membered heterocyclic ring. In some embodiments, Ring F is pyrrolidine, morpholine or piperidine; each represents a separate embodiment according to this invention. In some embodiments, Ring F is a substituted saturated 4-8 membered heterocyclic ring. In some embodiments, Ring F is 1-methylpyrrolidine, 3,3-difluoropyrrolidine, pyrrolidine-3-ol, 3-methoxypyrrolidine, 3-(difluoromethyl)pyrrolidine, or pyrrolidine-3-carbonitrile; each represents a separate embodiment according to this invention. In some embodiments, Ring F is a substituted or unsubstituted unsaturated, 4-8 membered heterocyclic ring. In some embodiments, Ring F is pyrrolidin-2-one, pyrrolidin-3-one, pyridine, piperidine-2-one, imidazole, pyrimidine, triazole, oxadiazole, or pyrazole; each represents a separate embodiment according to this invention.

In some embodiments, Ring F of formula I(h) and/or I(m) is absent. In some embodiments, Ring F is a substituted or unsubstituted, saturated or unsaturated, 4-8 membered heterocyclic ring. In some embodiments, Ring F is a substituted, saturated, 4-8 membered heterocyclic ring. In some embodiments, Ring F is a substituted unsaturated, 4-8 membered heterocyclic ring. In some embodiments, Ring F is an unsubstituted, saturated, 4-8 membered heterocyclic ring. In some embodiments, Ring F is an unsubstituted, unsaturated, 4-8 membered heterocyclic ring. In some embodiments, Ring F is pyrrolidine. In some embodiments, Ring F is pyrrolidine-2-one. In some embodiments, Ring F is piperidine. In some embodiments, Ring F is piperazine. In some embodiments, Ring F is morpholine. In some embodiments, Ring F is a pyridinyl. In other embodiments, Ring F is 2-pyridinyl. In other embodiments, Ring F is pyrimidine. In other embodiments, Ring F is imidazole. In other embodiments, Ring F is pyridazine. In other embodiments, Ring F is pyrazine. In other embodiments, Ring F is pyrazole. In other embodiments, Ring F is thiazole. In other embodiments, Ring F is isothiazolyl. In other embodiments, Ring F is thiadiazolyl. In other embodiments, Ring F is triazolyl. In other embodiments, Ring F is thiazolyl. In other embodiments, Ring F is oxazolyl. In other embodiments, Ring F is isoxazolyl. In other embodiments, Ring F is pyrrolyl. In other embodiments, Ring F is oxadiazolyl. In other embodiments, Ring F is 1,2,3-, 1,2,4-, 1,2,5- or 1,3,4-oxadiazolyl; each is a separate embodiment according to this invention. In other embodiments, Ring F is oxazolonyl. In other embodiments, Ring F is oxazolidonyl. In other embodiments, Ring F is thiazolonyl. In other embodiments, Ring F is isothiazolinonyl. In other embodiments, Ring F is isoxazolidinonyl. In other embodiments, Ring F is imidazolidinonyl. In other embodiments, Ring F is pyrazolonyl. In other embodiments, Ring F is 2H-pyrrol-2-onyl. In other embodiments, Ring F is triazolopyrimidine. In other embodiments, Ring F is 3H-[1,2,3]triazolo[4,5-d]pyrimidine, 1H-[1,2,3]triazolo[4,5-d]pyrimidine, [1,2,4]triazolo[4,3-c]pyrimidine, [1,2,4]triazolo[4,3-a]pyrimidine, [1,2,3]triazolo[1,5-a]pyrimidine, [1,2,4]triazolo[1,5-c]pyrimidine, [1,2,4]triazolo[1,5-a]pyrimidine or [1,2,4]triazolo[1,5-c]pyrimidine; each is a separate embodiment according to this invention. In other embodiments, Ring F is 6,7-dihydro-5H-pyrazolo[5,1-b][1,3]oxazine.

In some embodiments, $R_7$ of formula I(a) is O—$R_{20}$, substituted or unsubstituted 4-7 membered heterocyclic ring (e.g., morpholine, tetrahydrofuran, tetrahydropyran, oxetane, oxetan-3-ol, pyrrolidine, pyrrolidin-2-ol, pyrrolidin-3-ol, 3-methoxypyrrolidine, 1-methylpyrrolidine, pyrrolidin-2-one, pyrrolidin-3-one, pyrrolidine-3-carbonitrile, 3-cyanopyrrolidine, pyrrolidinone, imidazole, pyrazole, isoxazolidine, piperazine, piperidine, piperidin-3-ol, piperidin-4-ol, piperidine-2-one, piperidine-4-carbonitrile, 4-fluoropiperidine, oxadiazole, triazole, pyrazole, 2-oxopyrrolidine; each represents a separate embodiment according to this invention), or substituted or unsubstituted aryl. In some embodiments, $R_7$ of formula I(a) is represented by formula A, wherein $X_1$, $R_1$, $R_2$, $R_3$ and $R_4$ are as defined above except that $R_1$ and $R_2$ cannot be joined to form =O.

In some embodiments, $R_7'$ of formula I(c) is not H.

In some embodiments, $R_7'$ of formula I, II, I(a)-I(b) and/or I(d)-I(o) is H. In some embodiments, $R_7'$ of formula I, II and/or I(a)-I(o) is F, Cl, Br, I, OH, O—$R_{20}$, SH, $R_8$—OH, $R_8$—SH, —$R_8$—O—$R_{10}$, $R_8$—($C_3$-$C_8$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, C(O)N($R_{10}$)($R_{11}$), $SO_2R$, $SO_2N(R_{10})(R_1)$, $CH(CF_3)(NH$—$R_{10})$, $C_1$-$C_5$ linear or branched, substituted or unsubstituted alkyl, $C_1$-$C_5$ linear or branched, substituted or unsubstituted alkenyl, $C_1$-$C_5$ linear or branched, or $C_3$-$C_8$ cyclic haloalkyl, $C_1$-$C_5$ linear or branched, or $C_3$-$C_8$ cyclic alkoxy optionally wherein at least one methylene group ($CH_2$) in the alkoxy is replaced with an oxygen atom, methoxy, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_5$ cycloalkyl, cyclopropyl, cyclohexyl, substituted or unsubstituted 3-8 membered heterocyclic ring, morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine, substituted or unsubstituted aryl, or substituted or unsubstituted benzyl; each represents a separate embodiment according to this invention. In some embodiments, the heterocyclic ring is morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine; each represents a separate embodiment according to this invention. In some embodiments, $R_7'$ is morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine; each represents a separate embodiment according to this invention. In some embodiments, $R_7'$ is further substituted with at least one substitution selected from: F, Cl, Br, I, $C_1$-$C_5$ linear or branched alkyl, OH, alkoxy (e.g., OMe), amide (e.g., $C(O)N(R)_2$, C(O)-pyrrolidine, C(O)-piperidine, $N(R)_2$ $NH(R_{10})$, $N(R_{10})(R_{11})$), (e.g., $N(CH_3)_2$, $NH_2$), $CF_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and $NO_2$; each represents a separate embodiment according to this invention.

In some embodiments, $R_7'$ of formula I, II and/or I(a)-I(o) is H. In some embodiments, $R_7'$ is F. In some embodiments, $R_7'$ is Cl. In some embodiments, $R_7'$ is Br. In some embodiments, $R_7'$ is I. In some embodiments, $R_7'$ is $CF_3$. In some embodiments, $R_7'$ is $C_1$-$C_5$ linear or branched, substituted or unsubstituted alkyl. In some embodiments, $R_7'$ is $C_1$-$C_5$ linear or branched unsubstituted alkyl. In some embodiments, the alkyl is isopropyl, methyl, ethyl; each represents a separate embodiment according to this invention. In some embodiments, $R_7'$ is $C_1$-$C_5$ linear or branched substituted alkyl. In some embodiments, $R_7'$ is isopropyl. In some embodiments, $R_7'$ is methyl. In some embodiments, $R_7'$ is ethyl. In some embodiments, $R_7'$ is $C_1$-$C_5$ linear or branched, or $C_3$-$C_5$ cyclic haloalkyl. In some embodiments, $R_7'$ is $C_1$-$C_5$ linear or branched haloalkyl. In some embodiments, the haloalkyl is $CHF_2$. In some embodiments, $R_7'$ is $C_3$-$C_5$ cyclic haloalkyl. In some embodiments, $R_7'$ is substituted or unsubstituted $C_3$-$C_5$ cycloalkyl. In some embodiments, the cycloalkyl is cyclopropyl, cyclobutyl, cyclopentyl, cyclohexyl, or cycloheptyl; each represents a separate embodiment according to this invention. In some embodiments, the cycloalkyl is cyclopropyl. In some embodiments, the cycloalkyl is cyclohexyl. In some embodiments, $R_7'$ is morpholine. In some embodiments, $R_7'$ is pyran. In some embodiments, $R_7'$ is oxetane. In some embodiments, $R_7'$ is pyrrolidine. In some embodiments, $R_7'$ is 3,3-difluoropyrrolidine. In some embodiments, $R_7'$ is imidazole. In some embodiments, $R_7'$ is pyrazole. In some embodiments, $R_7'$ is triazole. In some embodiments, $R_7'$ is piperazine. In some embodiments, $R_7'$ is piperidine. In some embodiments, $R_7'$ is piperidin-2-one. In some embodiments, $R_7'$ is piperidin-4-ol. In some embodiments, $R_7'$ is dioxazole. In some embodiments, $R_7'$ is 2-oxopyrrolidine.

In some embodiments, $R_7$ and $R_7'$ of formula I, II, and/or I(a)-I(f) are joined to form a 3-8 membered substituted or unsubstituted, saturated, unsaturated or aromatic, carbocyclic or heterocyclic ring including but not limited to: cyclopentyl, cyclohexyl, piperidine, tetrahydrofuran, tetrahydropyran, pyrrolidine; each represents a separate embodiment according to this invention. In some embodiments, $R_7$ and $R_7'$ are joined to form a 5 or 6 membered substituted or unsubstituted, saturated, unsaturated or aromatic, carbocyclic or heterocyclic ring. In some embodiments, $R_7$ and $R_7'$ are joined to form a 5 membered unsubstituted saturated or unsaturated carbocyclic ring. In some embodiments, $R_7$ and $R_7'$ are joined to form 6 membered unsubstituted saturated or unsaturated carbocyclic ring. In some embodiments, $R_7$ and $R_7'$ are joined to form a cyclohexyl. In some embodiments, $R_7$ and $R_7'$ are joined to form a 5 membered substituted saturated or unsaturated carbocyclic ring. In some embodiments, $R_7$ and $R_7'$ are joined to form a cyclopentyl. In some embodiments, $R_7$ and $R_7'$ are joined to form 6 membered substituted saturated or unsaturated carbocyclic ring. In some embodiments, $R_7$ and $R_7'$ are joined to form a 6 membered substituted or unsubstituted, aromatic, carbocyclic ring. In some embodiments, $R_7$ and $R_7'$ are joined to form a 5 or 6 membered substituted or unsubstituted, aromatic, heterocyclic ring. In some embodiments, $R_7$ and $R_7'$ are joined to form a 5 or 6 membered substituted or unsubstituted, heterocyclic ring. In some embodiments, $R_7$ and $R_7'$ are joined to form a 6 membered substituted or unsubstituted, heterocyclic ring. In some embodiments, $R_7$ and $R_7'$ are joined to form a piperidine. In some embodiments, $R_7$ and $R_7'$ are joined to form a tetrahydropyran. In some embodiments, $R_7$ and $R_7'$ are joined to form a 5 membered substituted or unsubstituted, heterocyclic ring. In some embodiments, $R_7$ and $R_7'$ are joined to form a pyrrolidine. In some embodiments, $R_7$ and $R_7'$ are joined to form a tetrahydrofuran.

In some embodiments, $R_7$ and $R_7'$ of formula I(c) are different. In some embodiments, $R_7$ and $R_7'$ of formula I(c) are not H, F, Cl, $C_1$-$C_5$ linear or branched, or $C_3$-$C_8$ cyclic alkoxy, $C_1$-$C_5$ linear or branched haloalkoxy or $C_1$-$C_5$ linear or branched, substituted or unsubstituted alkyl; each represents a separate embodiment according to this invention.

In some embodiments, $R_7''$ of formula I(i)-I(o) is H. In some embodiments, $R_7''$ of formula I(i)-I(m) is F, Cl, Br, I, OH, O—$R_{20}$, SH, $R_8$—OH, $R_8$—SH, —$R_8$—O—$R_{10}$, $R_8$—($C_3$-$C_5$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl, $C_1$-$C_5$ linear or branched, substituted or unsubstituted alkenyl, $C_1$-$C_5$ linear or branched, or $C_3$-$C_8$ cyclic haloalkyl, $C_1$-$C_5$ linear or branched, or $C_3$-$C_8$ cyclic alkoxy optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted 3-8 membered heterocyclic ring, substituted or unsubstituted aryl, or substituted or unsubstituted benzyl; each represents a separate embodiment according to this invention. In some embodiments, $R_7''$ is further substituted with at least one substitution selected from: F, Cl, Br, I, $C_1$-$C_5$ linear or branched alkyl, OH, alkoxy (e.g., OMe), amide (e.g., $C(O)N(R)_2$, C(O)-pyrrolidine, C(O)-piperidine, $N(R)_2$ $NH(R_{10})$, $N(R_{10})(R_{11})$, (e.g., $N(CH_3)_2$, $NH_2$), $CF_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and $NO_2$; each represents a separate embodiment according to this invention.

In some embodiments, $R_7''$ of formula I(i)-I(o) is H. In some embodiments, $R_7''$ is F. In some embodiments, $R_7''$ is Cl. In some embodiments, $R_7''$ is Br. In some embodiments, $R_7''$ is I. In some embodiments, $R_7''$ is $CF_3$. In some embodiments, $R_7''$ is $C_1$-$C_5$ linear or branched, substituted or unsubstituted alkyl. In some embodiments, $R_7''$ is $C_1$-$C_5$ linear or branched unsubstituted alkyl. In some embodiments, the alkyl is isopropyl, methyl, ethyl; each represents a separate embodiment according to this invention. In some embodiments, $R_7''$ is $C_1$-$C_5$ linear or branched substituted alkyl. In some embodiments, $R_7''$ is isopropyl. In some embodiments, $R_7''$ is methyl. In some embodiments, $R_7''$ is ethyl. In some embodiments, $R_7''$ is $C_1$-$C_5$ linear or branched, or $C_3$-$C_5$ cyclic alkoxy optionally wherein at least one methylene group ($CH_2$) in the alkoxy is replaced with an oxygen atom. In some embodiments, $R_7''$ is $C_1$-$C_5$ linear or branched alkoxy. In some embodiments, $R_7''$ is methoxy. In some embodiments, $R_7''$ is $C_1$-$C_5$ linear or branched, or $C_3$-$C_5$ cyclic haloalkyl. In some embodiments, $R_7''$ is $C_1$-$C_5$ linear or branched haloalkyl. In some embodiments, the haloalkyl is $CHF_2$. In some embodiments, $R_7''$ is $C_3$-$C_5$ cyclic haloalkyl. In some embodiments, $R_7''$ is substituted or unsubstituted $C_3$-$C_5$ cycloalkyl. In some embodiments, the cycloalkyl is cyclopropyl, cyclobutyl, cyclopentyl, cyclohexyl, or cycloheptyl; each represents a separate embodiment according to this invention. In some embodiments, the cycloalkyl is cyclopropyl. In some embodiments, the cycloalkyl is cyclohexyl. In some embodiments, $R_7''$ is a substituted or unsubstituted 3-8 membered heterocyclic ring. In some embodiments, $R_7''$ is morpholine. In some embodiments, $R_7''$ is pyran. In some embodiments, $R_7''$ is oxetane. In some embodiments, $R_7''$ is pyrrolidine. In some embodiments, $R_7''''$ is 3,3-difluoropyrrolidine. In some embodiments, $R_7''$ is imidazole. In some embodiments, $R_7''''$ is pyrazole. In some embodiments, $R_7''$ is triazole. In some embodiments, $R_7''$ is piperazine. In some embodiments, $R_7''$ is piperidine. In some embodiments, $R_7''$ is piperidin-2-one. In some embodiments, $R_7''$ is piperidin-4-ol. In some embodiments, $R_7''$ is dioxazole. In some embodiments, $R_7''$ is 2-oxopyrrolidine.

In some embodiments, $R_7'$ and $R_7''$ of formula I(j)-I(o) are joined to form a 3-8 membered substituted or unsubstituted, saturated, unsaturated or aromatic, carbocyclic or heterocyclic ring including but not limited to: cyclopentyl, cyclohexyl, piperidine, tetrahydrofuran, tetrahydropyran, pyrrolidine; each represents a separate embodiment according to this invention. In some embodiments, $R_7'$ and $R_7''$ are joined to form a 5 or 6 membered substituted or unsubstituted, saturated, unsaturated or aromatic, carbocyclic or heterocyclic ring. In some embodiments, $R_7'$ and $R_7''$ are joined to form a membered unsubstituted saturated or unsaturated carbocyclic ring. In some embodiments, $R_7'$ and $R_7''$ are joined to form 6 membered unsubstituted saturated or unsaturated carbocyclic ring. In some embodiments, $R_7'$ and $R_7''$ are joined to form a cyclohexyl. In some embodiments, $R_7'$ and $R_7''$ are joined to form a 5 membered substituted saturated or unsaturated carbocyclic ring. In some embodiments, $R_7'$ and $R_7''$ are joined to form a cyclopentyl. In some embodiments, $R_7'$ and $R_7''$ are joined to form 6 membered substituted saturated or unsaturated carbocyclic ring. In some embodiments, $R_7'$ and $R_7''$ are joined to form a 6 membered substituted or unsubstituted, aromatic, carbocyclic ring. In some embodiments, $R_7'$ and $R_7''$ are joined to form a 5 or 6 membered substituted or unsubstituted, aromatic, heterocyclic ring. In some embodiments, $R_7'$ and $R_7''$ are joined to form a 5 or 6 membered substituted or unsubstituted, heterocyclic ring. In some embodiments, $R_7'$ and $R_7''$ are joined to form a 6 membered substituted or unsubstituted, heterocyclic ring. In some embodiments, $R_7'$ and $R_7''$ are joined to form a piperidine. In some embodiments, $R_7'$ and $R_7''$ are joined to form a tetrahydropyran. In some embodiments, $R_7'$ and $R_7''$ are joined to form a 5 membered substituted or unsubstituted, heterocyclic ring. In some embodiments, $R_7'$ and $R_7''$ are joined to form a pyrrolidine. In some embodiments, $R_7'$ and $R_7''$ are joined to form a tetrahydrofuran.

In some embodiments, $R_7'$ and $R_7''$ of formula I(c) and/or I(i)-I(o) are different. In some embodiments, $R_7$ and $R_7'$ of formula I(c) and/or I(i)-I(n) are not H, F, Cl, $C_1$-$C_5$ linear or branched, or $C_3$-$C_8$ cyclic alkoxy, $C_1$-$C_5$ linear or branched haloalkoxy or $C_1$-$C_5$ linear or branched, substituted or unsubstituted alkyl; each represents a separate embodiment according to this invention.

In some embodiments, $R_7'''$ of formula I(i) is H. In some embodiments, $R_7'''$ of formula I(i) is F, Cl, Br, I, OH, O—$R_{20}$, SH, $R_8$—OH, $R_8$—SH, —$R_8$—O—$R_{10}$, $R_8$—($C_3$-$C_8$ cycloalkyl), $R_8$—(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$—$R_8$—$N(R_{10})(R_{11})$, $B(OH)_2$, —$OC(O)CF_3$, —$OCH_2Ph$, NHC(O)—$R_{10}$, NHCO—$N(R_{10})(R_{11})$, COOH, —C(O)Ph, C(O)O—$R_{10}$, $R_8$—C(O)—$R_{10}$, C(O)H, C(O)—$R_{10}$, $C_1$-$C_5$ linear or branched C(O)-haloalkyl, —$C(O)NH_2$, C(O)NHR, $C(O)N(R_{10})(R_{11})$, $SO_2R$, $SO_2N(R_{10})(R_{11})$, $CH(CF_3)(NH$—$R_{10})$, $C_1$-$C_5$ linear or branched, substituted or unsubstituted alkyl, $C_1$-$C_5$ linear or branched, substituted or unsubstituted alkenyl, $C_1$-$C_5$ linear or branched, or $C_3$-$C_8$ cyclic haloalkyl, $C_1$-$C_5$ linear or branched, or $C_3$-$C_8$ cyclic alkoxy optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted 3-8 membered heterocyclic ring, substituted or unsubstituted aryl, or substituted or unsubstituted benzyl; each represents a separate embodiment according to this invention. In some embodiments, $R_7'''$ is further substituted with at least one substitution selected from: F, Cl, Br, I, $C_1$-$C_5$ linear or branched alkyl, OH, alkoxy (e.g., OMe), amide (e.g., C(O)N(R)$_2$, C(O)-pyrrolidine, C(O)-piperidine, N(R)$_2$ NH(R$_{10}$), N(R$_{10}$)(R$_{11}$), (e.g., N(CH$_3$)$_2$, NH$_2$), CF$_3$, aryl, phenyl, heteroaryl, substituted or unsubstituted $C_3$-$C_8$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and NO$_2$; each represents a separate embodiment according to this invention.

In some embodiments, $R_7'''$ of formula I(i) is H. In some embodiments, $R_7'''$ is F. In some embodiments, $R_7'''$ is Cl. In some embodiments, $R_7'''$ is Br. In some embodiments, $R_7'''$ is I. In some embodiments, $R_7'''$ is CF$_3$. In some embodiments, $R_7'''$ is $C_1$-$C_5$ linear or branched, substituted or unsubstituted alkyl. In some embodiments, $R_7'''$ is $C_1$-$C_5$ linear or branched unsubstituted alkyl. In some embodiments, the alkyl is isopropyl, methyl, ethyl; each represents a separate embodiment according to this invention. In some embodiments, $R_7'''$ is $C_1$-$C_5$ linear or branched substituted alkyl. In some embodiments, $R_7'''$ is isopropyl. In some embodiments, $R_7'''$ is methyl. In some embodiments, $R_7'''$ is ethyl. In some embodiments, $R_7'''$ is $C_1$-$C_5$ linear or branched, or $C_3$-$C_8$ cyclic alkoxy optionally wherein at least one methylene group (CH$_2$) in the alkoxy is replaced with an oxygen atom. In some embodiments, $R_7'''$ is $C_1$-$C_5$ linear or branched alkoxy. In some embodiments, $R_7'''$ is methoxy. In some embodiments, $R_7'''$ is $C_1$-$C_5$ linear or branched, or $C_3$-$C_8$ cyclic haloalkyl. In some embodiments, $R_{17}'''$ is $C_1$-$C_5$ linear or branched haloalkyl. In some embodiments, the haloalkyl is CHF$_2$. In some embodiments, $R_7'''$ is $C_3$-$C_8$ cyclic haloalkyl. In some embodiments, $R_7'''$ is substituted or unsubstituted $C_3$-$C_8$ cycloalkyl. In some embodiments, the cycloalkyl is cyclopropyl, cyclobutyl, cyclopentyl, cyclohexyl, or cycloheptyl; each represents a separate embodiment according to this invention. In some embodiments, $R_7'''$ is a substituted or unsubstituted 3-8 membered heterocyclic ring. In some embodiments, $R_7'''$ is morpholine. In some embodiments, $R_7'''$ is pyran. In some embodiments, $R_7'''$ is oxetane. In some embodiments, $R_7'''$ is pyrrolidine. In some embodiments, $R_7'''$ is 3,3-difluoropyrrolidine. In some embodiments, $R_7'''$ is imidazole. In some embodiments, $R_7'''$ is pyrazole. In some embodiments, $R_7'''$ is triazole. In some embodiments, $R_7''''$ is piperazine. In some embodiments, $R_7'''$ is piperidine. In some embodiments, $R_7'''$ is piperidin-2-one. In some embodiments, $R_7''''$ is piperidin-4-ol. In some embodiments, $R_7'''$ is dioxazole. In some embodiments, $R_7'''$ is 2-oxopyrrolidine.

In some embodiments, $R_7''''$ of formula I(i) is H. In some embodiments, $R_7''''$ of formula I(i) is F, Cl, Br, I, OH, O—R$_{20}$, SH, R$_8$—OH, R$_8$—SH, —R$_8$—O—R$_{10}$, R$_8$—(C$_3$-C$_5$ cycloalkyl), R$_8$—(3-8 membered heterocyclic ring), CF$_3$, CD$_3$, OCD$_3$, CN, NO$_2$, —CH$_2$CN, —R$_8$CN, NH$_2$, NHR, N(R)$_2$, NH(R$_{10}$), N(R$_{10}$)(R$_{11}$), R$_8$—N(R$_{10}$)(R$_{11}$), R$_9$—R$_8$—N(R$_{10}$)(R$_{11}$), B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, $C_1$-$C_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), CH(CF$_3$)(NH—R$_{10}$), $C_1$-$C_5$ linear or branched, substituted or unsubstituted alkyl, $C_1$-$C_5$ linear or branched, substituted or unsubstituted alkenyl, $C_1$-$C_5$ linear or branched, or $C_3$-$C_8$ cyclic haloalkyl, $C_1$-$C_5$ linear or branched, or $C_3$-$C_8$ cyclic alkoxy optionally wherein at least one methylene group (CH$_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted 3-8 membered heterocyclic ring, substituted or unsubstituted aryl, or substituted or unsubstituted benzyl; each represents a separate embodiment according to this invention. In some embodiments, $R_7''''$ is further substituted with at least one substitution selected from: F, Cl, Br, I, $C_1$-$C_5$ linear or branched alkyl, OH, alkoxy (e.g., OMe), amide (e.g., C(O)N(R)$_2$, C(O)-pyrrolidine, C(O)-piperidine, N(R)$_2$ NH(R$_{10}$), N(R$_{10}$)(R$_{11}$), (e.g., N(CH$_3$)$_2$, NH$_2$), CF$_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and NO$_2$; each represents a separate embodiment according to this invention.

In some embodiments, $R_7''''$ of formula I(i) is H. In some embodiments, $R_7''''$ is F. In some embodiments, $R_7''''$ is Cl. In some embodiments, $R_7''''$ is Br. In some embodiments, $R_7''''$ is I. In some embodiments, $R_{17}''''$ is CF$_3$. In some embodiments, $R_7''''$ is $C_1$-$C_5$ linear or branched, substituted or unsubstituted alkyl. In some embodiments, $R_7''''$ is $C_1$-$C_5$ linear or branched unsubstituted alkyl. In some embodiments, the alkyl is isopropyl, methyl, ethyl; each represents a separate embodiment according to this invention. In some embodiments, $R_7''''$ is $C_1$-$C_5$ linear or branched substituted alkyl. In some embodiments, $R_7''''$ is isopropyl. In some embodiments, $R_7''''$ is methyl. In some embodiments, $R_7''''$ is ethyl. In some embodiments, $R_7''''$ is $C_1$-$C_5$ linear or branched, or $C_3$-$C_5$ cyclic alkoxy optionally wherein at least one methylene group (CH$_2$) in the alkoxy is replaced with an oxygen atom. In some embodiments, $R_7''''$ is $C_1$-$C_5$ linear or branched alkoxy. In some embodiments, $R_7''$ is methoxy. In some embodiments, $R_7''''$ is $C_1$-$C_5$ linear or branched, or $C_3$-$C_5$ cyclic haloalkyl. In some embodiments, $R_7''''$ is $C_1$-$C_5$ linear or branched haloalkyl. In some embodiments, the haloalkyl is CHF$_2$. In some embodiments, $R_7''''$ is $C_3$-$C_5$ cyclic haloalkyl. In some embodiments, $R_7''''$ is substituted or unsubstituted $C_3$-$C_5$ cycloalkyl. In some embodiments, the cycloalkyl is cyclopropyl, cyclobutyl, cyclopentyl, cyclohexyl, or cycloheptyl; each represents a separate embodiment according to this invention. In some embodiments, $R_7''''$ is a substituted or unsubstituted 3-8 membered heterocyclic ring. In some embodiments, $R_7''''$ is morpholine. In some embodiments, $R_7''''$ is pyran. In some embodiments, $R_7''''$ is oxetane. In some embodiments, $R_7''''$ is pyrrolidine. In some embodiments, $R_7''''$ is 3,3-difluoropyrrolidine. In some embodiments, $R_7''''$ is imidazole. In some embodiments, $R_7''''$ is pyrazole. In some embodiments, $R_7''''$ is triazole. In some embodiments, $R_7''''$ is piperazine. In some embodiments, $R_7''''$ is piperidine. In some embodiments, $R_7''''$ is piperidin-2-one. In some embodiments, $R_7''''$ is piperidin-4-ol. In some embodiments, $R_7''''$ is dioxazole. In some embodiments, $R_7''''$ is 2-oxopyrrolidine.

In some embodiments, $R_7'$ and $R_7''$ of formula I(i) are joined to form a 3-8 membered substituted or unsubstituted, saturated, unsaturated or aromatic, carbocyclic or heterocyclic ring. In some embodiments, $R_7'$ and $R_7''$ are joined to form a 5 membered unsubstituted saturated or unsaturated carbocyclic ring. In some embodiments, $R_7'$ and $R_7''$ are joined to form a cyclopentane. In some embodiments, $R_7'$ and $R_7''$ are joined to form 6 membered unsubstituted saturated or unsaturated carbocyclic ring. In some embodiments, $R_7'$ and $R_7''$ are joined to form a cyclohexane. In some embodiments, $R_7'$ and $R_7''$ are joined to form a 5 membered substituted saturated or unsaturated carbocyclic ring. In some embodiments, $R_7'$ and $R_7''$ are joined to form 6 membered substituted saturated or unsaturated carbocyclic ring. In some embodiments, $R_7'$ and $R_7''$ are joined to form a 6 membered substituted or unsubstituted, aromatic, carbocyclic ring. In some embodiments, $R_7'$ and $R_7''$ are joined to form a 5 or 6 membered substituted or unsubstituted, aromatic, heterocyclic ring. In some embodiments, $R_7'$ and $R_7''$ are joined to form a 5 or 6 membered substituted or unsubstituted, heterocyclic ring. In some embodiments, $R_7'$ and $R_7''$ are joined to form a 6 membered substituted or unsubstituted, heterocyclic ring. In some embodiments, $R_7'$ and $R_7''$ are joined to form a piperidine. In some embodiments, $R_7'$ and $R_7''$ are joined to form a tetrahydropyran. In some embodiments, $R_7'$ and $R_7''$ are joined to form a 5 membered substituted or unsubstituted, heterocyclic ring. In some embodiments, $R_7'$ and $R_7''$ are joined to form a tetrahydrofuran. In some embodiments, $R_7'$ and $R_7''$ are joined to form a pyrrolidine.

In some embodiments, $R_7'$ and $R_7''$ of formula I(i) are different. In some embodiments, $R_7'$ and $R_7''$ of formula I(i) are not H, F, Cl, $C_1$-$C_5$ linear or branched, or $C_3$-$C_5$ cyclic alkoxy, $C_1$-$C_5$ linear or branched haloalkoxy or $C_1$-$C_5$ linear or branched, substituted or unsubstituted alkyl; each represents a separate embodiment according to this invention.

In some embodiments, $R_7''$ and $R_7$ of formula I(i) are joined to form a 3-8 membered substituted or unsubstituted, saturated, unsaturated or aromatic, carbocyclic or heterocyclic ring. In some embodiments, $R_7''$ and $R_7$ are joined to form a 5 membered unsubstituted saturated or unsaturated carbocyclic ring. In some embodiments, $R_7''$ and $R_7$ are joined to form a cyclopentane. In some embodiments, $R_7''$ and $R_7$ are joined to form 6 membered unsubstituted saturated or unsaturated carbocyclic ring. In some embodiments, $R_7''$ and $R_7$ are joined to form a cyclohexane. In some embodiments, $R_7''$ and $R_7$ are joined to form a 5 membered substituted saturated or unsaturated carbocyclic ring. In some embodiments, $R_7''$ and $R_7$ are joined to form 6 membered substituted saturated or unsaturated carbocyclic ring. In some embodiments, $R_7'$ and $R_7''$ are joined to form a 6 membered substituted or unsubstituted, aromatic, carbocyclic ring. In some embodiments, $R_7''$ and $R_7$ are joined to form a 5 or 6 membered substituted or unsubstituted, aromatic, heterocyclic ring. In some embodiments, $R_7''$ and $R_7$ are joined to form a 5 or 6 membered substituted or unsubstituted, heterocyclic ring. In some embodiments, $R_7''$ and $R_7$ are joined to form a 6 membered substituted or unsubstituted, heterocyclic ring. In some embodiments, $R_7''$ and $R_7$ are joined to form a piperidine. In some embodiments, $R_7''$ and $R_7$ are joined to form a tetrahydropyran. In some embodiments, $R_7''$ and $R_7$ are joined to form a 5 membered substituted or unsubstituted, heterocyclic ring. In some embodiments, $R_7''$ and $R_7$ are joined to form a tetrahydrofuran. In some embodiments, $R_7''$ and $R_7$ are joined to form a pyrrolidine.

In some embodiments, $R_7''$ and $R_7$ of formula I(i) are different. In some embodiments, $R_7''$ and $R_7$ of formula I(i) are not H, F, Cl, $C_1$-$C_5$ linear or branched, or $C_3$-$C_5$ cyclic alkoxy, $C_1$-$C_5$ linear or branched haloalkoxy or $C_1$-$C_5$ linear or branched, substituted or unsubstituted alkyl; each represents a separate embodiment according to this invention.

In some embodiments, $R_7$ and $R_7'''$ of formula I(i) are joined to form a 3-8 membered substituted or unsubstituted, saturated, unsaturated or aromatic, carbocyclic or heterocyclic ring. In some embodiments, $R_7$ and $R_7'''$ are joined to form a 5 membered unsubstituted saturated or unsaturated carbocyclic ring. In some embodiments, $R_7$ and $R_7'''$ are joined to form 6 membered unsubstituted saturated or unsaturated carbocyclic ring. In some embodiments, $R_7$ and $R_7'''$ are joined to form a 5 membered substituted saturated or unsaturated carbocyclic ring. In some embodiments, $R_7$ and $R_7'''$ are joined to form 6 membered substituted saturated or unsaturated carbocyclic ring. In some embodiments, $R_7$ and $R_7'''$ are joined to form a 6 membered substituted or unsubstituted, aromatic, carbocyclic ring. In some embodiments, $R_7$ and $R_7'''$ are joined to form a 5 or 6 membered substituted or unsubstituted, aromatic, heterocyclic ring. In some embodiments, $R_7$ and $R_7'''$ are joined to form a 5 or 6 membered substituted or unsubstituted, heterocyclic ring. In some embodiments, $R_7$ and $R_7'''$ are joined to form a 6 membered substituted or unsubstituted, heterocyclic ring. In some embodiments, $R_7$ and $R_7'''$ are joined to form a piperidine. In some embodiments, $R_7$ and $R_7'''$ are joined to form a tetrahydrofuran. In some embodiments, $R_7$ and $R_7'''$ are joined to form a tetrahydropyran. In some embodiments, $R_7$ and $R_7'''$ are joined to form a 5 membered substituted or unsubstituted, heterocyclic ring. In some embodiments, $R_7$ and $R_7'''$ are joined to form a pyrrolidine. In some embodiments, $R_7$ and $R_7'''$ are joined to form a cyclopentane. In some embodiments, $R_7$ and $R_7'''$ are joined to form a cyclohexane.

In some embodiments, $R_7$ and $R_7'''$ of formula I(i) are different. In some embodiments, $R_7$ and $R_7'''$ of formula I(i) are not H, F, Cl, $C_1$-$C_5$ linear or branched, or $C_3$-$C_5$ cyclic alkoxy, $C_1$-$C_5$ linear or branched haloalkoxy or $C_1$-$C_5$ linear or branched, substituted or unsubstituted alkyl; each represents a separate embodiment according to this invention.

In some embodiments, $R_7'''$ and $R_7''''$ of formula I(i) are joined to form a 3-8 membered substituted or unsubstituted, saturated, unsaturated or aromatic, carbocyclic or heterocyclic ring. In some embodiments, $R_7'''$ and $R_7''''$ are joined to form a 5 membered unsubstituted saturated or unsaturated carbocyclic ring. In some embodiments, $R_7'''$ and $R_7''''$ are joined to form 6 membered unsubstituted saturated or unsaturated carbocyclic ring. In some embodiments, $R_7'''$ and $R_7''''$ are joined to form a 5 membered substituted saturated or unsaturated carbocyclic ring. In some embodiments, $R_7'''$ and $R_7''''$ are joined to form 6 membered substituted saturated or unsaturated carbocyclic ring. In some embodiments, $R_7'''$ and $R_7''''$ are joined to form a 6 membered substituted or unsubstituted, aromatic, carbocyclic ring. In some embodiments, $R_7'''$ and $R_7''''$ are joined to form a 5 or 6 membered substituted or unsubstituted, aromatic, heterocyclic ring. In some embodiments, $R_7'''$ and $R_7''''$ are joined to form a 5 or 6 membered substituted or unsubstituted, heterocyclic ring. In some embodiments, $R_7'''$ and $R_7''''$ are joined to form a 6 membered substituted or unsubstituted, heterocyclic ring. In some embodiments, $R_7'''$ and $R_7''''$ are joined to form a piperidine. In some embodiments, $R_7'''$ and $R_7''''$ are joined to form a tetrahydrofuran. In some embodiments, $R_7'''$ and $R_7''''$ are joined to form a tetrahydropyran. In some embodiments, $R_7'''$ and $R_7''''$ are joined to form a 5 membered substituted or unsubstituted, heterocyclic ring. In some embodiments, $R_7'''$ and $R_7''''$ are joined to form a pyrrolidine. In some embodiments, $R_7'''$ and $R_7''''$ are joined to form a cyclopentane. In some embodiments, $R_7'''$ and $R_7''''$ are joined to form a cyclohexane.

In some embodiments, $R_7'''$ and $R_7''''$ of formula I(i) are different. In some embodiments, $R_7'''$ and $R_7''''$ of formula I(i) are not H, F, Cl, $C_1$-$C_5$ linear or branched, or $C_3$-$C_8$ cyclic alkoxy, $C_1$-$C_5$ linear or branched haloalkoxy or $C_1$-$C_5$ linear or branched, substituted or unsubstituted alkyl; each represents a separate embodiment according to this invention.

In some embodiments, at least two of $R_7$, $R_7'$, $R_7''$, $R_7'''$ and $R_7''''$ are not H. In some embodiments, at least three of $R_7$, $R_7'$, $R_7''$, $R_7'''$ and $R_7''''$ are not H In some embodiments, $R_{30}$ of formula I, II and/or I(a)-I(o) is H, $R_{20}$, F, Cl, Br, I, OH, SH, alkoxy, $N(R)_2$, $NH(R_{10})$, $N(R_{10})(R_{11})$, $CF_3$, CN, $NO_2$, $C_1$-$C_5$ linear or branched, substituted or unsubstituted alkyl, methyl, ethyl, $CH_2$—$CH_2$—O—$CH_2$—$CH_2$—O—$CH_3$, $CH_2$—O—$CH_2$—$CH_2$—O—$CH_3$, $C_1$-$C_5$ linear or branched alkoxy, $C_1$-$C_5$ linear or branched haloalkyl, $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—CH$(CH_3)_2$, $R_8$-aryl, —$R_8$—O—$R_8$—O—$R_{10}$, $(CH_2)_2$—O—$(CH_2)_2$O—$CH_3$, —$R_8$—O—$R_{10}$, —$R_8$—$R_{10}$, $(CH_2)_2$O—$CH_3$, substituted or unsubstituted aryl, phenyl, $CH_2$-Ph, substituted or unsubstituted heteroaryl, or pyridine; each represents a separate embodiment according to this invention.

In some embodiments, $R_{30}$ is further substituted with at least one substitution selected from: F, Cl, Br, I, $C_1$-$C_5$ linear or branched alkyl, OH, alkoxy (e.g., OMe), amide (e.g., $C(O)N(R)_2$, C(O)-pyrrolidine, C(O)-piperidine, $N(R)_2$ $NH(R_{10})$, $N(R_{10})(R_{11})$, (e.g., $N(CH_3)_2$, $NH_2$), $CF_3$, aryl, phenyl, heteroaryl, substituted or unsubstituted $C_3$-$C_8$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and $NO_2$; each represents a separate embodiment according to this invention. In some embodiments, $R_{30}$ is H. In some embodiments, $R_{30}$ is alkyl. In some embodiments, $R_{30}$ is methyl. In some embodiments, $R_{30}$ is $R_{20}$.

In some embodiments, R of formula I, II and/or I(a)-I(o) is H, F, Cl, Br, I, OH, SH, alkoxy, $NH(R_{10})$, $N(R_{10})(R_{11})$, $CF_3$, CN, $NO_2$, COOH, $C_1$-$C_5$ linear or branched, substituted or unsubstituted alkyl, $C_1$-$C_5$ linear or branched alkoxy, $C_1$-$C_5$ linear or branched haloalkyl, $R_8$-aryl, —$R_8$—O—$R_8$—O—$R_{10}$, —$R_8$—O—$R_{10}$, —$R_8$—$R_{10}$, substituted or unsubstituted aryl, or substituted or unsubstituted heteroaryl; each represents a separate embodiment according to this invention. In some embodiments, R is further substituted with at least one substitution selected from: F, Cl, Br, I, $C_1$-$C_5$ linear or branched alkyl, OH, alkoxy (e.g., OMe), amide (e.g., $C(O)N(R)_2$, C(O)-pyrrolidine, C(O)-piperidine, $N(R)_2$ $NH(R_{10})$, $N(R_{10})(R_{11})$, (e.g., $N(CH_3)_2$, $NH_2$), $CF_3$, aryl, phenyl, heteroaryl, substituted or unsubstituted $C_3$-$C_8$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and $NO_2$; each represents a separate embodiment according to this invention. In some embodiments, R is H. In some embodiments, R is $NH(R_{10})$. In some embodiments, R is NH—$CH_2$-cyclopropyl. In some embodiments, R is $C_1$-$C_5$ linear or branched, substituted or unsubstituted alkyl. In some embodiments, R is methyl. In some embodiments, R is ethyl. In some embodiments, R is propyl. In some embodiments, R is isopropyl. In some embodiments, R is butyl. In some embodiments, R is substituted alkyl. In some embodiments, R is $CH_2$—OH. In some embodiments, R is $CH_2$—$CH_2$—OH. In some embodiments, R is $C_3$-$C_8$ substituted or unsubstituted cycloalkyl. In some embodiments, R is cyclopropyl. In some embodiments, R is $C_1$-$C_5$ linear or branched alkoxy. In some embodiments, R is methoxy. In some embodiments, R is ethoxy. In some embodiments, R is propoxy. In some embodiments, R is isopropoxy. In some embodiments, R is COOH. In some embodiments, R is $R_8$—O—$R_{10}$. In some embodiments, R is $CH_2$—OH. In some embodiments, R is $CH_2$—$CH_2$—OH.

In various embodiments, each $R_8$ of compound of formula I, II and/or I(a)-I(o) is independently $CH_2$. In some embodiments, $R_8$ is $CH_2CH_2$. In some embodiments, $R_5$ is $CH_2CH_2CH_2$. In some embodiments, $R_8$ is $CH_2CH_2CH_2CH_2$.

In some embodiments, p of formula I, II and/or I(a)-I(o) is 1. In other embodiments, p is 2. In other embodiments, p is 3. In some embodiments, p is 4. In some embodiments, p is 5. In some embodiments, p is between 1 and 3. In some embodiments, p is between 1 and 5. In some embodiments, p is between 1 and 10.

In some embodiments, $R_9$ of formula I, II and/or I(a)-I(o) is C≡C. In some embodiments, $R_9$ is C≡C—C≡C. In some embodiments, $R_9$ is CH=CH. In some embodiments, $R_9$ is CH=CH—CH=CH.

In some embodiments, q of formula I, II and/or I(a)-I(o) is 2. In some embodiments, q is 4. In some embodiments, q is 6. In some embodiments, q is 8. In some embodiments, q is between 2 and 6.

In some embodiments, $R_{10}$ of formula I, II and/or I(a)-I(o) is H, $C_1$-$C_5$ substituted or unsubstituted linear or branched alkyl (e.g., methyl, ethyl, $CH_2$-cyclopropyl, $CH_2$—$CH_2$—O—$CH_3$; each represents a separate embodiment according to this invention), $C_1$-$C_5$ substituted or unsubstituted linear or branched haloalky, $CH_2CF_3$, $C_1$-$C_5$ linear or branched alkoxy (e.g., O—$CH_3$), $R_{20}$, C(O)R, or $S(O)_2R$; each represents a separate embodiment according to this invention. In some embodiments, $R_{10}$ is H. In some embodiments, $R_{10}$ is $C_1$-$C_5$ substituted or unsubstituted linear or branched alkyl. In some embodiments, $R_{10}$ is $C_1$-$C_5$ unsubstituted linear or branched alkyl. In other embodiments, $R_{10}$ is $CH_3$. In other embodiments, $R_{10}$ is $CH_2CH_3$. In other embodiments, $R_{10}$ is $CH_2CH_2CH_3$. In some embodiments, $R_{10}$ is isopropyl. In some embodiments, $R_{10}$ is butyl. In some embodiments, $R_{10}$ is isobutyl. In some embodiments, $R_{10}$ is t-butyl. In some embodiments, $R_{10}$ is pentyl. In some embodiments, $R_{10}$ is isopentyl. In some embodiments, $R_{10}$ is neopentyl. In some embodiments, $R_{10}$ is benzyl. In some embodiments, $R_{10}$ is $C_1$-$C_5$ substituted linear or branched alkyl. In other embodiments, $R_{10}$ is $CH_2$—$CH_2$—O—$CH_3$. In other embodiments, $R_{10}$ is $CH_2CF_3$. In other embodiments, $R_{10}$ is $C_1$-$C_5$ substituted or unsubstituted linear or branched haloalkyl. In other embodiments, $R_{10}$ is $C_1$-$C_5$ linear or branched alkoxy. In other embodiments, $R_{10}$ is O—$CH_3$. In other embodiments, $R_{10}$ is $R_{20}$. In other embodiments, $R_{10}$ is C(O)R. In other embodiments, $R_{10}$ is $S(O)_2R$. In some embodiments, $R_{10}$ is further substituted with at least one substitution selected from: F, Cl, Br, I, $C_1$-$C_5$ linear or branched alkyl, OH, alkoxy (e.g., OMe), amide (e.g., $C(O)N(R)_2$, C(O)-pyrrolidine, C(O)-piperidine, $N(R)_2$ $NH(R_{10})$, $N(R_{10})(R_{11})$, (e.g., $N(CH_3)_2$, $NH_2$), $CF_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and $NO_2$; each represents a separate embodiment according to this invention.

In some embodiments, $R_{11}$ of formula I, II and/or I(a)-I(o) is H, $C_1$-$C_5$ substituted or unsubstituted linear or branched alkyl (e.g., methyl, ethyl, $CH_2$—$CH_2$—O—$CH_3$, $CH_2CF_3$, $C_1$-$C_5$ linear or branched alkoxy (e.g., O—$CH_3$), C(O)R, or $S(O)_2R$; each represents a separate embodiment according to this invention. In some embodiments, $R_{11}$ is H. In some embodiments, $R_{11}$ is $C_1$-$C_5$ substituted or unsubstituted linear or branched alkyl. In some embodiments, $R_{11}$ is $C_1$-$C_5$ unsubstituted linear or branched alkyl. In other embodiments, $R_{11}$ is $CH_3$. In other embodiments, $R_{11}$ is $CH_2CH_3$. In other embodiments, $R_{11}$ is $CH_2CH_2CH_3$. In some embodiments, $R_{11}$ is isopropyl. In some embodiments, $R_{11}$ is butyl. In some embodiments, $R_{11}$ is isobutyl. In some embodiments, $R_{11}$ is t-butyl. In some embodiments, $R_{11}$ is pentyl. In some embodiments, $R_{11}$ is isopentyl. In some embodiments, $R_{11}$ is neopentyl. In some embodiments, $R_{11}$ is benzyl. In some embodiments, $R_{11}$ is $C_1$-$C_5$ substituted linear or branched alkyl. In other embodiments, $R_{11}$ is $CH_2$—$CH_2$—$O$—$CH_3$. In other embodiments, $R_{11}$ is $CH_2CF_3$. In other embodiments, $R_{11}$ is $C_1$-$C_5$ substituted or unsubstituted linear or branched haloalkyl. In other embodiments, $R_{11}$ is $C_1$-$C_5$ linear or branched alkoxy. In other embodiments, $R_{11}$ is $O$—$CH_3$. In other embodiments, $R_{11}$ is $R_{20}$. In other embodiments, $R_{11}$ is $C(O)R$. In other embodiments, $R_{11}$ is $S(O)_2R$. In some embodiments, $R_{11}$ is further substituted with at least one substitution selected from: F, Cl, Br, I, $C_1$-$C_5$ linear or branched alkyl, OH, alkoxy (e.g., OMe), amide (e.g., $C(O)N(R)_2$, $C(O)$-pyrrolidine, $C(O)$-piperidine, $N(R)_2$ $NH(R_{10})$, $N(R_{10})(R_{11})$, (e.g., $N(CH_3)_2$, $NH_2$), $CF_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and $NO_2$; each represents a separate embodiment according to this invention.

In some embodiments, $R_{10}$ and $R_{11}$ of formula I, II and/or I(a)-I(o) are joined to form a substituted or unsubstituted 3-8 membered heterocyclic ring. In other embodiments, $R_{10}$ and $R_{11}$ are joined to form a piperazine ring. In other embodiments, $R_{10}$ and $R_{11}$ are joined to form a piperidine ring. In some embodiments, substitutions include: F, Cl, Br, I, $C_1$-$C_5$ linear or branched alkyl, OH, alkoxy, OMe, amide, $C(O)N(R)_2$, $C(O)$-pyrrolidine, $C(O)$-piperidine, $N(R)_2$, $NH(R_{10})$, $N(R_{10})(R_{11})$, $N(CH_3)_2$, $NH_2$, $CF_3$, aryl, phenyl, heteroaryl, substituted or unsubstituted $C_3$-$C_5$ cycloalkyl, cyclobutanol, substituted or unsubstituted 3-8 membered heterocyclic ring pyran, oxetane, piperidine, pyrazole, methyl-pyrrazole, triazole, imidazole, halophenyl, (benzyloxy)phenyl, CN, and $NO_2$; each represents a separate embodiment according to this invention.

In some embodiments, n of formula I, II, I(a)-I(h) and/or I(j)-I(o) is an integer between 0 and 4. In some embodiments, n of formula I(c) is an integer between 1 and 4. In some embodiments, n of formula I, II, I(a)-I(h) and/or I(j)-I(n) is 0. In some embodiments, n of formula I, II, I(a)-I(h) and/or I(j)-I(n) is 1. In some embodiments, n of formula I, II, I(a)-I(h) and/or I(j)-I(n) is 2. In some embodiments, n of formula I, II, I(a)-I(h) and/or I(j)-I(n) is 3. In some embodiments, n of formula I, II, I(a)-I(h) and/or I(j)-I(n) is 4. In some embodiments, n of formula I, II, I(a)-I(h) and/or I(j)-I(n) is 1 or 2.

In some embodiments, A' of formula I(f) is a 3-8 membered single or fused saturated, unsaturated or aromatic heterocyclic ring. In some embodiments, A' is a 3-8 membered single heterocyclic ring. In some embodiments, A' is a fused 4-10 membered heterocyclic ring. In some embodiments, A' is a single aromatic 3-8 membered heterocyclic ring. In some embodiments, A' is a fused aromatic 3-10 membered heterocyclic ring. In some embodiments, A' is a saturated 3-8 membered single heterocyclic ring. In some embodiments, A' is piperidine. In some embodiments, A' is pyrrolidine. In some embodiments, A' is piperazine. In some embodiments, A' is morpholine. In some embodiments, A' is a pyridinyl. In other embodiments, A' is 2-pyridinyl. In other embodiments, A' is 3-pyridinyl. In other embodiments, A' is 4-pyridinyl. In other embodiments, A' is pyrimidine. In other embodiments, A' is pyridazine. In other embodiments, A' is pyrazine. In other embodiments, A' is pyrazole. In other embodiments, A' is benzothiazolyl. In other embodiments, A' is benzimidazolyl. In other embodiments, A' is quinolinyl. In other embodiments, A' is isoquinolinyl. In other embodiments, A' is indolyl. In other embodiments, A' is indenyl. In other embodiments, A' is benzofuran-2(3H)-one. In other embodiments, A' is benzo[d][1,3]dioxole. In other embodiments, A' is tetrahydrothiophenel, 1-dioxide. In other embodiments, A' is thiazole. In other embodiments, A' is benzimidazole. In others embodiment, A' is piperidine. In other embodiments, A' is imidazole. In other embodiments, A' is thiophene. In other embodiments, A' is isoquinoline. In other embodiments, A' is indole. In other embodiments, A' is 1,3-dihydroisobenzofuran. In other embodiments, A' is benzofuran. In other embodiments, A' is tetrahydro-2H-pyran. In other embodiments, A' is isothiazolyl. In other embodiments, A' is thiadiazolyl. In other embodiments, A' is triazolyl. In other embodiments, A' is thiazolyl. In other embodiments, A' is oxazolyl. In other embodiments, A' is isoxazolyl. In other embodiments, A' is pyrrolyl. In other embodiments, A' is furanyl. In other embodiments, A' is oxadiazolyl. In other embodiments, A' is 1,2,3-, 1,2,4-, 1,2,5- or 1,3,4-oxadiazolyl; each is a separate embodiment according to this invention. In other embodiments, A' is tetrahydrofuranyl. In other embodiments, A' is oxazolonyl. In other embodiments, A' is oxazolidonyl. In other embodiments, A' is thiazolonyl. In other embodiments, A' is isothiazolinonyl. In other embodiments, A' is isoxazolidinonyl. In other embodiments, A' is imidazolidinonyl. In other embodiments, A' is pyrazolonyl. In other embodiments, A' is 2H-pyrrol-2-onyl. In other embodiments, A' is furanonyl. In other embodiments, A' is thiophenonyl. In other embodiments, A' is thiane 1,1 dioxide. In other embodiments, A' is triazolopyrimidine. In other embodiments, A' is 3H-[1,2,3]triazolo[4,5-d]pyrimidine, 1H-[1,2,3]triazolo[4,5-d]pyrimidine, [1,2,4]triazolo[4,3-c]pyrimidine, [1,2,4]triazolo[4,3-a]pyrimidine, [1,2,4]triazolo[1,5-a]pyrimidine, [1,2,3]triazolo[1,5-c]pyrimidine, [1,2,4]triazolo[1,5-a]pyrimidine or [1,2,4]triazolo[1,5-c]pyrimidine; each is a separate embodiment according to this invention. In other embodiments, A' is 6,7-dihydro-5H-pyrazolo[5,1-b][1,3]oxazine. In other embodiments, A' is 1,2,3,4-tetrahydronaphthalene. In other embodiments, A' is chroman. In other embodiments, A' is isochroman. In other embodiments, A' is 1,2,3,4-tetrahydroquinoline. In other embodiments, A' is 1,2,3,4-tetrahydroisoquinoline. In other embodiments, A' is 2,3-dihydro-1H-indene. In other embodiments, A' is 2,3-dihydrobenzofuran. In other embodiments, A' is 1,3-dihydroisobenzofuran. In other embodiments, A' is isoindoline. In other embodiments, A' is indoline. In some embodiments, A' of formula I(f) is not a phenyl.

In some embodiments, $R_{100}$ of formula I(g) is H, $C_1$-$C_5$ substituted or unsubstituted linear or branched alkyl (e.g., methyl, ethyl), $R_8$—OH (e.g., $(CH_2)_2$—OH), —$R_8$—O—$R_{10}$ (e.g., $(CH_2)_2O$—$CH_3$), $R_8$—$N(R_{10})(R_{11})$ (e.g., $(CH_2)_2$—$NH(CH_3)$, $(CH_2)_2$—$NH_2$), $R_{20}$, or a substituted or unsubstituted 3-8 membered heterocyclic ring (e.g., pyrrolidine, piperidine); each represents a separate embodiment according to this invention. In some embodiments, $R_{100}$ is H. In some embodiments, $R_{100}$ is $C_1$-$C_5$ substituted or unsubstituted linear or branched alkyl. In some embodiments, $R_{100}$ is $C_1$-$C_5$ unsubstituted linear or branched alkyl. In other embodiments, $R_{100}$ is $CH_3$. In other embodiments, $R_{100}$ is $CH_2CH_3$. In other embodiments, $R_{100}$ is $CH_2CH_2CH_3$. In some embodiments, $R_{100}$ is isopropyl. In some embodiments, $R_{100}$ is butyl. In some embodiments, $R_{100}$ is isobutyl. In some embodiments, $R_{100}$ is t-butyl. In some embodiments, $R_{100}$ is pentyl. In some embodiments, $R_{100}$ is isopentyl. In some embodiments, $R_{100}$ is neopentyl. In some embodiments, $R_{100}$ is benzyl. In some embodiments, $R_{100}$ is $C_1$-$C_5$ substituted linear or branched alkyl. In other embodiments, $R_{100}$ is $CH_2$—$CH_2$—$O$—$CH_3$. In other embodiments, $R_{100}$ is $CH_2$—$CH_2$—$OH$. In other embodiments, $R_{100}$ is $R_8$—$OH$. In other embodiments, $R_{100}$ is $(CH_2)_2$—$OH$. In other embodiments, $R_{100}$ is —$R_8$—$O$—$R_{10}$. In other embodiments, $R_{100}$ is $(CH_2)_2O$—$CH_3$. In other embodiments, $R_{100}$ is $R_8$—$N(R_{10})(R_{11})$. In other embodiments, $R_{100}$ is $(CH_2)_2$—$NH(CH_3)$. In other embodiments, $R_{100}$ is $(CH_2)_2$—$NH_2$. In other embodiments, $R_{100}$ is $R_{20}$ as defined hereinabove. In other embodiments, $R_{100}$ is a substituted or unsubstituted 3-8 membered heterocyclic ring. In other embodiments, $R_{100}$ is pyrrolidine. In other embodiments, $R_{100}$ is piperidine. In other embodiments, $R_{100}$ is $C_1$-$C_5$ substituted or unsubstituted linear or branched haloalkyl. In other embodiments, $R_{100}$ is $C_1$-$C_5$ linear or branched alkoxy. In other embodiments, $R_{100}$ is $O$—$CH_3$. In other embodiments, $R_{100}$ is $C(O)R$. In other embodiments, $R_{100}$ is $S(O)_2R$. In some embodiments, $R_{100}$ is further substituted with at least one substitution selected from: F, Cl, Br, I, $C_1$-$C_5$ linear or branched alkyl, OH, alkoxy (e.g., OMe), amide (e.g., $C(O)N(R)_2$, $C(O)$-pyrrolidine, $C(O)$-piperidine, $N(R)_2$ $NH(R_{10})$, $N(R_{10})(R_{11})$, (e.g., $N(CH_3)_2$, $NH_2$), $CF_3$, aryl, phenyl, heteroaryl, substituted or unsubstituted $C_3$-$C_8$ cycloalkyl (e.g., cyclobutanol), substituted or unsubstituted 3-8 membered heterocyclic ring (e.g. pyran, oxetane, piperidine, pyrazole, methyl-pyrrazole, triazole, imidazole), halophenyl, (benzyloxy)phenyl, CN and $NO_2$; each represents a separate embodiment according to this invention.

In some embodiments, Ring W of formula I(j) and/or I(n) is a 3-10 membered single, fused, bridged or spiro, saturated, unsaturated or aromatic, carbocyclic or heterocyclic ring. In some embodiments, Ring W is a 3-8 membered single saturated heterocyclic ring. In some embodiments, Ring W is morpholine (e.g., 2 or 3-morpholine), tetrahydrofuran, tetrahydropyran, oxetane, pyrrolidine, piperazine, piperidine; each represents a separate embodiment according to this invention. In some embodiments, Ring W is further substituted with $R_{200}$ to form a substituted heterocyclic ring, including but not limited to: oxetan-3-ol, pyrrolidin-2-ol, pyrrolidin-3-ol, 3-methoxypyrrolidine, 3-cyanopyrrolidine, 1-methylpyrrolidine, 3-(difluoromethyl) pyrrolidine, 3,3-difluoropyrrolidine, piperidin-3-ol, piperidin-4-ol, piperidine-4-carbonitrile, 4-fluoropiperidine, 2,2-dimethylpyrrolidine, pyrrolidin-3-one-O-methyloxime, 3,3-dimethylmorpholine or 1-methylpiperazine; each represents a separate embodiment according to this invention. In some embodiments, Ring W is a 3-8 membered single unsaturated heterocyclic ring. In some embodiments, Ring W is a pyrrolidin-2-one, pyrrolidin-3-one, pyrrolidinone, pyrrolidin-3-one-O-methyloxime, imidazole, pyrazole, isoxazolidine, piperidine-2-one, piperazine-2-one, oxadiazole, triazole, 2-oxopyrrolidine; each represents a separate embodiment according to this invention. In some embodiments, Ring W is a 3-10 membered spiro, saturated, heterocyclic ring. In some embodiments, Ring W is 4-azaspiro[2.4]heptane, 2-oxa-5-azaspiro[3.4]octane, 1,4-dioxa-6-azaspiro[4.4]nonane, 4,7-diazaspiro[2.5]octane; each represents a separate embodiment according to this invention. In some embodiments, Ring W is a 3-10 membered bridged, saturated, heterocyclic ring. In some embodiments, Ring W is bicyclo[1.1.1]pentane, 2,5-diazabicyclo[2.2.1]heptane; each represents a separate embodiment according to this invention. In some embodiments, Ring W is a 3-8 membered single saturated carbocyclic ring (i.e., cycloalkyl). In some embodiments, Ring W is cyclopropyl.

In some embodiments, $R_{200}$ of formula I(j), I(k), I(l) and/or I(n) is H, $R_{20}$, F, Cl, Br, I, OH, SH, alkoxy, $NH_2$, $N(R)_2$, $NH(R_{10})$, $N(R_{10})(R_{11})$, $CF_3$, CN, $NO_2$, $C_1$-$C_5$ linear or branched, substituted or unsubstituted alkyl, methyl, ethyl, $CH_2$—$CH_2$—$O$—$CH_2$—$CH_2$—$O$—$CH_3$, $CH_2$—$O$—$CH_2$—$CH_2$—$O$—$CH_3$, $C_1$-$C_5$ linear or branched alkoxy, methoxy, $C_1$-$C_5$ linear or branched haloalkyl, $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $R_8$-aryl, $CH_2$-Ph, —$R_8$— $O$—$R_8$—$O$—$R_{10}$, $(CH_2)_2$—$O$—$(CH_2)_2O$—$CH_3$, —$R_8$— $O$—$R_{10}$, —$R_8$—$R_{10}$, $(CH_2)_2O$—$CH_3$, substituted or unsubstituted aryl, phenyl, substituted or unsubstituted heteroaryl, pyridine, 2, 3, or 4-pyridine; each represents a separate embodiment according to this invention. In some embodiments, $R_{200}$ is H. In some embodiments, $R_{200}$ is F. In some embodiments, $R_{200}$ is Cl. In some embodiments, $R_{200}$ is Br. In some embodiments, $R_{200}$ is I. In some embodiments, $R_{200}$ is OH. In some embodiments, $R_{200}$ is SH. In some embodiments, $R_{200}$ is alkoxy. In some embodiments, $R_{200}$ is $NH_2$. In some embodiments, $R_{200}$ is $N(R_{10})(R_{11})$. In some embodiments, $R_{200}$ is $CF_3$. In some embodiments, $R_{200}$ is CN. In some embodiments, $R_{200}$ is $NO_2$. In some embodiments, $R_{200}$ is $C_1$-$C_5$ linear or branched, substituted or unsubstituted alkyl. In some embodiments, $R_{200}$ is methyl or ethyl. In some embodiments, $R_{200}$ is $C_1$-$C_5$ linear or branched alkoxy. In some embodiments, $R_{200}$ is methoxy. In some embodiments, $R_{200}$ is $C_1$-$C_5$ linear or branched haloalkyl. In some embodiments, $R_{200}$ is $CHF_2$. In some embodiments, $R_{200}$ and the carbon atom to which it is connected are $C=O$. In some embodiments, $R_{200}$ and the carbon atom to which it is connected are $C=N$—$O(R)$. In some embodiments, $R_{200}$ and the carbon atom to which it is connected are $C=NO$—$CH_3$. In some embodiments, $R_{200}$ and the carbon atom to which it is connected are $C(R)_2$. In some embodiments, $R_{200}$ and the carbon atom to which it is connected are $C(CH_3)_2$. In some embodiments, $R_{200}$ and the carbon atom to which it is connected are $CF_2$.

In some embodiments, $W_1$ of formula I(j), I(k) and/or I(m) is $CH_2$. In some embodiments, $W_1$ is $C=O$. In some embodiments, $W_1$ is $CH(R_{10})$. In some embodiments, $W_1$ is $CHCH_3$.

In some embodiments, $Q_1$ of formula I(k) is O. In some embodiments, $Q_1$ is NH. In some embodiments, $Q_1$ is $CH_2$. In some embodiments, $Q_1$ is $CH(R)$. In some embodiments, $Q_1$ is $C(R)_2$. In some embodiments, $Q_1$ is S. In some embodiments, $Q_1$ is $S=O$. In some embodiments, $Q_1$ is $SO_2$. In some embodiments, $Q_1$ is $C=O$.

In some embodiments, $Q_2$ of formula I(k) is $C=O$. In some embodiments, $Q_2$ is NH. In some embodiments, $Q_2$ is $CH_2$. In some embodiments, $Q_2$ is O. In some embodiments, $Q_2$ is $CH(R)$. In some embodiments, $Q_2$ is $C(R)_2$. In some embodiments, $Q_2$ is S. In some embodiments, $Q_2$ is $S=O$. In some embodiments, $Q_2$ is $SO_2$.

In some embodiments, t of formula I(k) is an integer between 0 and 4. In some embodiments, t is 0. In some embodiments, t is 1. In some embodiments, t is 2. In some embodiments, t is 1 or 2. In some embodiments, t is between 1 and 3. In some embodiments, t is between 0 and 2.

In various embodiments, this invention is directed to the compounds presented in Table 1, pharmaceutical compositions and/or method of use thereof, each represents a separate embodiment according to this invention:

TABLE 1

| Comp. No. | Structure | Compound Name |
|---|---|---|
| 101 | 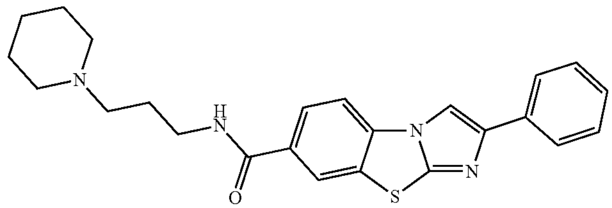 [SMILES: O=C(NCCCN1CCCCC1)c1ccc2c(c1)sc1nc(-c3ccccc3)cn12] | 2-phenyl-N-(3-(piperidin-1-yl)propyl)benzo[d]imidazo[2,1-b]thiazole-7-carboxamide |
| 102 | 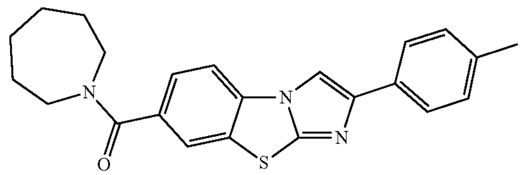 [SMILES: Cc1ccc(-c2cn3c(n2)sc2cc(C(=O)N4CCCCCC4)ccc23)cc1] | Azepan-1-yl(2-(p-tolyl)benzo[d]imidazo[2,1-b]thiazol-7-yl)methanone |
| 103 | 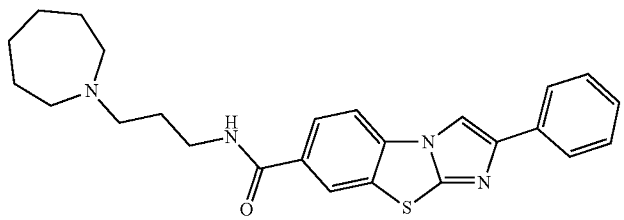 [SMILES: O=C(NCCCN1CCCCCC1)c1ccc2c(c1)sc1nc(-c3ccccc3)cn12] | N-(3-(azepan-1-yl)propyl)-2-phenylbenzo[d]imidazo[2,1-b]thiazole-7-carboxamide |
| 104 | 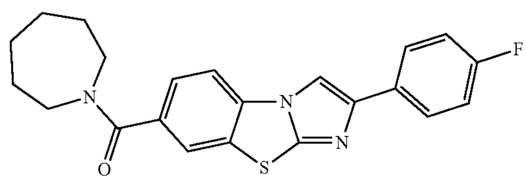 [SMILES: O=C(c1ccc2c(c1)sc1nc(-c3ccc(F)cc3)cn12)N1CCCCCC1] | azepan-1-yl(2-(4-fluorophenyl)benzo[d]imidazo[2,1-b]thiazol-7-yl)methanone |
| 105 | 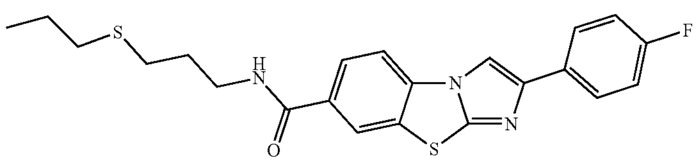 [SMILES: CCCSCCCNC(=O)c1ccc2c(c1)sc1nc(-c3ccc(F)cc3)cn12] | 2-(4-fluorophenyl)-N-(3-(propylthio)propyl)benzo[d]imidazo[2,1-b]thiazole-7-carboxamide |
| 106 | 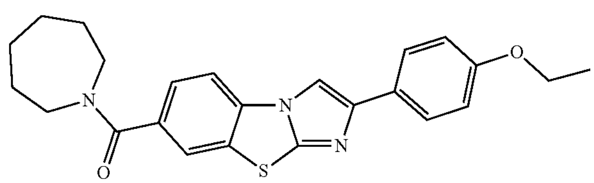 [SMILES: CCOc1ccc(-c2cn3c(n2)sc2cc(C(=O)N4CCCCCC4)ccc23)cc1] | azepan-1-yl(2-(4-ethoxyphenyl)benzo[d]imidazo[2,1-b]thiazol-7-yl)methanone |
| 107 | 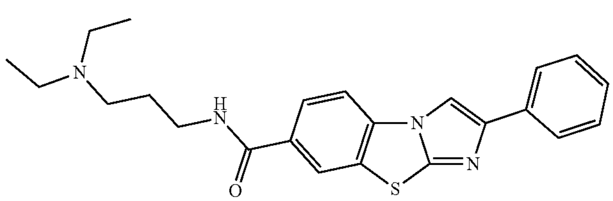 [SMILES: CCN(CC)CCCNC(=O)c1ccc2c(c1)sc1nc(-c3ccccc3)cn12] | N-(3-(diethylamino)propyl)-2-phenylbenzo[d]imidazo[2,1-b]thiazole-7-carboxamide |
| 108 | 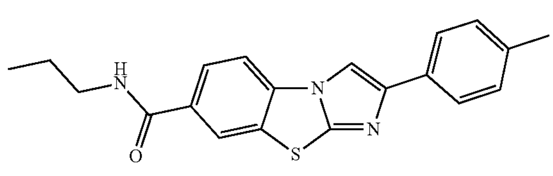 [SMILES: CCCNC(=O)c1ccc2c(c1)sc1nc(-c3ccc(C)cc3)cn12] | N-propyl-2-(p-tolyl)benzo[d]imidazo[2,1-b]thiazole-7-carboxamide |

TABLE 1-continued

| Comp. No. | Structure | Compound Name |
|---|---|---|
| 109 | 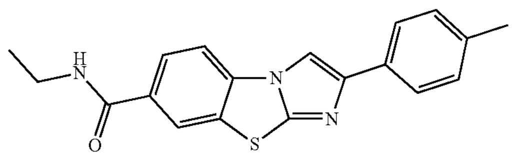 [SMILES: CCNC(=O)c1ccc2c(c1)sc1nc(-c3ccc(C)cc3)cn12] | N-ethyl-2-(p-tolyl)benzo[d]imidazo[2,1-b]thiazole-7-carboxamide |
| 110 | 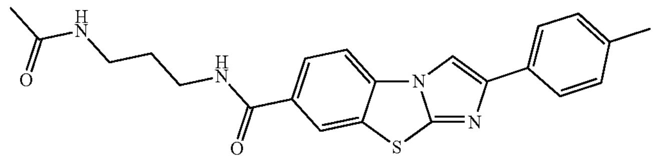 [SMILES: CC(=O)NCCCNC(=O)c1ccc2c(c1)sc1nc(-c3ccc(C)cc3)cn12] | N-(3-acetamidopropyl)-2-(p-tolyl)benzo[d]imidazo[2,1-b]thiazole-7-carboxamide |
| 111 | 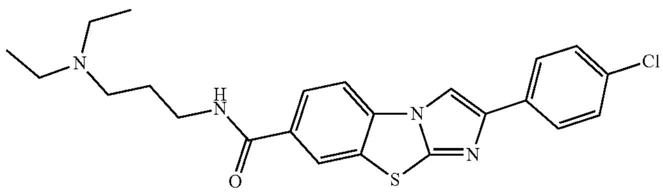 [SMILES: CCN(CC)CCCNC(=O)c1ccc2c(c1)sc1nc(-c3ccc(Cl)cc3)cn12] | 2-(4-chlorophenyl)-N-(3-(diethylamino)propyl)benzo[d]imidazo[2,1-b]thiazole-7-carboxamide |
| 114 | 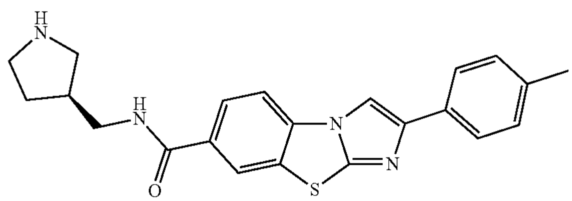 [SMILES: Cc1ccc(-c2cn3c(n2)sc2cc(C(=O)NC[C@H]4CCNC4)ccc23)cc1] | (S)-N-(pyrrolidin-3-ylmethyl)-2-(p-tolyl)benzo[d]imidazo[2,1-b]thiazole-7-carboxamide formate |
| 115 | 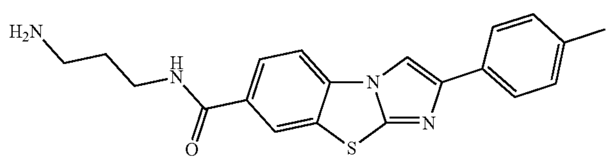 [SMILES: Cc1ccc(-c2cn3c(n2)sc2cc(C(=O)NCCCN)ccc23)cc1] | N-(3-aminopropyl)-2-(p-tolyl)benzo[d]imidazo[2,1-b]thiazole-7-carboxamide |
| 116 | 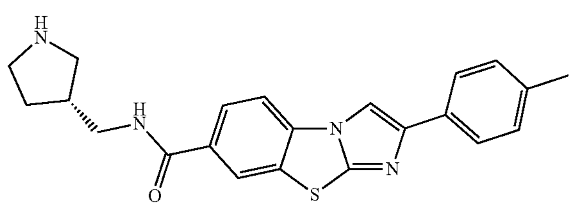 [SMILES: Cc1ccc(-c2cn3c(n2)sc2cc(C(=O)NC[C@@H]4CCNC4)ccc23)cc1] | (R)-N-(pyrrolidin-3-ylmethyl)-2-(p-tolyl)benzo[d]imidazo[2,1-b]thiazole-7-carboxamide formate |
| 117 | 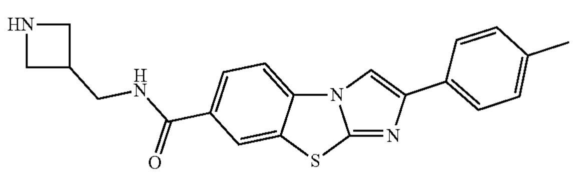 [SMILES: Cc1ccc(-c2cn3c(n2)sc2cc(C(=O)NCC4CNC4)ccc23)cc1] | N-(azetidin-3-ylmethyl)-2-(p-tolyl)benzo[d]imidazo[2,1-b]thiazole-7-carboxamide |
| 118 | 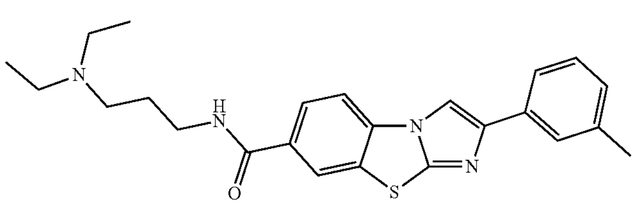 [SMILES: CCN(CC)CCCNC(=O)c1ccc2c(c1)sc1nc(-c3cccc(C)c3)cn12] | N-(3-(diethylamino)propyl)-2-(m-tolyl)benzo[d]imidazo[2,1-b]thiazole-7-carboxamide |

TABLE 1-continued

| Comp. No. | Structure | Compound Name |
|---|---|---|
| 119 | 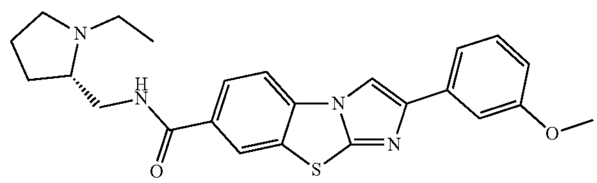 [SMILES: CCN1CCC[C@H]1CNC(=O)c1ccc2c(c1)sc1nc(-c3cccc(OC)c3)cn12] | (S)-N-((1-ethylpyrrolidin-2-yl)methyl)-2-(3-methoxyphenyl)benzo[d]imidazo[2,1-b]thiazole-7-carboxamide |
| 122 | 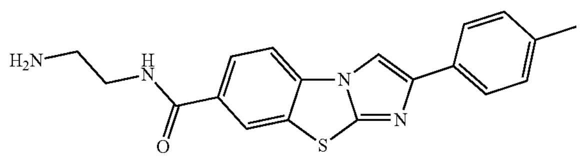 [SMILES: Cc1ccc(-c2cn3c(n2)sc2cc(C(=O)NCCN)ccc23)cc1] | N-(2-aminoethyl)-2-(p-tolyl)benzo[d]imidazo[2,1-b]thiazole-7-carboxamide |
| 123 | 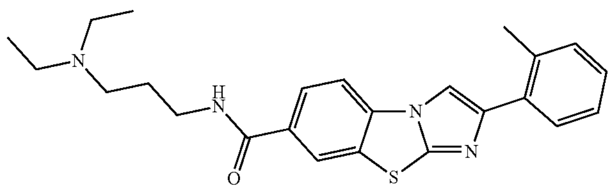 [SMILES: CCN(CC)CCCNC(=O)c1ccc2c(c1)sc1nc(-c3ccccc3C)cn12] | N-(3-(diethylamino)propyl)-2-(o-tolyl)benzo[d]imidazo[2,1-b]thiazole-7-carboxamide |
| 124 | 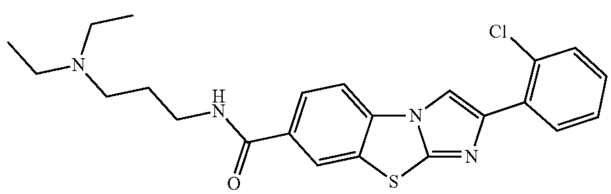 [SMILES: CCN(CC)CCCNC(=O)c1ccc2c(c1)sc1nc(-c3ccccc3Cl)cn12] | 2-(2-ehlorophenyl)-N-(3-(diethylamino)propyl)benzo[d]imidazo[2,1-b]thiazole-7-carboxamide |
| 125 | 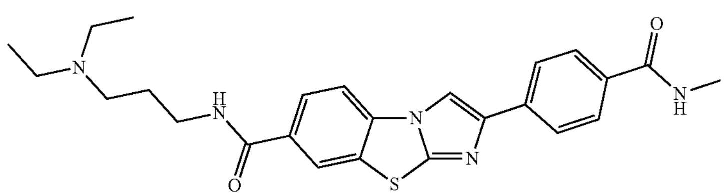 | N-(3-(diethylamino)propyl)-2-(4-(methylcarbamoyl)phenyl)benzo[d]imidazo[2,1-b]thiazole-7-carboxamide |
| 126 | 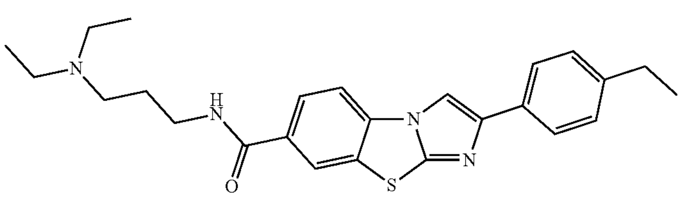 | N-(3-(diethylamino)propyl)-2-(4-ethylphenyl)benzo[d]imidazo[2,1-b]thiazole-7-carboxamide |
| 127 | 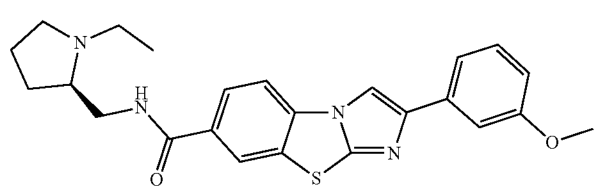 [SMILES: CCN1CCC[C@@H]1CNC(=O)c1ccc2c(c1)sc1nc(-c3cccc(OC)c3)cn12] | (R)-N-((1-ethylpyrrolidin-2-yl)methyl)-2-(3-methoxyphenyl)benzo[d]imidazo[2,1-b]thiazole-7-carboxamide |
| 129 | 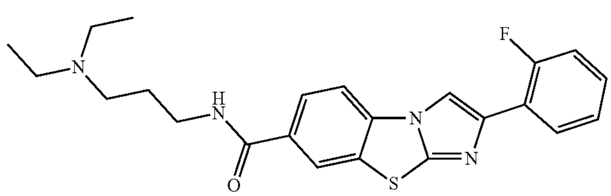 [SMILES: CCN(CC)CCCNC(=O)c1ccc2c(c1)sc1nc(-c3ccccc3F)cn12] | N-(3-(diethylamino)propyl)-2-(2-fluorophenyl)benzo[d]imidazo[2,1-b]thiazole-7-carboxamide |

TABLE 1-continued

| Comp. No. | Structure | Compound Name |
|---|---|---|
| 130 | 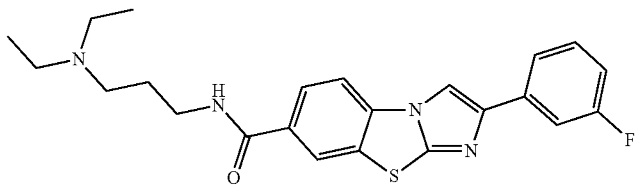 [SMILES: CCN(CC)CCCNC(=O)c1ccc2c(c1)sc1nc(-c3cccc(F)c3)cn12] | N-(3-(diethylamino)propyl)-2-(3-fluorophenyl)benzo[d]imidazo[2,1-b]thiazole-7-carboxamide |
| 131 | 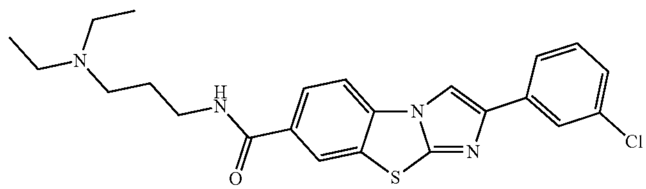 [SMILES: CCN(CC)CCCNC(=O)c1ccc2c(c1)sc1nc(-c3cccc(Cl)c3)cn12] | 2-(3-chlorophenyl)-N-(3-(diethylamino)propyl)benzo[d]imidazo[2,1-b]thiazole-7-carboxamide |
| 132 | 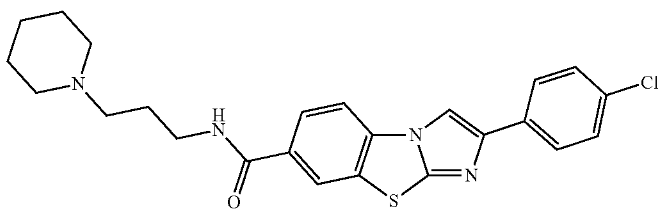 [SMILES: O=C(NCCCN1CCCCC1)c1ccc2c(c1)sc1nc(-c3ccc(Cl)cc3)cn12] | 2-(4-chlorophenyl)-N-(3-(piperidin-1-yl)propyl)benzo[d]imidazo[2,1-b]thiazole-7-carboxamide |
| 133 | 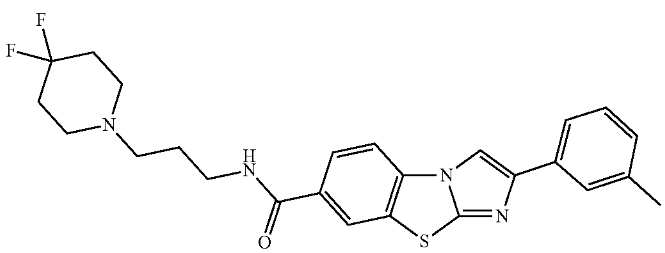 [SMILES: Cc1cccc(-c2cn3c(n2)sc2cc(C(=O)NCCCN4CCC(F)(F)CC4)ccc23)c1] | N-(3-(4,4-difluoropiperidin-1-yl)propyl)-2-(m-tolyl)benzo[d]imidazo[2,1-b]thiazole-7-carboxamide |
| 134 | 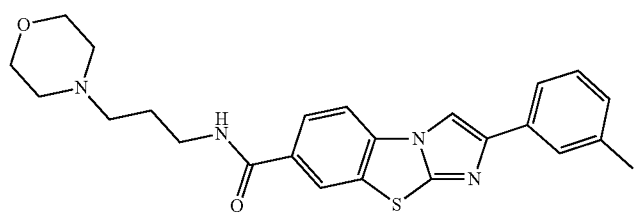 [SMILES: Cc1cccc(-c2cn3c(n2)sc2cc(C(=O)NCCCN4CCOCC4)ccc23)c1] | N-(3-morpholinopropyl)-2-(m-tolyl)benzo[d]imidazo[2,1-b]thiazole-7-carboxamide |
| 135 | 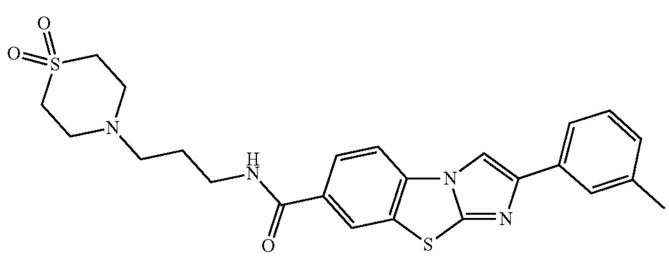 [SMILES: Cc1cccc(-c2cn3c(n2)sc2cc(C(=O)NCCCN4CCS(=O)(=O)CC4)ccc23)c1] | N-(3-(1,1-dioxidothiomorpholino)propyl)-2-(m-tolyl)benzo[d]imidazo[2,1-b]thiazole-7-carboxamide |
| 136 | 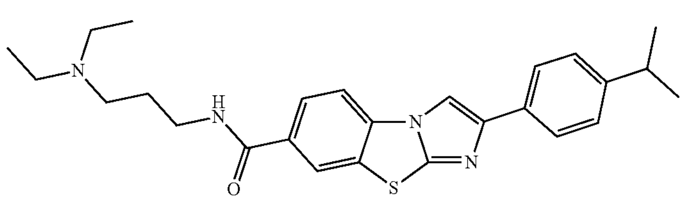 | N-(3-(diethylamino)propyl)-2-(4-isopropylphenyl)benzo[d]imidazo[2,1-b]thiazole-7-carboxamide formate |

TABLE 1-continued

| Comp. No. | Structure | Compound Name |
|---|---|---|
| 137 | 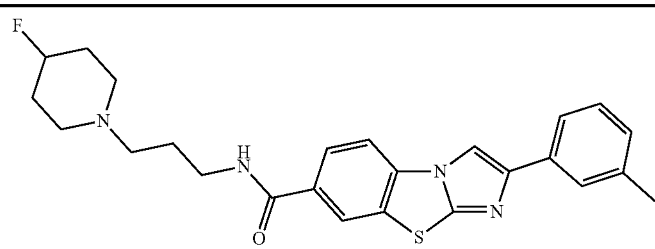 | N-(3-(4-fluoropiperidin-1-yl)propyl)-2-(m-tolyl)benzo[d]imidazo[2,1-b]thiazole-7-carboxamide |
| 138 | 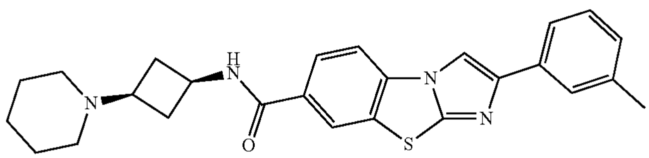 [SMILES: Cc1cccc(-c2cn3c(n2)sc2cc(C(=O)N[C@H]4C[C@@H](N5CCCCC5)C4)ccc23)c1] | N-((1s,3s)-3-(piperidin-1-yl)cyclobutyl)-2-(m-tolyl)benzo[d]imidazo[2,1-b]thiazole-7-carboxamide |
| 139 | 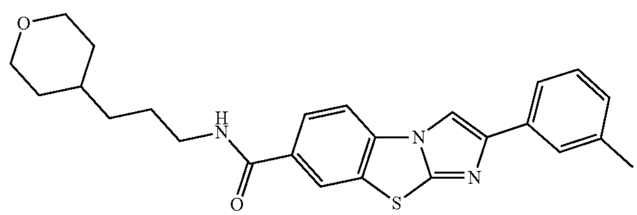 [SMILES: Cc1cccc(-c2cn3c(n2)sc2cc(C(=O)NCCCC4CCOCC4)ccc23)c1] | N-(3-(tetrahydro-2H-pyran-4-yl)propyl)-2-(m-tolyl)benzo[d]imidazo[2,1-b]thiazole-7-carboxamide |
| 140 | 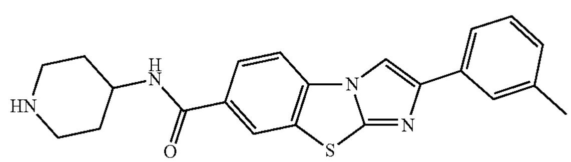 [SMILES: Cc1cccc(-c2cn3c(n2)sc2cc(C(=O)NC4CCNCC4)ccc23)c1] | N-(piperidin-4-yl)-2-(m-tolyl)benzo[d]imidazo[2,1-b]thiazole-7-carboxamide |
| 141 | 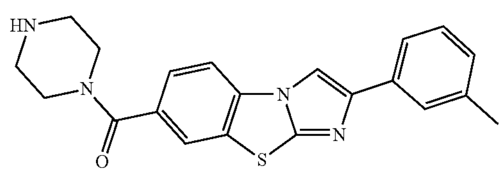 [SMILES: Cc1cccc(-c2cn3c(n2)sc2cc(C(=O)N4CCNCC4)ccc23)c1] | piperazin-1-yl(2-(m-tolyl)benzo[d]imidazo[2,1-b]thiazol-7-yl)methanone |
| 142 | 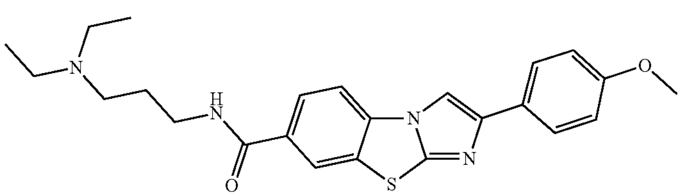 [SMILES: CCN(CC)CCCNC(=O)c1ccc2c(c1)sc1nc(-c3ccc(OC)cc3)cn12] | N-(3-(diethylamino)propyl)-2-(4-methoxyphenyl)benzo[d]imidazo[2,1-b]thiazole-7-carboxamide |
| 143 | 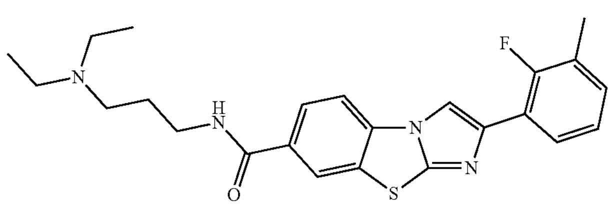 [SMILES: CCN(CC)CCCNC(=O)c1ccc2c(c1)sc1nc(-c3cccc(C)c3F)cn12] | N-(3-(diethylamino)propyl)-2-(2-fluoro-3-methylphenyl)benzo[d]imidazo[2,1-b]thiazole-7-carboxamide |
| 144 | 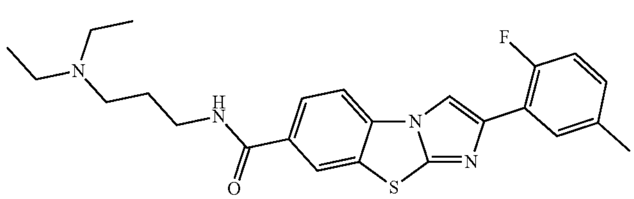 [SMILES: CCN(CC)CCCNC(=O)c1ccc2c(c1)sc1nc(-c3cc(C)ccc3F)cn12] | N-(3-(diethylamino)propyl)-2-(2-fluoro-5-methylphenyl)benzo[d]imidazo[2,1-b]thiazole-7-carboxamide |

TABLE 1-continued

| Comp. No. | Structure | Compound Name |
|---|---|---|
| 145 | 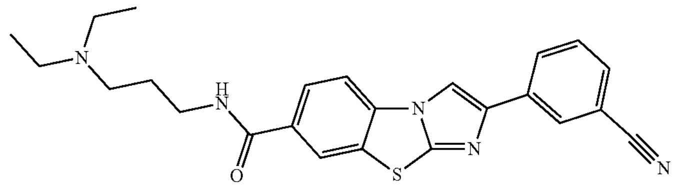 [SMILES: CCN(CC)CCCNC(=O)c1ccc2c(c1)sc1nc(-c3cccc(C#N)c3)cn12] | 2-(3-cyanophenyl)-N-(3-(diethylamino)propyl)benzo[d]imidazo[2,1-b]thiazole-7-carboxamide |
| 149 | 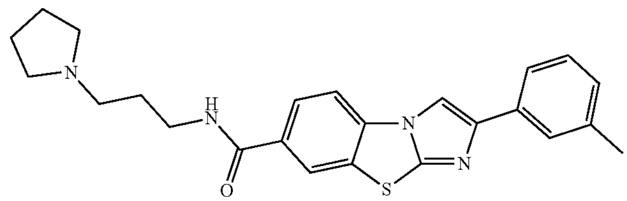 [SMILES: Cc1cccc(-c2cn3c(n2)sc2cc(C(=O)NCCCN4CCCC4)ccc23)c1] | N-(3-(pyrrolidin-1-yl)propyl)-2-(m-tolyl)benzo[d]imidazo[2,1-b]thiazole-7-carboxamide |
| 150 | 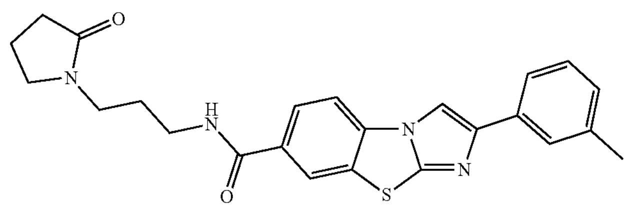 [SMILES: Cc1cccc(-c2cn3c(n2)sc2cc(C(=O)NCCCN4CCCC4=O)ccc23)c1] | N-(3-(2-oxopyrrolidin-1-yl)propyl)-2-(m-tolyl)benzo[d]imidazo[2,1-b]thiazole-7-carboxamide |
| 151 | 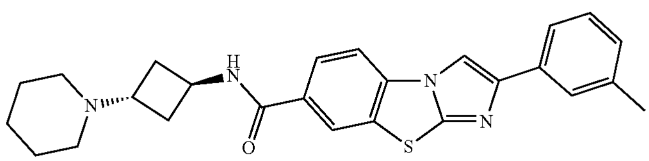 [SMILES: Cc1cccc(-c2cn3c(n2)sc2cc(C(=O)N[C@H]4C[C@H](N5CCCCC5)C4)ccc23)c1] | N-((1r,3r)-3-(piperidin-1-yl)cyclobutyl)-2-(m-tolyl)benzo[d]imidazo[2,1-b]thiazole-7-carboxamide |
| 152 | 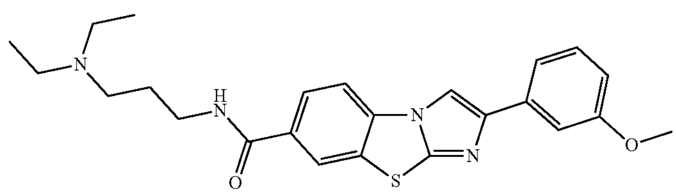 [SMILES: CCN(CC)CCCNC(=O)c1ccc2c(c1)sc1nc(-c3cccc(OC)c3)cn12] | N-(3-(diethylamino)propyl)-2-(3-methoxyphenyl)benzo[d]imidazo[2,1-b]thiazole-7-carboxamide |
| 153 | 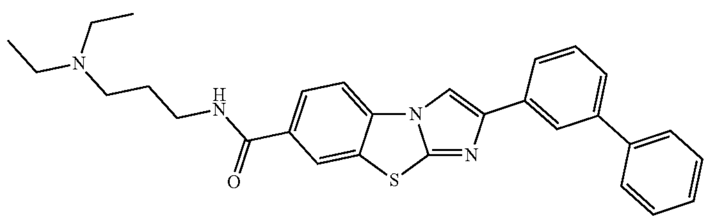 [SMILES: CCN(CC)CCCNC(=O)c1ccc2c(c1)sc1nc(-c3cccc(-c4ccccc4)c3)cn12] | 2-([1,1'-biphenyl]-3-yl)-N-(3-(diethylamino)propyl)benzo[d]imidazo[2,1-b]thiazole-7-carboxamide |
| 154 | 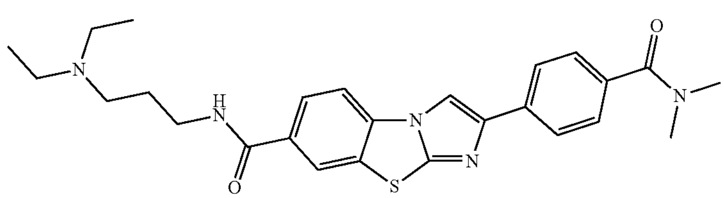 [SMILES: CCN(CC)CCCNC(=O)c1ccc2c(c1)sc1nc(-c3ccc(C(=O)N(C)C)cc3)cn12] | N-(3-(diethylamino)propyl)-2-(4-(dimethylcarbamoyl)phenyl)benzo[d]imidazo[2,1-b]thiazole-7-carboxamide formate |
| 155 | 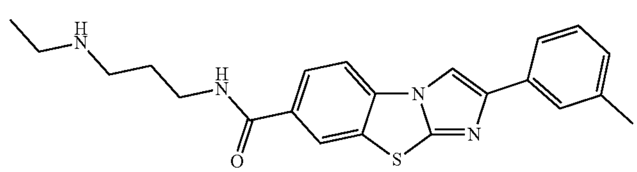 [SMILES: CCNCCCNC(=O)c1ccc2c(c1)sc1nc(-c3cccc(C)c3)cn12] | N-(3-(ethylamino)propyl)-2-tolyl)benzo[d]imidazo[2,1-b]thiazole-7-carboxamide |

TABLE 1-continued

| Comp. No. | Structure | Compound Name |
|---|---|---|
| 156 | 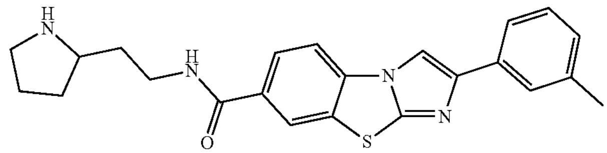 [SMILES: Cc1cccc(-c2cn3c(n2)sc2cc(C(=O)NCCC4CCCN4)ccc23)c1] | N-(2-(pyrrolidin-2-yl)ethyl)-2-(m-tolyl)benzo[d]imidazo[2,1-b]thiazole-7-carboxamide |
| 157 | 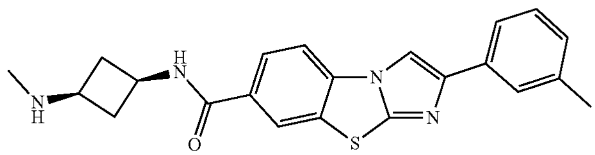 | N-((1s,3s)-3-(methylamino)cyclobutyl)-2-(m-tolyl)benzo[d]imidazo[2,1-b]thiazole-7-carboxamide formate |
| 158 | 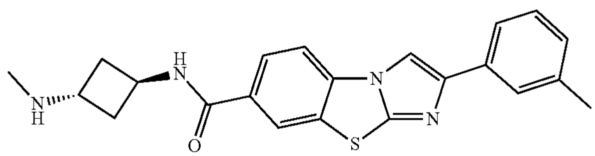 | N-((1r,3r)-3-(methylamino)cyclobutyl)-2-(m-tolyl)benzo[d]imidazo[2,1-b]thiazole-7-carboxamide formate |
| 159 | 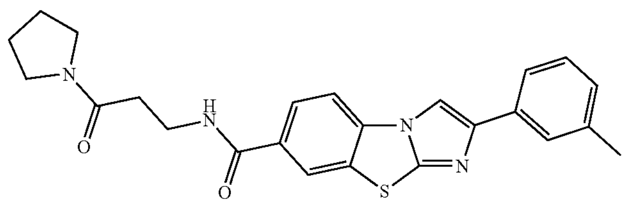 [SMILES: Cc1cccc(-c2cn3c(n2)sc2cc(C(=O)NCCC(=O)N4CCCC4)ccc23)c1] | N-(3-oxo-3-(pyrrolidin-1-yl)propyl)-2-(m-tolyl)benzo[d]imidazo[2,1-b]thiazole-7-carboxamide |
| 160 | 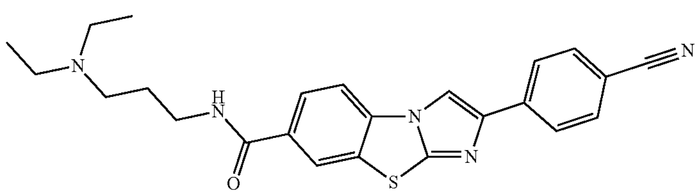 [SMILES: CCN(CC)CCCNC(=O)c1ccc2c(c1)sc1nc(-c3ccc(C#N)cc3)cn12] | 2-(4-cyanophenyl)-N-(3-(diethylamino)propyl)benzo[d]imidazo[2,1-b]thiazole-7-carboxamide |
| 161 | 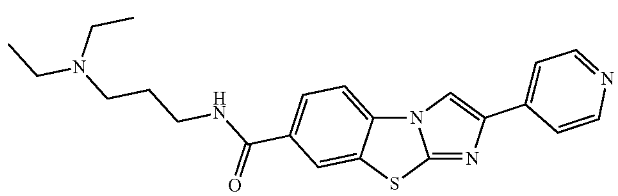 [SMILES: CCN(CC)CCCNC(=O)c1ccc2c(c1)sc1nc(-c3ccncc3)cn12] | N-(3-(diethylamino)propyl)-2-(pyridin-4-yl)benzo[d]imidazo[2,1-b]thiazole-7-carboxamide |
| 162 | 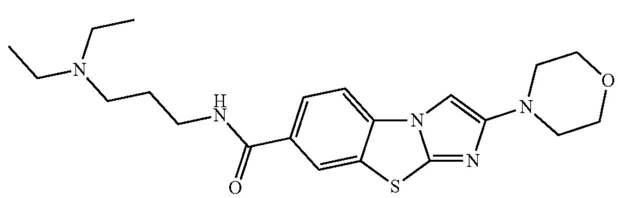 [SMILES: CCN(CC)CCCNC(=O)c1ccc2c(c1)sc1nc(N3CCOCC3)cn12] | N-(3-(diethylamino)propyl)-2-morpholinobenzo[d]imidazo[2,1-b]thiazole-7-carboxamide |
| 163 | 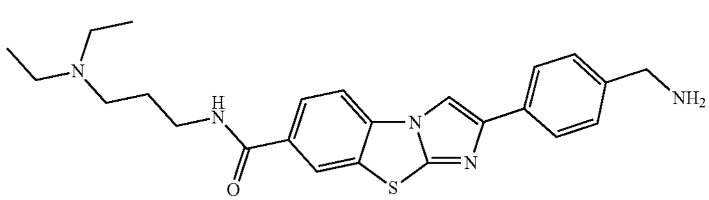 [SMILES: CCN(CC)CCCNC(=O)c1ccc2c(c1)sc1nc(-c3ccc(CN)cc3)cn12] | 2-(4-(aminomethyl)phenyl)-N-(3-(diethylamino)propyl)benzo[d]imidazo[2,1-b]thiazole-7-carboxamide |

TABLE 1-continued

| Comp. No. | Structure | Compound Name |
|---|---|---|
| 164 | 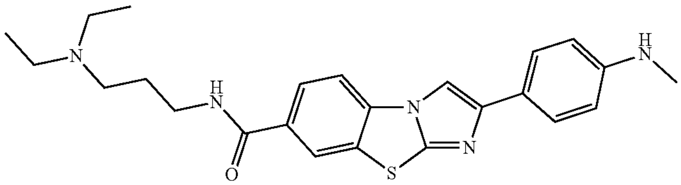 [SMILES: CCN(CC)CCCNC(=O)c1ccc2c(c1)sc1nc(-c3ccc(NC)cc3)cn12] | N-(3-(diethylamino)propyl)-2-(4-(methylamino)phenyl)benzo[d]imidazo[2,1-b]thiazole-7-carboxamide |
| 165 | 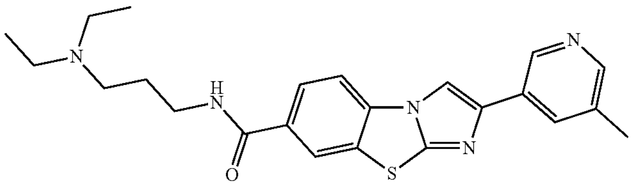 [SMILES: CCN(CC)CCCNC(=O)c1ccc2c(c1)sc1nc(-c3cncc(C)c3)cn12] | N-(3-(diethylamino)propyl)-2-(5-methylpyridin-3-yl)benzo[d]imidazo[2,1-b]thiazole-7-carboxamide |
| 166 | 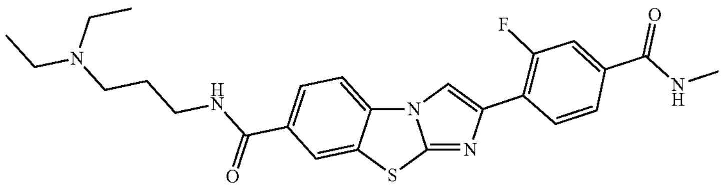 [SMILES: CCN(CC)CCCNC(=O)c1ccc2c(c1)sc1nc(-c3ccc(C(=O)NC)cc3F)cn12] | N-(3-(diethylamino)propyl)-2-(2-fluoro-4-(methylcarbamoyl)phenyl)benzo[d]imidazo[2,1-b]thiazole-7-carboxamide |
| 167 | 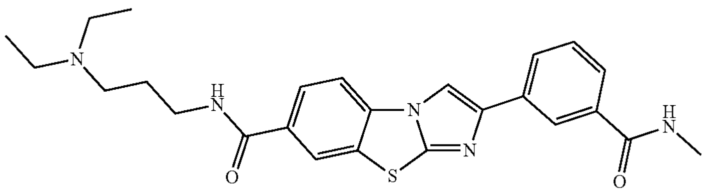 [SMILES: CCN(CC)CCCNC(=O)c1ccc2c(c1)sc1nc(-c3cccc(C(=O)NC)c3)cn12] | N-(3-(diethylamino)propyl)-2-(3-(methylcarbamoyl)phenyl)benzo[d]imidazo[2,1-b]thiazole-7-carboxamide |
| 168 | 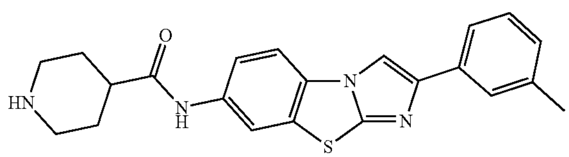 | N-(2-(m-tolyl)benzo[d]imidazo[2,1-b]thiazol-7-yl)piperidine-4-carboxamide |
| 169 | 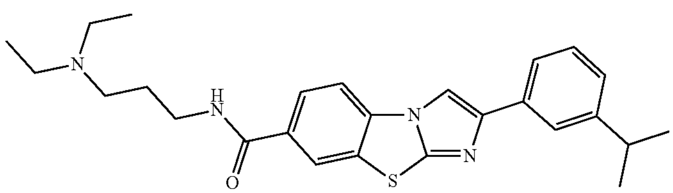 [SMILES: CCN(CC)CCCNC(=O)c1ccc2c(c1)sc1nc(-c3cccc(C(C)C)c3)cn12] | N-(3-(diethylamino)propyl)-2-(3-isopropylphenyl)benzo[d]imidazo[2,1-b]thiazole-7-carboxamide |
| 170 | 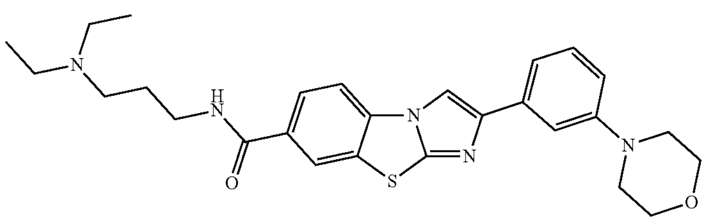 [SMILES: CCN(CC)CCCNC(=O)c1ccc2c(c1)sc1nc(-c3cccc(N4CCOCC4)c3)cn12] | N-(3-(diethylamino)propyl)-2-(3-morpholinophenyl)benzo[d]imidazo[2,1-b]thiazole-7-carboxamide |
| 171 | 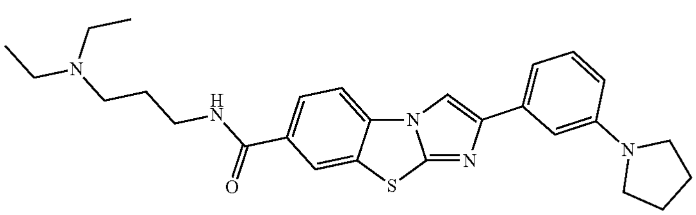 [SMILES: CCN(CC)CCCNC(=O)c1ccc2c(c1)sc1nc(-c3cccc(N4CCCC4)c3)cn12] | N-(3-(diethylamino)propyl)-2-(3-(pyrrolidin-1-yl)phenyl)benzo[d]imidazo[2,1-b]thiazole-7-carboxamide |

TABLE 1-continued

| Comp. No. | Structure | Compound Name |
|---|---|---|
| 172 | 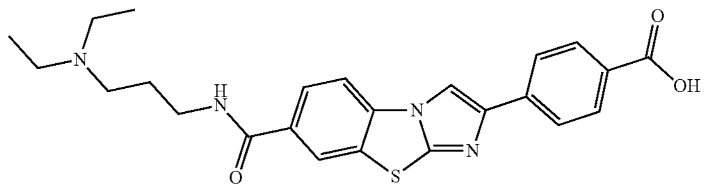 [SMILES: CCN(CC)CCCNC(=O)c1ccc2c(c1)sc1nc(-c3ccc(C(=O)O)cc3)cn12] | 4-(7-((3-(diethylamino)propyl)carbamoyl)benzo[d]imidazo[2,1-b]thiazol-2-yl)benzoic acid |
| 173 | 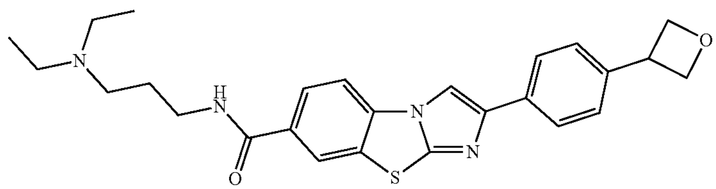 [SMILES: CCN(CC)CCCNC(=O)c1ccc2c(c1)sc1nc(-c3ccc(C4COC4)cc3)cn12] | N-(3-(diethylamino)propyl)-2-(4-(oxetan-3-yl)phenyl)benzo[d]imidazo[2,1-b]thiazole-7-carboxamide |
| 174 | 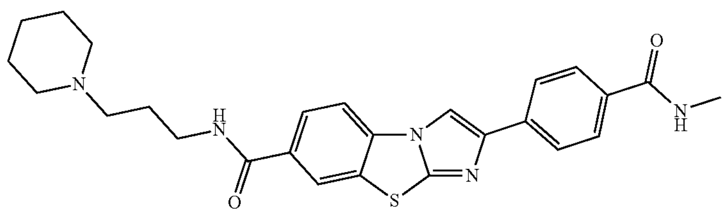 [SMILES: CNC(=O)c1ccc(-c2cn3c(n2)sc2cc(C(=O)NCCCN4CCCCC4)ccc23)cc1] | 2-(4-(methylcarbamoyl)phenyl)-N-(3-(piperidin-1-yl)propyl)benzo[d]imidazo[2,1-b]thiazole-7-carboxamide |
| 175 | 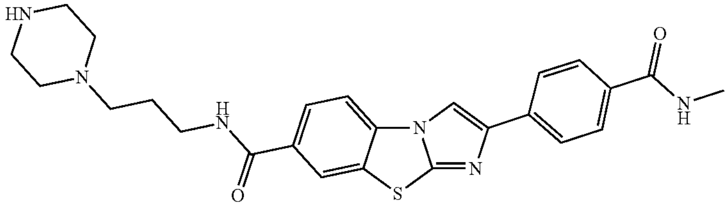 [SMILES: CNC(=O)c1ccc(-c2cn3c(n2)sc2cc(C(=O)NCCCN4CCNCC4)ccc23)cc1] | 2-(4-(methylcarbamoyl)phenyl)-N-(3-(piperazin-1-yl)propyl)benzo[d]imidazo[2,1-b]thiazole-7-carboxamide |
| 176 | 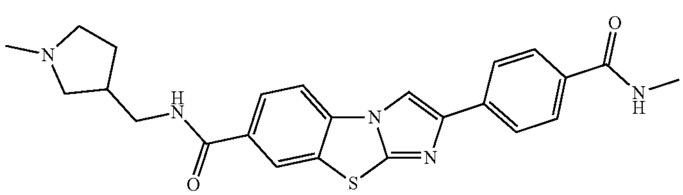 | 2-(4-(methylcarbamoyl)phenyl)-N-((1-methylpyrrolidin-3-yl)methyl)benzo[d]imidazo[2,1-b]thiazole-7-carboxamide |
| 177 | 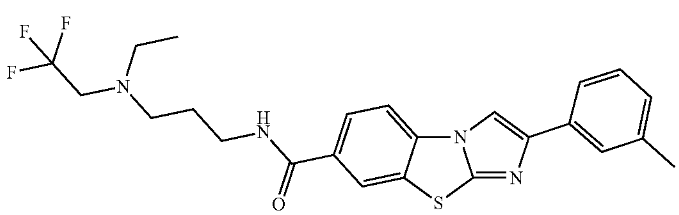 [SMILES: CCN(CCCNC(=O)c1ccc2c(c1)sc1nc(-c3cccc(C)c3)cn12)CC(F)(F)F] | N-(3-(ethyl(2,2,2-trifluoroethyl)amino)propyl)-2-(m-tolyl)benzo[d]imidazo[2,1-b]thiazole-7-carboxamide |
| 178 | 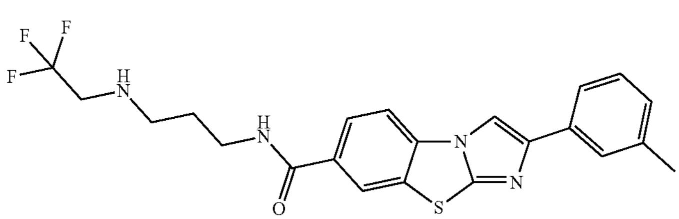 [SMILES: Cc1cccc(-c2cn3c(n2)sc2cc(C(=O)NCCCNCC(F)(F)F)ccc23)c1] | 2-(m-tolyl)-N-(3-((2,2,2-trifluoroethyl)amino)propyl)benzo[d]imidazo[2,1-b]thiazole-7-carboxamide |

TABLE 1-continued

| Comp. No. | Structure | Compound Name |
|---|---|---|
| 179 | 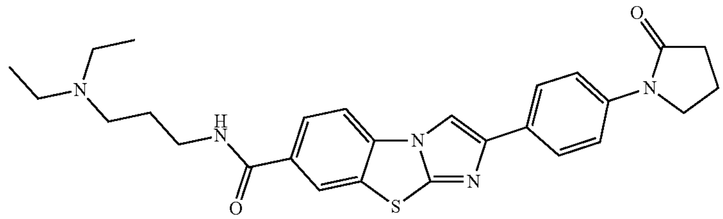 [SMILES: CCN(CC)CCCNC(=O)c1ccc2c(c1)sc1nc(-c3ccc(N4CCCC4=O)cc3)cn12] | N-(3-(diethylamino)propyl)-2-(4-(2-oxopyrrolidin-1-yl)phenyl)benzo[d]imidazo[2,1-b]thiazole-7-carboxamide |
| 180 | 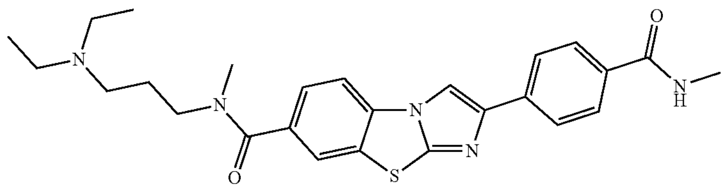 [SMILES: CCN(CC)CCCN(C)C(=O)c1ccc2c(c1)sc1nc(-c3ccc(C(=O)NC)cc3)cn12] | N-(3-(diethylamino)propyl)-N-methyl-2-(4-(methylcarbamoyl)phenyl)benzo[d]imidazo[2,1-b]thiazole-7-carboxamide |
| 181 | 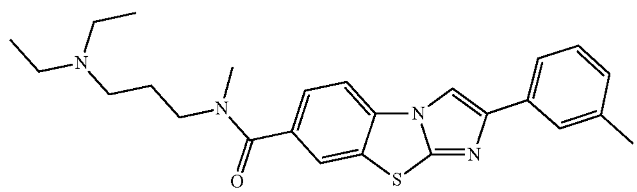 [SMILES: CCN(CC)CCCN(C)C(=O)c1ccc2c(c1)sc1nc(-c3cccc(C)c3)cn12] | N-(3-(diethylamino)propyl)-N-methyl-2-(m-tolyl)benzo[d]imidazo[2,1-b]thiazole-7-carboxamide |
| 182 | 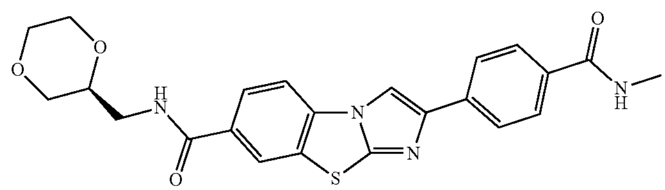 [SMILES: CNC(=O)c1ccc(-c2cn3c(n2)sc2cc(C(=O)NC[C@H]4COCCO4)ccc23)cc1] | (S)-N-((1,4-dioxan-2-yl)methyl)-2-(4-(methylcarbamoyl)phenyl)benzo[d]imidazo[2,1-b]thiazole-7-carboxamide |
| 183 | 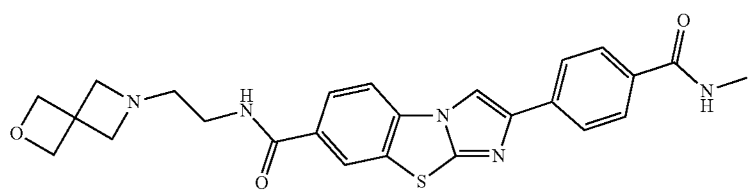 [SMILES: CNC(=O)c1ccc(-c2cn3c(n2)sc2cc(C(=O)NCCN4CC5(COC5)C4)ccc23)cc1] | N-(2-(2-oxa-6-azaspiro[3.3]heptan-6-yl)ethyl)-2-(4-(methylcarbamoyl)phenyl)benzo[d]imidazo[2,1-b]thiazole-7-carboxamide |
| 184 | 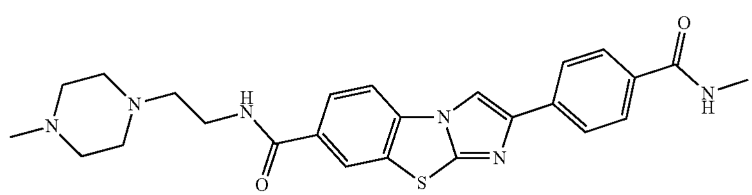 | 2-(4-(methylcarbamoyl)phenyl)-N-(2-(4-methylpiperazin-1-yl)ethyl)benzo[d]imidazo[2,1-b]thiazole-7-carboxamide |
| 185 | 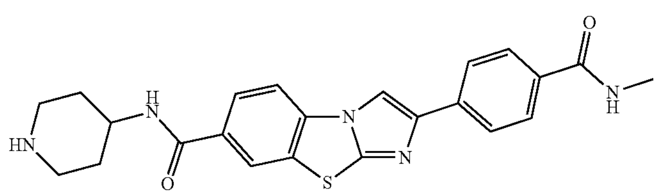 [SMILES: CNC(=O)c1ccc(-c2cn3c(n2)sc2cc(C(=O)NC4CCNCC4)ccc23)cc1] | 2-(4-(methylcarbamoyl)phenyl)-N-(piperidin-4-yl)benzo[d]imidazo[2,1-b]thiazole-7-carboxamide |
| 186 | 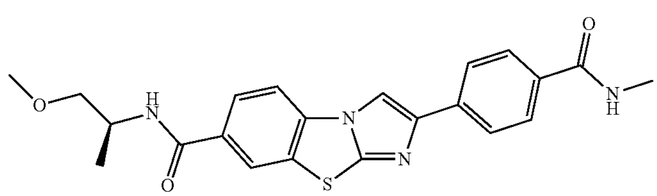 | (S)-N-(1-methoxypropan-2-(methylcarbamoyl)phenyl)benzo[d]imidazo[2,1-b]thiazole-7-carboxamide |

TABLE 1-continued

| Comp. No. | Structure | Compound Name |
|---|---|---|
| 187 | 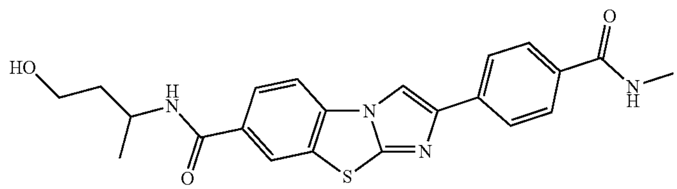 [SMILES: CNC(=O)c1ccc(-c2cn3c(n2)sc2cc(C(=O)NC(C)CCO)ccc23)cc1] | N-(4-hydroxybutan-2-yl)-2-(4-(methylcarbamoyl)phenyl)benzo[d]imidazo[2,1-b]thiazole-7-carboxamide |
| 188 | 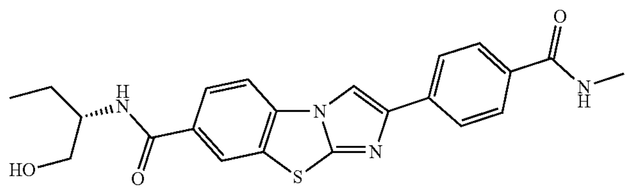 [SMILES: CC[C@@H](CO)NC(=O)c1ccc2c(c1)sc1nc(-c3ccc(C(=O)NC)cc3)cn12] | (S)-N-(1-hydroxybutan-2-yl)-2-(4-(methylcarbamoyl)phenyl)benzo[d]imidazo[2,1-b]thiazole-7-carboxamide |
| 189 | 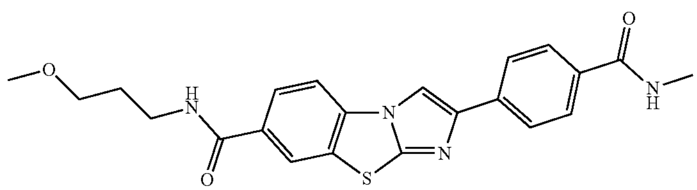 | N-(3-methoxypropyl)-2-(4-(methylcarbamoyl)phenyl)benzo[d]imidazo[2,1-b]thiazole-7-carboxamide |
| 190 | 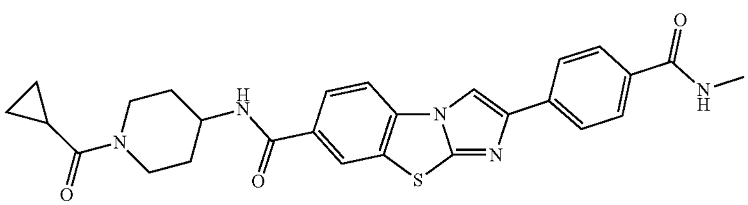 [SMILES: CNC(=O)c1ccc(-c2cn3c(n2)sc2cc(C(=O)NC4CCN(C(=O)C5CC5)CC4)ccc23)cc1] | N-(1-(cyclopropanecarbonyl)piperidin-4-yl)-2-(4-(methylcarbamoyl)phenyl)benzo[d]imidazo[2,1-b]thiazole-7-carboxamide |
| 191 | 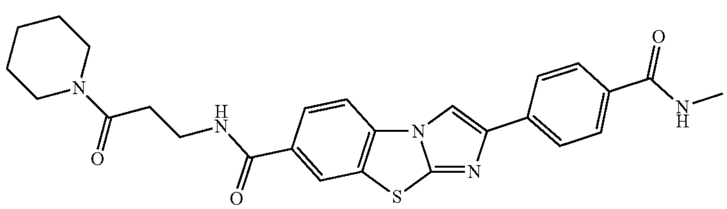 [SMILES: CNC(=O)c1ccc(-c2cn3c(n2)sc2cc(C(=O)NCCC(=O)N4CCCCC4)ccc23)cc1] | 2-(4-(methylcarbamoyl)phenyl)-N-(3-oxo-3-(piperidin-1-yl)propyl)benzo[d]imidazo[2,1-b]thiazole-7-carboxamide |
| 192 | 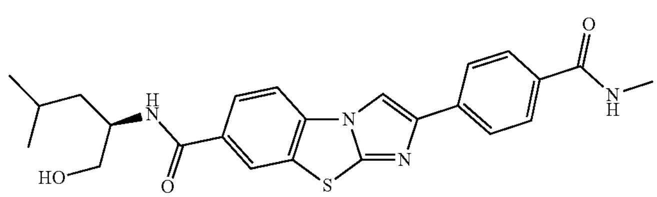 [SMILES: CNC(=O)c1ccc(-c2cn3c(n2)sc2cc(C(=O)N[C@@H](CO)CC(C)C)ccc23)cc1] | (R)-N-(1-hydroxy-4-methylpentan-2-yl)-2-(4-(methylcarbamoyl)phenyl)benzo[d]imidazo[2,1-b]thiazole-7-carboxamide |
| 193 | 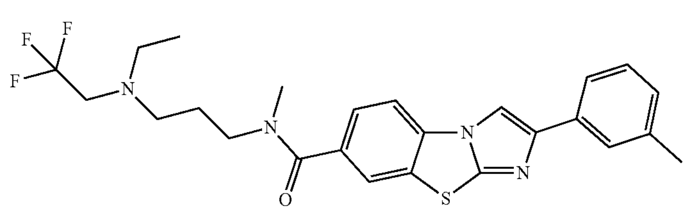 [SMILES: CCN(CCCN(C)C(=O)c1ccc2c(c1)sc1nc(-c3cccc(C)c3)cn12)CC(F)(F)F] | N-(3-(ethyl(2,2,2-trifluoroethyl)amino)propyl)-N-methyl-2-(m-tolyl)benzo[d]imidazo[2,1-b]thiazole-7-carboxamide |

TABLE 1-continued

| Comp. No. | Structure | Compound Name |
|---|---|---|
| 194 | 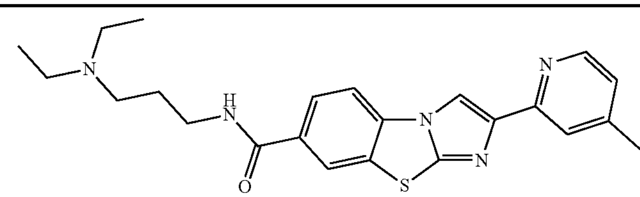 | N-(3-(diethylamino)propyl)-2-(4-methylpyridin-2-yl)benzo[d]imidazo[2,1-b]thiazole-7-carboxamide |
| 195 | 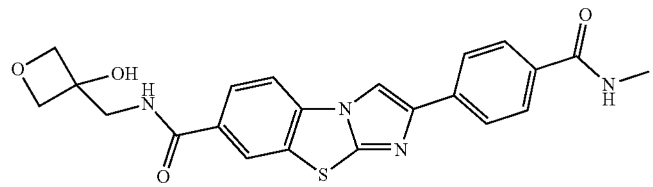 [SMILES: CNC(=O)c1ccc(-c2cn3c(n2)sc2cc(C(=O)NCC4(O)COC4)ccc23)cc1] | N-((3-hydroxyoxetan-3-yl)methyl)-2-(4-(methylcarbamoyl)phenyl)benzo[d]imidazo[2,1-b]thiazole-7-carboxamide |
| 196 | 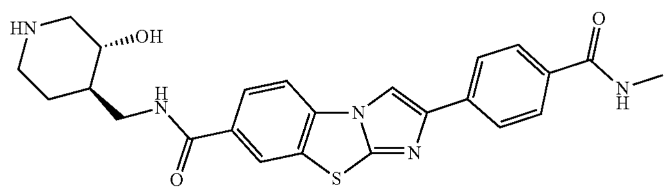 [SMILES: CNC(=O)c1ccc(-c2cn3c(n2)sc2cc(C(=O)NC[C@H]4CCNC[C@@H]4O)ccc23)cc1] | N-(((3R,4R)-3-hydroxypiperidin-4-yl)methyl)-2-(4-(methylcarbamoyl)phenyl)benzo[d]imidazo[2,1-b]thiazole-7-carboxamide |
| 197 | 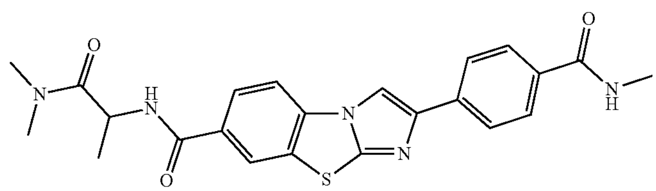 | N-(1-(dimethylamino)-1-oxopropan-2-yl)-2-(4-(methylcarbamoyl)phenyl)benzo[d]imidazo[2,1-b]thiazole-7-carboxamide |
| 198 | 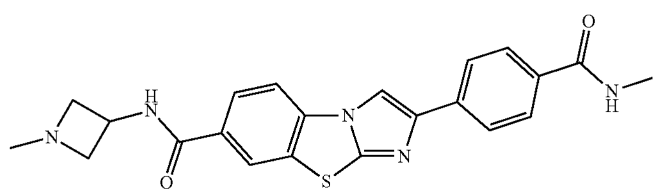 | N-(1-methylazetidin-3-yl)-2-(4-(methylcarbamoyl)phenyl)benzo[d]imidazo[2,1-b]thiazole-7-carboxamide |
| 199 | 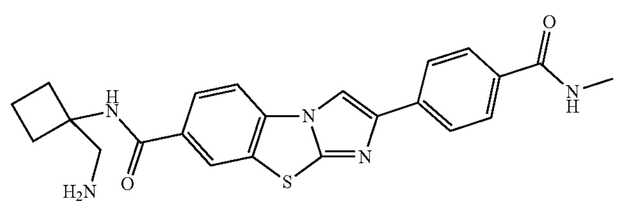 [SMILES: CNC(=O)c1ccc(-c2cn3c(n2)sc2cc(C(=O)NC4(CN)CCC4)ccc23)cc1] | N-(1-(aminomethyl)cyclobutyl)-2-(4-(methylcarbamoyl)phenyl)benzo[d]imidazo[2,1-b]thiazole-7-carboxamide |
| 200 | 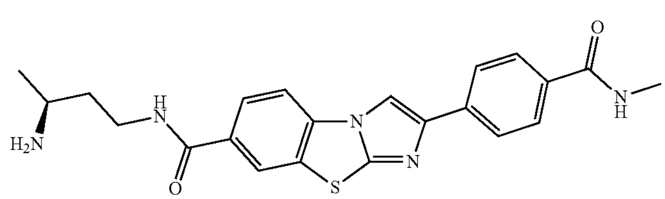 [SMILES: CNC(=O)c1ccc(-c2cn3c(n2)sc2cc(C(=O)NCC[C@H](C)N)ccc23)cc1] | (S)-N-(3-aminobutyl)-2-(4-(methylcarbamoyl)phenyl)benzo[d]imidazo[2,1-b]thiazole-7-carboxamide |
| 201 | 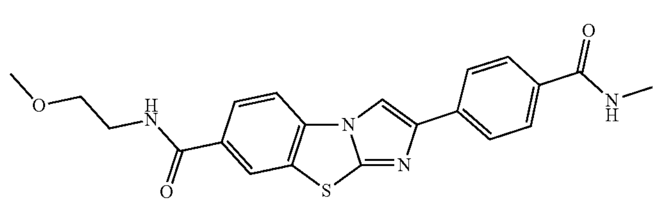 | N-(2-methoxyethyl)-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 202 | 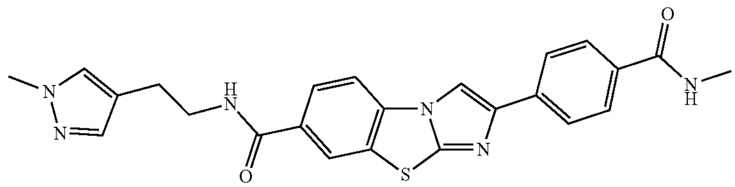 | N-(2-(1-methyl-1H-pyrazol-4-yl)ethyl)-2-(4-(methylcarbamoyl)phenyl)benzo[d]imidazo[2,1-b]thiazole-7-carboxamide |
| 203 | 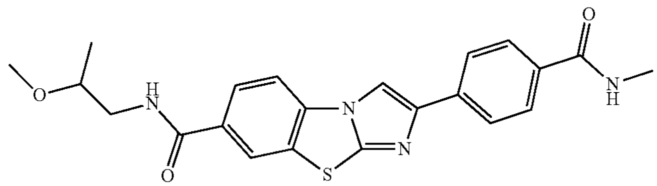 | N-(2-methoxypropyl)-2-(4-(methylcarbamoyl)phenyl)benzo[d]imidazo[2,1-b]thiazole-7-carboxamide |
| 204 | 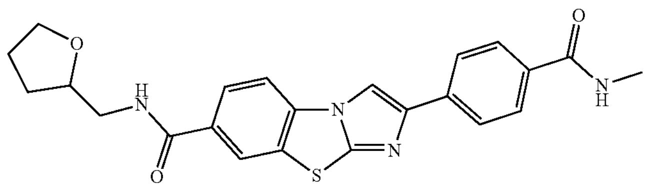 [SMILES: CNC(=O)c1ccc(-c2cn3c(n2)sc2cc(C(=O)NCC4CCCO4)ccc23)cc1] | 2-(4-(methylcarbamoyl)phenyl)-N-((tetrahydrofuran-2-yl)methyl)benzo[d]imidazo[2,1-b]thiazole-7-carboxamide |
| 205 | 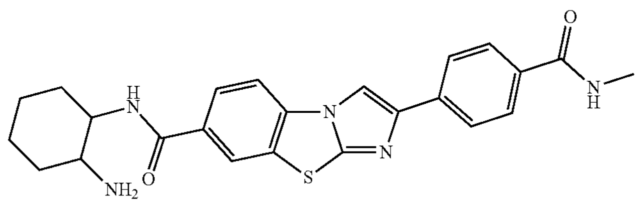 [SMILES: CNC(=O)c1ccc(-c2cn3c(n2)sc2cc(C(=O)NC4CCCCC4N)ccc23)cc1] | N-(2-aminocyclohexyl)-2-(4-(methylcarbamoyl)phenyl)benzo[d]imidazo[2,1-b]thiazole-7-carboxamide |
| 206 | 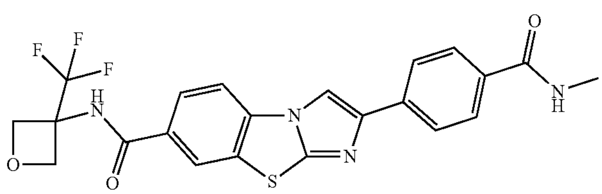 [SMILES: CNC(=O)c1ccc(-c2cn3c(n2)sc2cc(C(=O)NC4(C(F)(F)F)COC4)ccc23)cc1] | 2-(4-(methylcarbamoyl)phenyl)-N-(3-(trifluoromethyl)oxetan-3-yl)benzo[d]imidazo[2,1-b]thiazole-7-carboxamide |
| 207 | 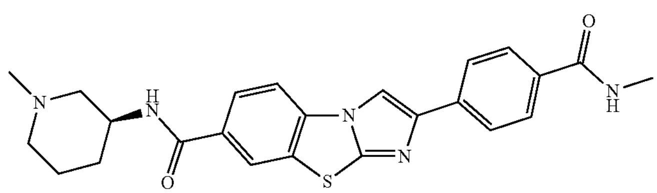 | (S)-2-(4-(methylcarbamoyl)phenyl)-N-(1-methylpiperidin-3-yl)benzo[d]imidazo[2,1-b]thiazole-7-carboxamide |
| 208 | 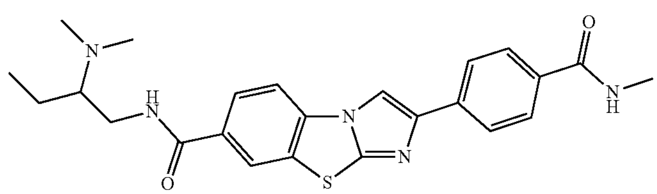 [SMILES: CCC(CNC(=O)c1ccc2c(c1)sc1nc(-c3ccc(C(=O)NC)cc3)cn12)N(C)C] | N-(2-(dimethylamino)butyl)-2-(4-(methylcarbamoyl)phenyl)benzo[d]imidazo[2,1-b]thiazole-7-carboxamide |
| 209 | 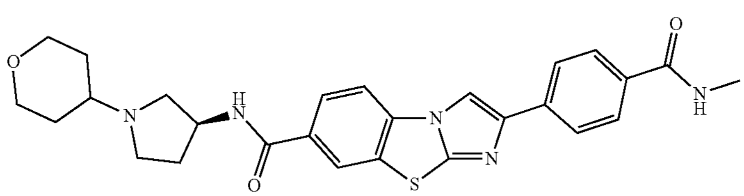 [SMILES: CNC(=O)c1ccc(-c2cn3c(n2)sc2cc(C(=O)N[C@H]4CCN(C5CCOCC5)C4)ccc23)cc1] | (S)-2-(4-(methylcarbamoyl)phenyl)-N-(1-(tetrahydro-2H-pyran-4-yl)pyrrolidin-3-yl)benzo[d]imidazo[2,1-b]thiazole-7-carboxamide |

TABLE 1-continued

| Comp. No. | Structure | Compound Name |
|---|---|---|
| 210 | 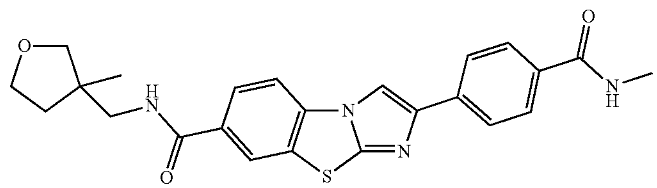 [SMILES: CNC(=O)c1ccc(-c2cn3c(n2)sc2cc(C(=O)NCC4(C)CCOC4)ccc23)cc1] | 2-(4-(methylcarbamoyl)phenyl)-N-((3-methyltetrahydrofuran-3-yl)methyl)benzo[d]imidazo[2,1-b]thiazole-7-carboxamide |
| 211 | 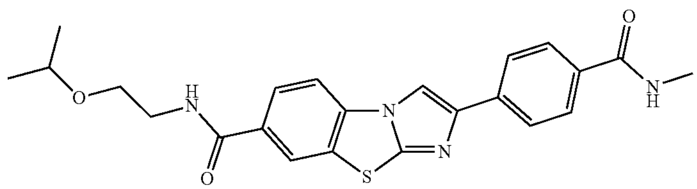 [SMILES: CNC(=O)c1ccc(-c2cn3c(n2)sc2cc(C(=O)NCCOC(C)C)ccc23)cc1] | N-(2-isopropalyethyl)-2-(4-(methylcarbamoyl)phenyl)benzo[d]imidazo[2,1-b]thiazole-7-carboxamide |
| 212 | 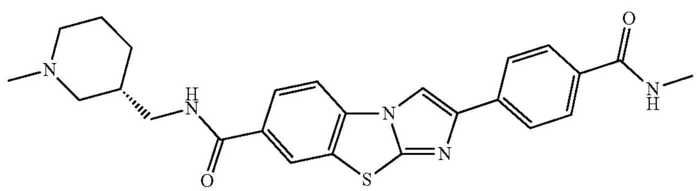 | (R)-2-(4-(methylcarbamoyl)phenyl)-N-((1-methylpiperidin-3-yl)methyl)benzo[d]imidazo[2,1-b]thiazole-7-carboxamide |
| 213 | 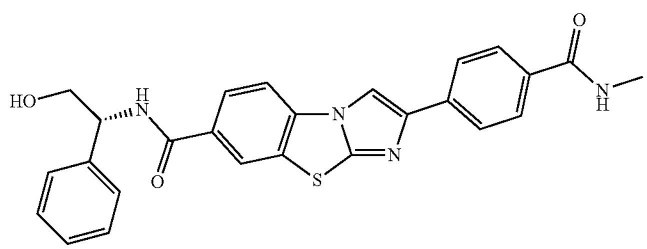 [SMILES: CNC(=O)c1ccc(-c2cn3c(n2)sc2cc(C(=O)N[C@@H](CO)c4ccccc4)ccc23)cc1] | (R)-N-(2-hydroxy-1-phenylethyl)-2-(4-(methylcarbamoyl)phenyl)benzo[d]imidazo[2,1-b]thiazole-7-carboxamide |
| 214 | 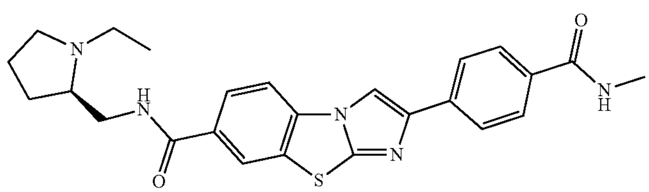 [SMILES: CCN1CCC[C@@H]1CNC(=O)c1ccc2c(c1)sc1nc(-c3ccc(C(=O)NC)cc3)cn12] | (R)-N-((1-ethylpyrrolidin-2-yl)methyl)-2-(4-(methylcarbamoyl)phenyl)benzo[d]imidazo[2,1-b]thiazole-7-carboxamide |
| 215 | 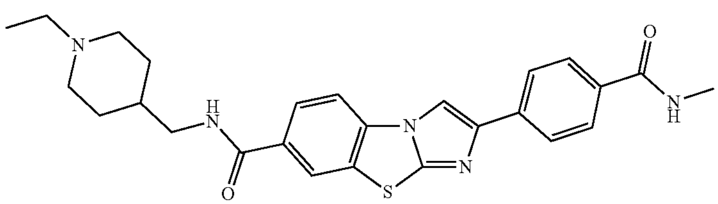 [SMILES: CCN1CCC(CNC(=O)c2ccc3c(c2)sc2nc(-c4ccc(C(=O)NC)cc4)cn23)CC1] | N-((1-ethylpiperidin-4-yl)methyl)-2-(4-(methylcarbamoyl)phenyl)benzo[d]imidazo[2,1-b]thiazole-7-carboxamide |
| 216 | 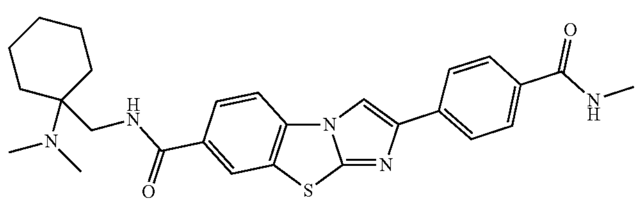 | N-((1-(dimethylamino)cyclohexyl)methyl)-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 217 | 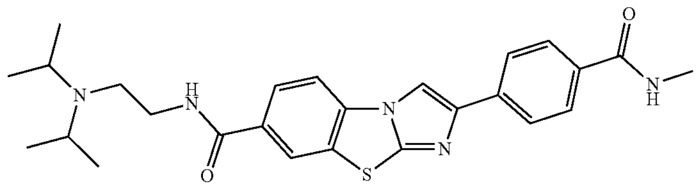 [SMILES: CNC(=O)c1ccc(-c2cn3c(n2)sc2cc(C(=O)NCCN(C(C)C)C(C)C)ccc23)cc1] | N-(2-(diisopropylamino)ethyl)-2-(4-(methylcarbamoyl)phenyl)benzo[d]imidazo[2,1-b]thiazole-7-carboxamide |
| 218 | 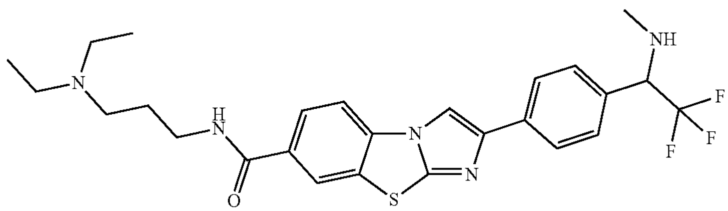 [SMILES: CCN(CC)CCCNC(=O)c1ccc2c(c1)sc1nc(-c3ccc(C(NC)C(F)(F)F)cc3)cn12] | N-(3-(diethylamino)propyl)-2-(4-(2,2,2-trifluoro-1-(methylamino)ethyl)phenyl)benzo[d]imidazo[2,1-b]thiazole-7-carboxamide |
| 219 | 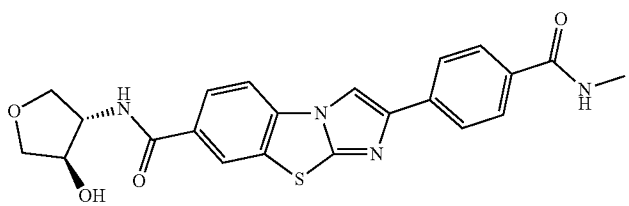 [SMILES: CNC(=O)c1ccc(-c2cn3c(n2)sc2cc(C(=O)N[C@H]4COC[C@@H]4O)ccc23)cc1] | N-((3S,4R)-4-hydroxytetrahydrofuran-3-yl)-2-(4-(methylcarbamoyl)phenyl)benzo[d]imidazo[2,1-b]thiazole-7-carboxamide |
| 220 | 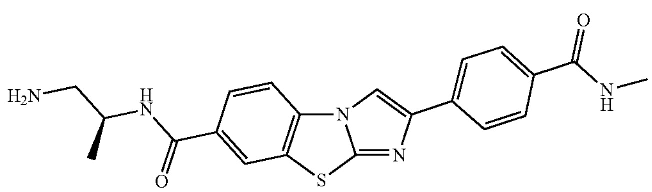 [SMILES: CNC(=O)c1ccc(-c2cn3c(n2)sc2cc(C(=O)N[C@@H](C)CN)ccc23)cc1] | (S)-N-(1-aminopropan-2-yl)-2-(4-(methylcarbamoyl)phenyl)benzo[d]imidazo[2,1-b]thiazole-7-carboxamide |
| 221 | 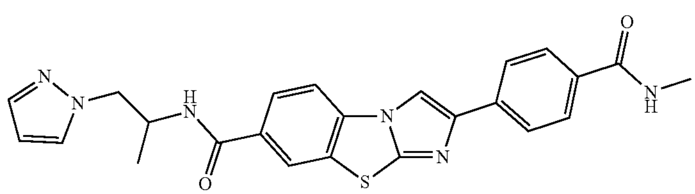 [SMILES: CNC(=O)c1ccc(-c2cn3c(n2)sc2cc(C(=O)NC(C)Cn4cccn4)ccc23)cc1] | N-(1-(1H-pyrazol-1-yl)propan-2-yl)-2-(4-(methylcarbamoyl)phenyl)benzo[d]imidazo[2,1-b]thiazole-7-carboxamide |
| 222 | 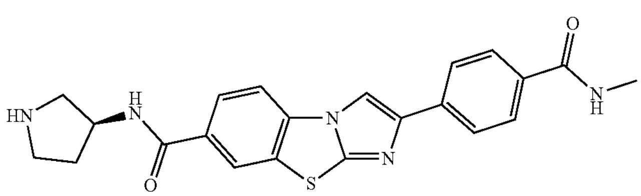 [SMILES: CNC(=O)c1ccc(-c2cn3c(n2)sc2cc(C(=O)N[C@H]4CCNC4)ccc23)cc1] | (S)-2-(4-(methylcarbamoyl)phenyl)-N-(pyrrolidin-3-yl)benzo[d]imidazo[2,1-b]thiazole-7-carboxamide |
| 223 | 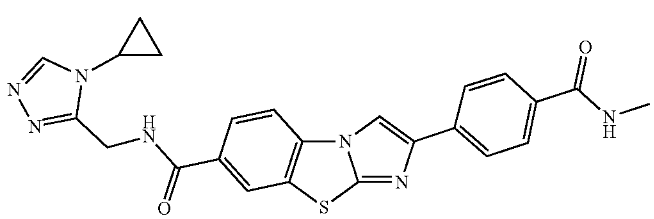 [SMILES: CNC(=O)c1ccc(-c2cn3c(n2)sc2cc(C(=O)NCc4nncn4C4CC4)ccc23)cc1] | N-((4-cyclopropyl-4H-1,2,4-triazol-3-yl)methyl)-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 224 | 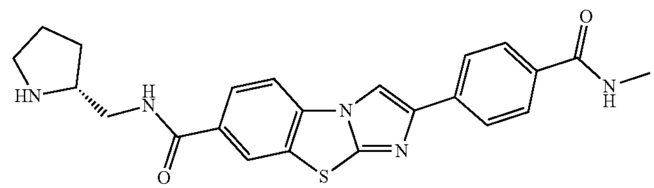 [SMILES: CNC(=O)c1ccc(-c2cn3c(n2)sc2cc(C(=O)NC[C@H]4CCCN4)ccc23)cc1] | (R)-2-(4-(methylcarbamoyl)phenyl)-N-(pyrrolidin-2-ylmethyl)benzo[d]imidazo[2,1-b]thiazole-7-carboxamide |
| 225 | 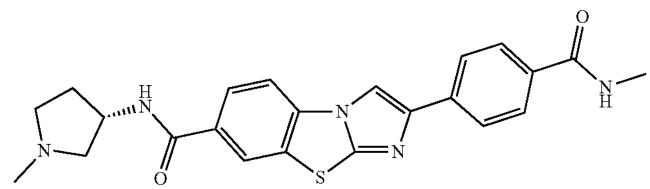 | (S)-2-(4-(methylcarbamoyl)phenyl)-N-(1-methylpyrrolidin-3-yl)benzo[d]imidazo[2,1-b]thiazole-7-carboxamide |
| 226 | 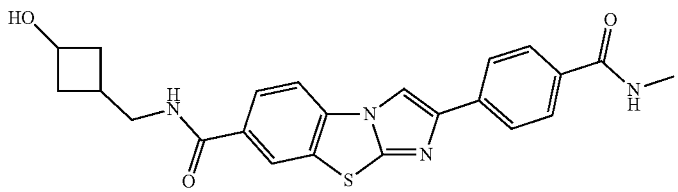 [SMILES: CNC(=O)c1ccc(-c2cn3c(n2)sc2cc(C(=O)NCC4CC(O)C4)ccc23)cc1] | N-((3-hydroxycyclobutyl)methyl)-2-(4-(methylcarbamoyl)phenyl)benzo[d]imidazo[2,1-b]thiazole-7-carboxamide |
| 227 | 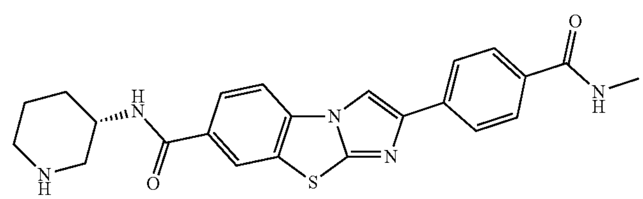 [SMILES: CNC(=O)c1ccc(-c2cn3c(n2)sc2cc(C(=O)N[C@H]4CCCNC4)ccc23)cc1] | (S)-2-(4-(methylcarbamoyl)phenyl)-N-(piperidin-3-yl)benzo[d]imidazo[2,1-b]thiazole-7-carboxamide |
| 228 | 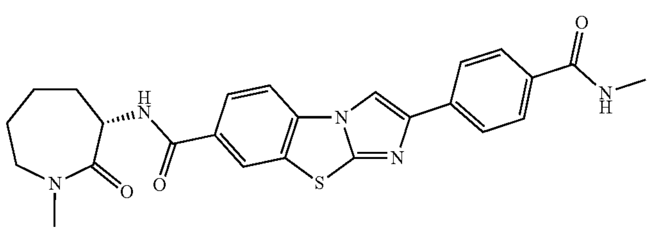 [SMILES: CNC(=O)c1ccc(-c2cn3c(n2)sc2cc(C(=O)N[C@H]4CCCCN(C)C4=O)ccc23)cc1] | (S)-N-(1-methyl-2-oxoazepan-3-yl)-2-(4-(methylcarbamoyl)phenyl)benzo[d]imidazo[2,1-b]thiazole-7-carboxamide |
| 229 | 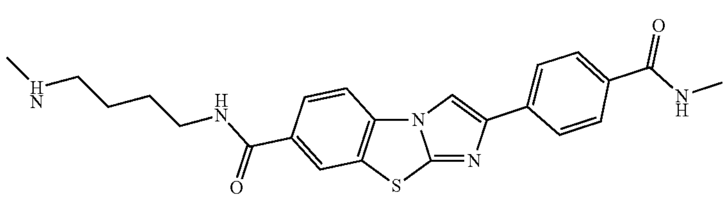 | N-(4-(methylamino)butyl)-2-(4-(methylcarbamoyl)phenyl)benzo[d]imidazo[2,1-b]thiazole-7-carboxamide |
| 230 | 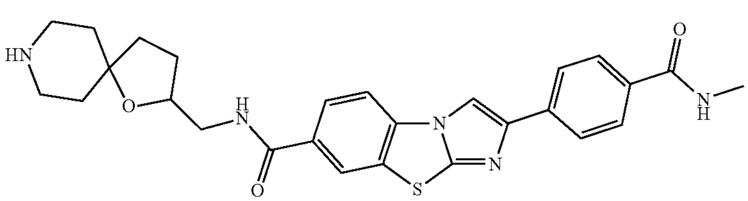 [SMILES: CNC(=O)c1ccc(-c2cn3c(n2)sc2cc(C(=O)NCC4CCC5(CCNCC5)O4)ccc23)cc1] | N-((1-oxa-8-azaspiro[4.5]decan-2-yl)methyl)-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 231 | 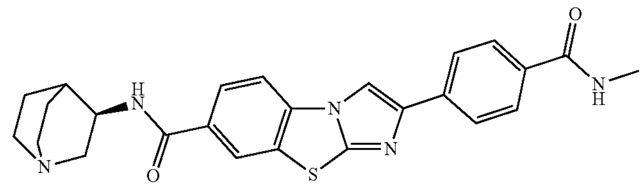 [SMILES: CNC(=O)c1ccc(-c2cn3c(n2)sc2cc(C(=O)N[C@H]4CN5CCC4CC5)ccc23)cc1] | (R)-2-(4-(methylcarbamoyl)phenyl)-N-(quinuclidin-3-yl)benzo[d]imidazo[2,1-b]thiazole-7-carboxamide |
| 232 | 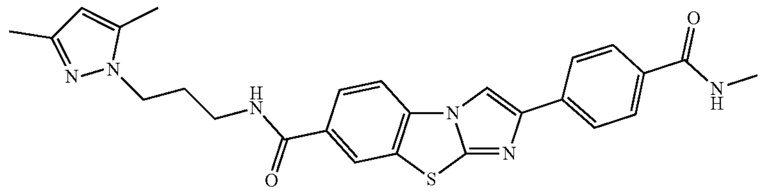 | N-(3-(3,5-dimethyl-1H-pyrazol-1-yl)propyl)-2-(4-(methylcarbamoyl)phenyl)benzo[d]imidazo[2,1-b]thiazole-7-carboxamide |
| 233 | 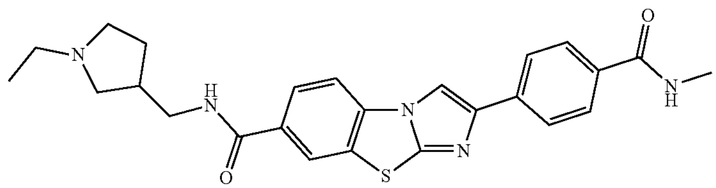 [SMILES: CCN1CCC(CNC(=O)c2ccc3c(c2)sc2nc(-c4ccc(C(=O)NC)cc4)cn23)C1] | N-((1-ethylpyrrolidin-3-yl)methyl)-2-(4-(methylcarbamoyl)phenyl)benzo[d]imidazo[2,1-b]thiazole-7-carboxamide |
| 234 | 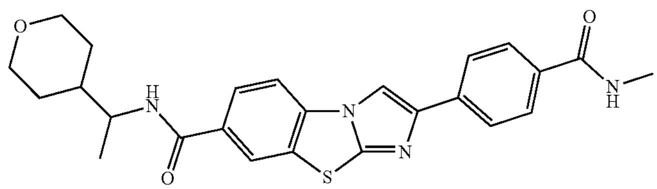 [SMILES: CNC(=O)c1ccc(-c2cn3c(n2)sc2cc(C(=O)NC(C)C4CCOCC4)ccc23)cc1] | 2-(4-(methylcarbamoyl)phenyl)-N-(1-(tetrahydro-2H-pyran-4-yl)ethyl)benzo[d]imidazo[2,1-b]thiazole-7-carboxamide |
| 235 | 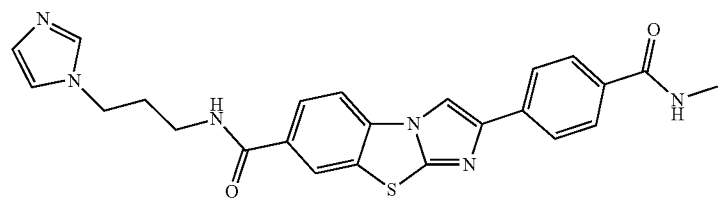 [SMILES: CNC(=O)c1ccc(-c2cn3c(n2)sc2cc(C(=O)NCCCn4ccnc4)ccc23)cc1] | N-(3-(1H-imidazol-1-yl)propyl)-2-(4-(methylcarbamoyl)phenyl)benzo[d]imidazo[2,1-b]thiazole-7-carboxamide |
| 236 | 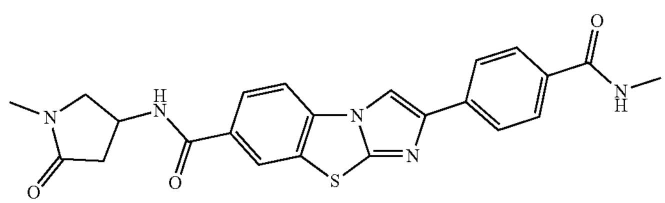 | N-(1-methyl-5-oxopyrrolidin-3-yl)-2-(4-(methylcarbamoyl)phenyl)benzo[d]imidazo[2,1-b]thiazole-7-carboxamide |
| 237 | 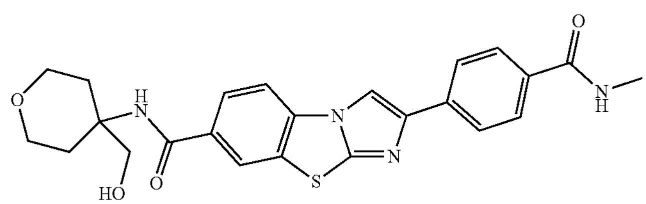 [SMILES: CNC(=O)c1ccc(-c2cn3c(n2)sc2cc(C(=O)NC4(CO)CCOCC4)ccc23)cc1] | N-(4-(hydroxymethyl)tetrahydro-2H-pyran-4-yl)-2-(4-(methylcarbamoyl)phenyl)benzo[d]imidazo[2,1-b]thiazole-7-carboxamide |
| 238 | 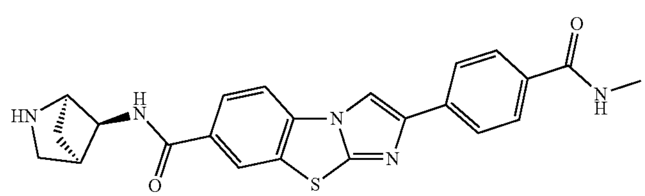 [SMILES: CNC(=O)c1ccc(-c2cn3c(n2)sc2cc(C(=O)N[C@H]4[C@H]5CN[C@@H]4C5)ccc23)cc1] | N-((1R,4R,5S)-2-azabicyclo[2.1.1]hexan-5-(methylcarbamoyl)phenyl)benzo[d]imidazo[2,1-b]thiazole-7-carboxamide |

TABLE 1-continued

| Comp. No. | Structure | Compound Name |
|---|---|---|
| 239 | 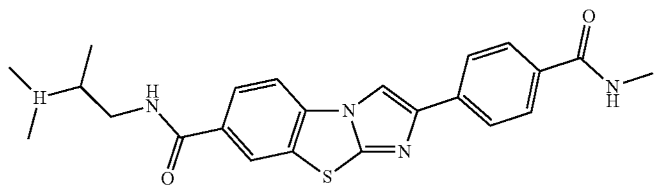 | N-(2-(dimethylamino)propyl)-2-(4-(methylcarbamoyl)phenyl)benzo[d]imidazo[2,1-b]thiazole-7-carboxamide |
| 240 | 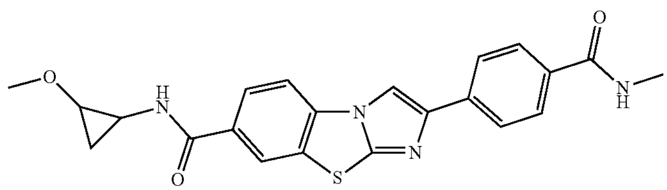 | N-(2-methoxycyclopropyl)-2-(4-(methylcarbamoyl)phenyl)benzo[d]imidazo[2,1-b]thiazole-7-carboxamide |
| 241 | 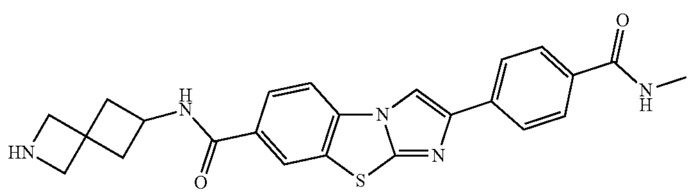 [SMILES: CNC(=O)c1ccc(-c2cn3c(n2)sc2cc(C(=O)NC4CC5(CNC5)C4)ccc23)cc1] | 2-(4-(methylcarbamoyl)phenyl)-N-(2-azaspiro[3.3]heptan-6-yl)benzo[d]imidazo[2,1-b]thiazole-7-carboxamide |
| 242 | 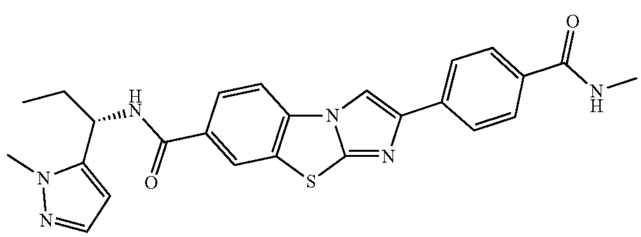 | (S)-N-(1-(1-methyl-1H-pyrazol-5-yl)propyl)-2-(4-(methylcarbamoyl)phenyl)benzo[d]imidazo[2,1-b]thiazole-7-carboxamide |
| 243 | 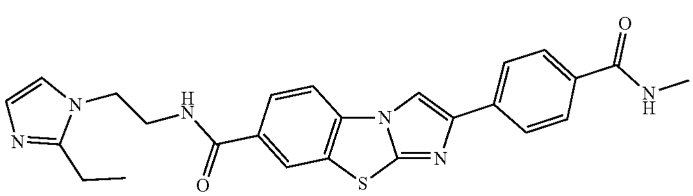 [SMILES: CCc1nccn1CCNC(=O)c1ccc2c(c1)sc1nc(-c3ccc(C(=O)NC)cc3)cn12] | N-(2-(2-ethyl-1H-imidazol-1-yl)ethyl)-2-(4-(methylcarbamoyl)phenyl)benzo[d]imidazo[2,1-b]thiazole-7-carboxamide |
| 244 | 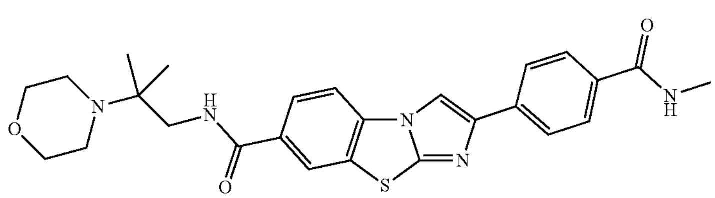 [SMILES: CNC(=O)c1ccc(-c2cn3c(n2)sc2cc(C(=O)NCC(C)(C)N4CCOCC4)ccc23)cc1] | N-(2-methyl-2-morpholinopropyl)-2-(4-(methylcarbamoyl)phenyl)benzo[d]imidazo[2,1-b]thiazole-7-carboxamide |
| 245 | 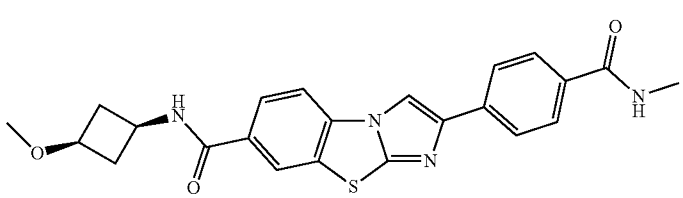 | N-((1s,3s)-3-methoxycyclobutyl)-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 246 | 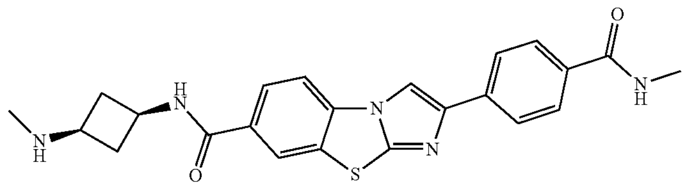 | N-((1s,3s)-3-(methylamino)cyclobutyl)-2-(4-(methylcarbamoyl)phenyl)benzo[d]imidazo[2,1-b]thiazole-7-carboxamide |
| 247 | 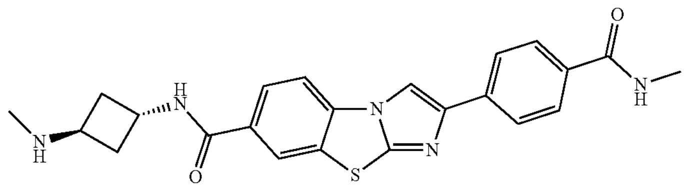 | N-((1r,3r)-3-(methylamino)cyclobutyl)-2-(4-(methylcarbamoyl)phenyl)benzo[d]imidazo[2,1-b]thiazole-7-carboxamide |
| 248 | 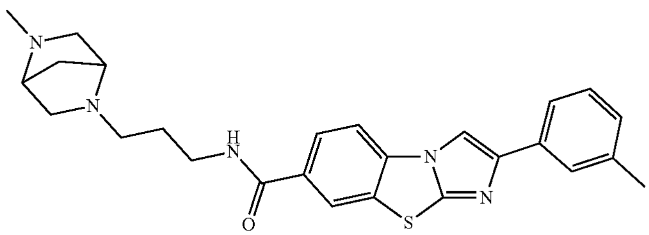 | N-(3-(5-methyl-2,5-diazabicyclo[2.2.1]heptan-2-yl)propyl)-2-(m-tolyl)benzo[d]imidazo[2,1-b]thiazole-7-carboxamide |
| 249 | 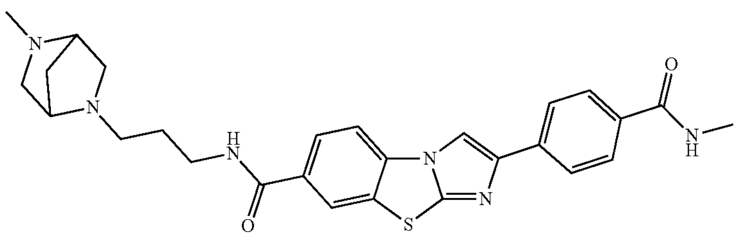 | N-(3-(5-methyl-2,5-diazabicyclo[2.2.1]heptan-2-yl)propyl)-2-(4-(methylcarbamoyl)phenyl)benzo[d]imidazo[2,1-b]thiazole-7-carboxamide |
| 250 | 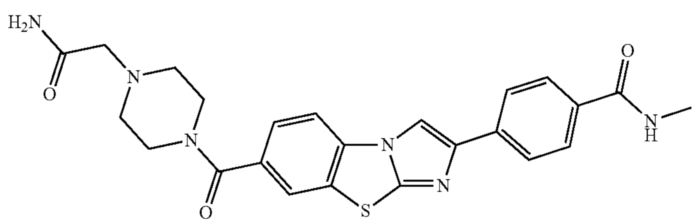 [SMILES: CNC(=O)c1ccc(-c2cn3c(n2)sc2cc(C(=O)N4CCN(CC(N)=O)CC4)ccc23)cc1] | 4-(7-(4-(2-amino-2-oxoethyl)piperazine-1-carbonyl)benzo[d]imidazo[2,1-b]thiazol-2-yl)-N-methylbenzamide |
| 251 | 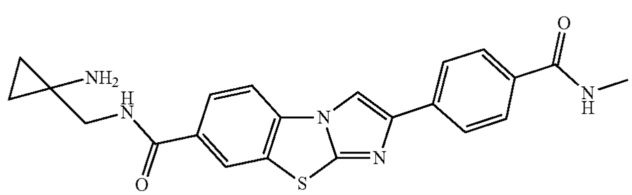 [SMILES: CNC(=O)c1ccc(-c2cn3c(n2)sc2cc(C(=O)NCC4(N)CC4)ccc23)cc1] | N-((1-aminocyclopropyl)methyl)-2-(4-(methylcarbamoyl)phenyl)benzo[d]imidazo[2,1-b]thiazole-7-carboxamide |
| 252 | 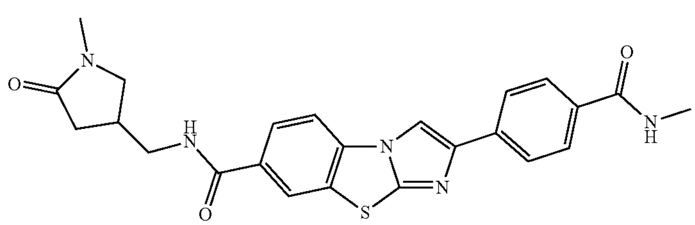 [SMILES: CNC(=O)c1ccc(-c2cn3c(n2)sc2cc(C(=O)NCC4CC(=O)N(C)C4)ccc23)cc1] | N-((1-methyl-5-oxopyrrolidin-3-yl)methyl)-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 253 | 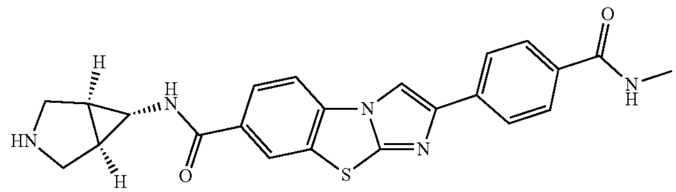 [SMILES: CNC(=O)c1ccc(-c2cn3c(n2)sc2cc(C(=O)N[C@H]4[C@@H]5CNC[C@@H]54)ccc23)cc1] | N-((1R,5S,6s)-3-azabicyclo[3.1.0]hexan-6-yl)-2-(4-(methylcarbamoyl)phenyl)benzo[d]imidazo[2,1-b]thiazole-7-carboxamide |
| 254 | 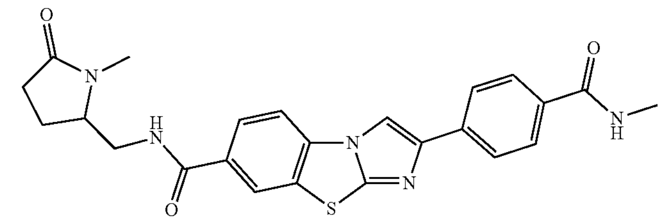 [SMILES: CNC(=O)c1ccc(-c2cn3c(n2)sc2cc(C(=O)NCC4CCC(=O)N4C)ccc23)cc1] | N-((1-methyl-5-oxopyrrolidin-2-yl)methyl)-2-(4-(methylcarbamoyl)phenyl)benzo[d]imidazo[2,1-b]thiazole-7-carboxamide |
| 255 | 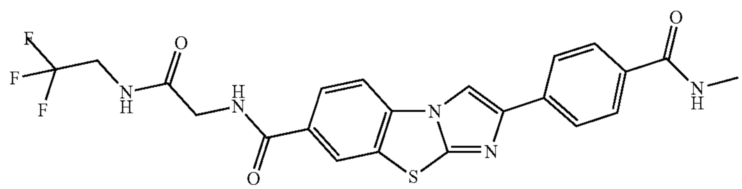 | 2-(4-(methylcarbamoyl)phenyl)-N-(2-oxo-2-((2,2,2-trifluoroethyl)amino)ethyl)benzo[d]imidazo[2,1-b]thiazole-7-carboxamide |
| 256 | 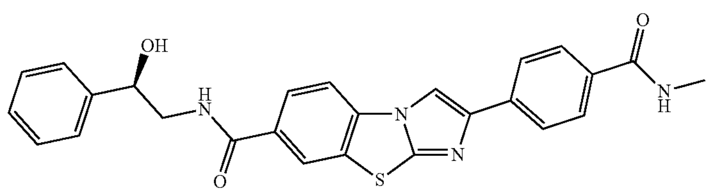 [SMILES: CNC(=O)c1ccc(-c2cn3c(n2)sc2cc(C(=O)NC[C@H](O)c4ccccc4)ccc23)cc1] | (R)-N-(2-hydroxy-2-phenylethyl)-2-(4-(methylcarbamoyl)phenyl)benzo[d]imidazo[2,1-b]thiazole-7-carboxamide |
| 257 | 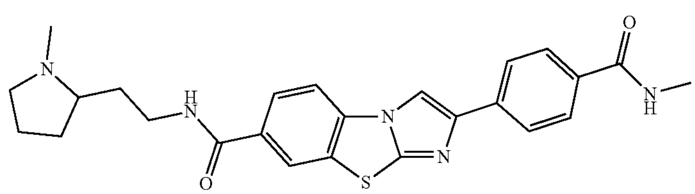 [SMILES: CNC(=O)c1ccc(-c2cn3c(n2)sc2cc(C(=O)NCCC4CCCN4C)ccc23)cc1] | 2-(4-(methylcarbamoyl)phenyl)-N-(2-(1-methylpyrrolidin-2-yl)ethyl)benzo[d]imidazo[2,1-b]thiazole-7-carboxamide |
| 258 | 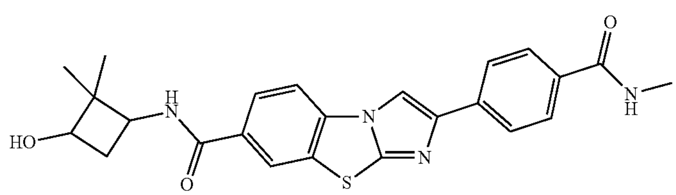 [SMILES: CNC(=O)c1ccc(-c2cn3c(n2)sc2cc(C(=O)NC4CC(O)C4(C)C)ccc23)cc1] | N-(3-hydroxy-2,2-dimethylcyclobutyl)-2-(4-(methylcarbamoyl)phenyl)benzo[d]imidazo[2,1-b]thiazole-7-carboxamide |
| 259 | 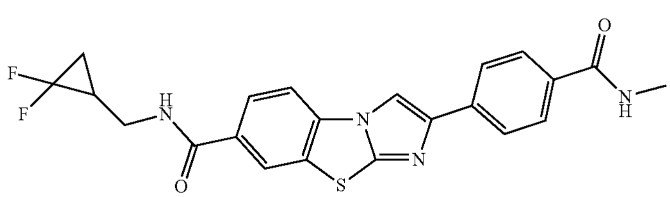 [SMILES: CNC(=O)c1ccc(-c2cn3c(n2)sc2cc(C(=O)NCC4CC4(F)F)ccc23)cc1] | N-((2,2-difluorocyclopropyl)methyl)-2-(4-(methylcarbamoyl)phenyl)benzo[d]imidazo[2,1-b]thiazole-7-carboxamide |
| 260 | 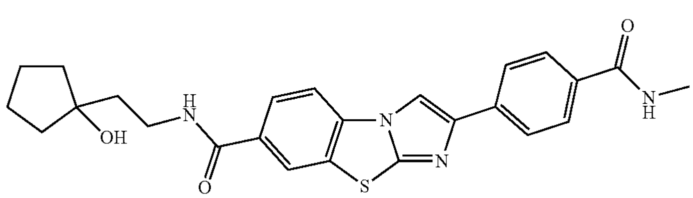 [SMILES: CNC(=O)c1ccc(-c2cn3c(n2)sc2cc(C(=O)NCCC4(O)CCCC4)ccc23)cc1] | N-(2-(1-hydroxycyclopentyl)ethyl)-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 261 | 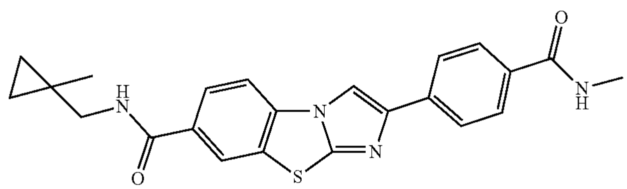 [SMILES: CNC(=O)c1ccc(-c2cn3c(n2)sc2cc(C(=O)NCC4(C)CC4)ccc23)cc1] | 2-(4-(methylcarbamoyl)phenyl) N-((1-methylcyclopropyl)methyl) benzo[d]imidazo[2,1-b]thiazole-7-carboxamide |
| 262 | 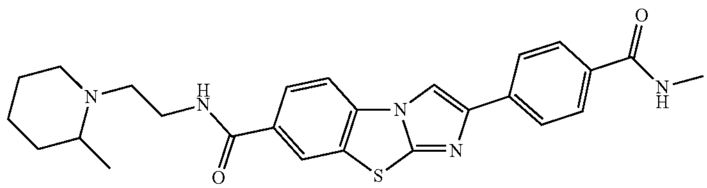 [SMILES: CNC(=O)c1ccc(-c2cn3c(n2)sc2cc(C(=O)NCCN4CCCCC4C)ccc23)cc1] | 2-(4-(methylcarbamoyl)phenyl) N-(2-(2-methylpiperidin-1-yl)ethyl)benzo[d]imidazo [2,1-b]thiazole-7-carboxamide |
| 263 | 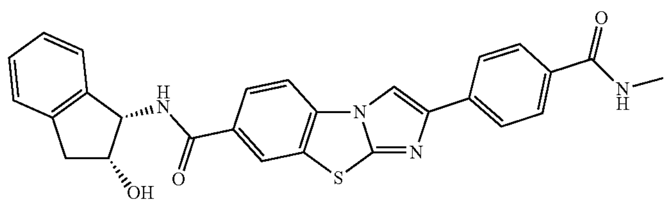 [SMILES: CNC(=O)c1ccc(-c2cn3c(n2)sc2cc(C(=O)N[C@H]4c5ccccc5C[C@H]4O)ccc23)cc1] | N-((1S,2R)-2-hydroxy-2,3-dihydro-1H-inden-1-yl)-2-(4-(methylcarbamoyl)phenyl) benzo[d]imidazo[2,1-b]thiazole-7-carboxamide |
| 264 | 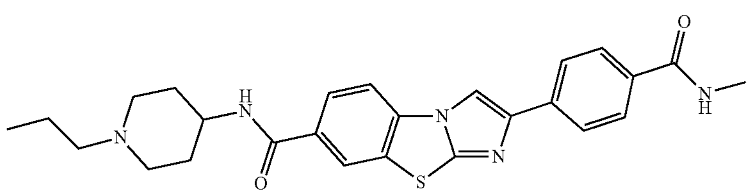 [SMILES: CCCN1CCC(NC(=O)c2ccc3c(c2)sc2nc(-c4ccc(C(=O)NC)cc4)cn23)CC1] | 2-(4-(methylcarbamoyl)phenyl)-N-(1-propylpiperidin-4-yl)benzo[d]imidazo[2,1-b]thiazole-7-carboxamide |
| 265 | 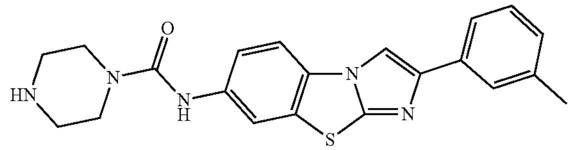 [SMILES: Cc1cccc(-c2cn3c(n2)sc2cc(NC(=O)N4CCNCC4)ccc23)c1] | N-(2-(m-tolyl)benzo[d]imidazo[2,1-b]thiazol-7-yl)piperazine-1-carboxamide |
| 266 | 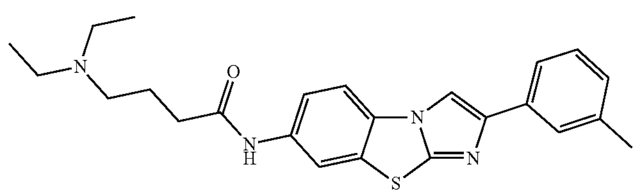 [SMILES: CCN(CC)CCCC(=O)Nc1ccc2c(c1)sc1nc(-c3cccc(C)c3)cn12] | 4-(diethylamino)-N-(2-(m-tolyl) benzo[d]imidazo[2,1-b]thiazol-7-yl)butanamide |
| 267 | 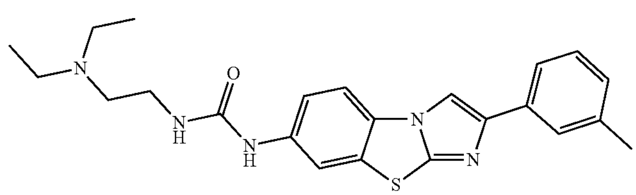 [SMILES: CCN(CC)CCNC(=O)Nc1ccc2c(c1)sc1nc(-c3cccc(C)c3)cn12] | 1-(2-(diethylamino)ethyl)-3-(2-(m-tolyl)benzo[d]imidazo[2,1-b]thiazol-7-yl)urea |
| 268 | 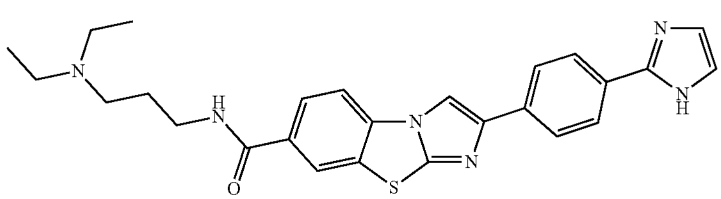 [SMILES: CCN(CC)CCCNC(=O)c1ccc2c(c1)sc1nc(-c3ccc(-c4ncc[nH]4)cc3)cn12] | 2-(4-(1H-imidazol-2-yl)phenyl)-N-(3-(diethylamino)propyl) benzo[d]imidazo[2,1-b]thiazole-7-carboxamide |

TABLE 1-continued

| Comp. No. | Structure | Compound Name |
|---|---|---|
| 269 | 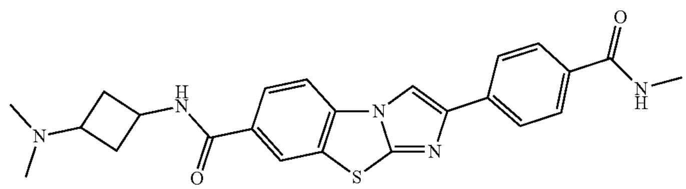 | N-(3-(dimethylamino)cyclobutyl)-2-(4-(methylcarbamoyl)phenyl)benzo[d]imidazo[2,1-b]thiazole-7-carboxamide |
| 270 | 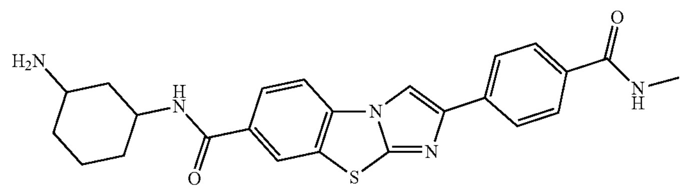 [SMILES: CNC(=O)c1ccc(-c2cn3c(n2)sc2cc(C(=O)NC4CCCC(N)C4)ccc23)cc1] | N-(3-aminocyclohexyl)-2-(4-(methylcarbamoyl)phenyl)benzo[d]imidazo[2,1-b]thiazole-7-carboxamide |
| 271 | 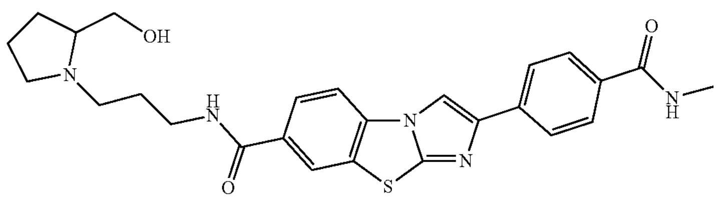 [SMILES: CNC(=O)c1ccc(-c2cn3c(n2)sc2cc(C(=O)NCCCN4CCCC4CO)ccc23)cc1] | N-(3-(2-(hydroxymethyl)pyrrolidin-1-yl)propyl)-2-(4-(methylcarbamoyl)phenyl)benzo[d]imidazo[2,1-b]thiazole-7-carboxamide |
| 272 | 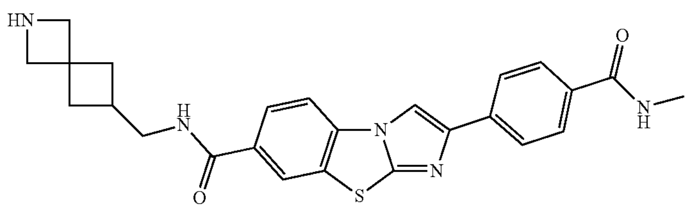 [SMILES: CNC(=O)c1ccc(-c2cn3c(n2)sc2cc(C(=O)NCC4CC5(CNC5)C4)ccc23)cc1] | N-((2-azaspiro[3.3]heptan-6-yl)methyl)-2-(4-(methylcarbamoyl)phenyl)benzo[d]imidazo[2,1-b]thiazole-7-carboxamide |
| 273 | 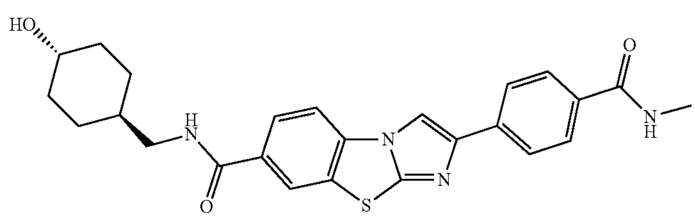 [SMILES: CNC(=O)c1ccc(-c2cn3c(n2)sc2cc(C(=O)NC[C@H]4CC[C@H](O)CC4)ccc23)cc1] | N-(((1r,4r)-4-hydroxycyclohexyl)methyl)-2-(4-(methylcarbamoyl)phenyl)benzo[d]imidazo[2,1-b]thiazole-7-carboxamide |
| 274 | 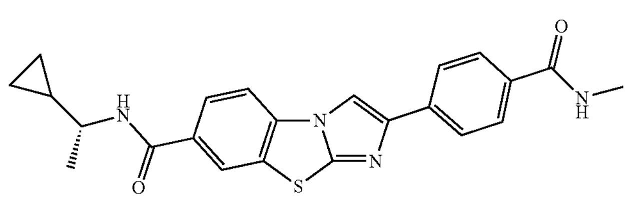 [SMILES: CNC(=O)c1ccc(-c2cn3c(n2)sc2cc(C(=O)N[C@H](C)C4CC4)ccc23)cc1] | (R)-N-(1-cyclopropylethyl)-2-(4-(methylcarbamoyl)phenyl)benzo[d]imidazo[2,1-b]thiazole-7-carboxamide |
| 275 | 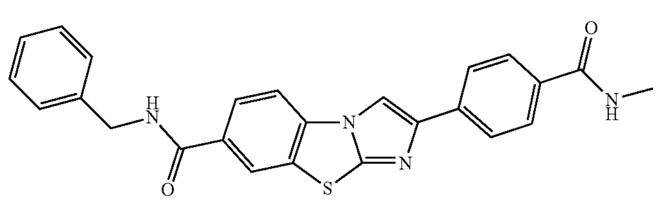 [SMILES: CNC(=O)c1ccc(-c2cn3c(n2)sc2cc(C(=O)NCc4ccccc4)ccc23)cc1] | N-benzyl-2-(4-(methylcarbamoyl)phenyl)benzo[d]imidazo[2,1-b]thiazole-7-carboxamide |

TABLE 1-continued

| Comp. No. | Structure | Compound Name |
|---|---|---|
| 276 | 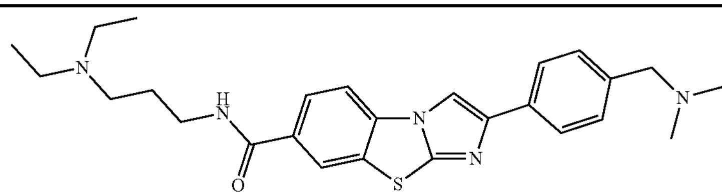 | N-(3-(diethylamino)propyl)-2-(4-((dimethylamino)methyl)phenyl)benzo[d]imidazo[2,1-b]thiazole-7-carboxamide |
| 277 | 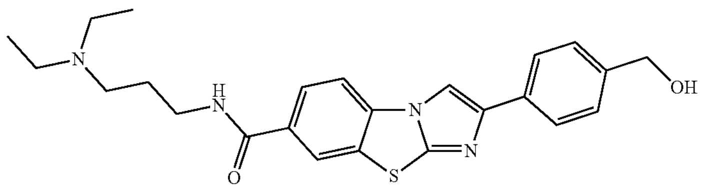 [SMILES: CCN(CC)CCCNC(=O)c1ccc2c(c1)sc1nc(-c3ccc(CO)cc3)cn12] | N-(3-(diethylamino)propyl)-2-(4-(hydroxymethyl)phenyl)benzo[d]imidazo[2,1-b]thiazole-7-carboxamide |
| 278 | 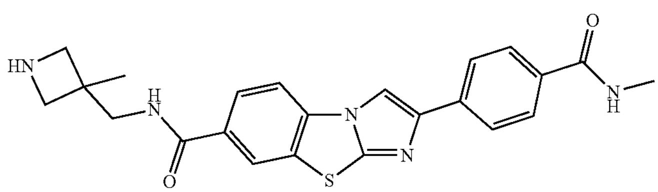 [SMILES: CNC(=O)c1ccc(-c2cn3c(n2)sc2cc(C(=O)NCC4(C)CNC4)ccc23)cc1] | N-((3-methylazetidin-3-yl)methyl)-2-(4-(methylcarbamoyl)phenyl)benzo[d]imidazo[2,1-b]thiazole-7-carboxamide |
| 279 | 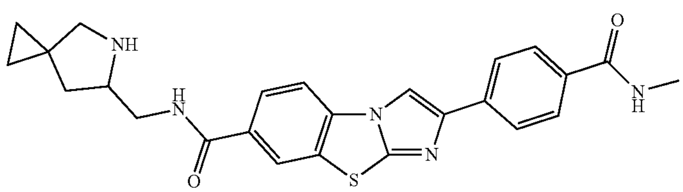 [SMILES: CNC(=O)c1ccc(-c2cn3c(n2)sc2cc(C(=O)NCC4CC5(CC5)CN4)ccc23)cc1] | N-((5-azaspiro[2.4]heptan-6-yl)methyl)-2-(4-(methylcarbamoyl)phenyl)benzo[d]imidazo[2,1-b]thiazole-7-carboxamide |
| 280 | 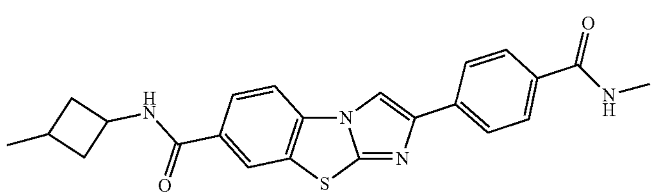 | 2-(4-(methylcarbamoyl)phenyl)-N-(3-methylcyclobutyl)benzo[d]imidazo[2,1-b]thiazole-7-carboxamide |
| 281 | 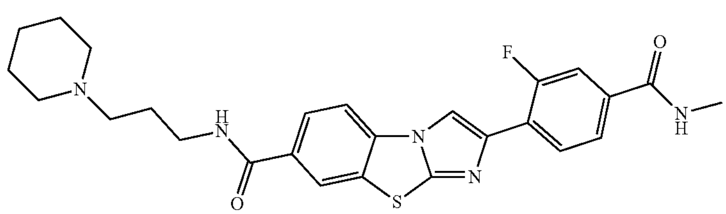 [SMILES: CNC(=O)c1ccc(-c2cn3c(n2)sc2cc(C(=O)NCCCN4CCCCC4)ccc23)c(F)c1] | 2-(2-fluoro-4-(methylcarbamoyl)phenyl)-N-(3-(piperidin-1-yl)propyl)benzo[d]imidazo[2,1-b]thiazole-7-carboxamide |
| 282 | 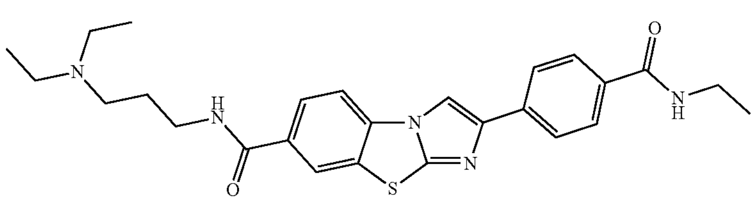 [SMILES: CCNC(=O)c1ccc(-c2cn3c(n2)sc2cc(C(=O)NCCCN(CC)CC)ccc23)cc1] | N-(3-(diethylamino)propyl)-2-(4-(ethylcarbamoyl)phenyl)benzo[d]imidazo[2,1-b]thiazole-7-carboxamide |
| 283 | 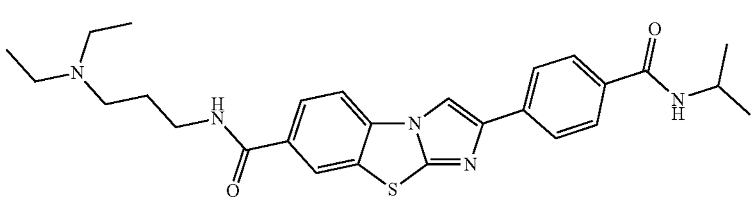 [SMILES: CCN(CC)CCCNC(=O)c1ccc2c(c1)sc1nc(-c3ccc(C(=O)NC(C)C)cc3)cn12] | N-(3-(diethylamino)propyl)-2-(4-(isopropylcarbamoyl)phenyl)benzo[d]imidazo[2,1-b]thiazole-7-carboxamide |

TABLE 1-continued

| Comp. No. | Structure | Compound Name |
|---|---|---|
| 284 | 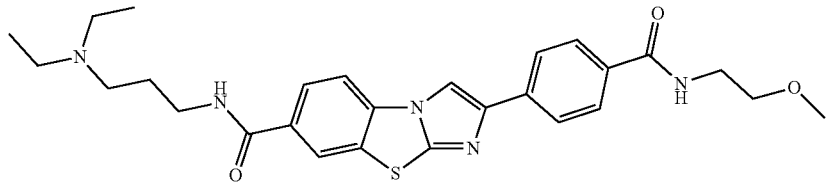 [SMILES: CCN(CC)CCCNC(=O)c1ccc2c(c1)sc1nc(-c3ccc(C(=O)NCCOC)cc3)cn12] | N-(3-(diethylamino)propyl)-2-(4-((2-methoxyethyl)carbamoyl)phenyl)benzo[d]imidazo[2,1-b]thiazole-7-carboxamide |
| 285 | 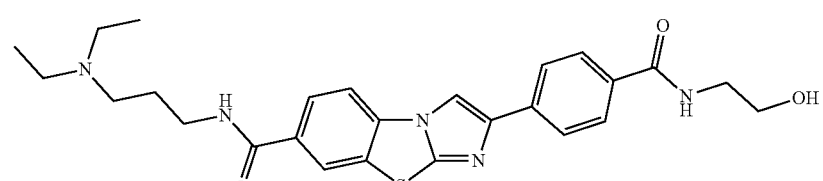 | N-(3-(diethylamino)propyl)-2-(4-((2-hydroxyethyl)carbamoyl)phenyl)benzo[d]imidazo[2,1-b]thiazole-7-carboxamide |
| 286 | 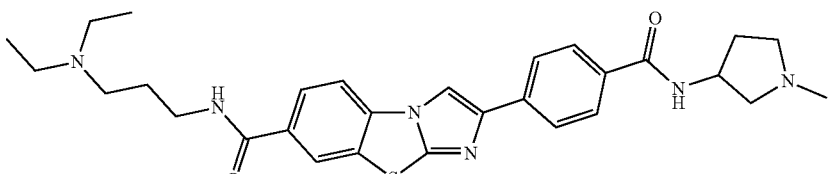 | N-(3-(diethylamino)propyl)-2-(4-((1-methylpyrrolidin-3-yl)carbamoyl)phenyl)benzo[d]imidazo[2,1-b]thiazole-7-carboxamide |
| 287 | 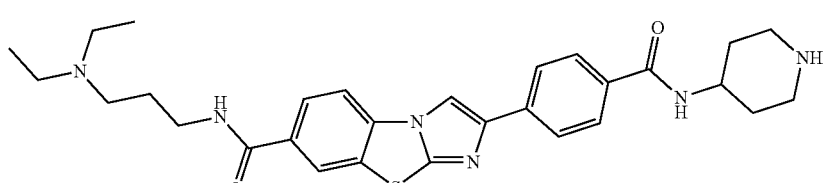 | N-(3-(diethylamino)propyl)-2-(4-(piperidin-4-ylcarbamoyl)phenyl)benzo[d]imidazo[2,1-b]thiazole-7-carboxamide |
| 288 | 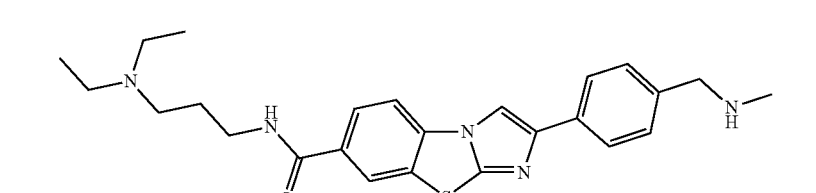 | N-(3-(diethylamino)propyl)-2-(4-((methylamino)methyl)phenyl)benzo[d]imidazo[2,1-b]thiazole-7-carboxamide |
| 289 | 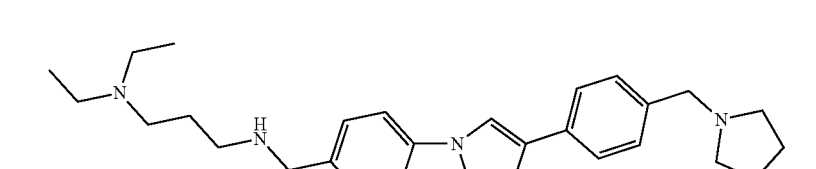 | N-(3-(diethylamino)propyl)-2-(4-(pyrrolidin-1-ylmethyl)phenyl)benzo[d]imidazo[2,1-b]thiazole-7-carboxamide |
| 290 | 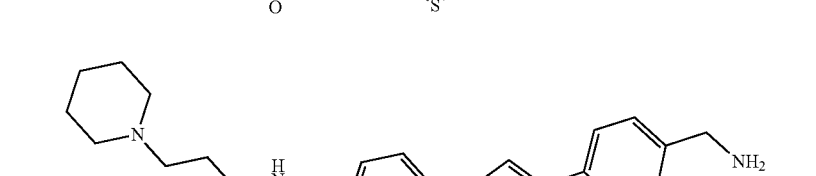 | 2-(4-(aminomethyl)phenyl)-N-(3-(piperidin-1-yl)propyl)benzo[d]imidazo[2,1-b]thiazole-7-carboxamide |

TABLE 1-continued

| Comp. No. | Structure | Compound Name |
|---|---|---|
| 291 | 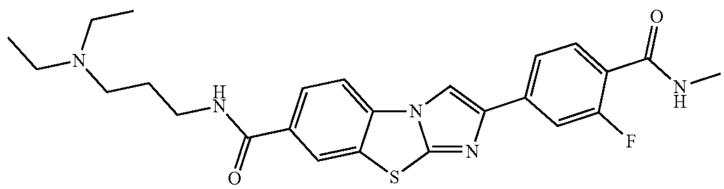 [SMILES: CCN(CC)CCCNC(=O)c1ccc2c(c1)sc1nc(-c3ccc(C(=O)NC)c(F)c3)cn12] | N-(3-(diethylamino)propyl)-2-(3-fluoro-4-(methylcarbamoyl)phenyl)benzo[d]imidazo[2,1-b]thiazole-7-carboxamide |
| 292 | 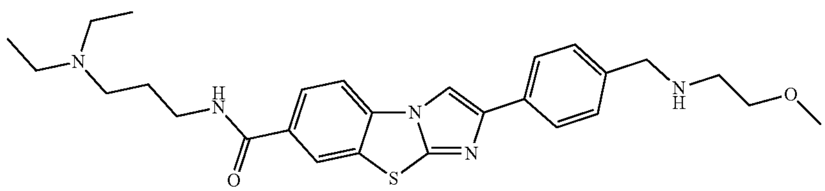 [SMILES: CCN(CC)CCCNC(=O)c1ccc2c(c1)sc1nc(-c3ccc(CNCCOC)cc3)cn12] | N-(3-(diethylamino)propyl)-2-(4-(((2-methoxyethyl)amino)methyl)phenyl)benzo[d]imidazo[2,1-b]thiazole-7-carboxamide |
| 293 | 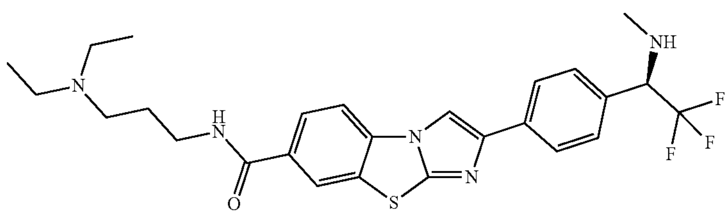 [SMILES: CCN(CC)CCCNC(=O)c1ccc2c(c1)sc1nc(-c3ccc([C@@H](NC)C(F)(F)F)cc3)cn12] | (R)-N-(3-(diethylamino)propyl)-2-(4-(2,2,2-trifluoro-1-(methylamino)ethyl)phenyl)benzo[d]imidazo[2,1-b]thiazole-7-carboxamide |
| 294 | 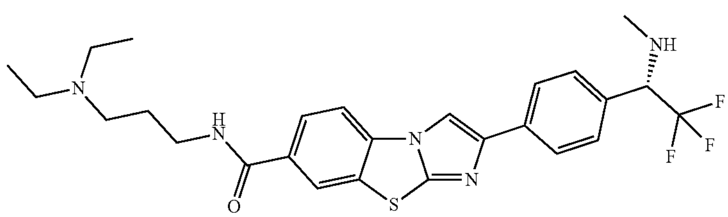 [SMILES: CCN(CC)CCCNC(=O)c1ccc2c(c1)sc1nc(-c3ccc([C@H](NC)C(F)(F)F)cc3)cn12] | (S)-N-(3-(diethylamino)propyl)-2-(4-(2,2,2-trifluoro-1-(methylamino)ethyl)phenyl)benzo[d]imidazo[2,1-b]thiazole-7-carboxamide |
| 295 | 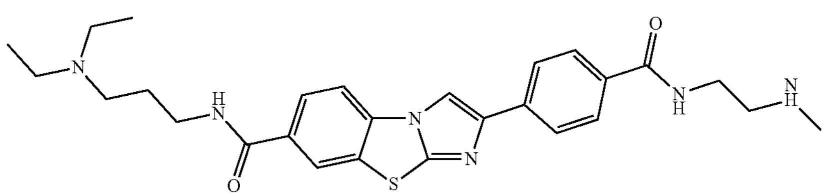 [SMILES: CCN(CC)CCCNC(=O)c1ccc2c(c1)sc1nc(-c3ccc(C(=O)NCCNC)cc3)cn12] | N-(3-(diethylamino)propyl)-2-(4-((2-(methylamino)ethyl)carbamoyl)phenyl)benzo[d]imidazo[2,1-b]thiazole-7-carboxamide |
| 296 | 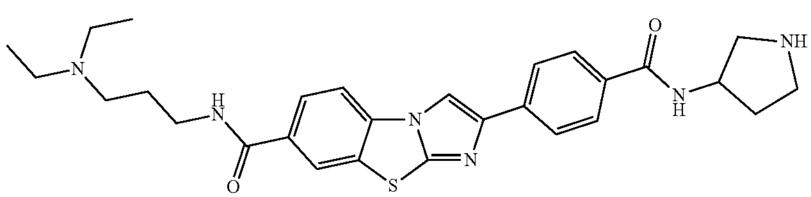 [SMILES: CCN(CC)CCCNC(=O)c1ccc2c(c1)sc1nc(-c3ccc(C(=O)NC4CCNC4)cc3)cn12] | N-(3-(diethylamino)propyl)-2-(4-(pyrrolidin-3-ylcarbamoyl)phenyl)benzo[d]imidazo[2,1-b]thiazole-7-carboxamide |
| 297 | 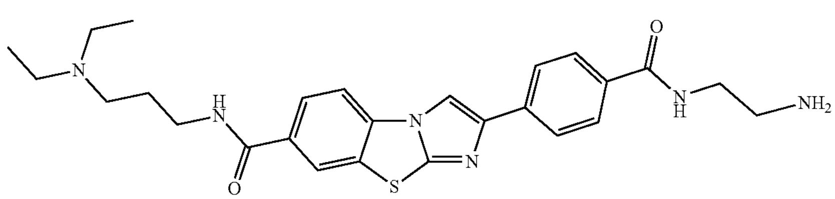 [SMILES: CCN(CC)CCCNC(=O)c1ccc2c(c1)sc1nc(-c3ccc(C(=O)NCCN)cc3)cn12] | 2-(4-((2-aminoethyl)carbamoyl)phenyl)-N-(3-(diethylamino)propyl)benzo[d]imidazo[2,1-b]thiazole-7-carboxamide |

TABLE 1-continued

| Comp. No. | Structure | Compound Name |
|---|---|---|
| 298 | 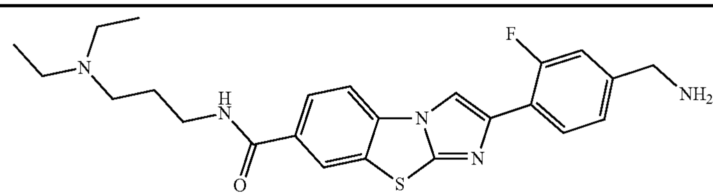 | 2-(4-(aminomethyl)-2-fluorophenyl)-N-(3-(diethylamino)propyl)benzo[d]imidazo[2,1-b]thiazole-7-carboxamide |
| 299 | 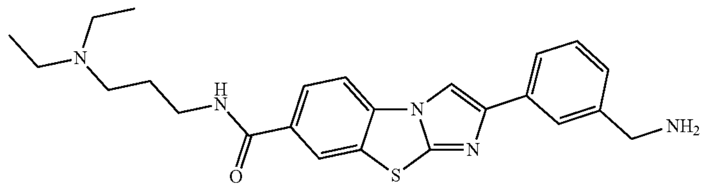 [SMILES: CCN(CC)CCCNC(=O)c1ccc2c(c1)sc1nc(-c3cccc(CN)c3)cn12] | 2-(3-(aminomethyl)phenyl)-N-(3-(diethylamino)propyl)benzo[d]imidazo[2,1-b]thiazole-7-carboxamide |
| 300 | 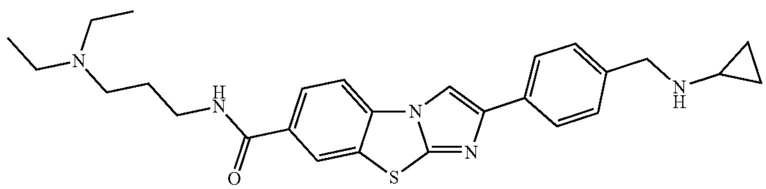 [SMILES: CCN(CC)CCCNC(=O)c1ccc2c(c1)sc1nc(-c3ccc(CNC4CC4)cc3)cn12] | 2-(4-((cyclopropylamino)methyl)phenyl)-N-(3-(diethylamino)propyl)benzo[d]imidazo[2,1-b]thiazole-7-carboxamide |
| 301 | 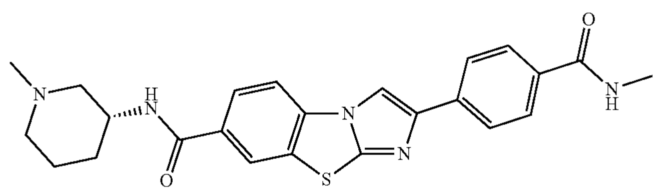 | (R)-2-(4-(methylcarbamoyl)phenyl)-N-(1-methylpiperidin-3-yl)benzo[d]imidazo[2,1-b]thiazole-7-carboxamide |
| 302 | 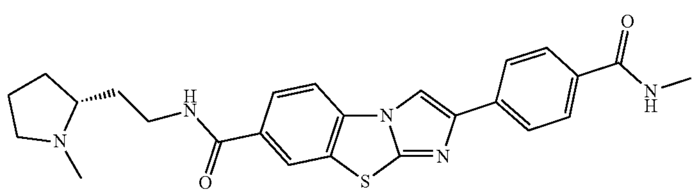 [SMILES: CNC(=O)c1ccc(-c2cn3c(n2)sc2cc(C(=O)NCC[C@H]4CCCN4C)ccc23)cc1] | (R)-2-(4-(methylcarbamoyl)phenyl)-N-(2-(1-methylpyrrolidin-2-yl)ethyl)benzo[d]imidazo[2,1-b]thiazole-7-carboxamide |
| 303 | 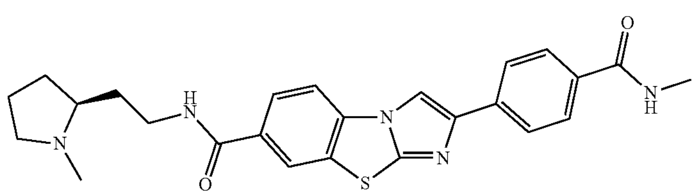 [SMILES: CNC(=O)c1ccc(-c2cn3c(n2)sc2cc(C(=O)NCC[C@@H]4CCCN4C)ccc23)cc1] | (S)-2-(4-(methylcarbamoyl)phenyl)-N-(2-(1-methylpyrrolidin-2-yl)ethyl)benzo[d]imidazo[2,1-b]thiazole-7-carboxamide |
| 304 | 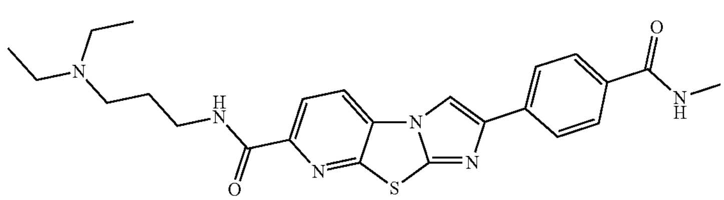 [SMILES: CCN(CC)CCCNC(=O)c1ccc2c(n1)sc1nc(-c3ccc(C(=O)NC)cc3)cn12] | N-(3-(diethylamino)propyl)-2-(4-(methylcarbamoyl)phenyl)imidazo[2',1':2,3]thiazolo[5,4-b]pyridine-7-carboxamide |
| 305 | 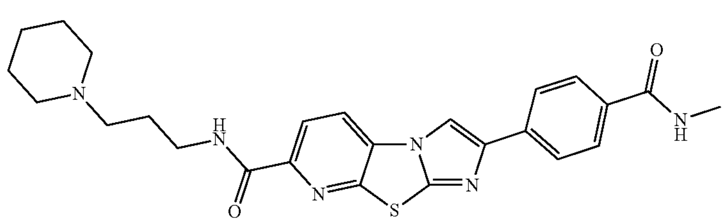 [SMILES: CNC(=O)c1ccc(-c2cn3c(n2)sc2nc(C(=O)NCCCN4CCCCC4)ccc23)cc1] | 2-(4-(methylcarbamoyl)phenyl)-N-(3-(piperidin-1-yl)propyl)imidazo[2',1':2,3]thiazolo[5,4-b]pyridine-7-carboxamide |

TABLE 1-continued

| Comp. No. | Structure | Compound Name |
|---|---|---|
| 306 | 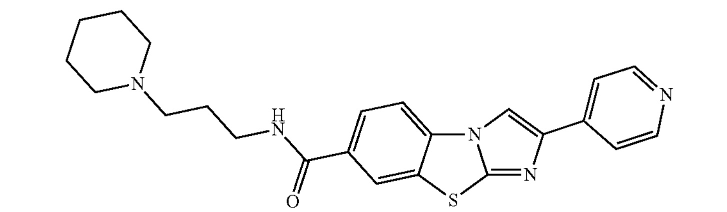 [SMILES: O=C(NCCCN1CCCCC1)c1ccc2c(c1)sc1nc(-c3ccncc3)cn12] | N-(3-(piperidin-1-yl)propyl)-2-(pyridin-4-yl)benzo[d]imidazo[2,1-b]thiazole-7-carboxamide |
| 307 | 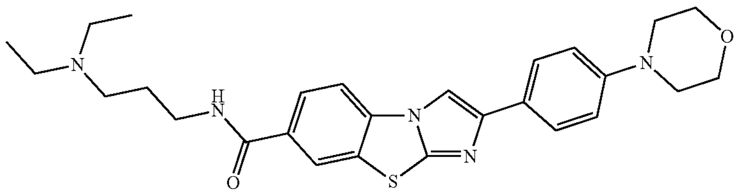 [SMILES: CCN(CC)CCCNC(=O)c1ccc2c(c1)sc1nc(-c3ccc(N4CCOCC4)cc3)cn12] | N-(3-(diethylamino)propyl)-2-(4-morpholinophenyl)benzo[d]imidazo[2,1-b]thiazole-7-carboxamide |
| 308 | 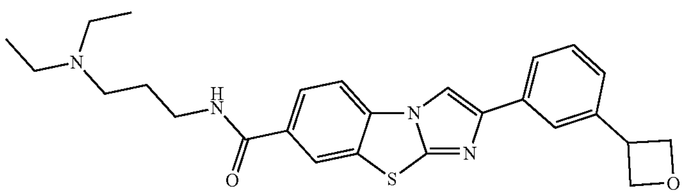 [SMILES: CCN(CC)CCCNC(=O)c1ccc2c(c1)sc1nc(-c3cccc(C4COC4)c3)cn12] | N-(3-(diethylamino)propyl)-2-(3-(oxetan-3-yl)phenyl)benzo[d]imidazo[2,1-b]thiazole-7-carboxamide |
| 309 | 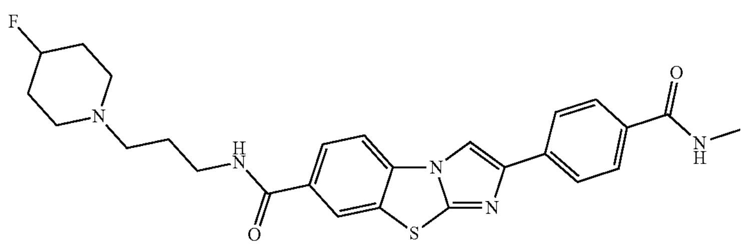 [SMILES: CNC(=O)c1ccc(-c2cn3c(n2)sc2cc(C(=O)NCCCN4CCC(F)CC4)ccc23)cc1] | N-(3-(4-fluoropiperidin-1-yl)propyl)-2-(4-(methylcarbamoyl)phenyl)benzo[d]imidazo[2,1-b]thiazole-7-carboxamide |
| 310 | 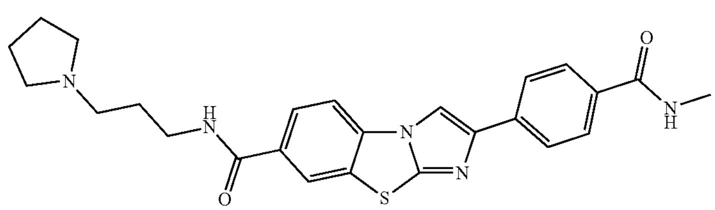 [SMILES: CNC(=O)c1ccc(-c2cn3c(n2)sc2cc(C(=O)NCCCN4CCCC4)ccc23)cc1] | 2-(4-(methylcarbamoyl)phenyl)-N-(3-(pyrrolidin-1-yl)propyl)benzo[d]imidazo[2,1-b]thiazole-7-carboxamide |
| 311 | 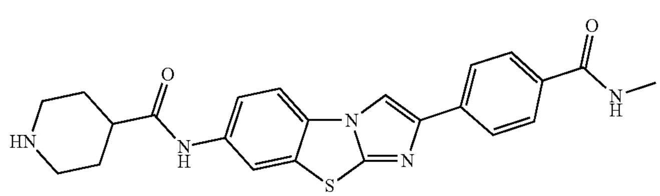 [SMILES: CNC(=O)c1ccc(-c2cn3c(n2)sc2cc(NC(=O)C4CCNCC4)ccc23)cc1] | (N-(2-(4-methylcarbamoyl)phenyl)benzo[d]imidazo[2,1-b]thiazol-7-yl)piperidine-4-carboxamide |
| 312 | 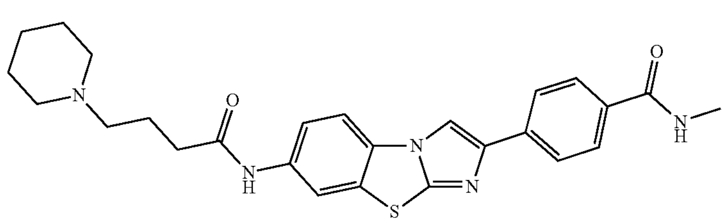 [SMILES: CNC(=O)c1ccc(-c2cn3c(n2)sc2cc(NC(=O)CCCN4CCCCC4)ccc23)cc1] | N-methyl-4-(7-(4-(piperidin-1-yl)butanamido)benzo[d]imidazo[2,1-b]thiazol-2-yl)benzamide |

| Comp. No. | Structure | Compound Name |
|---|---|---|
| 313 | 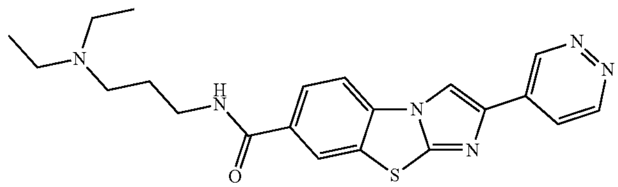 [SMILES: CCN(CC)CCCNC(=O)c1ccc2c(c1)sc1nc(-c3ccnnc3)cn12] | N-(3-(diethylamino)propyl)-2-(pyridazin-4-yl)benzo[d]imidazo[2,1-b]thiazole-7-carboxamide |
| 314 | 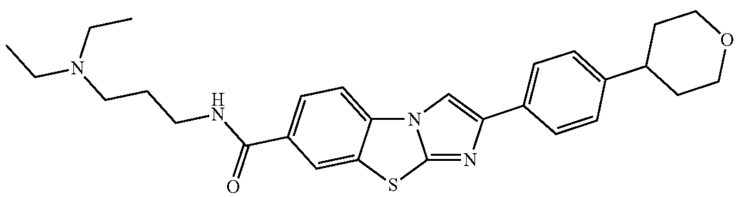 [SMILES: CCN(CC)CCCNC(=O)c1ccc2c(c1)sc1nc(-c3ccc(C4CCOCC4)cc3)cn12] | N-(3-(diethylamino)propyl)-2-(4-(tetrahydro-2H-pyran-4-yl)phenyl)benzo[d]imidazo[2,1-b]thiazole-7-carboxamide |
| 315 | 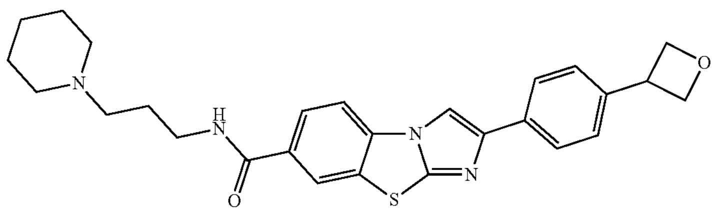 [SMILES: O=C(NCCCN1CCCCC1)c1ccc2c(c1)sc1nc(-c3ccc(C4COC4)cc3)cn12] | 2-(4-(oxetan-3-yl)phenyl)-N-(3-(piperidin-1-yl)propyl)benzo[d]imidazo[2,1-b]thiazole-7-carboxamide |
| 316 | 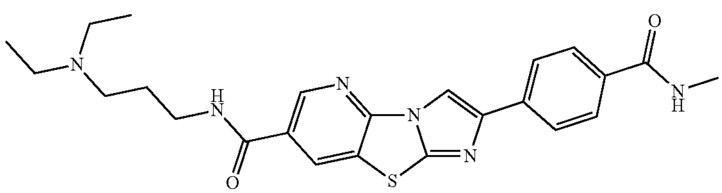 [SMILES: CCN(CC)CCCNC(=O)c1cnc2c(c1)sc1nc(-c3ccc(C(=O)NC)cc3)cn12] | N-(3-(diethylamino)propyl)-2-(4-(methylcarbamoyl)phenyl)imidazo[2',1':2,3]thiazolo[4,5-b]pyridine-7-carboxamide |
| 317 | 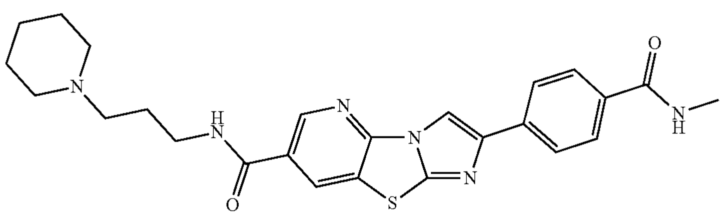 | 2-(4-(methylcarbamoyl)phenyl)-N-(3-(piperidin-1-yl)propyl)imidazo[2',1':2,3]thiazolo[4,5-b]pyridine-7-carboxamide |
| 318 | 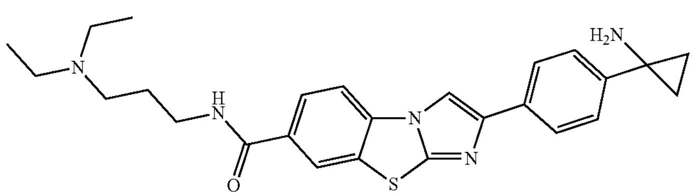 [SMILES: CCN(CC)CCCNC(=O)c1ccc2c(c1)sc1nc(-c3ccc(C4(N)CC4)cc3)cn12] | 2-(4-(1-aminocyclopropyl)phenyl)-N-(3-(diethylamino)propyl)benzo[d]imidazo[2,1-b]thiazole-7-carboxamide |
| 319 | 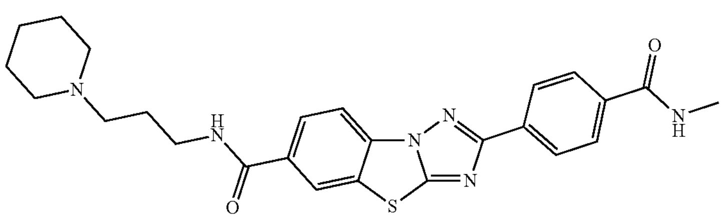 [SMILES: CNC(=O)c1ccc(-c2nc3sc4cc(C(=O)NCCCN5CCCCC5)ccc4n3n2)cc1] | 2-(4-(methylcarbamoyl)phenyl)-N-(3-(piperidin-1-yl)propyl)benzo[4,5]thiazolo[3,2-b][1,2,4]triazole-6-carboxamide |

TABLE 1-continued

| Comp. No. | Structure | Compound Name |
|---|---|---|
| 320 | 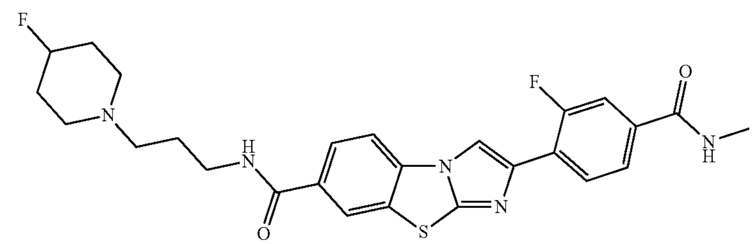 [SMILES: CNC(=O)c1ccc(-c2cn3c(n2)sc2cc(C(=O)NCCCN4CCC(F)CC4)ccc23)c(F)c1] | 2-(2-fluoro-4-(methylcarbamoyl)phenyl)-N-(3-(4-fluoropiperidin-1-yl)propyl)benzo[d]imidazo[2,1-b]thiazole-7-carboxamide |
| 321 | 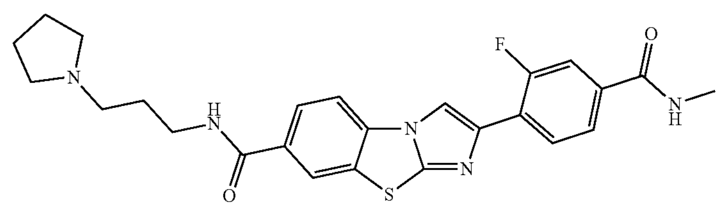 [SMILES: CNC(=O)c1ccc(-c2cn3c(n2)sc2cc(C(=O)NCCCN4CCCC4)ccc23)c(F)c1] | 2-(2-fluoro-4-(methylcarbamoyl)phenyl)-N-(3-(pyrrolidin-1-yl)propyl)benzo[d]imidazo[2,1-b]thiazole-7-carboxamide |
| 322 | 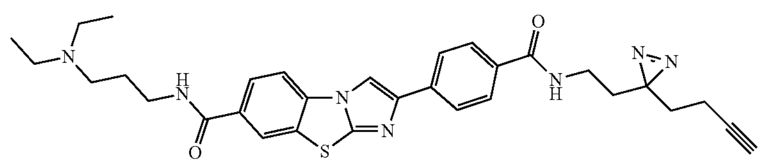 [SMILES: C#CCCC1(CCNC(=O)c2ccc(-c3cn4c(n3)sc3cc(C(=O)NCCCN(CC)CC)ccc34)cc2)N=N1] | 2-(4-((2-(3-(but-3-yn-1-yl)-3H-diazirin-3-yl)ethyl)carbamoyl)phenyl)-N-(3-(diethylamino)propyl)benzo[d]imidazo[2,1-b]thiazole-7-carboxamide |
| 323 | 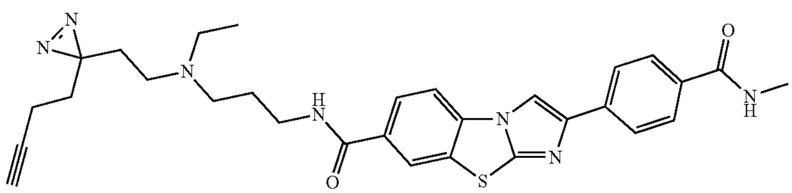 [SMILES: C#CCCC1(CCN(CC)CCCNC(=O)c2ccc3c(c2)sc2nc(-c4ccc(C(=O)NC)cc4)cn23)N=N1] | N-(3-((2-(3-(but-3-yn-1-yl)-3H-diazirin-3-yl)ethyl)(ethyl)amino)propyl)-2-(4-(methylcarbamoyl)phenyl)benzo[d]imidazo[2,1-b]thiazole-7-carboxamide |
| 324 | 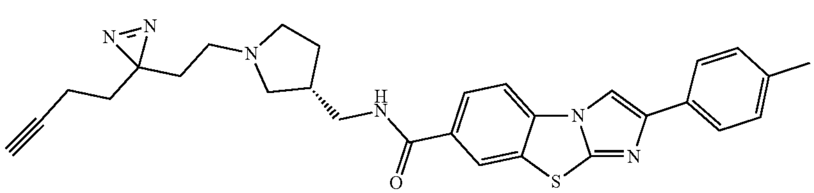 [SMILES: C#CCCC1(CCN2CC[C@H](CNC(=O)c3ccc4c(c3)sc3nc(-c5ccc(C)cc5)cn34)C2)N=N1] | (R)-N-((1-(2-(3-(but-3-yn-1-yl)-3H-diazirin-3-yl)ethyl)pyrrolidin-3-yl)methyl)-2-(p-tolyl)benzo[d]imidazo[2,1-b]thiazole-7-carboxamide |
| 325 | 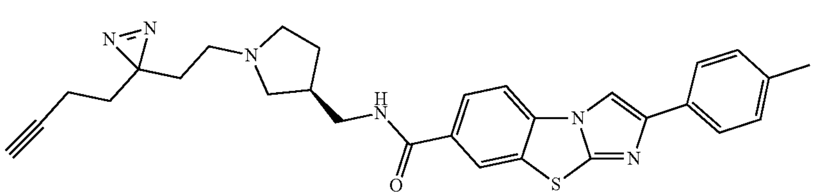 [SMILES: C#CCCC1(CCN2CC[C@@H](CNC(=O)c3ccc4c(c3)sc3nc(-c5ccc(C)cc5)cn34)C2)N=N1] | (S)-N-((1-(2-(3-(but-3-yn-1-yl)-3H-diazirin-3-yl)ethyl)pyrrolidin-3-yl)methyl)-2-(p-tolyl)benzo[d]imidazo[2,1-b]thiazole-7-carboxamide |
| 326 | 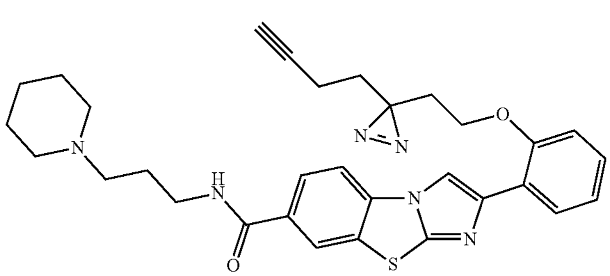 [SMILES: C#CCCC1(CCOc2ccccc2-c2cn3c(n2)sc2cc(C(=O)NCCCN4CCCCC4)ccc23)N=N1] | 2-(2-(2-(3-(but-3-yn-1-yl)-3H-diazirin-3-yl)ethoxy)phenyl)-N-(3-(piperidin-1-yl)propyl)benzo[d]imidazo[2,1-b]thiazole-7-carboxamide |

TABLE 1-continued

| Comp. No. | Structure | Compound Name |
|---|---|---|
| 327 | 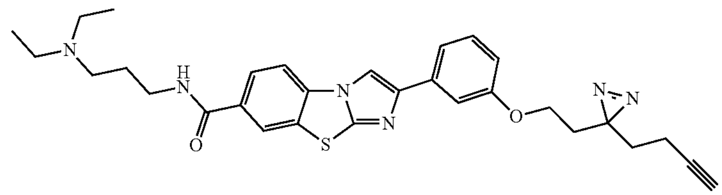 [SMILES: C#CCCC1(CCOc2cccc(-c3cn4c(n3)sc3cc(C(=O)NCCCN(CC)CC)ccc34)c2)N=N1] | 2-(3-(2-(3-(but-3-yn-1-yl)-3H-diazirin-3-yl)ethoxy)phenyl)-N-(3-(diethylamino)propyl)benzo[d]imidazo[2,1-b]thiazole-7-carboxamide |
| 328 | 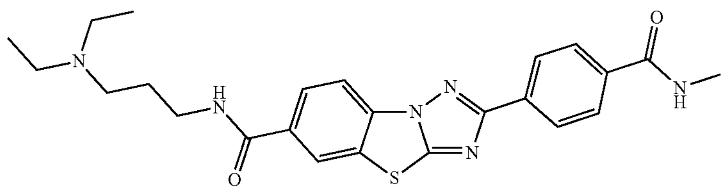 [SMILES: CCN(CC)CCCNC(=O)c1ccc2c(c1)sc1nc(-c3ccc(C(=O)NC)cc3)nn12] | N-(3-(diethylamino)propyl)-2-(4-(methylcarbamoyl)phenyl)benzo[4,5]thiazolo[3,2-b][1,2,4]triazole-6-carboxamide |
| 329 | 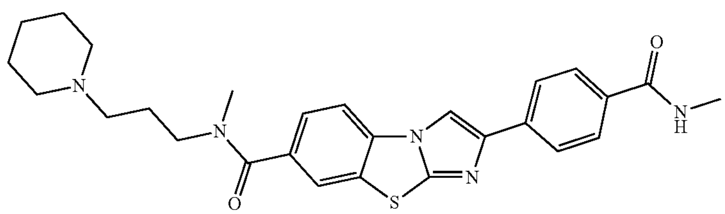 [SMILES: CNC(=O)c1ccc(-c2cn3c(n2)sc2cc(C(=O)N(C)CCCN4CCCCC4)ccc23)cc1] | N-methyl-2-(4-(methylcarbamoyl)phenyl)-N-(3-(piperidin-1-yl)propyl)benzo[d]imidazo[2,1-b]thiazole-7-carboxamide |
| 330 | 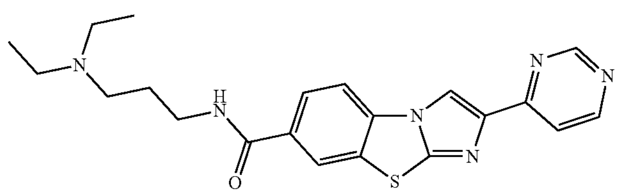 [SMILES: CCN(CC)CCCNC(=O)c1ccc2c(c1)sc1nc(-c3ccncn3)cn12] | N-(3-(diethylamino)propyl)-2-(pyrimidin-4-yl)benzo[d]imidazo[2,1-b]thiazole-7-carboxamide |
| 331 | 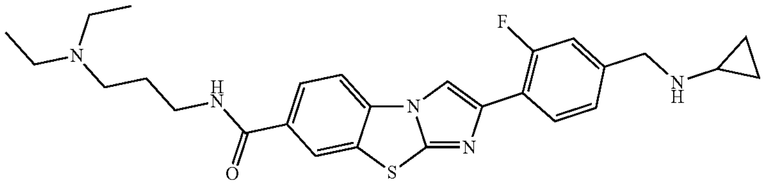 [SMILES: CCN(CC)CCCNC(=O)c1ccc2c(c1)sc1nc(-c3ccc(CNC4CC4)cc3F)cn12] | 2-(4-((cyclopropylamino)methyl)-2-fluorophenyl)-N-(3-(diethylamino)propyl)benzo[d]imidazo[2,1-b]thiazole-7-carboxamide |
| 332 | 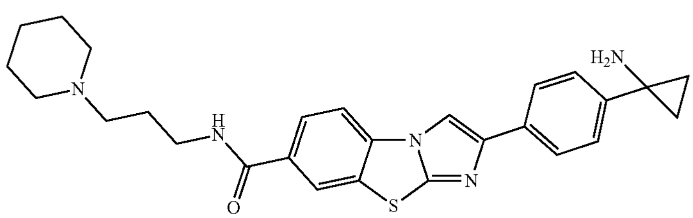 [SMILES: NC1(c2ccc(-c3cn4c(n3)sc3cc(C(=O)NCCCN5CCCCC5)ccc34)cc2)CC1] | 2-(4-(1-aminocyclopropyl)phenyl)-N-(3-(piperidin-1-yl)propyl)benzo[d]imidazo[2,1-b]thiazole-7-carboxamide |
| 333 | 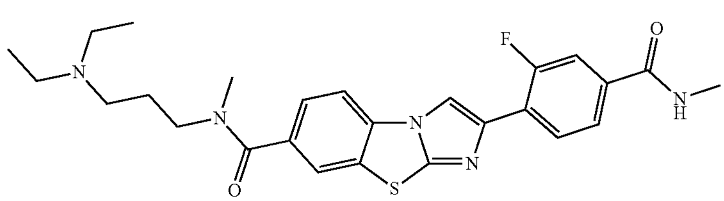 [SMILES: CCN(CC)CCCN(C)C(=O)c1ccc2c(c1)sc1nc(-c3ccc(C(=O)NC)cc3F)cn12] | N-(3-(diethylamino)propyl)-2-(2-fluoro-4-(methylcarbamoyl)phenyl)-N-methylbenzo[d]imidazo[2,1-b]thiazole-7-carboxamide |

TABLE 1-continued

| Comp. No. | Structure | Compound Name |
|---|---|---|
| 334 | 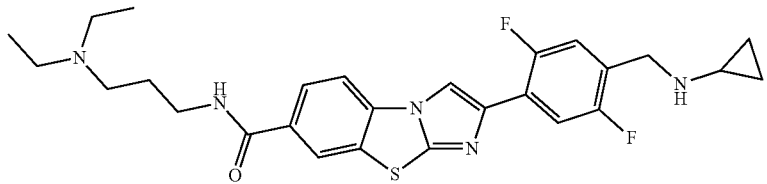 [SMILES: CCN(CC)CCCNC(=O)c1ccc2c(c1)sc1nc(-c3cc(F)c(CNC4CC4)cc3F)cn12] | 2-(4-((cyclopropylamino)methyl)-2,5-difluorophenyl)-N-(3-(diethylamino)propyl)benzo[d]imidazo[2,1-b]thiazole-7-carboxamide |
| 335 | 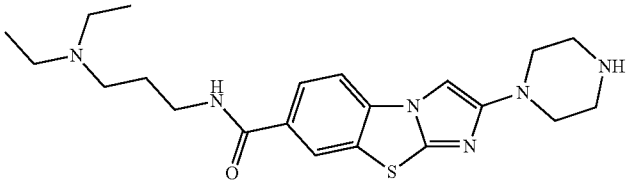 [SMILES: CCN(CC)CCCNC(=O)c1ccc2c(c1)sc1nc(N3CCNCC3)cn12] | N-3-(diethlamino)propyl)-2-(piperazin-1-yl)benzo[d]imidazo[2,1-b]thiazole-7-carboxamide |
| 336 | 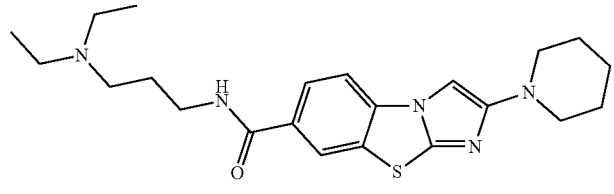 [SMILES: CCN(CC)CCCNC(=O)c1ccc2c(c1)sc1nc(N3CCCCC3)cn12] | N-(3-(diethylamino)propyl)-2-(piperidin-1-yl)benzo[d]imidazo[2,1-b]thiazole-7-carboxamide |
| 337 | 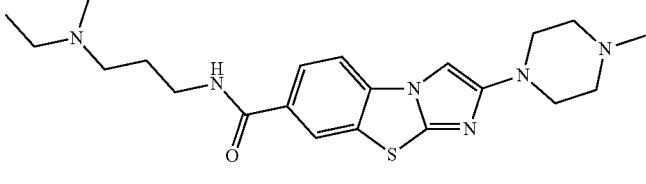 | N-(3-(diethylamino)propyl)-2-(4-methylpiperazin-1-yl)benzo[d]imidazo[2,1-b]thiazole-7-carboxamide |
| 338 | 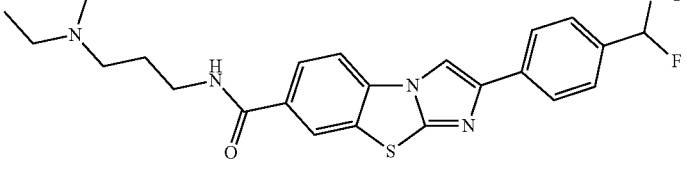 | 2-(4-(aminofluoromethyl)phenyl)-N-(3-(diethylamino)propyl)benzo[d]imidazo[2,1-b]thiazole-7-carboxamide |
| 339 | 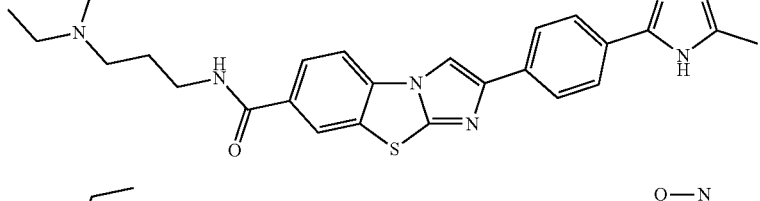 | N-(3-(diethylamino)propyl)-2-(4-(5-methyl-4H-1,2,4-triazol-3-yl)phenyl)benzo[d]imidazo[2,1-b]thiazole-7-carboxamide |
| 340 | 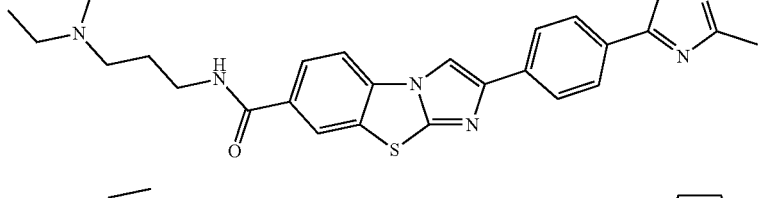 | N-(3-(diethylamino)propyl)-2-(4-(3-methyl-1,2,4-oxadiazol-5-yl)phenyl)benzo[d]imidazo[2,1-b]thiazole-7-carboxamide |
| 341 | 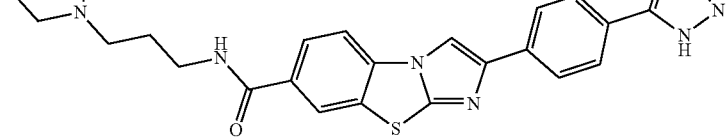 | 2-(4-(1H-pyrazol-5-yl)phenyl)-N-(3-(diethylamino)propyl)benzo[d]imidazo[2,1-b]thiazole-7-carboxamide |

TABLE 1-continued

| Comp. No. | Structure | Compound Name |
|---|---|---|
| 342 | 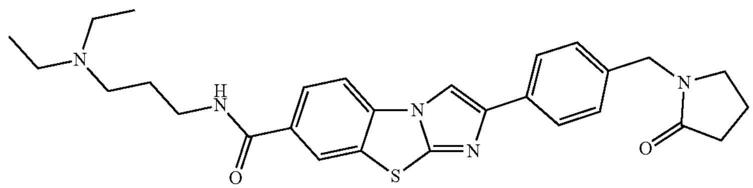 [SMILES: CCN(CC)CCCNC(=O)c1ccc2c(c1)sc1nc(-c3ccc(CN4CCCC4=O)cc3)cn12] | N-(3-(diethylamino)propyl)-2-(4-((2-oxopyrrolidin-1-yl)methyl)phenyl)benzo[d]imidazo[2,1-b]thiazole-7-carboxamide |
| 343 | 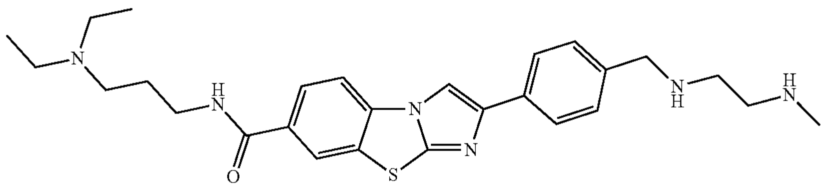 [SMILES: CCN(CC)CCCNC(=O)c1ccc2c(c1)sc1nc(-c3ccc(CNCCNC)cc3)cn12] | N-(3-(diethylamino)propyl)-2-(4-(((2-(methylamino)ethyl)amino)methyl)phenyl)benzo[d]imidazo[2,1-b]thiazole-7-carboxamide |
| 344 | 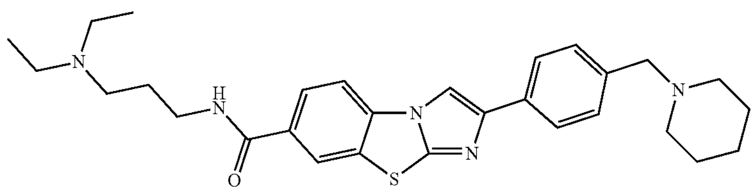 [SMILES: CCN(CC)CCCNC(=O)c1ccc2c(c1)sc1nc(-c3ccc(CN4CCCCC4)cc3)cn12] | N-(3-(diethylamino)propyl)-2-(4-(piperidin-1-ylmethyl)phenyl)benzo[d]imidazo[2,1-b]thiazole-7-carboxamide |
| 345 | 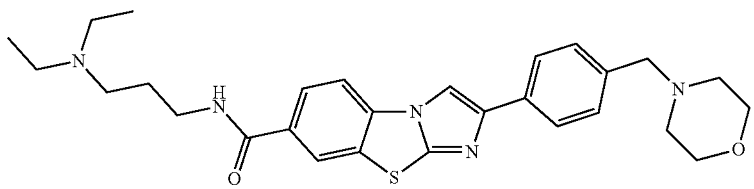 [SMILES: CCN(CC)CCCNC(=O)c1ccc2c(c1)sc1nc(-c3ccc(CN4CCOCC4)cc3)cn12] | N-(3-(diethylamino)propyl)-2-(4-(morpholinomethyl)phenyl)benzo[d]imidazo[2,1-b]thiazole-7-carboxamide |
| 346 | 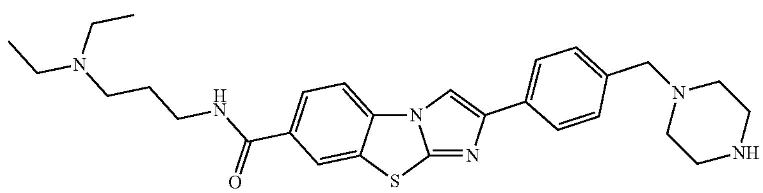 [SMILES: CCN(CC)CCCNC(=O)c1ccc2c(c1)sc1nc(-c3ccc(CN4CCNCC4)cc3)cn12] | N-(3-(diethylamino)propyl)-2-(4-(piperazin-1-ylmethyl)phenyl)benzo[d]imidazo[2,1-b]thiazole-7-carboxamide |
| 347 | 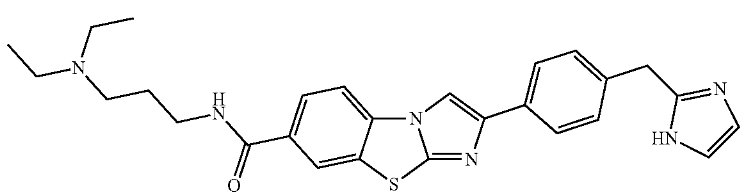 [SMILES: CCN(CC)CCCNC(=O)c1ccc2c(c1)sc1nc(-c3ccc(Cc4ncc[nH]4)cc3)cn12] | 2-(4-((1H-imidazol-2-yl)methyl)phenyl)-N-(3-(diethylamino)propyl)benzo[d]imidazo[2,1-b]thiazole-7-carboxamide |
| 348 | 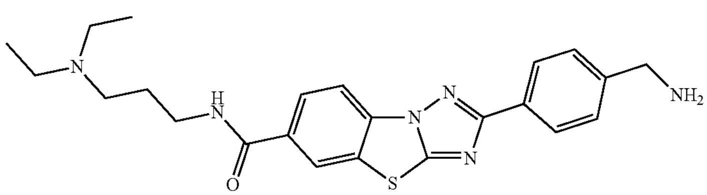 [SMILES: CCN(CC)CCCNC(=O)c1ccc2c(c1)sc1nc(-c3ccc(CN)cc3)nn12] | 2-(4-(aminomethyl)phenyl)-N-(3-(diethylamino)propyl)benzo[4,5]thiazolo[3,2-b][1,2,4]triazole-6-carboxamide |
| 349 | 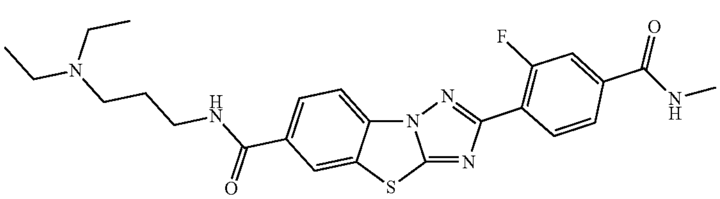 [SMILES: CCN(CC)CCCNC(=O)c1ccc2c(c1)sc1nc(-c3ccc(C(=O)NC)cc3F)nn12] | N-(3-(diethylamino)propyl)-2-(2-fluoro-4-(methylcarbamoyl)phenyl)benzo[4,5]thiazolo[3,2-b][1,2,4]triazole-6-carboxamide |

TABLE 1-continued

| Comp. No. | Structure | Compound Name |
|---|---|---|
| 350 | 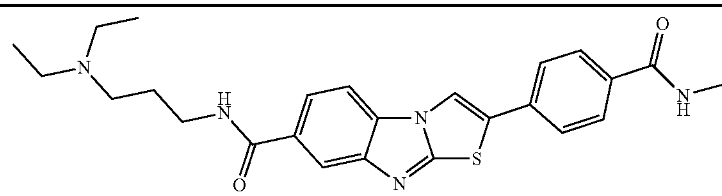 | N-(3-(diethylamino)propyl)-2-(4-(methylcarbamoyl)phenyl)benzo[4,5]imidazo[2,1-b]thiazole-7-carboxamide |
| 351 | 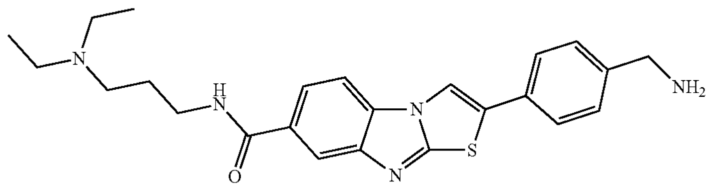 [SMILES: CCN(CC)CCCNC(=O)c1ccc2c(c1)nc1sc(-c3ccc(CN)cc3)cn12] | 2-(4-(aminomethyl)phenyl)-N-(3-(diethylamino)propyl)benzo[4,5]imidazo[2,1-b]thiazole-7-carboxamide |
| 352 | 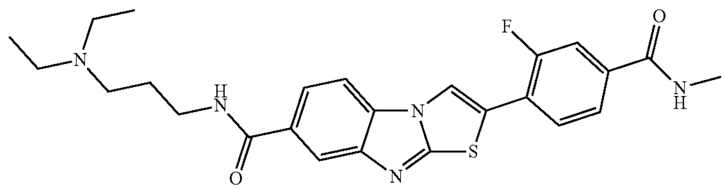 [SMILES: CCN(CC)CCCNC(=O)c1ccc2c(c1)nc1sc(-c3ccc(C(=O)NC)cc3F)cn12] | N-(3-(diethylamino)propyl)-2-(2-fluoro-4-(methylcarbamoyl)phenyl)benzo[4,5]imidazo[2,1-b]thiazole-7-carboxamide |
| 353 | 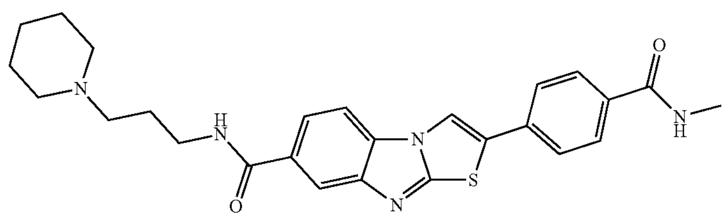 [SMILES: CNC(=O)c1ccc(-c2cn3c(nc4cc(C(=O)NCCCN5CCCCC5)ccc43)s2)cc1] | 2-(4-(methylcarbamoyl)phenyl)-N-(3-(piperidin-1-yl)propyl)benzo[4,5]imidazo[2,1-b]thiazole-7-carboxamide |
| 354 | 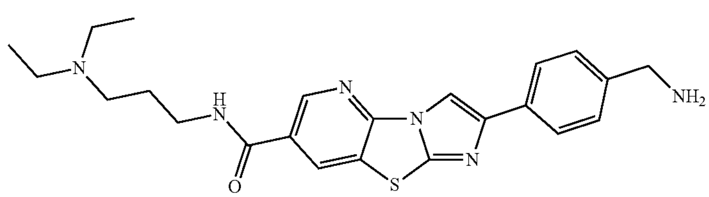 [SMILES: CCN(CC)CCCNC(=O)c1cnc2c(c1)sc1nc(-c3ccc(CN)cc3)cn12] | 2-(4-(aminomethyl)phenyl)-N-(3-(diethylamino)propyl)imidazo[2',1':2,3]thiazolo[4,5-b]pyridine-7-carboxamide |
| 355 | 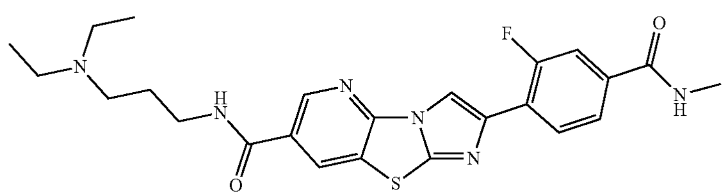 [SMILES: CCN(CC)CCCNC(=O)c1cnc2c(c1)sc1nc(-c3ccc(C(=O)NC)cc3F)cn12] | N-(3-(diethylamino)propyl)-2-(2-fluoro-4-(methylcarbamoyl)phenyl)imidazo[2',1':2,3]thiazolo[4,5-b]pyridine-7-carboxamide |
| 356 | 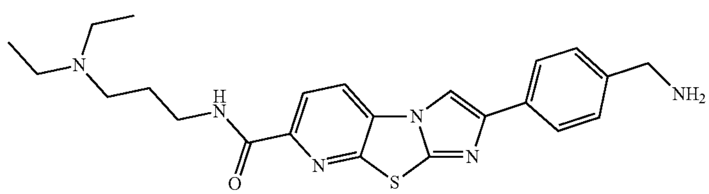 [SMILES: CCN(CC)CCCNC(=O)c1ccc2c(n1)sc1nc(-c3ccc(CN)cc3)cn12] | 2-(4-(aminomethyl)phenyl)-N-(3-(diethylamino)propyl)imidazo[2',1':2,3]thiazolo[5,4-b]pyridine-7-carboxamide |
| 357 | 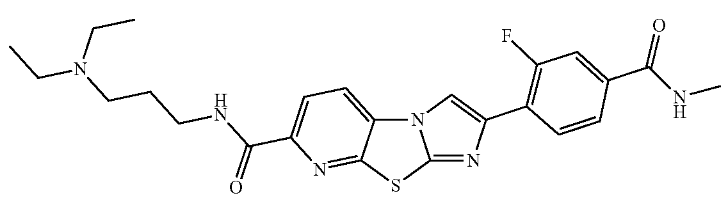 [SMILES: CCN(CC)CCCNC(=O)c1ccc2c(n1)sc1nc(-c3ccc(C(=O)NC)cc3F)cn12] | N-(3-(diethylamino)propyl)-2-(2-fluoro-4-(methylcarbamoyl)phenyl)imidazo[2',1':2,3]thiazolo[5,4-b]pyridine-7-carboxamide |

TABLE 1-continued

| Comp. No. | Structure | Compound Name |
|---|---|---|
| 358 | 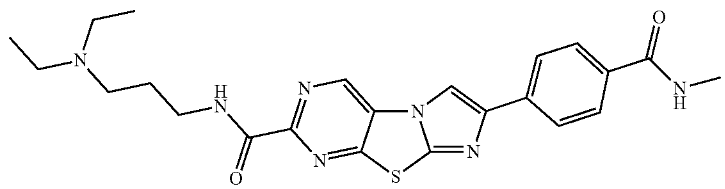 | N-(3-(diethylamino)propyl)-7-(4-(methylcarbamoyl)phenyl)imidazo[2',1':2,3]thiazolo[5,4-d]pyrimidine-2-carboxamide |
| 359 | 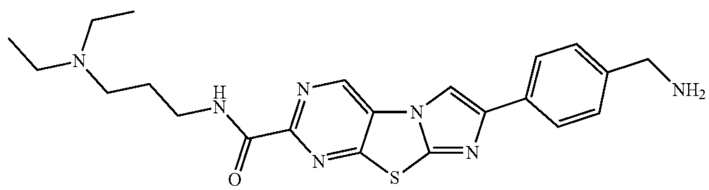 [SMILES: CCN(CC)CCCNC(=O)c1ncc2c(n1)sc1nc(-c3ccc(CN)cc3)cn12] | 7-(4-(aminomethyl)phenyl)-N-(3-(diethylamino)propyl)imidazo[2',1':2,3]thiazolo[5,4-d]pyrimidine-2-carboxamide |
| 360 | 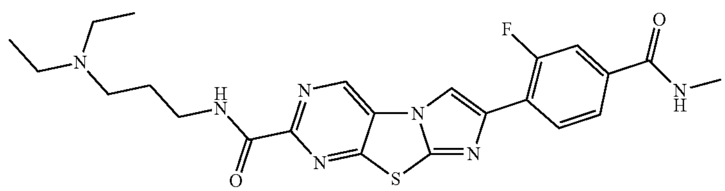 [SMILES: CCN(CC)CCCNC(=O)c1ncc2c(n1)sc1nc(-c3ccc(C(=O)NC)cc3F)cn12] | N-(3-(diethylamino)propyl)-7-(2-fluoro-4-(methylcarbamoyl)phenyl)imidazo[2',1':2,3]thiazolo[5,4-d]pyrimidine-2-carboxamide |
| 361 | 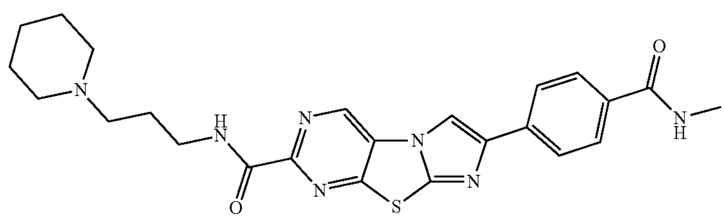 [SMILES: CNC(=O)c1ccc(-c2cn3c(n2)sc2nc(C(=O)NCCCN4CCCCC4)ncc23)cc1] | 7-(4-(methylcarbamoyl)phenyl)-N-(3-(piperidin-1-yl)propyl)imidazo[2',1':2,3]thiazolo[5,4-d]pyrimidine-2-carboxamide |
| 362 | 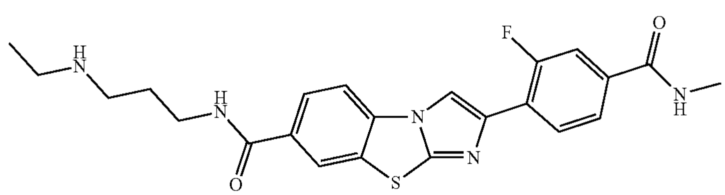 [SMILES: CCNCCCNC(=O)c1ccc2c(c1)sc1nc(-c3ccc(C(=O)NC)cc3F)cn12] | N-(3-(ethylamino)propyl)-2-(2-fluoro-4-(methylcarbamoyl)phenyl)benzo[d]imidazo[2,1-b]thiazole-7-carboxamide |
| 363 | 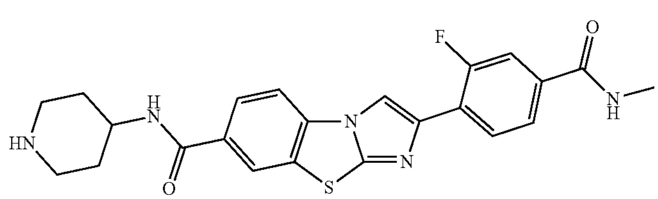 [SMILES: CNC(=O)c1ccc(-c2cn3c(n2)sc2cc(C(=O)NC4CCNCC4)ccc23)c(F)c1] | 2-(2-fluoro-4-(methylcarbamoyl)phenyl)-N-(piperidin-4-yl)benzo[d]imidazo[2,1-b]thiazole-7-carboxamide |
| 364 | 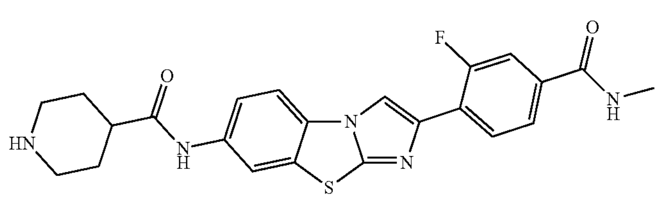 [SMILES: CNC(=O)c1ccc(-c2cn3c(n2)sc2cc(NC(=O)C4CCNCC4)ccc23)c(F)c1] | N-(2-(2-fluoro-4-(methylcarbamoyl)phenyl)benzo[d]imidazo[2,1-b]thiazol-7-yl)piperidine-4-carboxamide |

TABLE 1-continued

| Comp. No. | Structure | Compound Name |
|---|---|---|
| 365 | 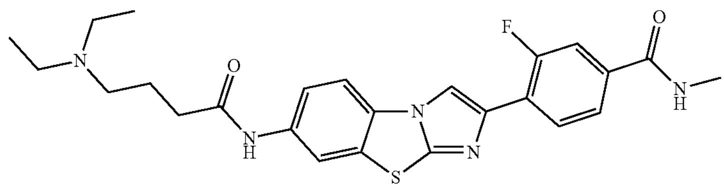 [SMILES: CCN(CC)CCCC(=O)Nc1ccc2c(c1)sc1nc(-c3ccc(C(=O)NC)cc3F)cn12] | 4-(7-(4-(diethylamino)butanamido)benzo[d]imidazo[2,1-b]thiazol-2-yl)-3-fluoro-N-methylbenzamide |
| 366 | 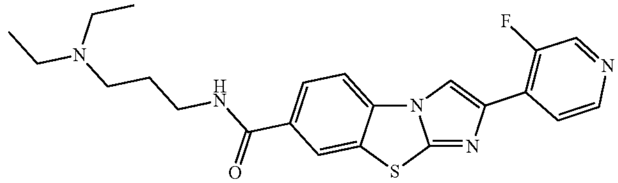 [SMILES: CCN(CC)CCCNC(=O)c1ccc2c(c1)sc1nc(-c3ccncc3F)cn12] | N-(3-(diethylamino)propyl)-2-(3-fluoropyridin-4-yl)benzo[d]imidazo[2,1-b]thiazole-7-carboxamide |
| 367 | 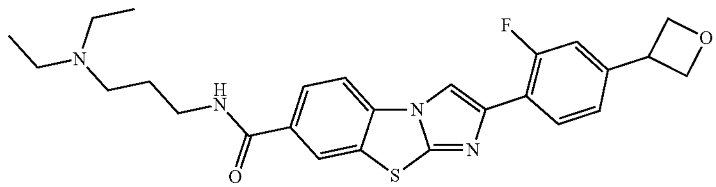 [SMILES: CCN(CC)CCCNC(=O)c1ccc2c(c1)sc1nc(-c3ccc(C4COC4)cc3F)cn12] | N-(3-(diethylamino)propyl)-2-(2-fluoro-4-(oxetan-3-yl)phenyl)benzo[d]imidazo[2,1-b]thiazole-7-carboxamide |
| 368 | 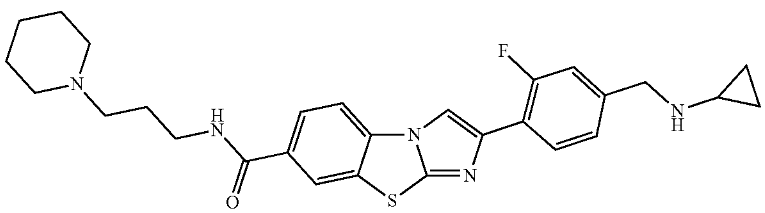 [SMILES: O=C(NCCCN1CCCCC1)c1ccc2c(c1)sc1nc(-c3ccc(CNC4CC4)cc3F)cn12] | 2-(4-((cyclopropylamino)methyl)-2-fluorophenyl)-N-(3-(piperidin-1-yl)propyl)benzo[d]imidazo[2,1-b]thiazole-7-carboxamide |
| 369 | 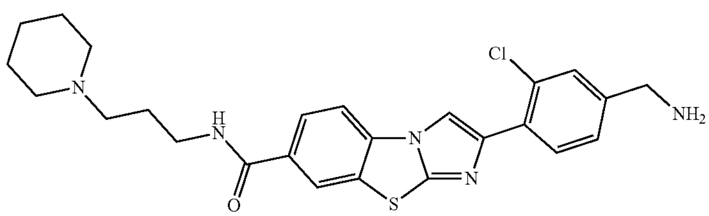 [SMILES: NCc1ccc(-c2cn3c(n2)sc2cc(C(=O)NCCCN4CCCCC4)ccc23)c(Cl)c1] | 2-(4-(aminomethyl)-2-chlorophenyl)-N-(3-(piperidin-1-yl)propyl)benzo[d]imidazo[2,1-b]thiazole-7-carboxamide |
| 370 | 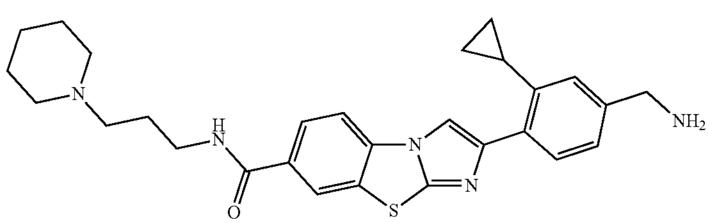 [SMILES: NCc1ccc(-c2cn3c(n2)sc2cc(C(=O)NCCCN4CCCCC4)ccc23)c(C2CC2)c1] | 2-(4-(aminomethyl)-2-cyclopropylphenyl)-N-(3-(piperidin-1-yl)propyl)benzo[d]imidazo[2,1-b]thiazole-7-carboxamide |
| 371 | 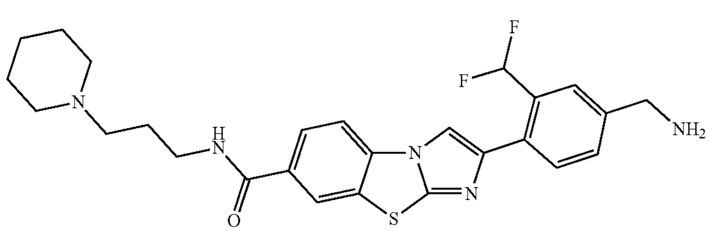 | 2-(4-(aminomethyl)-2-(difluoromethyl)phenyl)-N-(3-(piperidin-1-yl)propyl)benzo[d]imidazo[2,1-b]thiazole-7-carboxamide |

TABLE 1-continued

| Comp. No. | Structure | Compound Name |
|---|---|---|
| 372 | 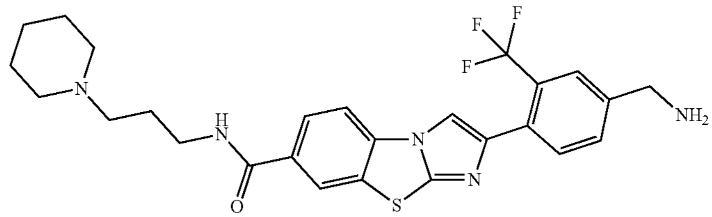 [SMILES: NCc1ccc(-c2cn3c(n2)sc2cc(C(=O)NCCCN4CCCCC4)ccc23)c(C(F)F)c1] | 2-(4-(aminomethyl)-2-(trifluoromethyl)phenyl)-N-(3-(piperidin-1-yl)propyl)benzo[d]imidazo[2,1-b]thiazole-7-carboxamide |
| 373 | 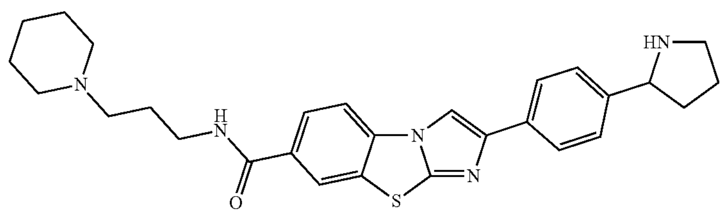 | N-(3-(piperidin-1-yl)propyl)-2-(4-(pyrrolidin-2-yl)phenyl)benzo[d]imidazo[2,1-b]thiazole-7-carboxamide |
| 374 | 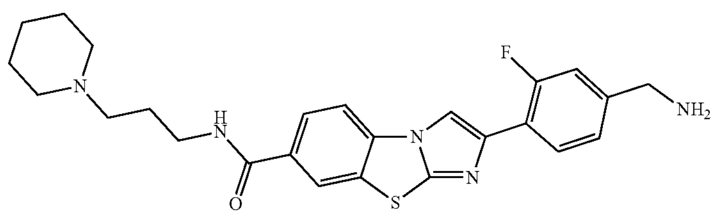 [SMILES: NCc1ccc(-c2cn3c(n2)sc2cc(C(=O)NCCCN4CCCCC4)ccc23)c(F)c1] | 2-(4-(aminomethyl)-2-fluorophenyl)-N-(3-(piperidin-1-yl)propyl)benzo[d]imidazo[2,1-b]thiazole-7-carboxamide |
| 375 | 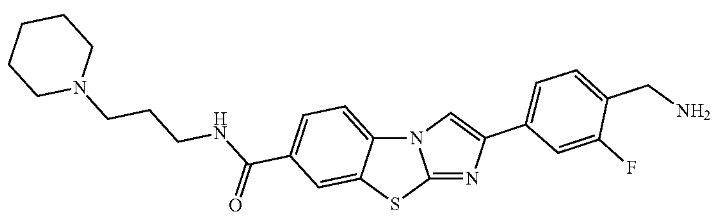 | 2-(4-(aminomethyl)-3-fluorophenyl)-N-(3-(piperidin-1-yl)propyl)benzo[d]imidazo[2,1-b]thiazole-7-carboxamide |
| 376 | 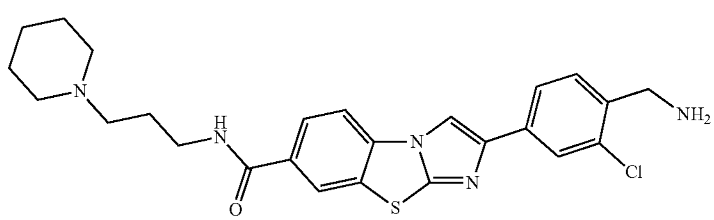 [SMILES: NCc1ccc(-c2cn3c(n2)sc2cc(C(=O)NCCCN4CCCCC4)ccc23)cc1Cl] | 2-(4-(aminomethyl)-3-chlorophenyl)-N-(3-(piperidin-1-yl)propyl)benzo[d]imidazo[2,1-b]thiazole-7-carboxamide |
| 377 | 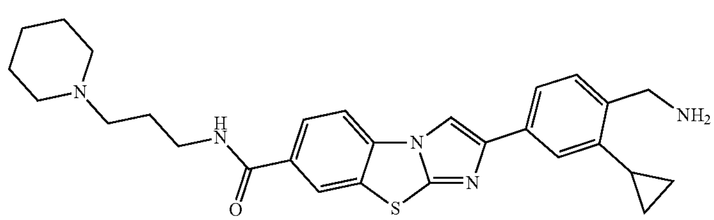 [SMILES: NCc1ccc(-c2cn3c(n2)sc2cc(C(=O)NCCCN4CCCCC4)ccc23)cc1C1CC1] | 2-(4-(aminomethyl)-3-cyclopropylphenyl)-N-(3-(piperidin-1-yl)propyl)benzo[d]imidazo[2,1-b]thiazole-7-carboxamide |
| 378 | 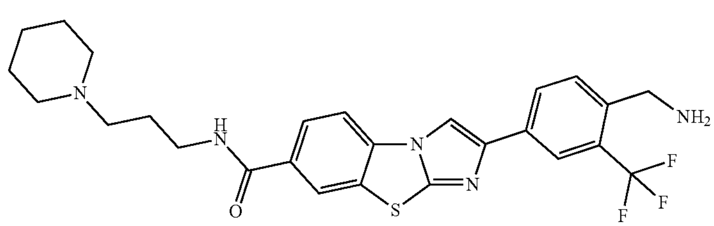 [SMILES: NCc1ccc(-c2cn3c(n2)sc2cc(C(=O)NCCCN4CCCCC4)ccc23)cc1C(F)(F)F] | 2-(4-(aminomethyl)-3-(trifluoromethyl)phenyl)-N-(3-(piperidin-1-yl)propyl)benzo[d]imidazo[2,1-b]thiazole-7-carboxamide |

TABLE 1-continued

| Comp. No. | Structure | Compound Name |
|---|---|---|
| 379 | 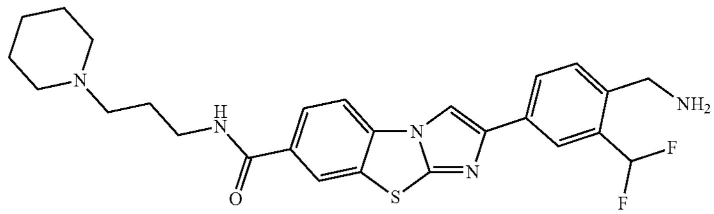 [SMILES: NCc1ccc(-c2cn3c(n2)sc2cc(C(=O)NCCCN4CCCCC4)ccc23)cc1C(F)F] | 2-(4-(aminomethyl)-3-(difluoromethyl)phenyl)-N-(3-(piperidin-1-yl)propyl)benzo[d]imidazo[2,1-b]thiazole-7-carboxamide |
| 380 | 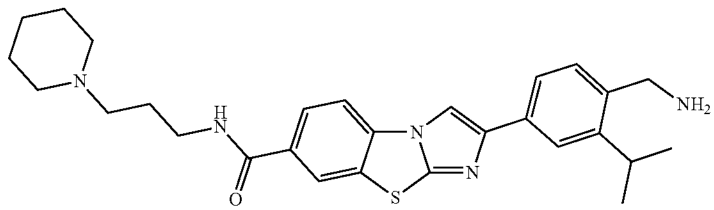 [SMILES: CC(C)c1cc(-c2cn3c(n2)sc2cc(C(=O)NCCCN4CCCCC4)ccc23)ccc1CN] | 2-(4-(aminomethyl)-3-isopropylphenyl)-N-(3-(piperidin-1-yl)propyl)benzo[d]imidazo[2,1-b]thiazole-7-carboxamide |
| 381 | 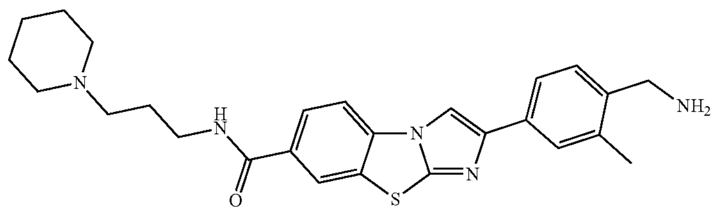 [SMILES: Cc1cc(-c2cn3c(n2)sc2cc(C(=O)NCCCN4CCCCC4)ccc23)ccc1CN] | 2-(4-(aminomethyl)-3-methylphenyl)-N-(3-(piperidin-1-yl)propyl)benzo[d]imidazo[2,1-b]thiazole-7-carboxamide |
| 382 | 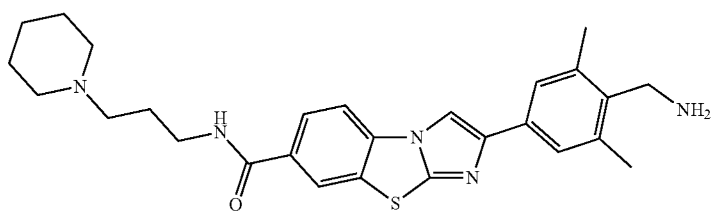 [SMILES: Cc1cc(-c2cn3c(n2)sc2cc(C(=O)NCCCN4CCCCC4)ccc23)cc(C)c1CN] | 2-(4-(aminomethyl)-3,5-dimethylphenyl)-N-(3-(piperidin-1-yl)propyl)benzo[d]imidazo[2,1-b]thiazole-7-carboxamide |
| 383 | 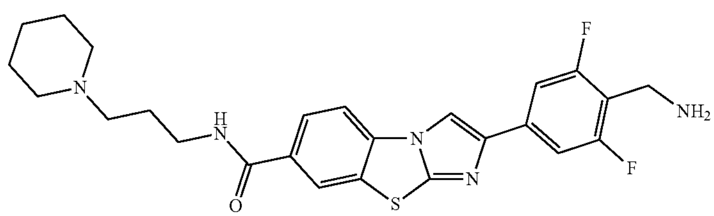 [SMILES: NCc1c(F)cc(-c2cn3c(n2)sc2cc(C(=O)NCCCN4CCCCC4)ccc23)cc1F] | 2-(4-(aminomethyl)-3,5-difluorophenyl)-N-(3-(piperidin-1-yl)propyl)benzo[d]imidazo[2,1-b]thiazole-7-carboxamide |
| 384 | 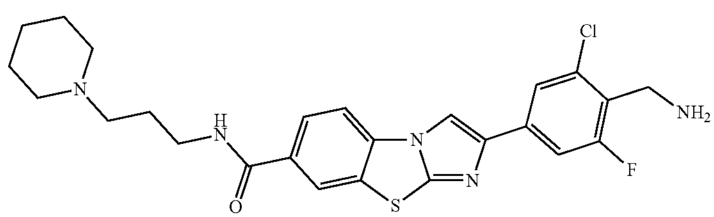 | 2-(4-(aminomethyl)-3-chloro-5-fluorophenyl)-N-(3-(piperidin-1-yl)propyl)benzo[d]imidazo[2,1-b]thiazole-7-carboxamide |
| 385 | 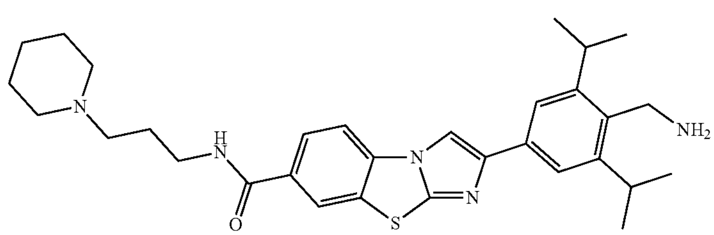 [SMILES: CC(C)c1cc(-c2cn3c(n2)sc2cc(C(=O)NCCCN4CCCCC4)ccc23)cc(C(C)C)c1CN] | 2-(4-(aminomethyl)-3,5-diisopropylphenyl)-N-(3-(piperidin-1-yl)propyl)benzo[d]imidazo[2,1-b]thiazole-7-carboxamide |

TABLE 1-continued

| Comp. No. | Structure | Compound Name |
|---|---|---|
| 386 | 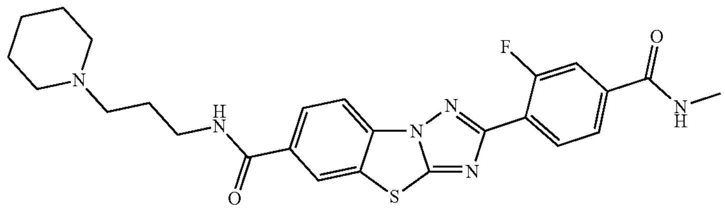 [SMILES: CNC(=O)c1ccc(-c2nc3sc4cc(C(=O)NCCCN5CCCCC5)ccc4n3n2)c(F)c1] | 2-(2-fluoro-4-(methylcarbamoyl)phenyl)-N-(3-(piperidin-1-yl)propyl)benzo[4,5]thiazolo[3,2-b][1,2,4]triazole-6-carboxamide |
| 387 | 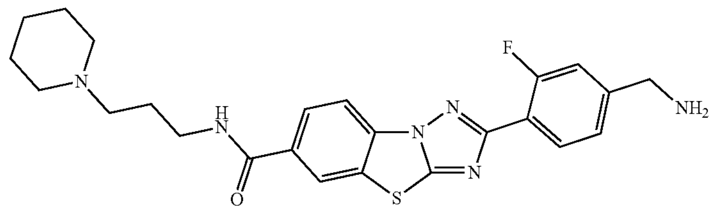 [SMILES: NCc1ccc(-c2nc3sc4cc(C(=O)NCCCN5CCCCC5)ccc4n3n2)c(F)c1] | 2-(4-(aminomethyl)-2-fluorophenyl)-N-(3-(piperidin-1-yl)propyl)benzo[4,5]thiazolo[3,2-b][1,2,4]triazole-6-carboxamide |
| 388 | 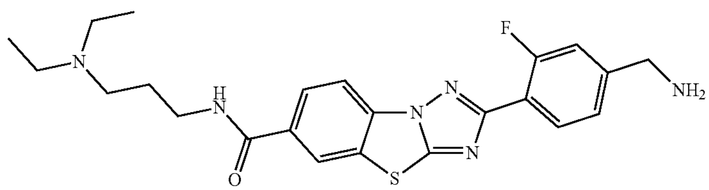 [SMILES: CCN(CC)CCCNC(=O)c1ccc2c(c1)sc1nc(-c3ccc(CN)cc3F)nn12] | 2-(4-(aminomethyl)-2-fluorophenyl)-N-(3-(diethylamino)propyl)benzo[4,5]thiazolo[3,2-b][1,2,4]triazole-6-carboxamide |
| 389 | 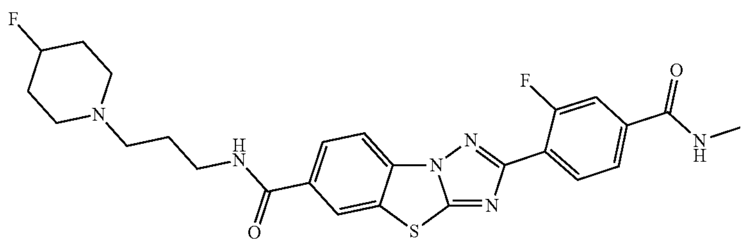 [SMILES: CNC(=O)c1ccc(-c2nc3sc4cc(C(=O)NCCCN5CCC(F)CC5)ccc4n3n2)c(F)c1] | 2-(2-fluoro-4-(methylcarbamoyl)phenyl)-N-(3-(4-fluoropiperidin-1-yl)propyl)benzo[4,5]thiazolo[3,2-b][1,2,4]triazole-6-carboxamide |
| 390 | 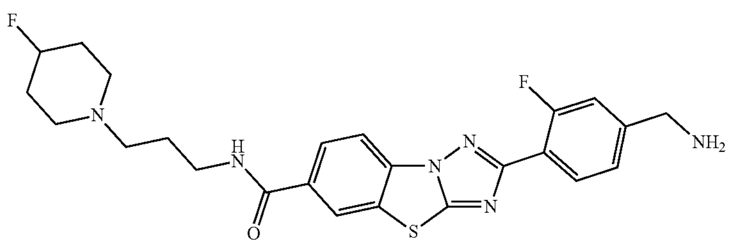 [SMILES: NCc1ccc(-c2nc3sc4cc(C(=O)NCCCN5CCC(F)CC5)ccc4n3n2)c(F)c1] | 2-(4-(aminomethyl)-2-fluorophenyl)-N-(3-(4-fluoropiperidin-1-yl)propyl)benzo[4,5]thiazolo[3,2-b][1,2,4]triazole-6-carboxamide |
| 391 | 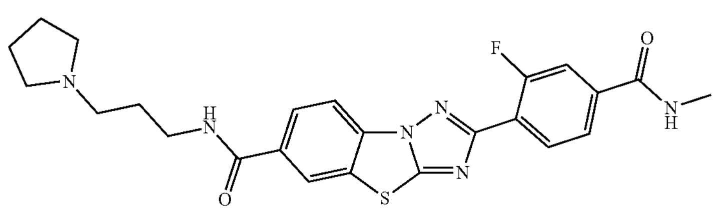 | 2-(2-fluoro-4-(methylcarbamoyl)phenyl)-N-(3-(pyrrolidin-1-yl)propyl)benzo[4,5]thiazolo[3,2-b][1,2,4]triazole-6-carboxamide |
| 392 | 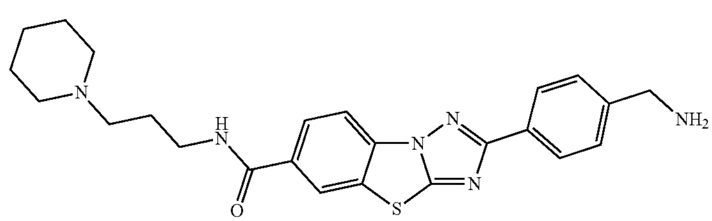 [SMILES: NCc1ccc(-c2nc3sc4cc(C(=O)NCCCN5CCCCC5)ccc4n3n2)cc1] | 2-(4-(aminomethyl)phenyl)-N-(3-(piperidin-1-yl)propyl)benzo[4,5]thiazolo[3,2-b][1,2,4]triazole-6-carboxamide |

TABLE 1-continued

| Comp. No. | Structure | Compound Name |
|---|---|---|
| 393 | 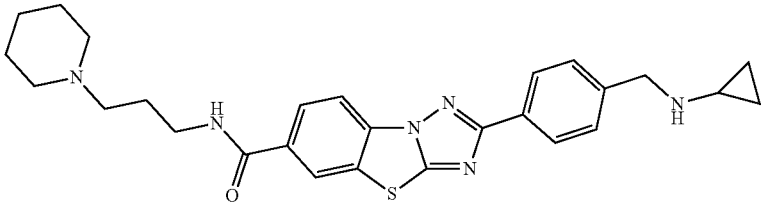 [SMILES: O=C(NCCCN1CCCCC1)c1ccc2c(c1)sc1nc(-c3ccc(CNC4CC4)cc3)nn12] | 2-(4-((cyclopropylamino)methyl)phenyl)-N-(3-(piperidin-1-yl)propyl)benzo[4,5]thiazolo[3,2-b][1,2,4]triazole-6-carboxamide |
| 394 | 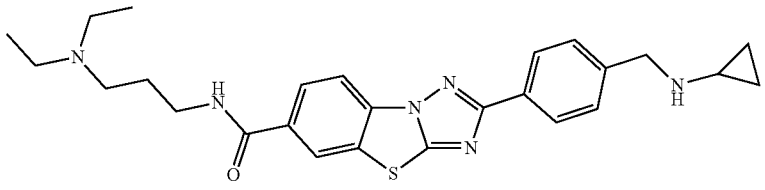 | 2-(4-((cyclopropylamino)methyl)phenyl)-N-(3-(diethylamino)propyl)benzo[4,5]thiazolo[3,2-b][1,2,4]triazole-6-carboxamide |
| 395 | 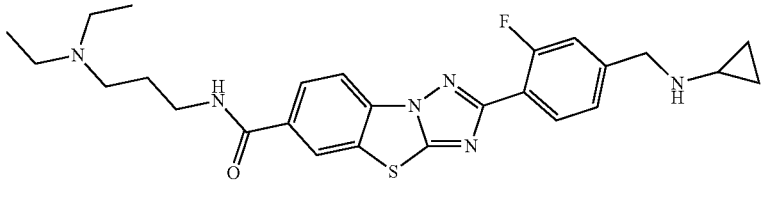 [SMILES: CCN(CC)CCCNC(=O)c1ccc2c(c1)sc1nc(-c3ccc(CNC4CC4)cc3F)nn12] | 2-(4-((cyclopropylamino)methyl)-2-fluorophenyl)-N-(3-(diethylamino)propyl)benzo[4,5]thiazolo[3,2-b][1,2,4]triazole-6-carboxamide |
| 396 | 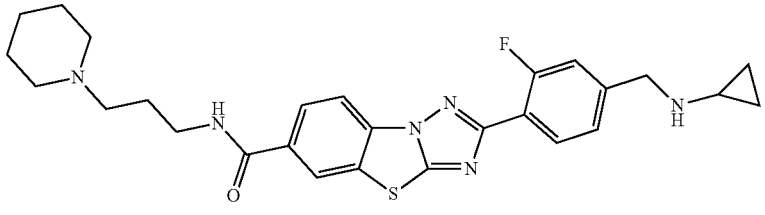 [SMILES: O=C(NCCCN1CCCCC1)c1ccc2c(c1)sc1nc(-c3ccc(CNC4CC4)cc3F)nn12] | 2-(4-((cyclopropylamino)methyl)-2-fluorophenyl)-N-(3-(piperidin-1-yl)propyl)benzo[4,5]thiazolo[3,2-b][1,2,4]triazole-6-carboxamide |
| 397 | 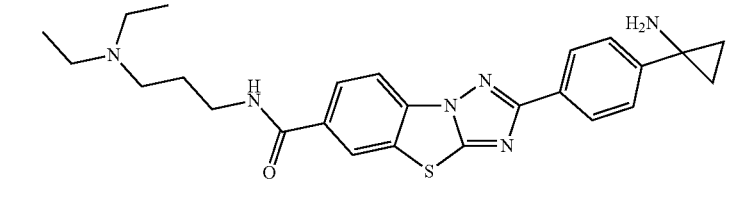 [SMILES: CCN(CC)CCCNC(=O)c1ccc2c(c1)sc1nc(-c3ccc(C4(N)CC4)cc3)nn12] | 2-(4-(1-aminocyclopropyl)phenyl)-N-(3-(diethylamino)propyl)benzo[4,5]thiazolo[3,2-b][1,2,4]triazole-6-carboxamide |
| 398 | 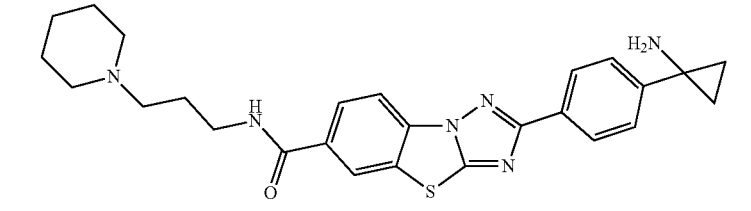 [SMILES: NC1(c2ccc(-c3nc4sc5cc(C(=O)NCCCN6CCCCC6)ccc5n4n3)cc2)CC1] | 2-(4-(1-aminocyclopropyl)phenyl)-N-(3-(piperidin-1-yl)propyl)benzo[4,5]thiazolo[3,2-b][1,2,4]triazole-6-carboxamide |
| 399 | 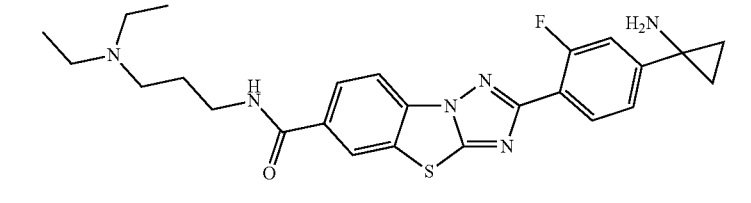 [SMILES: CCN(CC)CCCNC(=O)c1ccc2c(c1)sc1nc(-c3ccc(C4(N)CC4)cc3F)nn12] | 2-(4-(1-aminocyclopropyl)-2-fluorophenyl)-N-(3-(diethylamino)propyl)benzo[4,5]thiazolo[3,2-b][1,2,4]triazole-6-carboxamide |

TABLE 1-continued

| Comp. No. | Structure | Compound Name |
|---|---|---|
| 400 | 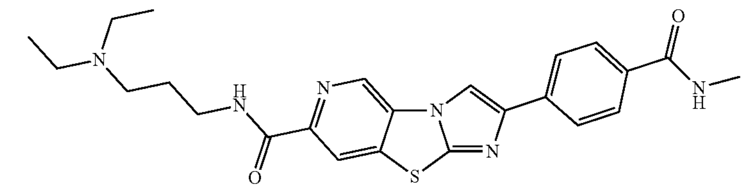 [SMILES: CCN(CC)CCCNC(=O)c1cc2sc3nc(-c4ccc(C(=O)NC)cc4)cn3c2cn1] | N-(3-(diethylamino)propyl)-2-(4-(methylcarbamoyl)phenyl)imidazo[2',1':2,3]thiazolo[4,5-c]pyridine-7-carboxamide |
| 401 | 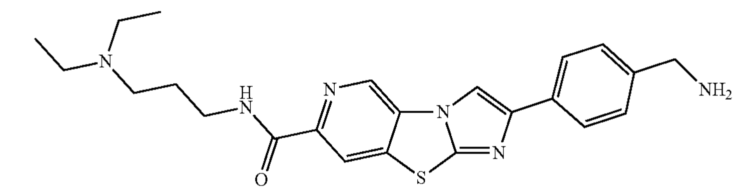 [SMILES: CCN(CC)CCCNC(=O)c1cc2sc3nc(-c4ccc(CN)cc4)cn3c2cn1] | 2-(4-(aminomethyl)phenyl)-N-(3-(diethylamino)propyl)imidazo[2',1':2,3]thiazolo[4,5-c]pyridine-7-carboxamide |
| 402 | 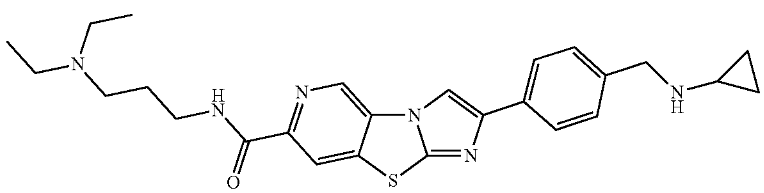 [SMILES: CCN(CC)CCCNC(=O)c1cc2sc3nc(-c4ccc(CNC5CC5)cc4)cn3c2cn1] | 2-(4-((cyclopropylamino)methyl)phenyl)-N-(3-(diethylamino)propyl)imidazo[2',1':2,3]thiazolo[4,5-c]pyridine-7-carboxamide |
| 403 | 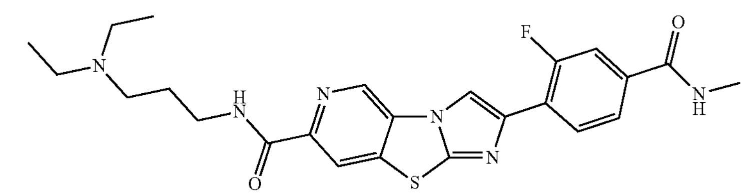 [SMILES: CCN(CC)CCCNC(=O)c1cc2sc3nc(-c4ccc(C(=O)NC)cc4F)cn3c2cn1] | N-(3-(diethylamino)propyl)-2-(2-fluoro-4-(methylcarbamoyl)phenyl)imidazo[2',1':2,3]thiazolo[4,5-c]pyridine-7-carboxamide |
| 404 | 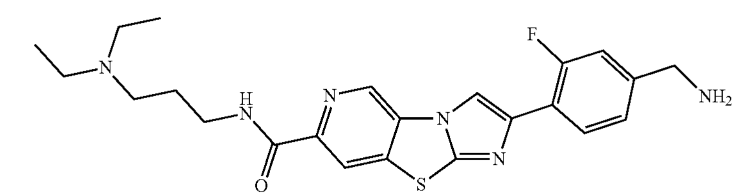 [SMILES: CCN(CC)CCCNC(=O)c1cc2sc3nc(-c4ccc(CN)cc4F)cn3c2cn1] | 2-(4-(aminomethyl)-2-fluorophenyl)-N-(3-(diethylamino)propyl)imidazo[2',1':2,3]thiazolo[4,5-c]pyridine-7-carboxamide |
| 405 | 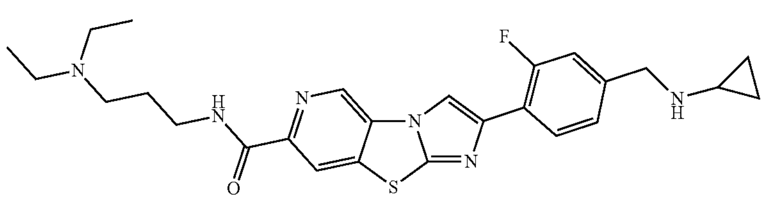 [SMILES: CCN(CC)CCCNC(=O)c1cc2sc3nc(-c4ccc(CNC5CC5)cc4F)cn3c2cn1] | 2-(4-((cyclopropylamino)methyl)-2-fluorophenyl)-N-(3-(diethylamino)propyl)imidazo[2'1':2,3]thiazolo[4,5-c]pyridine-7-carboxamide |
| 406 | 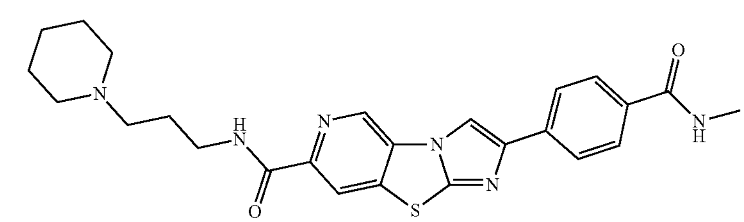 [SMILES: CNC(=O)c1ccc(-c2cn3c(n2)sc2cc(C(=O)NCCCN4CCCCC4)ncc23)cc1] | 2-(4-(methylcarbamoyl)phenyl)-N-(3-(piperidin-1-yl)propyl)imidazo[2',1':2,3]thiazolo[4,5-c]pyridine-7-carboxamide |

TABLE 1-continued

| Comp. No. | Structure | Compound Name |
|---|---|---|
| 407 | 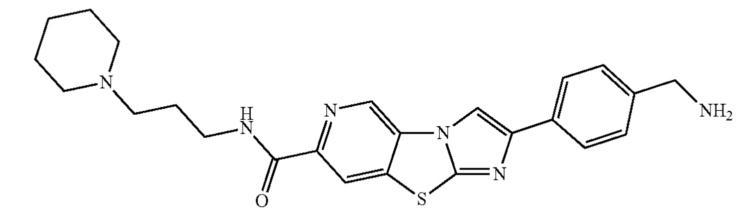 [SMILES: NCc1ccc(-c2cn3c(n2)sc2cc(C(=O)NCCCN4CCCCC4)ncc23)cc1] | 2-(4-(aminomethyl)phenyl)-N-(3-(piperidin-1-yl)propyl)imidazo[2',1':2,3]thiazolo[4,5-c]pyridine-7-carboxamide |
| 408 | 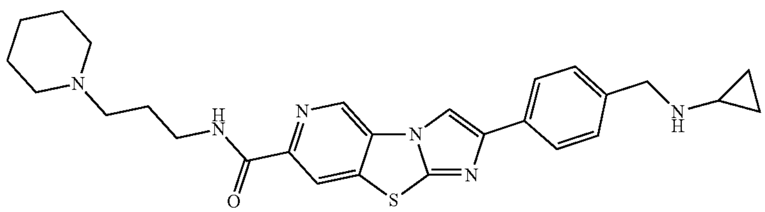 [SMILES: O=C(NCCCN1CCCCC1)c1cc2sc3nc(-c4ccc(CNC5CC5)cc4)cn3c2cn1] | 2-(4-((cyclopropylamino)methyl)phenyl)-N-(3-(piperidin-1-yl)propyl)imidazo[2',1':2,3]thiazolo[4,5-c]pyridine-7-carboxamide |
| 409 | 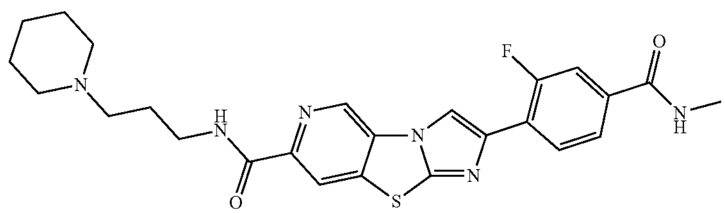 [SMILES: CNC(=O)c1ccc(-c2cn3c(n2)sc2cc(C(=O)NCCCN4CCCCC4)ncc23)c(F)c1] | 2-(2-fluoro-4-(methylcarbamoyl)phenyl)-N-(3-(piperidin-1-yl)propyl)imidazo[2',1':2,3]thiazolo[4,5-c]pyridine-7-carboxamide |
| 410 | 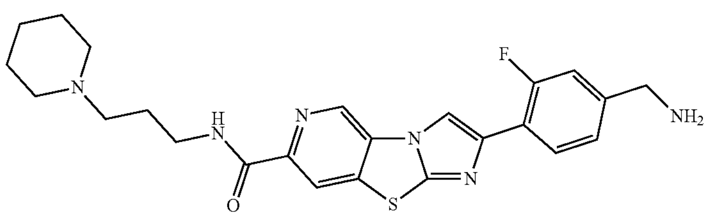 [SMILES: NCc1ccc(-c2cn3c(n2)sc2cc(C(=O)NCCCN4CCCCC4)ncc23)c(F)c1] | 2-(4-(aminomethyl)-2-fluorophenyl)-N-(3-(piperidin-1-yl)propyl)imidazo[2',1':2,3]thiazolo[4,5-c]pyridine-7-carboxamide |
| 411 | 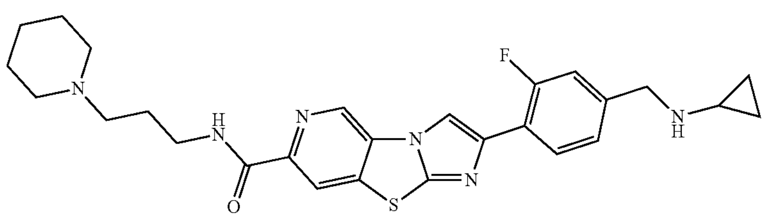 [SMILES: O=C(NCCCN1CCCCC1)c1cc2sc3nc(-c4ccc(CNC5CC5)cc4F)cn3c2cn1] | 2-(4-((cyclopropylamino)methyl)-2-fluorophenyl)-N-(3-(piperidin-1-yl)propyl)imidazo[2',1':2,3]thiazolo[4,5-c]pyridine-7-carboxamide |
| 412 | 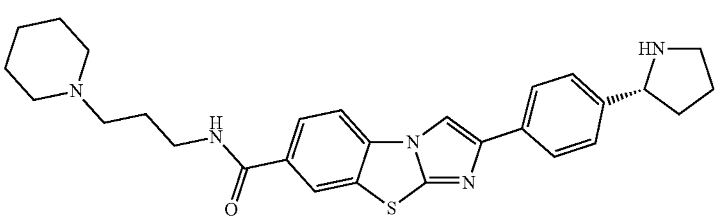 [SMILES: O=C(NCCCN1CCCCC1)c1ccc2c(c1)sc1nc(-c3ccc([C@H]4CCCN4)cc3)cn12] | (R)-N-(3-(piperidin-1-yl)propyl)-2-(4-(pyrrolidin-2-yl)phenyl)benzo[d]imidazo[2,1-b]thiazole-7-carboxamide |
| 413 | 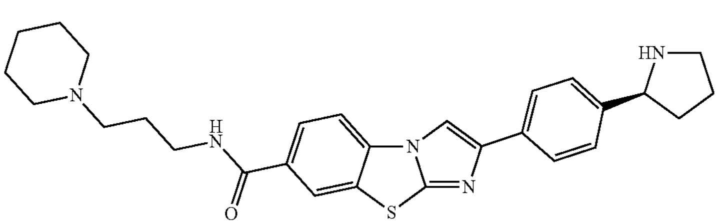 [SMILES: O=C(NCCCN1CCCCC1)c1ccc2c(c1)sc1nc(-c3ccc([C@@H]4CCCN4)cc3)cn12] | (S)-N-(3-(piperidin-1-yl)propyl)-2-(4-(pyrrolidin-2-yl)phenyl)benzo[d]imidazo[2,1-b]thiazole-7-carboxamide |

TABLE 1-continued

| Comp. No. | Structure | Compound Name |
|---|---|---|
| 414 | 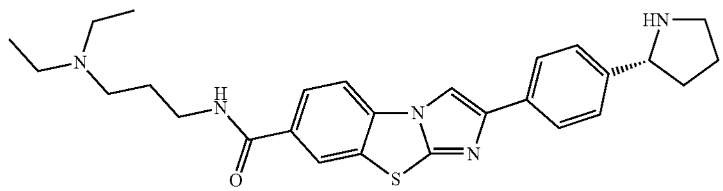 [SMILES: CCN(CC)CCCNC(=O)c1ccc2c(c1)sc1nc(-c3ccc([C@H]4CCCN4)cc3)cn12] | (R)-N-(3-(diethylamino)propyl)-2-(4-(pyrrolidin-2-yl)phenyl)benzo[d]imidazo[2,1-b]thiazole-7-carboxamide |
| 415 | 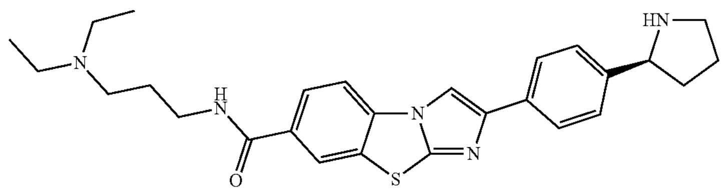 [SMILES: CCN(CC)CCCNC(=O)c1ccc2c(c1)sc1nc(-c3ccc([C@@H]4CCCN4)cc3)cn12] | (S)-N-(3-(diethylamino)propyl)-2-(4-(pyrrolidin-2-yl)phenyl)benzo[d]imidazo[2,1-b]thiazole-7-carboxamide |
| 416 | 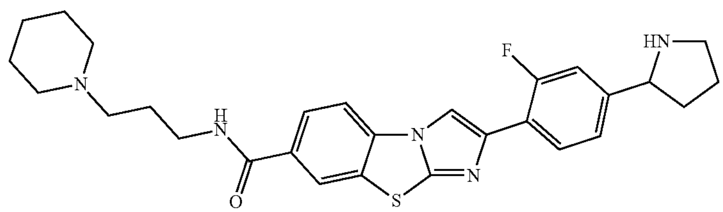 | 2-(2-fluoro-4-(pyrrolidin-2-yl)phenyl)-N-(3-(piperidin-1-yl)propyl)benzo[d]imidazo[2,1-b]thiazole-7-carboxamide |
| 417 | 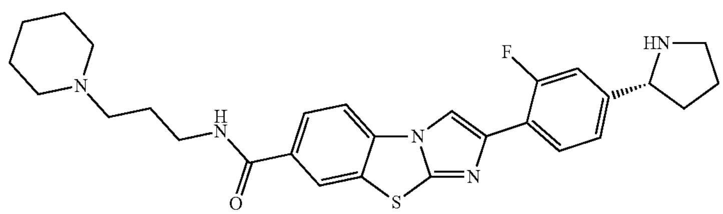 | (R)-2-(2-fluoro-4-(pyrrolidin-2-yl)phenyl)-N-(3-(piperidin-1-yl)propyl)benzo[d]imidazo[2,1-b]thiazole-7-carboxamide |
| 418 | 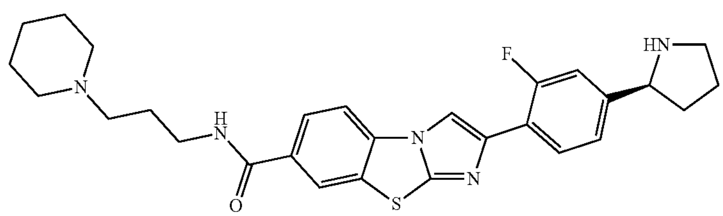 [SMILES: O=C(NCCCN1CCCCC1)c1ccc2c(c1)sc1nc(-c3ccc([C@@H]4CCCN4)cc3F)cn12] | (S)-2-(2-fluoro-4-(pyrrolidin-2-yl)phenyl)-N-(3-(piperidin-1-yl)propyl)benzo[d]imidazo[2,1-b]thiazole-7-carboxamide |
| 419 | 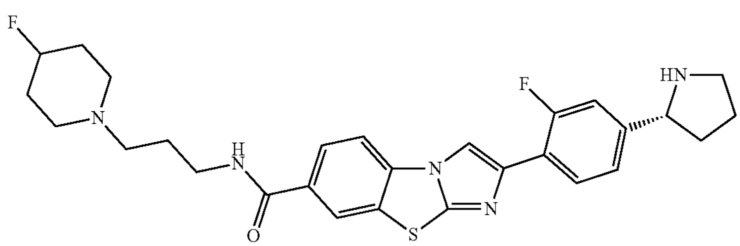 [SMILES: O=C(NCCCN1CCC(F)CC1)c1ccc2c(c1)sc1nc(-c3ccc([C@H]4CCCN4)cc3F)cn12] | (R)-2-(2-fluoro-4-(pyrrolidin-2-yl)phenyl)-N-(3-(4-fluoropiperidin-1-yl)propyl)benzo[d]imidazo[2,1-b]thiazole-7-carboxamide |
| 420 | 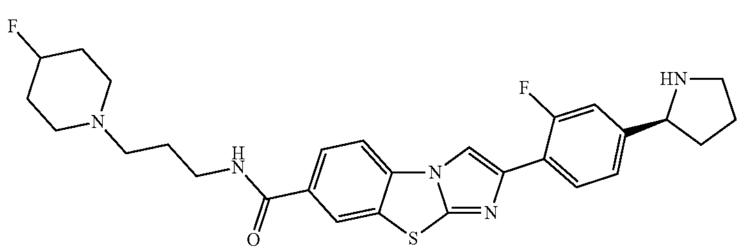 [SMILES: O=C(NCCCN1CCC(F)CC1)c1ccc2c(c1)sc1nc(-c3ccc([C@@H]4CCCN4)cc3F)cn12] | (S)-2-(2-fluoro-4-(pyrrolidin-2-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 421 | 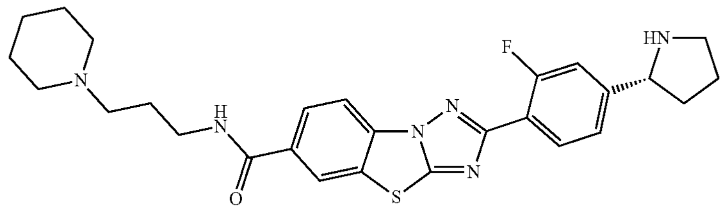 [SMILES: O=C(NCCCN1CCCCC1)c1ccc2c(c1)sc1nc(-c3ccc([C@H]4CCCN4)cc3F)nn12] | (R)-2-(2-fluoro-4-(pyrrolidin-2-yl)phenyl)-N-(3-(piperidin-1-yl)propyl)benzo[4,5]thiazolo[3,2-b][1,2,4]triazole-6-carboxamide |
| 422 | 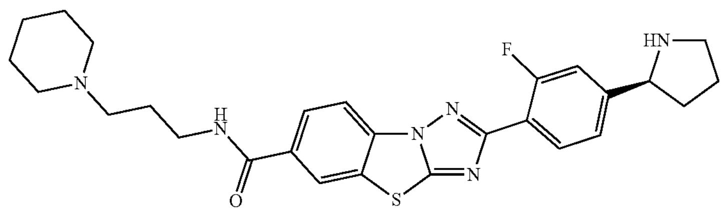 [SMILES: O=C(NCCCN1CCCCC1)c1ccc2c(c1)sc1nc(-c3ccc([C@@H]4CCCN4)cc3F)nn12] | (S)-2-(2-fluoro-4-(pyrrolidin-2-yl)phenyl)-N-(3-(piperidin-1-yl)propyl)benzo[4,5]thiazolo[3,2-b][1,2,4]triazole-6-carboxamide |
| 423S | 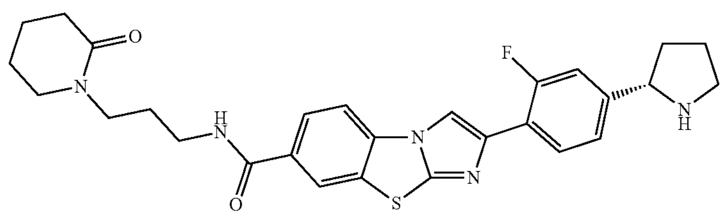 [SMILES: O=C(NCCCN1CCCCC1=O)c1ccc2c(c1)sc1nc(-c3ccc([C@@H]4CCCN4)cc3F)cn12] | (S)-2-(2-fluoro-4-(pyrrolidin-2-yl)phenyl)-N-(3-(2-oxopiperidin-1-yl)propyl)benzo[d]imidazo[2,1-b]othiazole-7-carboxamide |
| 423R | 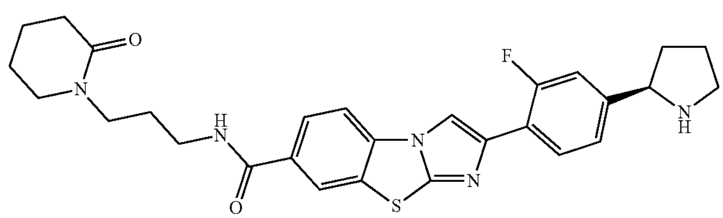 [SMILES: O=C(NCCCN1CCCCC1=O)c1ccc2c(c1)sc1nc(-c3ccc([C@H]4CCCN4)cc3F)cn12] | (R)-2-(2-fluoro-4-(pyrrolidin-2-yl)phenyl)-N-(3-(2-oxopiperidin-1-yl)propyl)benzo[d]imidazo[2,1-b]thiazole-7-carboxamide |
| 424 | 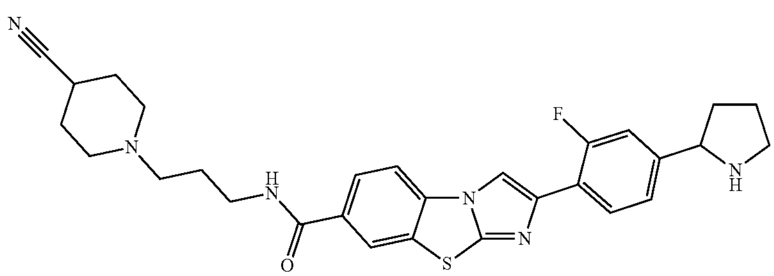 [SMILES: N#CC1CCN(CCCNC(=O)c2ccc3c(c2)sc2nc(-c4ccc(C5CCCN5)cc4F)cn23)CC1] | N-(3-(4-cyanopiperidin-1-yl)propyl)-2-(2-fluoro-4-(pyrrolidin-2-yl)phenyl)benzo[d]imidazo[2,1-b]thiazole-7-carboxamide |
| 425 | 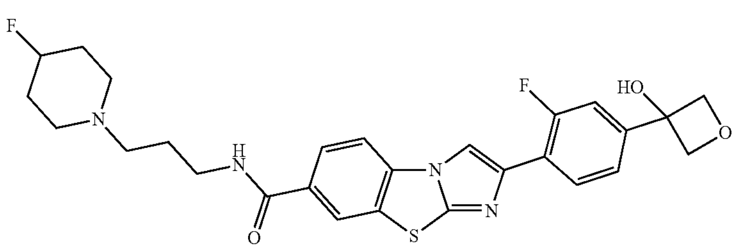 [SMILES: O=C(NCCCN1CCC(F)CC1)c1ccc2c(c1)sc1nc(-c3ccc(C4(O)COC4)cc3F)cn12] | 2-(2-fluoro-4-(3-hydroxyoxetan-3-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 426 | 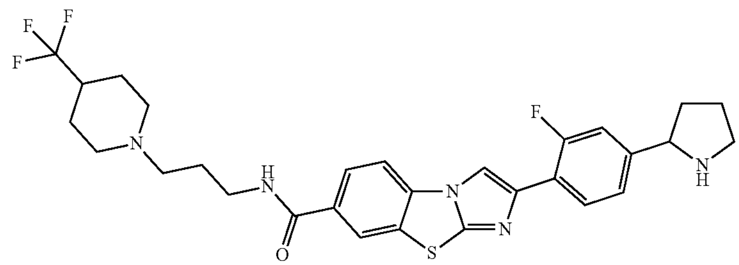 [SMILES: O=C(NCCCN1CCC(C(F)(F)F)CC1)c1ccc2c(c1)sc1nc(-c3ccc(C4CCCN4)cc3F)cn12] | 2-(2-fluoro-4-(pyrrolidin-2-yl)phenyl)-N-(3-(4-(trifluoromethyl)piperidin-1-yl)propyl)benzo[d]imidazo[2,1-b]thiazole-7-carboxamide |
| 427S | 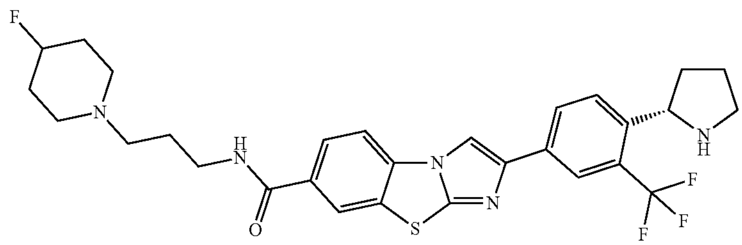 [SMILES: O=C(NCCCN1CCC(F)CC1)c1ccc2c(c1)sc1nc(-c3ccc([C@@H]4CCCN4)c(C(F)(F)F)c3)cn12] | (S)-N-(3-(4-fluoropiperidin-1-yl)propyl)-2-(4-(pyrrolidin-2-yl)-3-(trifluoromethyl)phenyl)benzo[d]imidazo[2,1-b]thiazole-7-carboxamide |
| 427R | 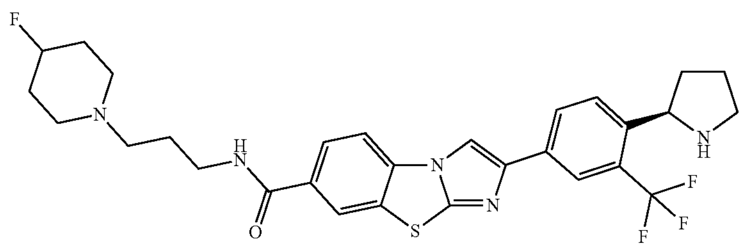 [SMILES: O=C(NCCCN1CCC(F)CC1)c1ccc2c(c1)sc1nc(-c3ccc([C@H]4CCCN4)c(C(F)(F)F)c3)cn12] | (R)-N-(3-(4-fluoropiperidin-1-yl)propyl)-2-(4-(pyrrolidin-2-yl)-3-(trifluoromethyl)phenyl)benzo[d]imidazo[2,1-b]thiazole-7-carboxamide |
| 428S | 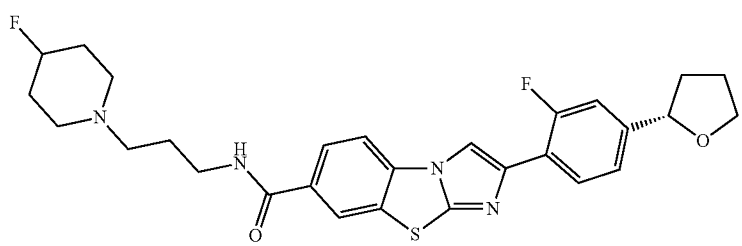 [SMILES: O=C(NCCCN1CCC(F)CC1)c1ccc2c(c1)sc1nc(-c3ccc([C@@H]4CCCO4)cc3F)cn12] | (S)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide |
| 428R | 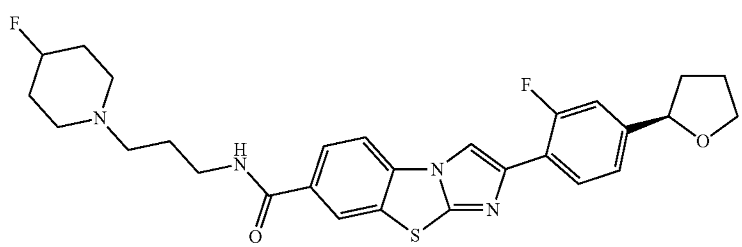 | (R)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide |
| 429S | 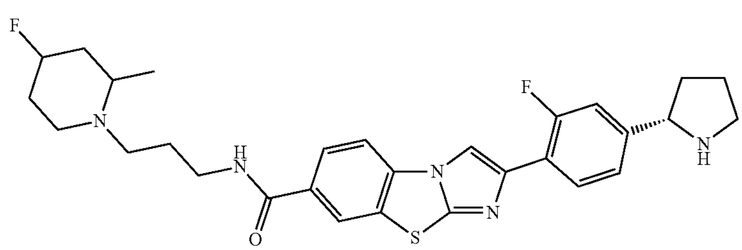 [SMILES: CC1CC(F)CCN1CCCNC(=O)c1ccc2c(c1)sc1nc(-c3ccc([C@@H]4CCCN4)cc3F)cn12] | N-(3-(4-fluoro-2-methylpiperidin-1-yl)propyl)-2-(2-fluoro-4-((S)-pyrrolidin-2-yl)phenyl)benzo[d]imidazo[2,1-b]thiazole-7-carboxamide |

TABLE 1-continued

| Comp. No. | Structure | Compound Name |
|---|---|---|
| 429R | 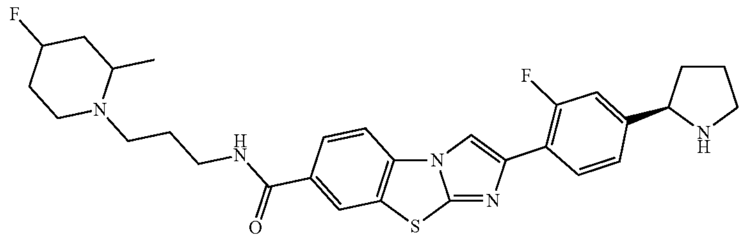 [SMILES: CC1CC(F)CCN1CCCNC(=O)c1ccc2c(c1)sc1nc(-c3ccc([C@H]4CCCN4)cc3F)cn12] | N-(3-(4-fluoro-2-methylpiperidin-1-yl)propyl)-2-(2-fluoro-4-((R)-pyrrolidin-2-yl)phenyl)benzo[d]imidazo[2,1-b]thiazole-7-carboxamide |
| 430S | 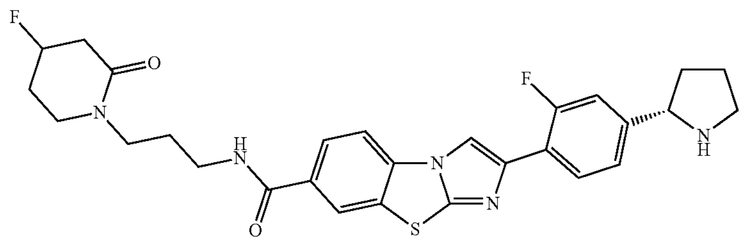 [SMILES: O=C(NCCCN1CCC(F)CC1=O)c1ccc2c(c1)sc1nc(-c3ccc([C@@H]4CCCN4)cc3F)cn12] | N-(3-(4-fluoro-2-oxopiperidin-1-yl)propyl)-2-(2-fluoro-4-((S)-pyrrolidin-2-yl)phenyl)benzo[d]imidazo[2,1-b]thiazole-7-carboxamide |
| 430R | 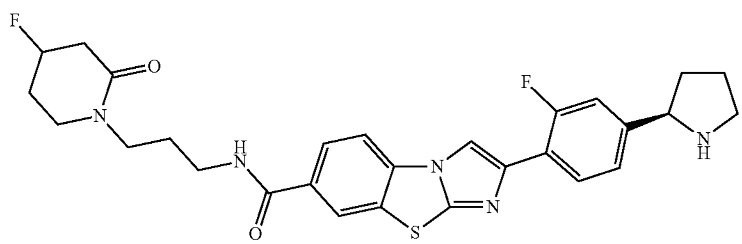 [SMILES: O=C(NCCCN1CCC(F)CC1=O)c1ccc2c(c1)sc1nc(-c3ccc([C@H]4CCCN4)cc3F)cn12] | N-(3-(4-fluoro-2-oxopiperidin-1-yl)propyl)-2-(2-fluoro-4-((R)-pyrrolidin-2-yl)phenyl)benzo[d]imidazo[2,1-b]thiazole-7-carboxamide |
| 431S | 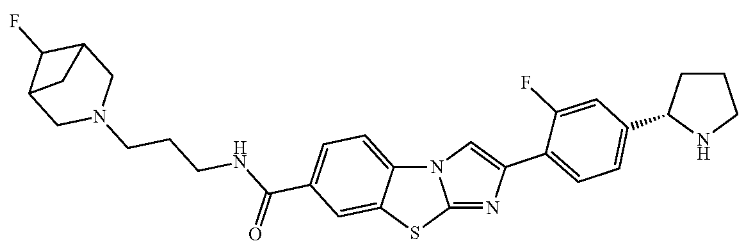 [SMILES: O=C(NCCCN1CC2CC(C1)C2F)c1ccc2c(c1)sc1nc(-c3ccc([C@@H]4CCCN4)cc3F)cn12] | N-(3-(6-fluoro-3-azabicyclo[3.1.1]heptan-3-yl)propyl)-2-(2-fluoro-4-((S)-pyrrolidin-2-yl)phenyl)benzo[d]imidazo[2,1-b]thiazole-7-carboxamide |
| 431R | 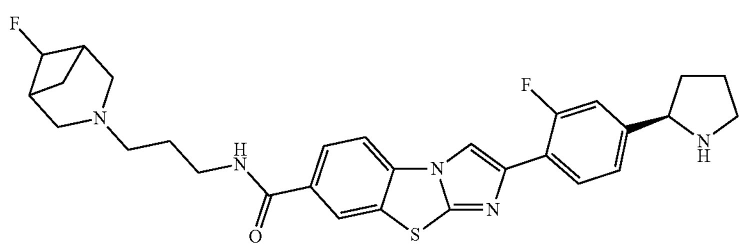 [SMILES: O=C(NCCCN1CC2CC(C1)C2F)c1ccc2c(c1)sc1nc(-c3ccc([C@H]4CCCN4)cc3F)cn12] | N-(3-(6-fluoro-3-azabicyclo[3.1.1]heptan-3-yl)propyl)-2-(2-fluoro-4-((R)-pyrrolidin-2-yl)phenyl)benzo[d]imidazo[2,1-b]thiazole-7-carboxamide |
| 432S | 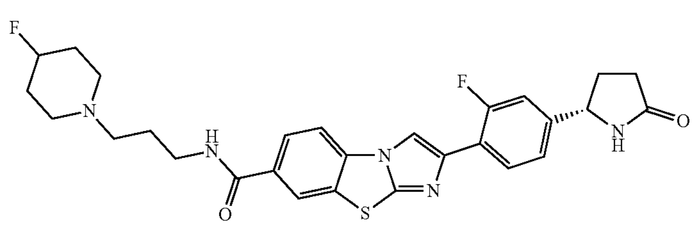 [SMILES: O=C1CC[C@@H](c2ccc(-c3cn4c(n3)sc3cc(C(=O)NCCCN5CCC(F)CC5)ccc34)c(F)c2)N1] | (S)-2-(2-fluoro-4-(5-oxopyrrolidin-2-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 432R | 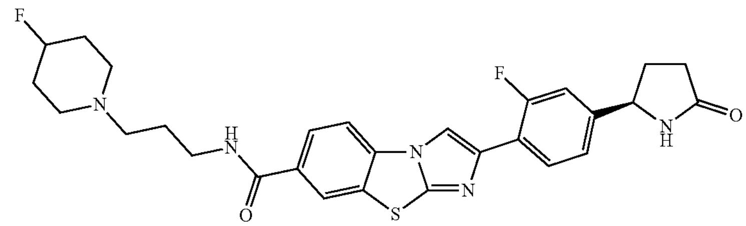 [SMILES: O=C1CC[C@H](c2ccc(-c3cn4c(n3)sc3cc(C(=O)NCCCN5CCC(F)CC5)ccc34)c(F)c2)N1] | (R)-2-(2-fluoro-4-(5-oxopyrrolidin-2-yl)phenyl)-N-(3-(4-fluoropiperidin-1-yl)propyl)benzo[d]imidazo[2-,1-b]thiazole-7-carboxamide |
| 433S | 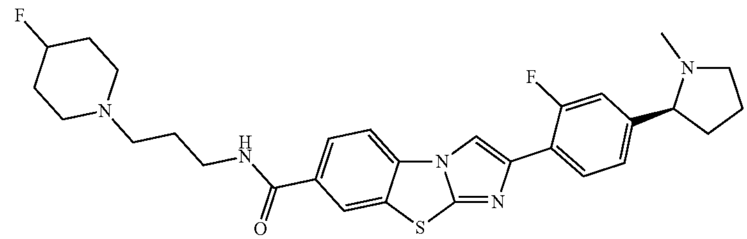 [SMILES: CN1CCC[C@H]1c1ccc(-c2cn3c(n2)sc2cc(C(=O)NCCCN4CCC(F)CC4)ccc23)c(F)c1] | (S)-2-(2-fluoro-4-(1-methylpyrrolidin-2-yl)phenyl)-N-(3-(4-fluoropiperidin-1-yl)propyl)benzo[d]imidazo[2,1-b]thiazole-7-carboxamide |
| 433R | 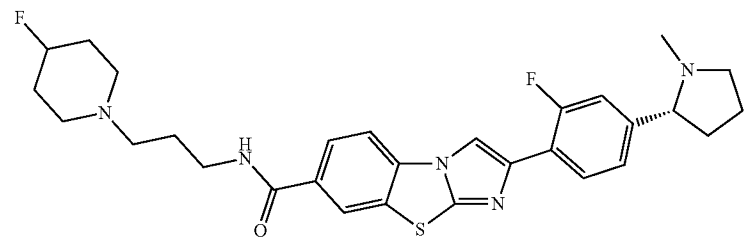 | (R)-2-(2-fluoro-4-(1-methylpyrrolidin-2-yl)phenyl)-N-(3-(4-fluoropiperidin-1-yl)propyl)benzo[d]imidazo[2,1-b]thiazole-7-carboxamide |
| 434S | 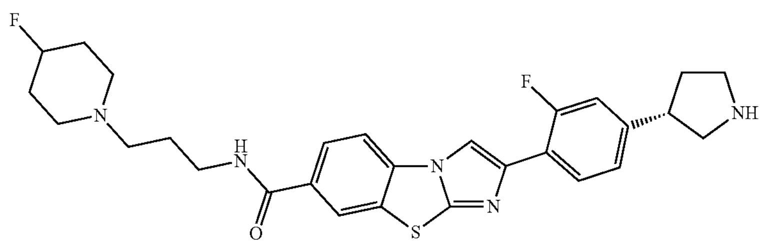 [SMILES: O=C(NCCCN1CCC(F)CC1)c1ccc2c(c1)sc1nc(-c3ccc([C@@H]4CCNC4)cc3F)cn12] | (S)-2-(2-fluoro-4-(pyrrolidin-3-yl)phenyl)-N-(3-(4-fluoropiperidin-1-yl)propyl)benzo[d]imidazo[2,1-b]thiazole-7-carboxamide |
| 434R | 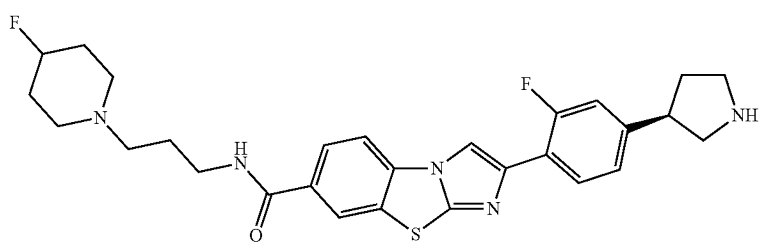 [SMILES: O=C(NCCCN1CCC(F)CC1)c1ccc2c(c1)sc1nc(-c3ccc([C@H]4CCNC4)cc3F)cn12] | (R)-2-(2-fluoro-4-(pyrrolidin-3-yl)phenyl)-N-(3-(4-fluoropiperidin-1-yl)propyl)benzo[d]imidazo[2,1-b]thiazole-7-carboxamide |
| 435S | 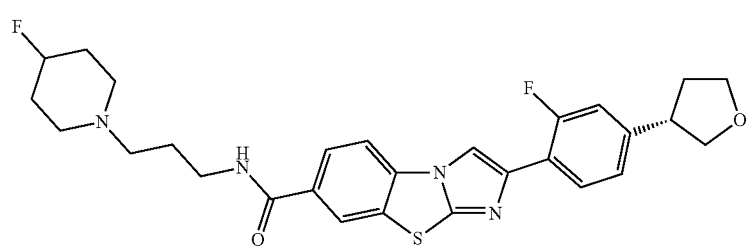 [SMILES: O=C(NCCCN1CCC(F)CC1)c1ccc2c(c1)sc1nc(-c3ccc([C@@H]4CCOC4)cc3F)cn12] | (S)-2-(2-fluoro-4-(tetrahydrofuran-3-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 435R | 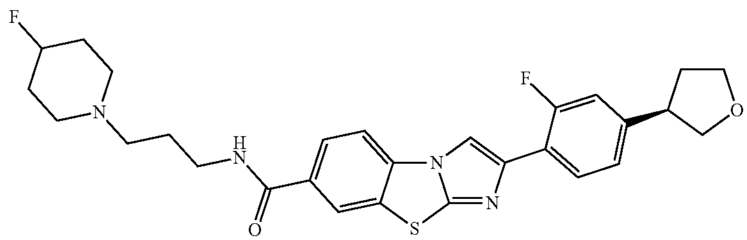 [SMILES: O=C(NCCCN1CCC(F)CC1)c1ccc2c(c1)sc1nc(-c3ccc([C@H]4CCOC4)cc3F)cn12] | (R)-2-(2-fluoro-4-(tetrahydrofuran-3-yl)phenyl)-N-(3-(4-fluoropiperidin-1-yl)propyl)benzo[d]imidazo[2,1-b]thiazole-7-carboxamide |
| 436S | 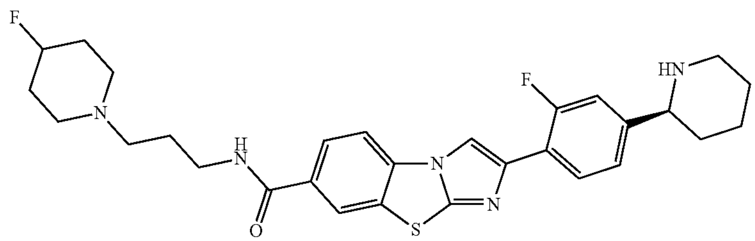 [SMILES: O=C(NCCCN1CCC(F)CC1)c1ccc2c(c1)sc1nc(-c3ccc([C@@H]4CCCCN4)cc3F)cn12] | (S)-2-(2-fluoro-4-(piperidin-2-yl)phenyl)-N-(3-(4-fluoropiperidin-1-yl)propyl)benzo[d]imidazo[2,1-b]thiazole-7-carboxamide |
| 436R | 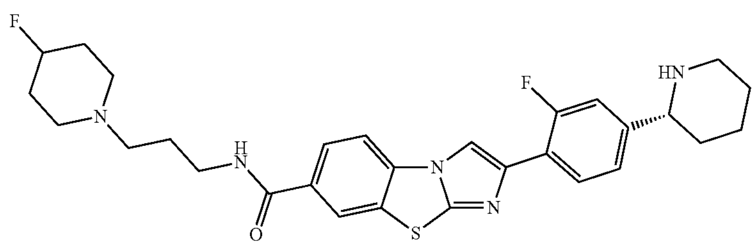 [SMILES: O=C(NCCCN1CCC(F)CC1)c1ccc2c(c1)sc1nc(-c3ccc([C@H]4CCCCN4)cc3F)cn12] | (R)-2-(2-fluoro-4-(piperidin-2-yl)phenyl)-N-(3-(4-fluoropiperidin-1-yl)propyl)benzo[d]imidazo[2,1-b]thiazole-7-carboxamide |
| 437S | 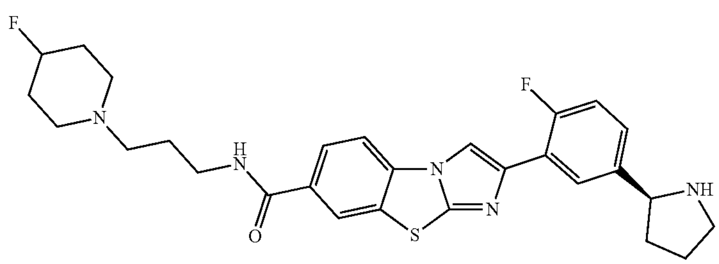 [SMILES: O=C(NCCCN1CCC(F)CC1)c1ccc2c(c1)sc1nc(-c3cc([C@@H]4CCCN4)ccc3F)cn12] | (S)-2-(2-fluoro-5-(pyrrolidin-2-yl)phenyl)-N-(3-(4-fluoropiperidin-1-yl)propyl)benzo[d]imidazo[2,1-b]thiazole-7-carboxamide |
| 437R | 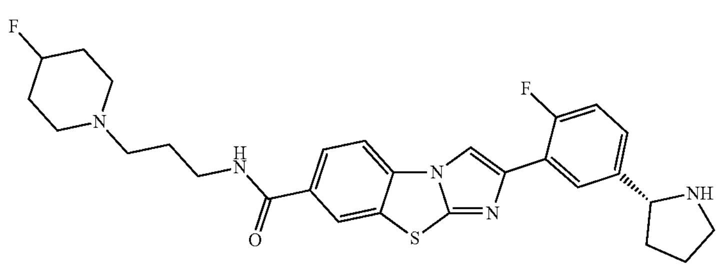 [SMILES: O=C(NCCCN1CCC(F)CC1)c1ccc2c(c1)sc1nc(-c3cc([C@H]4CCCN4)ccc3F)cn12] | (R)-2-(2-fluoro-5-(pyrrolidin-2-yl)phenyl)-N-(3-(4-fluoropiperidin-1-yl)propyl)benzo[d]imidazo[2,1-b]thiazole-7-carboxamide |
| 438S | 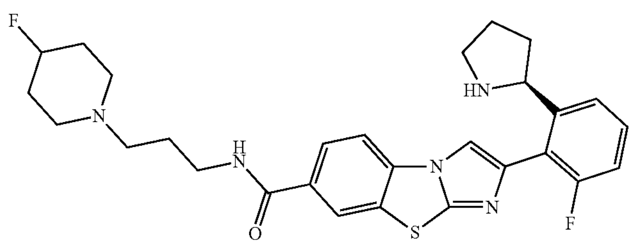 [SMILES: O=C(NCCCN1CCC(F)CC1)c1ccc2c(c1)sc1nc(-c3c(F)cccc3[C@@H]3CCCN3)cn12] | (S)-2-(2-fluoro-6-(pyrrolidin-2-yl)phenyl)-N-(3-(4-fluoropiperidin-1-yl)propyl)benzo[d]imidazo[2,1-b]thiazole-7-carboxamide |

| Comp. No. | Structure | Compound Name |
|---|---|---|
| 438R | 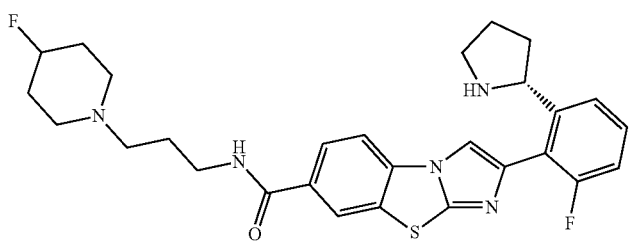 [SMILES: O=C(NCCCN1CCC(F)CC1)c1ccc2c(c1)sc1nc(-c3c(F)cccc3[C@H]3CCCN3)cn12] | (R)-2-(2-fluoro-6-(pyrrolidin-2-yl)phenyl)-N-(3-(4-fluoropiperidin-1-yl)propyl)benzo[d]imidazo[2,1-b]thiazole-7-carboxamide |
| 439S | 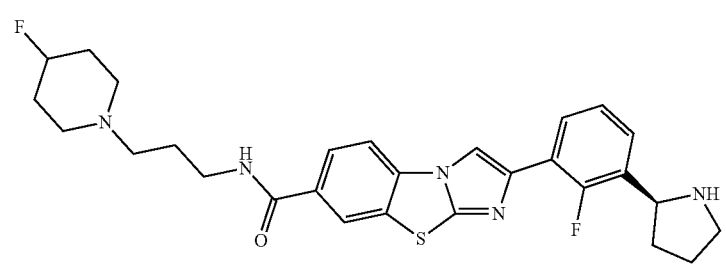 [SMILES: O=C(NCCCN1CCC(F)CC1)c1ccc2c(c1)sc1nc(-c3cccc([C@@H]4CCCN4)c3F)cn12] | (S)-2-(2-fluoro-3-(pyrrolidin-2-yl)phenyl)-N-(3-(4-fluoropiperidin-1-yl)propyl)benzo[d]imidazo[2,1-b]thiazole-7-carboxamide |
| 439R | 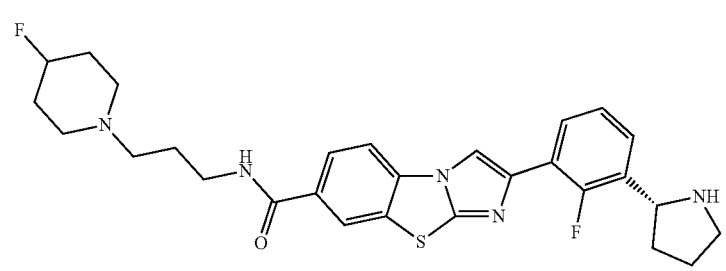 [SMILES: O=C(NCCCN1CCC(F)CC1)c1ccc2c(c1)sc1nc(-c3cccc([C@H]4CCCN4)c3F)cn12] | (R)-2-(2-fluoro-3-(pyrrolidin-2-yl)phenyl)-N-(3-(4-fluoropiperidin-1-yl)propyl)benzo[d]imidazo[2,1-b]thiazole-7-carboxamide |
| 440 | 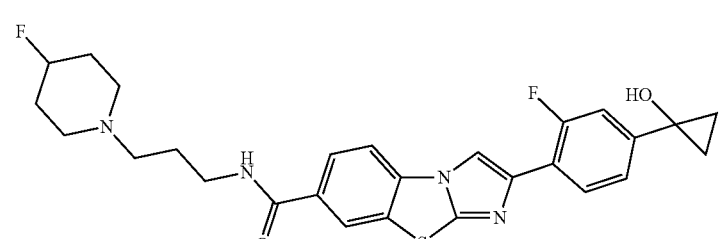 | 2-(2-fluoro-4-(1-hydroxycyclopropyl)phenyl)-N-(3-(4-fluoropiperidin-1-yl)propyl)benzo[d]imidazo[2,1-b]thiazole-7-carboxamide |
| 442 | 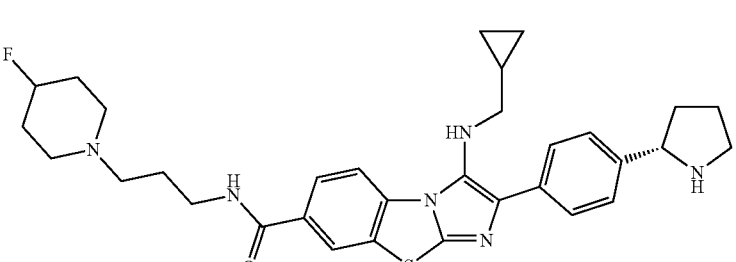 | (S)-3-((cyclopropylmethyl)amino)-N-(3-(4-fluoropiperidin-1-yl)propyl)-2-(4-(pyrrolidin-2-yl)phenyl)benzo[d]imidazo[2,1-b]thiazole-7-carboxamide |
| 443 | 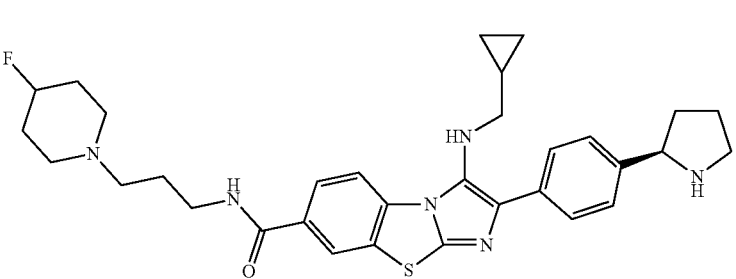 [SMILES: O=C(NCCCN1CCC(F)CC1)c1ccc2c(c1)sc1nc(-c3ccc([C@H]4CCCN4)cc3)c(NCC3CC3)n12] | (R)-3-((cyclopropylmethyl)amino)-N-(3-(4-fluoropiperidin-1-yl)propyl)-2-(4-(pyrrolidin-2-yl)phenyl)benzo[d]imidazo[2,1-b]thiazole-7-carboxamide |

TABLE 1-continued

| Comp. No. | Structure | Compound Name |
|---|---|---|
| 444 | 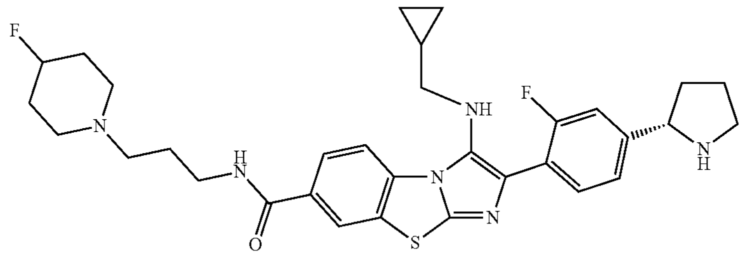 [SMILES: O=C(NCCCN1CCC(F)CC1)c1ccc2c(c1)sc1nc(-c3ccc([C@@H]4CCCN4)cc3F)c(NCC3CC3)n12] | (S)-3-((cyclopropylmethyl)amino)-2-(2-fluoro-4-(pyrrolidin-2-yl)phenyl)-N-(3-(4-fluoropiperidin-1-yl)propyl)benzo[d]imidazo[2,1-b]thiazole-7-carboxamide |
| 445 | 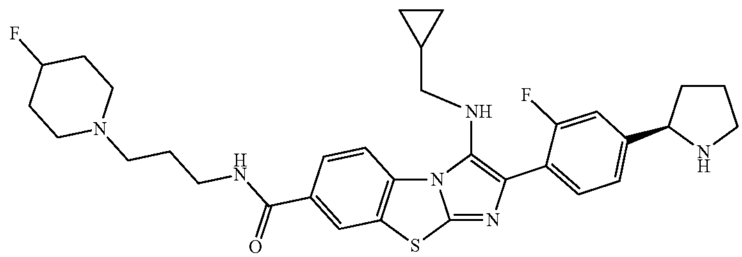 [SMILES: O=C(NCCCN1CCC(F)CC1)c1ccc2c(c1)sc1nc(-c3ccc([C@H]4CCCN4)cc3F)c(NCC3CC3)n12] | (R)-3-((cyclopropylmethyl)amino)-2-(2-fluoro-4-(pyrrolidin-2-yl)phenyl)-N-(3-(4-fluoropiperidin-1-yl)propyl)benzo[d]imidazo[2,1-b]thiazole-7-carboxamide |
| 446 | 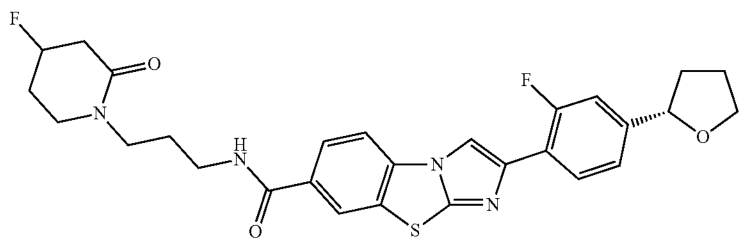 [SMILES: O=C(NCCCN1CCC(F)CC1=O)c1ccc2c(c1)sc1nc(-c3ccc([C@@H]4CCCO4)cc3F)cn12] | N-(3-(4-fluoro-2-oxopiperidin-1-yl)propyl)-2-(2-fluoro-4-((S)-tetrahydrofuran-2-yl)phenyl)benzo[d]imidazo[2,1-b]thiazole-7-carboxamide |
| 447 | 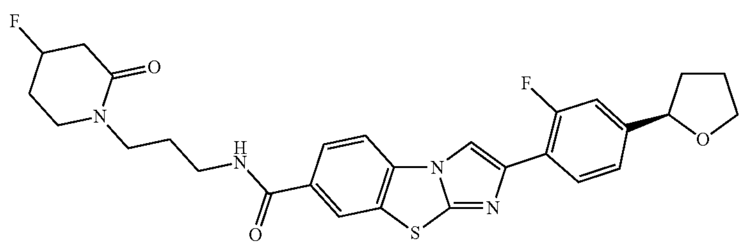 [SMILES: O=C(NCCCN1CCC(F)CC1=O)c1ccc2c(c1)sc1nc(-c3ccc([C@H]4CCCO4)cc3F)cn12] | N-(3-(4-fluoro-2-oxopiperidin-1-yl)propyl)-2-(2-fluoro-4-((S)-tetrahydrofuran-2-yl)phenyl)benzo[d]imidazo[2,1-b]thiazole-7-carboxamide |
| 448 | 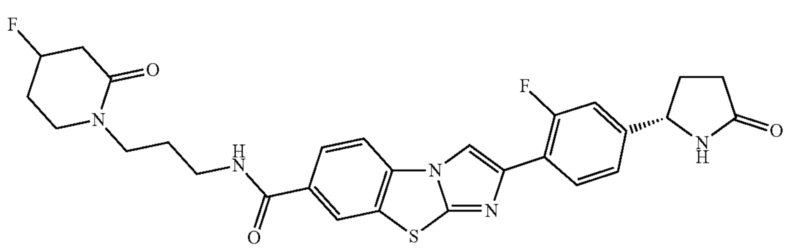 [SMILES: O=C1CC[C@@H](c2ccc(-c3cn4c(n3)sc3cc(C(=O)NCCCN5CCC(F)CC5=O)ccc34)c(F)c2)N1] | N-(3-(4-fluoro-2-oxopiperidin-1-yl)propyl)-2-(2-fluoro-4-((S)-5-oxopyrrolidin-2-yl)phenyl)benzo[d]imidazo[2,1-b]thiazole-7-carboxamide |
| 449 | 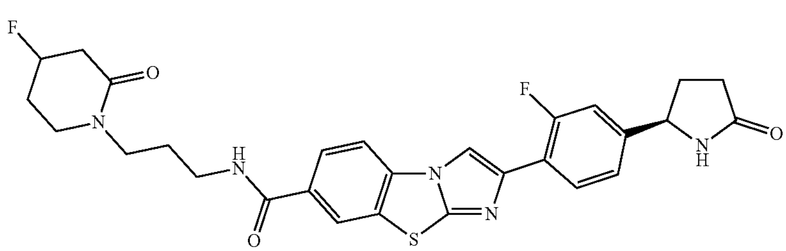 [SMILES: O=C1CC[C@H](c2ccc(-c3cn4c(n3)sc3cc(C(=O)NCCCN5CCC(F)CC5=O)ccc34)c(F)c2)N1] | N-(3-(4-fluoro-2-oxopiperidin-1-yl)propyl)-2-(2-fluoro-4-((R)-5-oxopyrrolidin-2-yl)phenyl)benzo[d]imidazo[2,1-b]thiazole-7-carboxamide |

TABLE 1-continued

| Comp. No. | Structure | Compound Name |
|---|---|---|
| 450S | 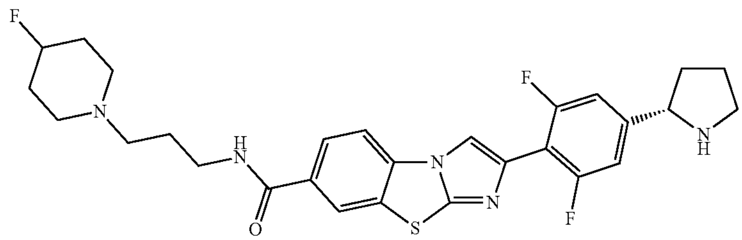 [SMILES: O=C(NCCCN1CCC(F)CC1)c1ccc2c(c1)sc1nc(-c3c(F)cc([C@@H]4CCCN4)cc3F)cn12] | (S)-2-(2,6-difluoro-4-(pyrrolidin-2-yl)phenyl)-N-(3-(4-fluoropiperidin-1-yl)propyl)benzo[d]imidazo[2,1-b]thiazole-7-carboxamide |
| 450R | 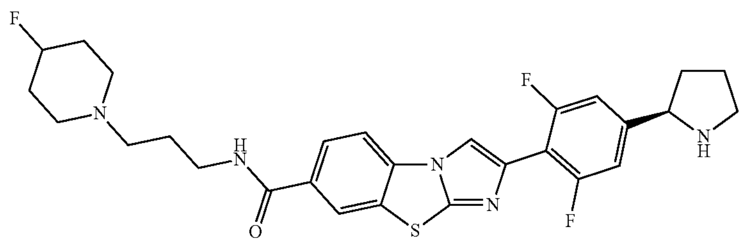 [SMILES: O=C(NCCCN1CCC(F)CC1)c1ccc2c(c1)sc1nc(-c3c(F)cc([C@H]4CCCN4)cc3F)cn12] | (R)-2-(2,6-difluoro-4-(pyrrolidin-2-yl)phenyl)-N-(3-(4-fluoropiperidin-1-yl)propyl)benzo[d]imidazo[2,1-b]thiazole-7-carboxamide |
| 451S | 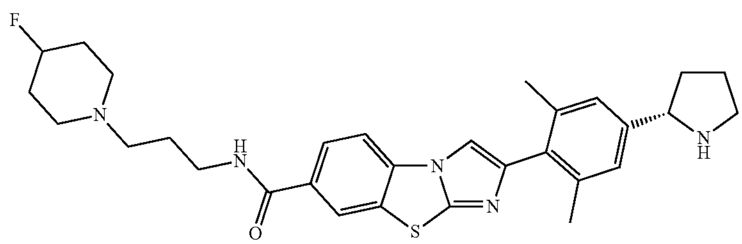 [SMILES: Cc1cc([C@@H]2CCCN2)cc(C)c1-c1cn2c(n1)sc1cc(C(=O)NCCCN3CCC(F)CC3)ccc12] | (S)-2-(2,6-dimethyl-4-(pyrrolidin-2-yl)phenyl)-N-(3-(4-fluoropiperidin-1-yl)propyl)benzo[d]imidazo[2,1-b]thiazole-7-carboxamide |
| 451R | 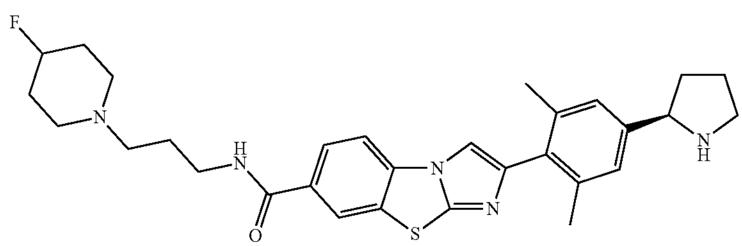 | (R)-2-(2,6-dimethyl-4-(pyrrolidin-2-yl)phenyl)-N-(3-(4-fluoropiperidin-1-yl)propyl)benzo[d]imidazo[2,1-b]thiazole-7-carboxamide |
| 452S | 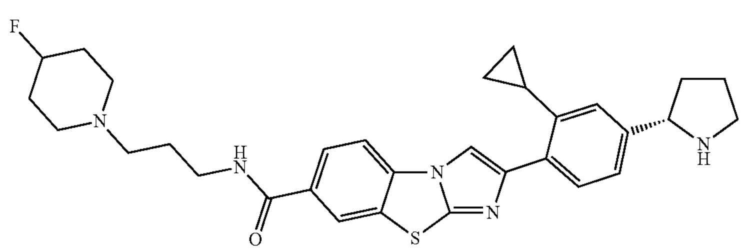 [SMILES: O=C(NCCCN1CCC(F)CC1)c1ccc2c(c1)sc1nc(-c3ccc([C@@H]4CCCN4)cc3C3CC3)cn12] | (S)-2-(2-cyclopropyl-4-(pyrrolidin-2-yl)phenyl)-N-(3-(4-fluoropiperidin-1-yl)propyl)benzo[d]imidazo[2,1-b]thiazole-7-carboxamide |
| 452R | 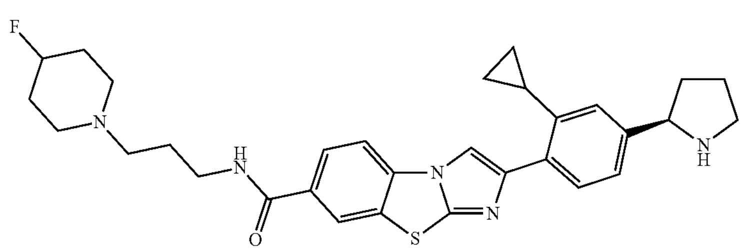 [SMILES: O=C(NCCCN1CCC(F)CC1)c1ccc2c(c1)sc1nc(-c3ccc([C@H]4CCCN4)cc3C3CC3)cn12] | (R)-2-(2-cyclopropyl-4-(pyrrolidin-2-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 453S | 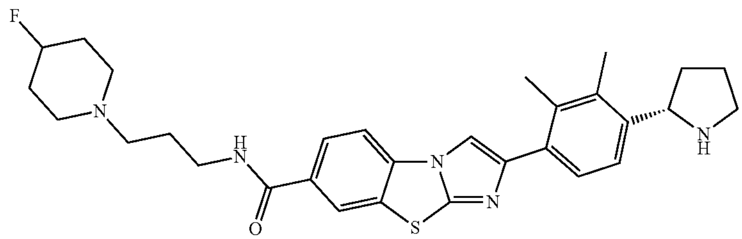 [SMILES: Cc1c(-c2cn3c(n2)sc2cc(C(=O)NCCCN4CCC(F)CC4)ccc23)ccc([C@@H]2CCCN2)c1C] | (S)-2-(2,3-dimethyl-4-(pyrrolidin-2-yl)phenyl)-N-(3-(4-fluoropiperidin-1-yl)propyl)benzo[d]imidazo[2,1-b]thiazole-7-carboxamide |
| 453R | 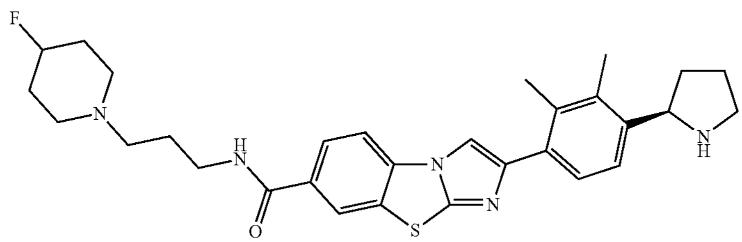 [SMILES: Cc1c(-c2cn3c(n2)sc2cc(C(=O)NCCCN4CCC(F)CC4)ccc23)ccc([C@H]2CCCN2)c1C] | (R)-2-(2,3-dimethyl-4-(pyrrolidin-2-yl)phenyl)-N-(3-(4-fluoropiperidin-1-yl)propyl)benzo[d]imidazo[2,1-b]thiazole-7-carboxamide |
| 454 | 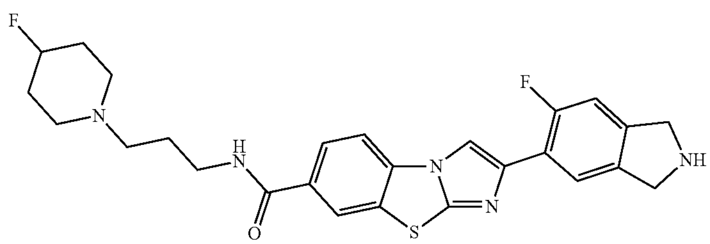 [SMILES: O=C(NCCCN1CCC(F)CC1)c1ccc2c(c1)sc1nc(-c3cc4c(cc3F)CNC4)cn12] | 2-(6-fluoroisoindolin-5-yl)-N-(3-(4-fluoropiperidin-1-yl)propyl)benzo[d]imidazo[2,1-b]thiazole-7-carboxamide |
| 455 | 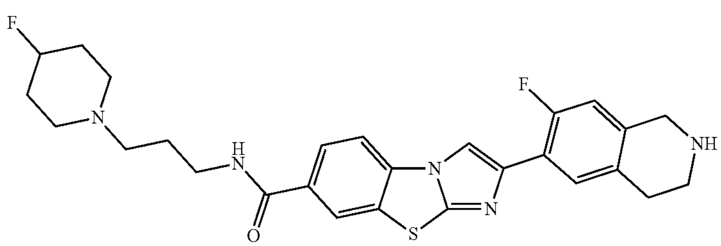 [SMILES: O=C(NCCCN1CCC(F)CC1)c1ccc2c(c1)sc1nc(-c3cc4c(cc3F)CNCC4)cn12] | 2-(7-fluoro-1,2,3,4-tetrahydroisoquinolin-6-yl)-N-(3-(4-fluoropiperidin-1-yl)propyl)benzo[d]imidazo[2,1-b]thiazole-7-carboxamide |
| 456 | 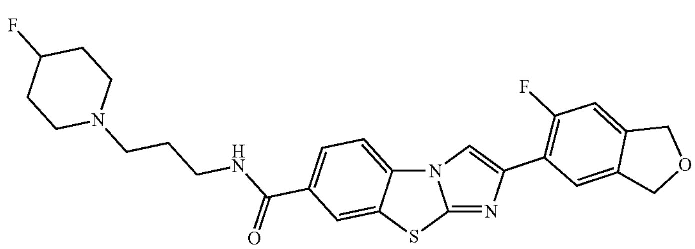 [SMILES: O=C(NCCCN1CCC(F)CC1)c1ccc2c(c1)sc1nc(-c3cc4c(cc3F)COC4)cn12] | 2-(6-fluoro-1,3-dihydroisobenzofuran-5-yl)-N-(3-(4-fluoropiperidin-1-yl)propyl)benzo[d]imidazo[2,1-b]thiazole-7-carboxamide |
| 457 | 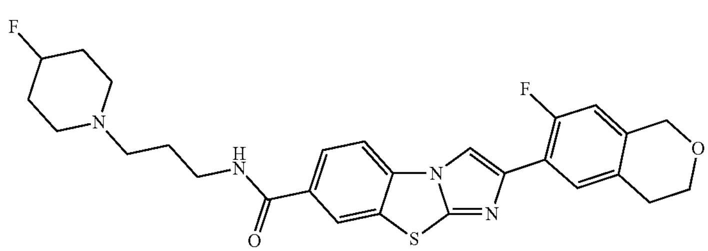 [SMILES: O=C(NCCCN1CCC(F)CC1)c1ccc2c(c1)sc1nc(-c3cc4c(cc3F)COCC4)cn12] | 2-(7-fluoroisochroman-6-yl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 458 | 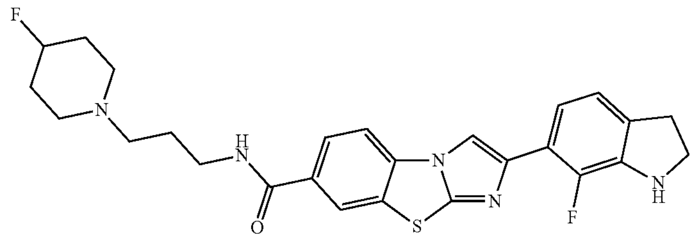 [SMILES: O=C(NCCCN1CCC(F)CC1)c1ccc2c(c1)sc1nc(-c3ccc4c(c3F)NCC4)cn12] | 2-(7-fluoroindolin-6-yl)-N-(3-(4-fluoropiperidin-1-yl)propyl)benzo[d]imidazo[2,1-b]thiazole-7-carboxamide |
| 459 | 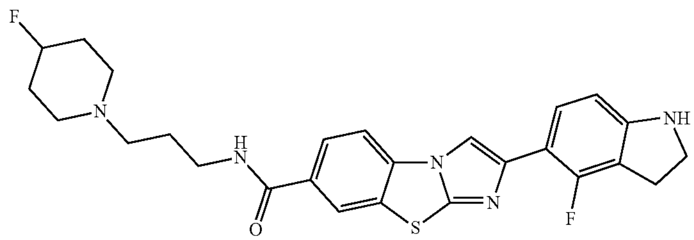 [SMILES: O=C(NCCCN1CCC(F)CC1)c1ccc2c(c1)sc1nc(-c3ccc4c(c3F)CCN4)cn12] | 2-(4-fluoroindolin-5-yl)-N-(3-(4-fluoropiperidin-1-yl)propyl)benzo[d]imidazo[2,1-b]thiazole-7-carboxamide |
| 460S | 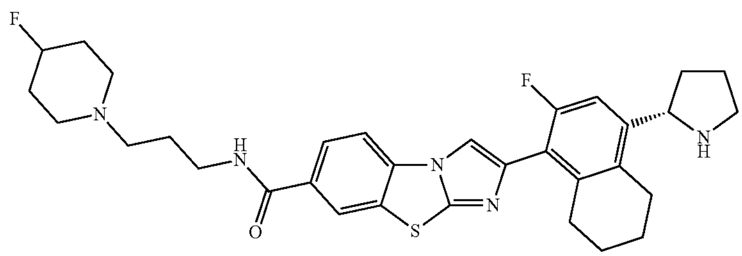 [SMILES: O=C(NCCCN1CCC(F)CC1)c1ccc2c(c1)sc1nc(-c3c(F)cc([C@@H]4CCCN4)c4c3CCCC4)cn12] | (S)-2-(2-fluoro-4-(pyrrolidin-2-yl)-5,6,7,8-tetrahydronaphthalen-1-yl)-N-(3-(4-fluoropiperidin-1-yl)propyl)benzo[d]imidazo[2,1-b]thiazole-7-carboxamide |
| 460R | 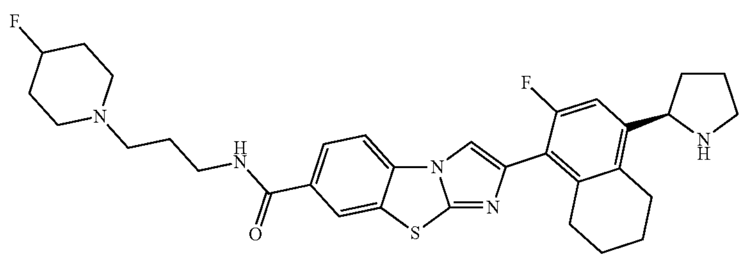 [SMILES: O=C(NCCCN1CCC(F)CC1)c1ccc2c(c1)sc1nc(-c3c(F)cc([C@H]4CCCN4)c4c3CCCC4)cn12] | (R)-2-(2-fluoro-4-(pyrrolidin-2-yl)-5,6,7,8-tetrahydronaphthalen-1-yl)-N-(3-(4-fluoropiperidin-1-yl)propyl)benzo[d]imidazo[2,1-b]thiazole-7-carboxamide |
| 461S | 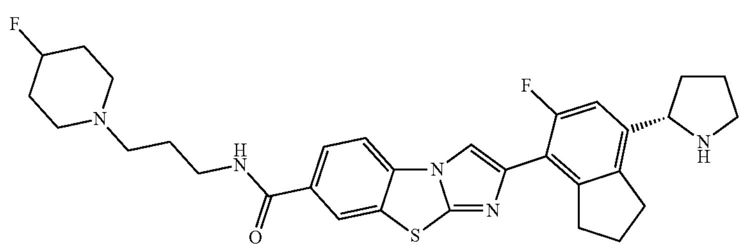 [SMILES: O=C(NCCCN1CCC(F)CC1)c1ccc2c(c1)sc1nc(-c3c(F)cc([C@@H]4CCCN4)c4c3CCC4)cn12] | (S)-2-(5-fluoro-7-(pyrrolidin-2-yl)-2,3-dihydro-1H-inden-4-yl)-N-(3-(4-fluoropiperidin-1-yl)propyl)benzo[d]imidazo[2,1-b]thiazole-7-carboxamide |
| 461R | 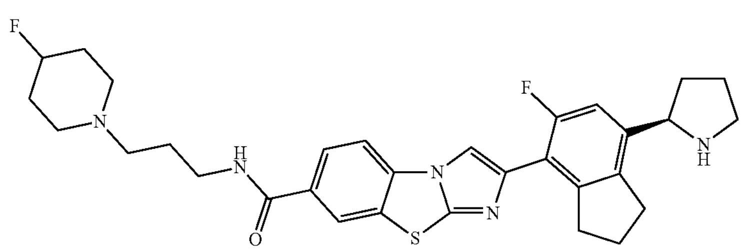 [SMILES: O=C(NCCCN1CCC(F)CC1)c1ccc2c(c1)sc1nc(-c3c(F)cc([C@H]4CCCN4)c4c3CCC4)cn12] | (R)-2-(5-fluoro-7-(pyrrolidin-2-yl)-2,3-dihydro-1H-inden-4-yl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 462S | 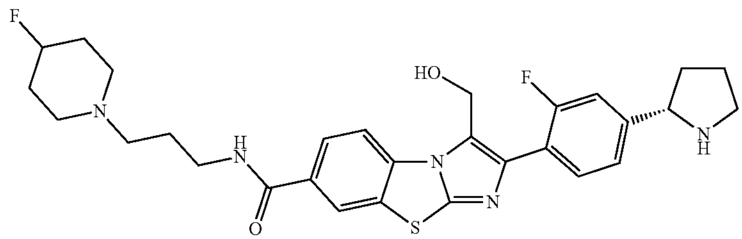 [SMILES: O=C(NCCCN1CCC(F)CC1)c1ccc2c(c1)sc1nc(-c3ccc([C@@H]4CCCN4)cc3F)c(CO)n12] | (S)-2-(2-fluoro-4-(pyrrolidin-2-yl)phenyl)-N-(3-(4-fluoropiperidin-1-yl)propyl)-3-(hydroxymethyl)benzo[d]imidazo[2,1-b]thiazole-7-carboxamide |
| 462R | 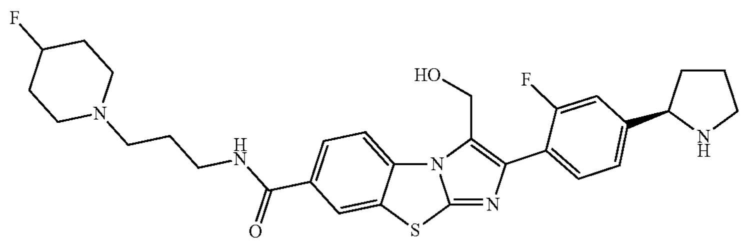 [SMILES: O=C(NCCCN1CCC(F)CC1)c1ccc2c(c1)sc1nc(-c3ccc([C@H]4CCCN4)cc3F)c(CO)n12] | (R)-2-(2-fluoro-4-(pyrrolidin-2-yl)phenyl)-N-(3-(4-fluoropiperidin-1-yl)propyl)-3-(hydroxymethyl)benzo[d]imidazo[2,1-b]thiazole-7-carboxamide |
| 463S | 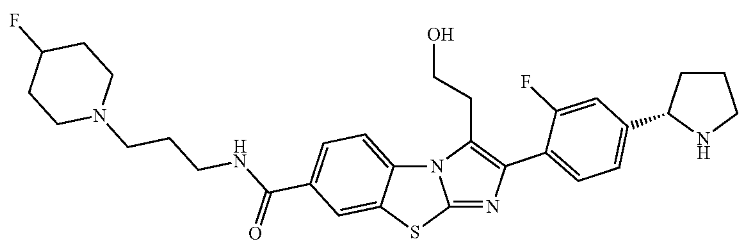 [SMILES: O=C(NCCCN1CCC(F)CC1)c1ccc2c(c1)sc1nc(-c3ccc([C@@H]4CCCN4)cc3F)c(CCO)n12] | (S)-2-(2-fluoro-4-(pyrrolidin-2-yl)phenyl)-N-(3-(4-fluoropiperidin-1-yl)propyl)-3-(2-hydroxyethyl)benzo[d]imidazo[2,1-b]thiazole-7-carboxamide |
| 463R | 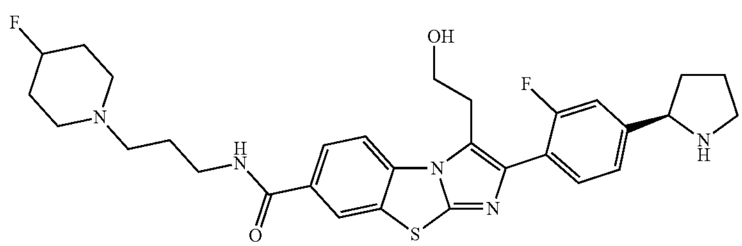 [SMILES: O=C(NCCCN1CCC(F)CC1)c1ccc2c(c1)sc1nc(-c3ccc([C@H]4CCCN4)cc3F)c(CCO)n12] | (R)-2-(2-fluoro-4-(pyrrolidin-2-yl)phenyl)-N-(3-(4-fluoropiperidin-1-yl)propyl)-3-(2-hydroxyethyl)benzo[d]imidazo[2,1-b]thiazole-7-carboxamide |
| 464S | 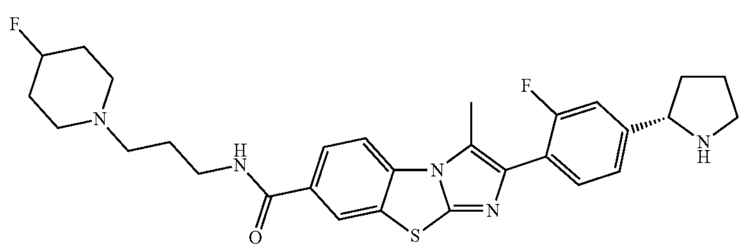 [SMILES: Cc1c(-c2ccc([C@@H]3CCCN3)cc2F)nc2sc3cc(C(=O)NCCCN4CCC(F)CC4)ccc3n12] | (S)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide |
| 464R | 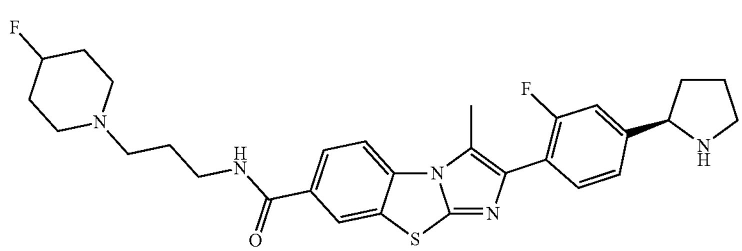 [SMILES: Cc1c(-c2ccc([C@H]3CCCN3)cc2F)nc2sc3cc(C(=O)NCCCN4CCC(F)CC4)ccc3n12] | (R)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide |

TABLE 1-continued

| Comp. No. | Structure | Compound Name |
|---|---|---|
| 465 | 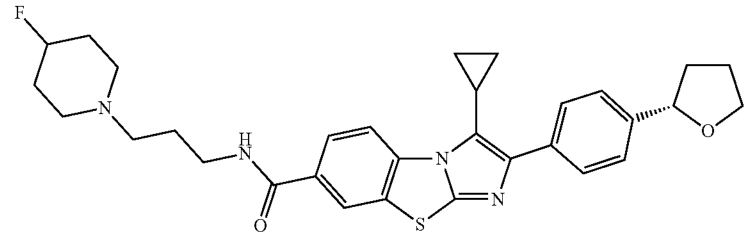 [SMILES: O=C(NCCCN1CCC(F)CC1)c1ccc2c(c1)sc1nc(-c3ccc([C@@H]4CCCO4)cc3)c(C3CC3)n12] | (S)-3-cyclopropyl-N-(3-(4-fluoropiperidin-1-yl)propyl)-2-(4-(tetrahydrofuran-2-yl)phenyl)benzo[d]imidazo[2,1-b]thiazole-7-carboxamide |
| 466 | 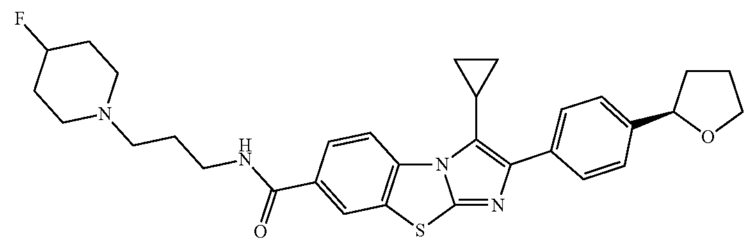 [SMILES: O=C(NCCCN1CCC(F)CC1)c1ccc2c(c1)sc1nc(-c3ccc([C@H]4CCCO4)cc3)c(C3CC3)n12] | (R)-3-cyclopropyl-N-(3-(4-fluoropiperidin-1-yl)propyl)-2-(4-(tetrahydrofuran-2-yl)phenyl)benzo[d]imidazo[2,1-b]thiazole-7-carboxamide |
| 467 | 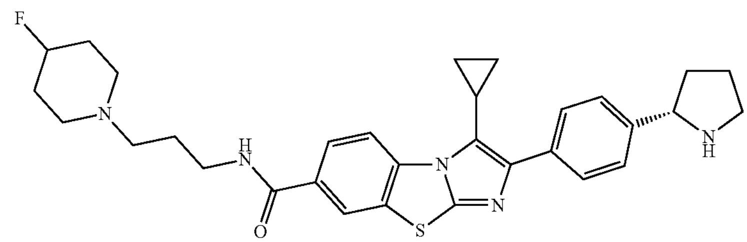 [SMILES: O=C(NCCCN1CCC(F)CC1)c1ccc2c(c1)sc1nc(-c3ccc([C@@H]4CCCN4)cc3)c(C3CC3)n12] | (S)-3-cyclopropyl-N-(3-(4-fluoropiperidin-1-yl)propyl)-2-(4-(pyrrolidin-2-yl)phenyl)benzo[d]imidazo[2,1-b]thiazole-7-carboxamide |
| 468 | 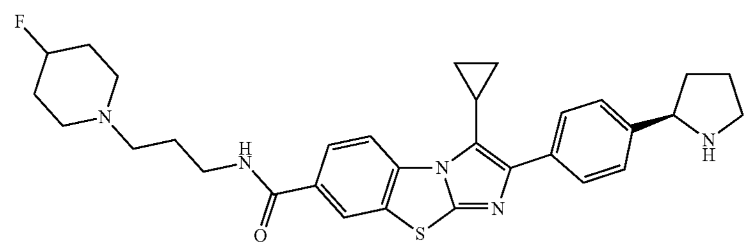 [SMILES: O=C(NCCCN1CCC(F)CC1)c1ccc2c(c1)sc1nc(-c3ccc([C@H]4CCCN4)cc3)c(C3CC3)n12] | (R)-3-cyclopropyl-N-(3-(4-fluoropiperidin-1-yl)propyl)-2-(4-(pyrrolidin-2-yl)phenyl)benzo[d]imidazo[2,1-b]thiazole-7-carboxamide |
| 469S | 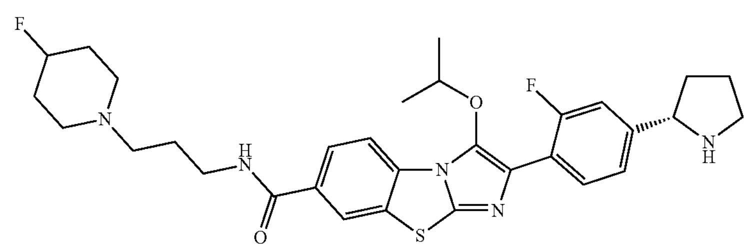 [SMILES: CC(C)Oc1c(-c2ccc([C@@H]3CCCN3)cc2F)nc2sc3cc(C(=O)NCCCN4CCC(F)CC4)ccc3n12] | (S)-2-(2-fluoro-4-(pyrrolidin-2-yl)phenyl)-N-(3-(4-fluoropiperidin-1-yl)propyl)-3-isopropoxybenzo[d]imidazo[2,1-b]thiazole-7-carboxamide |
| 469R | 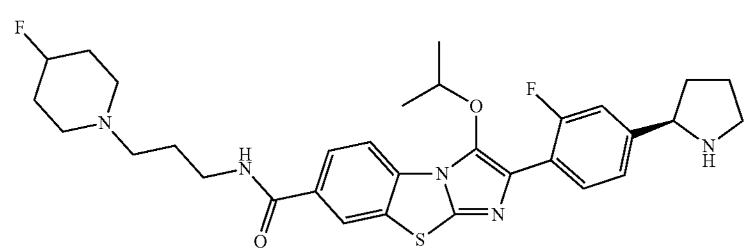 [SMILES: CC(C)Oc1c(-c2ccc([C@H]3CCCN3)cc2F)nc2sc3cc(C(=O)NCCCN4CCC(F)CC4)ccc3n12] | (R)-2-(2-fluoro-4-(pyrrolidin-2-yl)phenyl)-N-(3-(4-fluoropiperidin-1-yl)propyl)-3-isopropoxybenzo[d]imidazo[2,1-b]thiazole-7-carboxamide |

TABLE 1-continued

| Comp. No. | Structure | Compound Name |
|---|---|---|
| 470S | 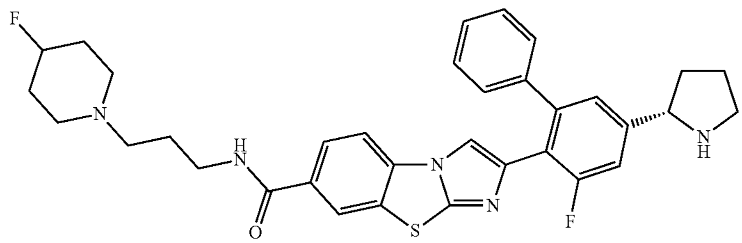 [SMILES: O=C(NCCCN1CCC(F)CC1)c1ccc2c(c1)sc1nc(-c3c(F)cc([C@@H]4CCCN4)cc3-c3ccccc3)cn12] | (S)-2-(3-fluoro-5-(pyrrolidin-2-yl)-[1,1'-biphenyl]-2-yl)-N-(3-(4-fluoropiperidin-1-yl)propyl)benzo[d]imidazo[2,1-b]thiazole-7-carboxamide |
| 470R | 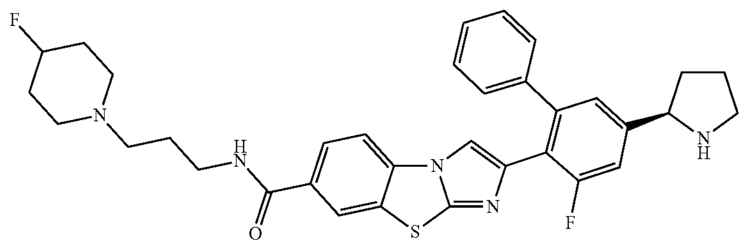 [SMILES: O=C(NCCCN1CCC(F)CC1)c1ccc2c(c1)sc1nc(-c3c(F)cc([C@H]4CCCN4)cc3-c3ccccc3)cn12] | (R)-2-(3-fluoro-5-(pyrrolidin-2-yl)-[1,1'-biphenyl]-2-yl)-N-(3-(4-fluoropiperidin-1-yl)propyl)benzo[d]imidazo[2,1-b]thiazole-7-carboxamide |
| 471S | 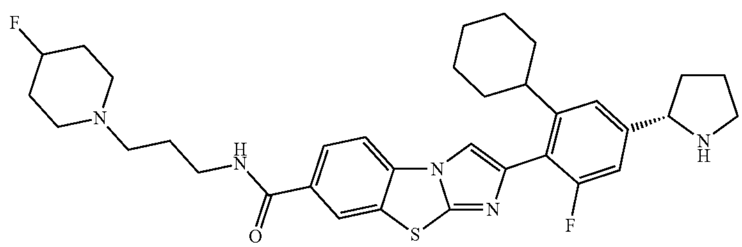 [SMILES: O=C(NCCCN1CCC(F)CC1)c1ccc2c(c1)sc1nc(-c3c(F)cc([C@@H]4CCCN4)cc3C3CCCCC3)cn12] | (S)-2-(2-cyclohexyl-6-fluoro-4-(pyrrolidin-2-yl)phenyl)-N-(3-(4-fluoropiperidin-1-yl)propyl)benzo[d]imidazo[2,1-b]thiazole-7-carboxamide |
| 471R | 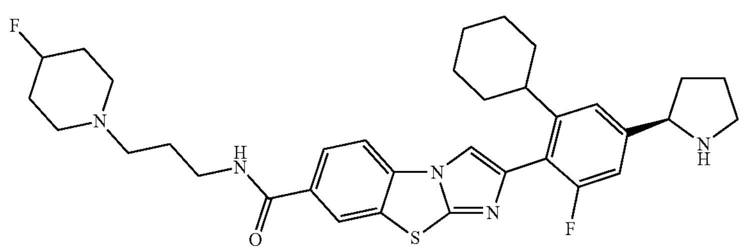 [SMILES: O=C(NCCCN1CCC(F)CC1)c1ccc2c(c1)sc1nc(-c3c(F)cc([C@H]4CCCN4)cc3C3CCCCC3)cn12] | (R)-2-(2-cyclohexyl-6-fluoro-4-(pyrrolidin-2-yl)phenyl)-N-(3-(4-fluoropiperidin-1-yl)propyl)benzo[d]imidazo[2,1-b]thiazole-7-carboxamide |
| 472S | 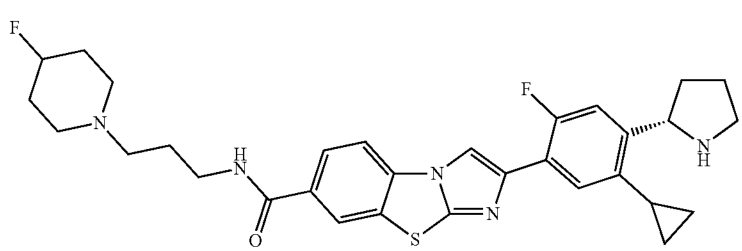 [SMILES: O=C(NCCCN1CCC(F)CC1)c1ccc2c(c1)sc1nc(-c3cc(C4CC4)c([C@@H]4CCCN4)cc3F)cn12] | (S)-2-(5-cyclopropyl-2-fluoro-4-(pyrrolidin-2-yl)phenyl)-N-(3-(4-fluoropiperidin-1-yl)propyl)benzo[d]imidazo[2,1-b]thiazole-7-carboxamide |
| 472R | 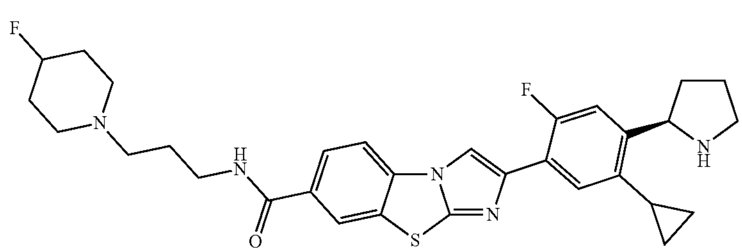 [SMILES: O=C(NCCCN1CCC(F)CC1)c1ccc2c(c1)sc1nc(-c3cc(C4CC4)c([C@H]4CCCN4)cc3F)cn12] | (R)-2-(5-cyclopropyl-2-fluoro-4-(pyrrolidin-2-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 473S | 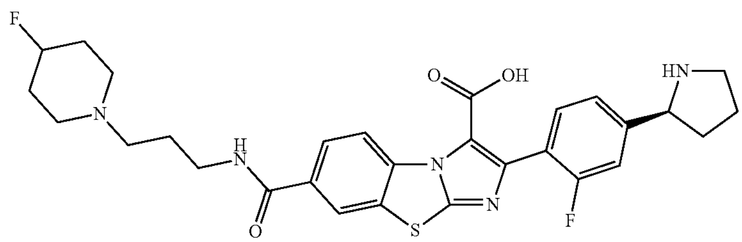 [SMILES: O=C(NCCCN1CCC(F)CC1)c1ccc2c(c1)sc1nc(-c3ccc([C@@H]4CCCN4)cc3F)c(C(=O)O)n12] | (S)-2-(2-fluoro-4-(pyrrolidin-2-yl)phenyl)-7-((3-(4-fluoropiperidin-1-yl)propyl)carbamoyl)benzo[d]imidazo[2,1-b]thiazole-3-carboxylic acid |
| 473R | 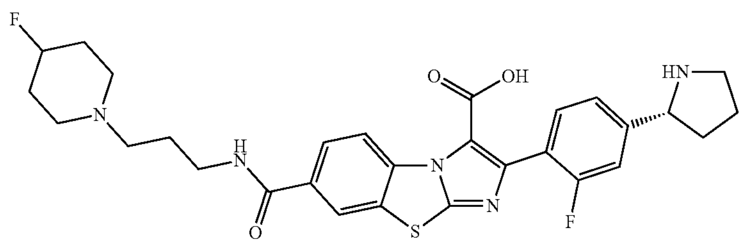 [SMILES: O=C(NCCCN1CCC(F)CC1)c1ccc2c(c1)sc1nc(-c3ccc([C@H]4CCCN4)cc3F)c(C(=O)O)n12] | (R)-2-(2-fluoro-4-(pyrrolidin-2-yl)phenyl)-7-((3-(4-fluoropiperidin-1-yl)propyl)carbamoyl)benzo[d]imidazo[2,1-b]thiazole-3-carboxylic acid |
| 474 | 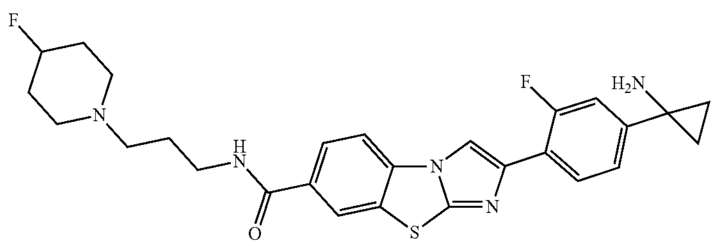 [SMILES: NC1(c2ccc(-c3cn4c(n3)sc3cc(C(=O)NCCCN5CCC(F)CC5)ccc34)c(F)c2)CC1] | 2-(4-(1-aminocyclopropyl)-2-fluorophenyl)-N-(3-(4-fluoropiperidin-1-yl)propyl)benzo[d]imidazo[2,1-b]thiazole-7-carboxamide |
| 475 | 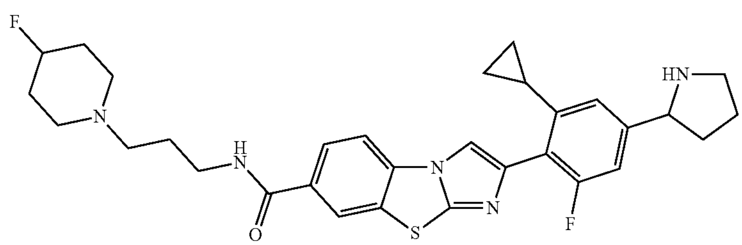 [SMILES: O=C(NCCCN1CCC(F)CC1)c1ccc2c(c1)sc1nc(-c3c(F)cc(C4CCCN4)cc3C3CC3)cn12] | 2-(2-cyclopropyl-6-fluoro-4-(pyrrolidin-2-yl)phenyl)-N-(3-(4-fluoropiperidin-1-yl)propyl)benzo[d]imidazo[2,1-b]thiazole-7-carboxamide |
| 476 | 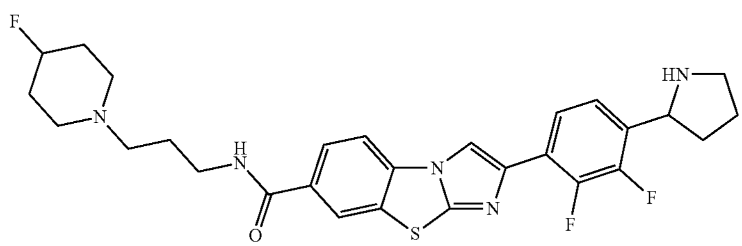 [SMILES: O=C(NCCCN1CCC(F)CC1)c1ccc2c(c1)sc1nc(-c3ccc(C4CCCN4)c(F)c3F)cn12] | 2-(2,3-difluoro-4-(pyrrolidin-2-yl)phenyl)-N-(3-(4-fluoropiperidin-1-yl)propyl)benzo[d]imidazo[2,1-b]thiazole-7-carboxamide |
| 477 | 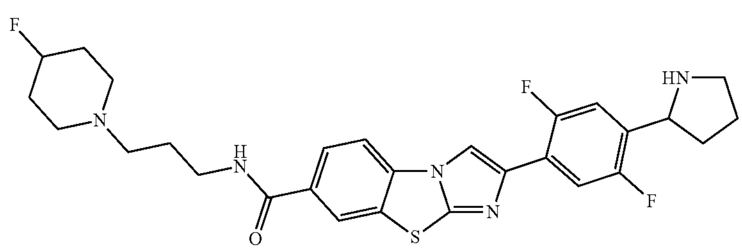 [SMILES: O=C(NCCCN1CCC(F)CC1)c1ccc2c(c1)sc1nc(-c3cc(F)c(C4CCCN4)cc3F)cn12] | 2-(2,5-difluoro-4-(pyrrolidin-2-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 478 | 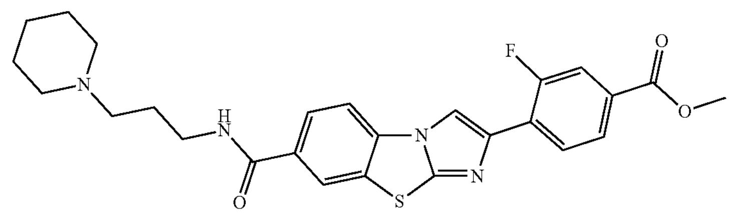 [SMILES: COC(=O)c1ccc(-c2cn3c(n2)sc2cc(C(=O)NCCCN4CCCCC4)ccc23)c(F)c1] | methyl 3-fluoro-4-(7-((3-(4-fluoropiperidin-1-yl)propyl)carbamoyl)benzo[d]imidazo[2,1-b]thiazol-2-yl)benzoate |
| 479 | 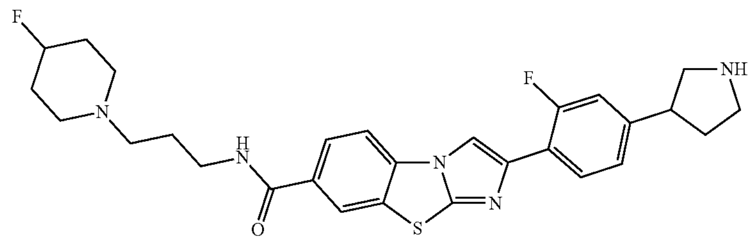 [SMILES: O=C(NCCCN1CCC(F)CC1)c1ccc2c(c1)sc1nc(-c3ccc(C4CCNC4)cc3F)cn12] | 2-(2-fluoro-4-(pyrrolidin-3-yl)phenyl)-N-(3-(4-fluoropiperidin-1-yl)propyl)benzo[d]imidazo[2,1-b]thiazole-7-carboxamide |
| 480 | 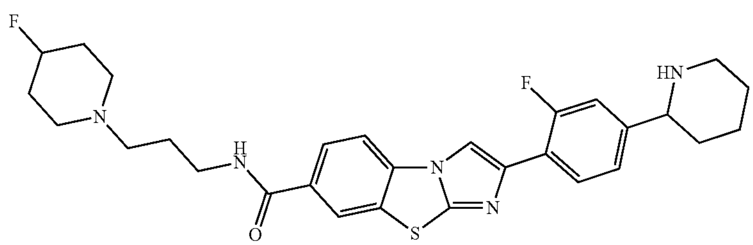 [SMILES: O=C(NCCCN1CCC(F)CC1)c1ccc2c(c1)sc1nc(-c3ccc(C4CCCCN4)cc3F)cn12] | 2-(2-fluoro-4-piperidin-2-yl)phenyl)-N-(3-(4-fluoropiperidin-1-yl)propyl)benzo[d]imidazo[2,1-b]thiazole-7-carboxamide |
| 481 | 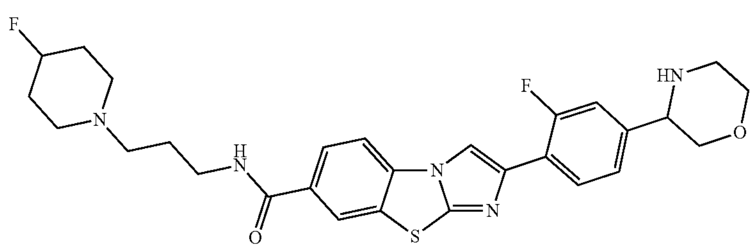 [SMILES: O=C(NCCCN1CCC(F)CC1)c1ccc2c(c1)sc1nc(-c3ccc(C4COCCN4)cc3F)cn12] | 2-(2-fluoro-4-(morpholin-3-yl)phenyl)-N-(3-(4-fluoropiperidin-1-yl)propyl)benzo[d]imidazo[2,1-b]thiazole-7-carboxamide |
| 482 | 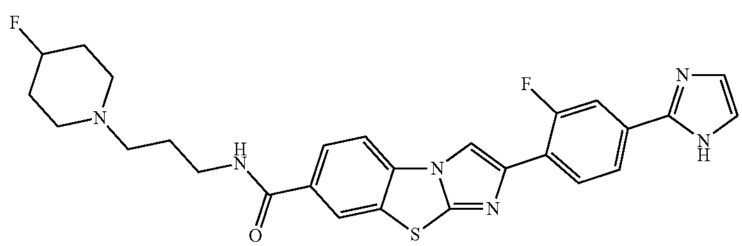 [SMILES: O=C(NCCCN1CCC(F)CC1)c1ccc2c(c1)sc1nc(-c3ccc(-c4ncc[nH]4)cc3F)cn12] | 2-(2-fluoro-4-(1H-imidazol-2-yl)phenyl)-N-(3-(4-fluoropiperidin-1-yl)propyl)benzo[d]imidazo[2,1-b]thiazole-7-carboxamide |
| 483 | 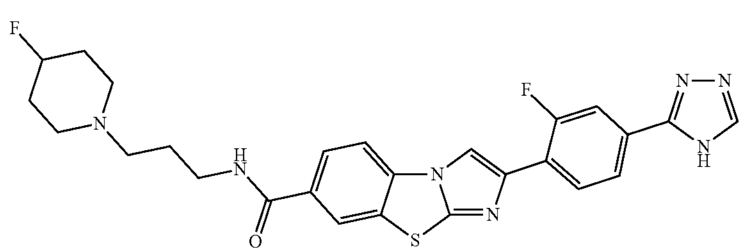 [SMILES: O=C(NCCCN1CCC(F)CC1)c1ccc2c(c1)sc1nc(-c3ccc(-c4nnc[nH]4)cc3F)cn12] | 2-(2-fluoro-4-(4H-1,2,4-triazol-3-yl)phenyl)-N-(3-(4-fluoropiperidin-1-yl)propyl)benzo[d]imidazo[2,1-b]thiazole-7-carboxamide |

TABLE 1-continued

| Comp. No. | Compound Name |
|---|---|
| 484 | 2-(3-fluoro-4-(pyrrolidin-2-yl)phenyl)-N-(3-(4-fluoropiperidin-1-yl)propyl)benzo[d]imidazo[2,1-b]thiazole-7-carboxamide |
| 485 | 2-(3-chloro-5-fluoro-4-(pyrrolidin-2-yl)phenyl)-N-(3-(4-fluoropiperidin-1-yl)propyl)benzo[d]imidazo[2,1-b]thiazole-7-carboxamide |
| 486 | 2-(2-fluoro-4-(6-oxopiperidin-2-yl)phenyl)-N-(3-(4-fluoropiperidin-1-yl)propyl)benzo[d]imidazo[2,1-b]thiazole-7-carboxamide |
| 487 | 2-(2-fluoro-4-(1H-pyrazol-5-yl)phenyl)-N-(3-(4-fluoropiperidin-1-yl)propyl)benzo[d]imidazo[2,1-b]thiazole-7-carboxamide |
| 488 | 2-(2-fluoro-4-(2H-1,2,3-triazol-4-yl)phenyl)-N-(3-(4-fluoropiperidin-1-yl)propyl)benzo[d]imidazo[2,1-b]thiazole-7-carboxamide |
| 489 | 2-(2-fluoro-5-methoxy-4-(pyrrolidin-2-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 490 | 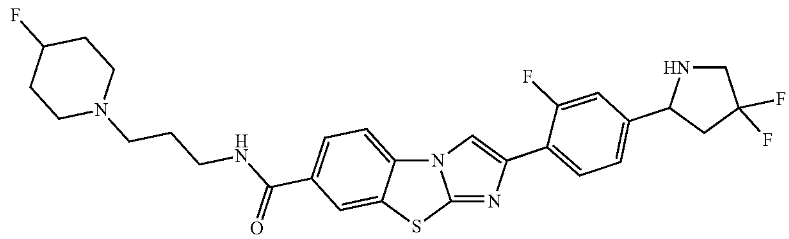 [SMILES: O=C(NCCCN1CCC(F)CC1)c1ccc2c(c1)sc1nc(-c3ccc(C4CC(F)(F)CN4)cc3F)cn12] | 2-(4-(4,4-difluoropyrrolidin-2-yl)-2-fluorophenyl)-N-(3-(4-fluoropiperidin-1-yl)propyl)benzo[d]imidazo[2,1-b]thiazole-7-carboxamide |
| 491R | 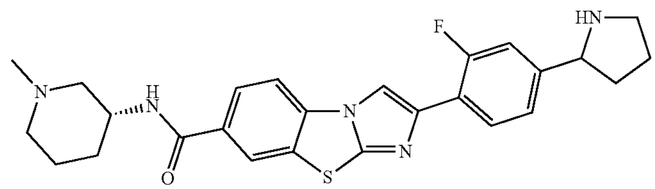 [SMILES: CN1CCC[C@@H](NC(=O)c2ccc3c(c2)sc2nc(-c4ccc(C5CCCN5)cc4F)cn23)C1] | 2-(2-fluoro-4-(pyrrolidin-2-yl)phenyl)-N-((R)-1-methylpiperidin-3-yl)benzo[d]imidazo[2,1-b]thiazole-7-carboxamide |
| 491S | 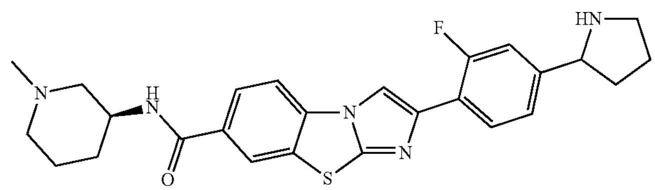 [SMILES: CN1CCC[C@H](NC(=O)c2ccc3c(c2)sc2nc(-c4ccc(C5CCCN5)cc4F)cn23)C1] | 2-(2-fluoro-4-(pyrrolidin-2-yl)phenyl)-N-((S)-1-methylpiperidin-3-yl)benzo[d]imidazo[2,1-b]thiazole-7-carboxamide |
| 492 | 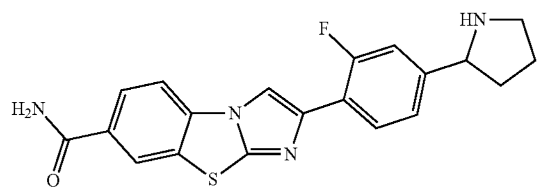 [SMILES: NC(=O)c1ccc2c(c1)sc1nc(-c3ccc(C4CCCN4)cc3F)cn12] | 2-(2-fluoro-4-(pyrrolidin-2-yl)phenyl)benzo[d]imidazo[2,1-b]thiazole-7-carboxamide |
| 493 | 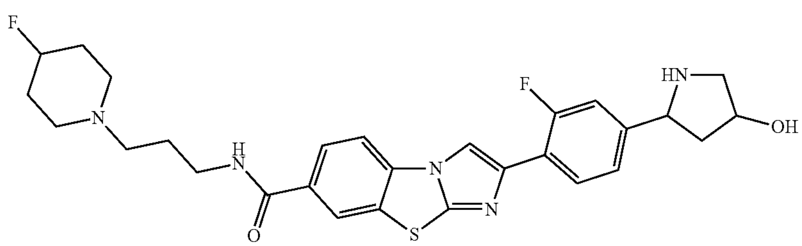 [SMILES: O=C(NCCCN1CCC(F)CC1)c1ccc2c(c1)sc1nc(-c3ccc(C4CC(O)CN4)cc3F)cn12] | 2-(2-fluoro-4-(4-hydroxypyrrolidin-2-yl)phenyl)-N-(3-(4-fluoropiperidin-1-yl)propyl)benzo[d]imidazo[2,1-b]thiazole-7-carboxamide |
| 494 | 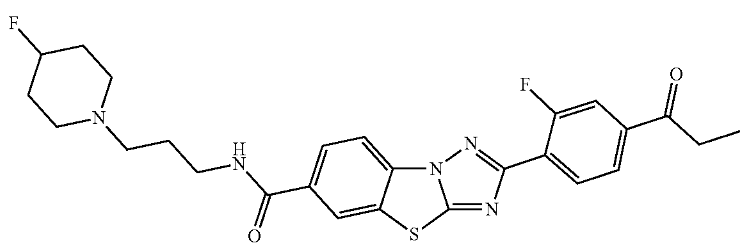 [SMILES: CCC(=O)c1ccc(-c2nc3sc4cc(C(=O)NCCCN5CCC(F)CC5)ccc4n3n2)c(F)c1] | 2-(2-fluoro-4-propionylphenyl)-N-(3-(4-fluoropiperidin-1-yl)propyl)benzo[d]imidazo[2,1-b]thiazole-7-carboxamide |
| 495 | 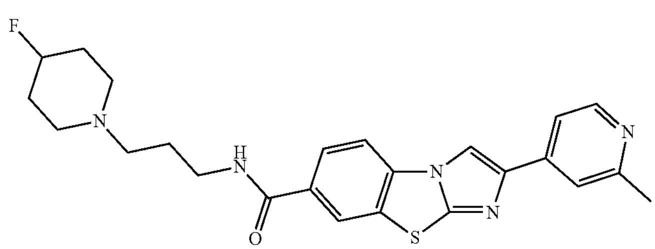 [SMILES: Cc1cc(-c2cn3c(n2)sc2cc(C(=O)NCCCN4CCC(F)CC4)ccc23)ccn1] | N-(3-(4-fluoropiperidin-1-yl)propyl)-2-(2-methylpyridin-4-yl)benzo[d]imidazo[2,1-b]thiazole-7-carboxamide |

TABLE 1-continued

| Comp. No. | Structure | Compound Name |
|---|---|---|
| 496 | 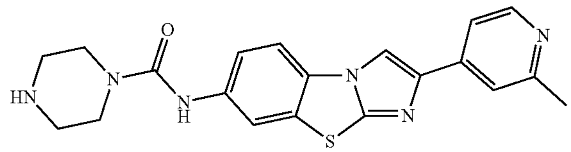 [SMILES: Cc1cc(-c2cn3c(n2)sc2cc(NC(=O)N4CCNCC4)ccc23)ccn1] | 2-(2-methylpyridin-4-yl)-N-(piperidin-4-yl)benzo[d]imidazo[2,1-b]thiazole-7-carboxamide |
| 497 | 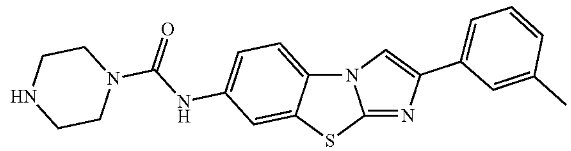 [SMILES: Cc1cccc(-c2cn3c(n2)sc2cc(NC(=O)N4CCNCC4)ccc23)c1] | N-(piperidin-4-yl)-2-(m-tolyl)benzo[4,5]thiazolo[3,2-b][1,2,4]triazole-6-carboxamide |
| 498 | 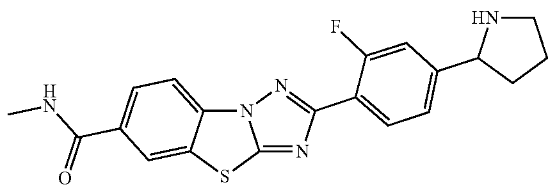 [SMILES: CNC(=O)c1ccc2c(c1)sc1nc(-c3ccc(C4CCCN4)cc3F)nn12] | 2-(2-fluoro-4-(pyrrolidin-2-yl)phenyl)-N-methylbenzo[d]imidazo[2,1-b]thiazole-7-carboxamide |
| 499 | 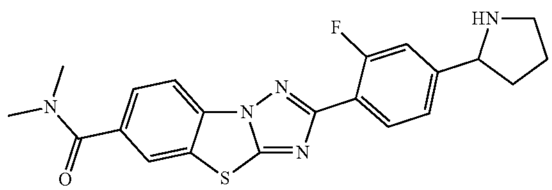 [SMILES: CN(C)C(=O)c1ccc2c(c1)sc1nc(-c3ccc(C4CCCN4)cc3F)nn12] | 2-(2-fluoro-4-(pyrrolidin-2-yl)phenyl)-N,N-dimethylbenzo[d]imidazo[2,1-b]thiazole-7-carboxamide |
| 500 | 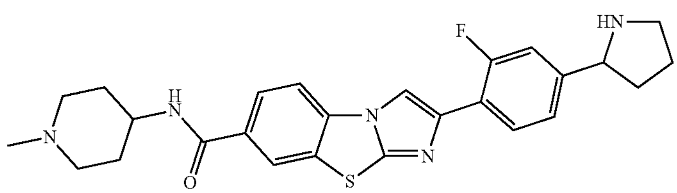 [SMILES: CN1CCC(NC(=O)c2ccc3c(c2)sc2nc(-c4ccc(C5CCCN5)cc4F)cn23)CC1] | 2-(2-fluoro-4-(pyrrolidin-2-yl)phenyl)-N-(1-methylpiperidin-4-yl)benzo[d]imidazo[2,1-b]thiazole-7-carboxamide |
| 501 | 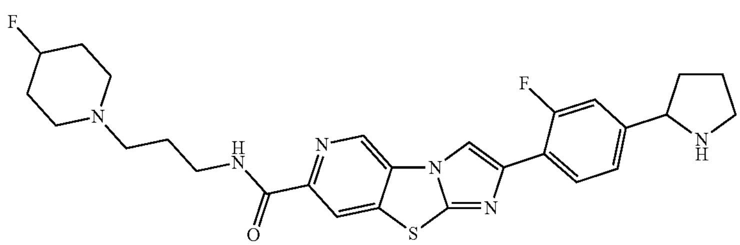 | 2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide |
| 502 | 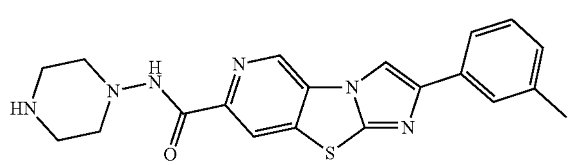 [SMILES: Cc1cccc(-c2cn3c(n2)sc2cc(C(=O)NN4CCNCC4)ncc23)c1] | N-(piperidin-4-yl)-2-(m-tolyl)imidazo[2',1':2,3]thiazolo[4,5-c]pyridine-7-carboxamide |
| 503S | 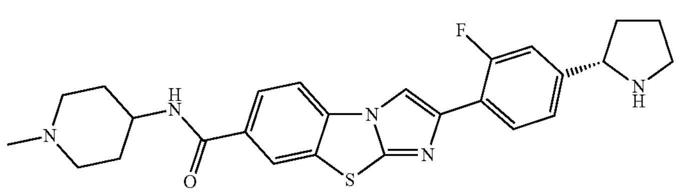 [SMILES: CN1CCC(NC(=O)c2ccc3c(c2)sc2nc(-c4ccc([C@@H]5CCCN5)cc4F)cn23)CC1] | (S)-2-(2-fluoro-4-(pyrrolidin-2-yl)phenyl)-N-(1-methylpiperidin-4-yl)benzo[d]imidazo[2,1-b]thiazole-7-carboxamide |

TABLE 1-continued

| Comp. No. | Structure | Compound Name |
|---|---|---|
| 503R | 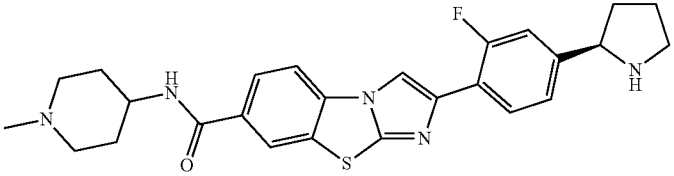 [SMILES: CN1CCC(NC(=O)c2ccc3c(c2)sc2nc(-c4ccc([C@H]5CCCN5)cc4F)cn23)CC1] | (R)-2-(2-fluoro-4-(pyrrolidin-2-yl)phenyl)-N-(1-methylpiperidin-4-yl)benzo[d]imidazo[2,1-b]thiazole-7-carboxamide |
| 504 | 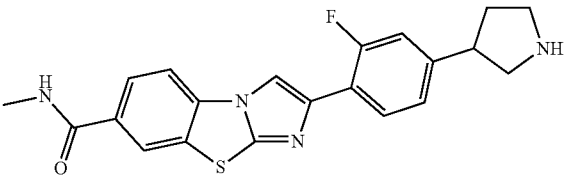 [SMILES: CNC(=O)c1ccc2c(c1)sc1nc(-c3ccc(C4CCNC4)cc3F)cn12] | 2-(2-fluoro-4-(pyrrolidin-3-yl)phenyl)-N-methylbenzo[d]imidazo[2,1-b]thiazole-7-carboxamide |
| 505 | 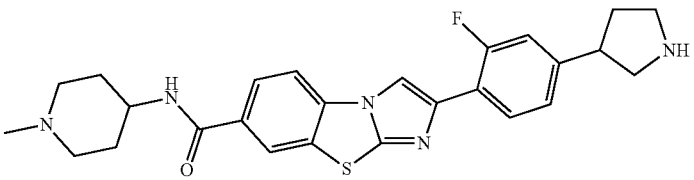 [SMILES: CN1CCC(NC(=O)c2ccc3c(c2)sc2nc(-c4ccc(C5CCNC5)cc4F)cn23)CC1] | 2-(2-fluoro-4-(pyrrolidin-3-yl)phenyl)-N-(1-methylpiperidin-4-yl)benzo[d]imidazo[2,1-b]thiazole-7-carboxamide |
| 506 | 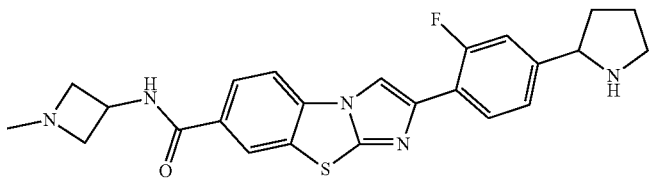 [SMILES: CN1CC(NC(=O)c2ccc3c(c2)sc2nc(-c4ccc(C5CCCN5)cc4F)cn23)C1] | 2-(2-fluoro-4-(pyrrolidin-2-yl)phenyl)-N-(1-methylazetidin-3-yl)benzo[d]imidazo[2,1-b]thiazole-7-carboxamide |
| 507 | 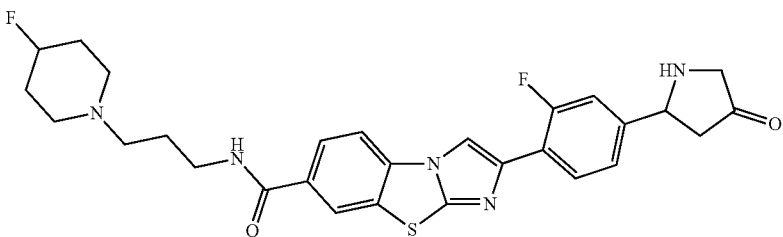 [SMILES: O=C1CNC(c2ccc(-c3cn4c(n3)sc3cc(C(=O)NCCCN5CCC(F)CC5)ccc34)c(F)c2)C1] | 2-(2-fluoro-4-(4-oxopyrrolidin-2-yl)phenyl)-N-(3-(4-fluoropiperidin-1-yl)propyl)benzo[d]imidazo[2,1-b]thiazole-7-carboxamide |
| 508 | 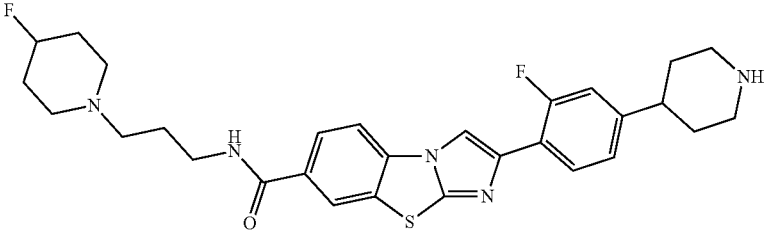 [SMILES: O=C(NCCCN1CCC(F)CC1)c1ccc2c(c1)sc1nc(-c3ccc(C4CCNCC4)cc3F)cn12] | 2-(2-fluoro-4-(piperidin-4-yl)phenyl)-N-(3-(4-fluoropiperidin-1-yl)propyl)benzo[d]imidazo[2,1-b]thiazole-7-carboxamide |
| 509R | 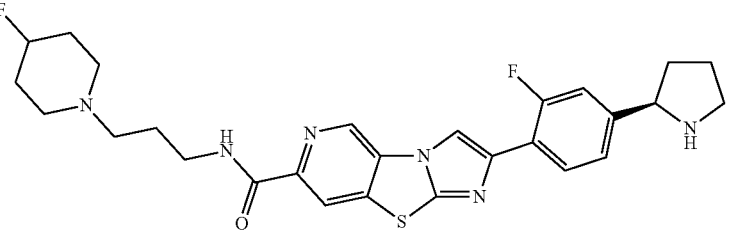 | (R)-2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide |

TABLE 1-continued

| Comp. No. | Structure | Compound Name |
|---|---|---|
| 510 | 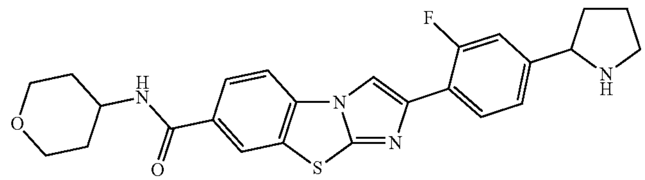 [SMILES: O=C(NC1CCOCC1)c1ccc2c(c1)sc1nc(-c3ccc(C4CCCN4)cc3F)cn12] | 2-(2-fluoro-4-(pyrrolidin-2-yl)phenyl)-N-(tetrahydro-2H-pyran-4-yl)benzo[d]imidazo[2,1-b]thiazole-7-carboxamide |
| 511 | 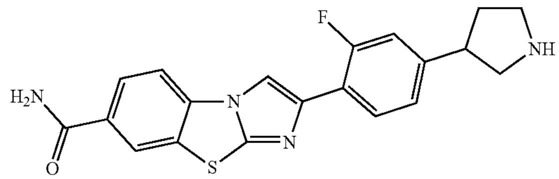 [SMILES: NC(=O)c1ccc2c(c1)sc1nc(-c3ccc(C4CCNC4)cc3F)cn12] | 2-(2-fluoro-4-(pyrrolidin-3-yl)phenyl)benzo[d]imidazo[2,1-b]thiazole-7-carboxamide |
| 512 | 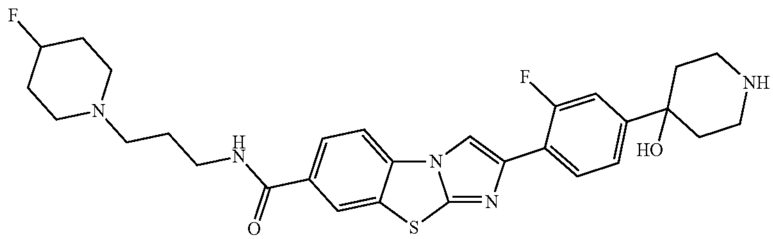 [SMILES: O=C(NCCCN1CCC(F)CC1)c1ccc2c(c1)sc1nc(-c3ccc(C4(O)CCNCC4)cc3F)cn12] | 2-(2-fluoro-4-4-hydroxypiperidin-4-yl)phenyl)-N-(3-(4-fluoropiperidin-1-yl)propyl)benzo[d]imidazo[2,1-b]thiazole-7-carboxamide |
| 513 | 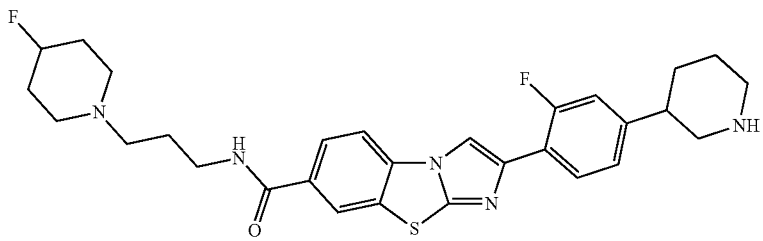 [SMILES: O=C(NCCCN1CCC(F)CC1)c1ccc2c(c1)sc1nc(-c3ccc(C4CCCNC4)cc3F)cn12] | 2-(2-fluoro-4-(piperidin-3-yl)phenyl)-N-(3-(4-fluoropiperidin-1-yl)propyl)benzo[d]imidazo[2,1-b]thiazole-7-carboxamide |
| 514 | 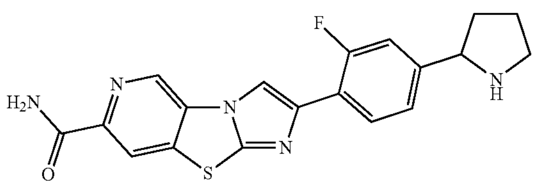 [SMILES: NC(=O)c1cc2sc3nc(-c4ccc(C5CCCN5)cc4F)cn3c2cn1] | 2-(2-fluoro-4-(pyrrolidin-2-yl)phenyl)imidazo[2',1':2,3]thiazolo[4,5-c]pyridine-7-carboxamide |
| 515 | 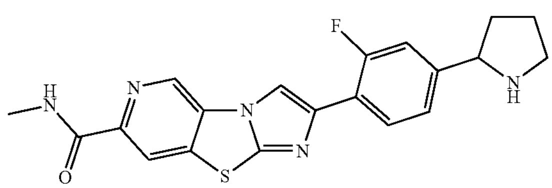 | 2-(2-fluoro-4-(pyrrolidin-2-yl)phenyl)-N-methylimidazo[2',1':2,3]thiazolo[4,5-c]pyridine-7-carboxamide |
| 516 | 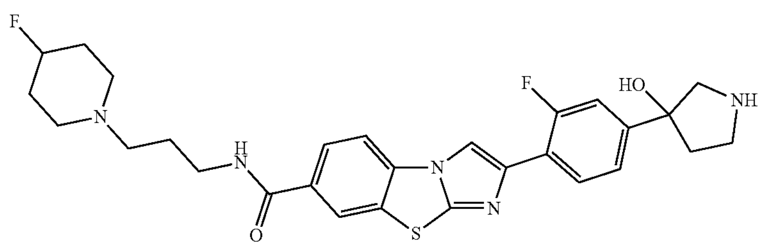 [SMILES: O=C(NCCCN1CCC(F)CC1)c1ccc2c(c1)sc1nc(-c3ccc(C4(O)CCNC4)cc3F)cn12] | 2-(2-fluoro-4-(3-hydroxypyrrolidin-3-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 517 | 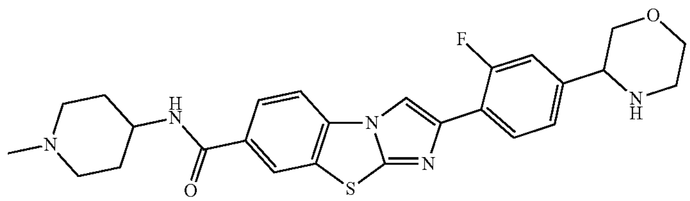 [SMILES: CN1CCC(NC(=O)c2ccc3c(c2)sc2nc(-c4ccc(C5COCCN5)cc4F)cn23)CC1] | 2-(2-fluoro-4-(morpholin-3-yl)phenyl)-N-(1-methylpiperidin-4-yl)benzo[d]imidazo[2,1-b]thiazole-7-carboxamide |
| 518 | 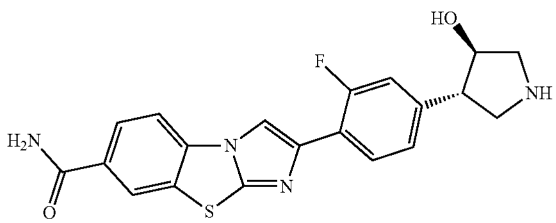 [SMILES: NC(=O)c1ccc2c(c1)sc1nc(-c3ccc([C@H]4CNC[C@@H]4O)cc3F)cn12] | 2-(2-fluoro-4-((3S,4R)-4-hydroxypyrrolidin-3-yl)phenyl)-N-methylbenzo[d]imidazo[2,1-b]thiazole-7-carboxamide |
| 519 | 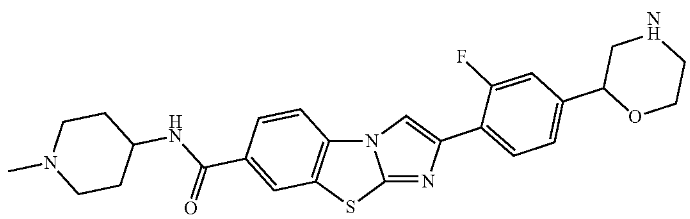 [SMILES: CN1CCC(NC(=O)c2ccc3c(c2)sc2nc(-c4ccc(C5CNCCO5)cc4F)cn23)CC1] | 2-(2-fluoro-4-(morpholin-2-yl)phenyl)-N-(1-methylpiperidin-4-yl)benzo[d]imidazo[2,1-b]thiazole-7-carboxamide |
| 520 | 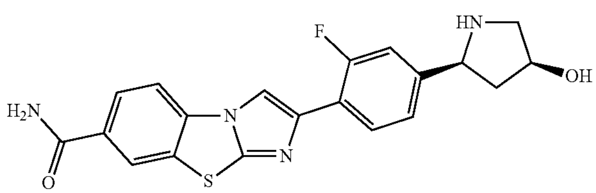 [SMILES: NC(=O)c1ccc2c(c1)sc1nc(-c3ccc([C@@H]4C[C@H](O)CN4)cc3F)cn12] | 2-(2-fluoro-4-((2S,4S)-4-hydroxypyrrolidin-2-yl)phenyl)benzo[d]imidazo[2,1-b]thiazole-7-carboxamide |
| 521 | 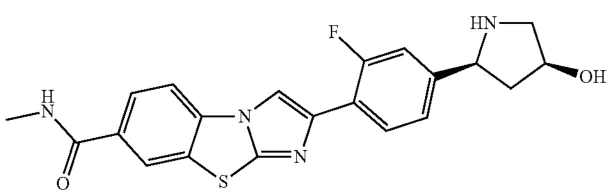 [SMILES: CNC(=O)c1ccc2c(c1)sc1nc(-c3ccc([C@@H]4C[C@H](O)CN4)cc3F)cn12] | 2-(2-fluoro-4-((2S,4S)-4-hydroxypyrrolidin-2-yl)phenyl)-N-methylbenzo[d]imidazo[2,1-b]thiazole-7-carboxamide |
| 522S | 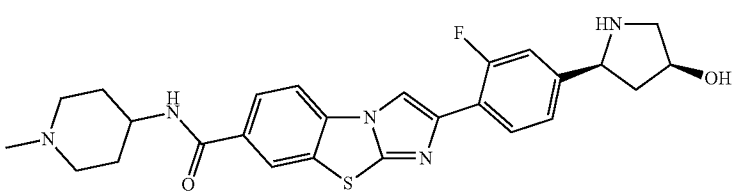 [SMILES: CN1CCC(NC(=O)c2ccc3c(c2)sc2nc(-c4ccc([C@@H]5C[C@H](O)CN5)cc4F)cn23)CC1] | 2-(2-fluoro-4-((2S,4S)-4-hydroxypyrrolidin-2-yl)phenyl)-N-(1-methylpiperidin-4-yl)benzo[d]imidazo[2,1-b]thiazole-7-carboxamide |
| 522R | 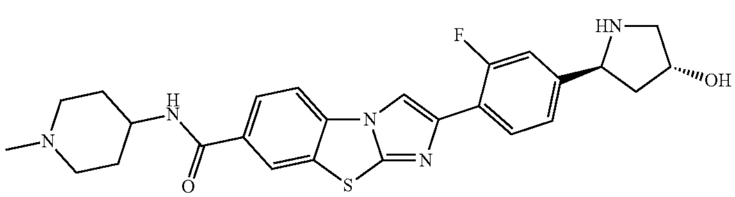 [SMILES: CN1CCC(NC(=O)c2ccc3c(c2)sc2nc(-c4ccc([C@@H]5C[C@@H](O)CN5)cc4F)cn23)CC1] | 2-(2-fluoro-4-((2S,4R)-4-hydroxypyrrolidin-2-yl)phenyl)-N-(1-methylpiperidin-4-yl)benzo[d]imidazo[2,1-b]thiazole-7-carboxamide |

TABLE 1-continued

| Comp. No. | Structure | Compound Name |
|---|---|---|
| 523 | 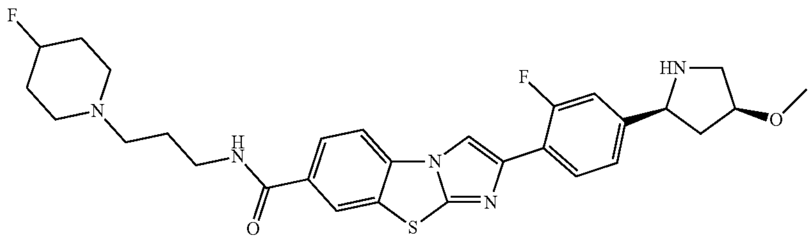 [SMILES: CO[C@@H]1CN[C@H](c2ccc(-c3cn4c(n3)sc3cc(C(=O)NCCCN5CCC(F)CC5)ccc34)c(F)c2)C1] | 2-(2-fluoro-4-((2S,4S)-4-methoxypyrrolidin-2-yl)phenyl)-N-(3-(4-fluoropiperidin-1-yl)propyl)benzo[d]imidazo[2,1-b]thiazole-7-carboxamide |
| 524S | 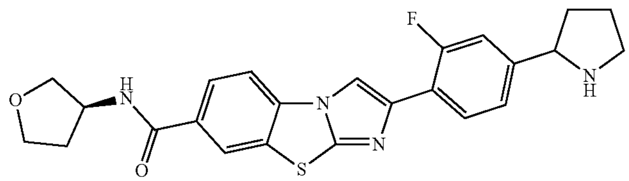 [SMILES: O=C(N[C@H]1CCOC1)c1ccc2c(c1)sc1nc(-c3ccc(C4CCCN4)cc3F)cn12] | 2-(2-fluoro-4-(pyrrolidin-2-yl)phenyl)-N-((S)-tetrahydrofuran-3-yl)benzo[d]imidazo[2,1-b]thiazole-7-carboxamide |
| 524R | 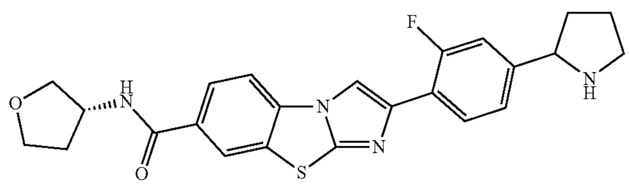 [SMILES: O=C(N[C@@H]1CCOC1)c1ccc2c(c1)sc1nc(-c3ccc(C4CCCN4)cc3F)cn12] | 2-(2-fluoro-4-(pyrrolidin-2-yl)phenyl)-N-((R)-tetrahydrofuran-3-yl)benzo[d]imidazo[2,1-b]thiazole-7-carboxamide |
| 525 | 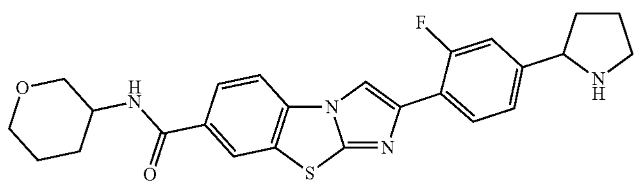 [SMILES: O=C(NC1CCCOC1)c1ccc2c(c1)sc1nc(-c3ccc(C4CCCN4)cc3F)cn12] | 2-(2-fluoro-4-(pyrrolidin-2-yl)phenyl)-N-(tetrahydro-2H-pyran-3-yl)benzo[d]imidazo[2,1-b]thiazole-7-carboxamide |
| 526 | 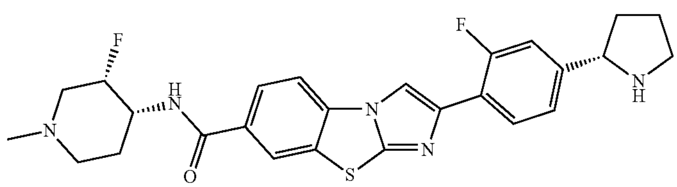 [SMILES: CN1CC[C@@H](NC(=O)c2ccc3c(c2)sc2nc(-c4ccc([C@@H]5CCCN5)cc4F)cn23)[C@@H](F)C1] | N-((3S,4R)-3-fluoro-1-methylpiperidin-4-yl)-2-(2-fluoro-4-(pyrrolidin-2-yl)phenyl)benzo[d]imidazo[2,1-b]thiazole-7-carboxamide |
| 527 | 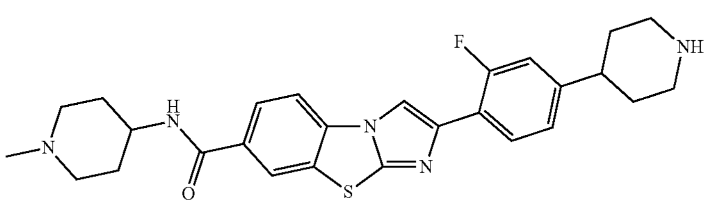 [SMILES: CN1CCC(NC(=O)c2ccc3c(c2)sc2nc(-c4ccc(C5CCNCC5)cc4F)cn23)CC1] | 2-(2-fluoro-4-(piperidin-4-yl)phenyl)-N-(1-methylpiperidin-4-yl)benzo[d]imidazo[2,1-b]thiazole-7-carboxamide |
| 528 | 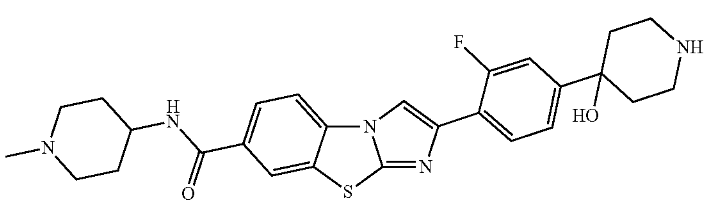 [SMILES: CN1CCC(NC(=O)c2ccc3c(c2)sc2nc(-c4ccc(C5(O)CCNCC5)cc4F)cn23)CC1] | 2-(2-fluoro-4-(4-hydroxypiperidin-4-yl)phenyl)-N-(1-methylpiperidin-4-yl)benzo[d]imidazo[2,1-b]thiazole-7-carboxamide |

TABLE 1-continued

| Comp. No. | Structure | Compound Name |
|---|---|---|
| 529 | 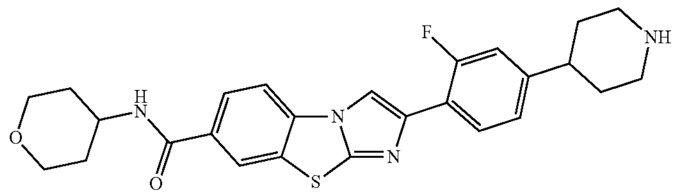 [SMILES: O=C(NC1CCOCC1)c1ccc2c(c1)sc1nc(-c3ccc(C4CCNCC4)cc3F)cn12] | 2-(2-fluoro-4-(piperidin-4-yl)phenyl)-N-(tetrahydro-2H-pyran-4-yl)benzo[d]imidazo[2,1-b]thiazole-7-carboxamide |
| 530 | 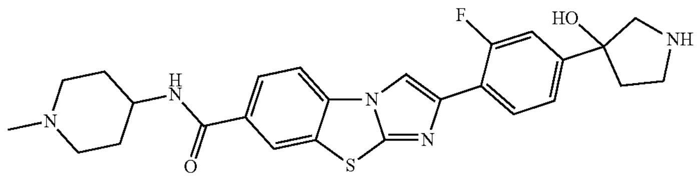 [SMILES: CN1CCC(NC(=O)c2ccc3c(c2)sc2nc(-c4ccc(C5(O)CCNC5)cc4F)cn23)CC1] | 2-(2-fluoro-4-(3-hydroxypyrrolidin-3-yl)phenyl)-N-(1-methylpiperidin-4-yl)benzo[d]imidazo[2,1-b]thiazole-7-carboxamide |
| 531 | 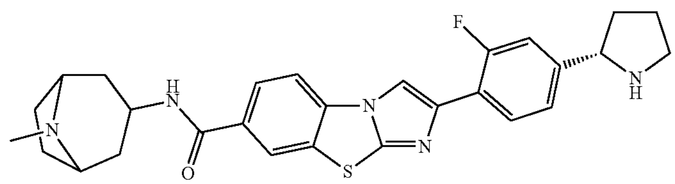 [SMILES: CN1C2CCC1CC(NC(=O)c1ccc3c(c1)sc1nc(-c4ccc([C@@H]5CCCN5)cc4F)cn13)C2] | 2-(2-fluoro-4-(pyrrolidin-2-yl)phenyl)-N-(8-methyl-8-azabicyclo[3.2.1]octan-3-yl)benzo[d]imidazo[2,1-b]thiazole-7-carboxamide |
| 532 | 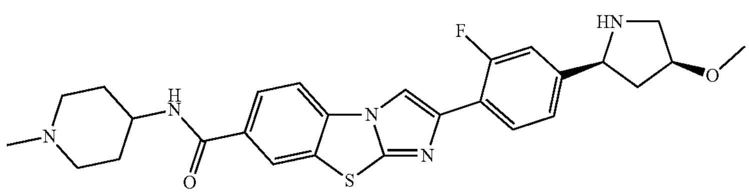 | 2-(2-fluoro-4-((2s,4S)-4-methoxypyrrolidin-2-yl)phenyl)-N-(1-methylpiperidin-4-yl)benzo[d]imidazo[2,1-b]thiazole-7-carboxamide |
| 533 | 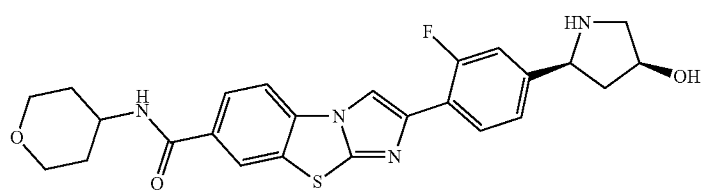 [SMILES: O=C(NC1CCOCC1)c1ccc2c(c1)sc1nc(-c3ccc([C@@H]4C[C@H](O)CN4)cc3F)cn12] | 2-(2-fluoro-4-((2S,4S)-4-hydroxypyrrolidin-2-yl)phenyl)-N-(tetrahydro-2H-pyran-4-yl)benzo[d]imidazo[2,1-b]thiazole-7-carboxamide |
| 534 | 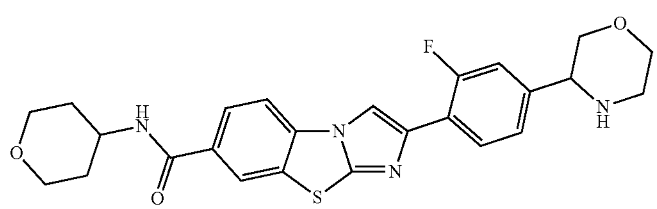 [SMILES: O=C(NC1CCOCC1)c1ccc2c(c1)sc1nc(-c3ccc(C4COCCN4)cc3F)cn12] | 2-(2-fluoro-4-(morpholin-3-yl)phenyl)-N-(tetrahydro-2H-pyran-4-yl)benzo[d]imidazo[2,1-b]thiazole-7-carboxamide |
| 535 | 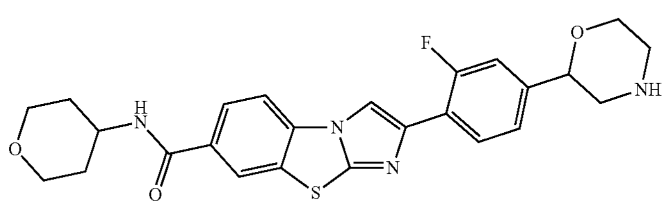 [SMILES: O=C(NC1CCOCC1)c1ccc2c(c1)sc1nc(-c3ccc(C4CNCCO4)cc3F)cn12] | 2-(2-fluoro-4-(morpholin-2-yl)phenyl)-N-(tetrahydro-2H-pyran-4-yl)benzo[d]imidazo[2,1-b]thiazole-7-carboxamide |
| 536 | 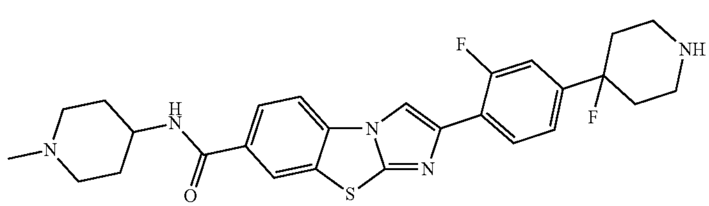 [SMILES: CN1CCC(NC(=O)c2ccc3c(c2)sc2nc(-c4ccc(C5(F)CCNCC5)cc4F)cn23)CC1] | 2-(2-fluoro-4-(4-fluoropiperidin-4-yl)phenyl)-N-(1-methylpiperidin-4-yl)benzo[d]imidazo[2,1-b]thiazole-7-carboxamide |

TABLE 1-continued

| Comp. No. | Structure | Compound Name |
|---|---|---|
| 537 | 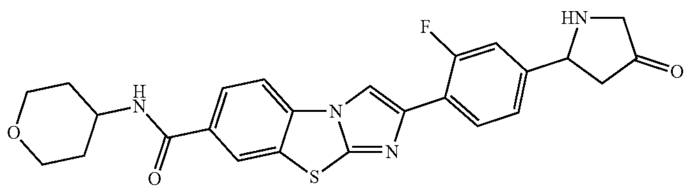 [SMILES: O=C1CNC(c2ccc(-c3cn4c(n3)sc3cc(C(=O)NC5CCOCC5)ccc34)c(F)c2)C1] | 2-(2-fluoro-4-(4-oxopyrrolidin-2-yl)phenyl)-N-(tetrahydro-2H-pyran-4-yl)benzo[d]imidazo[2,1-b]thiazole-7-carboxamide |
| 538 | 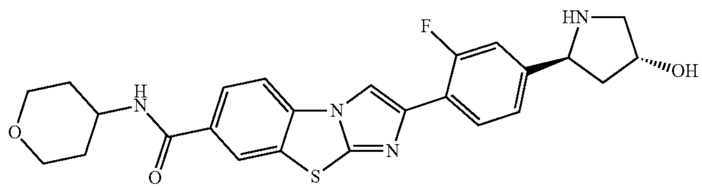 [SMILES: O=C(NC1CCOCC1)c1ccc2c(c1)sc1nc(-c3ccc([C@@H]4C[C@@H](O)CN4)cc3F)cn12] | 2-(2-fluoro-4-((2S,4R)-4-hydroxypyrrolidin-2-yl)phenyl)-N-(tetrahydro-2H-pyran-4-yl)benzo[d]imidazo[2,1-b]thiazole-7-carboxamide |
| 539 | 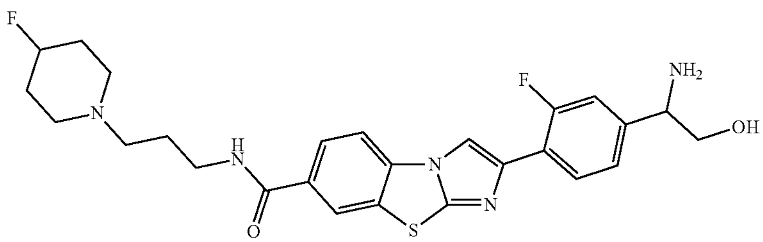 [SMILES: NC(CO)c1ccc(-c2cn3c(n2)sc2cc(C(=O)NCCCN4CCC(F)CC4)ccc23)c(F)c1] | 2-(4-(1-amino-2-hydroxyethyl)-2-fluorophenyl)-N-(3-(4-fluoropiperidin-1-yl)propyl)benzo[d]imidazo[2,1-b]thiazole-7-carboxamide |
| 540 | 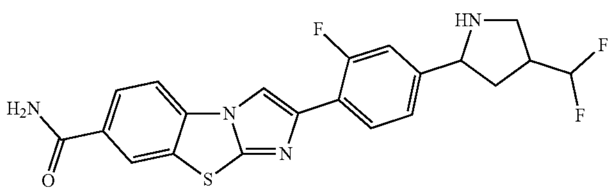 [SMILES: NC(=O)c1ccc2c(c1)sc1nc(-c3ccc(C4CC(C(F)F)CN4)cc3F)cn12] | 2-(4-(4-(difluoromethyl)pyrrolidin-2-yl)-2-fluorophenyl)benzo[d]imidazo[2,1-b]thiazole-7-carboxamide |
| 541 | 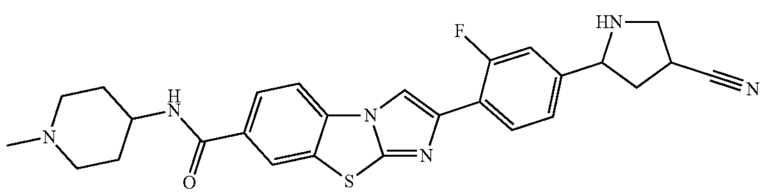 [SMILES: CN1CCC(NC(=O)c2ccc3c(c2)sc2nc(-c4ccc(C5CC(C#N)CN5)cc4F)cn23)CC1] | 2-(4-(4-cyanopyrrolidin-2-yl)-2-fluorophenyl)-N-(1-methylpiperidin-4-yl)benzo[d]imidazo[2,1-b]thiazole-7-carboxamide |
| 542 | 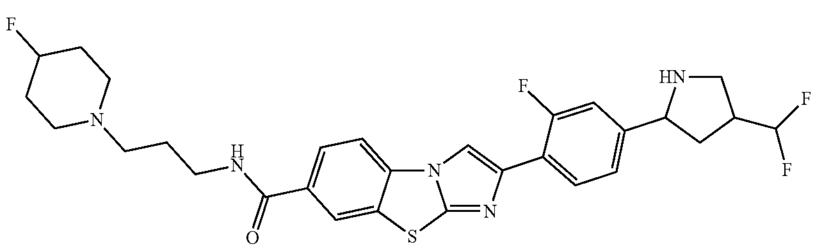 [SMILES: O=C(NCCCN1CCC(F)CC1)c1ccc2c(c1)sc1nc(-c3ccc(C4CC(C(F)F)CN4)cc3F)cn12] | 2-(4-(4-(difluoromethyl)pyrrolidin-2-yl)-2-fluorophenyl)-N-(3-(4-fluoropiperidin-1-yl)propyl)benzo[d]imidazo[2,1-b]thiazole-7-carboxamide |
| 543 | 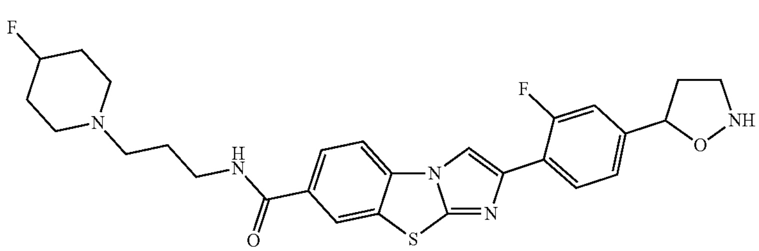 [SMILES: O=C(NCCCN1CCC(F)CC1)c1ccc2c(c1)sc1nc(-c3ccc(C4CCNO4)cc3F)cn12] | 2-(2-fluoro-4-(isoxazolidin-5-yl)phenyl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 544 | 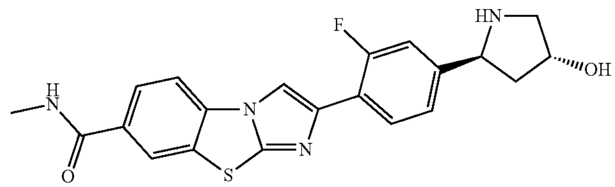 [SMILES: CNC(=O)c1ccc2c(c1)sc1nc(-c3ccc([C@@H]4C[C@@H](O)CN4)cc3F)cn12] | 2-(2-fluoro-4-((2S,4R)-4-hydroxypyrrolidin-2-yl)phenyl)-N-methylbenzo[d]imidazo[2,1-b]thiazole-7-carboxamide |
| 545 | 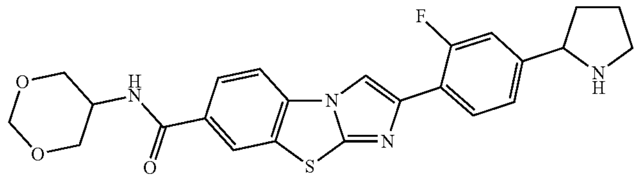 [SMILES: O=C(NC1COCOC1)c1ccc2c(c1)sc1nc(-c3ccc(C4CCCN4)cc3F)cn12] | N-(1,3-dioxan-5-yl)-2-(2-fluoro-4-(pyrrolidin-2-yl)phenyl)benzo[d]imidazo[2,1-b]thiazole-7-carboxamide |
| 546 | 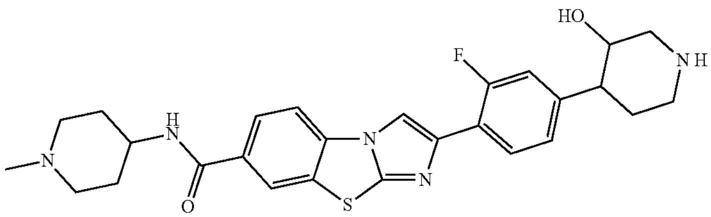 | 2-(2-fluoro-4-(3-hydroxypiperidin-4-yl)phenyl)-N-(1-methylpiperidin-4-yl)benzo[d]imidazo[2,1-b]thiazole-7-carboxamide |
| 547 | 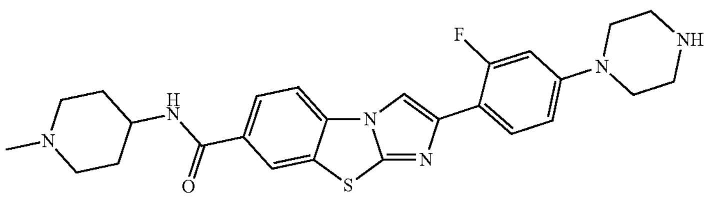 [SMILES: CN1CCC(NC(=O)c2ccc3c(c2)sc2nc(-c4ccc(N5CCNCC5)cc4F)cn23)CC1] | 2-(2-fluoro-4-(piperazin-1-yl)phenyl)-N-(1-methylpiperidin-4-yl)benzo[d]imidazo[2,1-b]thiazole-7-carboxamide |
| 548 | 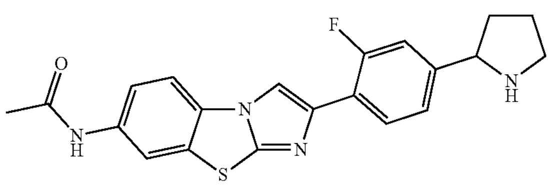 [SMILES: CC(=O)Nc1ccc2c(c1)sc1nc(-c3ccc(C4CCCN4)cc3F)cn12] | N-(2-(2-fluoro-4-(pyrrolidin-2-yl)phenyl)benzo[d]imidazo[2,1-b]thiazol-7-yl)acetamide |
| 549R | 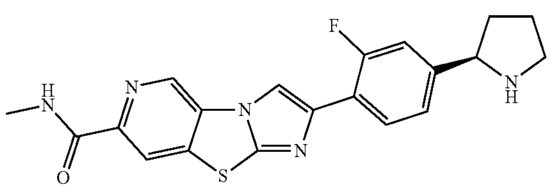 [SMILES: CNC(=O)c1cc2sc3nc(-c4ccc([C@H]5CCCN5)cc4F)cn3c2cn1] | (R)-2-(2-fluoro-4-(pyrrolidin-2-yl)phenyl)-N-methylimidazo[2',1':2,3]thiazolo[4,5-c]pyridine-7-carboxamide |
| 549S | 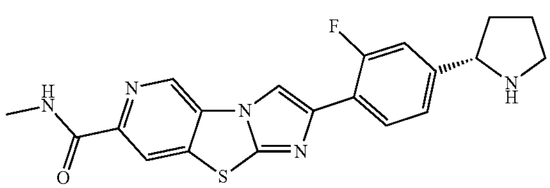 [SMILES: CNC(=O)c1cc2sc3nc(-c4ccc([C@@H]5CCCN5)cc4F)cn3c2cn1] | (S)-2-(2-fluoro-4-(pyrrolidin-2-yl)phenyl)-N-methylimidazo[2',1':2,3]thiazolo[4,5-c]pyridine-7-carboxamide |
| 550 | 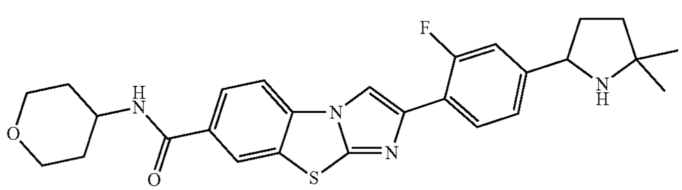 [SMILES: CC1(C)CCC(c2ccc(-c3cn4c(n3)sc3cc(C(=O)NC5CCOCC5)ccc34)c(F)c2)N1] | 2-(4-(5,5-dimethylpyrrolidin-2-yl)-2-fluorophenyl)-N-(tetrahydro-2H-pyran-4-yl)benzo[d]imidazo[2,1-b]thiazole-7-carboxamide |

TABLE 1-continued

| Comp. No. | Structure | Compound Name |
|---|---|---|
| 551 | 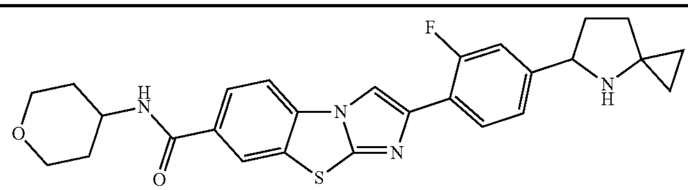 | 2-(2-fluoro-4-(4-azaspiro[2.4]heptan-5-yl)phenyl)-N-(tetrahydro-2H-pyran-4-yl)benzo[d]imidazo[2,1-b]thiazole-7-carboxamide |
| 552 | 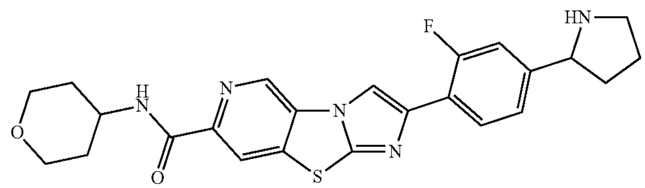 [SMILES: O=C(NC1CCOCC1)c1cc2sc3nc(-c4ccc(C5CCCN5)cc4F)cn3c2cn1] | 2-(2-fluoro-4-(pyrrolidin-2-yl)phenyl)-N-(tetrahydro-2H-pyran-4-yl)imidazo[2',1':2,3]thiazolo[4,5-c]pyridine-7-carboxamide |
| 553 | 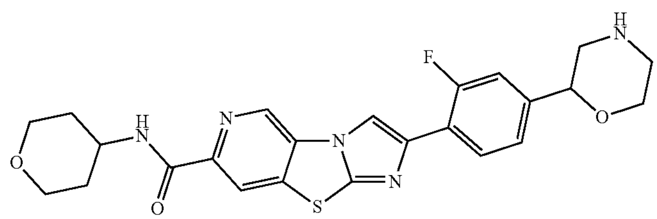 [SMILES: O=C(NC1CCOCC1)c1cc2sc3nc(-c4ccc(C5CNCCO5)cc4F)cn3c2cn1] | 2-(2-fluoro-4-(morpholin-2-yl)phenyl)-N-(tetrahydro-2H-pyran-4-yl)imidazo[2',1':2,3]thiazolo[4,5-c]pyridine-7-carboxamide |
| 554 | 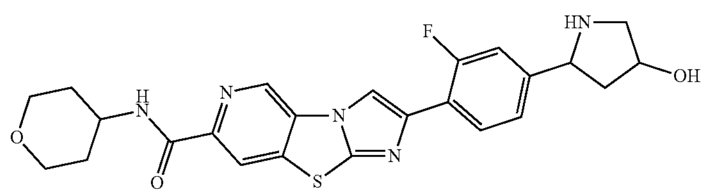 [SMILES: O=C(NC1CCOCC1)c1cc2sc3nc(-c4ccc(C5CC(O)CN5)cc4F)cn3c2cn1] | 2-(2-fluoro-4-(4-hydroxypyrrolidin-2-yl)phenyl)-N-(tetrahydro-2H-pyran-4-yl)imidazo[2',1':2,3]thiazolo[4,3-c]pyridine-7-carboxamide |
| 555 | 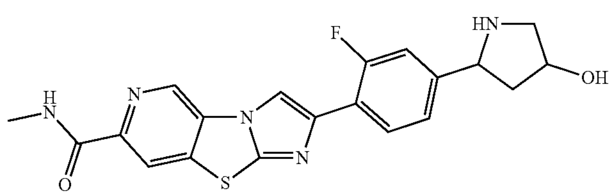 [SMILES: CNC(=O)c1cc2sc3nc(-c4ccc(C5CC(O)CN5)cc4F)cn3c2cn1] | 2-(2-fluoro-4-(4-hydroxypyrrolidin-2-yl)phenyl)-N-methylimidazo[2',1':2,3]thiazolo[4,5-c]pyridine-7-carboxamide |
| 556 | 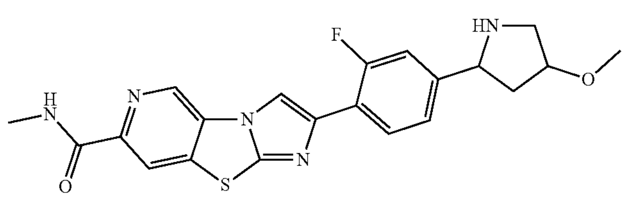 | 2-(2-fluoro-4-(4-methoxypyrrolidin-2-yl)phenyl)-N-methylimidazo[2',1':2,3]thiazolo[4,5-c]pyridine-7-carboxamide |
| 557 | 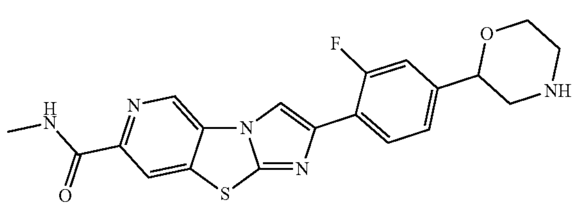 [SMILES: CNC(=O)c1cc2sc3nc(-c4ccc(C5CNCCO5)cc4F)cn3c2cn1] | 2-(2-fluoro-4-(morpholin-2-yl)phenyl)-N-methylimidazo[2',1':2,3]thiazolo[4,5-c]pyridine-7-carboxamide |
| 558 | 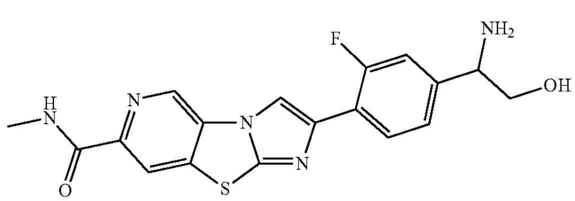 [SMILES: CNC(=O)c1cc2sc3nc(-c4ccc(C(N)CO)cc4F)cn3c2cn1] | 2-(4-(1-amino-2-hydroxyethyl)-2-fluorophenyl)-N-methylimidazo[2',1':2,3]thiazolo[4,5-c]pyridine-7-carboxamide |

TABLE 1-continued

| Comp. No. | Structure | Compound Name |
|---|---|---|
| 559 | 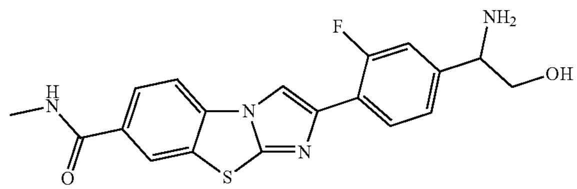 [SMILES: CNC(=O)c1ccc2c(c1)sc1nc(-c3ccc(C(N)CO)cc3F)cn12] | 2-(4-(1-amino-2-hydroxyethyl)-2-fluorophenyl)-N-methylbenzo[d]imidazo[2,1-b]thiazole-7-carboxamide |
| 560 | 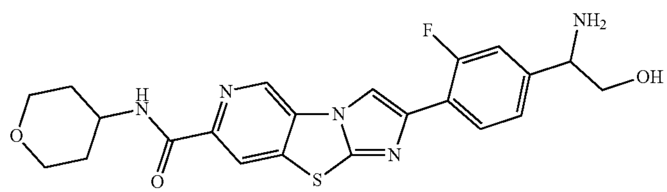 [SMILES: NC(CO)c1ccc(-c2cn3c(n2)sc2cc(C(=O)NC4CCOCC4)ncc23)c(F)c1] | 2-(4-(1-amino-2-hydroxyethyl)-2-fluorophenyl)-N-(tetrahydro-2H-pyran-4-yl)imidazo[2',1':2,3]thiazolo[4,3-c]pyridine-7-carboxamide |
| 561 | 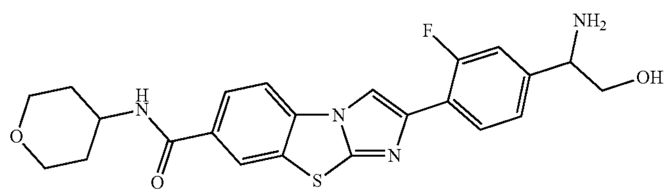 [SMILES: NC(CO)c1ccc(-c2cn3c(n2)sc2cc(C(=O)NC4CCOCC4)ccc23)c(F)c1] | 2-(4-(1-amino-2-hydroxyethyl)-2-fluorophenyl)-N-(tetrahydro-2H-pyran-4-yl)benzo[d]imidazo[2,1-b]thiazole-7-carboxamide |
| 562 | 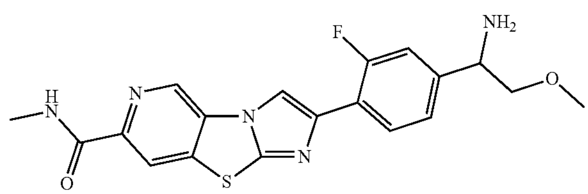 | 2-(4-(1-amino-2-methoxyethyl)-2-fluorophenyl)-N-methylimidazo[2',1':2,3]thiazolo[4,5-c]pyridine-7-carboxamide |
| 563 | 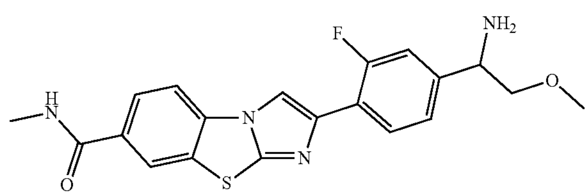 | 2-(4-(1-amino-2-methoxyethyl)-2-fluorophenyl)-N-methylbenzo[d]imidazo[2,1-b]thiazole-7-carboxamide |
| 564 | 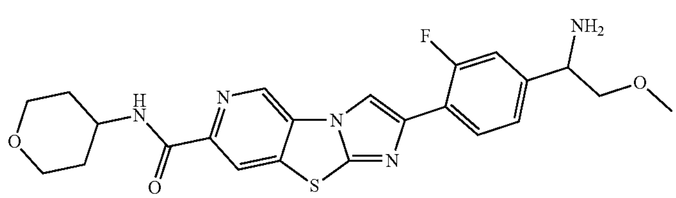 [SMILES: COCC(N)c1ccc(-c2cn3c(n2)sc2cc(C(=O)NC4CCOCC4)ncc23)c(F)c1] | 2-(4-(1-amino-2-methoxyethyl)-2-fluorophenyl)-N-(tetrahydro-2-pyran-4-yl)imidazo[2',1':2,3]thiazolo[4,3-c]pyridine-7-carboxamide |
| 565 | 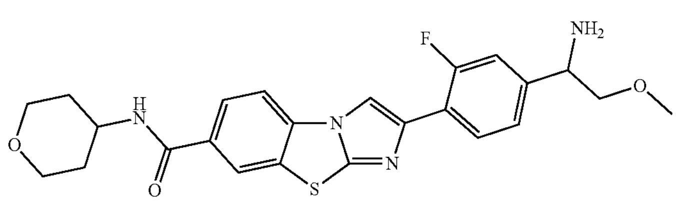 [SMILES: COCC(N)c1ccc(-c2cn3c(n2)sc2cc(C(=O)NC4CCOCC4)ccc23)c(F)c1] | 2-(4-(1-amino-2-methoxyethyl)-2-fluorophenyl)-N-(tetrahydro-2H-pyran-4-yl)benzo[d]imidazo[2,1-b]thiazole-7-carboxamide |
| 566 | 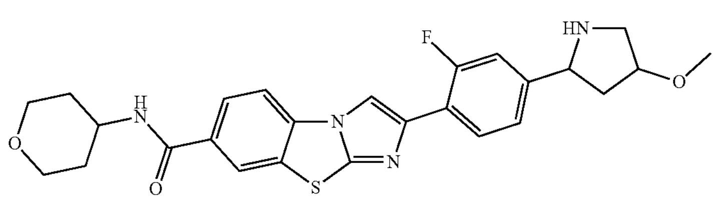 [SMILES: COC1CNC(c2ccc(-c3cn4c(n3)sc3cc(C(=O)NC5CCOCC5)ccc34)c(F)c2)C1] | 2-(2-fluoro-4-(4-methoxypyrrolidin-2-yl)phenyl)-N-(tetrahydro-2H-pyran-4-yl)benzo[d]imidazo[2,1-b]thiazole-7-carboxamide |

TABLE 1-continued

| Comp. No. | Structure | Compound Name |
|---|---|---|
| 567 | 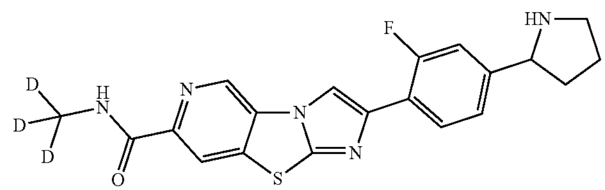 [SMILES: [2H]C([2H])([2H])NC(=O)c1cc2sc3nc(-c4ccc(C5CCCN5)cc4F)cn3c2cn1] | 2-(2-fluoro-4-(pyrrolidin-2-yl)phenyl)-N-(methyl-d3)imidazo[2',1':2,3]thiazolo[4,5-c]pyridine-7-carboxamide |
| 568 | 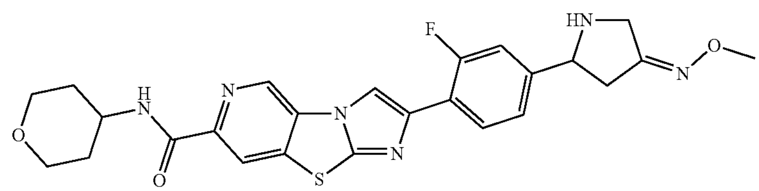 [SMILES: CO/N=C1\CNC(c2ccc(-c3cn4c(n3)sc3cc(C(=O)NC5CCOCC5)ncc34)c(F)c2)C1] | (Z)-2-(2-fluoro-4-(4-(methoxyimino)pyrrolidin-2-yl)phenyl)-N-(tetrahydro-2H-pyran-4-yl)benzo[d]imidazo[2,1-b]thiazole-7-carboxamide |
| 569 | 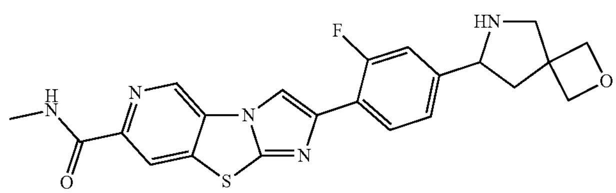 [SMILES: CNC(=O)c1cc2sc3nc(-c4ccc(C5CC6(CN5)COC6)cc4F)cn3c2cn1] | 2-(2-fluoro-4-(2-oxa-6-azaspiro[3.4]octan-7-yl)phenyl)-N-methylimidazo[2',1':2,3]thiazolo[4,5-c]pyridine-7-carboxamide |
| 570 | 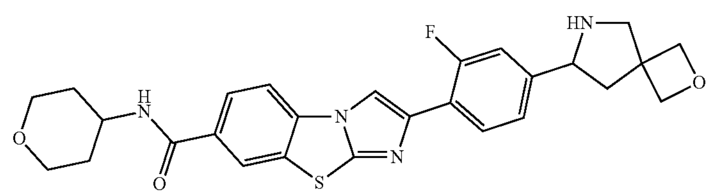 [SMILES: O=C(NC1CCOCC1)c1ccc2c(c1)sc1nc(-c3ccc(C4CC5(CN4)COC5)cc3F)cn12] | 2-(2-fluoro-4-(2-oxa-6-azaspiro[3.4]octan-7-yl)phenyl)-N-(tetrahydro-2H-pyran-4-yl)benzo[d]imidazo[2,1-b]thiazole-7-carboxamide |
| 571 | 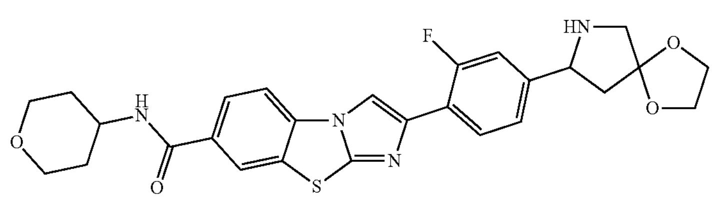 [SMILES: O=C(NC1CCOCC1)c1ccc2c(c1)sc1nc(-c3ccc(C4CC5(CN4)OCCO5)cc3F)cn12] | 2-(2-fluoro-4-(1,4-dioxa-7-azaspiro[4.4]nonan-8-yl)phenyl)-N-(tetrahydro-2H-pyran-4-yl)benzo[d]imidazo[2,1-b]thiazole-7-carboxamide |
| 572 | 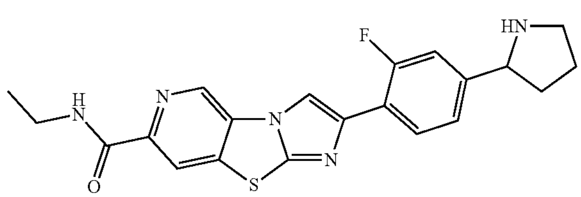 [SMILES: CCNC(=O)c1cc2sc3nc(-c4ccc(C5CCCN5)cc4F)cn3c2cn1] | N-ethyl-2-(2-fluoro-4-(pyrrolidin-2-yl)phenyl)imidazo[2'1':2,3]thiazolo[4,5-c]pyridine-7-carboxamide |
| 573 | 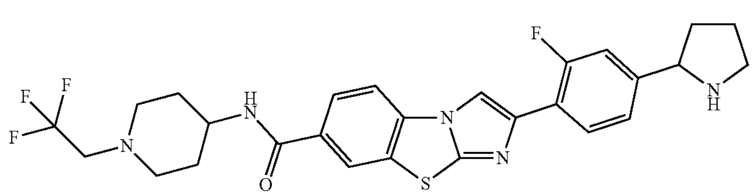 [SMILES: O=C(NC1CCN(CC(F)(F)F)CC1)c1ccc2c(c1)sc1nc(-c3ccc(C4CCCN4)cc3F)cn12] | 2-(2-fluoro-4-(pyrrolidin-2-yl)phenyl)-N-(1-(2,2,2-trifluoroethyl)piperidin-4-yl)benzo[d]imidazo[2,1-b]thiazole-7-carboxamide |
| 574 | 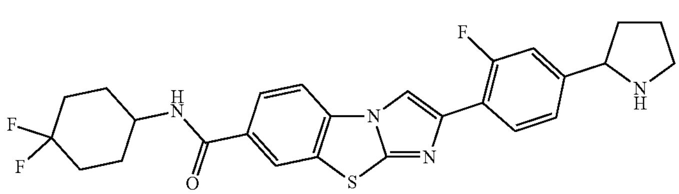 [SMILES: O=C(NC1CCC(F)(F)CC1)c1ccc2c(c1)sc1nc(-c3ccc(C4CCCN4)cc3F)cn12] | N-(4,4-difluorocyclohexyl)-2-(2-fluoro-4-(pyrrolidin-2-yl)phenyl)benzo[d]imidazo[2,1-b]thiazole-7-carboxamide |

TABLE 1-continued

| Comp. No. | Structure | Compound Name |
|---|---|---|
| 575 | 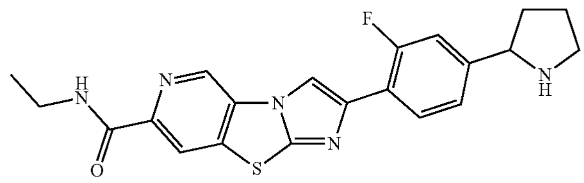 [SMILES: CCNC(=O)c1cc2sc3nc(-c4ccc(C5CCCN5)cc4F)cn3c2cn1] | 2-(2-fluoro-4-(pyrrolidin-2-yl)phenyl)-N-isopropylimidazo[2',1':2,3]thiazolo[4,5-c]pyridine-7-carboxamide |
| 576 | 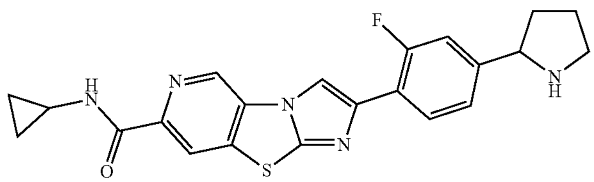 [SMILES: O=C(NC1CC1)c1cc2sc3nc(-c4ccc(C5CCCN5)cc4F)cn3c2cn1] | N-cyclopropyl-2-(2-fluoro-4-(pyrrolidin-2-yl)phenyl)imidazo[2',1':2,3]thiazolo[4,5-c]pyridine-7-carboxamide |
| 577 | 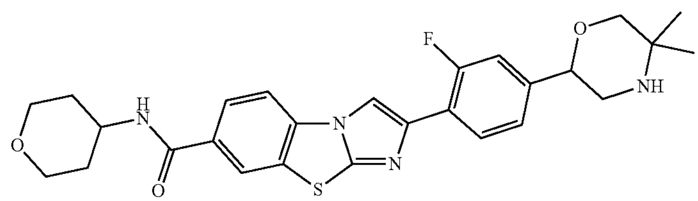 [SMILES: CC1(C)COC(c2ccc(-c3cn4c(n3)sc3cc(C(=O)NC5CCOCC5)ccc34)c(F)c2)CN1] | 2-(4-(5,5-dimethylmorpholin-2-yl)-2-fluorophenyl)-N-(tetrahydro-2H-pyran-4-yl)benzo[d]imidazo[2,1-b]thiazole-7-carboxamide |
| 578 | 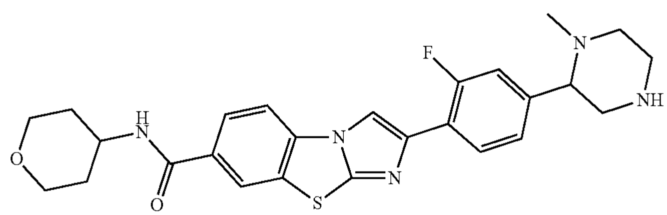 [SMILES: CN1CCNCC1c1ccc(-c2cn3c(n2)sc2cc(C(=O)NC4CCOCC4)ccc23)c(F)c1] | 2-(2-fluoro-4-(1-methylpiperazin-2-yl)phenyl)-N-(tetrahydro-2H-pyran-4-yl)benzo[d]imidazo[2,1-b]thiazole-7-carboxamide |
| 579 | 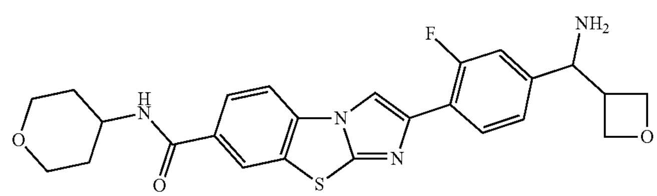 [SMILES: NC(c1ccc(-c2cn3c(n2)sc2cc(C(=O)NC4CCOCC4)ccc23)c(F)c1)C1COC1] | 2-(4-(amino(oxetan-3-yl)methyl)-2-fluorophenyl)-N-(tetrahydro-2H-pyran-4-yl)benzo[d]imidazo[2,1-b]thiazole-7-carboxamide |
| 580 | 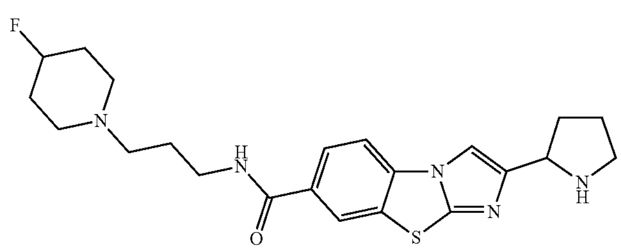 [SMILES: O=C(NCCCN1CCC(F)CC1)c1ccc2c(c1)sc1nc(C3CCCN3)cn12] | N-(3-(4-fluoropiperidin-1-yl)propyl)-2-(pyrrolidin-2-yl)benzo[d]imidazo[2,1-b]thiazole-7-carboxamide |
| 581 | 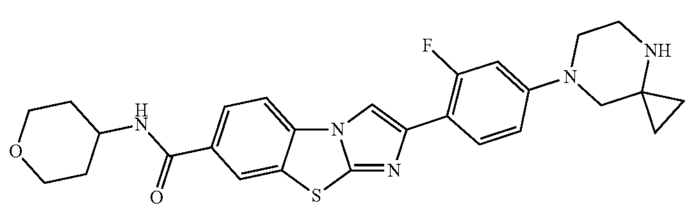 [SMILES: O=C(NC1CCOCC1)c1ccc2c(c1)sc1nc(-c3ccc(N4CCNC5(CC5)C4)cc3F)cn12] | 2-(2-fluoro-4-(4,7-diazaspiro[2.5]octan-7-yl)phenyl)-N-(tetrahydro-2H-pyran-4-yl)benzo[d]imidazo[2,1-b]thiazole-7-carboxamide |

TABLE 1-continued

| Comp. No. | Structure | Compound Name |
|---|---|---|
| 582 | 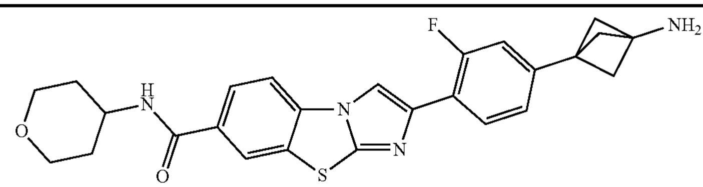 | 2-(4-(3-aminobicyclo[1.1.1]pentan-1-yl)-2-fluorophenyl)-N-(tetrahydro-2H-pyran-4-yl)benzo[d]imidazo[2,1-b]thiazole-7-carboxamide |
| 583 | 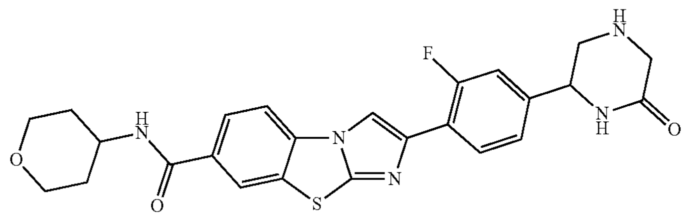 [SMILES: O=C1CNCC(c2ccc(-c3cn4c(n3)sc3cc(C(=O)NC5CCOCC5)ccc34)c(F)c2)N1] | 2-(2-fluoro-4-(6-oxopiperazin-2-yl)phenyl)-N-(tetrahydro-2H-pyran-4-yl)benzo[d]imidazo[2,1-b]thiazole-7-carboxamide |
| 584 | 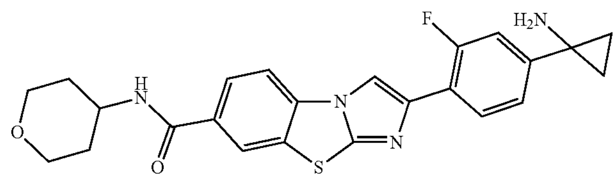 [SMILES: NC1(c2ccc(-c3cn4c(n3)sc3cc(C(=O)NC5CCOCC5)ccc34)c(F)c2)CC1] | 2-(4-(1-aminocyclopropyl)-2-fluorophenyl)-N-(tetrahydro-2-pyran-4-yl)benzo[d]imidazo[2,1-b]thiazole-7-carboxamide |
| 585 | 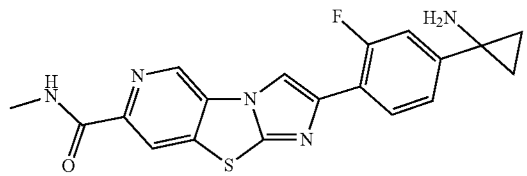 [SMILES: CNC(=O)c1cc2sc3nc(-c4ccc(C5(N)CC5)cc4F)cn3c2cn1] | 2-(4-(1-aminocyclopropyl)-2-fluorophenyl)-N-methylimidazo[2',1':2,3]thiazolo[4,5-c]pyridine-7-carboxamide |
| 586 | 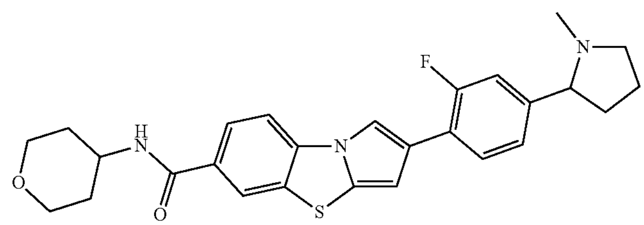 [SMILES: CN1CCCC1c1ccc(-c2cc3sc4cc(C(=O)NC5CCOCC5)ccc4n3c2)c(F)c1] | 2-(2-fluoro-4-(1-methylpyrrolidin-2-yl)phenyl)-N-(tetrahydro-2H-pyran-4-yl)benzo[d]imidazo[2,1-b]thiazole-7-carboxamide |
| 587 | 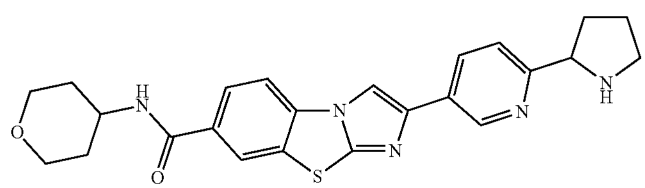 [SMILES: O=C(NC1CCOCC1)c1ccc2c(c1)sc1nc(-c3ccc(C4CCCN4)nc3)cn12] | 2-(6-(pyrrolidin-2-yl)pyridin-3-yl)-N-(tetrahydro-2H-pyran-4-yl)benzo[d]imidazo[2,1-b]thiazole-7-carboxamide |
| 588 | 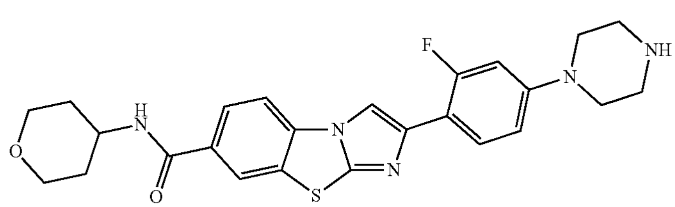 [SMILES: O=C(NC1CCOCC1)c1ccc2c(c1)sc1nc(-c3ccc(N4CCNCC4)cc3F)cn12] | 2-(2-fluoro-4-(piperazin-1-yl)phenyl)-N-(tetrahydro-2H-pyran-4-yl)benzo[d]imidazo[2,1-b]thiazole-7-carboxamide |
| 589 | 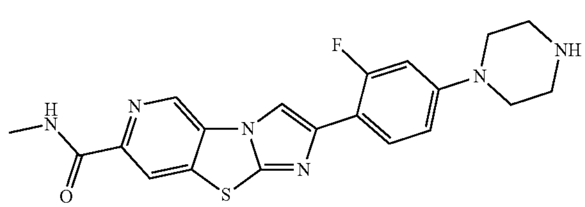 [SMILES: CNC(=O)c1cc2sc3nc(-c4ccc(N5CCNCC5)cc4F)cn3c2cn1] | 2-(2-fluoro-4-(piperazin-1-yl)phenyl)-N-methylimidazo[2',1':2,3]thiazolo[4,5-c]pyridine-7-carboxamide |

TABLE 1-continued

| Comp. No. | Structure | Compound Name |
|---|---|---|
| 590 | 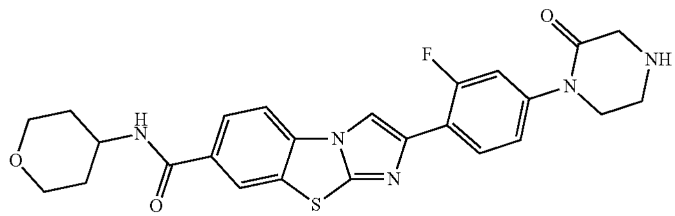 [SMILES: O=C(NC1CCOCC1)c1ccc2c(c1)sc1nc(-c3ccc(N4CCNCC4=O)cc3F)cn12] | 2-(2-fluoro-4-(2-oxopiperazin-1-yl)phenyl)-N-(tetrahydro-2-pyran-4-yl)benzo[d]imidazo[2,1-b]thiazole-7-carboxamide |
| 591 | 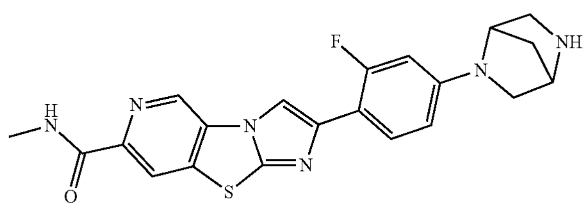 [SMILES: CNC(=O)c1cc2sc3nc(-c4ccc(N5CC6CC5CN6)cc4F)cn3c2cn1] | 2-(4-(2,5-diazabicyclo[2.2.1]heptan-2-yl)-2-fluorophenyl)-N-methylimidazo[2',1':2,3]thiazolo[4,5-c]pyridine-7-carboxamide |
| 592 | 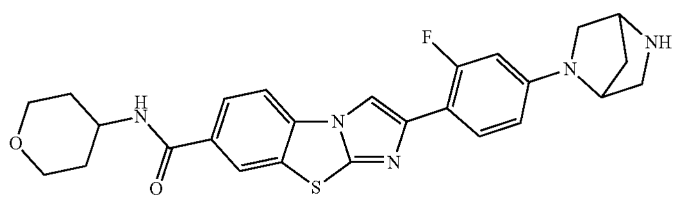 [SMILES: O=C(NC1CCOCC1)c1ccc2c(c1)sc1nc(-c3ccc(N4CC5CC4CN5)cc3F)cn12] | 2-(4-(2,5-diazabicyclo[2.2.1]heptan-2-yl)-2-fluorophenyl)-N-(tetrahydro-2H-pyran-4-yl)benzo[d]imidazo[2,1-b]thiazole-7-carboxamide |
| 593 | 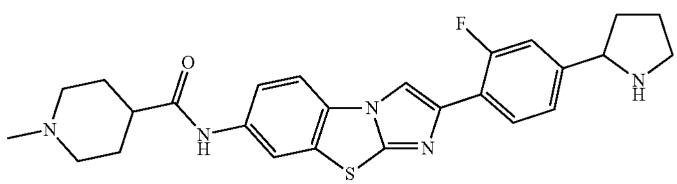 [SMILES: CN1CCC(C(=O)Nc2ccc3c(c2)sc2nc(-c4ccc(C5CCCN5)cc4F)cn23)CC1] | N-(2-(2-fluoro-4-(pyrrolidin-2-yl)phenyl)benzo[d]imidazo[2,1-b]thiazol-7-yl)-1-methylpiperidine-4-carboxamide |
| 594 | 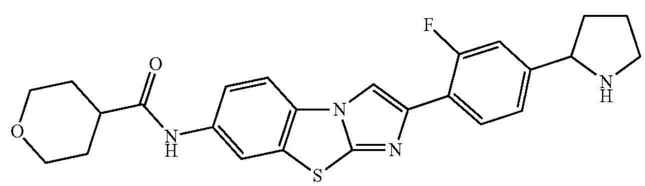 [SMILES: O=C(Nc1ccc2c(c1)sc1nc(-c3ccc(C4CCCN4)cc3F)cn12)C1CCOCC1] | N-(2-(2-fluoro-4-(pyrrolidin-2-yl)phenyl)benzo[d]imidazo[2,1-b]thiazol-7-yl)tetrahydro-2H-pyran-4-carboxamide |
| 600 | 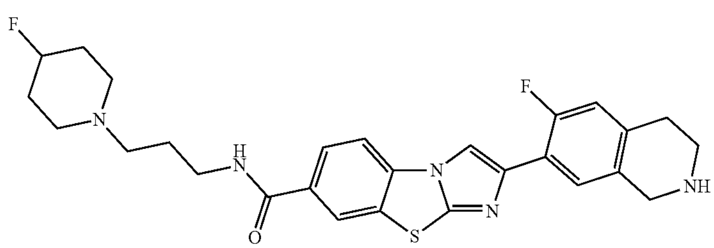 [SMILES: O=C(NCCCN1CCC(F)CC1)c1ccc2c(c1)sc1nc(-c3cc4c(cc3F)CCNC4)cn12] | 2-(6-fluoro-1,2,3,4-tetrahydroisoquinolin-7-yl)-N-(3-(4-fluropiperidin-1-yl)propyl)benzo[d]imidazo[2,1-b]thiazole-7-carboxamide |
| 601 | 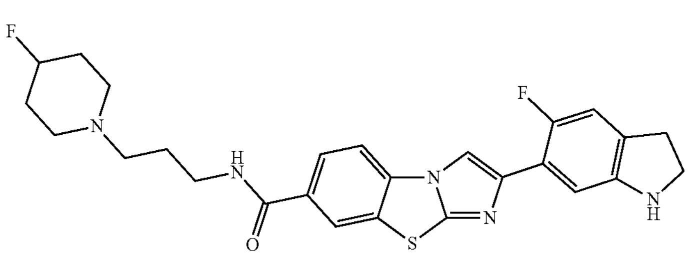 [SMILES: O=C(NCCCN1CCC(F)CC1)c1ccc2c(c1)sc1nc(-c3cc4c(cc3F)CCN4)cn12] | 2-(5-fluoroindolin-6-yl)-N-(3-(4-fluoropiperidin-1-yl)propyl)benzo[d]imidazo[2,1-b]thiazole-7-carboxamide |

TABLE 1-continued

| Comp. No. | Structure | Compound Name |
|---|---|---|
| 602 | 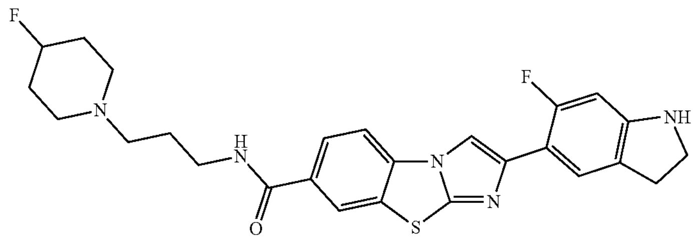 [SMILES: O=C(NCCCN1CCC(F)CC1)c1ccc2c(c1)sc1nc(-c3cc4c(cc3F)NCC4)cn12] | 2-(6-fluoroindolin-5-yl)-N-(3-(4-fluoropiperidin-1-yl)propyl-benzo[d]imidazo[2,1-b]thiazole-7-carboxamide |

It is well understood that in structures presented in this invention wherein the carbon atom has less than 4 bonds, H atoms are present to complete the valence of the carbon. It is well understood that in structures presented in this invention wherein the nitrogen atom has less than 3 bonds, H atoms are present to complete the valence of the nitrogen.

In some embodiments, this invention is directed to the compounds listed hereinabove, pharmaceutical compositions and/or method of use thereof, wherein the compound is pharmaceutically acceptable salt, stereoisomer, tautomer, hydrate, N-oxide, reverse amide analog, prodrug, isotopic variant (deuterated analog), PROTAC, pharmaceutical product or any combination thereof. In some embodiments, the compounds are c-MYC mRNA translation modulators. In some embodiments, the compounds are c-MYC mRNA translation inhibitors. In some embodiments, the compounds are c-MYC inhibitors. In various embodiments, the compounds are a c-MYC mRNA transcription regulators. In various embodiments, the compounds are any combination of c-MYC mRNA translation modulators, c-MYC mRNA transcription regulators and c-MYC inhibitors.

As used herein, the term "alkyl" can be any straight- or branched-chain alkyl group containing up to about 30 carbons unless otherwise specified. In various embodiments, an alkyl includes $C_1$-$C_5$ carbons. In some embodiments, an alkyl includes $C_1$-$C_6$ carbons. In some embodiments, an alkyl includes $C_1$-$C_5$ carbons. In some embodiments, an alkyl includes $C_1$-$C_5$ carbons. In some embodiments, an alkyl includes $C_1$-$C_{10}$ carbons. In some embodiments, an alkyl is a $C_1$-$C_{12}$ carbons. In some embodiments, an alkyl is a $C_1$-$C_{20}$ carbons. In some embodiments, branched alkyl is an alkyl substituted by alkyl side chains of 1 to 5 carbons. In various embodiments, the alkyl group may be unsubstituted.

In some embodiments, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, N(alkyl)$_2$, —OC(O)CF$_3$, —OCH$_2$Ph, —NHCO-alkyl, —C(O)Ph, C(O)O-alkyl, C(O)H, —C(O)NH$_2$ or any combination thereof.

The alkyl group can be a sole substituent, or it can be a component of a larger substituent, such as in an alkoxy, alkoxyalkyl, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, 2, 3, or 4-CH$_2$—C$_6$H$_4$—Cl, C(OH)(CH$_3$)(Ph), etc.

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. In some embodiments, the term aryl according to this invention, includes also heteroaryl. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, indolyl, phenylmethyl, phenylethyl, phenylamino, phenylamido, 3-methyl-4H-1,2,4-triazolyl, oxadiazolyl, 5-methyl-1,2,4-oxadiazolyl, isothiazolyl, thiadiazolyl, triazolyl, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, phenyl, halophenyl, CN, $NO_2$, —$CH_2CN$, $NH_2$, NH-alkyl, N(alkyl)$_2$, hydroxyl, —OC(O)CF$_3$, —OCH$_2$Ph, —NHCO-alkyl, COOH, —C(O)Ph, C(O)O-alkyl, C(O)H, —C(O)NH$_2$ or any combination thereof.

As used herein, the term "alkoxy" refers to an ether group substituted by an alkyl group as defined above. Alkoxy refers both to linear and to branched alkoxy groups. Nonlimiting examples of alkoxy groups are methoxy, ethoxy, propoxy, iso-propoxy, tert-butoxy.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are —N(Me)$_2$, —NHMe, —NH$_3$.

A "haloalkyl" group refers, in some embodiments, to an alkyl group as defined above, which is substituted by one or more halogen atoms, e.g. by F, Cl, Br or I. The term "haloalkyl" include but is not limited to fluoroalkyl, i.e., to an alkyl group bearing at least one fluorine atom. Nonlimiting examples of haloalkyl groups are $CF_3$, $CF_2CF_3$, $CF_2CH_3$, $CH_2CF_3$, $CF_2CH_2CH_3$, $CH_2CH_2CF_3$, $CF_2CH(CH_3)_2$ and $CF(CH_3)$—$CH(CH_3)_2$.

A "halophenyl" group refers, in some embodiments, to a phenyl substitutent which is substituted by one or more halogen atoms, e.g. by F, Cl, Br or I. In one embodiment, the halophenyl is 4-chlorophenyl.

An "alkoxyalkyl" group refers, in some embodiments, to an alkyl group as defined above, which is substituted by alkoxy group as defined above, e.g. by methoxy, ethoxy, propoxy, i-propoxy, t-butoxy etc. Nonlimiting examples of alkoxyalkyl groups are —CH$_2$—O—CH$_3$, —CH$_2$—O—CH(CH$_3$)$_2$, —CH$_2$—O—C(CH$_3$)$_3$, —CH$_2$—CH$_2$—O—CH$_3$, —CH$_2$—CH$_2$—O—CH(CH$_3$)$_2$, —CH$_2$—CH$_2$—O—C(CH$_3$)$_3$.

A "cycloalkyl" or "carbocyclic" group refers, in various embodiments, to a ring structure comprising carbon atoms as ring atoms, which may be either saturated or unsaturated, substituted or unsubstituted, single or fused. In some embodiments the cycloalkyl is a 3-10 membered ring. In some embodiments the cycloalkyl is a 3-12 membered ring. In some embodiments the cycloalkyl is a 6 membered ring. In some embodiments the cycloalkyl is a 5-7 membered ring. In some embodiments the cycloalkyl is a 3-8 membered ring. In some embodiments, the cycloalkyl group may be unsubstituted or substituted by a halogen, alkyl, haloalkyl, hydroxyl, alkoxy, carbonyl, amido, alkylamido, dialkylamido, cyano, nitro, CO$_2$H, amino, alkylamino, dialkylamino, carboxyl, thio, thioalkyl, C$_1$-C$_5$ linear or branched haloalkoxy, CF$_3$, phenyl, halophenyl, (benzyloxy)phenyl, —CH$_2$CN, NH$_2$, NH-alkyl, N(alkyl)$_2$, —OC(O)CF$_3$, —OCH$_2$Ph, —NHCO-alkyl, —C(O)Ph, C(O)O-alkyl, C(O)H, —C(O)NH$_2$ or any combination thereof. In some another embodiments, the cycloalkyl ring may be fused to another saturated or unsaturated cycloalkyl or heterocyclic 3-8 membered ring. In some embodiments, the cycloalkyl ring is a saturated ring. In some embodiments, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclopentadienyl, cyclobutyl, cyclobutenyl, cyclooctyl, cyclooctadienyl (COD), cyclooctaene (COE) etc.

A "heterocycle" or "heterocyclic" group refers, in various embodiments, to a ring structure comprising in addition to carbon atoms, sulfur, oxygen, nitrogen or any combination thereof, as part of the ring. A "heteroaromatic ring" refers in various embodiments, to an aromatic ring structure comprising in addition to carbon atoms, sulfur, oxygen, nitrogen or any combination thereof, as part of the ring. In some embodiments the heterocycle or heteroaromatic ring is a 3-10 membered ring. In some embodiments the heterocycle or heteroaromatic ring is a 3-12 membered ring. In some embodiments the heterocycle or heteroaromatic ring is a 6 membered ring. In some embodiments the heterocycle or heteroaromatic ring is a 5-7 membered ring. In some embodiments the heterocycle or heteroaromatic ring is a 3-8 membered ring. In some embodiments, the heterocycle group or heteroaromatic ring may be unsubstituted or substituted by a halogen, alkyl, haloalkyl, hydroxyl, alkoxy, carbonyl, amido, alkylamido, dialkylamido, cyano, nitro, CO$_2$H, amino, alkylamino, dialkylamino, carboxyl, thio, thioalkyl, C$_1$-C$_5$ linear or branched haloalkoxy, CF$_3$, phenyl, halophenyl, (benzyloxy)phenyl, —CH$_2$CN, NH$_2$, NH-alkyl, N(alkyl)$_2$, —OC(O)CF$_3$, —OCH$_2$Ph, —NHCO-alkyl, —C(O)Ph, C(O)O-alkyl, C(O)H, —C(O)NH$_2$ or any combination thereof. In some embodiments, the heterocycle ring or heteroaromatic ring may be fused to another saturated or unsaturated cycloalkyl or heterocyclic 3-8 membered ring. In some embodiments, the heterocyclic ring is a saturated ring. In some embodiments, the heterocyclic ring is an unsaturated ring. Non limiting examples of a heterocyclic ring or heteroaromatic ring systems comprise pyridine, piperidine, morpholine, piperazine, thiophene, pyrrole, benzodioxole, benzofuran-2(3H)-one, benzo[d][1,3]dioxole, indole, oxazole, isoxazole, imidazole and 1-methylimidazole, furane, triazole, pyrimidine, pyrazine, oxacyclobutane (1 or 2-oxacyclobutane), naphthalene, tetrahydrothiophene 1,1-dioxide, thiazole, benzimidazole, piperidine, 1-methylpiperidine, isoquinoline, 1,3-dihydroisobenzofuran, benzofuran, 3-methyl-4H-1,2,4-triazole, oxadiazolyl, 5-methyl-1,2,4-oxadiazole, pyrazole, isothiazole, thiadiazole, tetrahydrofurane, oxazolone, oxazolidone, thiazolone, isothiazolinone, isoxazolidinone, imidazolidinone, pyrazolone, 2H-pyrrol-2-one, furanone, thiophenone, thiane 1,1-dioxide, triazolopyrimidine, 6,7-dihydro-5H-pyrazolo[5,1-b][1,3]oxazine or indole.

In some embodiments, "heterocyclic ring" according to this invention refers to substituted or unsubstituted, 3 to 8 membered, saturated, unsaturated or aromatic, single, fused or spiro rings, which comprise at least one heteroatom selected from: N, O or S. In some embodiments, the heterocyclic ring may be substituted, unsubstituted, saturated, unsaturated, aromatic, single, fused or spiro ring; each represent a separate embodiment according to this invention. The heterocyclic ring(s) may be 3-10; 3-9; 3-8; 3-7; 3-6; 3-5; 4-6; 4-7; 4-8; 4-9; 5-6; 5-7; 5-8; 5-10 or 5-9 membered ring(s); each represents a separate embodiment according to this invention. Examples of heterocyclic rings include, but ot limited to: pyran, tetrahydropyran, pyrrazole, imidazole, furan, tetrahydrofuran, dioxane, oxetane, azetidine, pyridine, pyridazine, pyrimidine, piperidine, piperazine, triazole, oxadiazole, tetrahydrofuran (THF), tetrahydrofurane, morpholine, thiomorpholine 1,1-dioxide, oxa-azaspirodecane, azaspiroheptane, 5-azaspiro[2.4]heptane, 2-azaspiro[3.3]heptane, oxa-azaspiroheptane, 2-oxa-6-azaspiro[3.3]heptane pyrrol, pyrrolidine, pyrrolidine-2-one, 2-oxopyrrolidine, pyrrolidinone, quinuclidine, azepane, azepan-2-one, azabicyclohexane, 2-azabicyclo[2.1.1]hexane, 3-azabicyclo[3.1.0]hexane, 1-oxa-8-azaspiro[4.5]decane, diazabicyclo[2.2.1]heptane, 2,5-diazabicyclo[2.2.1]heptane. In some embodiments, the heterocyclic ring may be further substituted with at least one group selected from: F, Cl, Br, I, CF$_3$, R$_{20}$ as defined hereinbelow, C$_1$-C$_5$ linear or branched alkyl (e.g., methyl, ethyl, propyl), alkyleneamine (e.g., CH$_2$—NH$_2$), C$_1$-C$_5$ linear or branched haloalkyl (e.g., CH$_2$CF$_3$, CHF$_2$), OH, alkoxy (e.g., OCH$_3$), alkylene-OH (e.g., CH$_2$—OH), amide, alkylene-amide (e.g., CH$_2$—C(O)NH$_2$), C(O)-heterocyclic ring, amine (e.g., NH$_2$), alkylamine (e.g., NH(CH$_3$)), dialkylamine (e.g., N(CH$_3$)$_2$), CF$_3$, aryl, phenyl, halophenyl, heteroaryl, C$_3$-C$_5$ cycloalkyl (e.g., cyclopropyl, cyclohexyl), saturated, unsaturated, aromatic, single fused or spiral 3-8 membered heterocyclic ring, CN, and NO$_2$; each is a separate embodiment according to this invention.

In some embodiments, "single or fused saturated, unsaturated or aromatic heterocyclic ring" or "saturated, unsaturated, aromatic, single, fused or spiro heterocyclic ring" can be any such ring(s), which comprise at least one heteroatom selected from: N, O or S, including but not limited to: pyridinyl, (2-, 3-, and 4-pyridinyl), quinolinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, pyrazolyl, pyrrolyl, furanyl, thiophene-yl, quinolinyl, isoquinolinyl, 2,3-dihydroindenyl, indenyl, tetrahydronaphthyl, 3,4-dihydro-2H-benzo[b][1,4]dioxepine, benzodioxolyl, benzo[d][1,3]dioxole, tetrahydronaphthyl, indolyl, 1H-indole, isoindolyl, anthracenyl, benzimidazolyl, 2,3-dihydro-1H-benzo[d]imidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, 1,2,3,4-tetrahydroquinoxaline, 1-(pyridin-1(2H)-yl)ethanone, cinnolinyl, phthalazinyl, quinolinyl, isoquinolinyl, acridinyl, benzofuranyl, 1-benzofuran, isobenzofuranyl, benzofuran-2(3H)- one, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, 1,2,3-, 1,2,4-, 1,2,5- or 1,3,4-oxadiazolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, 3-methyl-4H-1,2,4-triazole, 5-methyl-1,2,4-oxadiazole etc. In some embodiments, the heterocyclic ring according to this invention includes: pyran, tetrahydropyran, pyrrazole, imidazole, furan, tetrahydrofuran, dioxane, oxetane, azetidine, pyridine, pyridazine, pyrimidine, piperidine, piperazine, triazole, oxadiazole, tetrahydrofuran (THF), tetrahydrofurane, morpholine, thiomorpholine 1,1-dioxide, oxa-azaspirodecane, azaspiroheptane, 5-azaspiro[2.4]heptane, 2-azaspiro[3.3]heptane, oxa-azaspiroheptane, pyrrol, pyrrolidine, pyrrolidine-2-one, 2-oxo-pyrrolidine, pyrrolidinone, quinuclidine, azepane, azepan-2-one, azabicyclohexane, 2-azabicyclo[2.1.1]hexane, 3-azabicyclo[3.1.0]hexane, 1-oxa-8-azaspiro[4.5]decane, and/or diazabicyclo[2.2.1]heptane; each represent a separate embodiment according to this invention. In some embodiments, the heterocyclic ring may be further substituted with at least one group selected from: F, Cl, Br, I, $CF_3$, $R_{20}$ as defined hereinbelow, $C_1$-$C_5$ linear or branched alkyl (e.g., methyl, ethyl, propyl), alkyleneamine (e.g., $CH_2$—$NH_2$), $C_1$-$C_5$ linear or branched haloalkyl (e.g., $CH_2CF_3$, $CHF_2$), OH, alkoxy (e.g., $OCH_3$), alkylene-OH (e.g., $CH_2$—OH), amide, alkylene-amide (e.g., $CH_2$—$C(O)NH_2$), C(O)-heterocyclic ring, amine (e.g., $NH_2$), alkylamine (e.g., $NH(CH_3)$), dialkylamine (e.g., $N(CH_3)_2$), $CF_3$, aryl, phenyl, halophenyl, heteroaryl, $C_3$-$C_5$ cycloalkyl (e.g., cyclopropyl, cyclohexyl), saturated, unsaturated, aromatice, single fused or spiral 3-8 membered heterocyclic ring, CN, and $NO_2$; each is a separate embodiment according to this invention.

In various embodiments, this invention provides a compound of this invention or its isomer, metabolite, pharmaceutically acceptable salt, pharmaceutical product, tautomer, hydrate, N-oxide, reverse amide analog, prodrug, isotopic variant (deuterated analog), PROTAC, polymorph, or crystal or combinations thereof. In various embodiments, this invention provides an isomer of the compound of this invention. In some embodiments, this invention provides a metabolite of the compound of this invention. In some embodiments, this invention provides a pharmaceutically acceptable salt of the compound of this invention. In some embodiments, this invention provides a pharmaceutical product of the compound of this invention. In some embodiments, this invention provides a tautomer of the compound of this invention. In some embodiments, this invention provides a hydrate of the compound of this invention. In some embodiments, this invention provides an N-oxide of the compound of this invention. In some embodiments, this invention provides a reverse amide analog of the compound of this invention. In some embodiments, "reverse amide analog" refers to acyclic amides or amides of acyclic amines. In some embodiments, this invention provides a prodrug of the compound of this invention. In some embodiments, this invention provides an isotopic variant (including but not limited to deuterated analog) of the compound of this invention. In some embodiments, this invention provides a PROTAC (Proteolysis targeting chimera) of the compound of this invention. In some embodiments, this invention provides a polymorph of the compound of this invention. In some embodiments, this invention provides a crystal of the compound of this invention.

In some embodiments, this invention provides composition comprising a compound of this invention, as described herein, or, In some embodiments, a combination of an isomer, metabolite, pharmaceutically acceptable salt, pharmaceutical product, tautomer, hydrate, N-oxide, reverse amide analog, prodrug, isotopic variant (deuterated analog), PROTAC, polymorph, or crystal of the compound of this invention.

In various embodiments, the term "isomer" includes, but is not limited to, stereoisomers including optical isomers and analogs, structural isomers and analogs, conformational isomers and analogs, and the like. In some embodiments, the isomer is a stereoisomer. In another embodiment, the isomer is an optical isomer.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

In various embodiments, this invention encompasses the use of various stereoisomers of the compounds of the invention. It will be appreciated by those skilled in the art that the compounds of the present invention may contain at least one chiral center. Accordingly, the compounds used in the methods of the present invention may exist in, and be isolated in, optically-active or racemic forms. The compounds according to this invention may further exist as stereoisomers which may be also optically-active isomers (e.g., enantiomers such as (R) or (S)), as enantiomerically enriched mixtures, racemic mixtures, or as single diastereomers, diastereomeric mixtures, or any other stereoisomers, including but not limited to: (R)(R), (R)(S), (S)(S), (S)(R), (R)(R)(R), (R)(R)(S), (R)(S)(R), (S)(R)(R), (R)(S)(S), (S)(R)(S), (S)(S)(R) or (S)(S)(S) stereoisomers. Some compounds may also exhibit polymorphism. It is to be understood that the present invention encompasses any racemic, optically-active, polymorphic, or stereroisomenc form, or mixtures thereof, which form possesses properties useful in the treatment of the various conditions described herein.

It is well known in the art how to prepare optically active forms (for example, by resolution of the racemic form by recrystallization techniques, by synthesis from optically-active starting materials, by chiral synthesis, or by chromatographic separation using a chiral stationary phase).

The compounds of the present invention can also be present in the form of a racemic mixture, containing substantially equivalent amounts of stereoisomers. In some embodiments, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 80% pure, more preferably at least about 95% pure, even more preferably at least about 98% pure, most preferably at least about 99% pure. In various embodiments, the compound according to the invention comprises a substantially pure stereoisomer. In some embodiments, the substantially pure stereoisomer is at least 70%; 75%; 80%; 85%; 90%; 93%; 95%; 97%; 98%; 99%; 99.5% pure; each represents a separate embodiment according to this invention.

In various embodiments, the compound comprises a single stereoisomer in a purity of >80%; >85%; >90%; >91%; >92%; >93%; >94%; >95%; >96%; >97%; >98%; >99%; >99.5% enantiomeric excess (ee); each represents a separate embodiment according to this invention. In various embodiments, the compound comprises a single stereoisomer in a purity >80%; >85%; >90%; >91%; >92%; >93%; >94%; >95%; >96%; >97%; >98%; >99%; >99.5% enantiomeric ratio (er); each represents a separate embodiment according to this invention. In various embodiments, the compound comprises a single stereoisomer in a purity higher than 80%>; 85%>; 90%>; 91%>; 92%>; 93%; 94%; 95%; 96%>; 97%; 98%>; 99%; 99.5%; each represents a separate embodiment according to this invention.

In various embodiments, the compound is a substantially pure single enantiomer. In various embodiments, the compound comprises a mixture of enantiomers. In various embodiments, the compound is a racemate.

In various embodiments, the compound has two chiral centers. In various embodiments, the compound comprises a mixture of stereoisomers. In various embodiments, the compound comprises a mixture of 2, 3, or 4 stereoisomers; each represents a separate embodiment according to this invention.

In various embodiments, the compound is a single stereoisomer. In various embodiments, the compound is a substantially pure single stereoisomer. In various embodiments, the substantially pure stereoisomer has at least 80%, 85%, 90%, 95%, 97%, 98%, 99% purity; each represents a separate embodiment according to this invention. In various embodiments, the compound is the substantially pure RR stereoisomer. In various embodiments, the compound is the substantially pure SS stereoisomer. In various embodiments, the compound is the substantially pure RS stereoisomer. In various embodiments, the compound is the substantially pure SR stereoisomer.

Compounds of the present invention can also be in the form of a hydrate, which means that the compound further includes a stoichiometric or non-stoichiometric amount of water bound by non-covalent intermolecular forces.

As used herein, when some chemical functional group (e.g., alkyl or aryl) is said to be "substituted", it is herein defined that one or more substitutions are possible. In some embodiments, the term "substituted" according to this invention, refers to but is not limited to at least one group selected from: halogen, $C_1$-$C_5$ linear or branched alkyl, OH, $C_1$-$C_5$ linear or branched alkyl-OH (e.g., $C(CH_3)_2CH_2$—OH, $CH_2CH_2$—OH), alkoxy (e.g., OMe), amide (e.g., C(O)N(R)$_2$, C(O)-pyrrolidine, C(O)-piperidine, N(R)$_2$, NH(R$_{10}$), N(R$_{10}$)(R$_{11}$), (e.g., N(CH$_3$)$_2$, NH$_2$), CF$_3$, aryl, phenyl, heteroaryl, substituted or unsubstituted $C_3$-$C_5$ cycloalkyl (e.g., cyclobutanol), substituted or unsubstituted 3-8 membered heterocyclic ring (e.g. pyran, oxetane, piperidine, pyrazole, methyl-pyrazole, triazole, imidazole), $C_1$-$C_5$ linear or branched haloalkyl (e.g., CHF$_2$, CH$_2$CF$_3$), halophenyl, (benzyloxy)phenyl, CN and NO$_2$; each represents a separate embodiment according to this invention.

Compounds of the present invention may exist in the form of one or more of the possible tautomers and depending on the conditions it may be possible to separate some or all of the tautomers into individual and distinct entities. It is to be understood that all of the possible tautomers, including all additional enol and keto tautomers and/or isomers are hereby covered. For example, the following tautomers, but not limited to these, are included: Tautomerization of the imidazole ring

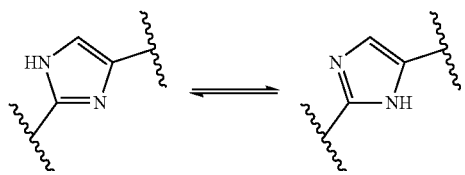 [SMILES: *c1c[nH]c(*)n1 ; *c1cnc(*)[nH]1]

Tautomerization of the Pyrazolone Ring:

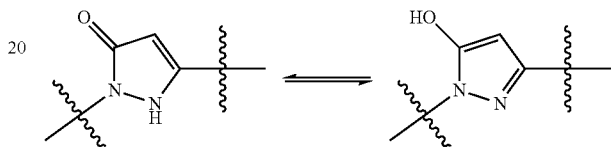

The invention includes "pharmaceutically acceptable salts" of the compounds of this invention, which may be produced, by reaction of a compound of this invention with an acid or base. Certain compounds, particularly those possessing acidic or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically acceptable salts of amines of the compounds of this invention may be prepared from an inorganic acid or from an organic acid. In various embodiments, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isethionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In various embodiments, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In various embodiments, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In some embodiments, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglumines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In various embodiments, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In some embodiments, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.10% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard- or soft-shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In various embodiments, the compounds of this invention are administered in combination with an anti-cancer therapy. Examples of such therapies include but are not limited to: chemotherapy, immunotherapy, radiotherapy, biological therapy, surgical intervention, and combinations thereof. In various embodiments, the compound is administered in combination with an anti-cancer agent by administering the compounds as herein described, alone or in combination with other agents.

When administering the compounds of the present invention, they can be administered systemically or, alternatively, they can be administered directly to a specific site where cancer is present. Thus, administering can be accomplished in any manner effective for delivering the compounds or the pharmaceutical compositions to the cancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

In various embodiments, the invention provides compounds and compositions, including any embodiment described herein, for use in any of the methods of this invention. In various embodiments, use of a compound of this invention or a composition comprising the same, will have utility in inhibiting, suppressing, enhancing, or stimulating a desired response in a subject, as will be understood by one skilled in the art. In some embodiments, the compositions may further comprise additional active ingredients, whose activity is useful for the particular application for which the compound of this invention is being administered.

The invention relates to the treatment, inhibition, and reduction of cancer, employing the use of a compound according to this invention or a pharmaceutically acceptable salt thereof. Accordingly, in various embodiments, this invention is directed to a method of treating, suppressing, reducing the severity, reducing the risk of developing or inhibiting cancer in a subject, comprising administering a compound according to this invention, to a subject suffering from cancer under conditions effective to treat, suppress, reduce the severity, reduce the risk of developing, or inhibit cancer in said subject. In some embodiments, the compound is a c-MYC mRNA translation modulator. In some embodiments, the compound is a c-MYC mRNA translation inhibitor. In some embodiments, the compound is a c-MYC inhibitor. In some embodiments, the compound is a c-MYC mRNA transcription regulator. In some embodiments, the compound is any combination of a c-MYC mRNA translation modulator, a c-MYC mRNA transcription regulator and a c-MYC inhibitor. In some embodiments, the compound is any one of the compounds listed in Table 1; each compound represents a separate embodiment according to this invention. In some embodiments, the cancer is early cancer. In some embodiments, the cancer is advanced cancer. In some embodiments, the cancer is invasive cancer. In some embodiments, the cancer is metastatic cancer. In some embodiments, the cancer is drug resistant cancer.

In some embodiments, the cancer is selected from the following list: bladder cancer (urothelial carcinoma), myelodysplasia, breast cancer, cervix cancer, endometrium cancer, esophagus cancer, head and neck cancer (squamous cell carcinoma), kidney cancer (e.g., renal cell carcinoma, clear cell renal cell carcinoma), liver cancer (hepatocellular carcinoma), lung cancer (e.g., metastatic, non-small cell, NSCLC, squamous cell carcinoma, small cell (SCLC)), metastatic cancer (e.g., to brain), nasopharynx cancer, solid tumor cancer, stomach cancer, adrenocortical carcinoma, Glioblastoma multiforme, acute myeloid leukemia, chronic lymphocytic leukemia, lymphoma (e.g., Hodgkin's (classical), diffuse large B-cell, primary central nervous system), malignant melanoma, uveal melanoma, meningioma, multiple myeloma, breast cancer, metastatic breast cancer, anus cancer (e.g. squamous cell), biliary cancer, bladder cancer, muscle invasive urothelial carcinoma, colorectal cancer, metastatic colorectal cancer, fallopian tube cancer, gastroesophageal junction cancer (e.g., adenocarcinoma), larynx cancer (e.g., squamous cell), merkel cell cancer, mouth cancer, ovary cancer (e.g., epithelial), pancreas cancer (e.g., adenocarcinoma, metastatic), penis cancer (e.g., squamous cell carcinoma), peritoneum cancer, prostate cancer (e.g., castration-resistant, metastatic), rectum cancer, skin cancer (e.g., basal cell carcinoma, squamous cell carcinoma), small intestine cancer (e.g., adenocarcinoma), testicular cancer, thymus cancer, anaplastic thyroid cancer, cholangiocarcinoma, chordoma, cutaneous T-cell lymphoma, digestive-gastrointestinal cancer, familial pheochromocytoma-paraganglioma, Glioma, HTLV-1-associated adult T-cell leukemia-lymphoma, hematologic-blood cancer, hepatitis C(HCV), papillomaviral respiratory Infection, uterine leiomyosarcoma, acute lymphocytic leukemia, chronic myeloid leukemia, T-cell Lymphoma, follicular lymphoma, primary mediastinal large B-cell lymphoma, diffuse large B-cell testicular lymphoma, melanoma, malignant mesothelioma, pleural mesothelioma, mycosis fungoides, neuroendocrine cancer, oral epithelial dysplasia, Sarcoma, severe sepsis, sezary syndrome, smoldering myeloma, soft tissue sarcoma, nasal natural killer (NK) cell T-cell lymphoma, peripheral T-cell lymphoma.

In some embodiments, the cancer is selected from a list including but not limited to: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer.

In some embodiments, the cancer may be selected from solid tumors and non-solid tumors.

In various embodiments, this invention is directed to a method for suppressing, reducing or inhibiting tumor growth in a subject, comprising administering a compound of this invention, to a subject under conditions effective to suppress, reduce or inhibit tumor growth in said subject.

In some embodiments, the tumor may be a solid tumor or a non-solid tumor.

In some embodiments, the solid tumor cancer is selected from a list including but not limited to: breast cancer, ovarian carcinoma, prostate cancer, colon cancer, gastric cancer, glioblastoma, medulloblastoma, melanoma, non-small cell lung carcinoma, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer.

In some embodiments, the non-solid tumors include but not limited to: hematological malignancies including leukemia, lymphoma or myeloma and inherited cancers such as retinoblastoma and Wilm's tumor.

In some embodiments, the non-solid tumor cancer is selected from a list including but not limited to: acute myeloid leukemia, chronic myelogenous leukemia, Hodgkin's and Burkitt's lymphoma, diffuse large Bcell lymphoma, primary central nervous system lymphoma, glioblastoma, medulloblastoma, germinal center-derived lymphomas, myeloma, retinoblastoma and Wilm's tumor.

Therefore, and in various embodiments, this invention is directed to a method of treating, suppressing, reducing the severity, reducing the risk of developing or inhibiting cancer comprising administering a compound of this invention to a subject suffering from cancer under conditions effective to treat, suppress, reduce the severity, reduce the risk of developing, or inhibit the cancer. In some embodiments, the cancer is early cancer. In some embodiments, the cancer is advanced cancer. In some embodiments, the cancer is invasive cancer. In some embodiments, the cancer is metastatic cancer. In some embodiments, the cancer is drug resistant cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting breast cancer comprising administering a compound of this invention to a subject suffering from breast cancer under conditions effective to treat, suppress, reduce the severity, reduce the risk of developing, or inhibit the breast cancer. In some embodiments, the breast cancer is early breast cancer. In some embodiments, the breast cancer is advanced breast cancer. In some embodiments, the breast cancer is invasive breast cancer. In some embodiments, the breast cancer is metastatic breast cancer. In some embodiments, the breast cancer is drug resistant breast cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting ovarian carcinoma comprising administering a compound of this invention to a subject suffering from ovarian carcinoma under conditions effective to treat, suppress, reduce the severity, reduce the risk of developing, or inhibit the ovarian carcinoma. In some embodiments, the ovarian carcinoma is early ovarian carcinoma. In some embodiments, the ovarian carcinoma is advanced ovarian carcinoma. In some embodiments, the ovarian carcinoma is invasive ovarian carcinoma. In some embodiments, the ovarian carcinoma is metastatic ovarian carcinoma. In some embodiments, the ovarian carcinoma is drug resistant ovarian carcinoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting acute myeloid leukemia comprising administering a compound of this invention to a subject suffering from acute myeloid leukemia under conditions effective to treat, suppress, reduce the severity, reduce the risk of developing, or inhibit the acute myeloid leukemia. In some embodiments, the acute myeloid leukemia is early acute myeloid leukemia. In some embodiments, the acute myeloid leukemia is advanced acute myeloid leukemia. In some embodiments, the acute myeloid leukemia is invasive acute myeloid leukemia. In some embodiments, the acute myeloid leukemia is metastatic acute myeloid leukemia. In some embodiments, the acute myeloid leukemia is drug resistant acute myeloid leukemia. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting chronic myelogenous leukemia comprising administering a compound of this invention to a subject suffering from chronic myelogenous leukemia under conditions effective to treat, suppress, reduce the severity, reduce the risk of developing, or inhibit the chronic myelogenous leukemia. In some embodiments, the chronic myelogenous leukemia is early chronic myelogenous leukemia. In some embodiments, the chronic myelogenous leukemia is advanced chronic myelogenous leukemia. In some embodiments, the chronic myelogenous leukemia is invasive chronic myelogenous leukemia. In some embodiments, the chronic myelogenous leukemia is metastatic chronic myelogenous leukemia. In some embodiments, the chronic myelogenous leukemia is drug resistant chronic myelogenous leukemia. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting Hodgkin's and/or Burkitt's lymphoma comprising administering a compound of this invention to a subject suffering from Hodgkin's and/or Burkitt's lymphoma under conditions effective to treat, suppress, reduce the severity, reduce the risk of developing, or inhibit the Hodgkin's and/or Burkitt's lymphoma. In some embodiments, the Hodgkin's and/or Burkitt's lymphoma is early Hodgkin's and/or Burkitt's lymphoma. In some embodiments, the Hodgkin's and/or Burkitt's lymphoma is advanced Hodgkin's and/or Burkitt's lymphoma. In some embodiments, the Hodgkin's and/or Burkitt's lymphoma is invasive Hodgkin's and/or Burkitt's lymphoma. In some embodiments, the Hodgkin's and/or Burkitt's lymphoma is metastatic Hodgkin's and/or Burkitt's lymphoma. In some embodiments, the Hodgkin's and/or Burkitt's lymphoma is drug resistant Hodgkin's and/or Burkitt's lymphoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting diffuse large Bcell lymphoma comprising administering a compound of this invention to a subject suffering from diffuse large Bcell lymphoma under conditions effective to treat, suppress, reduce the severity, reduce the risk of developing, or inhibit the diffuse large Bcell lymphoma. In some embodiments, the diffuse large Bcell lymphoma is early diffuse large Bcell lymphoma. In some embodiments, the diffuse large Bcell lymphoma is advanced diffuse large Bcell lymphoma. In some embodiments, the diffuse large Bcell lymphoma is invasive diffuse large Bcell lymphoma. In some embodiments, the diffuse large Bcell lymphoma is metastatic diffuse large Bcell lymphoma. In some embodiments, the diffuse large Bcell lymphoma is drug resistant diffuse large Bcell lymphoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting prostate cancer comprising administering a compound of this invention to a subject suffering from prostate cancer under conditions effective to treat, suppress, reduce the severity, reduce the risk of developing, or inhibit the prostate cancer. In some embodiments, the prostate cancer is early prostate cancer. In some embodiments, the prostate cancer is advanced prostate cancer. In some embodiments, the prostate cancer is invasive prostate cancer. In some embodiments, the prostate cancer is metastatic prostate cancer. In some embodiments, the prostate cancer is drug resistant prostate cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colon cancer comprising administering a compound of this invention to a subject suffering from colon cancer under conditions effective to treat, suppress, reduce the severity, reduce the risk of developing, or inhibit the colon cancer. In some embodiments, the colon cancer is early colon cancer. In some embodiments, the colon cancer is advanced colon cancer. In some embodiments, the colon cancer is invasive colon cancer. In some embodiments, the colon cancer is metastatic colon cancer. In some embodiments, the colon cancer is drug resistant colon cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting gastric cancer comprising administering a compound of this invention to a subject suffering from gastric cancer under conditions effective to treat, suppress, reduce the severity, reduce the risk of developing, or inhibit the gastric cancer. In some embodiments, the gastric cancer is early gastric cancer. In some embodiments, the gastric cancer is advanced gastric cancer. In some embodiments, the gastric cancer is invasive gastric cancer. In some embodiments, the gastric cancer is metastatic gastric cancer. In some embodiments, the gastric cancer is drug resistant gastric cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting lymphoma comprising administering a compound of this invention to a subject suffering from lymphoma under conditions effective to treat, suppress, reduce the severity, reduce the risk of developing, or inhibit the lymphoma. In some embodiments, the lymphoma is early lymphoma. In some embodiments, the lymphoma is advanced lymphoma. In some embodiments, the lymphoma is invasive lymphoma. In some embodiments, the lymphoma is metastatic lymphoma. In some embodiments, the lymphoma is drug resistant lymphoma. In some embodiments, the lymphoma is primary central nervous system lymphoma. In some embodiments, the lymphoma is germinal center-derived lymphoma. In some embodiments, the lymphoma is Hodgkin's lymphoma. In some embodiments, the lymphoma is Burkitt's lymphoma. In some embodiments, the lymphoma is diffuse large B-cell lymphoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting glioblastoma comprising administering a compound of this invention to a subject suffering from glioblastoma under conditions effective to treat, suppress, reduce the severity, reduce the risk of developing, or inhibit the glioblastoma. In some embodiments, the glioblastoma is early glioblastoma. In some embodiments, the glioblastoma is advanced glioblastoma. In some embodiments, the glioblastoma is invasive glioblastoma. In some embodiments, the glioblastoma is metastatic glioblastoma. In some embodiments, the glioblastoma is drug resistant glioblastoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting medulloblastoma comprising administering a compound of this invention to a subject suffering from medulloblastoma under conditions effective to treat, suppress, reduce the severity, reduce the risk of developing, or inhibit the medulloblastoma. In some embodiments, the medulloblastoma is early medulloblastoma. In some embodiments, the medulloblastoma is advanced medulloblastoma. In some embodiments, the medulloblastoma is invasive medulloblastoma. In some embodiments, the medulloblastoma is metastatic medulloblastoma. In some embodiments, the medulloblastoma is drug resistant medulloblastoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting melanoma comprising administering a compound of this invention to a subject suffering from melanoma under conditions effective to treat, suppress, reduce the severity, reduce the risk of developing, or inhibit the melanoma. In some embodiments, the melanoma is early melanoma. In some embodiments, the melanoma is advanced melanoma. In some embodiments, the melanoma is invasive melanoma. In some embodiments, the melanoma is metastatic melanoma. In some embodiments, the melanoma is drug resistant melanoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting non-small cell lung carcinoma comprising administering a compound of this invention to a subject suffering from non-small cell lung carcinoma under conditions effective to treat, suppress, reduce the severity, reduce the risk of developing, or inhibit the non-small cell lung carcinoma. In some embodiments, the non-small cell lung carcinoma is early non-small cell lung carcinoma. In some embodiments, the non-small cell lung carcinoma is advanced non-small cell lung carcinoma. In some embodiments, the non-small cell lung carcinoma is invasive non-small cell lung carcinoma. In some embodiments, the non-small cell lung carcinoma is metastatic non-small cell lung carcinoma. In some embodiments, the non-small cell lung carcinoma is drug resistant non-small cell lung carcinoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting esophageal squamous cell carcinoma comprising administering a compound of this invention to a subject suffering from esophageal squamous cell carcinoma under conditions effective to treat, suppress, reduce the severity, reduce the risk of developing, or inhibit the esophageal squamous cell carcinoma. In some embodiments, the esophageal squamous cell carcinoma is early esophageal squamous cell carcinoma. In some embodiments, the esophageal squamous cell carcinoma is advanced esophageal squamous cell carcinoma. In some embodiments, the esophageal squamous cell carcinoma is invasive esophageal squamous cell carcinoma. In some embodiments, the esophageal squamous cell carcinoma is metastatic esophageal squamous cell carcinoma. In some embodiments, the esophageal squamous cell carcinoma is drug resistant esophageal squamous cell carcinoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting osteosarcoma comprising administering a compound of this invention to a subject suffering from osteosarcoma under conditions effective to treat, suppress, reduce the severity, reduce the risk of developing, or inhibit the osteosarcoma. In some embodiments, the osteosarcoma is early osteosarcoma. In some embodiments, the osteosarcoma is advanced osteosarcoma. In some embodiments, the osteosarcoma is invasive osteosarcoma. In some embodiments, the osteosarcoma is metastatic osteosarcoma. In some embodiments, the osteosarcoma is drug resistant osteosarcoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting bladder cancer comprising administering a compound of this invention to a subject suffering from bladder cancer under conditions effective to treat, suppress, reduce the severity, reduce the risk of developing, or inhibit the bladder cancer. In some embodiments, the bladder cancer is early bladder cancer. In some embodiments, the bladder cancer is advanced bladder cancer. In some embodiments, the bladder cancer is invasive bladder cancer. In some embodiments, the bladder cancer is metastatic bladder cancer. In some embodiments, the bladder cancer is drug resistant bladder cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting pancreatic cancer comprising administering a compound of this invention to a subject suffering from pancreatic cancer under conditions effective to treat, suppress, reduce the severity, reduce the risk of developing, or inhibit the pancreatic cancer. In some embodiments, the pancreatic cancer is early pancreatic cancer. In some embodiments, the pancreatic cancer is advanced pancreatic cancer. In some embodiments, the pancreatic cancer is invasive pancreatic cancer. In some embodiments, the pancreatic cancer is metastatic pancreatic cancer. In some embodiments, the pancreatic cancer is drug resistant pancreatic cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting lung adenocarcinoma comprising administering a compound of this invention to a subject suffering from lung adenocarcinoma under conditions effective to treat, suppress, reduce the severity, reduce the risk of developing, or inhibit the lung adenocarcinoma. In some embodiments, the lung adenocarcinoma is early lung adenocarcinoma. In some embodiments, the lung adenocarcinoma is advanced lung adenocarcinoma. In some embodiments, the lung adenocarcinoma is invasive lung adenocarcinoma. In some embodiments, the lung adenocarcinoma is metastatic lung adenocarcinoma. In some embodiments, the lung adenocarcinoma is drug resistant lung adenocarcinoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting thyroid cancer comprising administering a compound of this invention to a subject suffering from thyroid cancer under conditions effective to treat, suppress, reduce the severity, reduce the risk of developing, or inhibit the thyroid cancer. In some embodiments, the thyroid cancer is early thyroid cancer. In some embodiments, the thyroid cancer is advanced thyroid cancer. In some embodiments, the thyroid cancer is invasive thyroid cancer. In some embodiments, the thyroid cancer is metastatic thyroid cancer. In some embodiments, the thyroid cancer is drug resistant thyroid cancer. In some embodiments, the thyroid cancer is BRAF V600E thyroid cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting choroid plexus carcinoma comprising administering a compound of this invention to a subject suffering from choroid plexus carcinoma under conditions effective to treat, suppress, reduce the severity, reduce the risk of developing, or inhibit the choroid plexus carcinoma. In some embodiments, the choroid plexus carcinoma is early choroid plexus carcinoma. In some embodiments, the choroid plexus carcinoma is advanced choroid plexus carcinoma. In some embodiments, the choroid plexus carcinoma is invasive choroid plexus carcinoma. In some embodiments, the choroid plexus carcinoma is metastatic choroid plexus carcinoma. In some embodiments, the choroid plexus carcinoma is drug resistant choroid plexus carcinoma. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colitis-associated cancer comprising administering a compound of this invention to a subject suffering from colitis-associated cancer under conditions effective to treat, suppress, reduce the severity, reduce the risk of developing, or inhibit the colitis-associated cancer. In some embodiments, the colitis-associated cancer is early colitis-associated cancer. In some embodiments, the colitis-associated cancer is advanced colitis-associated cancer. In some embodiments, the colitis-associated cancer is invasive colitis-associated cancer. In some embodiments, the colitis-associated cancer is metastatic colitis-associated cancer. In some embodiments, the colitis-associated cancer is drug resistant colitis-associated cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting ovarian cancer comprising administering a compound of this invention to a subject suffering from ovarian cancer under conditions effective to treat, suppress, reduce the severity, reduce the risk of developing, or inhibit the ovarian cancer. In some embodiments, the ovarian cancer is early ovarian cancer. In some embodiments, the ovarian cancer is advanced ovarian cancer. In some embodiments, the ovarian cancer is invasive ovarian cancer. In some embodiments, the ovarian cancer is metastatic ovarian cancer. In some embodiments, the ovarian cancer is drug resistant ovarian cancer. In some embodiments, the ovarian cancer is epithelial ovarian cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colorectal cancer comprising administering a compound of this invention to a subject suffering from colorectal cancer under conditions effective to treat, suppress, reduce the severity, reduce the risk of developing, or inhibit the colorectal cancer. In some embodiments, the colorectal cancer is early colorectal cancer. In some embodiments, the colorectal cancer is advanced colorectal cancer. In some embodiments, the colorectal cancer is invasive colorectal cancer. In some embodiments, the colorectal cancer is metastatic colorectal cancer. In some embodiments, the colorectal cancer is drug resistant colorectal cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting uterine cancer comprising administering a compound of this invention to a subject suffering from uterine cancer under conditions effective to treat, suppress, reduce the severity, reduce the risk of developing, or inhibit the uterine cancer. In some embodiments, the uterine cancer is early uterine cancer. In some embodiments, the uterine cancer is advanced uterine cancer. In some embodiments, the uterine cancer is invasive uterine cancer. In some embodiments, the uterine cancer is metastatic uterine cancer. In some embodiments, the uterine cancer is drug resistant uterine cancer. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the compound is any one of the compounds listed in Table 1; each compound represents a separate embodiment according to this invention.

In various embodiments, this invention provides methods for increasing the survival of a subject suffering from metastatic cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the cancer is breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, thyroid cancer, choroid plexus carcinoma, colitis-associated cancer, colorectal cancer, or uterine cancer; each represents a separate embodiment according to this invention.

In various embodiments, this invention provides methods for treating, suppressing, reducing the severity, reducing the risk, or inhibiting advanced cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is a c-MYC mRNA translation modulator. In some embodiments, the compound is a c-MYC mRNA translation inhibitor. In some embodiments, the compound is a c-MYC mRNA transcription regulator. In some embodiments, the compound is selective to c-MYC. In some embodiments, the compound reduces the amount of c-Myc protein in a cell. In some embodiments, the cancer is breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, thyroid cancer, choroid plexus carcinoma, colitis-associated cancer, colorectal cancer, or uterine cancer; each represents a separate embodiment according to this invention.

The compounds of the present invention are useful in the treatment, reducing the severity, reducing the risk of developing, or inhibition of early cancer, metastatic cancer, advanced cancer, drug resistant cancer, and various forms of cancer. In a preferred embodiment the cancer is breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, thyroid cancer, choroid plexus carcinoma, colitis-associated cancer, colorectal cancer, or uterine cancer; each represents a separate embodiment according to this invention. Based upon their believed mode of action, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In various embodiments, other types of cancers that may be treatable with the c-MYC mRNA translation modulators according to this invention include: adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, Kaposi's sarcoma, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, hepatocellular cancer, hematological cancer or any combination thereof. In some embodiments the cancer is invasive. In some embodiments the cancer is metastatic cancer. In some embodiments the cancer is advanced cancer. In some embodiments the cancer is drug resistant cancer.

In various embodiments "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In various embodiments "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism; g) Cells and tumors with activating RAS mutations are relatively resistant to most anti-cancer agents. Thus, the resistance to anticancer agents used in chemotherapy is the main cause of treatment failure in malignant disorders, provoking tumors to become resistant. Drug resistance is the major cause of cancer chemotherapy failure.

In various embodiments "resistant cancer" refers to drug-resistant cancer as described herein above. In some embodiments "resistant cancer" refers to cancer cells that acquire resistance to any treatment such as chemotherapy, radiotherapy or biological therapy.

In various embodiments, this invention is directed to treating, suppressing, reducing the severity, reducing the risk of developing, or inhibiting cancer in a subject, wherein the subject has been previously treated with chemotherapy, radiotherapy or biological therapy.

In various embodiments "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In various embodiments, "Radiotherapy" (also referred herein as "Radiation therapy") refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In various embodiments "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

When the compounds or pharmaceutical compositions of the present invention are administered to treat, suppress, reduce the severity, reduce the risk of developing, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

In various embodiments, the compound according to this invention, is administered in combination with an anti-cancer therapy. Examples of such therapies include but are not limited to: chemotherapy, immunotherapy, radiotherapy, biological therapy, surgical intervention, and combinations thereof.

In various embodiments, the compound is administered in combination with an anti-cancer agent by administering the compounds as herein described, alone or in combination with other agents.

In various embodiments, the composition for cancer treatment of the present invention can be used together with existing chemotherapy drugs or be made as a mixture with them. Such a chemotherapy drug includes, for example, alkylating agents, nitrosourea agents, antimetabolites, antitumor antibiotics, alkaloids derived from plant, topoisomerase inhibitors, hormone therapy medicines, hormone antagonists, aromatase inhibitors, P-glycoprotein inhibitors, platinum complex derivatives, other immunotherapeutic drugs, and other anticancer agents. Further, they can be used together with hypoleukocytosis (neutrophil) medicines that are cancer treatment adjuvant, thrombopenia medicines, antiemetic drugs, and cancer pain medicines for patient's QOL recovery or be made as a mixture with them.

In various embodiments, this invention provides a method of modulating c-MYC mRNA translation in a cell, comprising contacting a compound represented by the structure of formula I, II and/or I(a)-I(o) and/or by the structures listed in Table 1, as defined herein above, with a cell, thereby modulating c-MYC mRNA translation in said cell. In some embodiments, the method is carried out by regulating c-MYC mRNA splicing. In some embodiments, the method is carried out by inclusion or exclusion of untranslated region or alternative usage of exons. In some embodiments, the method is carried out by regulation of c-MYC mRNA modifications. In some embodiments, the method is carried out by regulation of the interaction of RNA binding protein with c-MYC mRNA thereby changing mRNA localization. In some embodiments, the method is carried out by regulating c-MYC mRNA localization in the cytoplasm. In some embodiments, the method is carried out by regulating ribosomes or ribosome accessory factor to c-MYC mRNA. In some embodiments, the method is carried out by reducing the amount of c-MYC protein in the cell.

This invention further provides a method of regulating c-MYC mRNA transcription in a cell, comprising contacting a compound represented by the structure of formula I, II and/or I(a)-I(o) and/or by the structures listed in Table 1, as defined herein above, with a cell, thereby regulating c-MYC mRNA transcription in said cell. In some embodiments, the method is carried out by regulating c-MYC mRNA splicing. In some embodiments, the method is carried out by inclusion or exclusion of untranslated region or alternative usage of exons. In some embodiments, the method is carried out by regulation of c-MYC mRNA modifications. In some embodiments, the method is carried out by regulation of the interaction of RNA binding protein with c-MYC mRNA thereby changing mRNA localization. In some embodiments, the method is carried out by regulating c-MYC mRNA localization in the cytoplasm. In some embodiments, the method is carried out by regulating ribosomes or ribosome accessory factor to c-MYC mRNA. In some embodiments, the method is carried out by reducing the amount of c-MYC protein in the cell.

In various embodiments, this invention is directed to a method of destroying a cancerous cell comprising providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture).

A still further aspect of the present invention relates to a method of treating or preventing a cancerous condition that includes providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to other embodiments, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

As used herein, subject or patient refers to any mammalian patient, including without limitation, humans and other primates, dogs, cats, horses, cows, sheep, pigs, rats, mice, and other rodents. In various embodiments, the subject is male. In some embodiments, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The following examples are presented in order to more fully illustrate the preferred embodiments of the invention. They should in no way, however, be construed as limiting the broad scope of the invention.

EXAMPLES

Example 1

General Synthetic Details for Compounds of the Invention (Schemes 1-22)
General Methods All reagents were commercial grade and were used as received without further purification, unless otherwise specified. Reagent grade solvents were used in all cases, unless otherwise specified. Thin layer chromatography was carried out using pre-coated silica gel F-254 plates (thickness 0.25 mm). $^1$H-NMR and $^{19}$F-NMR spectra were recorded on a Bruker Bruker Avance 400 MHz or Avance III 400 MHz spectrometer. The chemical shifts are expressed in ppm using the residual solvent as internal standard. Splitting patterns are designated as s (singlet), d (doublet), dd (doublet of doublets), t (triplet), dt (doublet of triplets), q (quartet), m (multiplet) and br s (broad singlet).

Abbreviations

AcOH Acetic acid
amphos Bis(di-tert-butyl(4-dimethylaminophenyl)phosphine
Boc tert-Butyloxycarbonyl
BuLi n-butyllithium
t-BuLi tert-butyllithium
DBU 1,8-Diazabicyclo[5.4.0]undec-7-ene
dppb 1,4-Bis(diphenylphosphino)butane
dppf 1,1'-Bis(diphenylphosphino)ferrocene
DCM Dichloromethane
DCE 1,2-Dichloroethane
DIBAL-H Diisobutylaluminum hydride
DIPEA N,N-Diisopropylethylamine
DMF N,N-Dimethylformamide
DMA N,N-Dimethylacetamide
DMAP 4-Dimethylaminopyridine
DME 1,2-Dimethoxyethane
DMSO Dimethylsulfoxide
DPPA Diphenyl phosphoryl azide
DTBF 1,1'-Bis(di-tert-butylphosphino)ferrocene
EDC·HCl N-(3-Dimethylaminopropyl)-N-ethylcarbodiimide hydrochloride HATU [O-(7-Azabenzotriazol-1-yl)-N,N,N',N'-tetramethyluronium-hexafluorphosphate]
HPLC High performance liquid chromatography
MsCl Methanesulfonyl chloride
NBS N-Bromosuccinimide
POBr₃ Phosphorus(V) oxybromide
Py-HBr₃ Pyridinium tribromide
SEM 2-(Trimethylsilyl)ethoxymethyl
T3P Propylphosphonic anhydride
TBAF Tetrabutylammonium fluoride
TCFH N,N,N,N-tetramethylchloroformamidinium hexafluorophosphate
TFA Trifluoroacetic acid
THF Tetrahydrofuran
TMS-OTf Trimethylsilyl trifluoromethanesulfonate General Synthesis of Compounds of the Invention

Synthesis of benzo[d]imidazo[2,1-b]thiazole Compounds, Structure I

Scheme 1. First generation synthesis of benzo[d]imidazo[2,1-b]thiazole compounds, Structure I.

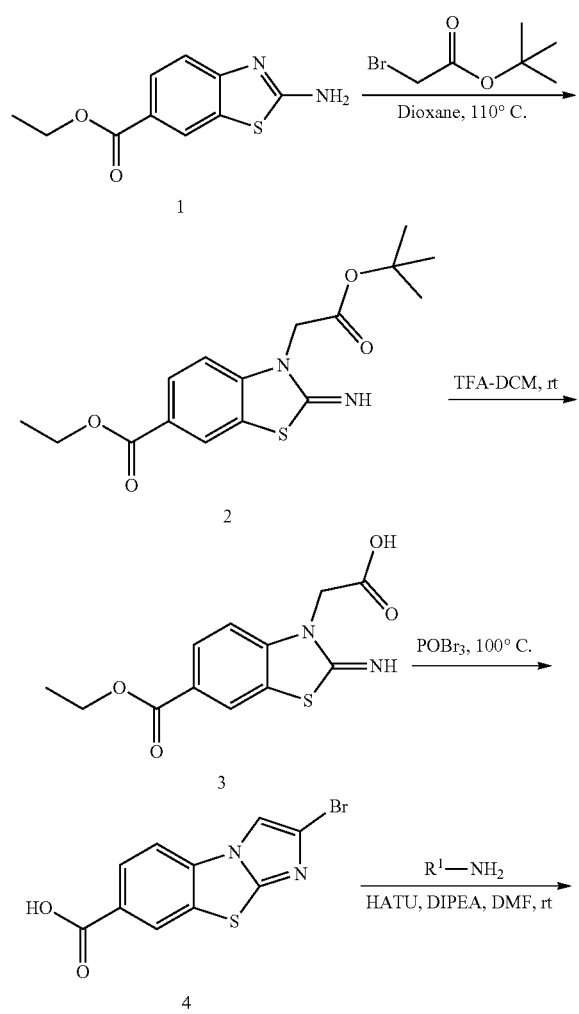

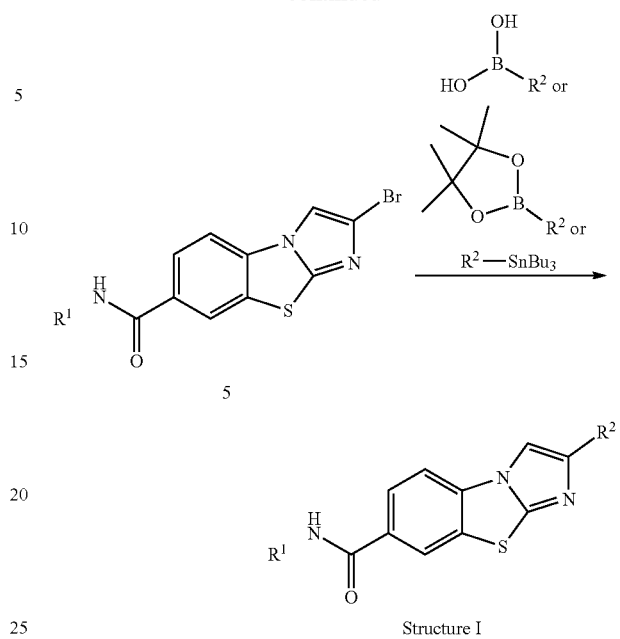

The first step of the synthesis involves alkylation of ethyl 2-aminobenzothiazole-6-carboxylate 1 with tert-butyl bromoacetate at elevated temperature affording alkylated intermediate 2. The tert-butyl group was removed using a mixture of TFA-DCM to generate the carboxylic acid intermediate 3. Treatment of the carboxylic acid intermediate 3 with phosphorus(V) oxybromide at elevated temperature results in intramolecular cyclization to form the benzo[d]imidazo[2,1-b]thiazole intermediate 4. The acid moiety of the left-hand side (LHS) of intermediate 4 was elaborated to the amides, by HATU mediated coupling with a variety of amines affording the amide intermediates 5. The final step of the synthetic sequence involves palladium catalyzed cross-coupling to introduce an aryl/heteroaryl component at the bromo substituent of the heterocyclic intermediate 5. Cross-coupling partners to introduce $R_2$ include various boronic acid/esters (Suzuki-Miyaura coupling) or various organostannane reagents (Stille coupling) to furnish the final compounds with various right-hand sides (RHS), Structure I.

Synthesis of benzo[d]imidazo[2,1-b]thiazole Compounds, Structure I

Scheme 2. Second generation synthesis of benzo[d]imidazo[2,1-b]thiazole compounds, Structure II.

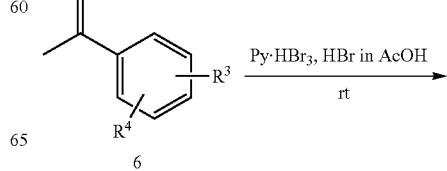

283
-continued

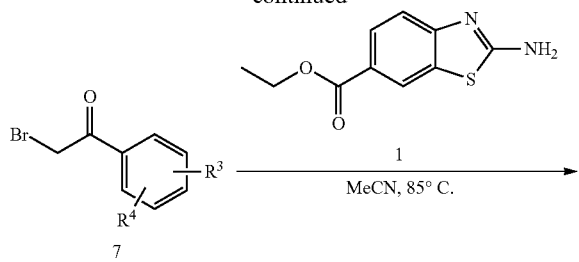

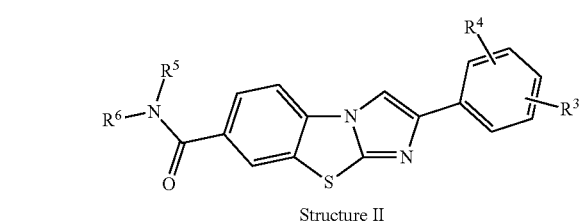

The first step of the synthesis involves bromination of the a-carbonyl position of various substituted aryl methyl ketones 6, using pyridinium tribromide in the presence of HBr in acetic acid affording substituted phenacyl bromide intermediates 7. These intermediates 7 facilitate ready diversification of the right-hand side (RHS) of the final Compounds, Structure II. Intermediate 7 undergoes a alkylation reaction followed by intramolecular cyclization with ethyl 2-aminobenzothiazole-6-carboxylate 1 at elevated temperature to from ester benzo[d]imidazo[2,1-b]thiazole intermediate 8. Hydrolysis of ester intermediate 8 with sodium hydroxide in water/THF mixture affords acid intermediate 9. The final step involves an amide coupling of various primary\secondary amines with acid intermediate 9, using HATU as a coupling reagent delivering the final compounds with various left-hand side (LHS) amides, Structure II.

284

Alternative Synthesis of benzo[d]imidazo[2,1-b]thiazole Compounds, Structure II Scheme 3. Alternative synthesis of benzo[d]imidazo[2,1-b]thiazole compounds, Structure II.

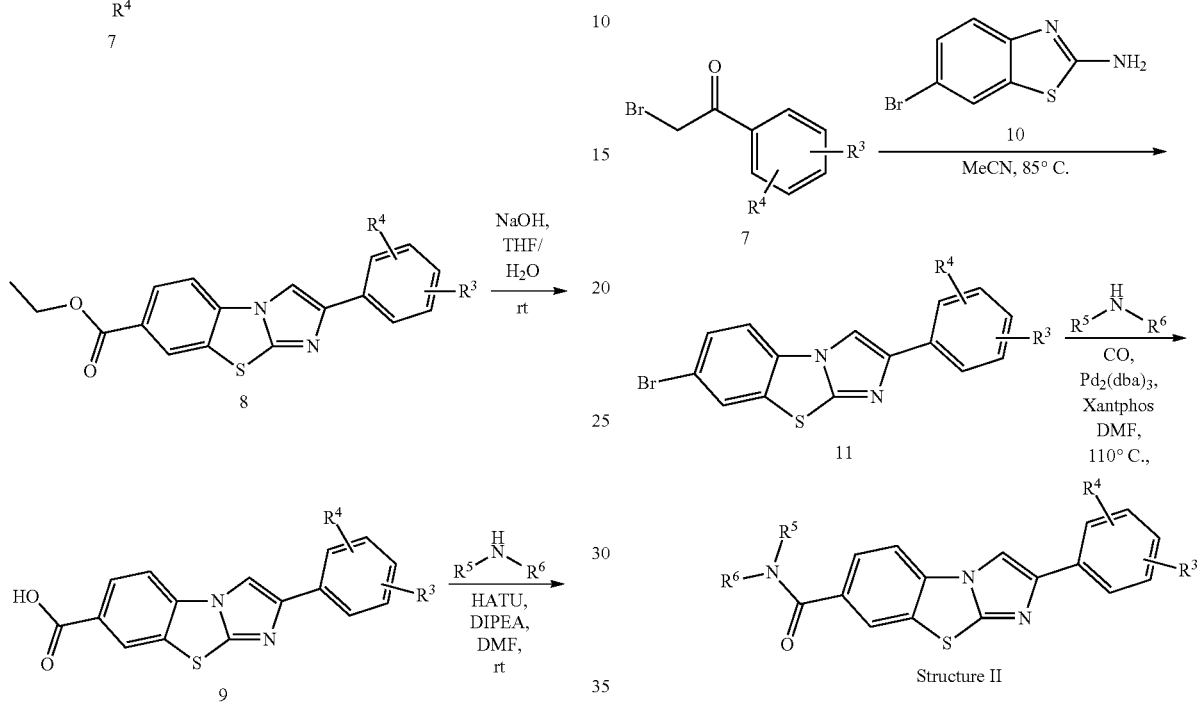

The first step involves a "one-pot" alkylation and intramolecular cyclization reaction between substituted phenacyl bromide intermediates 7 (as in Scheme 2) and 2-amino-6-bromobenzothiazole 10 at elevated temperature affording 7-bromo-2-aryl-1benzo[d]imidazo[2,1-b]thiazole intermediates 11. The bromo heterocyclic intermediate 11 is employed as the key starting material for the final palladium-catalyzed aminocarbonylation reaction at elevated temperature. Various primary\secondary amines are used in this final palladium-catalyzed aminocarbonylation reaction to provide a variety of left-hand side (LHS) amides, Structure II.

Synthesis of Reverse Amide benzo[d]imidazo[2,1-b]thiazole Compounds, Structure III Scheme 4. Synthesis of reverse amide benzo[d]imidazo[2,1-b]thiazole compounds, Structure III.

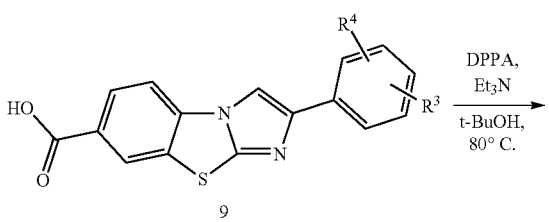

-continued

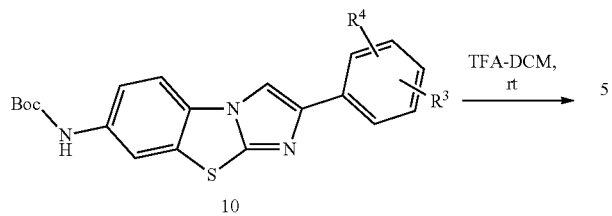

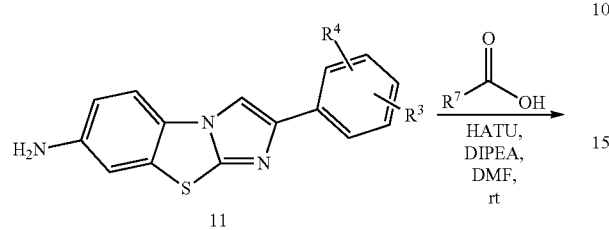

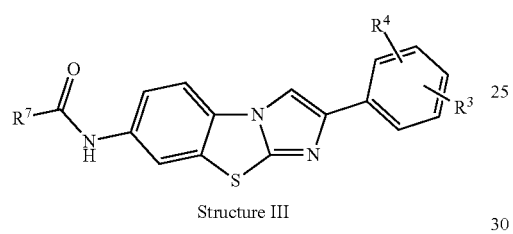

Structure III

The first step of the synthesis proceeds via a Curtius Rearrangement, using diphenyl phosphoryl azide (DPPA) and tert-butanol in the presence of triethylamine at elevated temperature affording N-Boc amine intermediate 10. N-Boc deprotection of intermediate 10 using a mixture of TFA in DCM enabled ready access to the 7-amino-2-aryl-lbenzo[d]imidazo[2,1-b]thiazole intermediate 11. The final step involves amide coupling of the amine intermediate 11 with a variety of carboxylic acids, using HATU as a coupling reagent to furnish the desired left-hand side (LHS) reverse amides, Structure III.

Synthesis of 4-(methylcarbamoyl)phenyl)benzo[4,5]imidazo[2,1-b]thiazole-7-carboxamide compounds, Structure IV Scheme 5.
Synthesis of 4-(methylcarbamoyl)phenyl)benzo[4,5]imidazo[2,1-b]thiazole-7-carboxamide compounds, Structure IV.

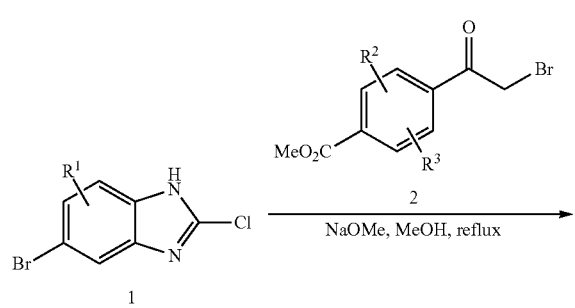

-continued

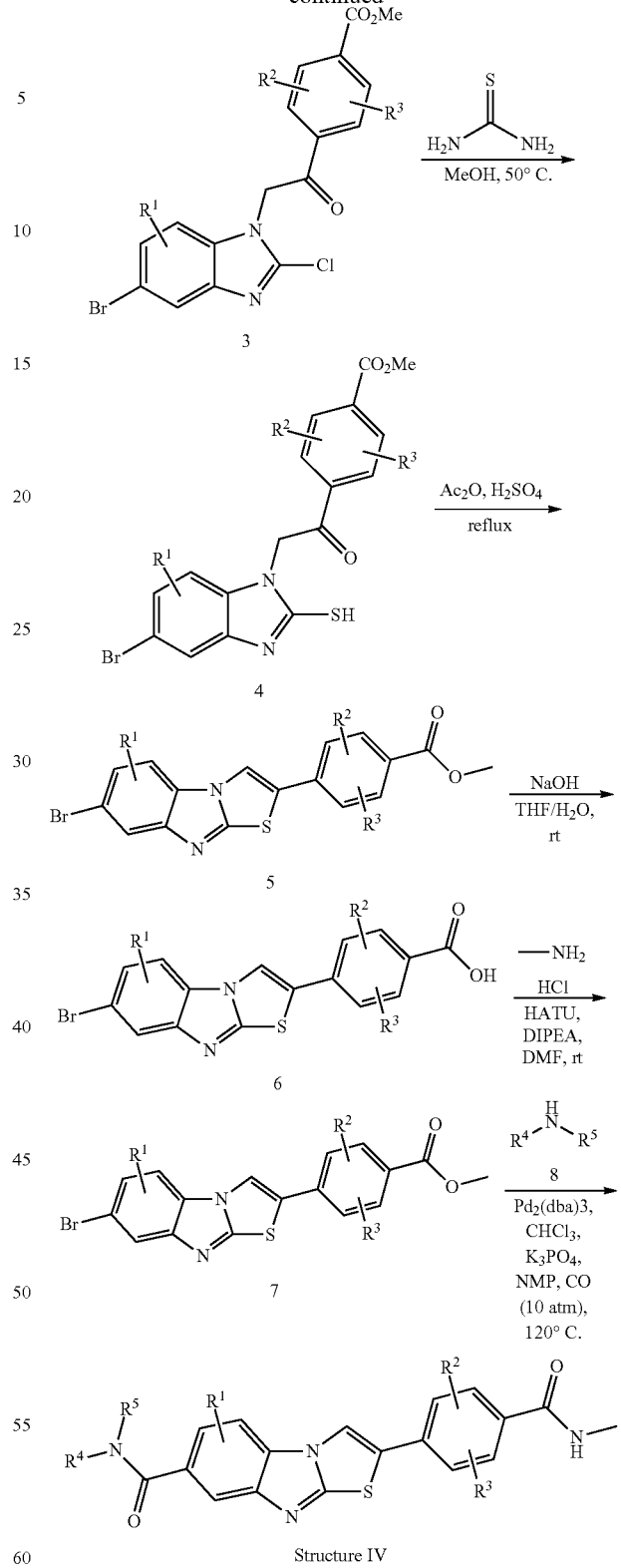

Structure IV

The first step of the synthesis involves alkylation of the $R^1$ substituted 5-bromo-2-chloro-1H-benzo[d]imidazole 1 with substituted phenacyl bromides 2 affording the N-alkylated intermediates 3. The thiol moiety is introduced by reaction of the 2-chlorobenzimidazole intermediate 3 with thiourea at elevated temperature to form intermediate 4. The third step involves "one pot" acetylation and intramolecular cyclization, using acetic anhydride and sulfuric acid to generate the tricyclic benzo[4,5]imidazo[2,1-b]thiazole ester intermediate 5. Hydrolysis of the methyl ester intermediate 5 using sodium hydroxide in a water/THF mixture gave carboxylic acid intermediate 6. Amide coupling reaction between carboxylic acid intermediate 6 and methylamine hydrochloride, using HATU as a coupling reagent affords the important methylamide intermediate 7. The bromo heteroaryl moiety of intermediate 7 is used in the final palladium-catalyzed aminocarbonylation reaction at elevated temperature with a variety of primary/secondary amines to deliver the final left-hand side (LHS) amides, Structure IV.

Synthesis of 4-(methylcarbamoyl)phenyl)benzo[4,5]thiazolo[3,2-b][1,2,4]triazole-6-carboxamide Compounds, Structure V

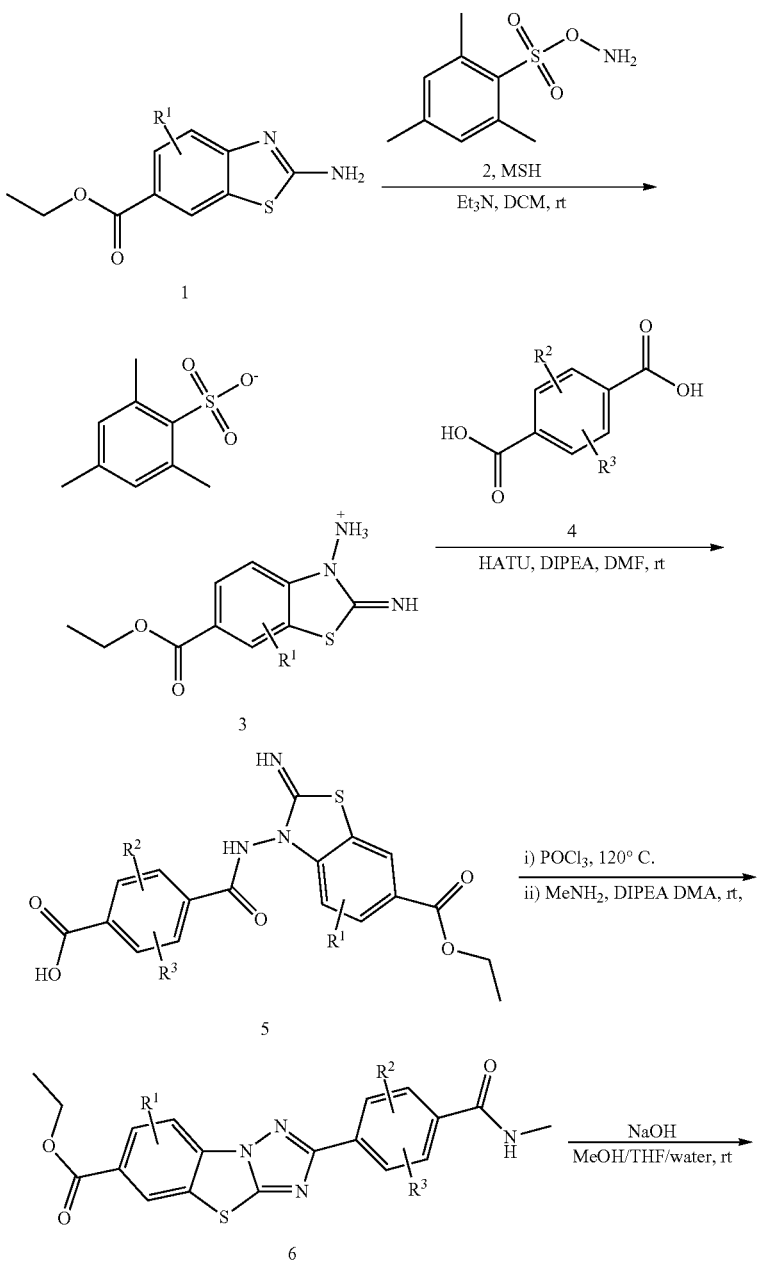

Scheme 6.
Synthesis of 4-(methylcarbamoyl)phenyl)benzo[4,5]thiazolo[3,2-b][1,2,4]triazole-6-carboxamide compounds, Structure V.

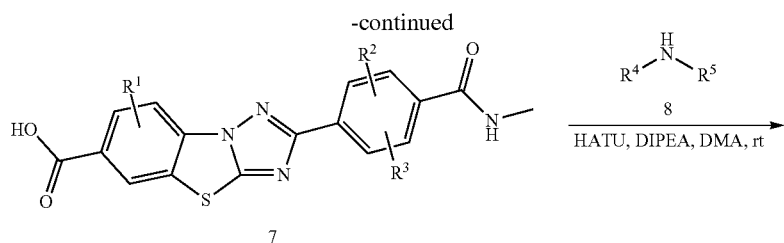

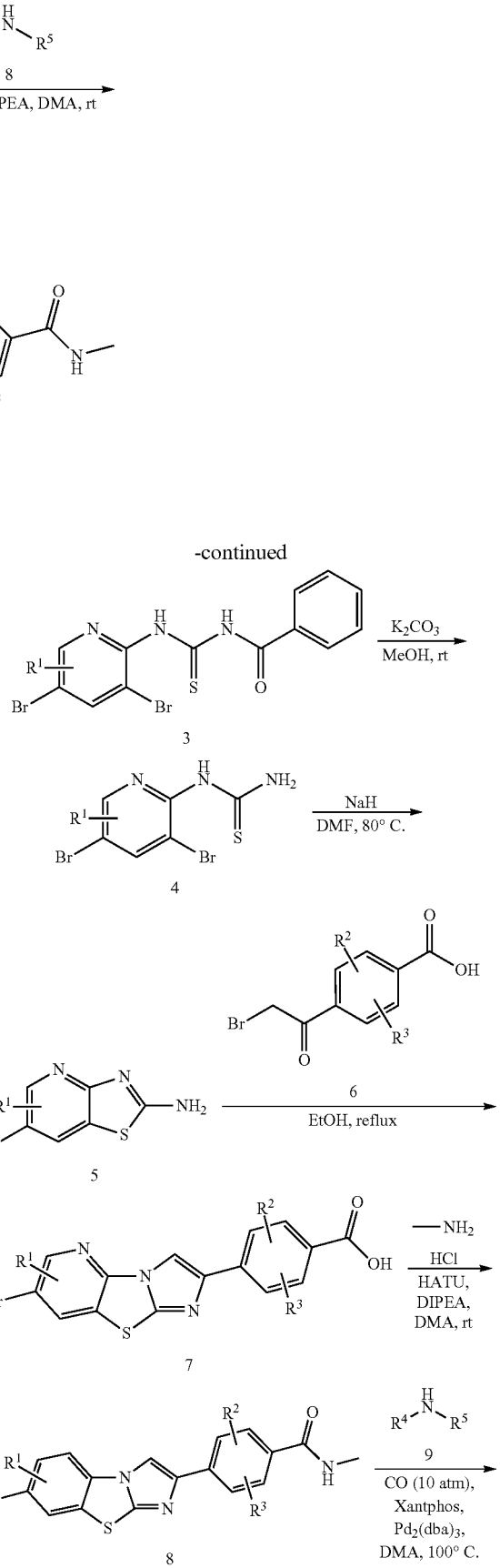

The first step of the synthesis involves electrophilic amination reaction of ethyl 2-aminobenzothiazole-6-carboxylate 1 with O-(2,4,6-trimethylbenzenesulfonyl)hydroxylamine (MSH) 2 in DCM affording the salt intermediate 3. The salt intermediate 3 undergoes an amide coupling reaction with various terephthalic acids 4, using HATU to provide the mono acylated intermediate 5. Intermediate 5 then undergoes a two-step sequence involving intramolecular cyclization and amidation, using phosphorus(V) oxychloride at elevated temperature followed by treatment with methylamine under basic conditions to afford the 4-(methylcarbamoyl)phenyl)benzo[4,5]thiazolo[3,2-b][1,2,4]triazole intermediate 6. Hydrolysis of the ethyl ester moiety of intermediate 6, using sodium hydroxide in water/THF/MeOH mixture provides the carboxylic acid intermediate 7. The final step involves amide coupling of the carboxylic acid intermediate 7 with a variety of primary/secondary amines, using HATU as a coupling reagent to furnish the final left-hand side (LHS) amides, Structure V.

Synthesis of 4-(methylcarbamoyl)phenyl)imidazo[2',1':2,3]thiazolo[4,5-b]pyridine-7-carboxamide Compounds, Structure VI Scheme 7.
Synthesis of 4-(methylcarbamoyl)phenyl)imidazo[2',1':2,3]thiazolo[4,5-b]pyridine-7-carboxamide compounds, Structure VI.

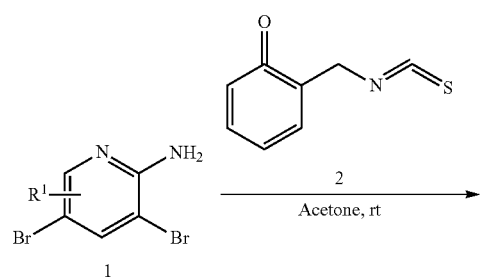

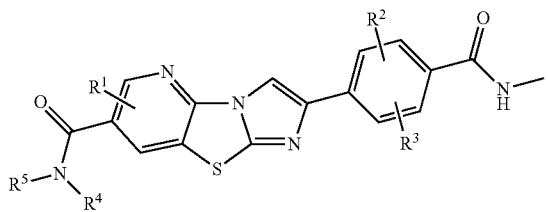

Structure VI

The first step of the synthesis involves reaction of benzoyl isothiocyanate 2 and 2-amino-3,5-dibromopyridine 1 in acetone affording benzoyl thiourea intermediate 3. Base-mediated methanolysis of the benzoyl thiourea intermediate 3 provides thiourea intermediate 4. Subsequently, intramolecular cyclization of thiourea intermediate 4 employing sodium hydride in DMF at elevated temperature furnishes the 6-bromothiazolo[4,5-b]pyridin-2-amine intermediate 5. Step four of the synthesis involves alkylation of the amino moiety of intermediate 5 with 4-carboxylic acid substituted phenacyl bromides 6 followed by intramolecular cyclization in refluxing ethanol to form the imidazothiazolo[4,5-b] pyridine benzoic acid intermediate 7. Amide coupling reaction of the benzoic acid intermediate 7 with methylamine hydrochloride using HATU as the coupling reagent affords the methylamide intermediate 8. In the final step, the 7-bromo heteroaryl moiety of intermediate 8 undergoes a palladium-catalyzed aminocarbonylation reaction at elevated temperature, using various primary/secondary amines to furnish the desired 4-(methylcarbamoyl)phenyl)imidazo[2,1':2,3]thiazolo[4,5-b]pyridine-7-carboxamide compounds, Structure VI.

Synthesis of 4-(methylcarbamoyl)phenyl)imidazo[2',1':2,3]thiazolo[5,4-b]pyridine-7-carboxamide Compounds, Structure VII Scheme 8.
Synthesis of 4-(methylcarbamoyl)phenyl)imidazo[2',1':2,3]thiazolo[5,4-b] pyridine-7-carboxamide compounds, Structure VII.

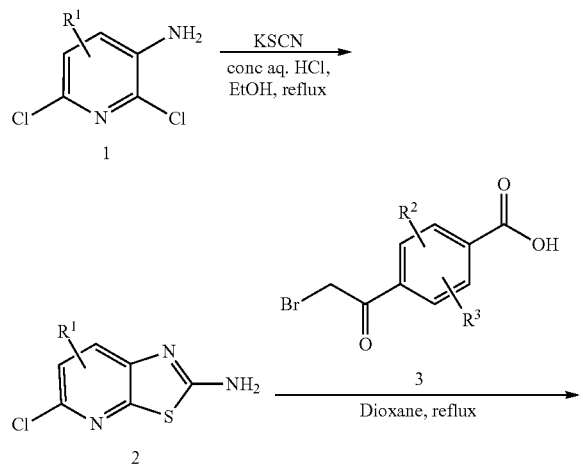

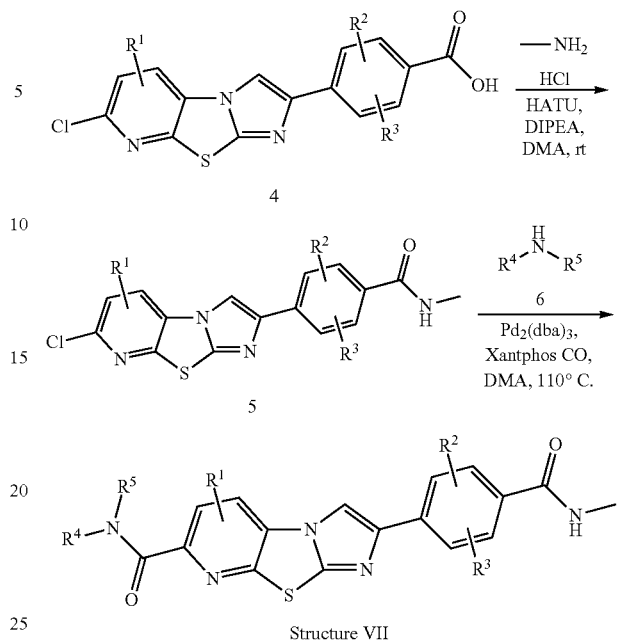

Structure VII

The first step of the synthesis involves reaction of potassium thiocyanate and substituted 2,6-dichloro-3-pyridinamine 1 in refluxing ethanol, in the presence of concentrated aqueous hydrochloric acid affording the 5-chlorothiazolo[5,4-b]pyridin-2-amine intermediate 2. The second step involves alkylation of the amino moiety of intermediate 2 with 4-carboxylic acid substituted phenacyl bromides 3 followed by intramolecular cyclization in refluxing dioxane to form the imidazothiazolo[5,4-b]pyridine benzoic acid intermediate 4. Amide coupling reaction of the benzoic acid intermediate 4 with methylamine hydrochloride, using HATU as the coupling reagent affords the methylamide intermediate 5. In the final step, the 7-chloro heteroaryl moiety of intermediate 5 undergoes a palladium-catalyzed aminocarbonylation reaction at elevated temperature, using various primary/secondary amines to furnish the desired 4-(methylcarbamoyl)phenyl)imidazo[2',1':2,3]thiazolo[5,4-b]pyridine-7-carboxamide Compounds, Structure VII.

Synthesis of 4-(methylcarbamoyl)phenyl)imidazo[2',1':2,3]thiazolo[5,4-d]pyrimidine-2-carboxamide Compounds, Structure VIII Scheme 9.
Synthesis of 4-(methylcarbamoyl)phenyl)imidazo[2',1':2,3]thiazolo[5,4-d] pyrimidine-2-carboxamide compounds, Structure VIII.

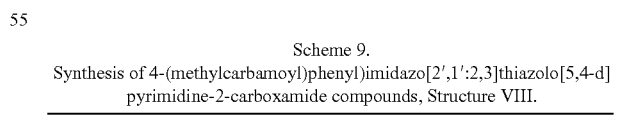

293
-continued

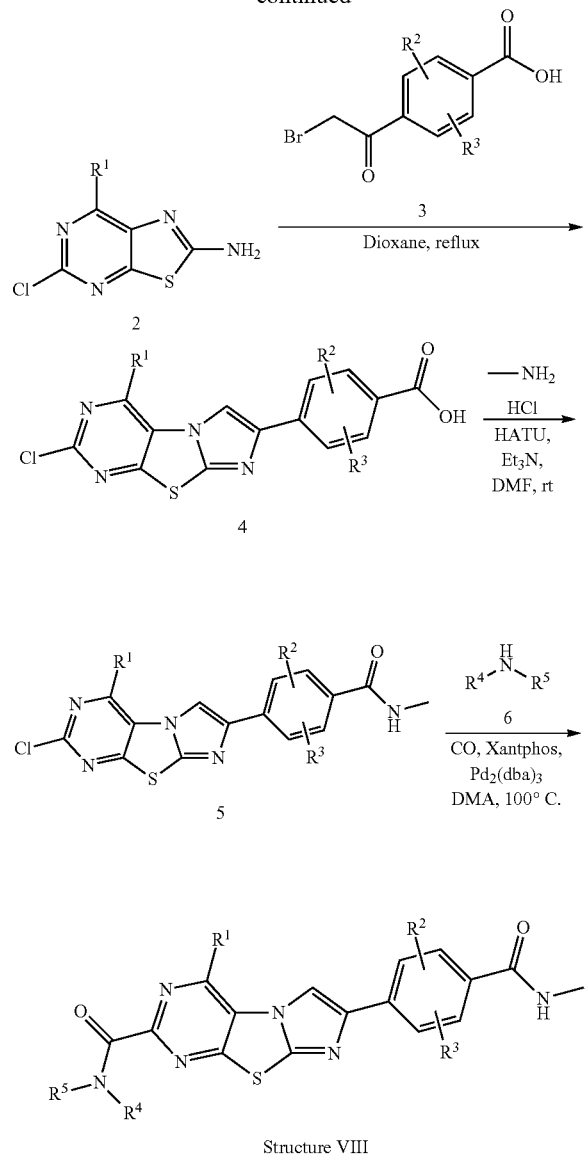

Structure VIII

The first step of the synthesis involves reaction of potassium thiocyanate with a 6-substituted 2,4-dichloropyrimidin-5-amine 1 in acetic acid at elevated temperature affording the 5-chlorothiazolo[5,4-d]pyrimidin-2-amine intermediate 2. The second step involves alkylation of the amino moiety of intermediate 2 with 4-carboxylic acid substituted phenacyl bromides 3 followed by intramolecular cyclization in refluxing dioxane to generate the imidazo[2',1':2,3]thiazolo[5,4-d]pyrimidin-7-yl)benzoic acid intermediate 4. Amide coupling reaction of the benzoic acid intermediate 4 with methylamine hydrochloride, using HATU as the coupling reagent affords the methylamide intermediate 5. In the final step, the 2-chloroimidazolo moiety of intermediate 5 undergoes a palladium-catalyzed aminocarbonylation reaction at elevated temperature, using various primary/secondary amines to deliver the desired 4-(methylcarbamoyl)phenyl)imidazo[2',1':2,3]thiazolo[5,4-d]pyrimidine-2-carboxamide Compounds, Structure VIII.

294
Synthesis of 4-(methylcarbamoyl)phenyl)imidazo[2',7':2,3]thiazolo[4,5-c]pyridine-7-carboxamide Compounds, Structure IX PGP-61

Scheme 10.
Synthesis of 4-(methylcarbamoyl)phenyl)imidazo[2',1':2,3]thiazolo[4,5-c]pyridine-7-carboxamide compounds, Structure IX.

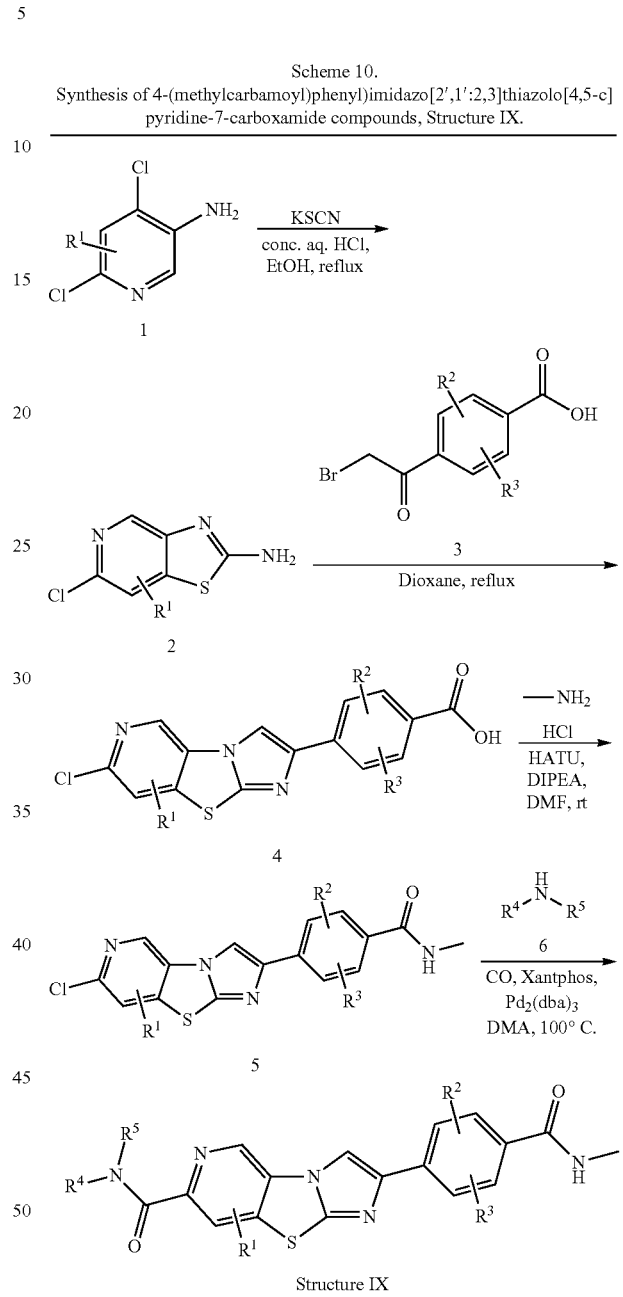

Structure IX

The first step of the synthesis involves reaction of potassium thiocyanate with a substituted 4,6-dichloropyridin-3-amine 1 in refluxing ethanol, in the presence of concentrated aqueous hydrochloric acid affording the 6-chlorothiazolo[4,5-c]pyridin-2-amine intermediate 2. The second step involves alkylation of the amino moiety of intermediate 2 with 4-carboxylic acid substituted phenacyl bromides 3 followed by intramolecular cyclization in refluxing dioxane to generate the imidazo[2',1':2,3]thiazolo[4,5-c]pyridin-2-yl)benzoic acid intermediate 4. Amide coupling reaction of the benzoic acid intermediate 4 with methylamine hydrochloride, using HATU as the coupling reagent affords the methylamide intermediate 5. In the final step, the 7-chloro heteroaryl moiety of intermediate undergoes a palladium-catalyzed aminocarbonylation reaction at elevated temperature, using various primary/secondary amines to deliver the desired 4-(methylcarbamoyl)phenyl)imidazo[2',1':2,3]thiazolo[4,5-c]pyridine-7-carboxamide compounds, Structure IX.

First Generation Synthesis of 4-(aminomethyl)phenyl)benzo[4,5]imidazo[2,1-b]thiazole-7-carboxamide Compounds, Structure X Scheme 11.
First generation synthesis of 4-(aminomethyl)phenyl)benzo[4,5]imidazo[2,1-b]thiazole-7-carboxamide compounds, Structure X.

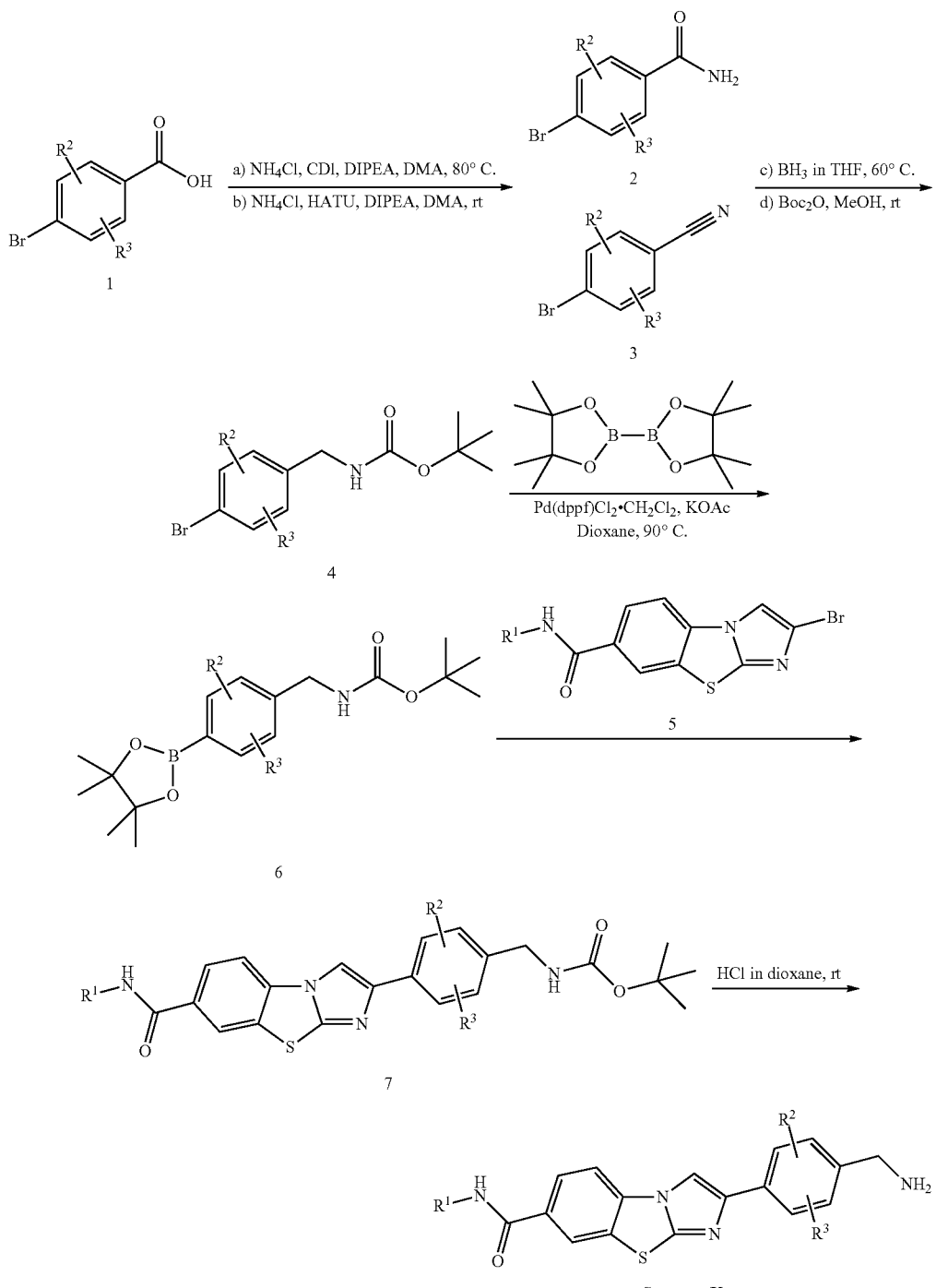

The first step of the synthesis involved primary amide formation from substituted aryl carboxylic acids 1. This was achieved using ammonium chloride and coupling reagents such as CDI or HATU to afford primary amide intermediates 2 and nitrile intermediates 3. Reduction of mixtures of 2 or 3 using borane in THF at elevated temperatures and subsequent protecting group strategy afforded intermediates 4. Palladium-mediated, Miyaura borylation of aryl bromide intermediates 4 gave the desired aryl boronic ester intermediates 6. Intermediates 6 were readily diversified with intermediates 5 to give protected final compounds 7. Acid mediated deprotection of 7 delivered Structure X.

An alternate synthetic sequence involved palladium-catalyzed Suzuki-Miyaura cross-coupling to introduce an aryl/heteroaryl component at the bromo substituted heterocyclic intermediates 5 to generate intermediates 7. The final step of the synthetic sequence involved acid mediated N-Boc deprotection of intermediates 7.

The first step of the synthesis involved primary amide formation from substituted aryl carboxylic acids 6 (as in Scheme 5). This was achieved using ammonium chloride and coupling reagents such as CDI or HATU to afford primary amide intermediates 9. Reduction of intermediates 9 using borane in THF at elevated temperatures and subsequent protecting group strategy afforded intermediates 10. Intermediates 10 were subjected to palladium-catalyzed aminocarbonylation with the desired amine (as in Scheme 3) at elevated temperature to provide intermediates 7. Acid mediated deprotection of intermediates 7 gave final Compounds, Structure X.

Second Generation Synthesis of 4-(aminomethyl) phenyl)benzo[4,5]imidazo[2,1-b]thiazole-7-carboxamide Compounds, Structure X Scheme 12.
Second generation synthesis of 4-(aminomethyl)phenyl)benzo[4,5]imidazo [2,1-b]thiazole-7-carboxamide compounds, Structure X.

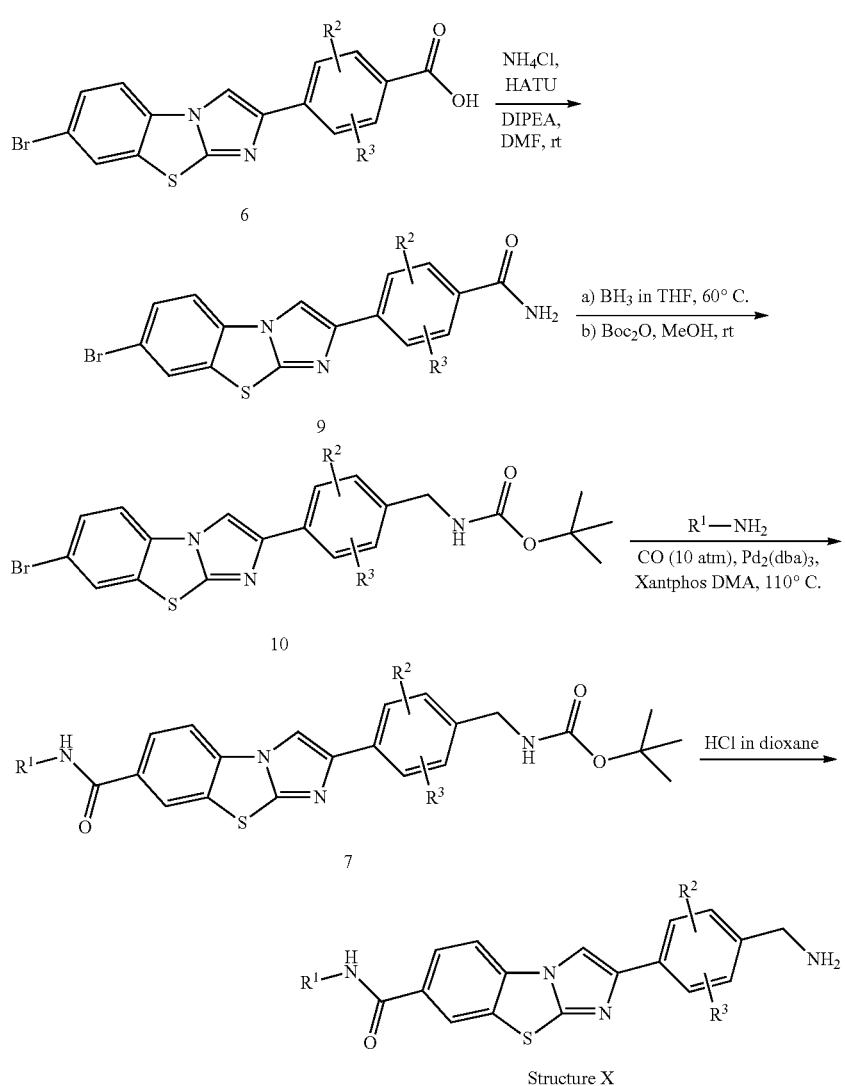

Synthesis of 4-(substituted aminomethyl)phenyl)benzo[4,5]imidazo[2,1-b]thiazole-7-carboxamide compounds, Structure XI

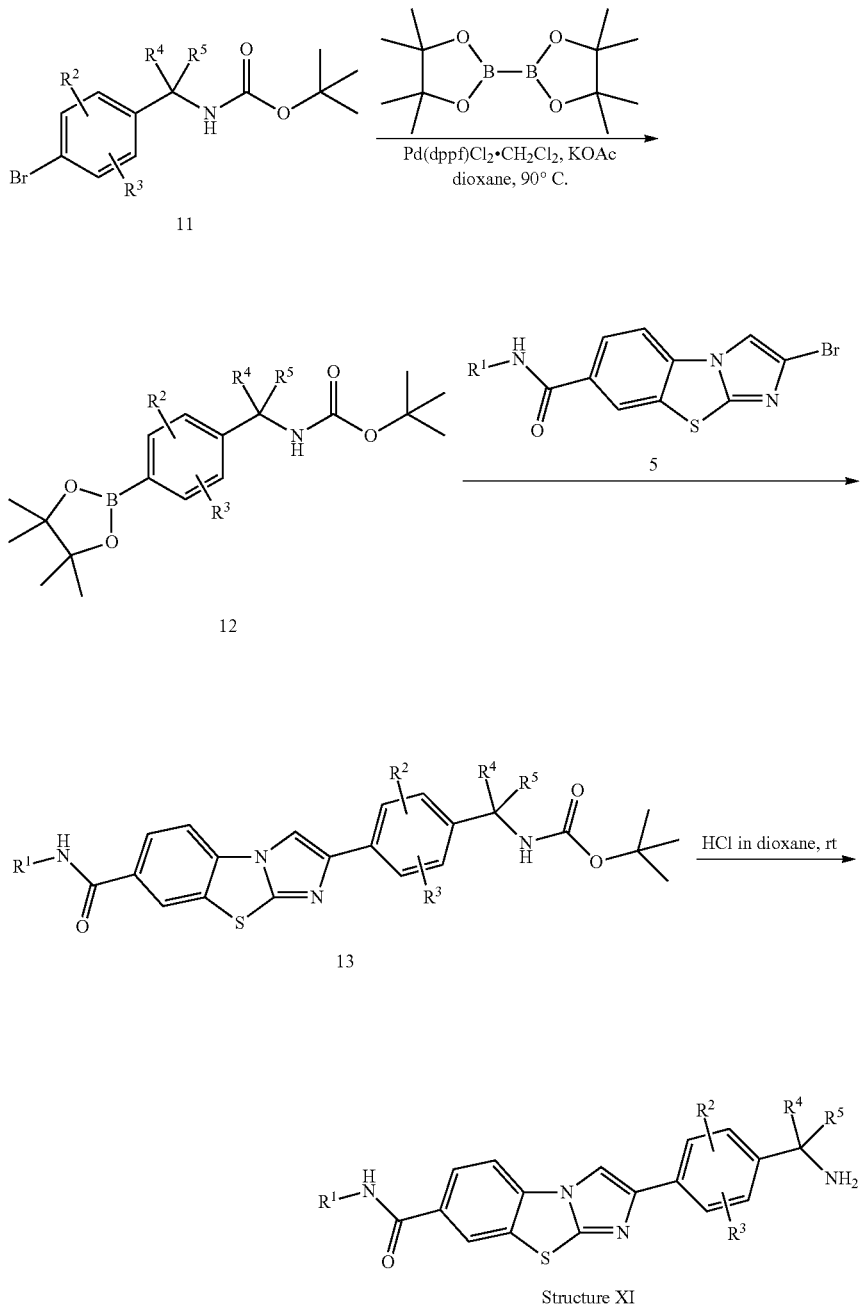

The first step of the synthesis involved palladium-mediated, Miyaura borylation of aryl bromide intermediates 11 to give desired aryl boronic ester intermediates 12. Intermediates 12 undergo palladium-mediated Suzuki-Miyaura cross-coupling, followed by acid mediated N-Boc deprotection reaction to generate the final Compounds, Structure XI.

Synthesis of 4-(N-substituted aminomethyl)phenyl)benzo[4,5]imidazo[2,1-b]thiazole-7-carboxamide Compounds, Structure XII

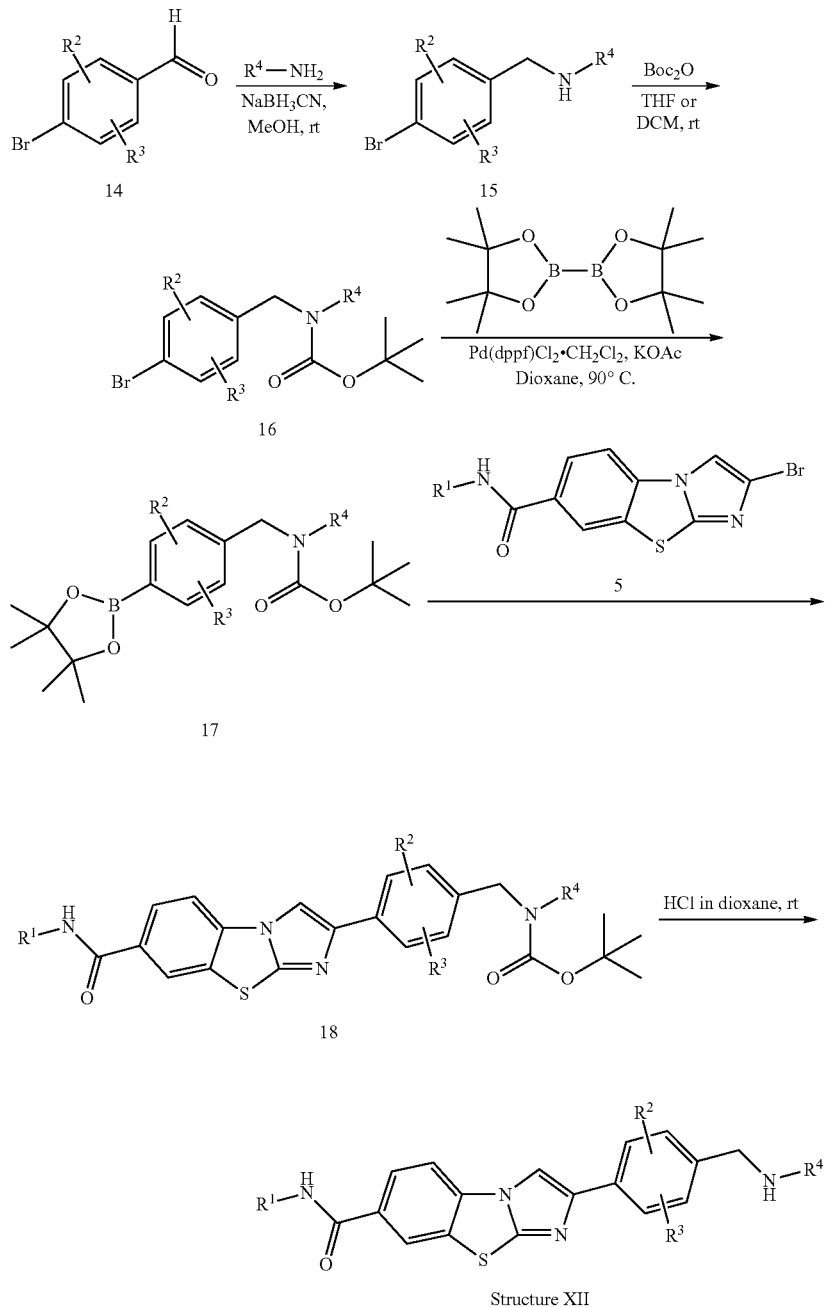

Scheme 14.
Synthesis of 4-(N-substituted aminomethyl)phenyl)benzo[4,5]imidazo[2,1-b]thiazole-7-carboxamide compounds, Structure XII.

The first step of the synthesis involved reductive amination of aldehyde intermediates 14 with various amines to generate intermediates 15. Intermediates 15 were subsequently protected to give intermediates 16. Intermediates 16 undergo the same synthetic procedure as outlined in Scheme 11 to generate the final Compounds, Structure XII.

Synthesis of 2-(4-(pyrrolidin-2-yl)phenyl)benzo[d]imidazo[2,1-b]thiazole-7-carboxamide compounds, Structure XIII
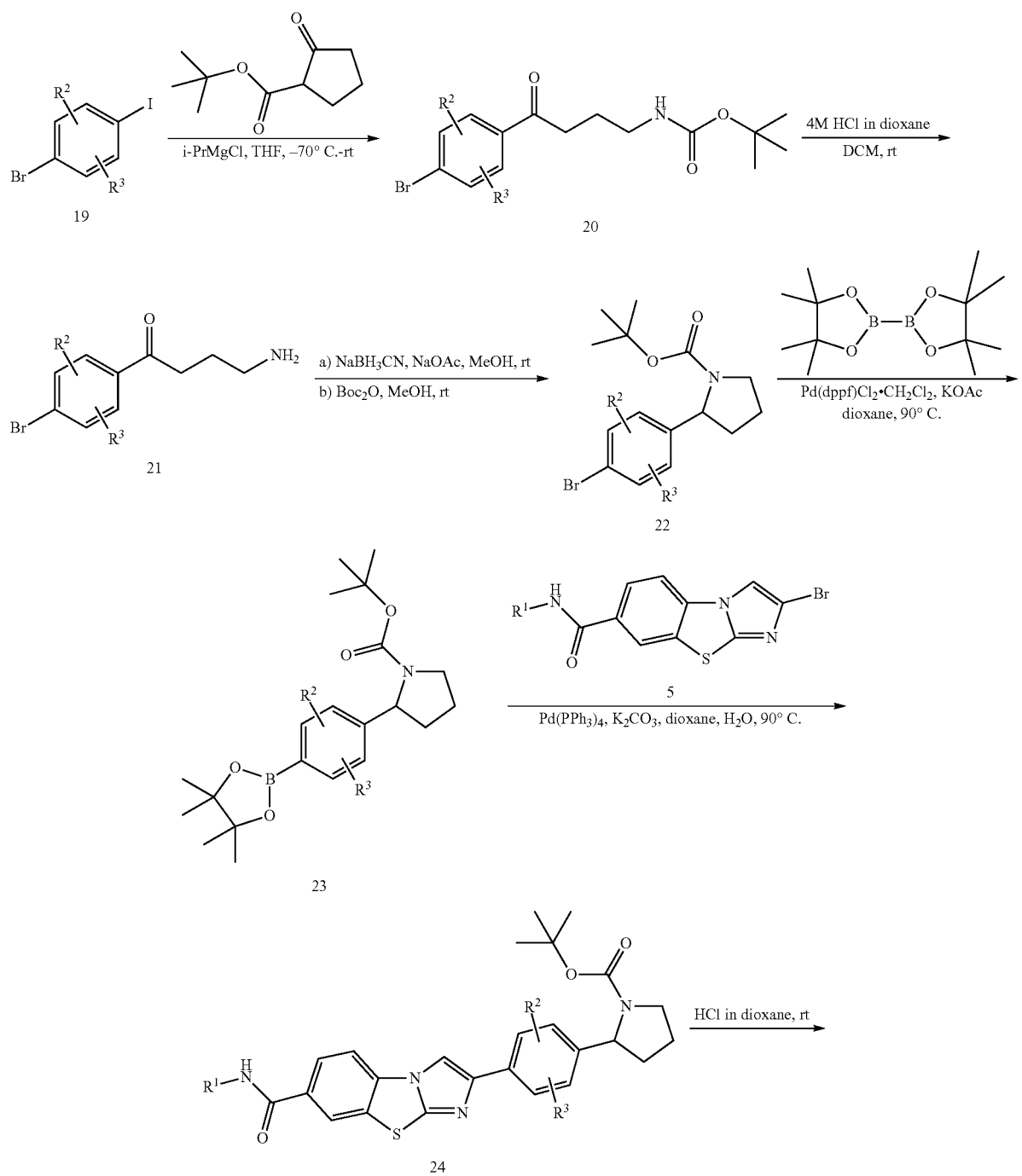
Scheme 15.
Synthesis of 2-(4-(pyrrolidin-2-yl)phenyl)benzo[d]imidazo[2,1-b]thiazole-7-carboxamide compounds, Structure XIII.

-continued

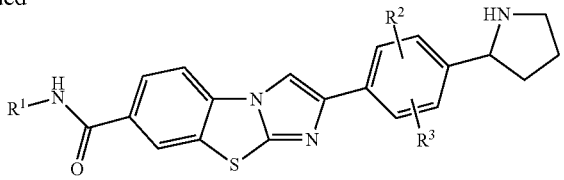

Structure XIII

The first step of the synthesis involved Grignard reagent formation of substituted aryl iodide intermediates 19. The resulting Grignard reagents were reacted with tert-butyl 2-oxopyrrolidine-1-carboxylate to give N-Boc aryl ketone intermediates 20. Intermediates 20 are deprotected under acidic conditions to generate intermediates 21. Intermediates 16 undergo the same synthetic procedure as outlined in Scheme 11 to generate final Compounds, Structure XIII.

If required, intermediates 24 were separated by chiral HPLC/SFC to generate two enantiomers. The resulting intermediates were deprotected using acidic conditions, to generate the enantiomers of Structure XIII.

Synthesis of benzo[d]imidazo[2,1-b]thiazole Compounds, Structure IXV

Scheme 16. Synthesis of benzo[d]imidazo[2,1-b]thiazole compounds, Structure IXV.

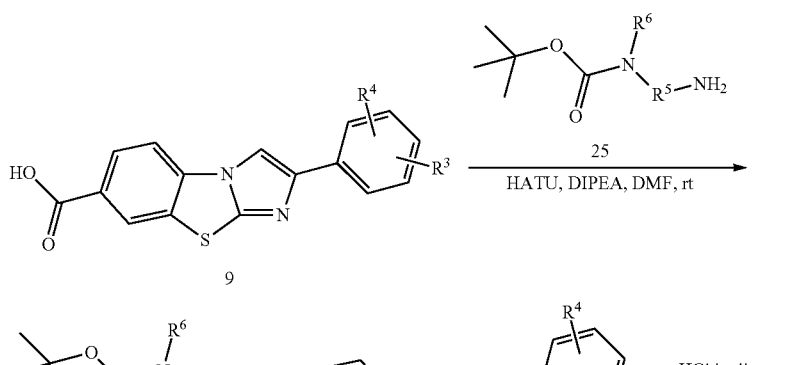

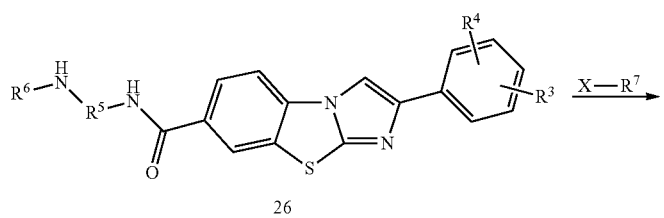

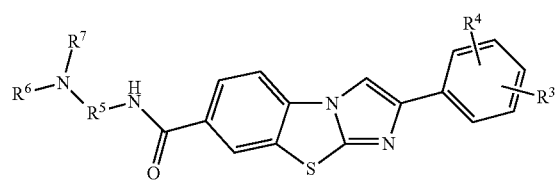

Structure IXV

The first step of the synthesis involved amide formation from substituted aryl carboxylic acids 1. Coupling was achieved using reagents such as CDI or HATU and a diverse selection of primary and secondary amines to afford Structure II (as in Scheme 3). Deprotection of Structure II was achieved via acidic conditions (as in Scheme 11) to generate intermediates 26. The final step of the synthesis involved alkylation of intermediates 26 with a variety of alkyl halides to give final compounds of Structure IXV.

Synthesis of Reverse Amide benzo[d]imidazo[2,1-b]thiazole Compounds, Structure XV

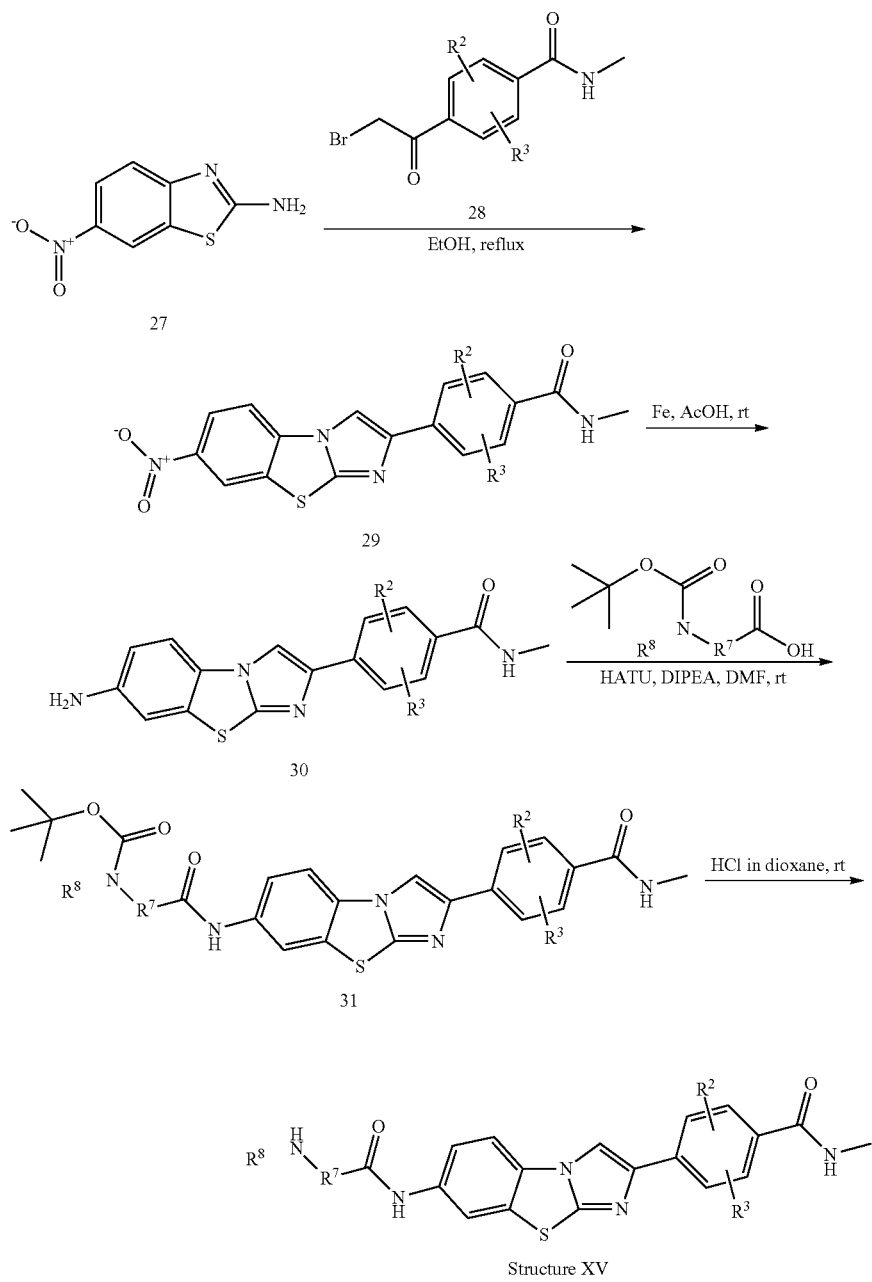

Scheme 17. Synthesis of reverse amide benzo[d]imidazo[1,1-b]thiazole compounds, Structure XV.

The first step involved a one-pot alkylation, intramolecular cyclization reaction between substituted alpha-bromo ketone intermediates 28 and 6-nitrobenzo[d]thiazol-2-amine 27 at elevated temperature affording intermediates 29. The nitro group was reduced using a mixture of iron in acetic acid to afford intermediates 30. Intermediates 30 were subjected to HATU mediated amide coupling with a variety of carboxylic acids to give intermediates 31. Acid mediated deprotection generated final compounds, Structure XV.

Alternative Synthesis of 7-nitro-2-aryl-lbenzo[d]imidazo[2,1-b]thiazole intermediate 29

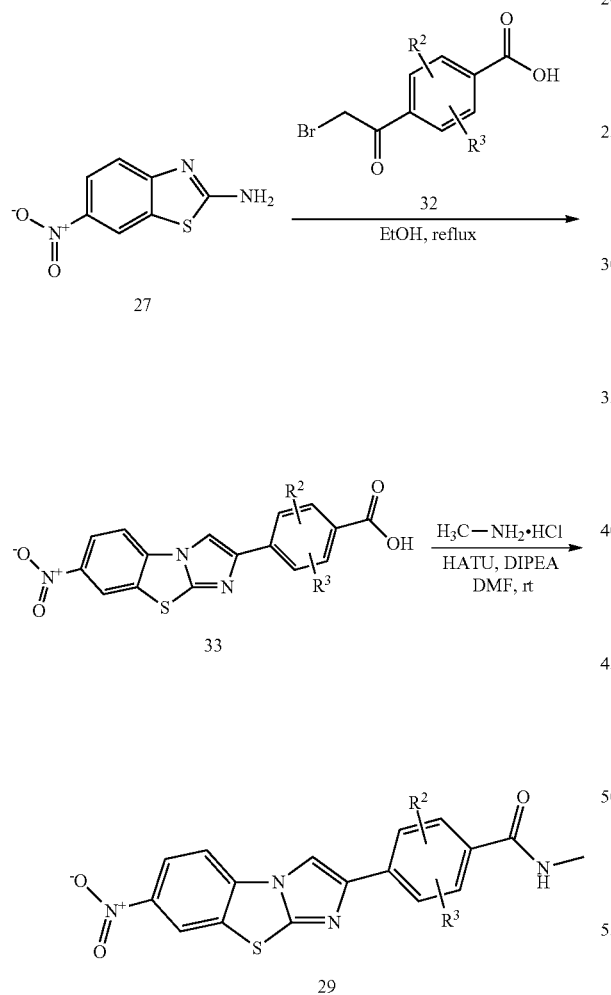

Alternative Synthesis of 6-chlorothiazolo[4,5-c]pyridin-2-amine intermediate 2

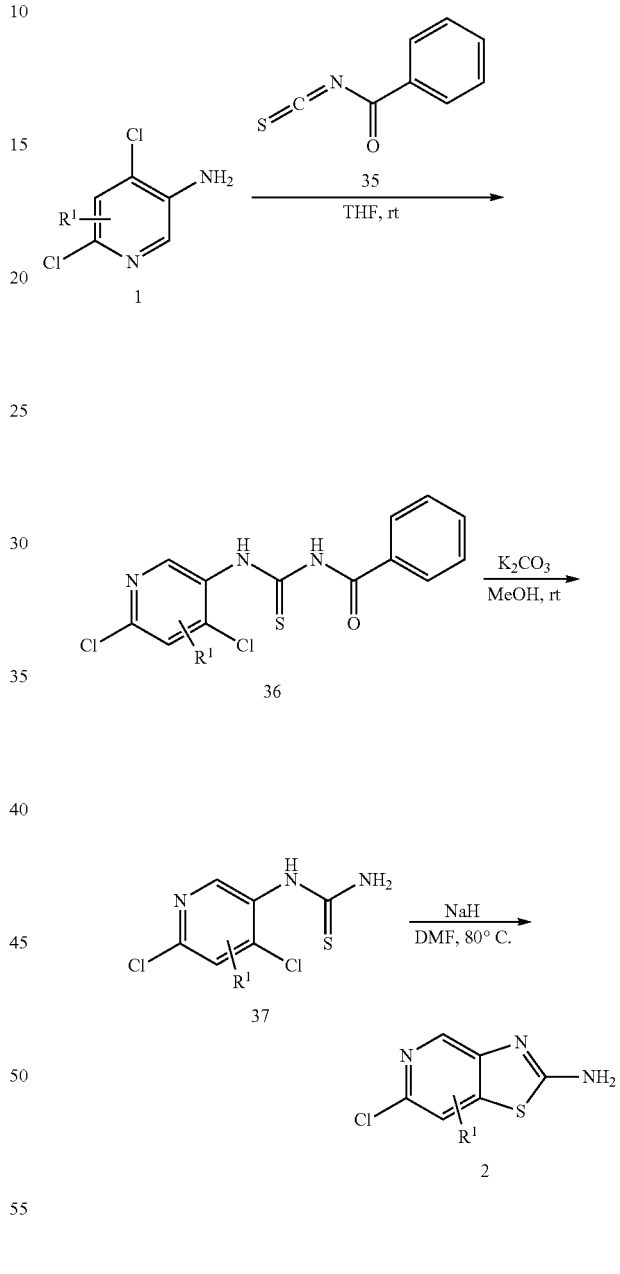

The first step involved a one-pot alkylation, intramolecular cyclization reaction between substituted alpha-bromo ketone intermediates 32 and 6-nitrobenzo[d]thiazol-2-amine 27 at elevated temperature affording intermediates 33. Intermediates 33 were subjected to HATU mediated amide coupling with a methylamine hydrochloride to give intermediate 29.

The first step of the synthesis involves reaction of benzoyl isothiocyanate 35 with substituted 4,6-dichloropyridin-3-amines 1 in THF to generate intermediates 36. Base-mediated deprotection of intermediates 36 provided thiourea intermediates 37. Intermediates 37 were subjected to intramolecular cyclization mediated by sodium hydride in DMF at elevated temperature to afford intermediates 2 (as in Scheme 10).

Synthesis of 4-(substituted aminomethyl)phenyl)benzo[4,5]thiazolo[3,2-b][1,2,4]triazole-6-carboxamide Compounds, Structure XVI
Scheme 20. Synthesis of 4-(substituted aminomethyl)phenyl)benzo[4,5]thiazolo[3,2-b][1,2,4]triazole-6-carboxamide compounds, Structure XVI.
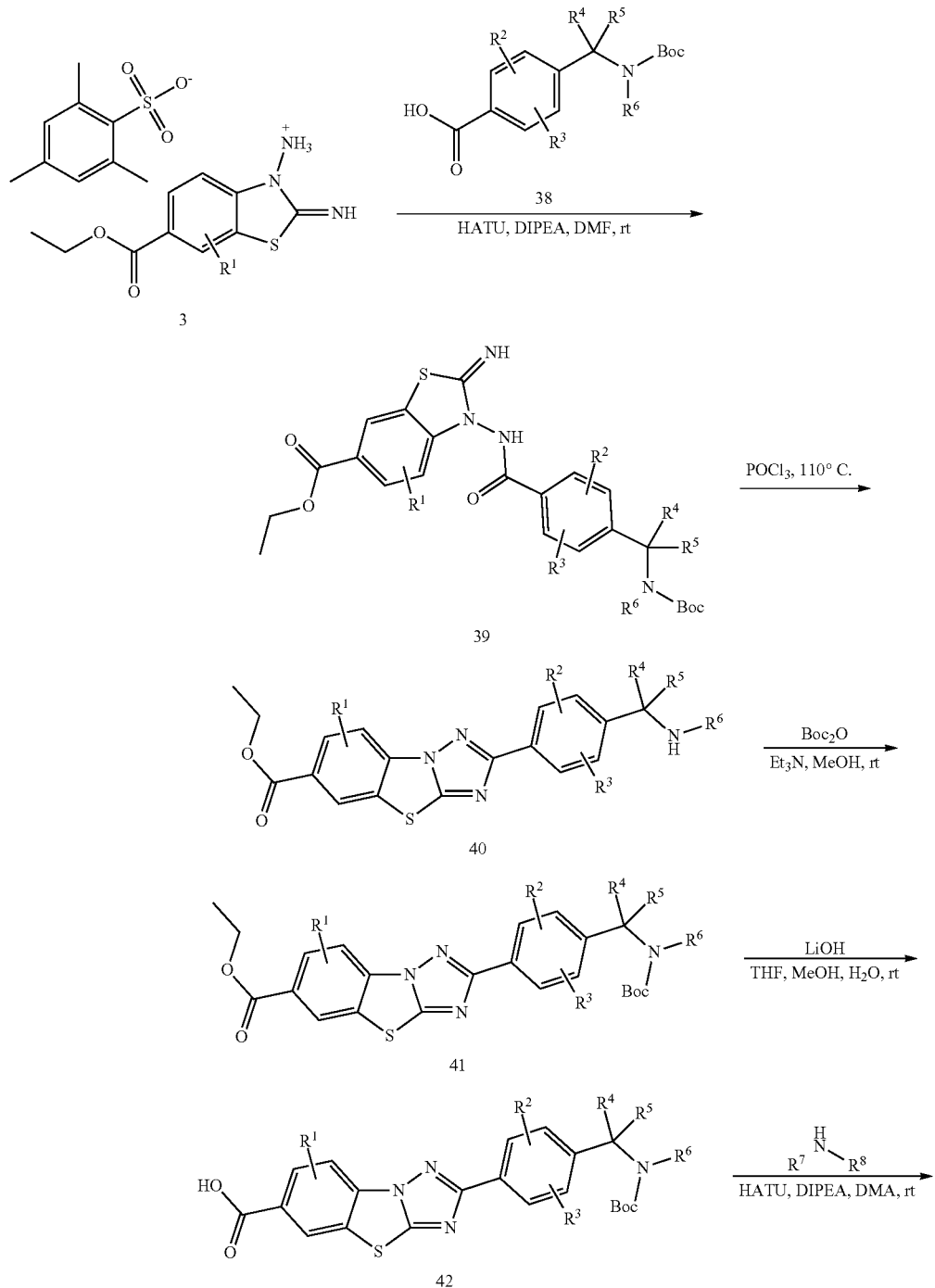

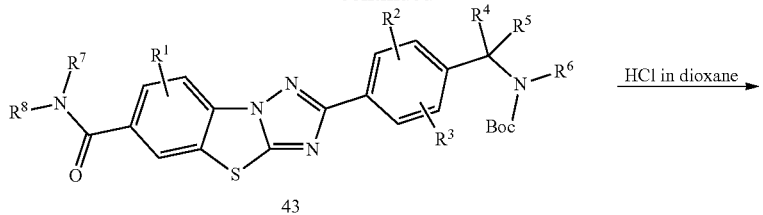

43

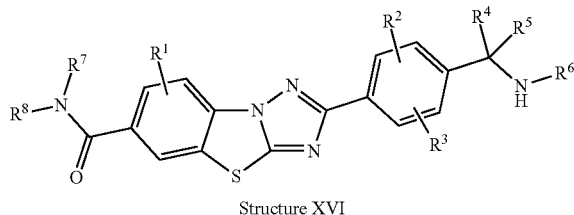

Structure XVI

The first step of the synthesis intermediates 3 were subjected to HATU mediated amide coupling with a variety of carboxylic acids to give intermediates 39. Intermediates 39 were subjected to intramolecular cyclization, using phosphorus(V) oxychloride at elevated temperature to generate intermediates 40. Intermediates 40 were then subsequently treated with Boc$_2$O under basic conditions to give intermediates 41. Hydrolysis of ester intermediates 41 with lithium hydroxide in a mixture of water/THF/MeOH afforded carboxylic acid intermediates 42. Intermediates 42 were subjected to HATU mediated amide coupling with a diverse range of primary/secondary amines, to generate intermediates 43. Acid mediated deprotection reaction gave Compounds, Structure XVI.

If required, intermediates 43 were separated by chiral HPLC/SFC to generate two enantiomers. The resulting intermediates were deprotected using acidic conditions, to generate the enantiomers of Structure XVI.

Second Generation Synthesis of Intermediates 41

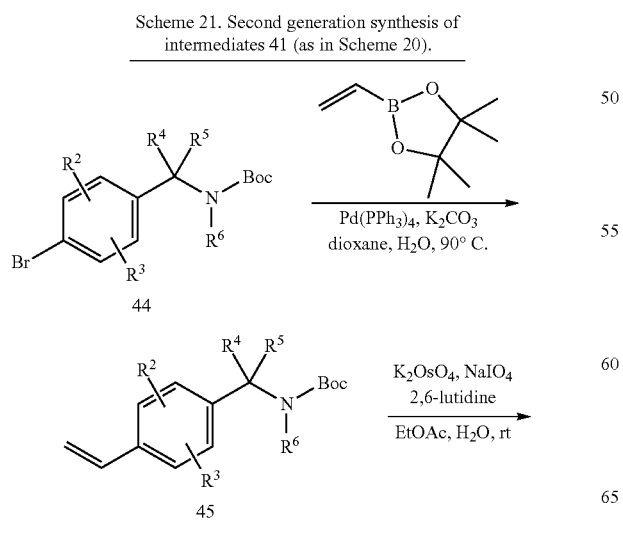

The first step of the synthesis involved a palladium-mediated Suzuki-Miyaura coupling reaction to introduce a vinyl substituent on intermediate 44 to generate intermediate 45. Intermediate 45 is subjected to oxidation to generate aldehyde intermediates 46. The final step of the synthesis involved an oxidative intermolecular cyclization between intermediates 46 and intermediate 3 to give ester intermediates 41.

Alternative Synthesis of Intermediates 46

Scheme 22. Alternative synthesis of intermediates 46 (as in Scheme 21).

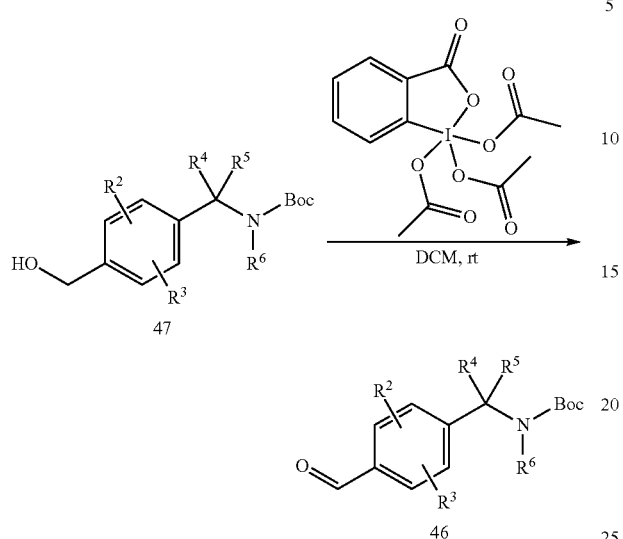

This step of the synthesis involved oxidation of benzyl alcohol intermediates 47 using Dess-Martin periodinane or other oxidants to generate aldehyde intermediates 46.

Example 2

General Synthetic Details for Additional Compounds of the Invention (Schemes 23-31)

General Synthesis of Additional Compounds of the Invention

Scheme 23. Synthesis of RHS modified phenyl trifluoromethanesulfonate analogues 10

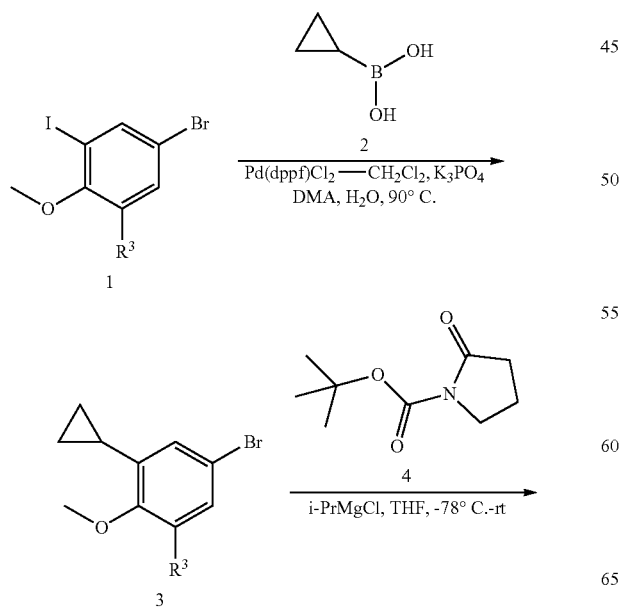

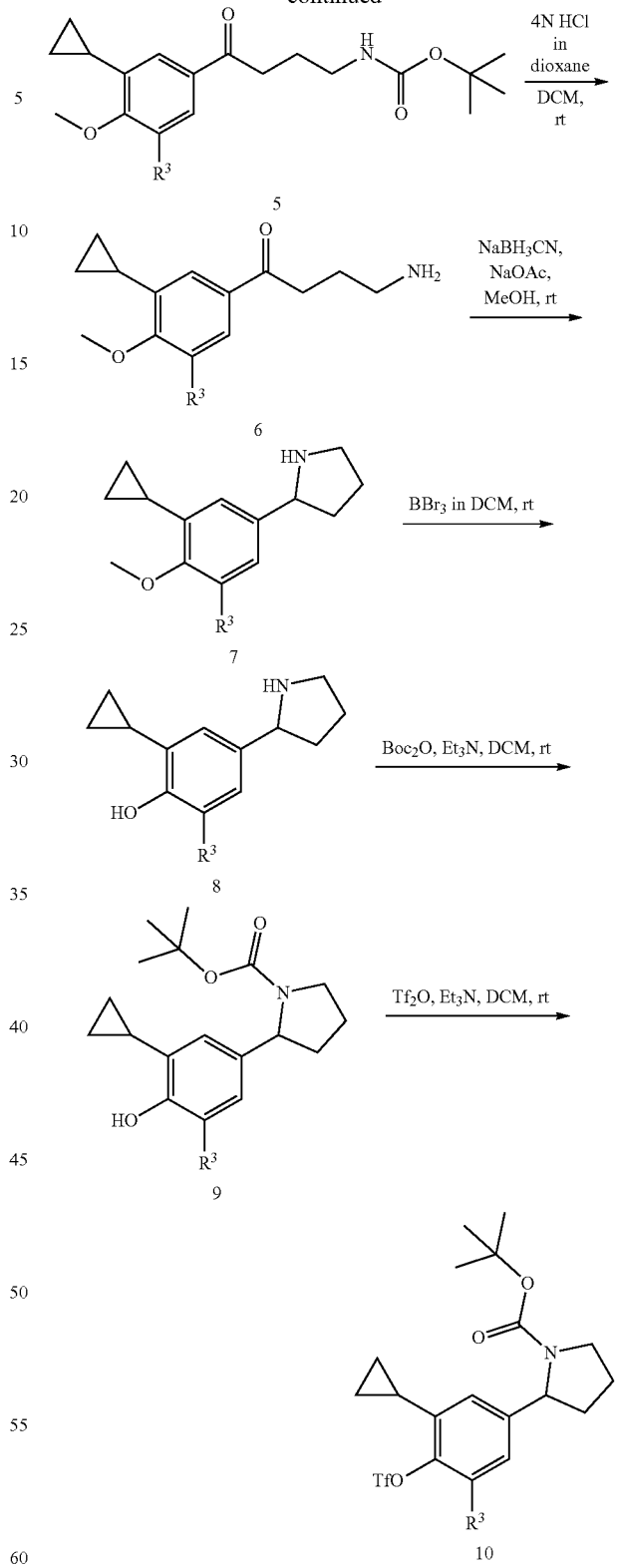

The first step of the synthesis involved a Suzuki coupling reaction between substituted iodobenzenes 1 and cyclopropylboronic acid 2 to afford intermediates 3. Halogen magnesium exchange of intermediates 3 by isopropylmagnesium bromide at a lower temperature formed new aryl magnesium reagents, which were treated with tert-butyl 2-oxopyrrolidine-1-carboxylate 4 to generate aryl alkyl ketones 5. Subsequently the N-Boc group was removed under acidic conditions to give amine intermediates 6 as hydrochloride salts or free bases. Intermediates 6 were subjected to an intramolecular reductive amination reaction to generate intermediates 7. The methoxy protecting groups of aryl methyl ethers were removed using boron tribromide to give amino polysubstituted phenols 8. Intermediates 8 were subjected to amino group protection with Boc groups to generate intermediates 9. In the final step the hydroxyl groups were converted to the corresponding trifluoromethanesulfonates by treatment with trifluoromethanesulfonic anhydride under basic conditions to give elaborated intermediates 10 (Scheme 23).

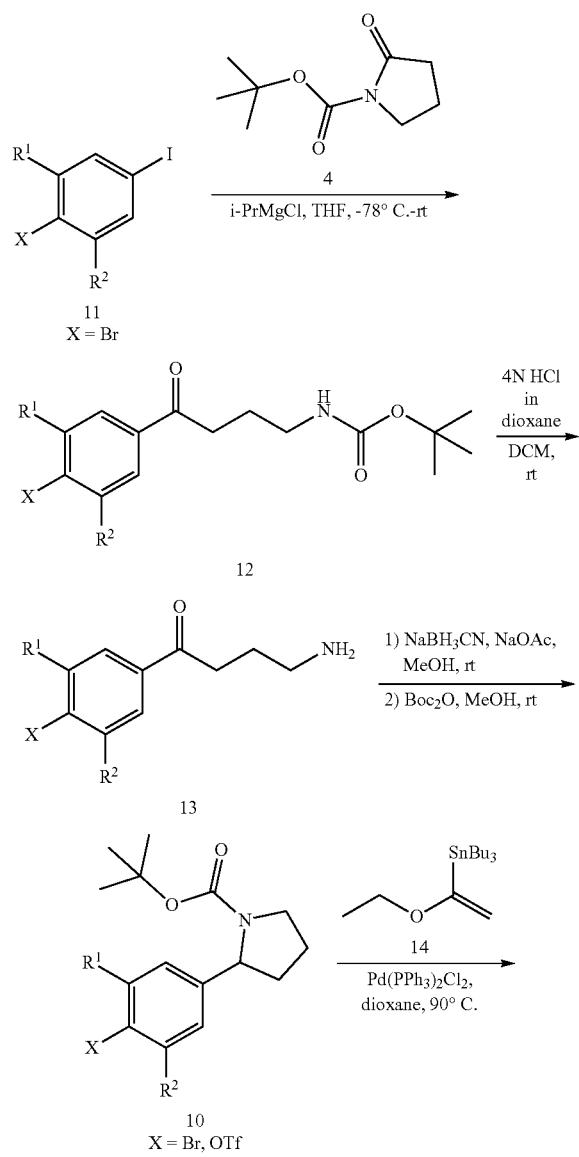

Scheme 24. Synthesis of RHS modified aromatic α-bromoketone analogues 16

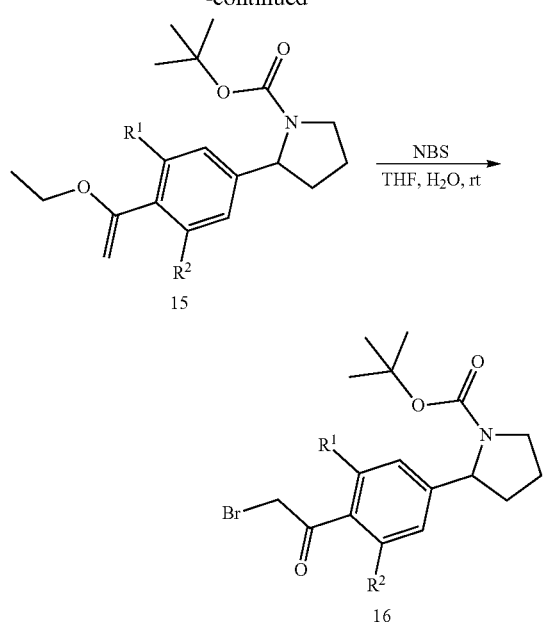

The first 3 steps were conducted using similar methodology the corresponding steps described in Scheme 23 to generate intermediates 10. Subsequently a 1-ethoxyvinyl group was introduced via Stille coupling of intermediates 10 with tributyl(1-ethoxyvinyl)stannane 14 affording intermediates 15. Intermediates 15 were treated with NBS in THF and water to give the corresponding aromatic a-bromoketones 16 (Scheme 24).

Scheme 25. Synthesis of RHS modified aromatic α-bromoketone analogues 19.

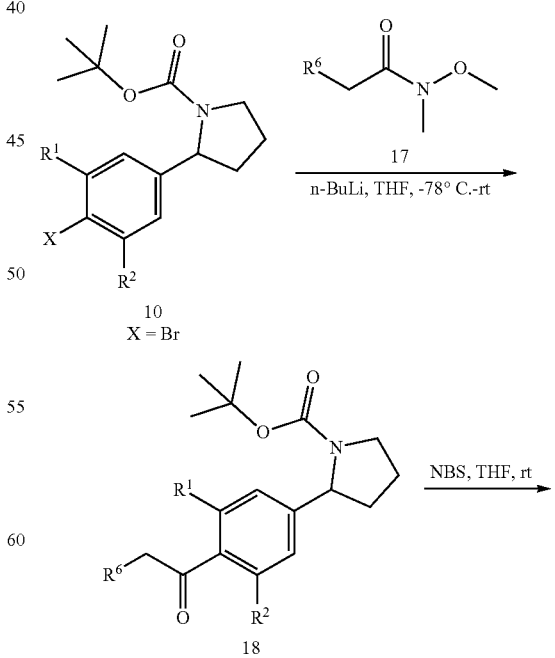

319
-continued

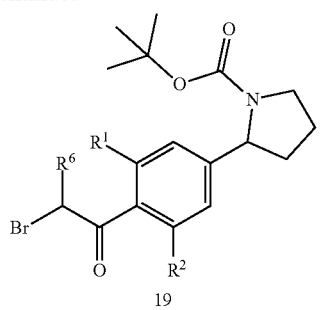
19

The corresponding step involved lithium halogen exchange of intermediates 10 with n-butyl lithium, followed by quenching with substituted Weinreb amides 17 forming a-substituted aromatic ketone intermediates 18. Subsequent bromination at a-position of ketone intermediates 18 with brominating reagents such as NBS generated modified a-bromoketones 19 (Scheme 25).

Scheme 26. Synthesis of 5-substituted methyl 2-aminobenzo[d]thiazole-6-carboxylate 21

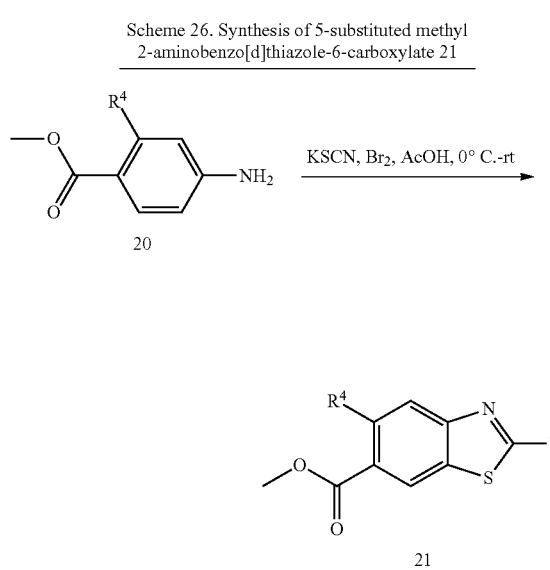

Intermediates 20 were treated with potassium thiocyanate and bromine in acetic acid to generate corresponding 2-aminobenzo[d]thiazoles 21 (Scheme 26).

Scheme 27. Synthesis of functionalized Anologues 26.

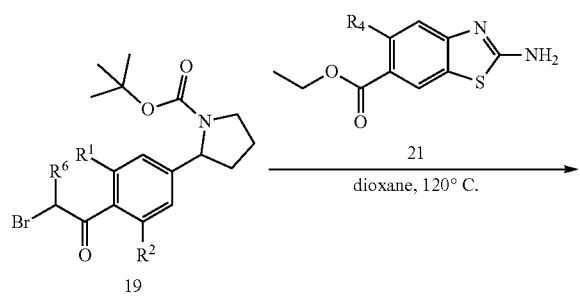

320
-continued

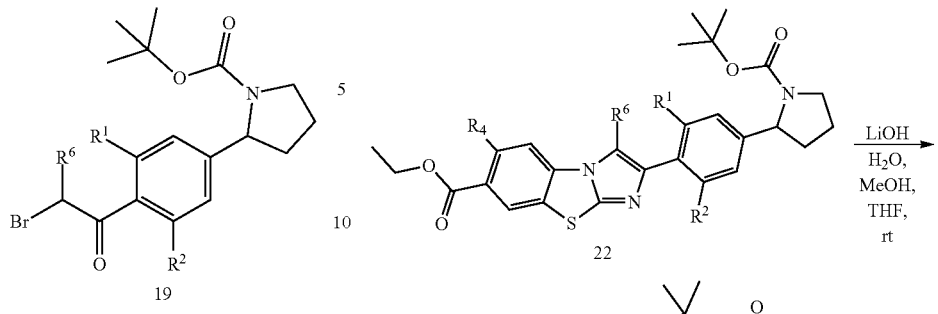

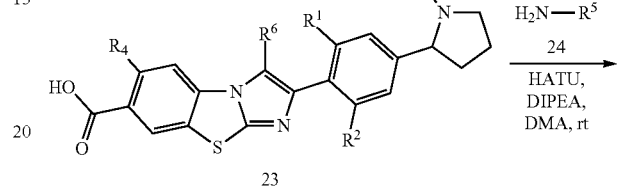

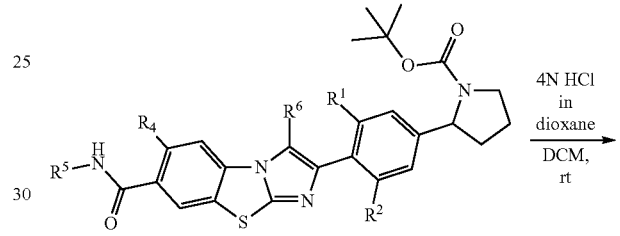

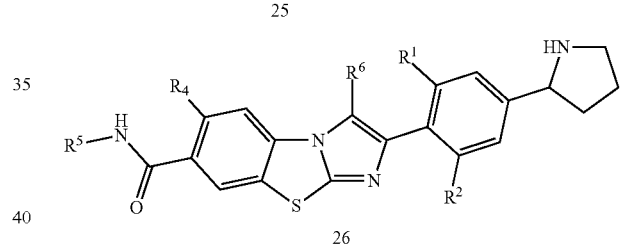

The initial step involved a cyclization reaction between modified a-bromoketone analogues 19 and corresponding 2-aminobenzo[d]thiazole 21 affording substituted tricyclic benzo[d]imidazo[2,1-b]thiazole intermediates 22. The carboxylic esters were hydrolyzed under basic conditions such as aqueous lithium hydroxide to afford carboxylic acids 23. Subsequent condensation reaction of intermediates 23 with corresponding amines afforded N-Boc protected amides 25. Intermediates 25 were deprotected under acidic conditions such as hydrogen chloride in dioxane solution to generate final compounds 26 (Scheme 27).

Scheme 28. Synthesis of N-Boc protected multi-substituted indoline 29.

$X^1$ = F, $X^2$ = Br
$X^1$ = Br, $X^2$ = F

-continued

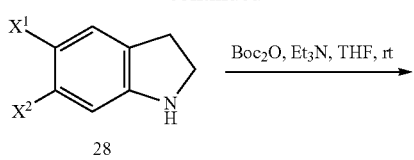

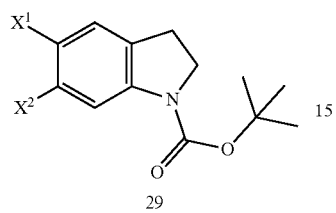

Substituted indoles 27 were reduced with triethylsilane under acidic conditions to afford indolines 28, which were Boc protected to generate corresponding intermediates 29 (Scheme 28).

Scheme 29. Synthesis of N-Boc protected substituted tetrahydroisoquinoline 32.

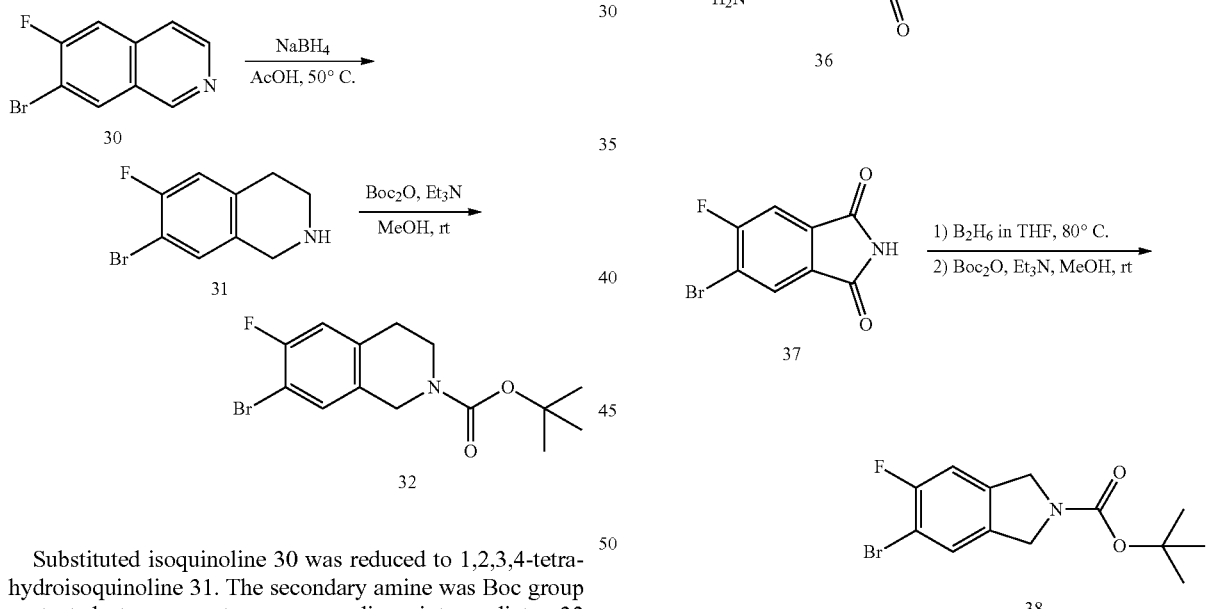

Substituted isoquinoline 30 was reduced to 1,2,3,4-tetrahydroisoquinoline 31. The secondary amine was Boc group protected to generate corresponding intermediate 32 (Scheme 29).

Scheme 30. Synthesis of N-Boc protected substituted isoindoline 38.

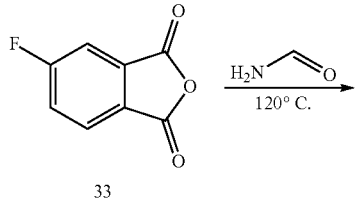

-continued

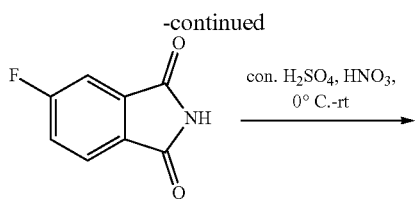

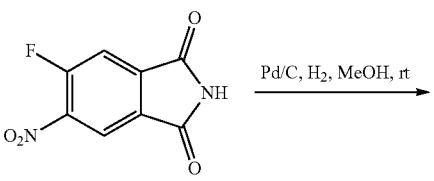

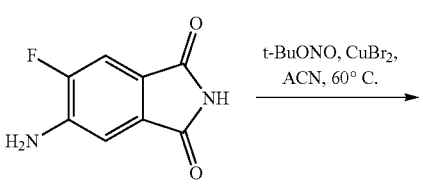

The first step of the synthesis involved reaction of 5-fluoroisobenzofuran-1,3-dione in formamide at elevated temperatures affording 5-fluoroisoindoline-1,3-dione intermediate 33. Intermediate 33 was subjected to regioselective nitration to generate intermediate 35. The nitro group was reduced using 10% palladium on activated carbon to give intermediate 36. Intermediate 36 was treated with t-butyl nitrite and copper(I) bromide to generate intermediate 37. The final step of the synthesis involved reduction of intermediate 37 with diborane in THF at elevated temperatures following by in-situ Boc protection affording intermediate 38 (Scheme 30).

Scheme 31.
Synthesis of functionalized Anologues 45.
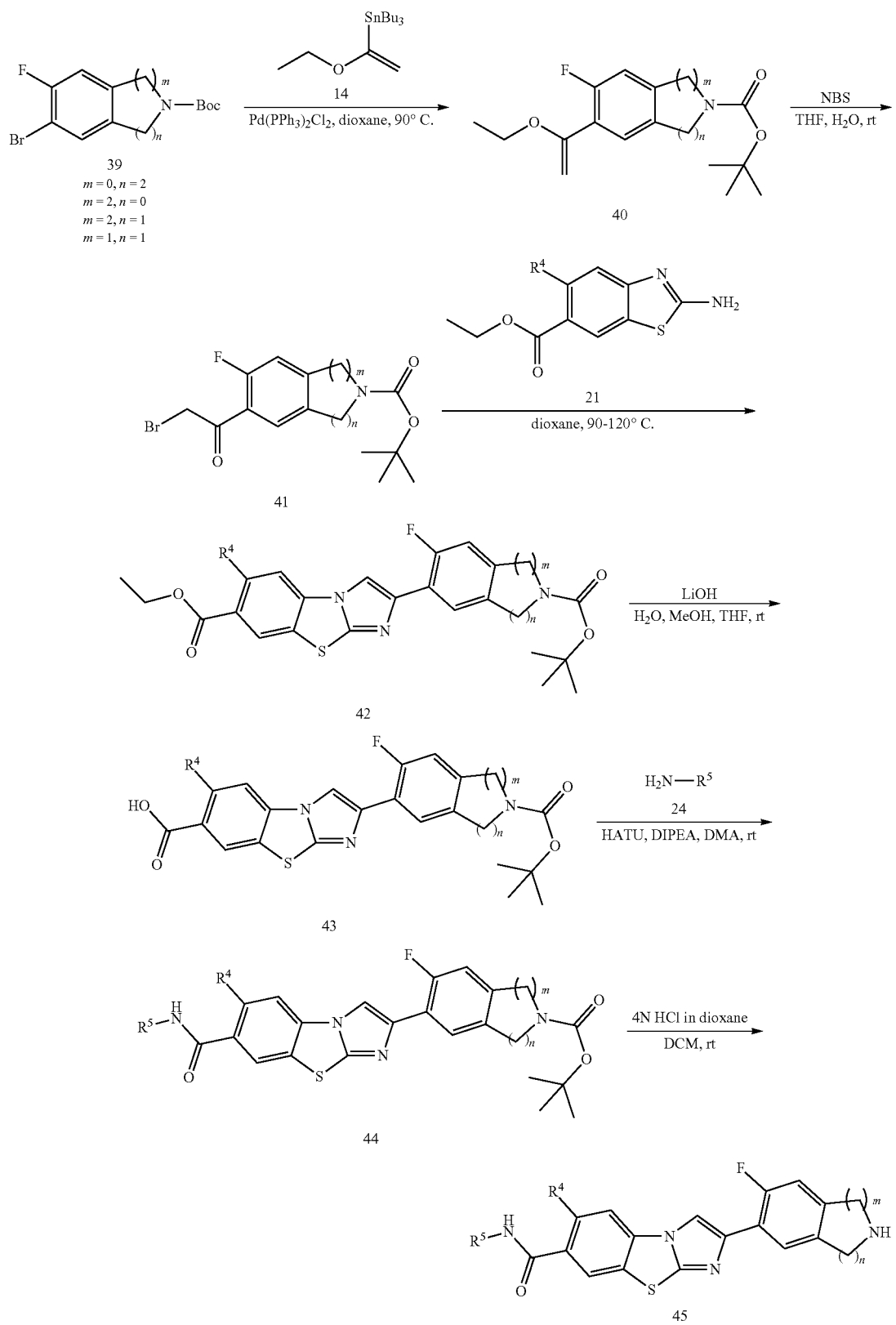

The first 2 steps are analogous to corresponding steps 4 and 5 as described in Scheme 24 to generate modified a-bromoketone intermediates 41. The subsequent 4 steps were also undertaken as described in Scheme 27 affording the final compounds 45 (Scheme 31).

Example 3

General Synthetic Details for Additional Compounds of the Invention (Schemes 32-58)
General Synthesis of Compounds of the Invention Scheme 32
General synthesis of right-hand side modified benzo[d]imidazo[2,1-b]thiazole-7-carboxamide analogues 10.

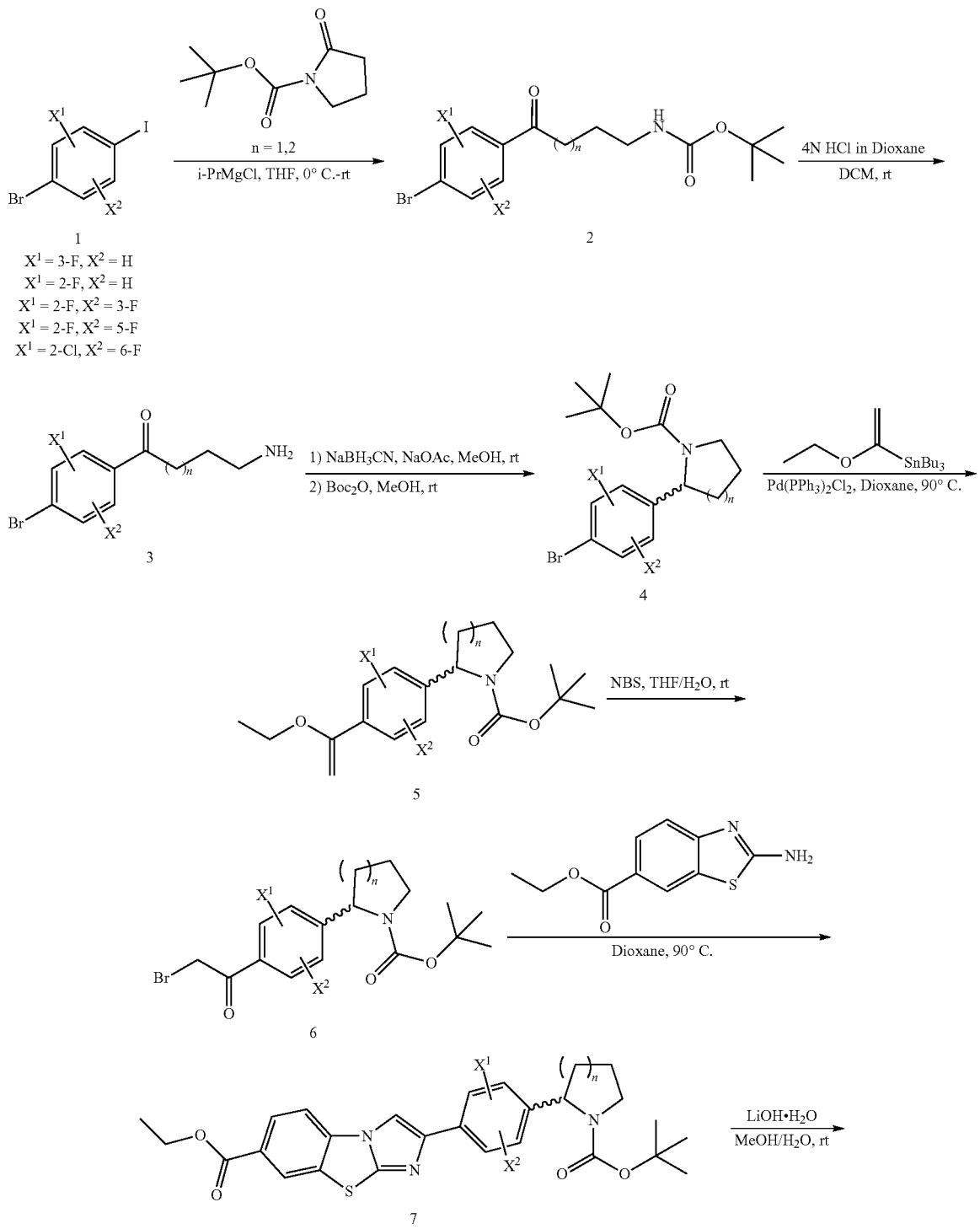

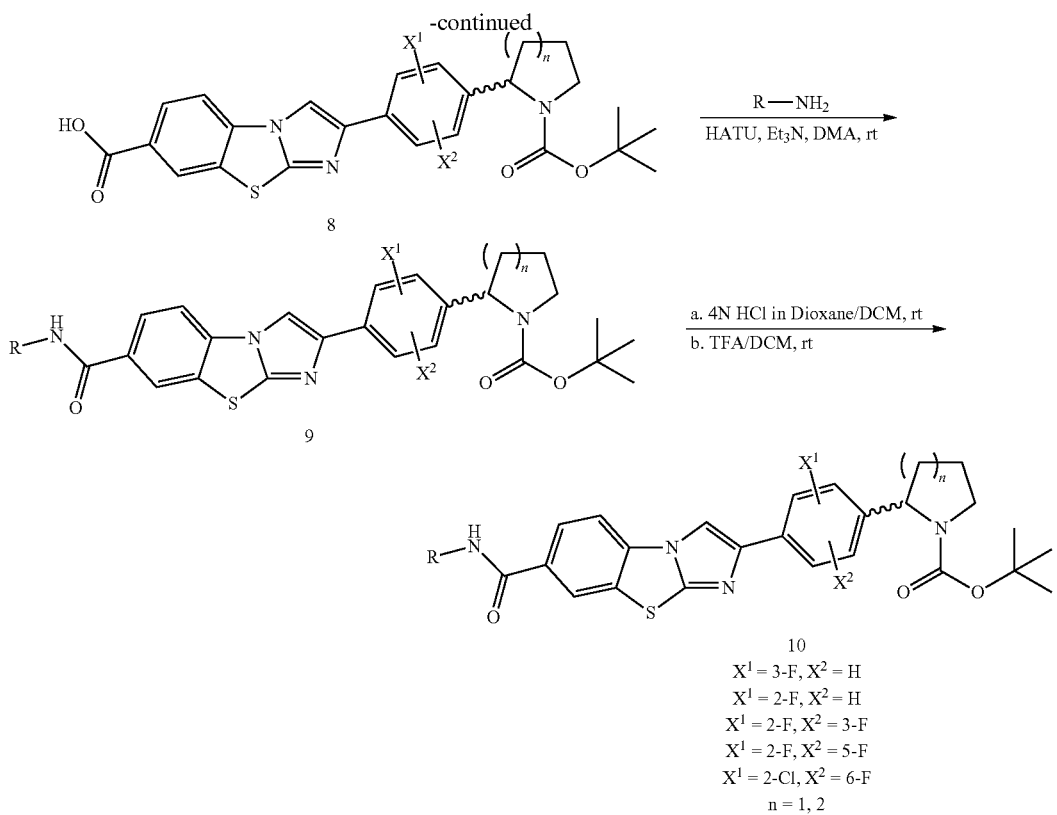

$X^1 = 3\text{-F}, X^2 = H$
$X^1 = 2\text{-F}, X^2 = H$
$X^1 = 2\text{-F}, X^2 = 3\text{-F}$
$X^1 = 2\text{-F}, X^2 = 5\text{-F}$
$X^1 = 2\text{-Cl}, X^2 = 6\text{-F}$
$n = 1, 2$ Reagents 1 (Scheme 32) were reacted with isopropylmagnesium bromide at low temperatures. This generated the corresponding phenylmagnesium bromides, which were then treated with N-Boc protected lactams to generate ketones 2. The N-Boc protecting group of 2 was removed under acidic conditions to generate terminal amines 3 as the hydrochloride salts. Then an intramolecular reductive amination reaction was carried out and the resulting endo-amines were protected as the Boc carbamates in-situ to generate intermediates 4. Reaction with tributyl(1-ethoxyvinyl)stannane in the presence of catalytic palladium at elevated temperatures generated vinyl ethyl ethers 5. Treatment with N-bromosuccinimide in aqueous conditions generated aromatic α-bromoketone analogues 6. This was followed by a cyclization with ethyl 2-aminobenzo[d]thiazole-6-carboxylate at elevated temperature to generate intermediates 7. The ester was hydrolyzed to carboxylic acids 8. Amide coupling reaction on 8 with various amines gave amides 9. The N-Boc protecting group was removed by 4 N hydrochloride in 1,4-dioxane or by trifluoroacetic acid to generate benzo[d]imidazo[2,1-b]thiazole-7-carboxamide analogues 10 as a free base or as the hydrochloride/formic acid salt. Chiral resolution was performed on N-Boc protected compounds 9 to generate, after subsequent N-Boc protecting group removal, the individual enantiomers if required.

Scheme 33. An alternative synthesis of N-Boc protected benzo[d]imidazo[2,1-b]thiazole-7-carboxamide compounds 9

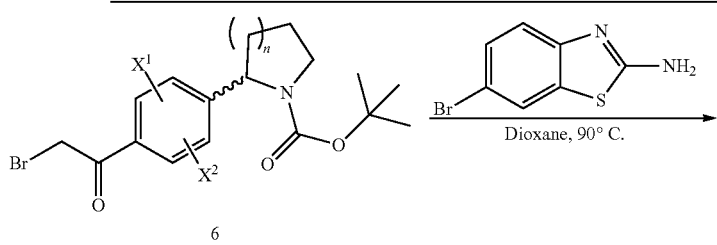

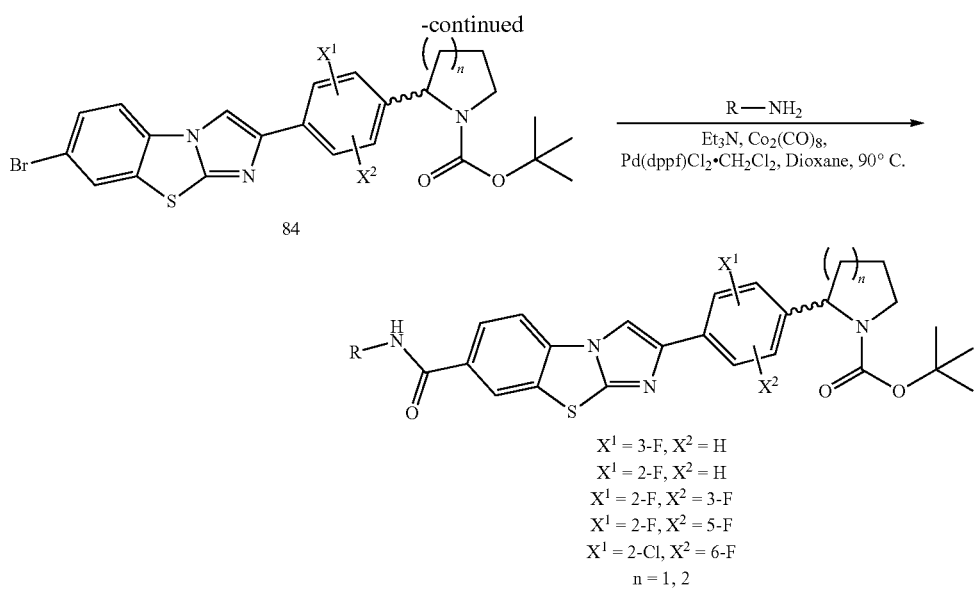

$X^1$ = 3-F, $X^2$ = H
$X^1$ = 2-F, $X^2$ = H
$X^1$ = 2-F, $X^2$ = 3-F
$X^1$ = 2-F, $X^2$ = 5-F
$X^1$ = 2-Cl, $X^2$ = 6-F
n = 1, 2

A cyclization of aromatic a-bromoketone analogues 6 (Scheme 33) with 6-bromobenzo[d]thiazol-2-amine at elevated temperature gave intermediates 84 (Scheme 33). The bromide of intermediates 84 was converted to various amides via aminocarbonylation reaction to generate intermediates 9. Chiral resolution was performed on N-Boc protected compounds 9 to generate the individual enantiomers if required.

A cyclization of aromatic a-bromoketone analogue 6 (Scheme 34) with commercial available N-(2-aminobenzo[d]thiazol-6-yl)amides at elevated temperature gave intermediates 11. The N-Boc protecting group was removed by 4 N hydrochloride in 1,4-dioxane to generate N-(benzo[d]imidazo[2,1-b]thiazol-7-yl)amide analogues 12 as the free base or as the hydrochloride salt. Chiral resolution was performed on N-Boc protected compounds 11 to generate, Scheme 34.
General synthesis of right-hand side modified reversed N-(benzo[d]imidazo[2,1-b]thiazole-7-yl)amide analogues 12.

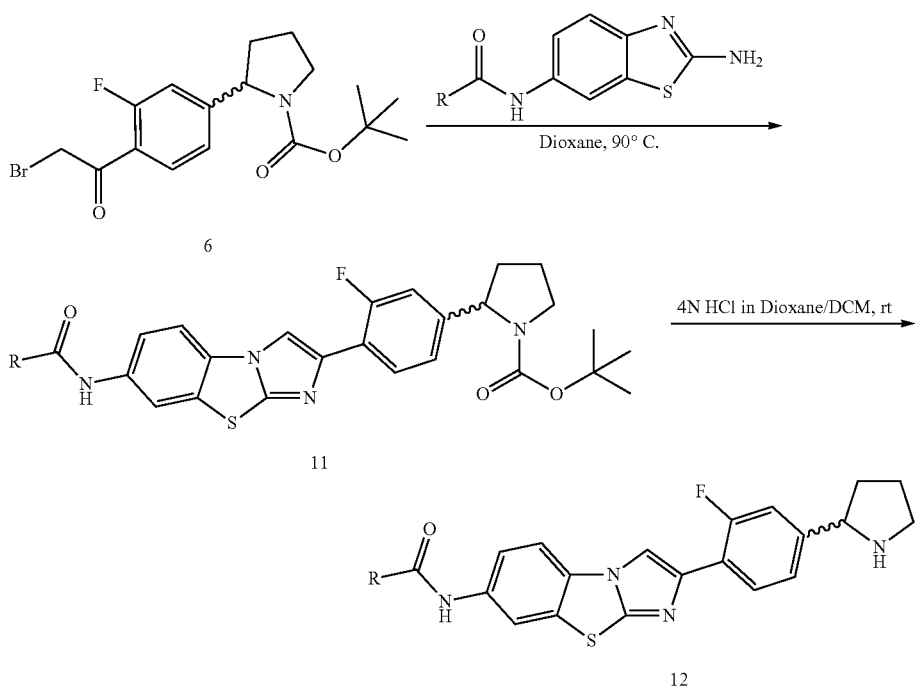

after subsequent N-Boc protecting group removal, the individual enantiomers if required.
Intermediate 13 (Scheme 35) was synthesized following the same synthetic method as described in Scheme 32 Step
Scheme 35.
A second alternative for general synthesis of right-hand side modified benzo[d]imidazo[2,1-b]thiazole-7-carboxamide analogues 20.
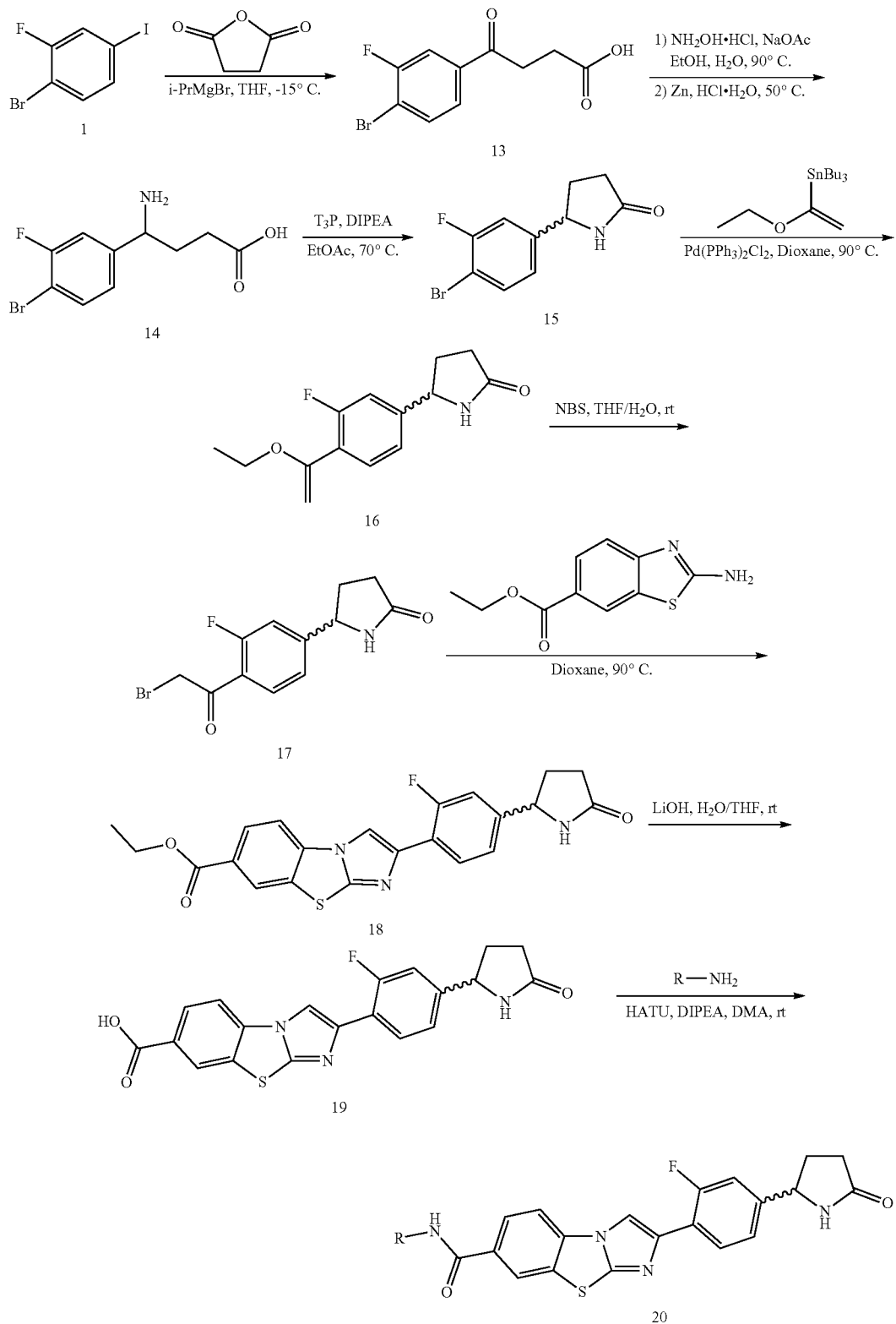

1 by reacting starting materials 1 with succinic anhydride. The ketone of 13 was converted to amine 14, via, in-situ reduction of an oxime using zinc powder. This was followed by intramolecular condensation reaction to generate lactam intermediate 15. Final compounds 20 were synthesized from intermediate 15 following the same procedure as described in Scheme 32. Compounds were isolated as the free base or as the hydrochloride salt. Chiral resolution was performed on lactam 15 to generate, after subsequent completion of the synthetic sequence, the individual enantiomers if required.

Scheme 36.
A third alternative for general synthesis of right-hand side modified benzo[d]imidazo[2,1-b]thiazole-7-carboxamide analogues 31.

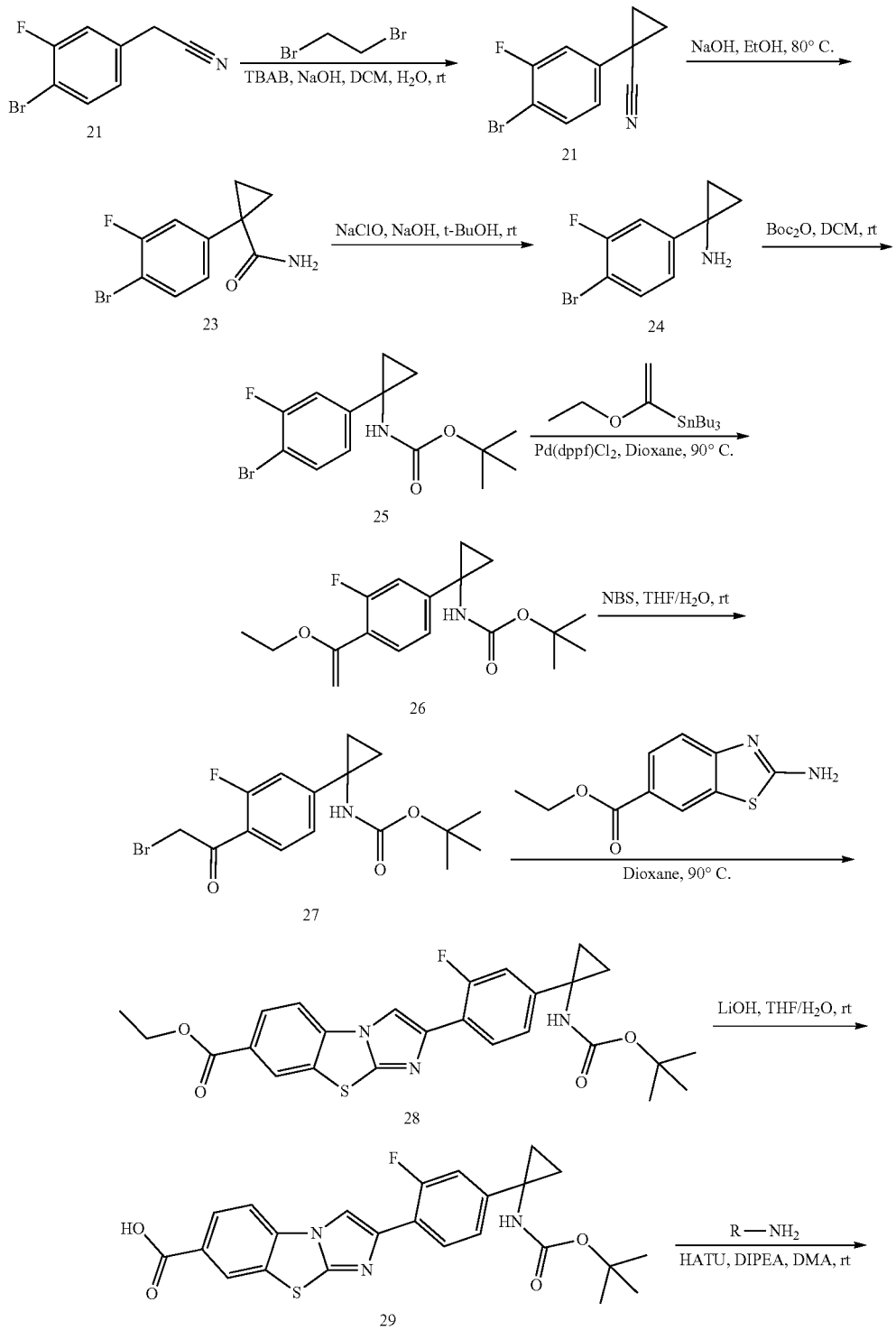

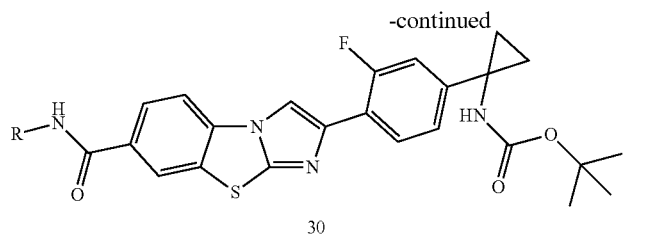

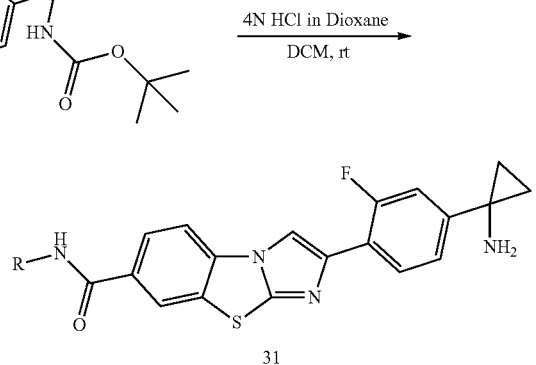

Cyclopropyl intermediates 22 (Scheme 36) was synthesized from phenylacetonitrile 21 and 1,2-dibromoethane under basic conditions. The cyano group was hydrolyzed to amide intermediate 23. Hoffman rearrangement and subsequent protection as the Boc carbamates generated N-Boc protected intermediate 25. Final compounds 31 were synthesized from intermediate 25 following the same synthetic sequence described in Scheme 32. The compounds were isolated as the free base or as the hydrochloride salt.

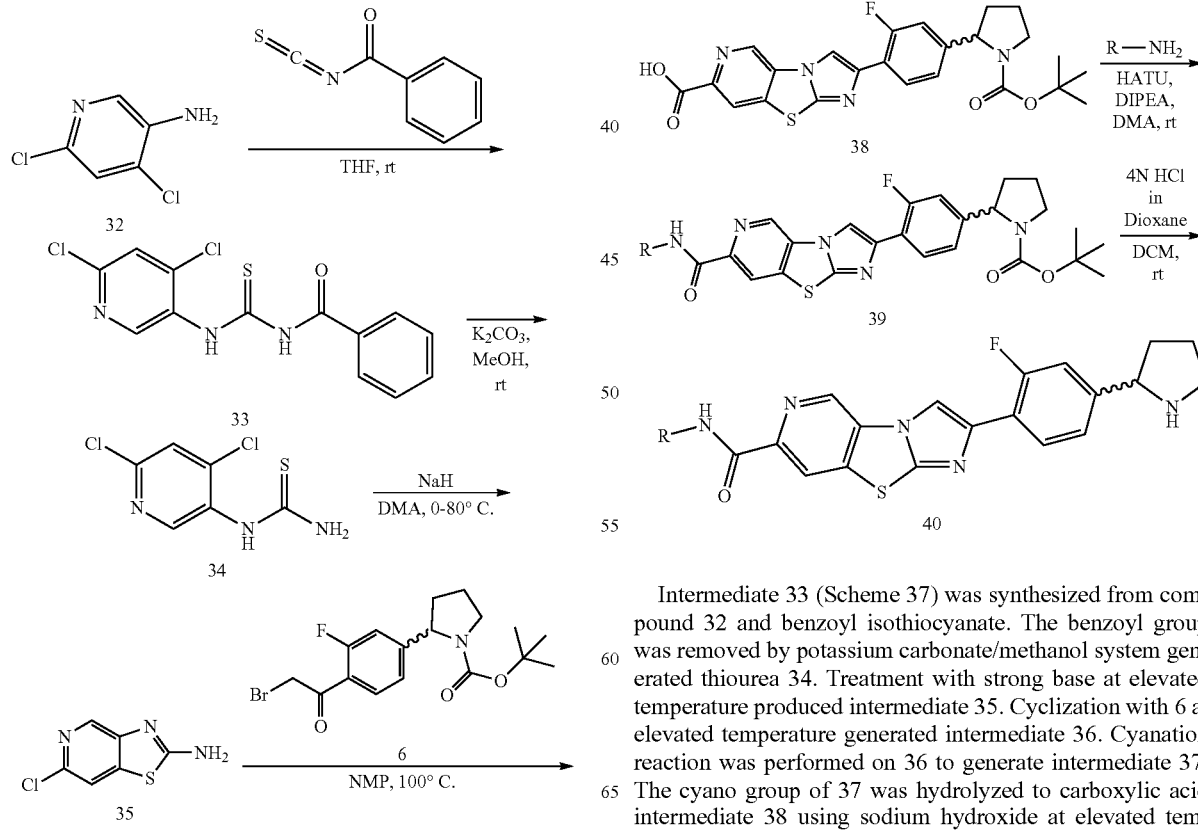

Intermediate 33 (Scheme 37) was synthesized from compound 32 and benzoyl isothiocyanate. The benzoyl group was removed by potassium carbonate/methanol system generated thiourea 34. Treatment with strong base at elevated temperature produced intermediate 35. Cyclization with 6 at elevated temperature generated intermediate 36. Cyanation reaction was performed on 36 to generate intermediate 37. The cyano group of 37 was hydrolyzed to carboxylic acid intermediate 38 using sodium hydroxide at elevated temperature. Final compounds 40 were synthesized from carboxylic acid 38 following the same synthetic sequence described in Scheme 32. The compounds were isolated as the free base or as the hydrochloride salt. Chiral resolution was performed on N-Boc protected compounds 39 to generate, after subsequent N-Boc protecting group removal, the individual enantiomers if required.

Scheme 38.
General synthesis of right-hand side fragment bromobenzene analogues 42.

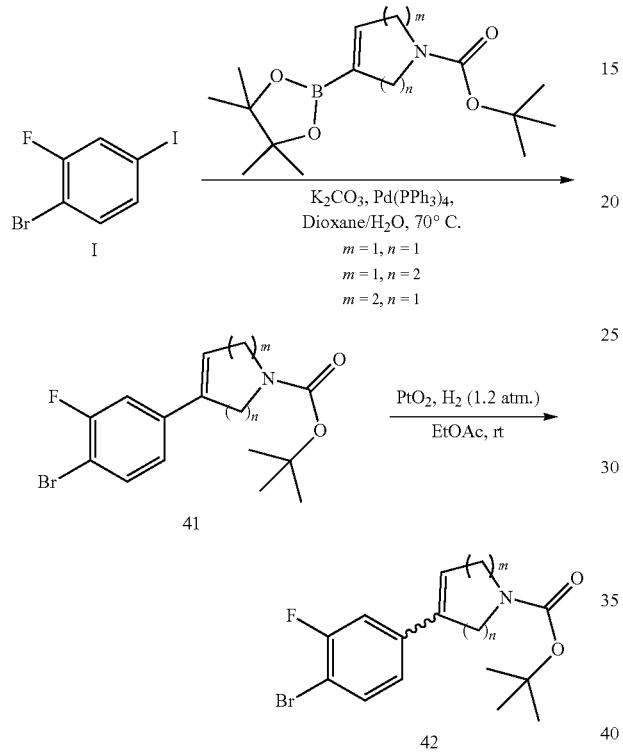

Compound 1 (Scheme 38) was reacted with various boronic esters/acids via Suzuki cross-coupling to generate styrene compounds 41. Reduction by hydrogenation reaction gave bromobenzene intermediates 42.

Scheme 39.
General synthesis of right-hand side fragment bromobenzene analogues 43.

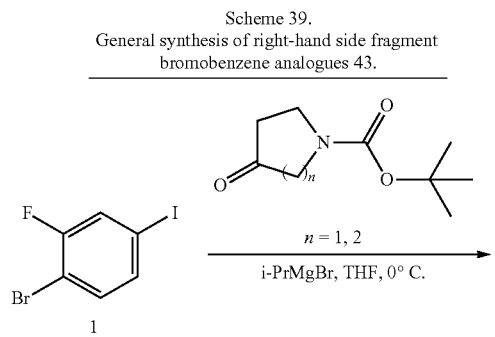

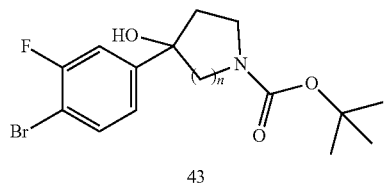

Intermediates 43 (Scheme 39) were synthesized following the same synthetic procedure described in Scheme 32 Step 1, by reacting starting materials 1 with various ketones.

Scheme 40.
General synthesis of right-hand side fragment bromobenzene analogue 44.

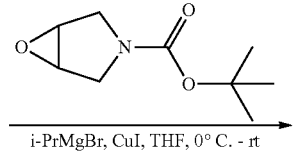

Intermediate 44 (Scheme 40) was synthesized following the same synthetic procedure described in Scheme 32 Step 1, by reaction of reagent 1 with the epoxide in the presence of copper (I) salt.

Scheme 41.
General synthesis of right-hand side fragment bromobenzene analogue 46.

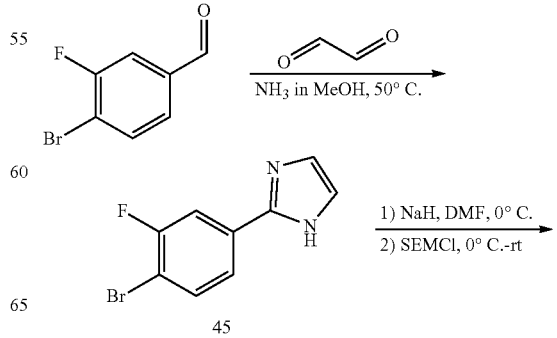

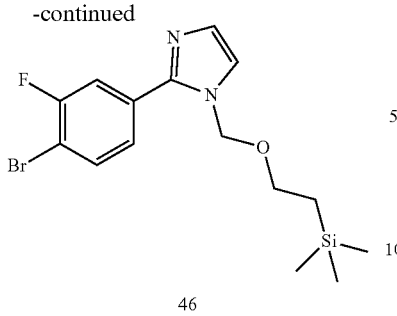

46

Imidazole intermediate 45 (Scheme 41) was synthesized from commercially available 4-bromo-3-fluorobenzaldehyde via a cyclization reaction. The imidazole was protected with a SEM group to generate intermediate 46.

Scheme 42.
General synthesis of right-hand side fragment bromobenzene analogue 49.

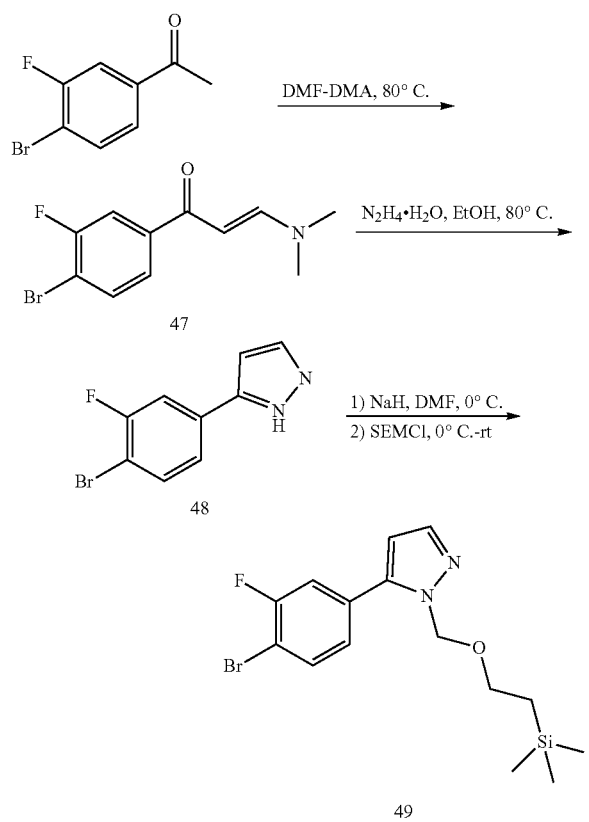

Reaction of commercially available 1-(4-bromo-3-fluorophenyl)ethan-1-one (Scheme 42) with DMF-DMA at elevated temperature generated intermediate 47 (Scheme 42). Cyclization with hydrazine hydrate gave pyrazole intermediate 48. The pyrazole was protected with a SEM group to generate intermediate 49.

Scheme 43.
General synthesis of right-hand side fragment bromobenzene analoogue 51.

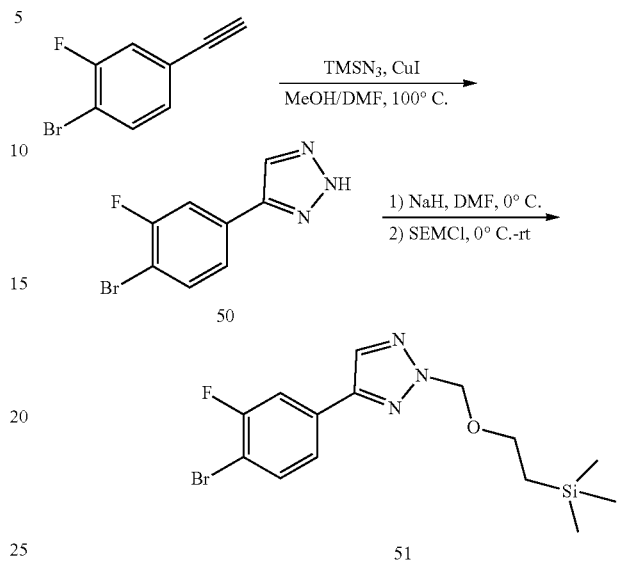

Click reaction was performed on commercially available 1-bromo-4-ethynyl-2-fluorobenzene (Scheme 43) to generate 1,2,3-triazole intermediate 50 (Scheme 43). The triazole was protected with a SEM group to generate intermediate 51.

Scheme 44.
General synthesis of right-hand side fragment bromobenzene analogue 54.

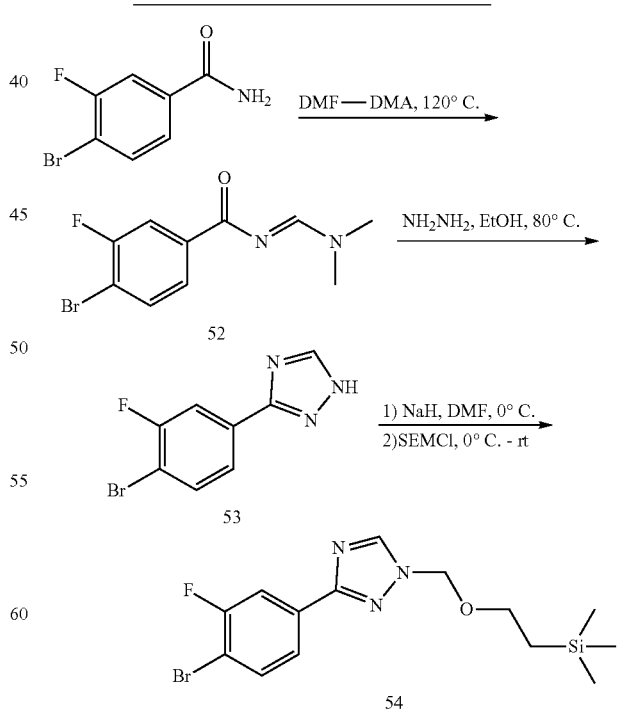

Reaction of commercially available 4-bromo-3-fluorobenzamide (Scheme 44) with DMF-DMA at elevated temperature generated intermediate 52. Cyclization with hydrazine hydrate gave 1,3,4-triazole intermediate 53. The triazole was protected with a SEM group to generate intermediate 54.

Scheme 45.
General synthesis of right-hand side fragment bromobenzene analogue 55.

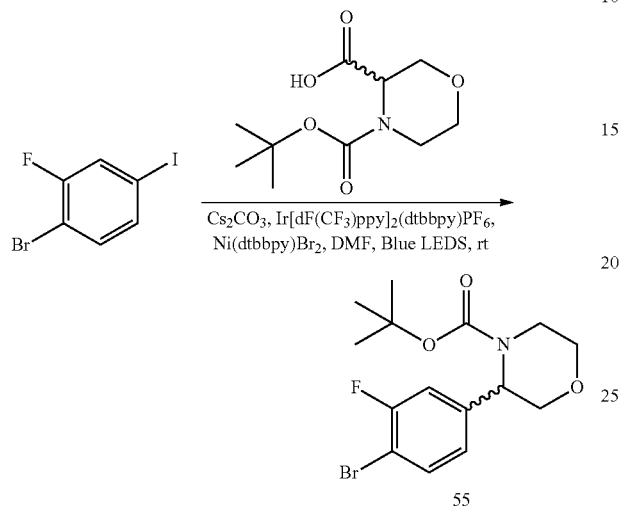

Intermediate 55 (Scheme 45) was synthesized by reaction of commercially available 1-bromo-2-fluoro-4-iodobenzene and the carboxylic acid via a photoredox cross-coupling reaction.

Scheme 46. General synthesis of right-hand side fragment bromobenzene analogue 57.

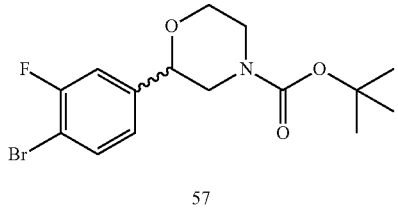

Condensation reaction was performed on commercially available 3R/3S-4-(1,1-Dimethylethyl)-3,4-morpholinedicarboxylate (Scheme 46) with 2-hydroxyisoindoline-1,3-dione to generate activated ester intermediate 56 (Scheme 46). A cross-coupling reaction with 1-bromo-2-fluoro-4-iodobenzene gave bromobenzene analogue 57.

Scheme 47. General synthesis of right-hand side fragment bromobenzene analogue 59, 60 and 61.

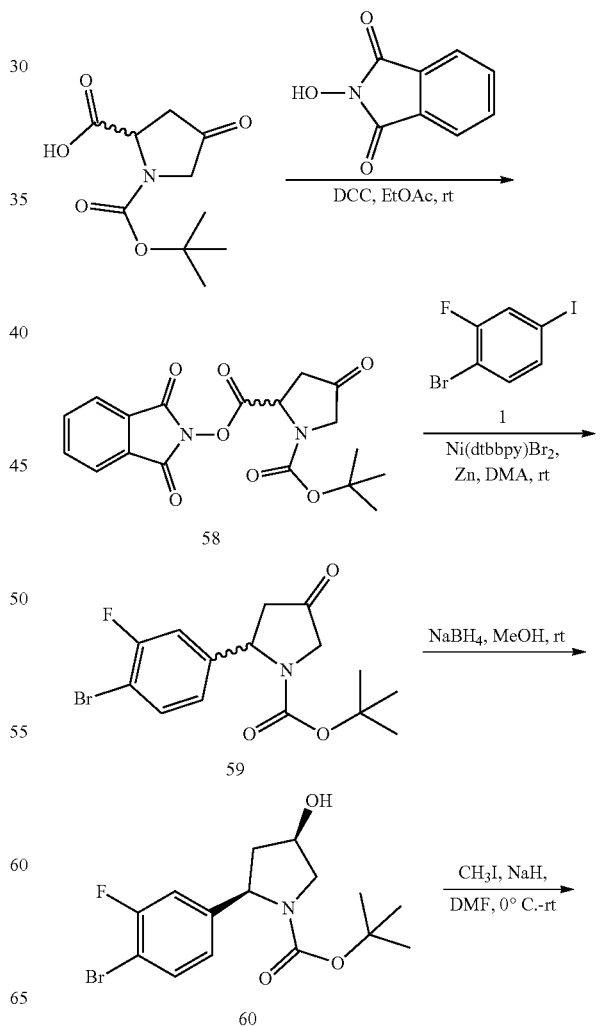

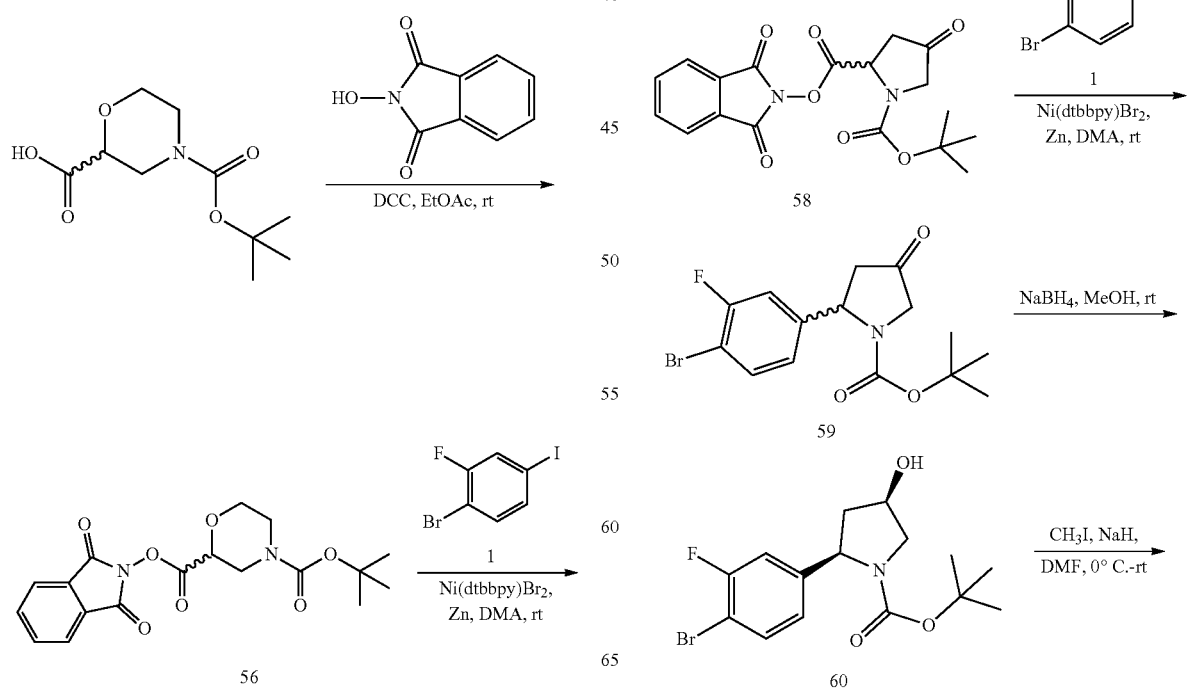

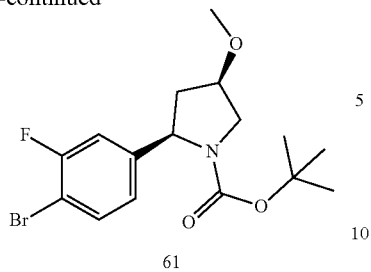

61

Intermediate 59 (Scheme 47) was synthesized from commercially available 2R/2S-1-(1,1-Dimethylethyl)-4-oxo-1,2-pyrrolidinedicarboxylate, following the same synthetic sequence described in Scheme 37. The ketone of 59 was reduced to give cis alcohol intermediate 60. A methyl group was introduced to give ether intermediate 61.

Scheme 48. General synthesis of right-hand side fragment bromobenzene analogue 67.

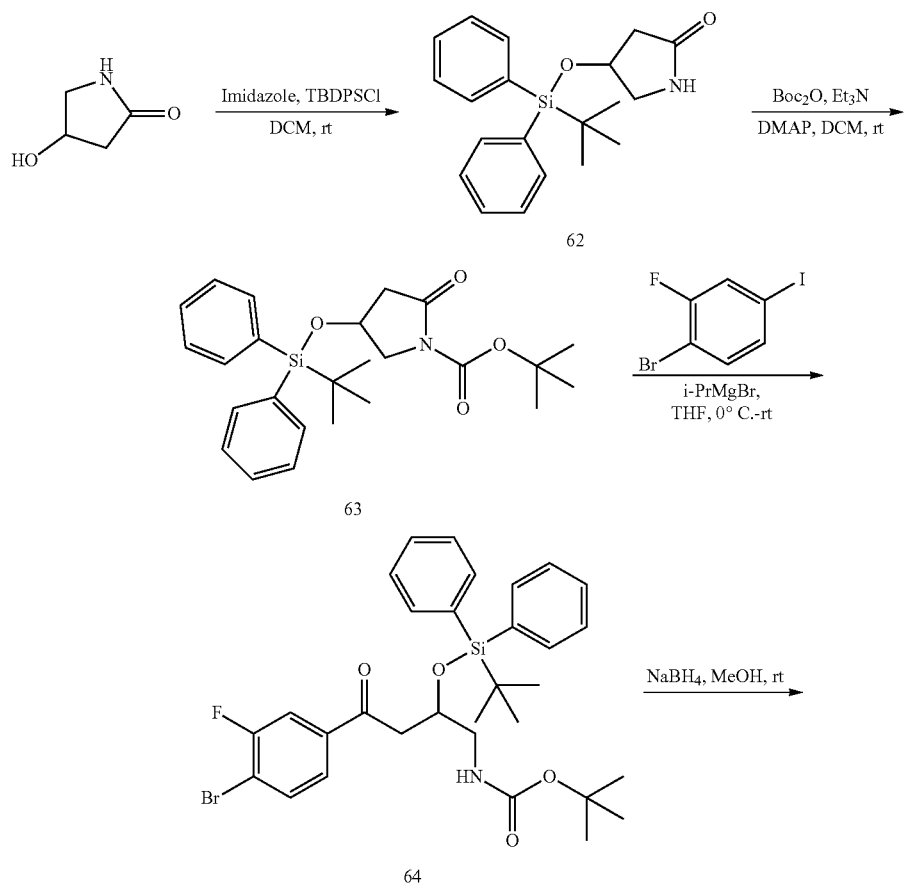

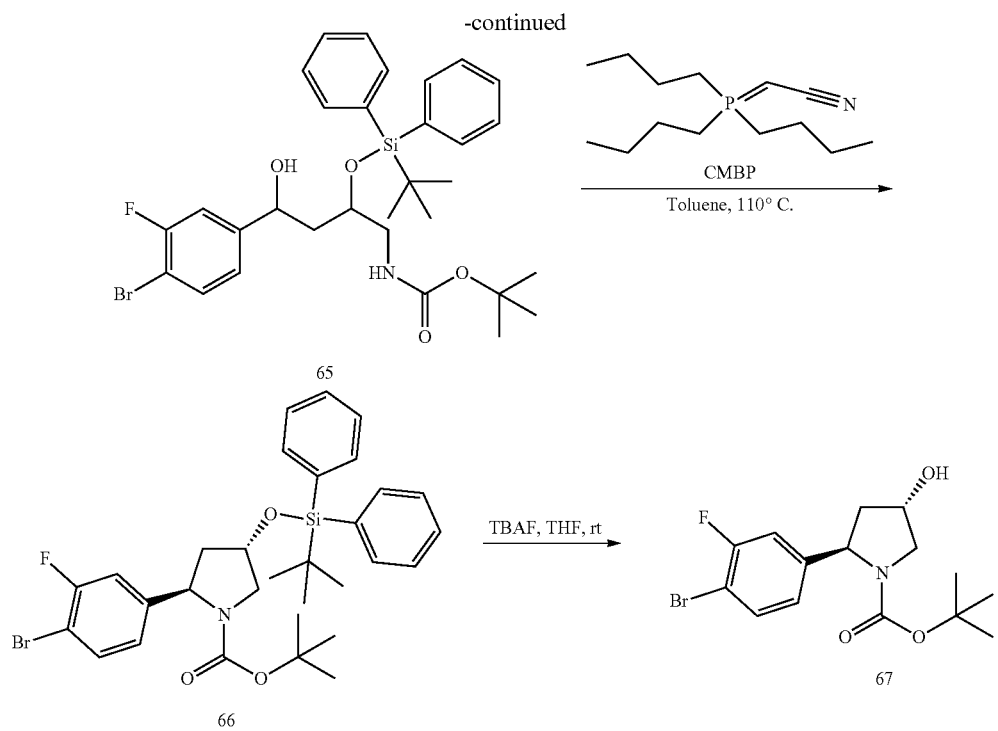

Hydroxyl group of 4-hydroxypyrrolidin-2-one (Scheme 48) was protected with a TBDPS group to generate intermediate 62. Boc protection of the lactam group gave intermediate 63. The ketone intermediate 64 was synthesized following the synthetic procedure described in Scheme 32 Step 1. Ketone reduction gave the alcohol intermediate 65. A Mitsunobu reaction was performed on 65 using the reagent CMBP to selectively generate trans intermediate 66. The TBDPS group was removed by reaction with TBAF to generate intermediate 67.

Scheme 49. General synthesis of right-hand side fragment boronic esters/acids analogues 68.

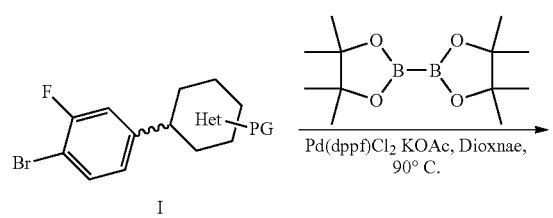

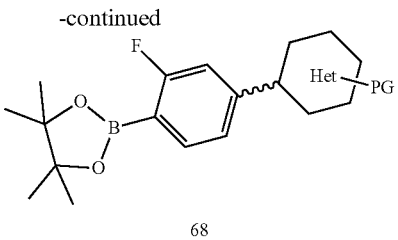

I = 4, 42, 43, 44, 46, 49, 51, 54, 55, 57, 59, 60, 61, 67
PG = Boc, SEM

Bromobenzene analogues I (Scheme 49) were converted to their corresponding boronic esters/acids analogues 68 via Miyaura borylation reaction.

Scheme 50. General synthesis of right-hand side modified benzo[d]imidazo[2,1-b]thiazole-7-carboxamide analogues 74.

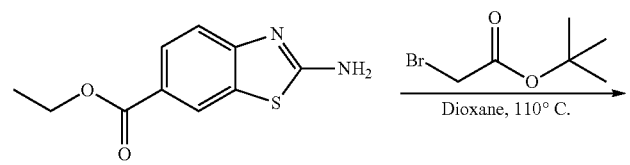

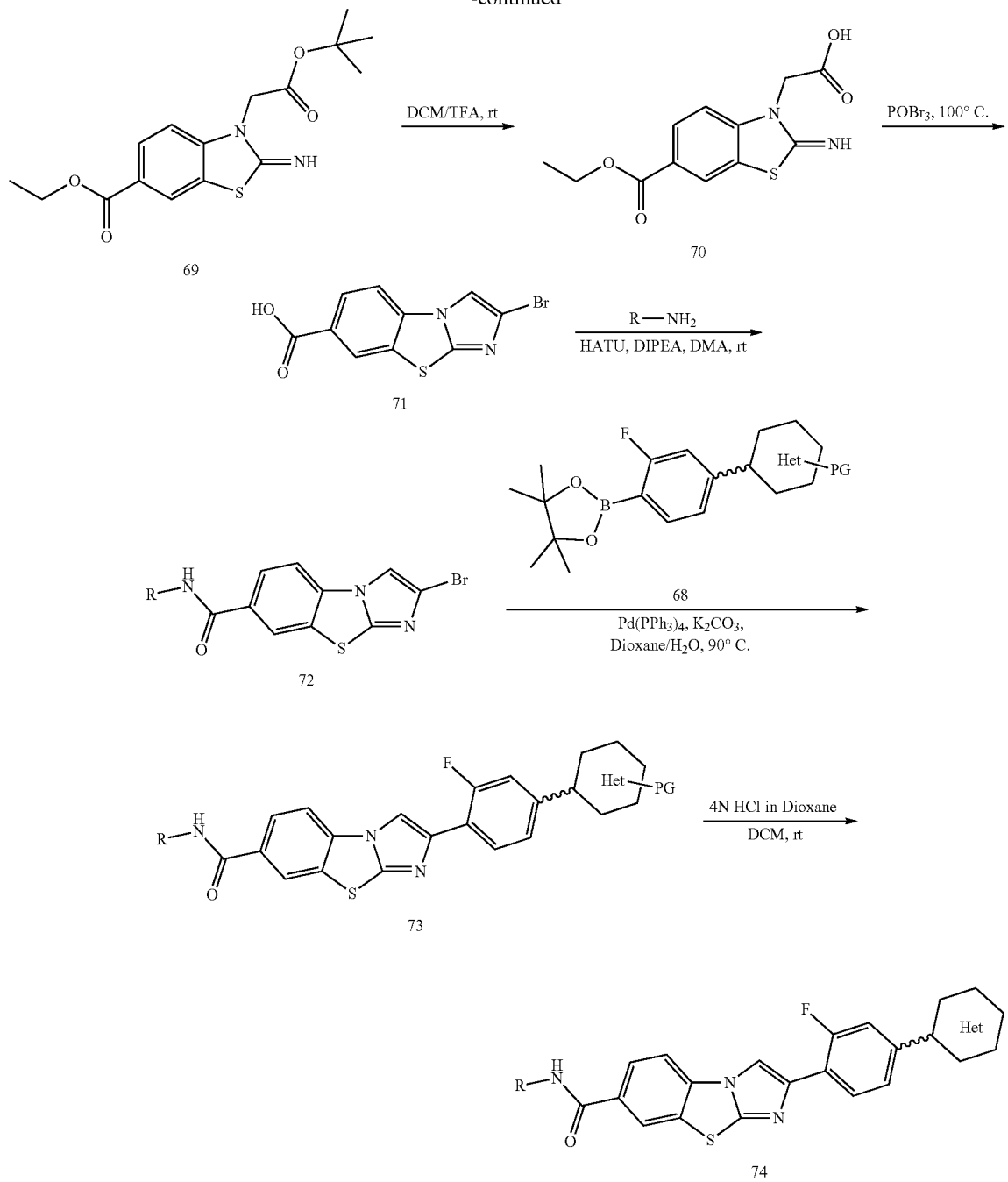

Alkylation of commercially available ethyl 2-aminobenzothiazole-6-carboxylate (Scheme 50) with tert-butyl bromoacetate at elevated temperature afforded intermediate 69. The tert-butyl ester was hydrolyzed using a mixture of TFA-DCM to generate the carboxylic acid intermediate 70. Treatment of the carboxylic acid intermediate 70 with phosphorus(V) oxybromide at elevated temperature resulted in intramolecular cyclization to form the 2-bromobenzo[d]imidazo[2,1-b]thiazole-7-carboxylic acid intermediate 71. Elaboration at the carboxylic acid terminus of intermediate 71, by HATU mediated coupling with numerous amines, afforded amide intermediates 72. Suzuki cross-coupling with various boronate esters 68, gave intermediates 73. The N-Boc protecting group was removed by 4 N hydrochloride in 1,4-dioxane to generate benzo[d]imidazo[2,1-b]thiazole-7-carboxamide analogues 74 as the free base or as the hydrochloride salt. Chiral resolution was performed on N-Boc protected compounds 73 to generate, after subsequent N-Boc protecting group removal, the individual enantiomers if required.

Scheme 51. General synthesis of right-hand side modified benzo[d]imidazo[2,1-b]thiazole-7-carboxamide analogues 76.

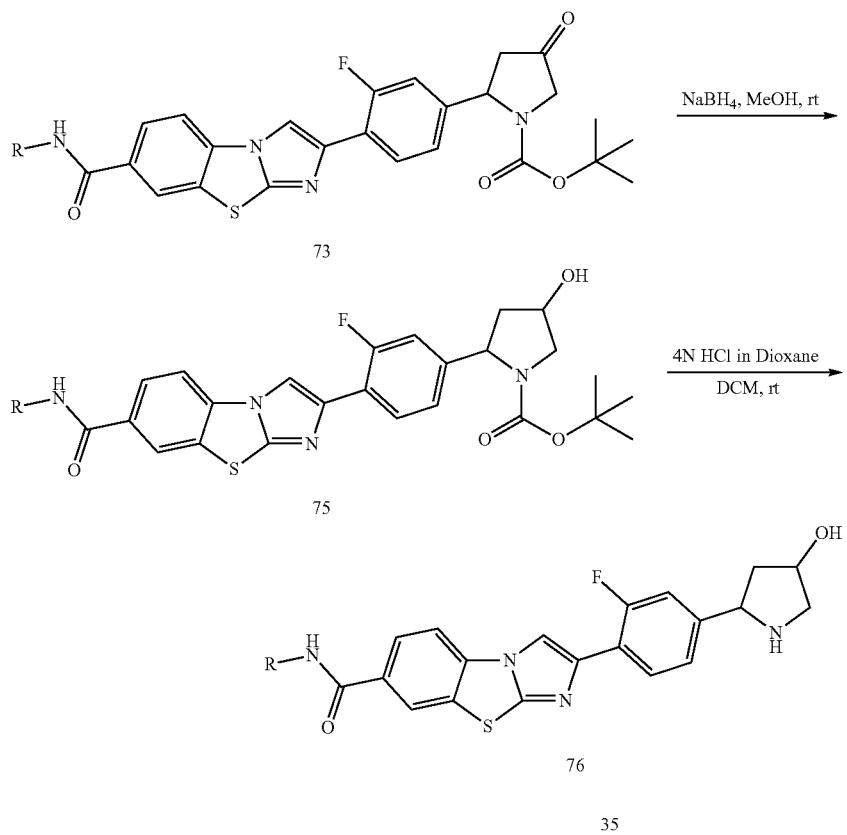

The ketone of intermediate 73 (Scheme 51) was reduced by sodium borohydride to generate alcohol intermediate 75. The N-Boc protecting group was removed by 4 N hydrochloride in 1,4-dioxane to generate benzo[d]imidazo[2,1-b]thiazole-7-carboxamide analogues 76 as the free base or as the hydrochloride salt.

Scheme 52. General synthesis of right-hand side modified benzo[d]imidazo[2,1-b]thiazole-7-carboxamide analogues 78.

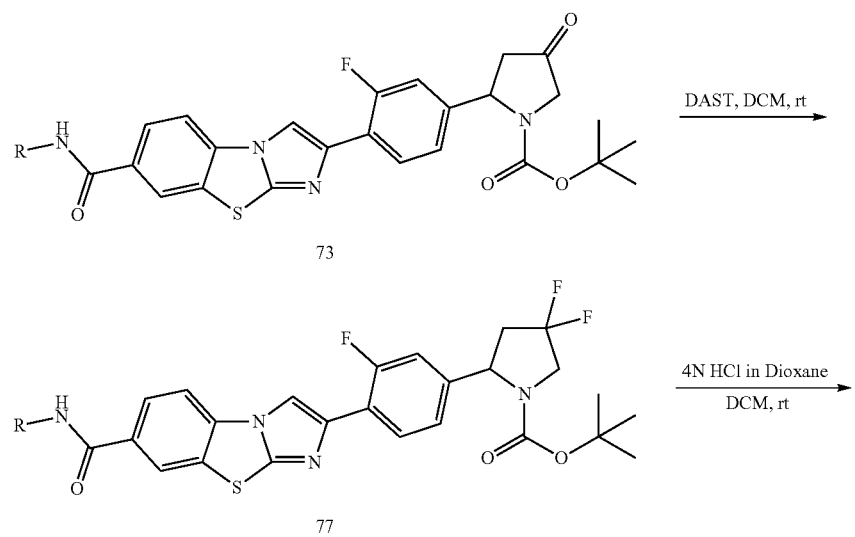

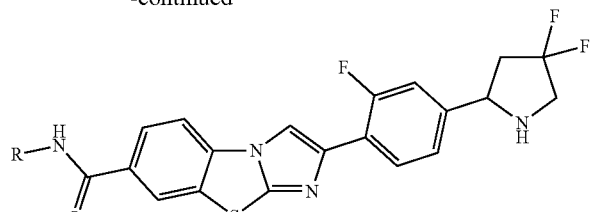
78
Difluoro intermediate 77 (Scheme 52) was synthesized from ketone intermediate 73 by reaction with DAST reagent. The N-Boc protecting group was removed by 4 N hydrochloride in 1,4-dioxane to generate benzo[d]imidazo[2,1-b]thiazole-7-carboxamide analogues 78 as the free base or as the hydrochloride salt.
Scheme 53. General synthesis of benzo[d]imidazo[2,1-b]thiazole-7-carboxamide analogue 83.
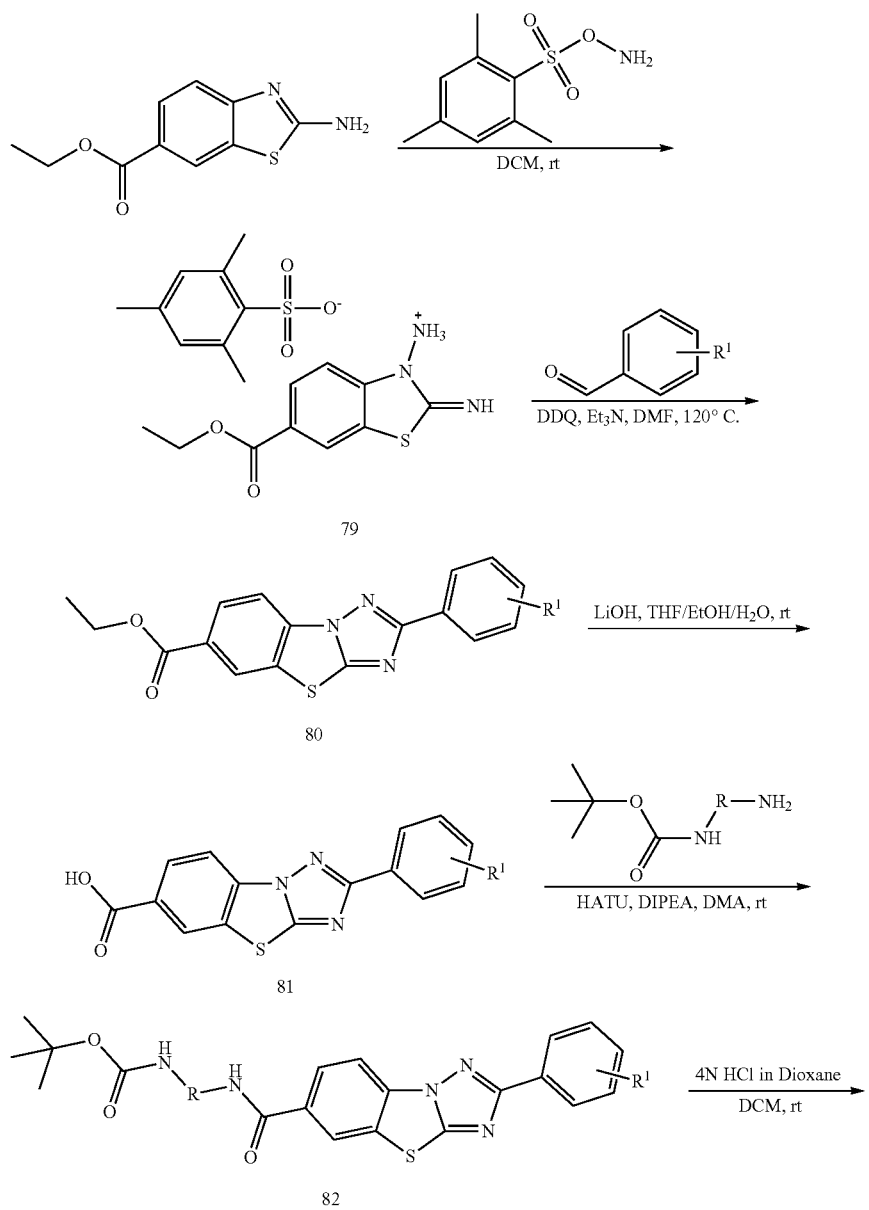

-continued

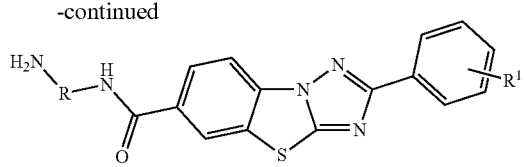

83

Electrophilic amination reaction of ethyl 2-aminobenzothiazole-6-carboxylate (Scheme 53) with O-(2,4,6-trimethylbenzenesulfonyl)hydroxylamine (MSH) in DCM afforded intermediate 79. An intermolecular oxidative cyclization between aldehydes and salt intermediate 79 afforded the tricyclic core intermediates 80. Final compounds 83 were synthesized from intermediates 80 following the same synthetic sequence described in Scheme 32. The compounds were isolated as the free base or as the hydrochloride salt.

Scheme 54. General synthesis of benzo[d]imidazo[2,1-b]thiazole-7-carboxamide analogue 85.

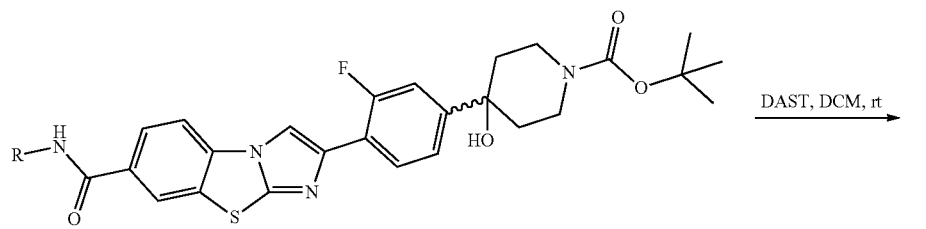

73

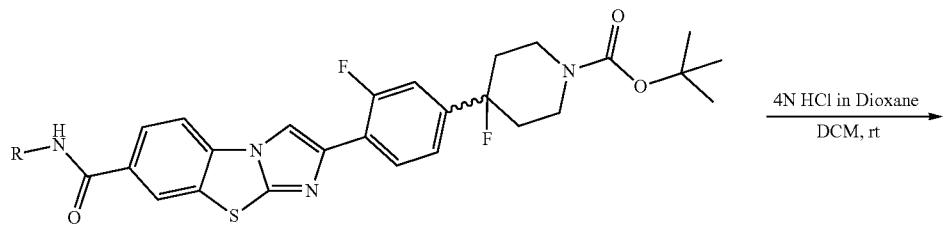

84

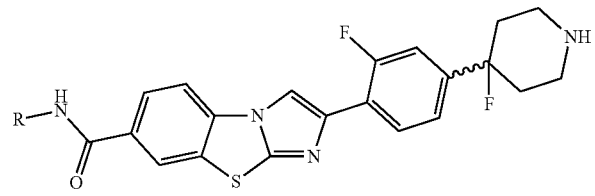

85

The hydroxyl group of intermediate 73 was converted to fluoride using DAST reagent, to generate intermediate 84. The N-Boc protecting group was removed by treatment with 4 N hydrochloride in 1,4-dioxane, to generate benzo[d]imidazo[2,1-b]thiazole-7-carboxamide analogues 85 as a free base or as the hydrochloride salt.

Scheme 55. General synthesis of benzo[d]imidazo[2,1-b]thiazole-7-carboxamide analogue 89.

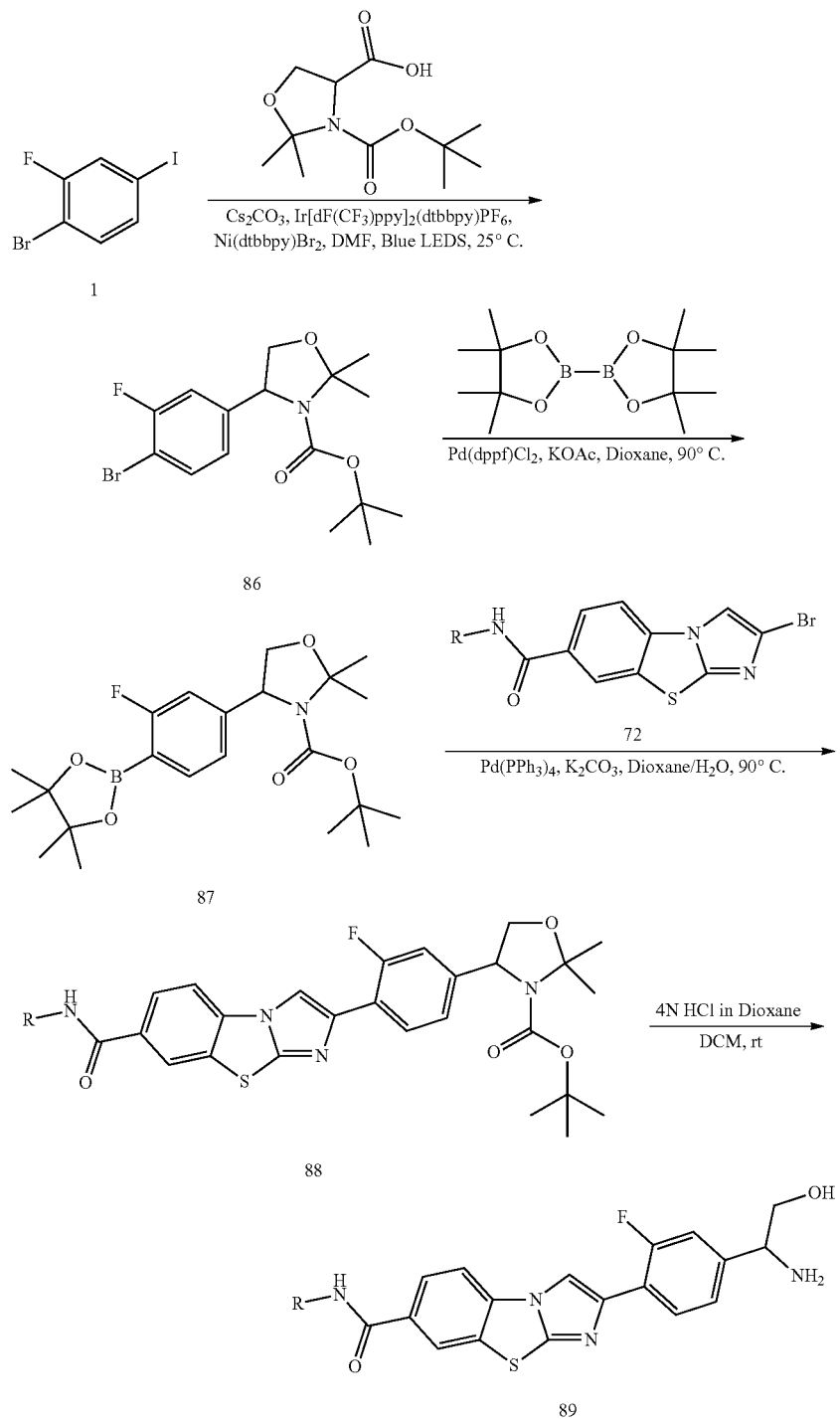

Intermediate 86 was synthesized from compound 1 and carboxylic acid by a decarboxylative coupling reaction. Miyaura borylation reaction generated boronic ester analogue 87. Final compounds 89 were synthesized from intermediates 87 and 72 following the procedure described in Scheme 50. The compounds were isolated as the free base or as the hydrochloride salt.

Scheme 56. General synthesis of benzo[d]imidazo[2,1-b]thiazole-7-carboxamide analogue 94.
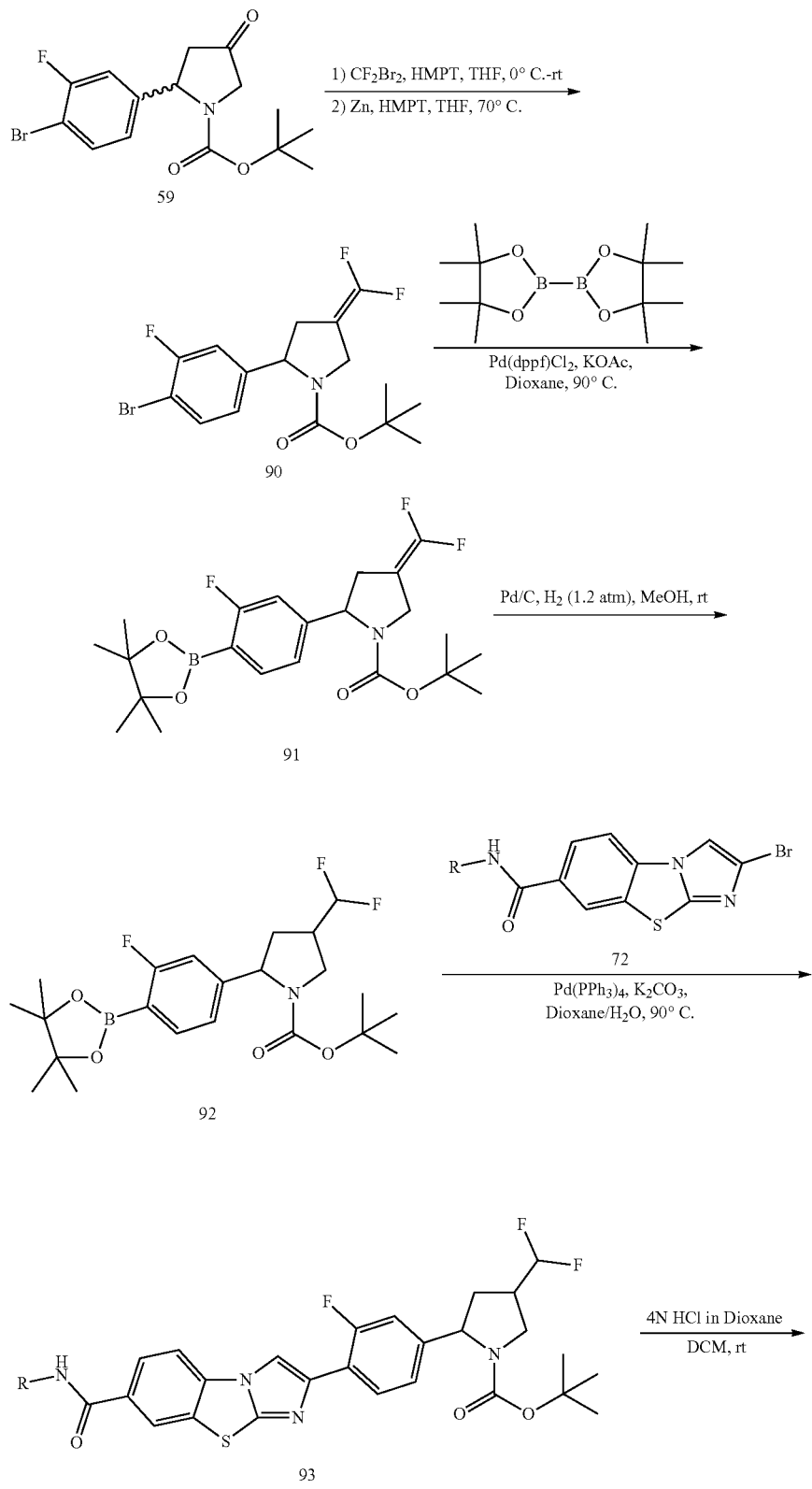

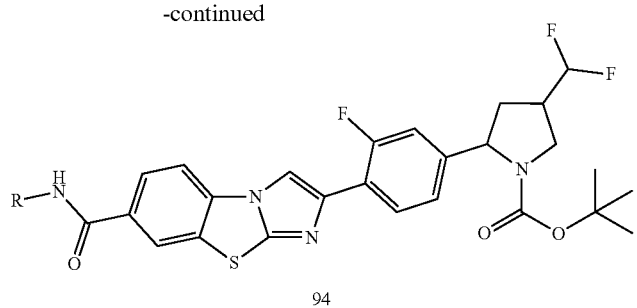

The ketone of intermediate 59 was converted to difluoroethylene intermediate 90. The Miyaura borylation reaction was performed on 90 to generate boronic ester intermediate 91. The double bond was reduced by hydrogenation to generate intermediate 92. Final compounds 94 were synthesized from intermediates 92 and 72 following the same procedure described in Scheme 50. The compounds were isolated as the free base or as the hydrochloride salt.

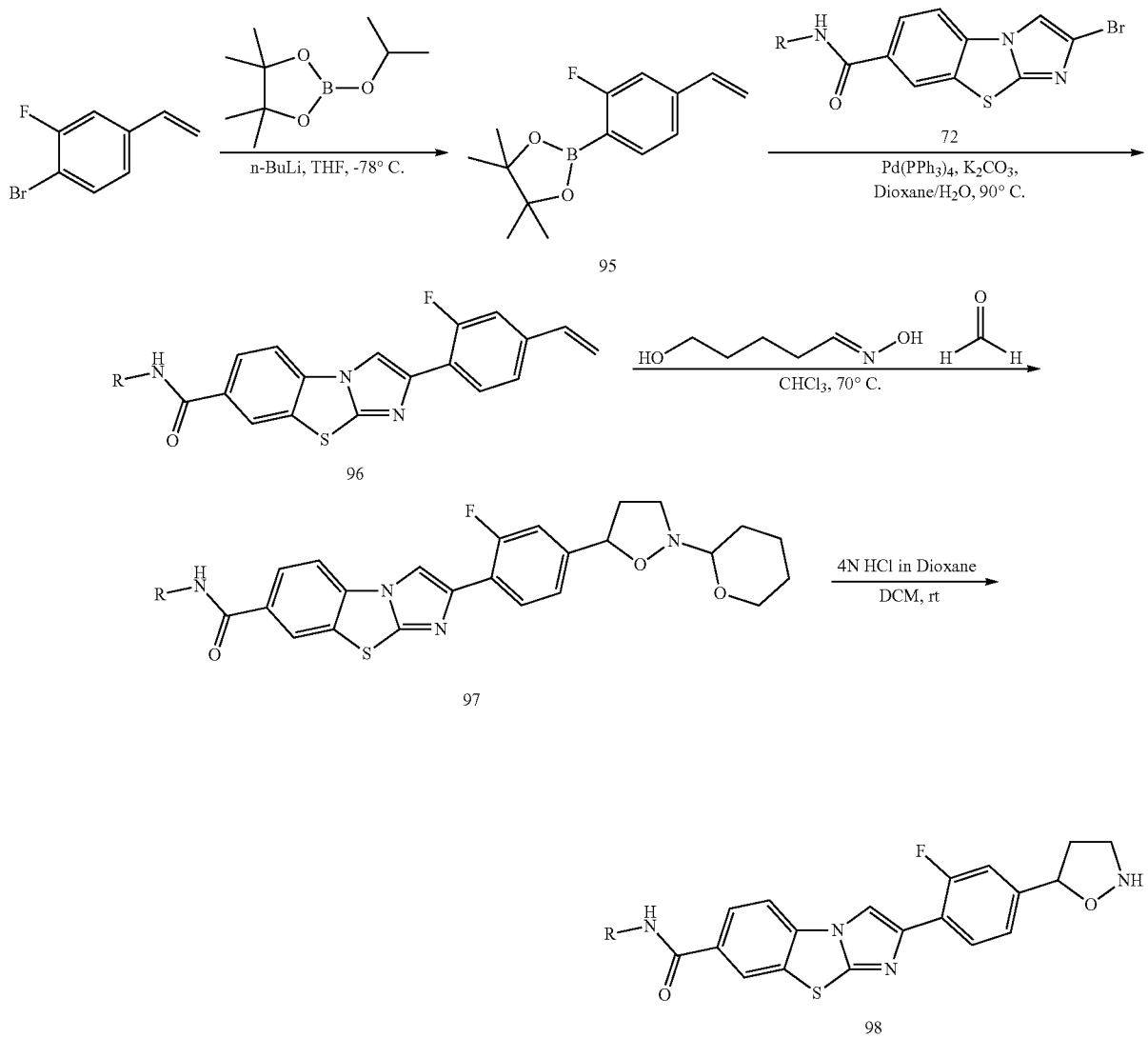

Commercially available 1-Bromo-4-ethenyl-2-fluorobenzene was converted to the corresponding borinic ester 95, using Lithium-halogen exchange and subsequent trapping with borate reagent. A Suzuki cross-coupling reaction was performed to generate intermediate 96. A cyclization reaction was carried out on intermediate 96 to convert the ethene group to N-THP protected isoxazolidine intermediate 97. The N-THP protecting group was removed by 4 N hydrochloride in 1,4-dioxane to generate benzo[d]imidazo[2,1-b]thiazole-7-carboxamide analogue 98 as a free base or as the hydrochloride salt.

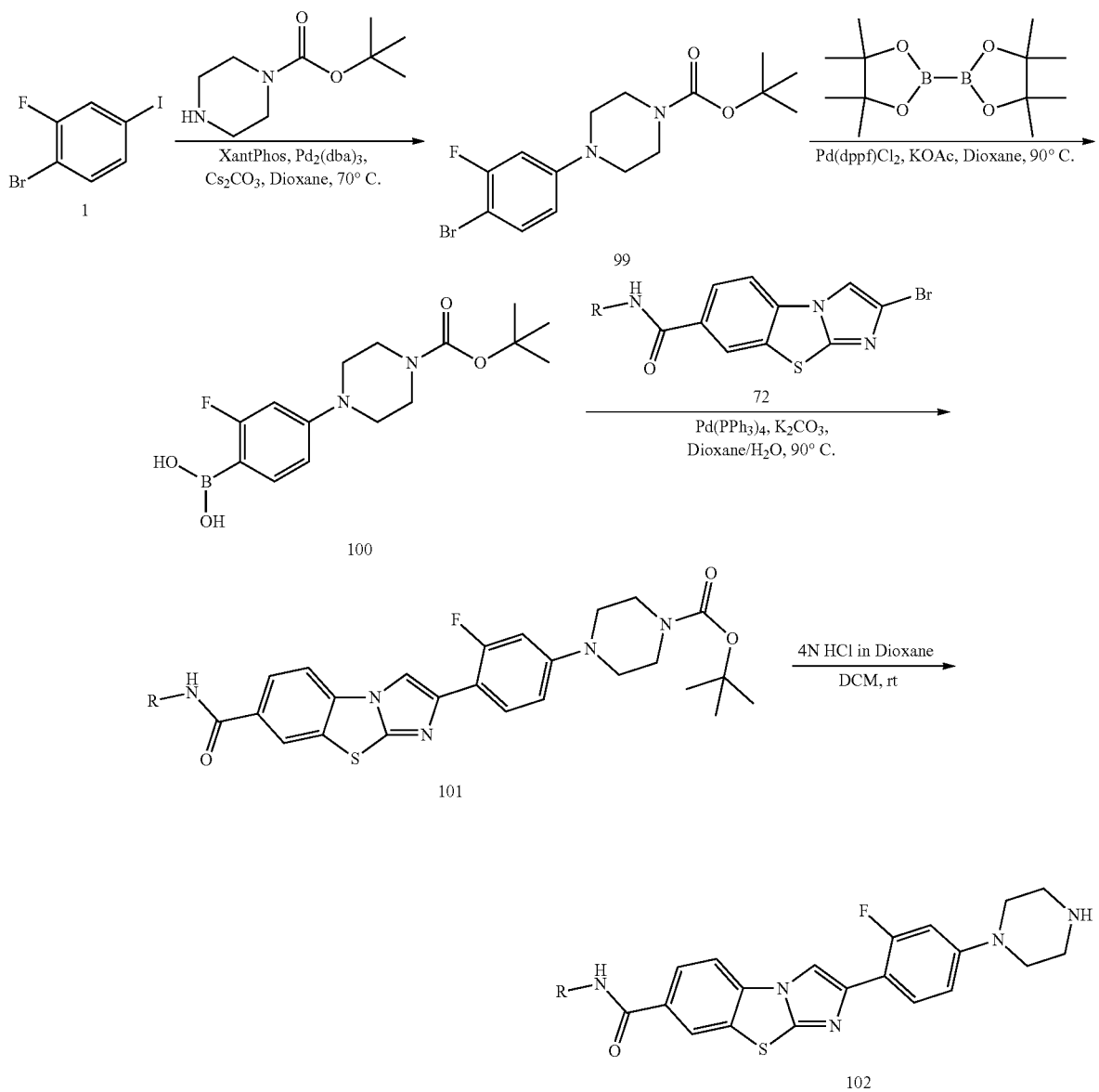

Scheme 58. General synthesis of benzo[d]imidazo[2,1-b]thiazole-7-carboxamide analogue 102.

A Buchwald cross-coupling reaction was performed on starting material 1 with amine to generate intermediate 99. Final compounds 102 were synthesized from intermediate 99 following the same procedure described in Scheme 55. The compounds were isolated as the free base or as the hydrochloride salt.

Example 4

Synthetic Details of Some Compounds of the Invention

Synthesis of (S)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide (Compound 428S)

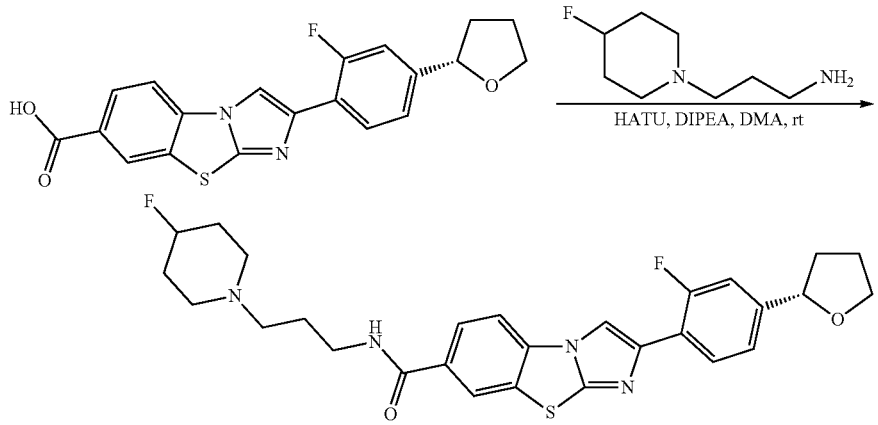

To a stirred solution of (S)-2-(2-fluoro-4-(tetrahydrofuran-2-yl)phenyl)benzo[d]imidazo[2,1-b]thiazole-7-carboxylic acid (110 mg, 0.288 mmol) and N,N,N',N'-tetramethyl-O-(7-azabenzotriazol-1-yl)uronium hexafluorophospate (164 mg, 0.431 mmol) in N,N-dimethylacetamide (5 mL) were added N-ethyl-N-isopropylpropan-2-amine (112 mg, 0.867 mmol) and 3-(4-fluoropiperidin-1-yl)propan-1-amine (92 mg, 0.574 mmol) at room temperature under a nitrogen atmosphere. The reaction solution was stirred for 3 h at room temperature under a nitrogen atmosphere and was purified by reverse phase flash chromatography with the following conditions: Column: Spherical C18, 20-40 μm, 120 g; Mobile Phase A: water (10 mM $NH_4HCO_3$); Mobile Phase B: acetonitrile; Flow rate: 80 mL/min; Gradient: 40% B—60% B in 20 min; Detector: 254 nm. The fractions containing desired product were collected at 50% B and concentrated under reduced pressure to afford (S)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide as a white solid.

Yield 30 mg (20%). $^1$H NMR (400 MHz, DMSO) δ 8.70 (d, J=3.6 Hz, 1H), 8.61 (t, J=5.6 Hz, 1H), 8.49 (d, J=1.6 Hz, 1H), 8.27 (d, J=8.4 Hz, 1H), 8.11 (dd, J=8.0 Hz, 1H), 8.01 (dd, J=1.6, 8.4 Hz, 1H), 7.27 (d, J=2.8 Hz, 1H), 7.25 (s, 1H), 4.91-4.84 (m, 1H), 4.77-4.58 (m, 1H), 4.07-3.97 (m, 1H), 3.89-3.78 (m, 1H), 3.36-3.29 (m, 2H), 2.56-2.48 (m, 2H), 2.40-2.24 (m, 5H), 2.01-1.91 (m, 2H), 1.91-1.77 (m, 2H), 1.76-1.64 (m, 5H). $^{19}$F NMR (376 MHz, $CD_3OD$) δ −115.13. m/z: [ESI$^+$]525 (M+H)$^+$. ($C_{28}H_{30}F_2N_4O_2S$)

Synthesis of (R)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide (Compound 428R)

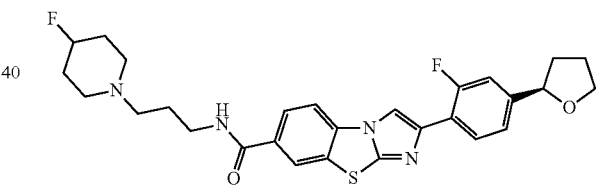

Compound (R)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide was prepared from (R)-2-(2-fluoro-4-(tetrahydrofuran-2-yl)phenyl)benzo[d]imidazo[2,1-b]thiazole-7-carboxylic acid (100 mg, 0.261 mmol) and 3-(4-fluoropiperidin-1-yl)propan-1-amine (84 mg, 0.524 mmol) following a similar procedure to that described for the synthesis of (S)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide, and was isolated as a white solid.

Yield 30 mg (22%). $^1$H NMR (400 MHz, DMSO) δ 8.70 (d, J=3.6 Hz, 1H), 8.61 (t, J=5.6 Hz, 1H), 8.49 (d, J=1.6 Hz, 1H), 8.27 (d, J=8.4 Hz, 1H), 8.11 (dd, J=8.0 Hz, 1H), 8.01 (dd, J=1.6, 8.4 Hz, 1H), 7.27 (d, J=2.8 Hz, 1H), 7.25 (s, 1H), 4.91-4.84 (m, 1H), 4.77-4.58 (m, 1H), 4.07-3.97 (m, 1H), 3.89-3.78 (m, 1H), 3.36-3.29 (m, 2H), 2.56-2.48 (m, 2H), 2.40-2.24 (m, 5H), 2.01-1.91 (m, 2H), 1.91-1.77 (m, 2H), 1.76-1.64 (m, 5H). $^{19}$F NMR (376 MHz, $CD_3OD$) δ −115.13. m/z: [ESI$^+$]525 (M+H)$^+$. ($C_{28}H_{30}F_2N_4O_2S$)

Example 5

Synthetic Details of Additional Compounds of the Invention (Intermediates, Schemes 60-81)
Intermediate Preparations Synthesis of tert-butyl (R)-2-(3-fluoro-4-(7-((1-methylpiperidin-4-yl)carbamoyl)benzo[d]imidazo[2,1-b]thiazol-2-yl)phenyl)pyrrolidine-1-carboxylate and tert-butyl (S)-2-(3-fluoro-4-(7-((1-methylpiperidin-4-yl)carbamoyl)benzo[d]imidazo[2,1-b]thiazol-2-yl)phenyl)pyrrolidine-1-carboxylate

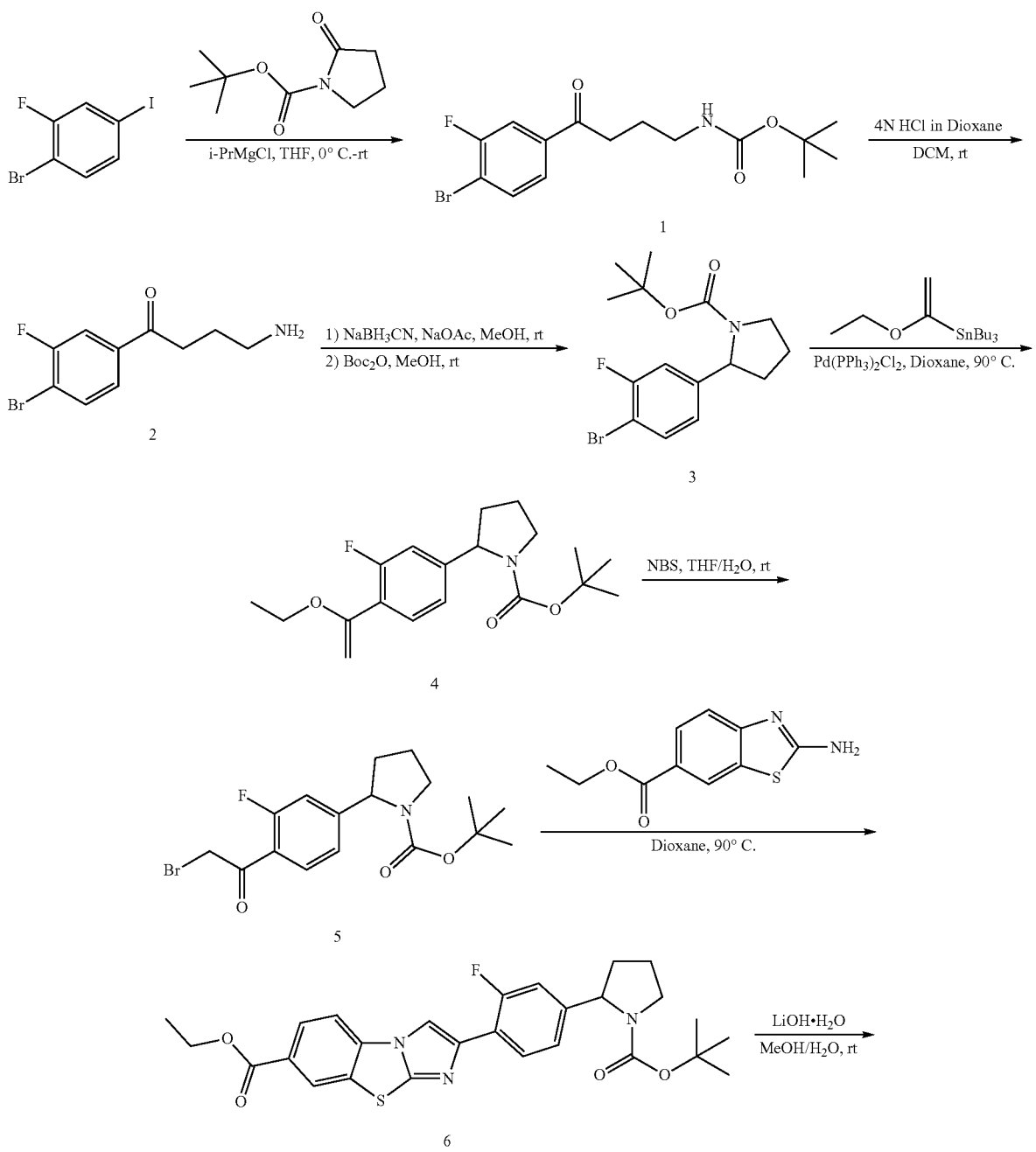

Scheme 60.

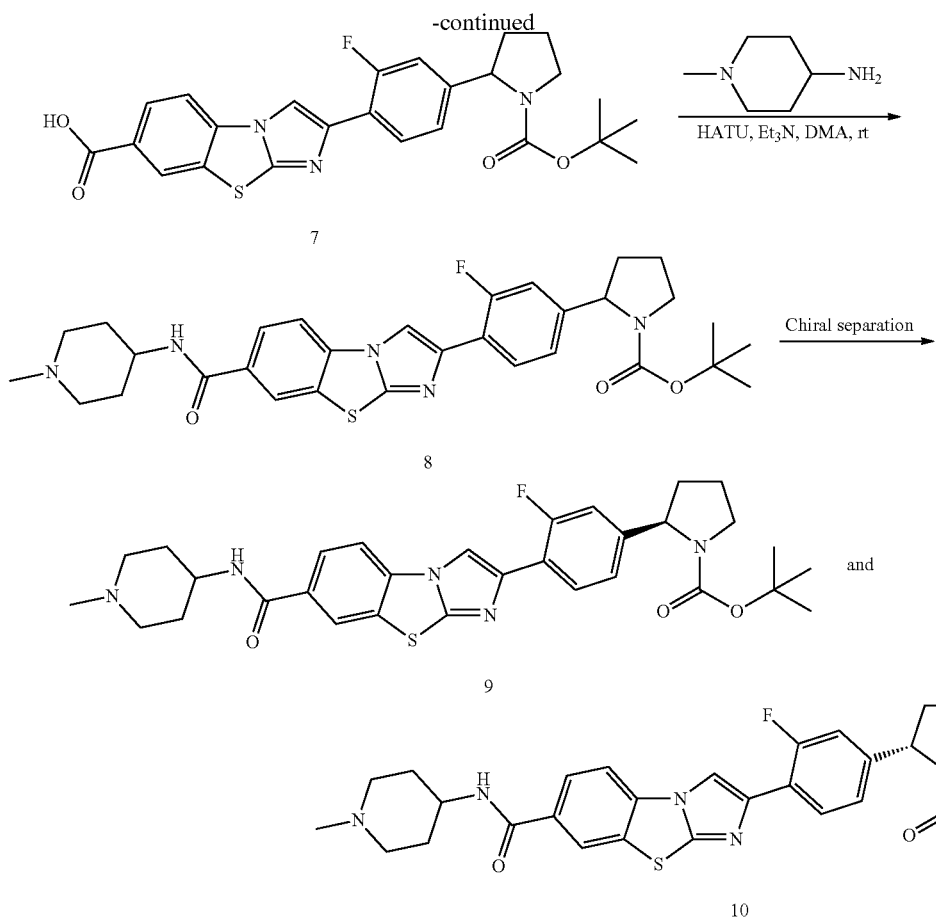

Synthesis of tert-butyl (4-(4-bromo-3-fluorophenyl)-4-oxobutyl)carbamate

To a stirred solution of 1-bromo-2-fluoro-4-iodobenzene (46.00 g, 152.88 mmol) in tetrahydrofuran (400 mL) was added isopropylmagnesium chloride (2.0 N in tetrahydrofuran, 84 mL, 168.00 mmol) dropwise, at 0° C. under a nitrogen atmosphere. The resulting solution was stirred for 3 h after which, a solution of tert-butyl 2-oxopyrrolidine-1-carboxylate (33.98 g, 183.46 mmol) in tetrahydrofuran (60 mL) was added dropwise, over 10 min. The reaction solution was stirred for an additional 1 h before being warmed up to room temperature and quenched with water (400 mL). The resulting mixture was extracted with ethyl acetate (3×400 mL). The combined organic layers were washed with brine (3×100 mL), dried over anhydrous sodium sulfate, filtered and concentrated under reduced pressure. The residue was purified by silica gel column chromatography (eluted with 1%-20% ethyl acetate in petroleum ether) to afford tert-butyl (4-(4-bromo-3-fluorophenyl)-4-oxobutyl)carbamate as a white solid.

Yield 22.00 g (40%). $^1$H NMR (400 MHz, CDCl$_3$) δ 7.74-7.56 (m, 3H), 4.69 (br s, 1H), 3.29-3.16 (m, 2H), 2.99 (t, J=7.2 Hz, 2H), 2.01-1.87 (m, 2H), 1.43 (s, 9H). m/z: [ESI$^+$]360, 362 (M+H)$^+$.

Synthesis of 4-amino-1-(4-bromo-3-fluorophenyl)butan-1-one hydrochloride

To a stirred solution of tert-butyl (4-(4-bromo-3-fluorophenyl)-4-oxobutyl)carbamate (8.53 g, 23.68 mmol) in dichloromethane (120 mL), was added a solution of 4.0 N hydrogen chloride in 1,4-dioxane (60 mL), dropwise at room temperature. The reaction mixture was stirred for 4 h resulting in the formation of a precipitate. After filtration, the filtered cake was washed with petroleum ether (3×50 mL) and oven dried to afford 4-amino-1-(4-bromo-3-fluorophenyl)butan-1-one hydrochloride as alight yellow solid.

Yield 6.10 g (87%). $^1$H NMR (400 MHz, DMSO) δ 8.03 (br s, 3H, NH$_3^+$), 7.97-7.85 (m, 2H), 7.75 (dd, J=2.0, 8.4 Hz, 1H), 3.21 (t, J=7.2 Hz, 2H), 2.91-2.80 (m, 2H), 1.96-1.85 (m, 2H). m/z: [ESI$^+$]260, 262 (M+H)$^+$.

Synthesis of tert-butyl 2-(4-bromo-3-fluorophenyl) pyrrolidine-1-carboxylate To a stirred solution of 4-amino-1-(4-bromo-3-fluorophenyl)butan-1-one hydrochloride (16.00 g, 53.95 mmol) in methanol (240 mL) were sequentially added sodium acetate trihydrate (22.02 g, 161.82 mmol) and sodium cyanoborohydride (6.78 g, 107.90 mmol), portionwise at 0° C. The reaction solution was warmed to room temperature and stirred for 16 h. To the reaction mixture was added di-tert-butyl dicarbonate (35.32 g, 161.83 mmol) and the resulting solution was stirred for an additional 16 h. The reaction mixture was concentrated under reduced pressure to give the crude residue, which was purified by reverse phase flash chromatography using the following conditions: Column: Spherical C18, 20-40 m, 330 g; Mobile Phase A: water (plus 10 mmol/L ammonium bicarbonate); Mobile Phase B: acetonitrile; Flow rate: 80 mL/min; Gradient: 75%-95% B in 20 min; Detector: UV 254/220 nm. The fractions containing desired product were collected at 90% B and concentrated under reduced pressure to afford tert-butyl 2-(4-bromo-3-fluorophenyl)pyrrolidine-1-carboxylate as a white solid.

Yield 17.75 g (96%). $^1$H NMR (400 MHz, CDCl$_3$) δ 7.51-7.45 (m, 1H), 6.97 (dd, J=2.0, 9.6 Hz, 1H), 6.88 (dd, J=2.0, 8.4 Hz, 1H), 4.96-4.69 (m, 1H), 3.71-3.47 (m, 2H), 2.43-2.25 (m, 1H), 1.94-1.85 (m, 2H), 1.84-1.74 (m, 1H), 1.45 (s, 4H), 1.25 (s, 5H). m/z: [ESI$^+$]288, 290 (M+H-56)$^+$.

Synthesis of tert-butyl 2-(4-(1-ethoxyvinyl)-3-fluorophenyl)pyrrolidine-1-carboxylate To a stirred solution of tert-butyl 2-(4-bromo-3-fluorophenyl)pyrrolidine-1-carboxylate (50.00 g, 145.26 mmol) and tributyl(1-ethoxyethenyl)stannane (62.95 g, 174.30 mmol) in 1,4-dioxane (1000 mL) was added bis(triphenylphosphine)palladium(II) chloride (10.20 g, 14.53 mmol) as a single portion, at room temperature under a nitrogen atmosphere. The reaction mixture was stirred for 1 h at 90° C. The mixture was then cooled to room temperature, diluted with water (500 mL) and extracted with ethyl acetate (3×500 mL). The combined organic layers were washed with brine (1 L) and dried over anhydrous sodium sulfate. After filtration, the filtrate was concentrated under reduced pressure to afford tert-butyl 2-(4-(1-ethoxyvinyl)-3-fluorophenyl)pyrrolidine-1-carboxylate as a brown oil, which was carried through to the next synthetic step without further purification Yield 40.00 g (82%). $^1$H NMR not run. m/z: [ESI$^+$]280 (M+H-56)$^+$.

Synthesis of tert-butyl 2-[4-(2-bromoacetyl)-3-fluorophenyl]pyrrolidine-1-carboxylate A mixture of tert-butyl 2-(4-(1-ethoxyvinyl)-3-fluorophenyl)pyrrolidine-1-carboxylate (34.00 g, 101.37 mmol) and N-bromosuccinimide (23.45 g, 131.75 mmol) in tetrahydrofuran/water (5:1, 600 mL), was stirred for 3 h at room temperature. The reaction mixture was concentrated under reduced pressure. The residue was purified by silica gel column chromatography (eluted with 0-6% ethyl acetate in petroleum ether) to afford tert-butyl 2-[4-(2-bromoacetyl)-3-fluorophenyl]pyrrolidine-1-carboxylate as a light yellow oil.

Yield 31.00 g (79%). $^1$H NMR (400 MHz, CDCl$_3$) δ 7.92 (dd, J=7.8, 8.0 Hz, 1H), 7.12 (dd, J=1.6, 8.0 Hz, 1H), 7.00 (dd, J=1.6, 12.4 Hz, 1H), 5.00-4.76 (m, 1H), 4.53 (s, 2H), 3.72-3.49 (m, 2H), 2.45-2.27 (m, 1H), 1.97-1.76 (m, 3H), 1.51-1.19 (m, 9H). m/z: [ESI$^+$]330, 332 (M+H-56)$^+$.

Synthesis of ethyl 2-(4-(1-(tert-butoxycarbonyl)pyrrolidin-2-yl)-2-fluorophenyl)benzo[d]imidazo[2,1-b]thiazole-7-carboxylate A mixture of tert-butyl 2-(4-(2-bromoacetyl)-3-fluorophenyl)pyrrolidine-1-carboxylate (10.00 g, 25.89 mmol) and ethyl 2-aminobenzo[d]thiazole-6-carboxylate (5.75 g, 25.87 mmol) in 1,4-dioxane (200 mL), was stirred for 16 h at 90° C. under a nitrogen atmosphere. The mixture was cooled to room temperature and concentrated under reduced pressure. The residue was purified by silica gel column chromatography (eluted with 50% ethyl acetate in petroleum ether) to afford ethyl 2-(4-(1-(tert-butoxycarbonyl)pyrrolidin-2-yl)-2-fluorophenyl)benzo[d]imidazo[2,1-b]thiazole-7-carboxylate as an off-white solid.

Yield 2.20 g (17%). $^1$H NMR (400 MHz, DMSO) δ 8.76-8.70 (m, 2H), 8.32-8.29 (m, 1H), 8.18-8.04 (m, 2H), 7.17-7.07 (m, 2H), 4.90-4.70 (m, 1H), 4.38 (q, J=7.2 Hz, 2H), 3.63-3.41 (m, 2H), 2.40-2.24 (m, 1H), 1.91-1.70 (m, 3H), 1.41-1.14 (m, 9H), 1.37 (t, J=7.2 Hz, 3H). m/z: [ESI$^+$]510 (M+H)$^+$.

Synthesis of 2-(4-(1-(tert-butoxycarbonyl)pyrrolidin-2-yl)-2-fluorophenyl)benzo[d]imidazo[2,1-b]thiazole-7-carboxylic acid A mixture of ethyl 2-(4-(1-(tert-butoxycarbonyl)pyrrolidin-2-yl)-2-fluorophenyl)benzo[d]imidazo[2,1-b]thiazole-7-carboxylate (2.22 g, 4.36 mmol) and lithium hydroxide monohydrate (0.55 g, 13.11 mmol) in methanol/water (1:1, 20 mL), was stirred for 2 h at room temperature. The reaction mixture was acidified to pH 6 with 2 N hydrochloric acid solution. The solids were collected by filtration, washed with water (3×10 mL) and oven dried to afford 2-(4-(1-(tert-butoxycarbonyl)pyrrolidin-2-yl)-2-fluorophenyl)benzo[d]imidazo[2,1-b]thiazole-7-carboxylic acid as a white solid.

Yield 1.50 g (72%). $^1$H NMR (400 MHz, DMSO) δ 13.11 (br s, 1H), 8.71 (d, J=3.6 Hz, 1H), 8.69-8.64 (m, 1H), 8.30-8.24 (m, 1H), 8.14-8.08 (m, 2H), 7.17-7.10 (m, 2H), 4.90-4.67 (m, 1H), 3.63-3.41 (m, 2H), 2.40-2.24 (m, 1H), 1.94-1.69 (m, 3H), 1.45-1.09 (m, 9H). m/z: [ESI$^+$]482 (M+H)$^+$.

Synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate To a stirred solution of 2-(4-(1-(tert-butoxycarbonyl)pyrrolidin-2-yl)-2-fluorophenyl)benzo[d]imidazo[2,1-b]thiazole-7-carboxylic acid (0.60 g, 1.25 mmol) and O-(7-azabenzotriazol-1-yl)-N,N,N',N'-tetramethyluronium hexafluorophosphate (HATU) (0.70 g, 1.84 mmol) in N,N-dimethylacetamide (10 mL) were sequentially added N,N-Diisopropylethylamine (0.50 g, 3.87 mmol) and 1-methylpiperidin-4-amine (0.15 g, 1.31 mmol), dropwise at room temperature under a nitrogen atmosphere. The reaction was stirred for 2 h. The resulting solution was purified directly by reverse phase flash chromatography using the following conditions Column: WelFlash™ C18-I, 20-40 μm, 330 g; Eluent A: water (plus 20 mmol/L ammonium bicarbonate); Eluent B: methanol; Gradient: 70%-90% B in 25 min; Flow rate: 80 mL/min; Detector: 215/254 nm. The desired fractions were collected at 82% B and concentrated under reduced pressure to afford tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate as a yellow solid.

Yield 0.50 g (69%). $^1$H NMR (400 MHz, DMSO) δ 8.70 (d, J=3.6 Hz, 1H), 8.50 (d, J=1.6 Hz, 1H), 8.38 (d, J=7.6 Hz, 1H), 8.26 (d, J=8.4 Hz, 1H), 8.13-8.05 (m, 1H), 8.03 (dd, J=1.6, 8.4 Hz, 1H), 7.18-7.08 (m, 2H), 4.90-4.69 (m, 1H), 3.85-3.70 (m, 1H), 3.63-3.40 (m, 2H), 2.84-2.75 (m, 2H), 2.39-2.24 (m, 1H), 2.19 (s, 3H), 2.05-1.92 (m, 2H), 1.92-1.71 (m, 5H), 1.68-1.51 (m, 2H), 1.43-1.10 (m, 9H). m/z: [ESI$^+$]578 (M+H)$^+$.

Synthesis of tert-butyl (R)-2-(3-fluoro-4-(7-((1-methylpiperidin-4-yl)carbamoyl)benzo[d]imidazo[2,1-b]thiazol-2-yl)phenyl)pyrrolidine-1-carboxylate and tert-butyl (S)-2-(3-fluoro-4-(7-((1-methylpiperidin-4-yl)carbamoyl)benzo[d]imidazo[2,1-b]thiazol-2-yl)phenyl)pyrrolidine-1-carboxylate Tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate (0.50 g, 0.87 mmol) was isolated after Prep-CHIRAL-HPLC using the following conditions; Column: CHIRALPAK IG, 2×25 cm, 5 μm; Mobile Phase A: Hexane (0.5% 2 Mammonia-methanol), Mobile Phase B: ethanol:dichloromethane=1:1; Flow rate: 20 mL/min; Gradient: 25% B in 24 min; UV Detector: 220/254 nm. One enantiomer was collected at 13.57 min and concentrated under reduced pressure to afford to afford tert-butyl (R)-2-(3-fluoro-4-(7-((1-methylpiperidin-4-yl)carbamoyl)benzo[d]imidazo[2,1-b]thiazol-2-yl)phenyl)pyrrolidine-1-carboxylate as a yellow solid.

Yield 0.15 g (30%). $^1$H NMR (400 MHz, DMSO) δ 8.70 (d, J=3.6 Hz, 1H), 8.50 (d, J=1.6 Hz, 1H), 8.38 (d, J=7.6 Hz, 1H), 8.26 (d, J=8.4 Hz, 1H), 8.13-8.05 (m, 1H), 8.03 (dd, J=1.6, 8.4 Hz, 1H), 7.18-7.08 (m, 2H), 4.90-4.69 (m, 1H), 3.85-3.70 (m, 1H), 3.63-3.40 (m, 2H), 2.84-2.75 (m, 2H), 2.39-2.24 (m, 1H), 2.19 (s, 3H), 2.05-1.92 (m, 2H), 1.92-1.71 (m, 5H), 1.68-1.51 (m, 2H), 1.43-1.10 (m, 9H). m/z: [ESI$^+$]578 (M+H)$^+$. [α]$^{25}_D$=+160° (c=1 mg/mL, methanol).

Second enantiomer was collected at 17.7 min and concentrated under reduced pressure to afford to afford tert-butyl (S)-2-(3-fluoro-4-(7-((1-methylpiperidin-4-yl)carbamoyl)benzo[d]imidazo[2,1-b]thiazol-2-yl)phenyl)pyrrolidine-1-carboxylate as a yellow solid.

Yield 0.25 g (50%). $^1$H NMR (400 MHz, DMSO) δ 8.70 (d, J=3.6 Hz, 1H), 8.50 (d, J=1.6 Hz, 1H), 8.38 (d, J=7.6 Hz, 1H), 8.26 (d, J=8.4 Hz, 1H), 8.13-8.05 (m, 1H), 8.03 (dd, J=1.6, 8.4 Hz, 1H), 7.18-7.08 (m, 2H), 4.90-4.69 (m, 1H), 3.85-3.70 (m, 1H), 3.63-3.40 (m, 2H), 2.84-2.75 (m, 2H), 2.39-2.24 (m, 1H), 2.19 (s, 3H), 2.05-1.92 (m, 2H), 1.92-1.71 (m, 5H), 1.68-1.51 (m, 2H), 1.43-1.10 (m, 9H). m/z: [ESI$^+$]578 (M+H)$^+$. [α]$_{25}^D$=−76° (c=1 mg/mL, methanol).

Synthesis of tert-butyl 2-(3-fluoro-4-(7-((tetrahydro-2H-pyran-4-yl)carbamoyl)benzo[d]imidazo[2,1-b]thiazol-2-yl)phenyl)pyrrolidine-1-carboxylate Compound tert-butyl 2-(3-fluoro-4-(7-((tetrahydro-2H-pyran-4-yl)carbamoyl)benzo[d]imidazo[2,1-b]thiazol-2-yl)phenyl)pyrrolidine-1-carboxylate was prepared from 2-(4-(1-(tert-butoxycarbonyl)pyrrolidin-2-yl)-2-fluorophenyl)benzo[d]imidazo[2,1-b]thiazole-7-carboxylic acid (200 mg, 0.415 mmol) and tetrahydro-2H-pyran-4-amine (60 mg, 0.593 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as an orange solid.

Yield 150 mg (64%). $^1$H NMR (300 MHz, DMSO) δ 8.70 (d, J=3.6 Hz, 1H), 8.51 (d, J=1.6 Hz, 1H), 8.43 (d, J=7.6 Hz, 1H), 8.27 (d, J=8.4 Hz, 1H), 8.15-8.06 (m, 1H), 8.04 (dd, J=1.6, 8.4 Hz, 1H), 7.18-7.09 (m, 2H), 4.90-4.67 (m, 1H), 4.12-3.98 (m, 1H), 3.97-3.81 (m, 2H), 3.64-3.48 (m, 2H), 3.48-3.35 (m, 2H), 2.40-2.23 (m, 1H), 1.90-1.70 (m, 5H), 1.70-1.51 (m, 2H), 1.43-1.12 (m, 9H). m/z: [ESI$^+$]565 (M+H)$^+$.

Synthesis of tert-butyl 2-(4-(7-carbamoylbenzo[d]imidazo[2,1-b]thiazol-2-yl)-3-fluorophenyl)pyrrolidine-1-carboxylate Compound tert-butyl 2-(4-(7-carbamoylbenzo[d]imidazo[2,1-b]thiazol-2-yl)-3-fluorophenyl)pyrrolidine-1-carboxylate was prepared from 2-(4-(1-(tert-butoxycarbonyl)pyrrolidin-2-yl)-2-fluorophenyl)benzo[d]imidazo[2,1-b]thiazole-7-carboxylic acid (100 mg, 0.208 mmol) and ammonium bicarbonate (90 mg, 1.138 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a brown oil.

Yield 60 mg (60%). $^1$H NMR (400 MHz, CDCl$_3$) δ 8.31-8.21 (m, 1H), 8.21-8.12 (m, 2H), 8.00-7.79 (m, 2H), 7.79-7.65 (m, 1H), 7.57-7.43 (m, 1H), 7.13-6.83 (m, 2H), 4.99-4.75 (m, 1H), 3.73-3.49 (m, 2H), 2.43-2.25 (m, 1H), 1.99-1.74 (m, 3H), 1.58-1.20 (m, 9H). m/z: [ESI$^+$]481 (M+H)$^+$.

Synthesis of tert-butyl 2-(3-fluoro-4-(7-(methylcarbamoyl)benzo[d]imidazo[2,1-b]thiazol-2-yl)phenyl)pyrrolidine-1-carboxylate Compound tert-butyl 2-(3-fluoro-4-(7-(methylcarbamoyl)benzo[d]imidazo[2,1-b]thiazol-2-yl)phenyl)pyrrolidine-1-carboxylate was prepared from 2-(4-(1-(tert-butoxycarbonyl)pyrrolidin-2-yl)-2-fluorophenyl)benzo[d]imidazo[2,1-b]thiazole-7-carboxylic acid (150 mg, 0.312 mmol) and methanamine hydrochloride (25 mg, 0.370 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a white solid.

Yield 100 mg (65%). $^1$H NMR (400 MHz, CDCl$_3$) δ 8.26-8.11 (m, 3H), 8.08-7.97 (m, 1H), 7.91-7.76 (m, 1H), 7.75-7.62 (m, 1H), 7.14-6.89 (m, 2H), 4.98-4.76 (m, 1H), 3.73-3.51 (m, 2H), 3.08 (d, J=4.8 Hz, 3H), 2.45-2.25 (m, 1H), 2.03-1.78 (m, 3H), 1.54-1.21 (m, 9H). m/z: [ESI$^+$]495 (M+H)$^+$.

Synthesis of tert-butyl 2-(3-fluoro-4-(7-(((S)-1-methylpiperidin-3-yl)carbamoyl)benzo[d]imidazo[2,1-b]thiazol-2-yl)phenyl)pyrrolidine-1-carboxylate Compound tert-butyl 2-(3-fluoro-4-(7-(((S)-1-methylpiperidin-3-yl)carbamoyl)benzo[d]imidazo[2,1-b]thiazol-2-yl)phenyl)pyrrolidine-1-carboxylate was prepared from 2-(4-(1-(tert-butoxycarbonyl)pyrrolidin-2-yl)-2-fluorophenyl)benzo[d]imidazo[2,1-b]thiazole-7-carboxylic acid (100 mg, 0.208 mmol) and (S)-1-methylpiperidin-3-amine (35 mg, 0.307 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a brown oil.

Yield 80 mg (67%). $^1$H NMR (400 MHz, CDCl$_3$) δ 8.32-8.09 (m, 2H), 8.01-7.80 (m, 2H), 7.80-7.64 (m, 1H), 7.58-7.39 (m, 1H), 7.15-6.81 (m, 2H), 4.98-4.75 (m, 1H), 3.73-3.49 (m, 4H), 3.06-3.00 (m, 1H), 2.76-2.45 (m, 1H), 2.43-2.15 (m, 4H), 2.01-1.59 (m, 8H), 1.59-1.17 (m, 9H). m/z: [ESI$^+$]578 (M+H)$^+$.

Synthesis of tert-butyl 2-(3-fluoro-4-(7-(((R)-1-methylpiperidin-3-yl)carbamoyl)benzo[d]imidazo[2,1-b]thiazol-2-yl)phenyl)pyrrolidine-1-carboxylate Compound tert-butyl 2-(3-fluoro-4-(7-(((R)-1-methylpiperidin-3-yl)carbamoyl)benzo[d]imidazo[2,1-b]thiazol-2-yl)

phenyl)pyrrolidine-1-carboxylate was prepared from 2-(4-(1-(tert-butoxycarbonyl)pyrrolidin-2-yl)-2-fluorophenyl)benzo[d]imidazo[2,1-b]thiazole-7-carboxylic acid (100 mg, 0.208 mmol) and (R)-1-methylpiperidin-3-amine (35 mg, 0.307 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a brown oil.

Yield 80 mg (67%). $^1$H NMR (400 MHz, CDCl$_3$) δ 8.32-8.09 (m, 2H), 8.01-7.80 (m, 2H), 7.80-7.64 (m, 1H), 7.58-7.39 (m, 1H), 7.15-6.81 (m, 2H), 4.98-4.75 (m, 1H), 3.73-3.49 (m, 4H), 3.06-3.00 (m, 1H), 2.76-2.45 (m, 1H), 2.43-2.15 (m, 4H), 2.01-1.59 (m, 8H), 1.59-1.17 (m, 9H). m/z: [ESI$^+$]578 (M+H)$^+$.

Synthesis of tert-butyl 2-(3-fluoro-4-(7-((1-methylazetidin-3-yl)carbamoyl)benzo[d]imidazo[2,1-b]thiazol-2-yl)phenyl)pyrrolidine-1-carboxylate Compound tert-butyl 2-(3-fluoro-4-(7-((1-methylazetidin-3-yl)carbamoyl)benzo[d]imidazo[2,1-b]thiazol-2-yl)phenyl)pyrrolidine-1-carboxylate was prepared from 2-(4-(1-(tert-butoxycarbonyl)pyrrolidin-2-yl)-2-fluorophenyl)benzo[d]imidazo[2,1-b]thiazole-7-carboxylic acid (200 mg, 0.415 mmol) and 1-methylazetidin-3-amine (45 mg, 0.522 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a light yellow solid.

Yield 90 mg (39%). $^1$H NMR (300 MHz, DMSO) δ 8.97-8.87 (m, 1H), 8.69 (d, J=3.6 Hz, 1H), 8.54-8.48 (m, 1H), 8.33-8.24 (m, 1H), 8.16-7.99 (m, 2H), 7.18-7.06 (m, 2H), 4.93-4.69 (m, 1H), 4.58-4.42 (m, 1H), 3.74-3.62 (m, 2H), 3.62-3.43 (m, 2H), 3.19-3.04 (m, 2H), 2.34 (s, 3H), 2.31-2.23 (m, 1H), 1.93-1.69 (m, 3H), 1.47-1.08 (m, 9H). m/z: [ESI$^+$]550 (M+H)$^+$.

Synthesis of tert-butyl 2-(3-fluoro-4-(7-((tetrahydro-2H-pyran-3-yl)carbamoyl)benzo[d]imidazo[2,1-b]thiazol-2-yl)phenyl)pyrrolidine-1-carboxylate Compound tert-butyl 2-(3-fluoro-4-(7-((tetrahydro-2H-pyran-3-yl)carbamoyl)benzo[d]imidazo[2,1-b]thiazol-2-yl)phenyl)pyrrolidine-1-carboxylate was prepared from 2-(4-(1-(tert-butoxycarbonyl)pyrrolidin-2-yl)-2-fluorophenyl)benzo[d]imidazo[2,1-b]thiazole-7-carboxylic acid (200 mg, 0.415 mmol) and tetrahydro-2H-pyran-3-amine (50 mg, 0.494 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as an off white solid.

Yield 130 mg (55%). $^1$H NMR (300 MHz, DMSO) δ 8.70 (d, J=3.6 Hz, 1H), 8.51 (d, J=1.5 Hz, 1H), 8.34 (d, J=7.8 Hz, 1H), 8.26 (d, J=8.4 Hz, 1H), 8.14-8.06 (m, 1H), 8.04 (dd, J=1.5, 8.4 Hz, 1H), 7.18-7.07 (m, 2H), 4.92-4.69 (m, 1H), 4.01-3.89 (m, 1H), 3.89-3.72 (m, 2H), 3.63-3.40 (m, 2H), 3.26-3.15 (m, 2H), 2.42-2.23 (m, 1H), 2.02-1.56 (m, 7H), 1.43-1.12 (m, 9H). m/z: [ESI$^+$]565 (M+H)$^+$.

Synthesis of 3-(4-fluoropiperidin-1-yl)propan-1-amine

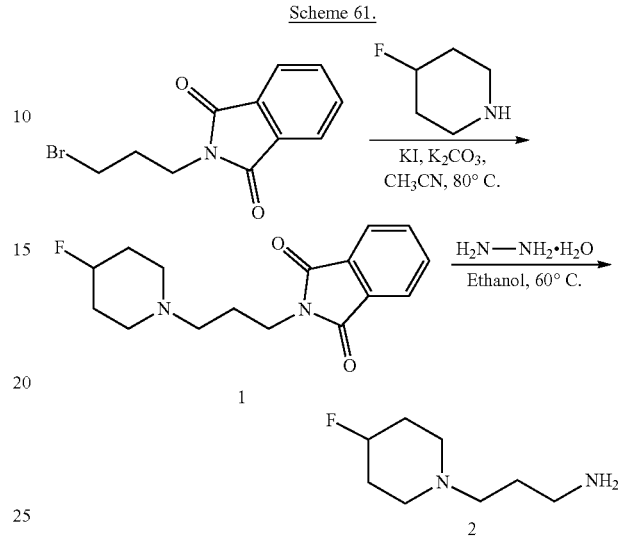

Scheme 61.

Synthesis of 2-(3-(4-fluoropiperidin-1-yl)propyl)isoindoline-1,3-dione

To a stirred mixture of 4-fluoropiperidine hydrochloride (50.00 g, 358.17 mmol) and 2-(3-bromopropyl)isoindoline-1,3-dione (96.03 g, 358.17 mmol) in acetonitrile (2500 mL) were added potassium iodide (59.46 g, 358.19 mmol) and potassium carbonate (99.00 g, 716.35 mmol) at room temperature. The reaction mixture was stirred for 16 h at 80° C. The mixture was cooled to room temperature and filtered. The filtrate was concentrated to dryness and the residue purified by silica gel column chromatography (eluted with 50% ethyl acetate in petroleum ether) to afford 2-(3-(4-fluoropiperidin-1-yl)propyl)isoindoline-1,3-dione as a white solid.

Yield 91.00 g (88%). $^1$H NMR (400 MHz, CDCl$_3$) δ 7.84 (dd, J=3.2, 5.6 Hz, 2H), 7.71 (dd, J=3.2, 5.6 Hz, 2H), 4.69-4.46 (m, 1H), 3.76 (t, J=6.8 Hz, 2H), 2.57-2.47 (m, 2H), 2.42 (t, J=6.8 Hz, 2H), 2.34-2.24 (m, 2H), 1.87 (p, J=6.8 Hz, 2H), 1.80-1.63 (m, 4H). m/z: [ESI$^+$]291 (M+H)$^+$.

Synthesis of 3-(4-fluoropiperidin-1-yl)propan-1-amine

To a stirred solution of 2-(3-(4-fluoropiperidin-1-yl)propyl)isoindoline-1,3-dione (90.00 g, 309.98 mmol) in ethanol (1500 mL) was added hydrazine hydrate (85%, 54.77 g, 929.97 mmol) at room temperature. The reaction solution was stirred for 3 h at 60° C. The resulting mixture was cooled to room temperature. The precipitated solids were filtered out and washed with dichloromethane (5×500 mL). The combined filtrates were concentrated under vacuum to afford 3-(4-fluoropiperidin-1-yl)propan-1-amine as a light yellow oil.

Yield 40.00 g (81%). $^1$H NMR (400 MHz, CDCl$_3$) δ 4.79-4.59 (m, 1H), 2.82-2.74 (m, 2H), 2.65-2.55 (m, 2H), 2.45-2.31 (m, 4H), 2.01-1.81 (m, 2H), 1.72-1.59 (m, 4H). NH$_2$ protons not observed. m/z: [ESI$^+$]161 (M+H)$^+$.

Synthesis of tert-butyl 2-(2,3-difluoro-4-(7-((3-(4-fluoropiperidin-1-yl)propyl)carbamoyl)benzo[d]imidazo[2,1-b]thiazol-2-yl)phenyl)pyrrolidine-1-carboxylate
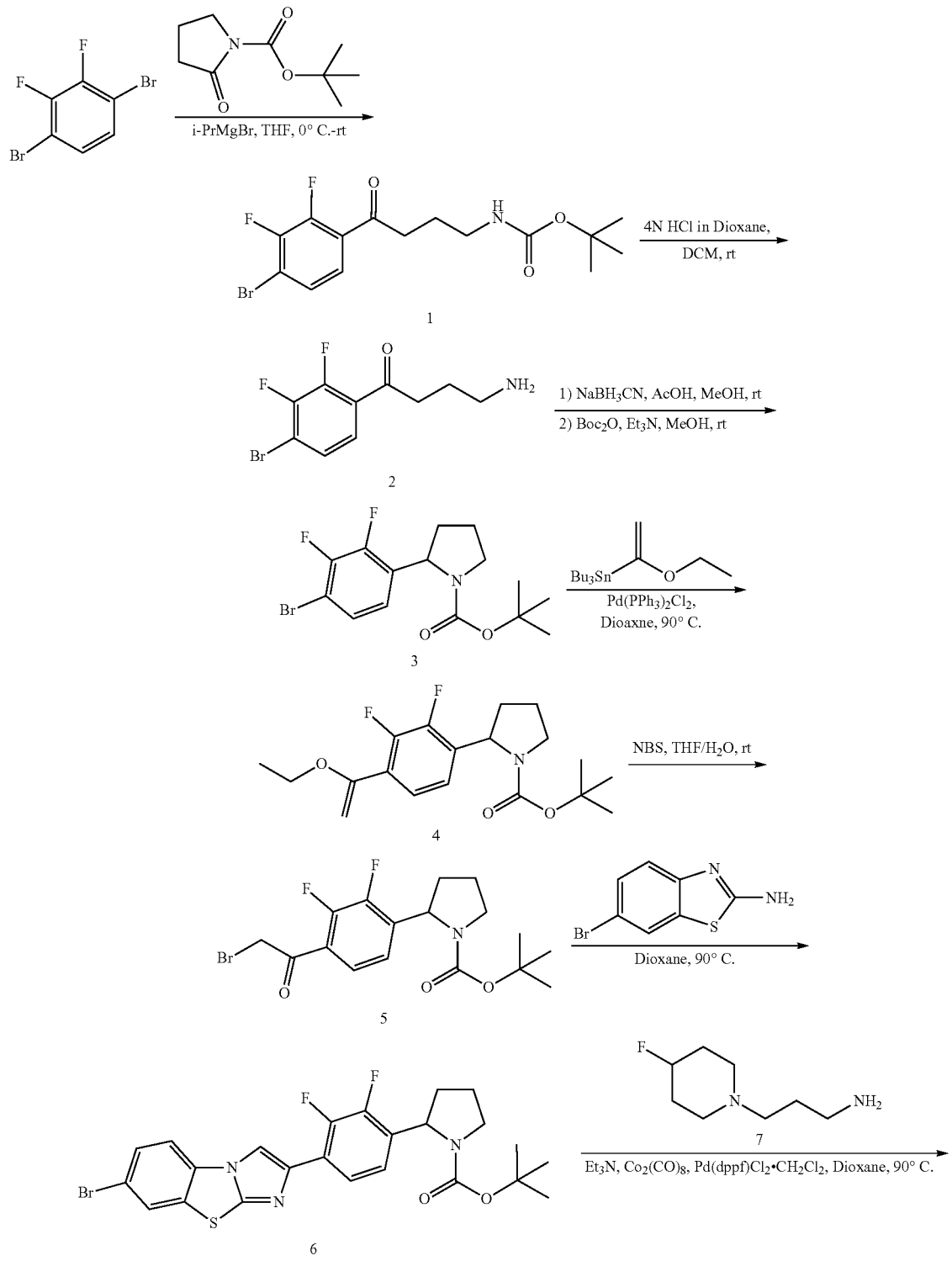
Scheme 62.

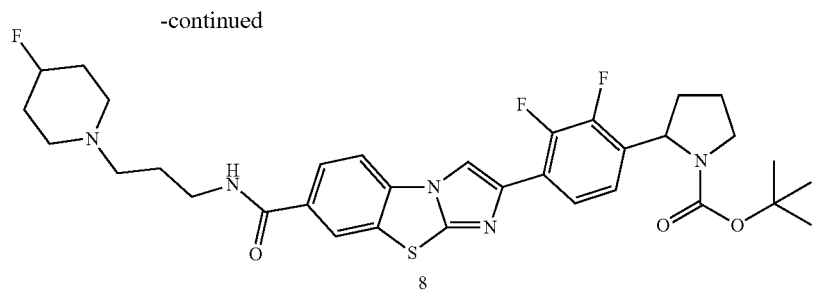

8

Synthesis of tert-butyl (4-(4-bromo-2,3-difluorophenyl)-4-oxobutyl)carbamate Compound tert-butyl (4-(4-bromo-2,3-difluorophenyl)-4-oxobutyl)carbamate was prepared from 1,4-dibromo-2,3-difluorobenzene (5.00 g, 18.39 mmol) and tert-butyl 2-oxopyrrolidine-1-carboxylate (4.43 g, 23.92 mmol), following a similar procedure to that described for the synthesis of tert-butyl (4-(4-bromo-3-fluorophenyl)-4-oxobutyl)carbamate and was isolated as a yellow oil.

Yield 2.30 g (33%). $^1$H NMR (300 MHz, CDCl$_3$) δ 7.60-7.51 (m, 1H), 7.46-7.39 (m, 1H), 4.62 (br s, 1H), 3.28-3.19 (m, 2H), 3.07-2.97 (m, 2H), 1.99-1.90 (m, 2H), 1.45 (s, 9H). m/z: [ESI$^+$]322, 324 (M+H-56)$^+$.

Synthesis of 4-amino-1-(4-bromo-2,3-difluorophenyl)butan-1-one hydrochloride Compound 4-amino-1-(4-bromo-2,3-difluorophenyl)butan-1-one hydrochloride was prepared from tert-butyl (4-(4-bromo-2,3-difluorophenyl)-4-oxobutyl)carbamate (2.30 g, 6.08 mmol), following a similar procedure to that described for the synthesis of 4-amino-1-(4-bromo-3-fluorophenyl)butan-1-one hydrochloride and was isolated as a white solid.

Yield 1.70 g (89%). $^1$H NMR not run. m/z: [ESI$^+$]278, 280 (M+H)$^+$.

Synthesis of tert-butyl 2-(4-bromo-2,3-difluorophenyl)pyrrolidine-1-carboxylate Compound tert-butyl 2-(4-bromo-2,3-difluorophenyl)pyrrolidine-1-carboxylate was prepared from 4-amino-1-(4-bromo-2,3-difluorophenyl)butan-1-one hydrochloride (1.70 g, 5.40 mmol), following a similar procedure to that described for the synthesis of tert-butyl 2-(4-bromo-3-fluorophenyl)pyrrolidine-1-carboxylate and was isolated as a colorless oil.

Yield 1.00 g (51%). $^1$H NMR (400 MHz, CDCl$_3$) δ 7.30-7.22 (m, 1H), 6.89-6.75 (m, 1H), 5.19-4.98 (m, 1H), 3.67-3.49 (m, 2H), 2.45-2.29 (m, 1H), 1.97-1.79 (m, 3H), 1.49-1.23 (m, 9H). m/z: [ESI$^+$]306, 308 (M+H-56)$^+$.

Synthesis of tert-butyl 2-(4-(1-ethoxyvinyl)-2,3-difluorophenyl)pyrrolidine-1-carboxylate Compound tert-butyl 2-(4-(1-ethoxyvinyl)-2,3-difluorophenyl)pyrrolidine-1-carboxylate was prepared from tert-butyl 2-(4-bromo-2,3-difluorophenyl)pyrrolidine-1-carboxylate (1.00 g, 2.76 mmol) and tributyl(1-ethoxyvinyl)stannane (1.20 g, 3.32 mmol), following a similar procedure to that described for the synthesis of tert-butyl 2-(4-(1-ethoxyvinyl)-3-fluorophenyl)pyrrolidine-1-carboxylate and was isolated as a brown oil. The crude product was carried through without further purification.

Yield 0.90 g (crude). $^1$H NMR not run. m/z: [ESI$^+$]354 (M+H)$^+$.

Synthesis of tert-butyl 2-(4-(2-bromoacetyl)-2,3-difluorophenyl)pyrrolidine-1-carboxylate Compound tert-butyl 2-(4-(2-bromoacetyl)-2,3-difluorophenyl)pyrrolidine-1-carboxylate was prepared from tert-butyl 2-(4-(1-ethoxyvinyl)-2,3-difluorophenyl)pyrrolidine-1-carboxylate (0.90 g, crude) and N-bromosuccinimide (0.55 g, 3.09 mmol), following a similar procedure to that described for the synthesis of tert-butyl 2-[4-(2-bromoacetyl)-3-fluorophenyl]pyrrolidine-1-carboxylate and was isolated as a light yellow oil.

Yield 0.88 g (79% over two steps). $^1$H NMR (400 MHz, CDCl$_3$) δ 7.72-7.61 (m, 1H), 7.14-6.98 (m, 1H), 5.25-5.06 (m, 1H), 4.51 (s, 2H), 3.75-3.52 (m, 2H), 2.51-2.33 (m, 1H), 2.01-1.79 (m, 3H), 1.47-1.22 (m, 9H). m/z: [ESI$^+$]348, 350 (M+H-56)$^+$.

Synthesis of tert-butyl 2-(4-(7-bromobenzo[d]imidazo[2,1-b]thiazol-2-yl)-2,3-difluorophenyl)pyrrolidine-1-carboxylate Compound tert-butyl 2-(4-(7-bromobenzo[d]imidazo[2,1-b]thiazol-2-yl)-2,3-difluorophenyl)pyrrolidine-1-carboxylate was prepared from tert-butyl 2-(4-(2-bromoacetyl)-2,3-difluorophenyl)pyrrolidine-1-carboxylate (0.50 g, 1.24 mmol) and 6-bromobenzo[d]thiazol-2-amine (0.34 g, 1.48 mmol), following a similar procedure to that described for the synthesis of ethyl 2-(4-(1-(tert-butoxycarbonyl)pyrrolidin-2-yl)-2-fluorophenyl)benzo[d]imidazo[2,1-b]thiazole-7-carboxylate and was isolated as a white solid.

Yield 0.50 g (76%). $^1$H NMR (400 MHz, CDCl$_3$) δ 8.17 (s, 1H), 8.00-7.90 (m, 2H), 7.71-7.57 (m, 2H), 7.08-6.98 (m, 1H), 5.28-5.06 (m, 1H), 3.70-3.51 (m, 2H), 2.48-2.34 (m, 1H), 1.97-1.86 (m, 3H), 1.50-1.24 (m, 9H). m/z: [ESI$^+$]534, 536 (M+H)$^+$.

Synthesis of tert-butyl 2-(2,3-difluoro-4-(7-((3-(4-fluoropiperidin-1-yl)propyl)carbamoyl)benzo[d]imidazo[2,1-b]thiazol-2-yl)phenyl)pyrrolidine-1-carboxylate To a stirred mixture of tert-butyl 2-(4-(7-bromobenzo[d]imidazo[2,1-b]thiazol-2-yl)-2,3-difluorophenyl)pyrrolidine-1-carboxylate (200 mg, 0.374 mmol), 3-(4-fluoropiperidin-1-yl)propan-1-amine (71 mg, 0.443 mmol) and triethylamine (113 mg, 1.117 mmol, 2.98 equiv) in 1,4-dioxane (5 mL) were sequentially added cobalt carbonyl (40 mg, 0.117 mmol) and 1,1'-bis(diphenylphosphino)ferrocene-palladium(II)dichloride dichloromethane complex (23 mg, 0.028 mmol) as single portions at room temperature under a nitrogen atmosphere. The reaction mixture was stirred for 16 h at 90° C. The mixture was cooled to room temperature and filtered. The filtrate was purified directly by silica gel column chromatography (eluted with 9% of methanol in dichloromethane) to afford tert-butyl 2-(2,3-difluoro-4-(7-((3-(4-fluoropiperidin-1-yl)propyl)carbamoyl)benzo[d]imidazo[2,1-b]thiazol-2-yl)phenyl)pyrrolidine-1-carboxylate as a light yellow solid.

Yield 160 mg (67%). $^1$H NMR not run. m/z: [ESI$^+$]642 (M+H)$^+$.

Synthesis of tert-butyl 2-(2-fluoro-4-(7-((3-(4-fluoropiperidin-1-yl)propyl)carbamoyl)benzo[d]imidazo[2,1-b]thiazol-2-yl)phenyl)pyrrolidine-1-carboxylate

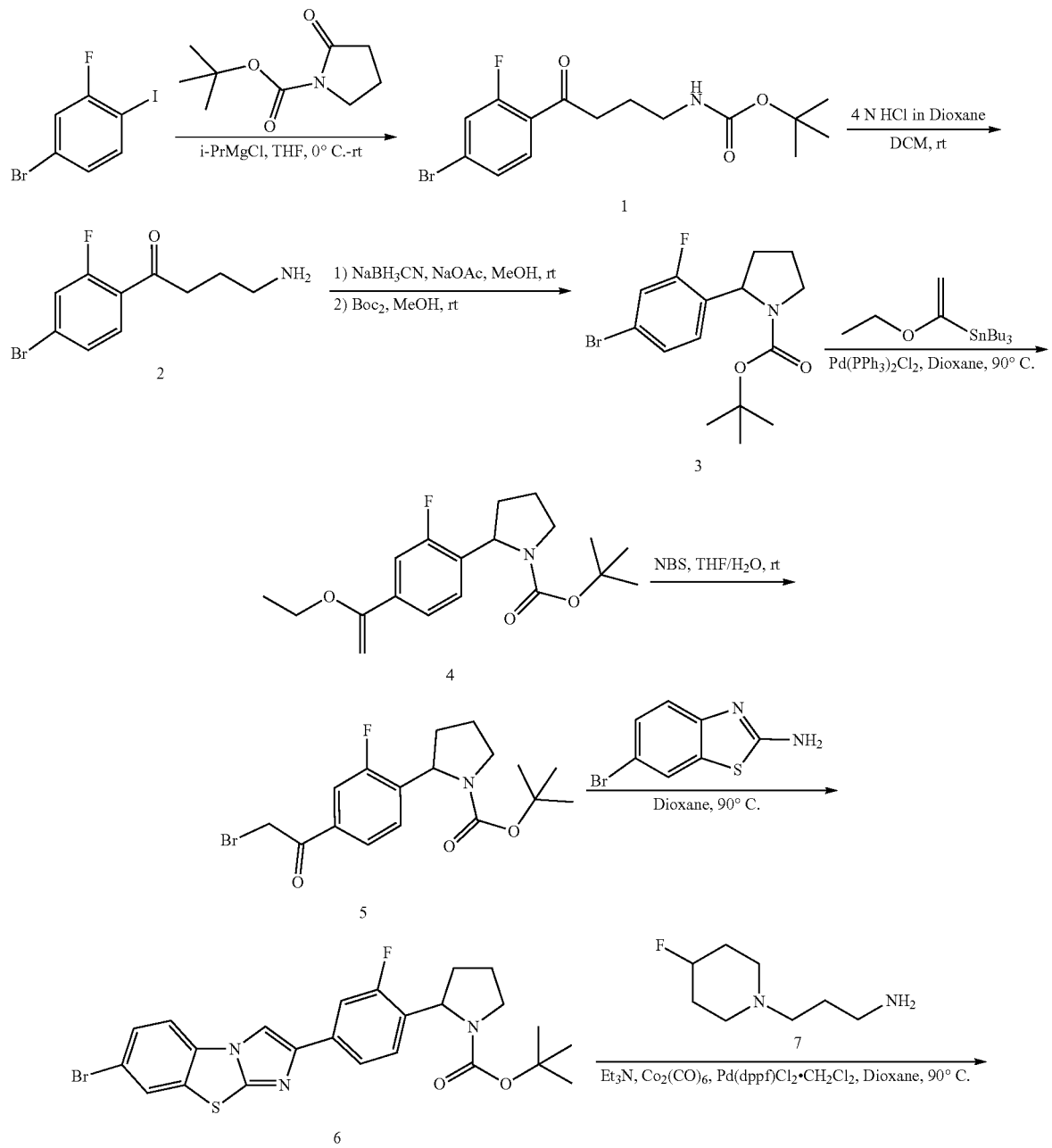

Scheme 63.

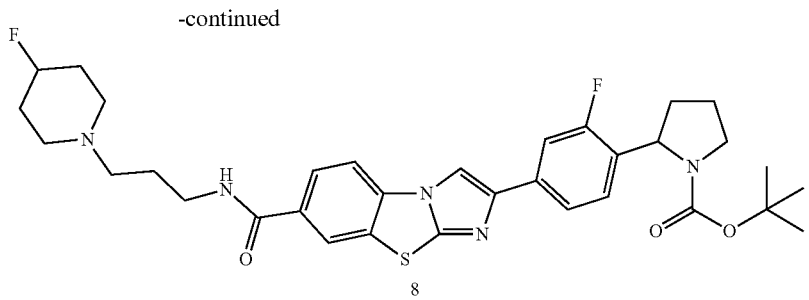

8

Synthesis of tert-butyl (4-(4-bromo-2-fluorophenyl)-4-oxobutyl)carbamate

Compound tert-butyl (4-(4-bromo-2-fluorophenyl)-4-oxobutyl)carbamate was prepared from 4-bromo-2-fluoro-1-iodobenzene (5.00 g, 16.62 mmol) and tert-butyl 2-oxopyrrolidine-1-carboxylate (4.00 g, 21.60 mmol), following a similar procedure to that described for the synthesis of tert-butyl (4-(4-bromo-3-fluorophenyl)-4-oxobutyl)carbamate and was isolated as a yellow solid.

Yield 3.50 g (58%). $^1$H NMR (400 MHz, CDCl$_3$) δ 7.81-7.64 (m, 1H), 7.41-7.24 (m, 2H), 4.82-4.64 (m, 1H), 3.27-3.05 (m, 2H), 3.05-2.86 (m, 2H), 1.98-1.77 (m, 2H), 1.39 (s, 9H). m/z: [ESI$^+$]304, 306 (M+H-56)$^+$.

Synthesis of 4-amino-1-(4-bromo-2-fluorophenyl)butan-1-one hydrochloride

Compound 4-amino-1-(4-bromo-2-fluorophenyl)butan-1-one hydrochloride was prepared from tert-butyl (4-(4-bromo-2-fluorophenyl)-4-oxobutyl)carbamate (3.50 g, 9.72 mmol), following a similar procedure to that described for the synthesis of 4-amino-1-(4-bromo-3-fluorophenyl)butan-1-one hydrochloride and was isolated as a white solid.

Yield 2.50 g (87%). $^1$H NMR (400 MHz, CD$_3$OD) δ 7.85-7.79 (m, 1H), 7.55-7.47 (m, 2H), 3.19-3.12 (m, 2H), 3.06-2.99 (m, 2H), 2.11-2.01 (m, 2H). m/z: [ESI$^+$]242, 244 (M+H-18)$^+$.

Synthesis of tert-butyl 2-(4-bromo-2-fluorophenyl)pyrrolidine-1-carboxylate

Compound tert-butyl 2-(4-bromo-2-fluorophenyl)pyrrolidine-1-carboxylate was prepared from 4-amino-1-(4-bromo-2-fluorophenyl)butan-1-one hydrochloride (2.00 g, 6.74 mmol), following a similar procedure to that described for the synthesis of tert-butyl 2-(4-bromo-3-fluorophenyl)pyrrolidine-1-carboxylate and was isolated as a white solid.

Yield 2.00 g (86%). $^1$H NMR (400 MHz, CDCl$_3$) δ 7.27-7.16 (m, 2H), 7.08-6.95 (m, 1H), 5.18-4.97 (m, 1H), 3.67-3.49 (m, 2H), 2.43-2.26 (m, 1H), 1.96-1.76 (m, 3H), 1.49-1.23 (m, 9H). m/z: [ESI$^+$]288, 290 (M+H-56)$^+$.

Synthesis of tert-butyl 2-(4-(1-ethoxyvinyl)-2-fluorophenyl)pyrrolidine-1-carboxylate Compound tert-butyl 2-(4-(1-ethoxyvinyl)-2-fluorophenyl)pyrrolidine-1-carboxylate was prepared from tert-butyl 2-(4-bromo-2-fluorophenyl)pyrrolidine-1-carboxylate (1.30 g, 3.78 mmol) and tributyl(1-ethoxyvinyl)stannane (1.62 g, 4.49 mmol), following a similar procedure to that described for the synthesis of tert-butyl 2-(4-(1-ethoxyvinyl)-3-fluorophenyl)pyrrolidine-1-carboxylate and was isolated as a white solid.

Yield 0.70 g (55%). $^1$H NMR (400 MHz, CDCl$_3$) δ 7.73-7.67 (m, 1H), 7.66-7.59 (m, 1H), 7.30-7.19 (m, 1H), 5.25-5.06 (m, 1H), 3.74 (q, J=7.2 Hz, 2H), 3.70-3.60 (m, 2H), 2.64-2.55 (m, 2H), 2.47-2.32 (m, 1H), 1.98-1.80 (m, 3H), 1.26 (t, J=7.2 Hz, 3H), 1.49-1.23 (m, 9H). m/z: [ESI$^+$]336 (M+H)$^+$.

Synthesis of tert-butyl 2-(4-(2-bromoacetyl)-2-fluorophenyl)pyrrolidine-1-carboxylate Compound tert-butyl 2-(4-(2-bromoacetyl)-2-fluorophenyl)pyrrolidine-1-carboxylate was prepared from tert-butyl 2-(4-(1-ethoxyvinyl)-2-fluorophenyl)pyrrolidine-1-carboxylate (700 mg, 2.087 mmol) and N-bromosuccinimide (450 mg, 2.53 mmol), following a similar procedure to that described for the synthesis of tert-butyl 2-[4-(2-bromoacetyl)-3-fluorophenyl]pyrrolidine-1-carboxylate and was isolated as a brown yellow solid.

Yield 330 mg (41%). $^1$H NMR (400 MHz, CDCl$_3$) δ 7.76-7.72 (m, 1H), 7.69-7.63 (m, 1H), 7.34-7.22 (m, 1H), 5.25-5.07 (m, 1H), 4.43 (s, 2H), 3.73-3.52 (m, 2H), 2.47-2.30 (m, 1H), 1.97-1.78 (m, 3H), 1.48-1.20 (m, 9H). m/z: [ESI$^+$]330, 332 (M+H-56)$^+$.

Synthesis of ethyl 2-(4-(1-(tert-butoxycarbonyl)pyrrolidin-2-yl)-3-fluorophenyl)benzo[d]imidazo[2,1-b]thiazole-7-carboxylate Compound ethyl 2-(4-(1-(tert-butoxycarbonyl)pyrrolidin-2-yl)-3-fluorophenyl)benzo[d]imidazo[2,1-b]thiazole-7-carboxylate was prepared from 6-bromobenzo[d]thiazol-2-amine (400 mg, 1.746 mmol) and tert-butyl 2-(4-(2-bromoacetyl)-2-fluorophenyl)pyrrolidine-1-carboxylate (700 mg, 1.812 mmol), following a similar procedure to that described for the synthesis of ethyl 2-(4-(1-(tert-butoxycarbonyl)pyrrolidin-2-yl)-2-fluorophenyl)benzo[d]imidazo[2,1-b]thiazole-7-carboxylate and was isolated as a white solid.

Yield 330 mg (37%). $^1$H NMR (400 MHz, CDCl$_3$) δ 8.01-7.95 (m, 1H), 7.93-7.88 (m, 1H), 7.66-7.50 (m, 4H), 7.24-7.18 (m, 1H), 5.26-5.05 (m, 1H), 3.72-3.59 (m, 2H), 2.44-2.31 (m, 1H), 1.99-1.84 (m, 3H), 1.51-1.25 (m, 9H). m/z: [ESI$^+$]516, 518 (M+H)$^+$.

Synthesis of tert-butyl 2-(2-fluoro-4-(7-((3-(4-fluoropiperidin-1-yl)propyl)carbamoyl)benzo[d]imidazo[2,1-b]thiazol-2-yl)phenyl)pyrrolidine-1-carboxylate Compound tert-butyl 2-(2-fluoro-4-(7-((3-(4-fluoropiperidin-1-yl)propyl)carbamoyl)benzo[d]imidazo[2,1-b]thiazol-2-yl)phenyl)pyrrolidine-1-carboxylate was prepared from tert-butyl 2-(4-(7-bromobenzo[d]imidazo[2,1-b]thiazol-2-yl)-2-fluorophenyl)pyrrolidine-1-carboxylate (330 mg, 0.639 mmol) and 3-(4-fluoropiperidin-1-yl)propan-1-amine (204 mg, 1.273 mmol), following a similar procedure to that described for the synthesis of tert-butyl 2-(2,3-difluoro-4-(7-((3-(4-fluoropiperidin-1-yl)propyl)carbamoyl)benzo[d]imidazo[2,1-b]thiazol-2-yl)phenyl)pyrrolidine-1-carboxylate and was isolated as a brown yellow solid.

Yield 130 mg (33%). $^1$H NMR (400 MHz, CDCl$_3$) δ 8.52-8.43 (m, 1H), 8.30-8.25 (m, 1H), 8.06-8.00 (m, 1H), 7.99-7.91 (m, 1H), 7.69-7.63 (m, 1H), 7.62-7.49 (m, 2H), 7.25-7.12 (m, 1H), 5.27-5.06 (m, 1H), 4.88-4.67 (m, 1H), 3.71-3.60 (m, 4H), 2.80-2.51 (m, 6H), 2.45-2.32 (m, 1H), 2.11-1.81 (m, 9H), 1.50-1.24 (m, 9H). m/z: [ESI$^+$]624 (M+H)$^+$.

Synthesis of tert-butyl (1-(3-fluoro-4-(7-((3-(4-fluoropiperidin-1-yl)propyl)carbamoyl)benzo[d]imidazo[2,1-b]thiazol-2-yl)phenyl)cyclopropyl)carbamate

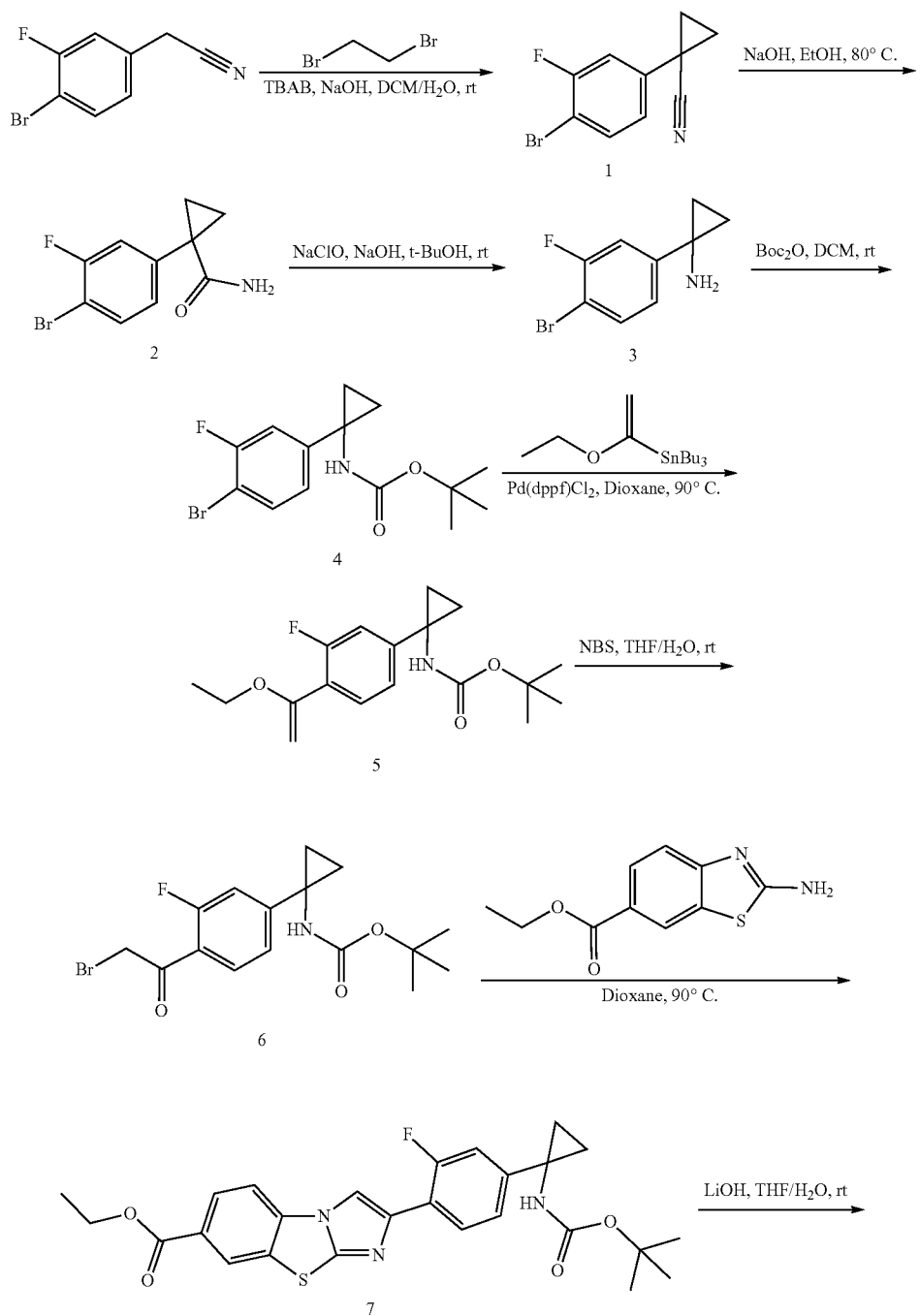

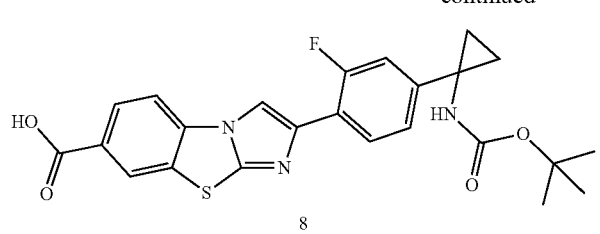
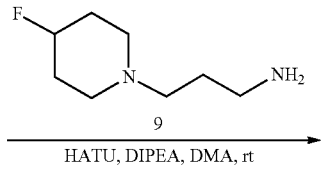
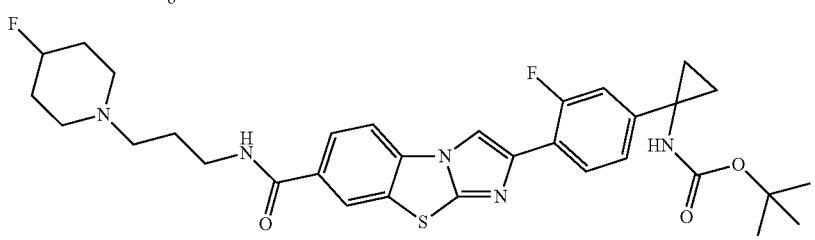

Synthesis of 1-(4-bromo-3-fluorophenyl)cyclopropane-1-carbonitrile

To a stirred solution of 2-(4-bromo-3-fluorophenyl)acetonitrile (25.00 g, 116.80 mmol) and dibromoethane (43.89 g, 233.63 mmol) in dichloromethane/water (1:1, 600 mL) were added sodium hydroxide (23.36 g, 584.00 mmol) and tetrabutylammonium bromide (75.31 g, 233.61 mmol) sequentially as single portions at room temperature. The resulting mixture was stirred for 16 h. The reaction mixture was diluted with water (200 mL) and extracted with dichloromethane (3×500 mL). The combined organic layers were washed with brine (3×200 mL) and dried over anhydrous sodium sulfate. After filtration, the filtrate was concentrated under reduced pressure. The residue was purified by silica gel column chromatography (eluted with 0-70% ethyl acetate in petroleum ether) to afford 1-(4-bromo-3-fluorophenyl)cyclopropane-1-carbonitrile as a pink solid.

Yield 21.00 g (75%). $^1$H NMR (400 MHz, CDCl$_3$) δ 7.54 (dd, J=7.2, 8.4 Hz, 1H), 7.05 (dd, J=2.4, 9.6 Hz, 1H), 7.00 (dd, J=2.4, 8.4 Hz, 1H), 1.83-1.77 (m, 2H), 1.45-1.40 (m, 2H). No LCMS mass.

Synthesis of 1-(4-bromo-3-fluorophenyl)cyclopropane-1-carboxamide

A mixture of 1-(4-bromo-3-fluorophenyl)cyclopropane-1-carbonitrile (2.00 g, 8.33 mmol) and sodium hydroxide (0.67 g, 16.75 mmol) in ethanol (20 mL) was stirred for 2 h at 80° C. After being cooled to room temperature, the precipitated solids were collected by filtration, washed with water (3×10 mL) and oven dried to afford 1-(4-bromo-3-fluorophenyl)cyclopropane-1-carboxamide as a pink solid.

Yield 1.60 g (74%). $^1$H NMR (300 MHz, CDCl$_3$) δ 7.49 (dd, J=7.2, 8.4 Hz, 1H), 7.14 (dd, J=2.4, 9.6 Hz, 1H), 7.04 (dd, J=2.4, 8.4 Hz, 1H), 1.75-1.67 (m, 2H), 1.31-1.23 (m, 2H). NH$_2$ protons not observed. m/z: [ESI-]256, 258 (M−H)$^-$.

Synthesis of 1-(4-bromo-3-fluorophenyl)cyclopropan-1-amine

To a stirred mixture of 1-(4-bromo-3-fluorophenyl)cyclopropane-1-carboxamide (1.60 g, 6.20 mmol) and sodium hydroxide (1.24 g, 31.00 mmol) in tert-butanol (20 mL), was added sodium hypochlorite aqueous solution (10%, 13.85 g, 18.60 mmol) dropwise at room temperature under a nitrogen atmosphere. The resulting mixture was stirred for 16 h. The reaction mixture was diluted with water (200 mL) and extracted with ethyl acetate (3×300 mL). The combined organic phase was washed with brine (200 mL) and dried over anhydrous sodium sulfate. After filtration, the filtrate was concentrated under reduced pressure. The residue was purified by silica gel column chromatography (eluted with 0-80% ethyl acetate in petroleum ether) to afford 1-(4-bromo-3-fluorophenyl)cyclopropan-1-amine as a yellow solid.

Yield 1.00 g (70%). $^1$H NMR not run. m/z: [ESI$^+$]230, 232 (M+H)$^+$.

Synthesis of tert-butyl (1-(4-bromo-3-fluorophenyl)cyclopropyl)carbamate

A solution of 1-(4-bromo-3-fluorophenyl)cyclopropan-1-amine (0.90 g, 3.91 mmol) and di-tert-butyl dicarbonate (1.28 g, 5.86 mmol) in dichloromethane (10 mL) was stirred for 2 h at room temperature. The reaction solution was purified directly by silica gel column chromatography (eluted with 0-70% ethyl acetate in petroleum ether) to afford tert-butyl (1-(4-bromo-3-fluorophenyl)cyclopropyl)carbamate as a white solid.

Yield 0.40 g (31%). $^1$H NMR (300 MHz, CDCl$_3$) δ 7.45 (dd, J=7.2, 8.4 Hz, 1H), 7.01 (dd, J=2.1, 10.2 Hz, 1H), 6.87 (dd, J=2.1, 8.4 Hz, 1H), 5.26 (br s, 1H), 1.45 (s, 9H), 1.36-1.27 (m, 2H), 1.27-1.17 (m, 2H). m/z: [ESI$^+$]330, 332 (M+H)$^+$.

Synthesis of tert-butyl (1-(4-(1-ethoxyvinyl)-3-fluorophenyl)cyclopropyl)carbamate Compound tert-butyl (1-(4-(1-ethoxyvinyl)-3-fluorophenyl)cyclopropyl)carbamate was prepared from tert-butyl (1-(4-bromo-3-fluorophenyl)cyclopropyl)carbamate (370 mg, 1.121 mmol) and tributyl(1-ethoxyvinyl)stannane (485 mg, 1.343 mmol), following a similar procedure to that described for the synthesis of tert-butyl 2-(4-(1-ethoxyvinyl)-3-fluorophenyl)pyrrolidine-1-carboxylate and was isolated as a dark oil. The compound was used directly in the next step without further purification.

Yield 350 mg (crude). $^1$H NMR not run. m/z: [ESI$^+$]322 (M+H)$^+$.

Synthesis of tert-butyl (1-(4-(2-bromoacetyl)-3-fluorophenyl)cyclopropyl)carbamate Compound tert-butyl (1-(4-(2-bromoacetyl)-3-fluorophenyl)cyclopropyl)carbamate was prepared from tert-butyl (1-(4-(1-ethoxyvinyl)-3-fluorophenyl)cyclopropyl)carbamate (350 mg, 1.089 mmol) and N-bromosuccinimide (290 mg, 1.629 mmol), following a similar procedure to that described for the synthesis of tert-butyl 2-[4-(2-bromoacetyl)-3-fluorophenyl]pyrrolidine-1-carboxylate and was isolated as a light yellow oil.

Yield 200 mg (49%). $^1$H NMR (300 MHz, CDCl$_3$) δ 7.93-7.85 (m, 1H), 7.04-6.95 (m, 2H), 5.30 (br s, 1H), 4.51 (s, 2H), 1.48 (s, 9H), 1.45-1.31 (m, 4H). m/z: [ESI$^+$]316, 318 (M+H-56)$^+$.

Synthesis of ethyl 2-(4-(1-((tert-butoxycarbonyl)amino)cyclopropyl)-2-fluorophenyl)benzo[d]imidazo[2,1-b]thiazole-7-carboxylate Compound ethyl 2-(4-(1-((tert-butoxycarbonyl)amino)cyclopropyl)-2-fluorophenyl)benzo[d]imidazo[2,1-b]thiazole-7-carboxylate was prepared from tert-butyl (1-(4-(2-bromoacetyl)-3-fluorophenyl)cyclopropyl)carbamate (200 mg, 0.537 mmol) and ethyl 2-aminobenzo[d]thiazole-6-carboxylate (143 mg, 0.643 mmol), following a similar procedure to that described for the synthesis of ethyl 2-(4-(1-(tert-butoxycarbonyl)pyrrolidin-2-yl)-2-fluorophenyl)benzo[d]imidazo[2,1-b]thiazole-7-carboxylate and was isolated as a light yellow solid.

Yield 60 mg (23%). $^1$H NMR (400 MHz, CDCl$_3$) δ 8.47-8.42 (m, 1H), 8.22-8.09 (m, 3H), 7.72-7.65 (m, 1H), 7.09-7.00 (m, 2H), 5.32 (br s, 1H), 4.45 (q, J=7.2 Hz, 2H), 1.49 (s, 9H), 1.45 (t, J=7.2 Hz, 3H), 1.39-1.26 (m, 4H). m/z: [ESI$^+$]496 (M+H)$^+$.

Synthesis of 2-(4-(1-((tert-butoxycarbonyl)amino)cyclopropyl)-2-fluorophenyl)benzo[d]imidazo[2,1-b]thiazole-7-carboxylic acid Compound 2-(4-(1-((tert-butoxycarbonyl)amino)cyclopropyl)-2-fluorophenyl)benzo[d]imidazo[2,1-b]thiazole-7-carboxylic acid was prepared from ethyl 2-(4-(1-((tert-butoxycarbonyl)amino)cyclopropyl)-2-fluorophenyl)benzo[d]imidazo[2,1-b]thiazole-7-carboxylate (60 mg, 0.121 mmol), following a similar procedure to that described for the synthesis of 2-(4-(1-(tert-butoxycarbonyl)pyrrolidin-2-yl)-2-fluorophenyl)benzo[d]imidazo[2,1-b]thiazole-7-carboxylic acid and was isolated as a light yellow solid.

Yield 50 mg (88%). $^1$H NMR (400 MHz, DMSO) δ 13.18 (br s, 1H), 8.68 (d, J=3.6 Hz, 1H), 8.66 (d, J=1.6 Hz, 1H), 8.27 (d, J=8.4 Hz, 1H), 8.11 (dd, J=1.6, 8.4 Hz, 1H), 8.08-8.00 (m, 1H), 7.77 (br s, 1H), 7.08-6.99 (m, 2H), 1.41 (s, 9H), 1.25-1.14 (m, 4H). m/z: [ESI$^+$]468 (M+H)$^+$.

Synthesis of tert-butyl (1-(3-fluoro-4-(7-((3-(4-fluoropiperidin-1-yl)propyl)carbamoyl)benzo[d]imidazo[2,1-b]thiazol-2-yl)phenyl)cyclopropyl)carbamate Compound tert-butyl (1-(3-fluoro-4-(7-((3-(4-fluoropiperidin-1-yl)propyl)carbamoyl)benzo[d]imidazo[2,1-b]thiazol-2-yl)phenyl)cyclopropyl)carbamate was prepared from 2-(4-(1-(((tert-butoxycarbonyl)amino)cyclopropyl)-2-fluorophenyl)benzo[d]imidazo[2,1-b]thiazole-7-carboxylic acid (50 mg, 0.107 mmol) and 3-(4-fluoropiperidin-1-yl)propan-1-amine (21 mg, 0.131 mmol), following a similar procedure to that described for the synthesis of tert-butyl 2-(3-fluoro-4-(7-(((1-methylpiperidin-4-yl)carbamoyl)benzo[d]imidazo[2,1-b]thiazol-2-yl)phenyl)pyrrolidine-1-carboxylate and was isolated as a white solid.

Yield 30 mg (46%). $^1$H NMR (400 MHz, DMSO) δ 8.67 (d, J=3.6 Hz, 1H), 8.60 (t, J=5.6 Hz, 1H), 8.51-8.45 (m, 1H), 8.29-8.22 (m, 1H), 8.09-7.98 (m, 2H), 7.77 (br s, 1H), 7.09-6.99 (m, 2H), 4.77-4.56 (m, 1H), 3.39-3.29 (m, 2H), 2.58-2.48 (m, 2H), 2.40-2.24 (m, 4H), 1.93-1.77 (m, 2H), 1.77-1.64 (m, 4H), 1.41 (s, 9H), 1.25-1.16 (m, 4H). m/z: [ESI$^+$]610 (M+H)$^+$.

Synthesis of tert-butyl 2-(4-(7-acetamidobenzo[d]imidazo[2,1-b]thiazol-2-yl)-3-fluorophenyl)pyrrolidine-1-carboxylate Compound tert-butyl 2-(4-(7-acetamidobenzo[d]imidazo[2,1-b]thiazol-2-yl)-3-fluorophenyl)pyrrolidine-1-carboxylate was prepared from N-(2-aminobenzo[d]thiazol-6-yl)acetamide (200 mg, 0.965 mmol) and tert-butyl 2-(4-(2-bromoacetyl)-3-fluorophenyl)pyrrolidine-1-carboxylate (450 mg, 1.165 mmol), following a similar procedure to that described for the synthesis of ethyl 2-(4-(1-(tert-butoxycarbonyl)pyrrolidin-2-yl)-2-fluorophenyl)benzo[d]imidazo[2,1-b]thiazole-7-carboxylate and was isolated as a light orange solid.

Yield 200 mg (42%). $^1$H NMR (400 MHz, CDCl$_3$) δ 9.37 (br s, 1H), 7.81-7.70 (m, 1H), 7.68-7.58 (m, 1H), 7.58-7.47 (m, 1H), 7.19-7.10 (m, 2H), 6.90-6.80 (m, 1H), 6.78-6.67 (m, 1H), 4.92-4.77 (m, 1H), 3.77-3.54 (m, 2H), 2.40-2.27 (m, 1H), 2.22 (s, 3H), 2.00-1.83 (m, 3H), 1.63-1.21 (m, 9H). m/z: [ESI$^+$]495 (M+H)$^+$.

Synthesis of (S)-2-(2-fluoro-4-(5-oxopyrrolidin-2-yl)phenyl)benzo[d]imidazo[2,1-b]thiazole-7-carboxylic acid Scheme 65.

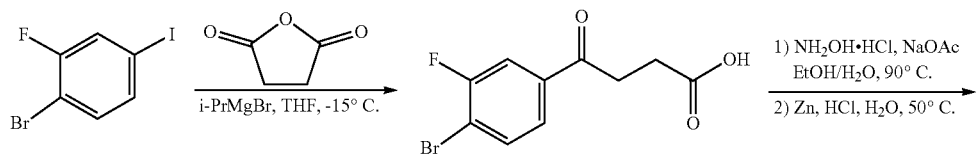

-continued

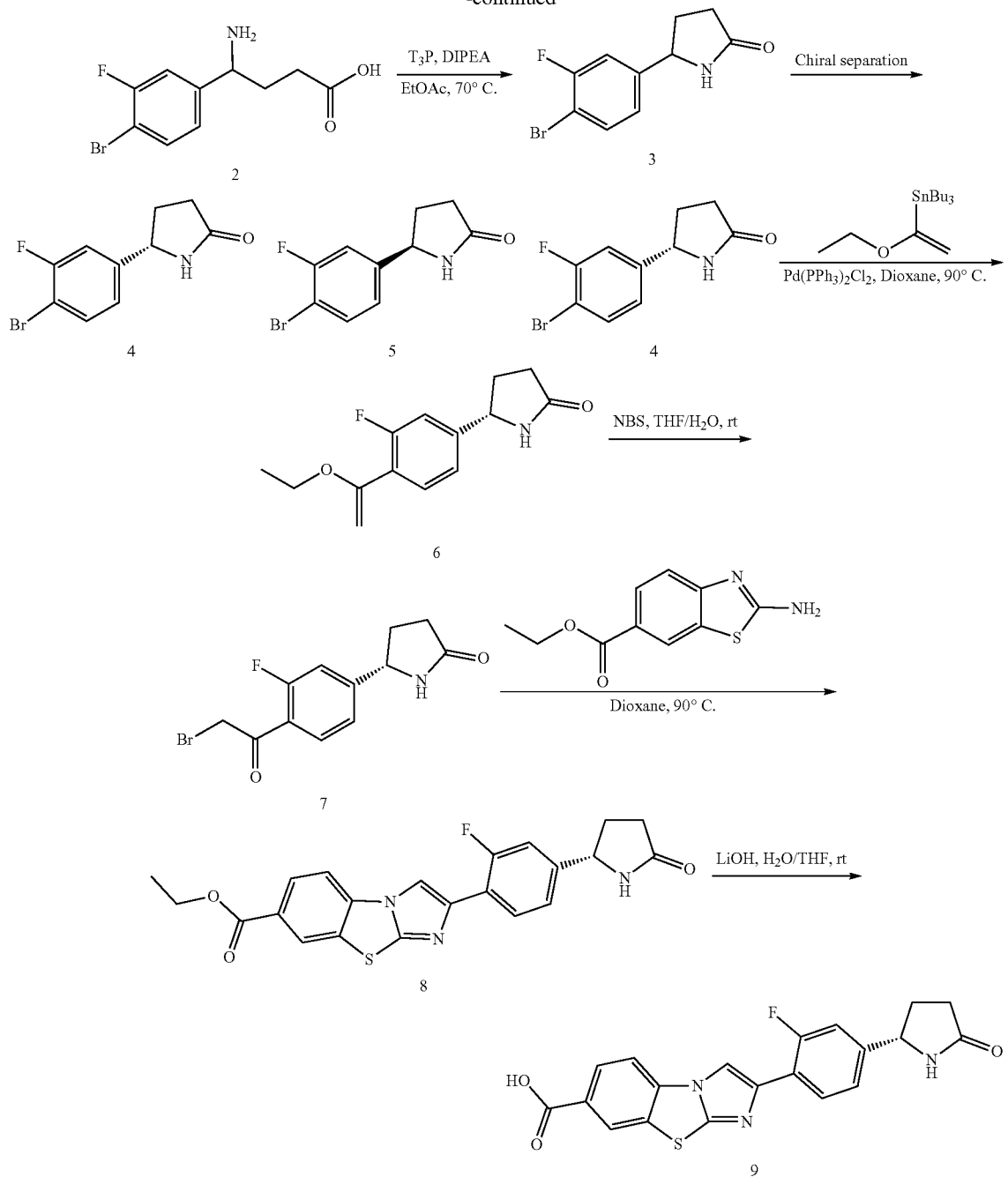

Synthesis of 4-(4-bromo-3-fluorophenyl)-4-oxobutanoic acid

Compound 4-(4-bromo-3-fluorophenyl)-4-oxobutanoic acid was prepared from 1-bromo-2-fluoro-4-iodobenzene (50.00 g, 166.17 mmol) and succinic anhydride (20.00 g, 199.85 mmol) at −15° C., following a similar procedure to that described for the synthesis of tert-butyl (4-(4-bromo-3-fluorophenyl)-4-oxobutyl)carbamate and was isolated as a white solid.

Yield: 6.40 g (14%). H NMR (400 MHz, DMSO) δ 12.18 (br s, 1H), 7.94-7.87 (m, 2H), 7.79-7.74 (m, 1H), 3.26 (t, J=6.0 Hz, 2H), 2.58 (t, J=6.0 Hz, 2H). m/z: [ESI-]273, 275 (M−H)⁻.

Synthesis of 4-amino-4-(4-bromo-3-fluorophenyl)butanoic acid

To a stirred solution of hydroxylamine hydrochloride (1.94 g, 27.92 mmol) and sodium acetate (2.86 g, 34.86 mmol) in water (60 mL), was added a solution of 4-(4- bromo-3-fluorophenyl)-4-oxobutanoic acid (6.40 g, 23.27 mmol) in ethanol (50 mL) dropwise over 3 min at room temperature. The reaction mixture was stirred for 16 h at 90° C. To the above solution were sequentially added hydrochloric acid (12 N, 4 mL) dropwise and zinc powder (7.40 g, 113.17 mmol) as a single portion at room temperature. The resulting mixture was stirred for an additional 2 h at 50° C. The mixture was cooled to room temperature and filtered. The filter cake was washed with ethanol (3×10 mL). The combined filtrates were concentrated under reduced pressure to afford 4-amino-4-(4-bromo-3-fluorophenyl)butanoic acid as light pink oil.

Yield 6.40 g (crude). $^1$H NMR not run. m/z: [ESI$^+$]276, 278 (M+H)$^+$.

Synthesis of 5-(4-bromo-3-fluorophenyl)pyrrolidin-2-one

To a stirred solution of 4-amino-4-(4-bromo-3-fluorophenyl)butanoic acid (6.40 g, crude) in ethyl acetate (40 mL), were sequentially added N,N-Diisopropylethylamine (41 mL, 235.38 mmol) and propanephosphonic acid cyclic anhydride (50% w/w in ethyl acetate, 40.00 g, 62.86 mmol) dropwise at room temperature. The reaction solution was stirred for 16 h at 70° C. The reaction mixture was cooled to room temperature and concentrated under reduced pressure. The residue was purified by silica gel column chromatography (eluted with 1%-5% of methanol in dichloromethane) to afford 5-(4-bromo-3-fluorophenyl)pyrrolidin-2-one as a white solid.

Yield 3.00 g (50% over two steps). $^1$H NMR (400 MHz, DMSO) δ 8.12 (br s, 1H), 7.70 (dd, J=8.0, 8.4 Hz, 1H), 7.31 (dd, J=2.0, 10.0 Hz, 1H), 7.12 (dd, J=2.0, 8.4 Hz, 1H), 4.74-4.64 (m, 1H), 2.49-2.42 (m, 1H), 2.27-2.20 (m, 2H), 1.80-1.70 (m, 1H). m/z: [ESI$^+$]258, 260 (M+H)$^+$.

Synthesis of (S)-5-(4-bromo-3-fluorophenyl)pyrrolidin-2-one and (R)-5-(4-bromo-3-fluorophenyl)pyrrolidin-2-one 5-(4-bromo-3-fluorophenyl)pyrrolidin-2-one (3.00 g, 11.62 mmol) was isolated after Prep-Chiral-HPLC using the following conditions; Column: CHIRALPAK IG, 5×25 cm, 10 um; Mobile Phase A: CO$_2$, Mobile Phase B: Methanol (plus 0.1% 2 N ammonia-methanol); Flow rate: 200 mL/min; Gradient: isocratic 20% B; Column Temperature (° C.): 35; Back Pressure (bar): 100; UV Detector: 220 nm. The faster eluting peak at 12.53 min was collected and concentrated under reduced pressure to afford (R)-5-(4-bromo-3-fluorophenyl)pyrrolidin-2-one as a pink solid.

Yield 1.30 g (43%). $^1$H NMR (400 MHz, CDCl$_3$) δ 7.57 (dd, J=7.6, 8.4 Hz, 1H), 7.10 (dd, J=2.0, 9.2 Hz, 1H), 7.01 (dd, J=2.0, 8.4 Hz, 1H), 6.56 (br s, 1H), 4.80-4.70 (m, 1H), 2.67-2.55 (m, 1H), 2.53-2.36 (m, 2H), 2.02-1.88 (m, 1H). m/z: [ESI$^+$]258, 260 (M+H)$^+$.

The slower peak was collected at 16 min and concentrated under reduced pressure to afford (S)-5-(4-bromo-3-fluorophenyl)pyrrolidin-2-one as a pink solid.

Yield 1.40 g (47%). $^1$H NMR (400 MHz, CDCl$_3$) δ 7.57 (dd, J=7.6, 8.4 Hz, 1H), 7.10 (dd, J=2.0, 9.2 Hz, 1H), 7.01 (dd, J=2.0, 8.4 Hz, 1H), 6.56 (br s, 1H), 4.80-4.70 (m, 1H), 2.67-2.55 (m, 1H), 2.53-2.36 (m, 2H), 2.02-1.88 (m, 1H). m/z: [ESI$^+$]258, 260 (M+H)$^+$.

Synthesis of (S)-5-(4-(1-ethoxyvinyl)-3-fluorophenyl)pyrrolidin-2-one

Compound (S)-5-(4-(1-ethoxyvinyl)-3-fluorophenyl)pyrrolidin-2-one was prepared from (S)-5-(4-bromo-3-fluorophenyl)pyrrolidin-2-one (0.60 g, 2.33 mmol) and tributyl(1-ethoxyethenyl)stannane (1.26 g, 3.49 mmol), following a similar procedure to that described for the synthesis of tert-butyl 2-(4-(1-ethoxyvinyl)-3-fluorophenyl)pyrrolidine-1-carboxylate and was isolated as a brown oil. The compound was used directly in the next step without further purification.

Yield 0.55 g (crude). m/z: [ESI$^+$]250 (M+H)$^+$.

Synthesis of(S)-5-(4-(2-bromoacetyl)-3-fluorophenyl)pyrrolidin-2-one

Compound (S)-5-(4-(2-bromoacetyl)-3-fluorophenyl) pyrrolidin-2-one was prepared from (S)-5-(4-(1-ethoxyvinyl)-3-fluorophenyl)pyrrolidin-2-one (550 mg, 2.206 mmol) and 1-bromopyrrolidine-2,5-dione (982 mg, 5.517 mmol), following a similar procedure to that described for the synthesis of tert-butyl 2-[4-(2-bromoacetyl)-3-fluorophenyl] pyrrolidine-1-carboxylate and was isolated as a white solid.

Yield 440 mg (63% over two steps). $^1$H NMR (400 MHz, CDCl$_3$) δ 7.98 (dd, J=7.6, 8.4 Hz, 1H), 7.24 (dd, J=2.0, 9.2 Hz, 1H), 7.16 (dd, J=2.0, 8.4 Hz, 1H), 6.36 (br s, 1H), 4.89-4.79 (m, 1H), 4.52 (d, J=2.4 Hz, 2H), 2.73-2.59 (m, 1H), 2.57-2.38 (m, 2H), 2.05-1.92 (m, 1H). m/z: [ESI$^+$]300, 302 (M+H)$^+$.

Synthesis of ethyl (S)-2-(2-fluoro-4-(5-oxopyrrolidin-2-yl)phenyl)benzo[d]imidazo[2,1-b]thiazole-7-carboxylate Compound ethyl (S)-2-(2-fluoro-4-(5-oxopyrrolidin-2-yl)phenyl)benzo[d]imidazo[2,1-b]thiazole-7-carboxylate was prepared from (S)-5-(4-(2-bromoacetyl)-3-fluorophenyl) pyrrolidin-2-one (440 mg, 1.466 mmol) and ethyl 2-aminobenzo[d]thiazole-6-carboxylate (326 mg, 1.467 mmol), following a similar procedure to that described for the synthesis of ethyl 2-(4-(1-(tert-butoxycarbonyl)pyrrolidin-2-yl)-2-fluorophenyl)benzo[d]imidazo[2,1-b]thiazole-7-carboxylate and was isolated as a white solid.

Yield: 190 mg (31%). $^1$H NMR (400 MHz, DMSO) δ 8.73 (d, J=3.6 Hz, 1H), 8.69 (d, J=1.6 Hz, 1H), 8.29 (d, J=8.4 Hz, 1H), 8.17-8.09 (m, 3H), 7.27 (dd, J=1.6, 6.8 Hz, 1H), 7.25 (d, J=2.0 Hz, 1H), 4.79-4.66 (m, 1H), 4.36 (q, J=7.2 Hz, 2H), 2.57-2.51 (m, 1H), 2.31-2.22 (m, 2H), 1.89-1.74 (m, 1H), 1.36 (t, J=7.2 Hz, 3H). m/z: [ESI$^+$]424 (M+H)$^+$.

Synthesis of (S)-2-(2-fluoro-4-(5-oxopyrrolidin-2-yl)phenyl)benzo[d]imidazo[2,1-b]thiazole-7-carboxylic acid Compound (S)-2-(2-fluoro-4-(5-oxopyrrolidin-2-yl)phenyl)benzo[d]imidazo[2,1-b]thiazole-7-carboxylic acid was prepared from ethyl (S)-2-(2-fluoro-4-(5-oxopyrrolidin-2-yl)phenyl)benzo[d]imidazo[2,1-b]thiazole-7-carboxylate (190 mg, 0.449 mmol), following a similar procedure to that described for the synthesis of 2-(4-(1-(tert-butoxycarbonyl) pyrrolidin-2-yl)-2-fluorophenyl)benzo[d]imidazo[2,1-b]thiazole-7-carboxylic acid and was isolated as a white solid.

Yield: 140 mg (79%). $^1$H NMR (400 MHz, DMSO) δ 13.23 (br s, 1H), 8.74 (dd, J=2.0, 4.0 Hz, 1H), 8.67 (d, J=2.0 Hz, 1H), 8.29 (dd, J=2.0, 8.4 Hz, 1H), 8.20-8.06 (m, 3H), 7.29-7.22 (m, 2H), 4.78-4.68 (m, 1H), 2.57-2.51 (m, 1H), 2.31-2.22 (m, 2H), 1.89-1.72 (m, 1H). m/z: [ESI$^+$]396 (M+H)$^+$.

Synthesis of (R)-2-(2-fluoro-4-(5-oxopyrrolidin-2-yl)phenyl)benzo[d]imidazo[2,1-b]thiazole-7-carboxylic acid

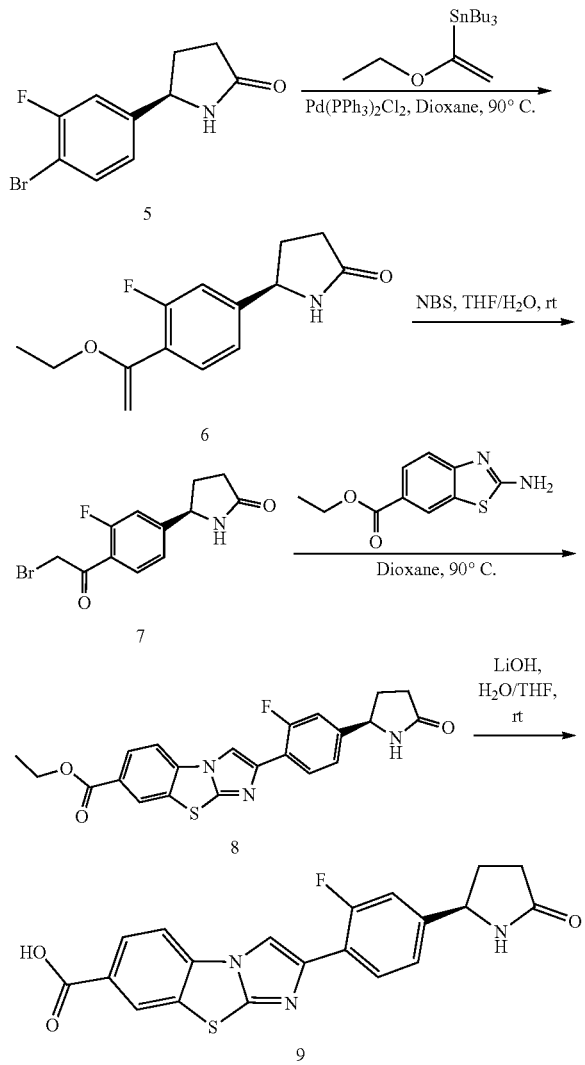

Synthesis of (R)-5-(4-(1-ethoxyvinyl)-3-fluorophenyl)pyrrolidin-2-one

Compound (R)-5-(4-(1-ethoxyvinyl)-3-fluorophenyl)pyrrolidin-2-one was prepared from (R)-5-(4-bromo-3-fluorophenyl)pyrrolidin-2-one (0.80 g, 3.10 mmol) and tributyl(1-ethoxyethenyl)stannane (1.68 g, 4.65 mmol), following a similar procedure to that described for the synthesis of tert-butyl 2-(4-(1-ethoxyvinyl)-3-fluorophenyl)pyrrolidine-1-carboxylate and was isolated as a brown oil. The compound was used directly in the next step without further purification.

Yield 0.75 g (crude). m/z: [ESI$^+$]250 (M+H)$^+$.

Synthesis of (R)-5-(4-(2-bromoacetyl)-3-fluorophenyl)pyrrolidin-2-one

Compound (R)-5-(4-(2-bromoacetyl)-3-fluorophenyl)pyrrolidin-2-one was prepared from (R)-5-(4-(1-ethoxyvi-nyl)-3-fluorophenyl)pyrrolidin-2-one (0.75 g, 3.01 mmol) and 1-bromopyrrolidine-2,5-dione (1.34 g, 7.52 mmol), following a similar procedure to that described for the synthesis of tert-butyl 2-[4-(2-bromoacetyl)-3-fluorophenyl]pyrrolidine-1-carboxylate and was isolated as a white solid.

Yield 0.72 g (83% over two steps). $^1$H NMR (400 MHz, CDCl$_3$) δ 7.98 (dd, J=7.6, 8.4 Hz, 1H), 7.24 (dd, J=2.0, 9.2 Hz, 1H), 7.16 (dd, J=2.0, 8.4 Hz, 1H), 6.36 (br s, 1H), 4.89-4.79 (m, 1H), 4.52 (d, J=2.4 Hz, 2H), 2.73-2.59 (m, 1H), 2.57-2.38 (m, 2H), 2.05-1.92 (m, 1H). m/z: [ESI$^+$]300, 302 (M+H)$^+$.

Synthesis of ethyl (R)-2-(2-fluoro-4-(5-oxopyrrolidin-2-yl)phenyl)benzo[d]imidazo[2,1-b]thiazole-7-carboxylate Compound ethyl (R)-2-(2-fluoro-4-(5-oxopyrrolidin-2-yl)phenyl)benzo[d]imidazo[2,1-b]thiazole-7-carboxylate was prepared from (R)-5-(4-(2-bromoacetyl)-3-fluorophenyl)pyrrolidin-2-one (720 mg, 2.399 mmol) and ethyl 2-aminobenzo[d]thiazole-6-carboxylate (533 mg, 2.398 mmol), following a similar procedure to that described for the synthesis of ethyl 2-(4-(1-(tert-butoxycarbonyl)pyrrolidin-2-yl)-2-fluorophenyl)benzo[d]imidazo[2,1-b]thiazole-7-carboxylate and was isolated as a white solid.

Yield: 142 mg (14%). $^1$H NMR (400 MHz, DMSO) δ 8.73 (d, J=3.6 Hz, 1H), 8.69 (d, J=1.6 Hz, 1H), 8.29 (d, J=8.4 Hz, 1H), 8.17-8.09 (m, 3H), 7.27 (dd, J=1.6, 6.8 Hz, 1H), 7.25 (d, J=2.0 Hz, 1H), 4.79-4.66 (m, 1H), 4.36 (q, J=7.2 Hz, 2H), 2.57-2.51 (m, 1H), 2.31-2.22 (m, 2H), 1.89-1.74 (m, 1H), 1.36 (t, J=7.2 Hz, 3H). m/z: [ESI$^+$]424 (M+H)$^+$.

Synthesis of (R)-2-(2-fluoro-4-(5-oxopyrrolidin-2-yl)phenyl)benzo[d]imidazo[2,1-b]thiazole-7-carboxylic acid Compound (R)-2-(2-fluoro-4-(5-oxopyrrolidin-2-yl)phenyl)benzo[d]imidazo[2,1-b]thiazole-7-carboxylic acid was prepared from ethyl (R)-2-(2-fluoro-4-(5-oxopyrrolidin-2-yl)phenyl)benzo[d]imidazo[2,1-b]thiazole-7-carboxylate (142 mg, 0.335 mmol), following a similar procedure to that described for the synthesis of 2-(4-(1-(tert-butoxycarbonyl)pyrrolidin-2-yl)-2-fluorophenyl)benzo[d]imidazo[2,1-b]thiazole-7-carboxylic acid and was isolated as a white solid.

Yield: 100 mg (75%). $^1$H NMR (400 MHz, DMSO) δ 13.23 (br s, 1H), 8.74 (dd, J=2.0, 4.0 Hz, 1H), 8.67 (d, J=2.0 Hz, 1H), 8.29 (dd, J=2.0, 8.4 Hz, 1H), 8.20-8.06 (m, 3H), 7.29-7.22 (m, 2H), 4.78-4.68 (m, 1H), 2.57-2.51 (m, 1H), 2.31-2.22 (m, 2H), 1.89-1.72 (m, 1H). m/z: [ESI$^+$]396 (M+H)$^+$.

Synthesis of 2-bromo-N-(3-(4-fluoropiperidin-1-yl)propyl)benzo[d]imidazo[2,1-b]thiazole-7-carboxamide

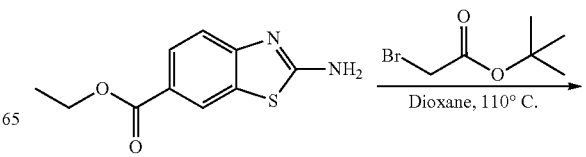

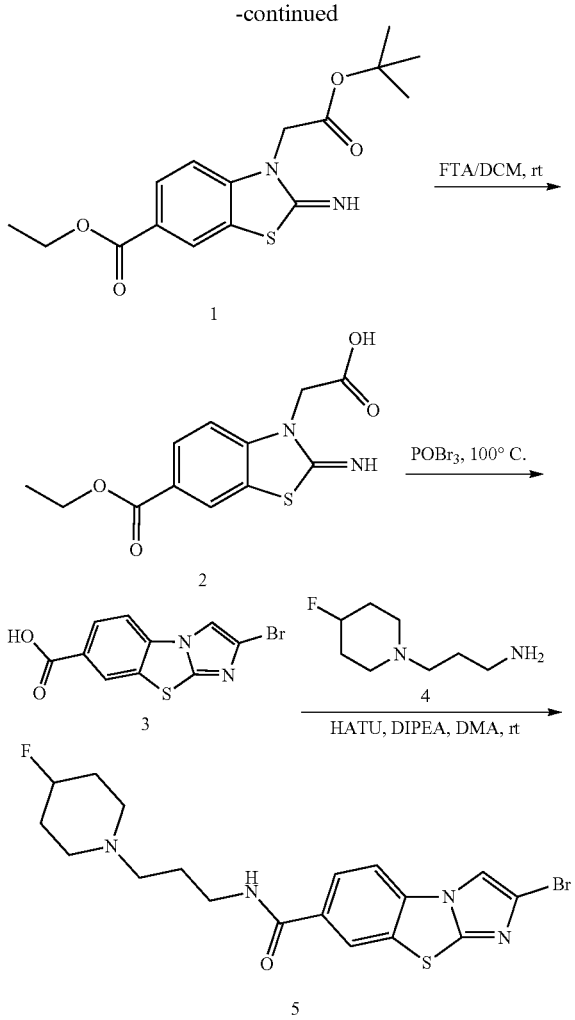

Synthesis of ethyl 3-(2-(tert-butoxy)-2-oxoethyl)-2-imino-2,3-dihydrobenzo[d]thiazole-6-carboxylate To a stirred solution of ethyl 2-aminobenzo[d]thiazole-6-carboxylate (75.00 g, 337.44 mmol) in dioxane (800 mL), was added tert-butyl 2-bromoacetate (78.98 g, 404.90 mmol) at room temperature under a nitrogen atmosphere. The resulting mixture was stirred at 110° C. for 16 h. Upon completion, the reaction mixture was cooled down to room temperature. The precipitated solids were collected by filtration, washed with ethanol (3×120 mL) and oven dried to afford ethyl 3-(2-(tert-butoxy)-2-oxoethyl)-2-imino-2,3-dihydrobenzo[d]thiazole-6-carboxylate as an off-white solid.

Yield: 97.50 g (86%). $^1$H NMR (400 MHz, DMSO) δ 10.68 (br s, 1H), 8.68 (d, J=1.8 Hz, 1H), 8.11 (dd, J=1.8, 8.6 Hz, 1H), 7.77 (d, J=8.6 Hz, 1H), 5.24 (s, 2H), 4.36 (q, J=7.2 Hz, 2H), 1.44 (s, 9H), 1.35 (t, J=7.2 Hz, 3H). m/z: [ESI$^+$]337 (M+H)$^+$.

Synthesis of 2-(6-(ethoxycarbonyl)-2-iminobenzo[d]thiazol-3(2H)-yl)acetic acid To a solution of ethyl 3-(2-(tert-butoxy)-2-oxoethyl)-2-imino-2,3-dihydrobenzo[d]thiazole-6-carboxylate (97.00 g, 288.34 mmol) in dichloromethane (600 mL) was added trifluoroacetic acid (300 mL). The resulting solution was stirred for 16 h at room temperature. The reaction solution was concentrated under reduced pressure. The residue was triturated with diethyl ether (400 mL) and oven dried to afford 2-(6-(ethoxycarbonyl)-2-iminobenzo[d]thiazol-3(2H)-yl)acetic acid as an off-white solid.

Yield 80.00 g (99%). $^1$H NMR (400 MHz, DMSO) δ 13.81 (br s, 1H), 10.72 (br s, 1H), 8.69 (d, J=1.8 Hz, 1H), 8.10 (dd, J=1.8, 8.6 Hz, 1H), 7.82 (d, J=8.6 Hz, 1H), 5.22 (s, 2H), 4.36 (q, J=7.2 Hz, 2H), 1.35 (t, J=7.2 Hz, 3H). m/z: [ESI$^+$]281 (M+H)$^+$.

Synthesis of 2-Bromobenzo[d]imidazo[2,1-b]thiazole-7-carboxylic acid

A mixture of 2-(6-(ethoxycarbonyl)-2-iminobenzo[d]thiazol-3(2H)-yl)acetic acid (80.00 g, 285.41 mmol) and phosphorus oxybromide (655.00 g, 2284.78 mmol) was stirred for 16 h at 100° C. under a nitrogen atmosphere. Upon completion, the reaction mixture was cooled down to room temperature and diluted with dioxane (600 mL). The precipitated solids were collected by filtration, washed with water (6×180 mL) and dried in the air to afford 2-bromobenzo[d]imidazo[2,1-b]thiazole-7-carboxylic acid as an off-white solid.

Yield 62.80 g (74%). $^1$H NMR (400 MHz, DMSO) δ 8.70 (d, J=1.6 Hz, 1H), 8.59 (s, 1H), 8.12 (dd, J=1.6, 8.4 Hz, 1H), 8.10 (d, J=8.4 Hz, 1H). OH proton not observed. m/z: [ESI$^+$]297, 299 (M+H)$^+$.

Synthesis of 2-bromo-N-(3-(4-fluoropiperidin-1-yl)propyl)benzo[d]imidazo[2,1-b]thiazole-7-carboxamide Compound 2-bromo-N-(3-(4-fluoropiperidin-1-yl)propyl)benzo[d]imidazo[2,1-b]thiazole-7-carboxamide was prepared from 2-bromobenzo[d]imidazo[2,1-b]thiazole-7-carboxylic acid (1.20 g, 4.04 mmol) and 3-(4-fluoropiperidin-1-yl)propan-1-amine (0.84 g, 5.24 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a white solid.

Yield 0.80 g (45%). $^1$H NMR (400 MHz, DMSO) δ 8.72 (t, J=5.6 Hz, 1H), 8.58 (s, 1H), 8.53 (d, J=1.6 Hz, 1H), 8.11 (d, J=8.4 Hz, 1H), 8.03 (dd, J=1.6, 8.4 Hz, 1H), 4.99-4.75 (m, 1H), 3.42-3.33 (m, 2H), 3.16-2.85 (m, 6H), 2.06-1.79 (m, 6H). m/z: [ESI$^+$]439, 441 (M+H)$^+$.

Synthesis of 2-bromobenzo[d]imidazo[2,1-b]thiazole-7-carboxamide

Compound 2-bromobenzo[d]imidazo[2,1-b]thiazole-7-carboxamide was prepared from 2-bromobenzo[d]imidazo[2,1-b]thiazole-7-carboxylic acid (5.00 g, 16.83 mmol) and ammonium bicarbonate (1.60 g, 20.24 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as an off-white solid.

Yield 2.60 g (52%). $^1$H NMR (400 MHz, DMSO) δ 8.56-8.55 (m, 1H), 8.55-8.54 (m, 1H), 8.10-8.05 (m, 3H), 7.52 (br s, 1H). m/z: [ESI$^+$]296, 298 (M+H)$^+$.

Synthesis of 2-bromo-N-methylbenzo[d]imidazo[2,1-b]thiazole-7-carboxamide

Compound 2-bromo-N-methylbenzo[d]imidazo[2,1-b]thiazole-7-carboxamide was prepared from 2-bromobenzo

[d]imidazo[2,1-b]thiazole-7-carboxylic acid (2.00 g, 6.73 mmol) and methanamine hydrochloride (0.70 g, 10.37 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as an off-white solid.

Yield 1.30 g (62%). $^1$H NMR (300 MHz, DMSO) δ 8.60-8.49 (m, 3H), 8.12-8.06 (m, 1H), 8.04-7.98 (m, 1H), 2.83 (d, J=4.5 Hz, 3H). m/z: [ESI$^+$]310, 312 (M+H)$^+$.

Synthesis of 2-bromo-N-(1-methylpiperidin-4-yl)benzo[d]imidazo[2,1-b]thiazole-7-carboxamide Compound 2-bromo-N-(1-methylpiperidin-4-yl)benzo[d]imidazo[2,1-b]thiazole-7-carboxamide was prepared from 2-bromobenzo[d]imidazo[2,1-b]thiazole-7-carboxylic acid (10.00 g, 33.66 mmol) and 1-methylpiperidin-4-amine (5.80 g, 50.79 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a yellow solid.

Yield 9.30 g (70%). $^1$H NMR (400 MHz, DMSO) δ 8.55 (s, 1H), 8.51 (d, J=1.6 Hz, 1H), 8.37 (d, J=7.6 Hz, 1H), 8.08 (d, J=8.4 Hz, 1H), 8.02 (dd, J=1.6, 8.4 Hz, 1H), 3.81-3.69 (m, 1H), 2.81-2.74 (m, 2H), 2.17 (s, 3H), 2.01-1.92 (m, 2H), 1.84-1.75 (m, 2H), 1.65-1.53 (m, 2H). m/z: [ESI$^+$]393, 395 (M+H)$^+$.

Synthesis of 2-bromo-N-(tetrahydro-2H-pyran-4-yl)benzo[d]imidazo[2,1-b]thiazole-7-carboxamide Compound 2-bromo-N-(tetrahydro-2H-pyran-4-yl)benzo[d]imidazo[2,1-b]thiazole-7-carboxamide was prepared from 2-bromobenzo[d]imidazo[2,1-b]thiazole-7-carboxylic acid (5.00 g, 16.83 mmol) and tetrahydro-2H-pyran-4-amine (2.50 g, 24.72 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a yellow solid.

Yield 2.50 g (39%). $^1$H NMR (300 MHz, DMSO) δ 8.56 (s, 1H), 8.52 (d, J=1.5 Hz, 1H), 8.43 (d, J=7.5 Hz, 1H), 8.09 (d, J=8.4 Hz, 1H), 8.03 (dd, J=1.5, 8.4 Hz, 1H), 4.12-3.95 (m, 1H), 3.95-3.84 (m, 2H), 3.47-3.36 (m, 2H), 1.89-1.74 (m, 2H), 1.69-1.51 (m, 2H). m/z: [ESI$^+$]380, 382 (M+H)$^+$.

Synthesis of tert-butyl 4-(3-fluoro-4-(7-((3-(4-fluoropiperidin-1-yl)propyl)carbamoyl)benzo[d]imidazo[2,1-b]thiazol-2-yl)phenyl)piperidine-1-carboxylate Scheme 68.

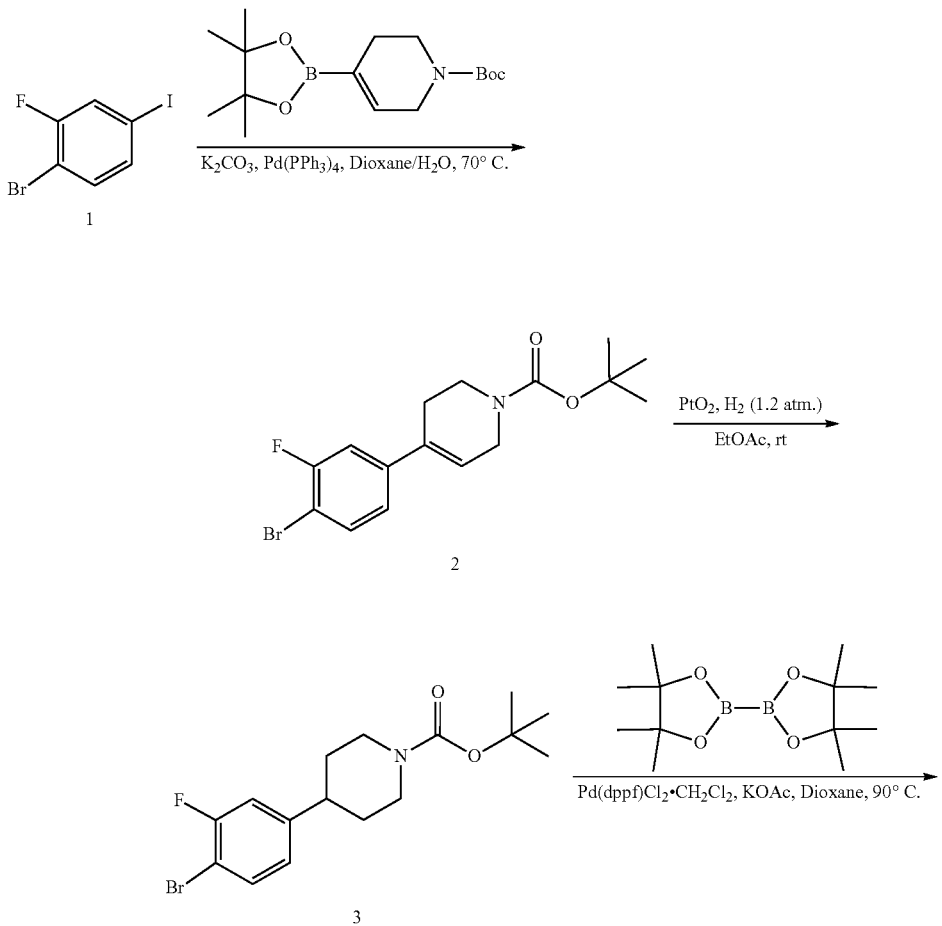

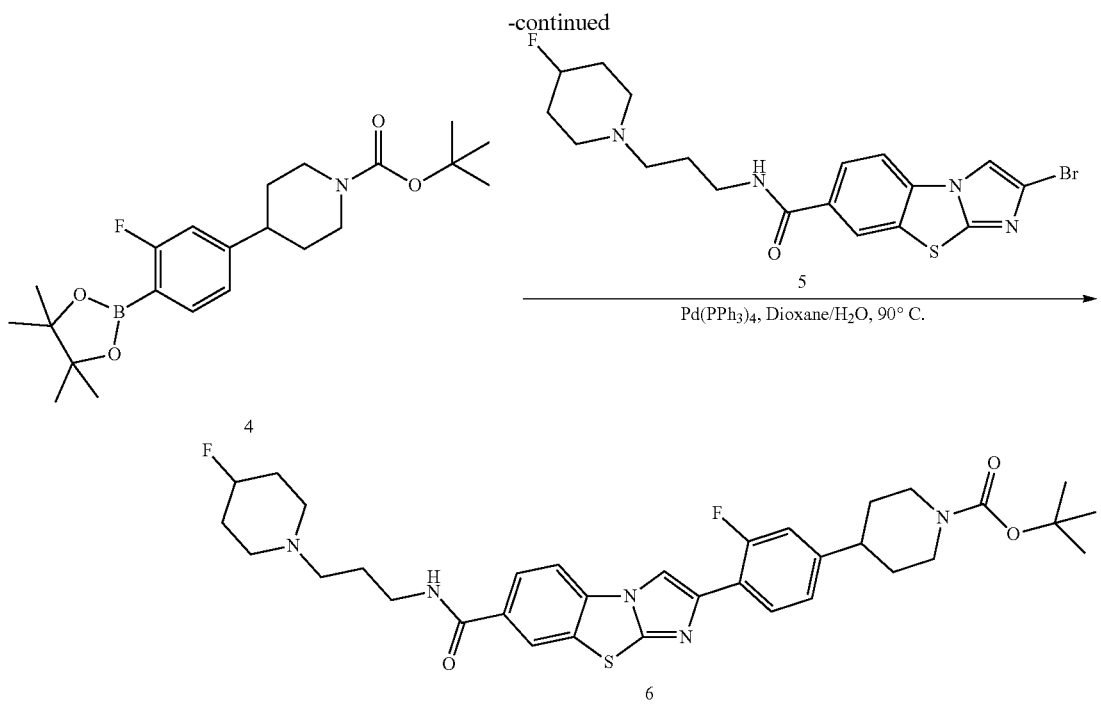

Synthesis of tert-butyl 4-(4-bromo-3-fluorophenyl)-3,6-dihydropyridine-1(2H)-carboxylate To a stirred mixture of 1-bromo-2-fluoro-4-iodobenzene (15.00 g, 49.85 mmol) and tert-butyl 4-(4,4,5,5-tetramethyl-1,3,2-dioxaborolan-2-yl)-3,6-dihydropyridine-1(2H)-carboxylate (18.00 g, 58.21 mmol) in 1,4-dioxane:water (7:1, 170 mL), were added potassium carbonate (21.00 g, 151.95 mmol) and tetrakis(triphenylphosphine)palladium (0) (5.70 g, 4.93 mmol) at room temperature under a nitrogen atmosphere. The reaction mixture was stirred for 4 h at 70° C. The mixture was cooled to room temperature, diluted with water (500 mL) and extracted with ethyl acetate (3×300 mL). The combined organic layers were washed with brine (300 mL) and dried over anhydrous sodium sulfate. After filtration, the filtrate was concentrated under reduced pressure. The residue was purified by silica gel column chromatography (25% ethyl acetate in petroleum ether) to afford tert-butyl 4-(4-bromo-3-fluorophenyl)-3,6-dihydropyridine-1(2H)-carboxylate as a white oil.

Yield 16.00 g (90%). $^1$H NMR (400 MHz, CD$_3$OD) δ 7.56 (dd, J=7.2, 8.4 Hz, 1H), 7.28 (dd, J=2.0, 10.4 Hz, 1H), 7.18 (dd, J=2.0, 8.4 Hz, 1H), 6.25-6.15 (m, 1H), 4.12-4.01 (m, 2H), 3.67-3.59 (m, 2H), 2.55-2.48 (m, 2H), 1.50 (s, 9H). m/z: [ESI$^+$]300, 302 (M+H-56)$^+$.

Synthesis of tert-butyl 4-(4-bromo-3-fluorophenyl)piperidine-1-carboxylate

A mixture of tert-butyl 4-(4-bromo-3-fluorophenyl)-3,6-dihydropyridine-1(2H)-carboxylate (10.00 g, 28.07 mmol) and platinum dioxide (1.00 g, 4.40 mmol) in ethyl acetate (15 mL) was stirred for 2 h at room temperature under a hydrogen atmosphere (1.2 atm.). After filtration, the filter cake was washed with ethyl acetate (3×50 mL). The combined filtrates were concentrated under reduced pressure. The residue was purified by silica gel column chromatography (30% ethyl acetate in petroleum ether) to afford tert-butyl 4-(4-bromo-3-fluorophenyl)piperidine-1-carboxylate as a colorless oil.

Yield 8.00 g (80%). $^1$H NMR (400 MHz, DMSO) δ 7.61 (dd, J=7.2, 8.4 Hz, 1H), 7.30 (dd, J=2.0, 10.4 Hz, 1H), 7.08 (dd, J=2.0, 8.4 Hz, 1H), 4.12-4.01 (m, 2H), 2.86-2.65 (m, 3H), 1.79-1.69 (m, 2H), 1.53-1.43 (m, 2H), 1.42 (s, 9H). m/z: [ESI$^+$]302, 304 (M+H-56)$^+$.

Synthesis of tert-butyl 4-(3-fluoro-4-(4,4,5,5-tetramethyl-1,3,2-dioxaborolan-2-yl)phenyl)piperidine-1-carboxylate A mixture of tert-butyl 4-(4-bromo-3-fluorophenyl)piperidine-1-carboxylate (1.00 g, 2.79 mmol), bis(pinacolato)diboron (1.00 g, 3.94 mmol), 1,1'-bis(diphenylphosphino)ferrocene-palladium(II)dichloride dichloromethane complex (0.23 g, 0.28 mmol) and potassium acetate (0.83 g, 8.46 mmol) in 1,4-dioxane (20 mL), was stirred for 2 h at 90° C. under a nitrogen atmosphere. The reaction mixture was cooled to room temperature, diluted with water (50 mL) and extracted with ethyl acetate (3×50 mL). The combined extracts were concentrated under reduced pressure to afford tert-butyl 4-(3-fluoro-4-(4,4,5,5-tetramethyl-1,3,2-dioxaborolan-2-yl)phenyl)piperidine-1-carboxylate as brown oil. The compound was used directly in the next step without further purification.

Yield 1.00 g (crude). $^1$H NMR not run. m/z: [ESI$^+$]350 (M+H-56)$^+$.

Synthesis of tert-butyl 4-(3-fluoro-4-(7-((3-(4-fluoropiperidin-1-yl)propyl)carbamoyl)benzo[d]imidazo[2,1-b]thiazol-2-yl)phenyl)piperidine-1-carboxylate Compound tert-butyl 4-(3-fluoro-4-(7-((3-(4-fluoropiperidin-1-yl)propyl)carbamoyl)benzo[d]imidazo[2,1-b]thiazol-2-yl)phenyl)piperidine-1-carboxylate was prepared from 2-bromo-N-(3-(4-fluoropiperidin-1-yl)propyl)benzo

[d]imidazo[2,1-b]thiazole-7-carboxamide (300 mg, 0.683 mmol) and tert-butyl 4-(3-fluoro-4-(4,4,5,5-tetramethyl-1,3,2-dioxaborolan-2-yl)phenyl)piperidine-1-carboxylate (500 mg, crude) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 400 mg (92%). ¹H NMR (300 MHz, DMSO) δ 8.66 (d, J=3.6 Hz, 1H), 8.63 (t, J=5.7 Hz, 1H), 8.49 (d, J=1.5 Hz, 1H), 8.26 (d, J=8.4 Hz, 1H), 8.12-8.05 (m, 1H), 8.02 (dd, J=1.5, 8.4 Hz, 1H), 7.28-7.16 (m, 2H), 4.87-4.57 (m, 1H), 4.16-3.99 (m, 2H), 3.43-3.22 (m, 4H), 2.90-2.66 (m, 6H), 2.53-2.32 (m, 3H), 1.87-1.66 (m, 6H), 1.62-1.47 (m, 2H), 1.43 (s, 9H). m/z: [ESI⁺]638 (M+H)⁺.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate Synthesis of tert-butyl (R)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate Synthesis of tert-butyl (S)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate Scheme 69.

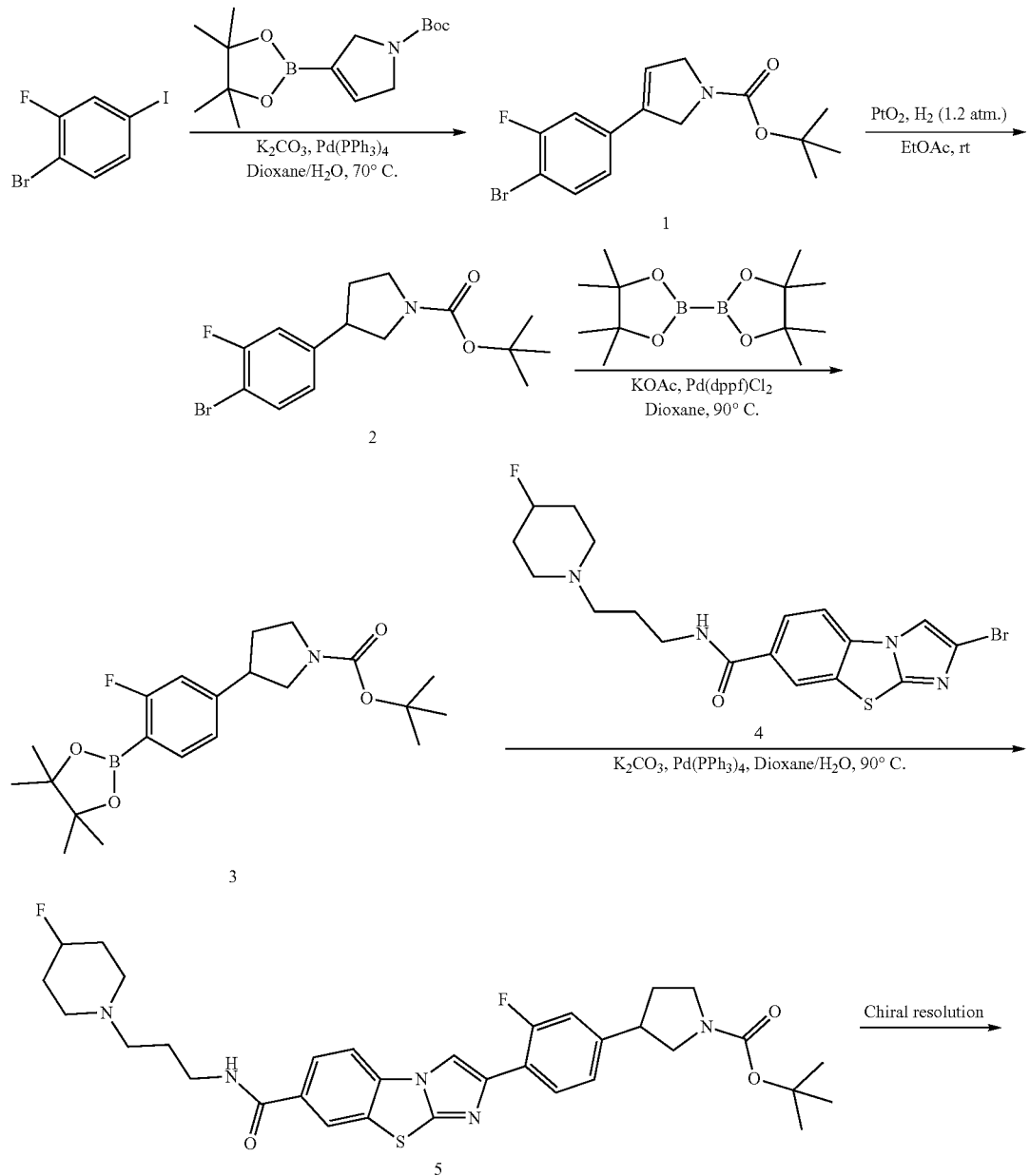

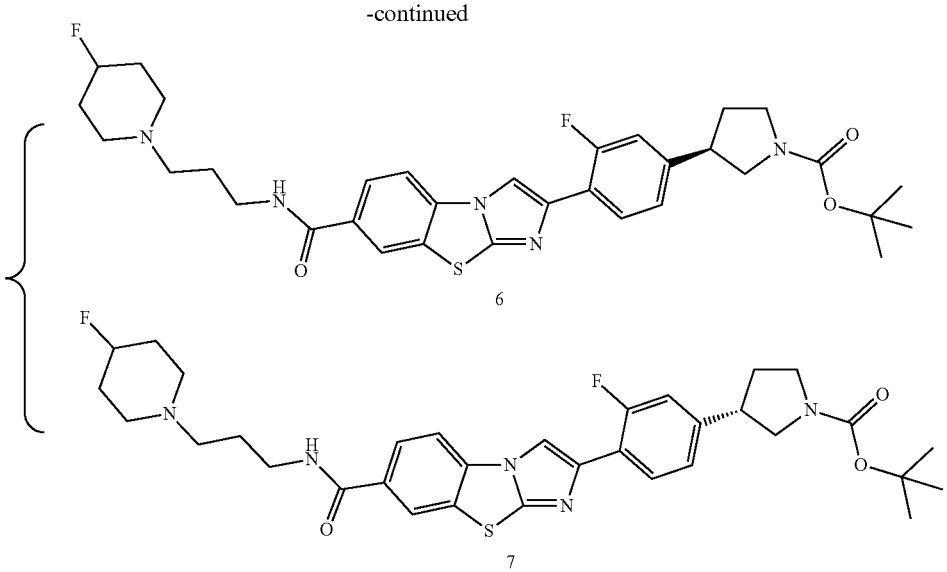

Synthesis of tert-butyl 3-(4-bromo-3-fluorophenyl)-2,5-dihydro-1H-pyrrole-1-carboxylate Compound tert-butyl 3-(4-bromo-3-fluorophenyl)-2,5-dihydro-1H-pyrrole-1-carboxylate was prepared from 1-bromo-2-fluoro-4-iodobenzene (10.19 g, 33.87 mmol) and tert-butyl 3-(4,4,5,5-tetramethyl-1,3,2-dioxaborolan-2-yl)-2,5-dihydro-1H-pyrrole-1-carboxylate (10.00 g, 33.88 mmol), following a similar procedure to that described for the synthesis of tert-butyl 4-(4-bromo-3-fluorophenyl)-3,6-dihydropyridine-1(2H)-carboxylate and was isolated as a yellow solid.

Yield 6.50 g (56%). $^1$H NMR (300 MHz, CDCl$_3$) δ 7.54 (dd, J=7.2, 8.4 Hz, 1H), 7.15 (dd, J=2.1, 9.6 Hz, 1H), 7.05 (dd, J=2.1, 8.4 Hz, 1H), 6.26-6.15 (m, 1H), 4.53-4.40 (m, 2H), 4.38-4.26 (m, 2H), 1.53 (s, 9H). m/z: [ESI$^+$]286, 288 (M+H-56)$^+$.

Synthesis of tert-butyl 3-(4-bromo-3-fluorophenyl)pyrrolidine-1-carboxylate

Compound tert-butyl 3-(4-bromo-3-fluorophenyl)pyrrolidine-1-carboxylate was prepared from tert-butyl 3-(4-bromo-3-fluorophenyl)-2,5-dihydro-1H-pyrrole-1-carboxylate (6.50 g, 18.99 mmol), following a similar procedure to that described for the synthesis of tert-butyl 4-(4-bromo-3-fluorophenyl)piperidine-1-carboxylate and was isolated as a colorless oil.

Yield 2.60 g (40%). $^1$H NMR (300 MHz, CDCl$_3$) δ 7.50 (dd, J=7.2, 8.4 Hz, 1H), 7.03 (dd, J=2.1, 9.6 Hz, 1H), 6.93 (dd, J=2.1, 8.4 Hz, 1H), 3.87-3.78 (m, 1H), 3.67-3.55 (m, 1H), 3.52-3.18 (m, 3H), 2.35-2.22 (m, 1H), 2.04-1.89 (m, 1H), 1.50 (s, 9H). m/z: [ESI$^+$]288, 290 (M+H-56)$^+$.

Synthesis of tert-butyl 3-(3-fluoro-4-(4,4,5,5-tetramethyl-1,3,2-dioxaborolan-2-yl)phenyl)pyrrolidine-1-carboxylate Compound tert-butyl 3-(3-fluoro-4-(4,4,5,5-tetramethyl-1,3,2-dioxaborolan-2-yl)phenyl)pyrrolidine-1-carboxylate was prepared from tert-butyl 3-(4-bromo-3-fluorophenyl)pyrrolidine-1-carboxylate (300 mg, 0.872 mmol) and bis(pinacolato)diboron (330 mg, 1.300 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown oil. The compound was used directly in the next step without further purification.

Yield 300 mg (crude). $^1$H NMR not run. m/z: [ESI$^+$]336 (M+H-56)$^+$.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate Compound tert-butyl 3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate was prepared from 2-bromo-N-(3-(4-fluoropiperidin-1-yl)propyl)benzo[d]imidazo[2,1-b]thiazole-7-carboxamide (300 mg, 0.683 mmol) and tert-butyl 3-(3-fluoro-4-(4,4,5,5-tetramethyl-1,3,2-dioxaborolan-2-yl)phenyl)pyrrolidine-1-carboxylate (300 mg, crude) at 90° C., following a similar procedure to that described for the synthesis of tert-butyl 4-(4-bromo-3-fluorophenyl)-3,6-dihydropyridine-1(2H)-carboxylate and was isolated as a light yellow oil.

Yield 200 mg (47%). $^1$H NMR (400 MHz, CDCl$_3$) δ 8.57-8.45 (m, 1H), 8.38-8.27 (m, 1H), 8.25-8.13 (m, 2H), 8.04-7.96 (m, 1H), 7.74-7.65 (m, 1H), 7.19-7.11 (m, 1H), 7.10-7.00 (m, 1H), 4.96-4.73 (m, 1H), 3.93-3.79 (m, 2H), 3.75-3.53 (m, 2H), 3.51-3.28 (m, 2H), 2.88-2.67 (m, 6H), 2.38-2.25 (m, 1H), 2.13-1.83 (m, 8H), 1.52-1.26 (m, 9H). m/z: [ESI$^+$]624 (M+H)$^+$.

Synthesis of tert-butyl (R)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate

Synthesis of tert-butyl (S)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate tert-butyl 3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (100 mg, 0.160 mmol) was separated by Chiral Prep-HPLC using the following conditions; Column: CHIRALPAK IF, 2×25 cm, 5 um; Mobile Phase A: tert-butyl methyl ether (plus 0.5% 2 Nammonia-methanol), Mobile Phase B: methanol:dichloromethane=1:1; Flow rate: 20 mL/min; Gradient: 10% B in 24 min; UV Detector: 220/254 nm. The faster eluting peak at 15.36 min was collected and concentrated under reduced pressure to afford tert-butyl (R)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate as a white solid.

Yield 30 mg (30%). $^1$H NMR (400 MHz, CDCl$_3$) δ 8.57-8.45 (m, 1H), 8.38-8.27 (m, 1H), 8.25-8.13 (m, 2H), 8.04-7.96 (m, 1H), 7.74-7.65 (m, 1H), 7.19-7.11 (m, 1H), 7.10-7.00 (m, 1H), 4.96-4.73 (m, 1H), 3.93-3.79 (m, 2H), 3.75-3.53 (m, 2H), 3.51-3.28 (m, 2H), 2.88-2.67 (m, 6H), 2.38-2.25 (m, 1H), 2.13-1.83 (m, 8H), 1.52-1.26 (m, 9H). m/z: [ESI$^+$]624 (M+H)$^+$.

The slower eluting peak at 20.33 min was collected and concentrated under reduced pressure to afford tert-butyl (S)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate as a white solid.

Yield 30 mg (30%). $^1$H NMR (400 MHz, CDCl$_3$) δ 8.57-8.45 (m, 1H), 8.38-8.27 (m, 1H), 8.25-8.13 (m, 2H), 8.04-7.96 (m, 1H), 7.74-7.65 (m, 1H), 7.19-7.11 (m, 1H), 7.10-7.00 (m, 1H), 4.96-4.73 (m, 1H), 3.93-3.79 (m, 2H), 3.75-3.53 (m, 2H), 3.51-3.28 (m, 2H), 2.88-2.67 (m, 6H), 2.38-2.25 (m, 1H), 2.13-1.83 (m, 8H), 1.52-1.26 (m, 9H). m/z: [ESI$^+$]624 (M+H)$^+$.

Synthesis of tert-butyl 3-(4-(7-carbamoylbenzo[d]imidazo[2,1-b]thiazol-2-yl)-3-fluorophenyl)pyrrolidine-1-carboxylate Compound tert-butyl 3-(4-(7-carbamoylbenzo[d]imidazo[2,1-b]thiazol-2-yl)-3-fluorophenyl)pyrrolidine-1-carboxylate was prepared from 2-bromobenzo[d]imidazo[2,1-b]thiazole-7-carboxamide (200 mg, 0.675 mmol) and tert-butyl 3-(3-fluoro-4-(4,4,5,5-tetramethyl-1,3,2-dioxaborolan-2-yl)phenyl)pyrrolidine-1-carboxylate (300 mg, crude) at 90° C., following a similar procedure to that described for the synthesis of tert-butyl 4-(4-bromo-3-fluorophenyl)-3,6-dihydropyridine-1(2H)-carboxylate and was isolated as a white solid.

Yield 50 mg (15%). $^1$H NMR (400 MHz, CDCl$_3$) δ 8.46-8.39 (m, 1H), 8.31-8.22 (m, 3H), 8.11-8.03 (m, 1H), 7.90-7.84 (m, 1H), 7.60-7.45 (m, 1H), 7.27-7.18 (m, 1H), 7.15-7.07 (m, 1H), 3.91-3.79 (m, 1H), 3.71-3.57 (m, 1H), 3.53-3.31 (m, 3H), 2.39-2.27 (m, 1H), 2.09-1.98 (m, 1H), 1.52 (s, 9H). m/z: [ESI$^+$]481 (M+H)$^+$.

Synthesis of tert-butyl 3-(3-fluoro-4-(7-(methylcarbamoyl)benzo[d]imidazo[2,1-b]thiazol-2-yl)phenyl)pyrrolidine-1-carboxylate Compound tert-butyl 3-(3-fluoro-4-(7-(methylcarbamoyl)benzo[d]imidazo[2,1-b]thiazol-2-yl)phenyl)pyrrolidine-1-carboxylate was prepared from 2-bromo-N-methylbenzo[d]imidazo[2,1-b]thiazole-7-carboxamide (342 mg, 1.103 mmol) and tert-butyl 3-(3-fluoro-4-(4,4,5,5-tetramethyl-1,3,2-dioxaborolan-2-yl)phenyl)pyrrolidine-1-carboxylate (400 mg, crude) at 90° C., following a similar procedure to that described for the synthesis of tert-butyl 4-(4-bromo-3-fluorophenyl)-3,6-dihydropyridine-1(2H)-carboxylate and was isolated as an orange solid.

Yield 120 mg (22%). $^1$H NMR (400 MHz, DMSO) δ 8.69 (d, J=3.6 Hz, 1H), 8.57 (d, J=4.8 Hz, 1H), 8.49 (d, J=1.6 Hz, 1H), 8.27 (d, J=8.4 Hz, 1H), 8.14-8.05 (m, 1H), 8.01 (dd, J=1.6, 8.4 Hz, 1H), 7.30 (d, J=12.8 Hz, 1H), 7.25 (d, J=8.0 Hz, 1H), 3.79-3.71 (m, 1H), 3.54-3.31 (m, 3H), 3.25-3.16 (m, 1H), 2.83 (d, J=4.8 Hz, 3H), 2.30-2.19 (m, 1H), 2.07-1.95 (m, 1H), 1.43 (s, 9H). m/z: [ESI$^+$]495 (M+H)$^+$.

Synthesis of tert-butyl 3-(3-fluoro-4-(7-((1-methylpiperidin-4-yl)carbamoyl)benzo[d]imidazo[2,1-b]thiazol-2-yl)phenyl)pyrrolidine-1-carboxylate Compound tert-butyl 3-(3-fluoro-4-(7-((1-methylpiperidin-4-yl)carbamoyl)benzo[d]imidazo[2,1-b]thiazol-2-yl)phenyl)pyrrolidine-1-carboxylate was prepared from 2-bromo-N-(1-methylpiperidin-4-yl)benzo[d]imidazo[2,1-b]thiazole-7-carboxamide (200 mg, 0.509 mmol) and tert-butyl 3-(3-fluoro-4-(4,4,5,5-tetramethyl-1,3,2-dioxaborolan-2-yl)phenyl)pyrrolidine-1-carboxylate (300 mg, crude) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 150 mg (51%). $^1$H NMR (400 MHz, CDCl$_3$) δ 8.25-8.16 (m, 3H), 7.87 (dd, J=1.6, 8.4 Hz, 1H), 7.70 (d, J=8.4 Hz, 1H), 7.15 (dd, J=1.6, 8.0 Hz, 1H), 7.06 (d, J=12.4 Hz, 1H), 6.03 (d, J=7.6 Hz, 1H), 4.11-4.00 (m, 1H), 3.93-3.80 (m, 1H), 3.74-3.56 (m, 1H), 3.49-3.26 (m, 3H), 2.97-2.84 (m, 2H), 2.40-2.27 (m, 4H), 2.27-2.15 (m, 2H), 2.15-1.98 (m, 3H), 1.72-1.59 (m, 2H), 1.52 (s, 9H). m/z: [ESI$^+$] 578 (M+H)$^+$.

Synthesis of tert-butyl 4-(3-fluoro-4-(7-((tetrahydro-2H-pyran-4-yl)carbamoyl)benzo[d]imidazo[2,1-b]thiazol-2-yl)phenyl)piperidine-1-carboxylate Compound tert-butyl 4-(3-fluoro-4-(7-((tetrahydro-2H-pyran-4-yl)carbamoyl)benzo[d]imidazo[2,1-b]thiazol-2-yl)phenyl)piperidine-1-carboxylate was prepared from 2-bromo-N-(tetrahydro-2H-pyran-4-yl)benzo[d]imidazo[2,1-b]thiazole-7-carboxamide (200 mg, 0.526 mmol) and tert-butyl 4-(3-fluoro-4-(4,4,5,5-tetramethyl-1,3-dioxolan-2-yl)phenyl)piperidine-1-carboxylate (300 mg, crude) at 90° C., following a similar procedure to that described for the synthesis of tert-butyl 4-(4-bromo-3-fluorophenyl)-3,6-dihydropyridine-1(2H)-carboxylate and was isolated as a white solid.

Yield 200 mg (66%). $^1$H NMR (300 MHz, DMSO) δ 8.67 (d, J=3.6 Hz, 1H), 8.50 (d, J=1.5 Hz, 1H), 8.43 (d, J=7.5 Hz, 1H), 8.27 (d, J=8.4 Hz, 1H), 8.12-8.02 (m, 2H), 7.30-7.17 (m, 2H), 4.17-3.98 (m, 3H), 3.97-3.89 (m, 1H), 3.50-3.36 (m, 2H), 2.91-2.69 (m, 4H), 1.87-1.76 (m, 4H), 1.70-1.49 (m, 4H), 1.43 (s, 9H). m/z: [ESI$^+$]579 (M+H)$^+$.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)piperidine-1-carboxylate

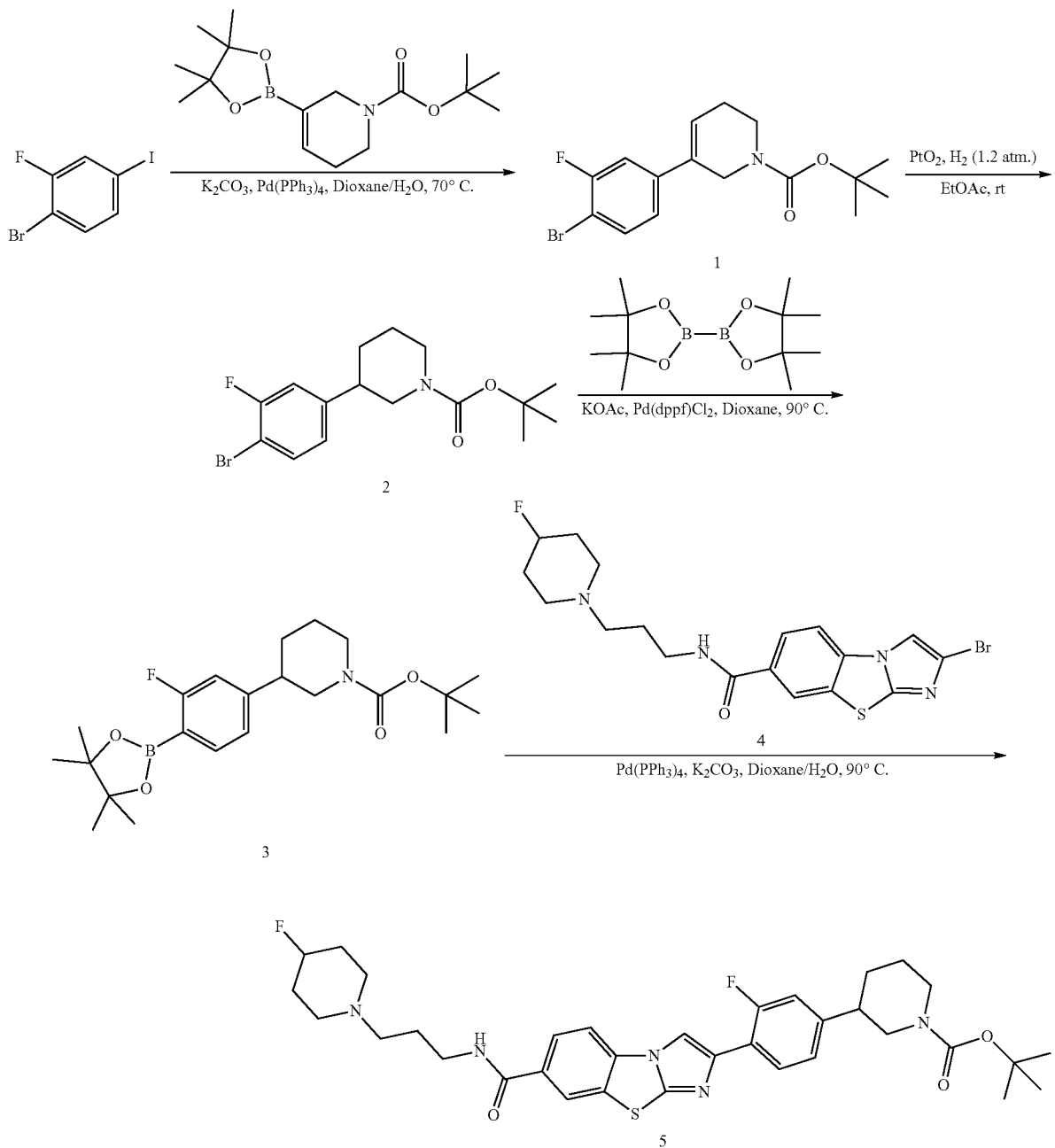

Scheme 70.

Synthesis of tert-butyl 5-(4-bromo-3-fluorophenyl)-3,6-dihydropyridine-1(2H)-carboxylate Compound tert-butyl 5-(4-bromo-3-fluorophenyl)-3,6-dihydropyridine-1(2H)-carboxylate was prepared from 1-bromo-2-fluoro-4-iodobenzene (3.30 g, 10.97 mmol) and tert-butyl 5-(4,4,5,5-tetramethyl-1,3,2-dioxaborolan-2-yl)-3,6-dihydropyridine-1(2H)-carboxylate (4.00 g, 12.94 mmol), following a similar procedure to that described for the synthesis of tert-butyl 4-(4-bromo-3-fluorophenyl)-3,6-dihydropyridine-1(2H)-carboxylate and was isolated as an off-white solid.

Yield 3.00 g (77%). $^1$H NMR (400 MHz, DMSO) δ 7.68 (dd, J=7.2, 8.4 Hz, 1H), 7.44 (dd, J=2.0, 10.4 Hz, 1H), 7.21 (dd, J=2.0, 8.4 Hz, 1H), 6.48-6.40 (m, 1H), 4.23-4.16 (m, 2H), 3.50-3.42 (m, 2H), 2.31-2.21 (m, 2H), 1.43 (s, 9H). m/z: [ESI$^+$]300, 302 (M+H-56)$^+$.

Synthesis of tert-butyl 3-(4-bromo-3-fluorophenyl)piperidine-1-carboxylate

Compound tert-butyl 3-(4-bromo-3-fluorophenyl)piperidine-1-carboxylate was prepared from tert-butyl 5-(4-bromo-3-fluorophenyl)-3,6-dihydropyridine-1(2H)-carboxylate (1.90 g, 5.33 mmol), following a similar procedure to that described for the synthesis of tert-butyl 4-(4-bromo-3-fluorophenyl)piperidine-1-carboxylate and was isolated as a colorless oil.

Yield 0.61 g (32%). $^1$H NMR (300 MHz, DMSO) δ 7.69-7.59 (m, 1H), 7.38-7.29 (m, 1H), 7.16-7.06 (m, 1H), 4.02-3.86 (m, 2H), 3.75-3.52 (m, 2H), 3.00-2.57 (m, 3H), 1.76-1.57 (m, 2H), 1.41 (s, 9H). m/z: [ESI$^+$]302, 304 (M+H-56)$^+$.

Synthesis of tert-butyl 3-(3-fluoro-4-(4,4,5,5-tetramethyl-1,3,2-dioxaborolan-2-yl)phenyl)piperidine-1-carboxylate Compound tert-butyl 3-(3-fluoro-4-(4,4,5,5-tetramethyl-1,3,2-dioxaborolan-2-yl)phenyl)piperidine-1-carboxylate was prepared from tert-butyl 3-(4-bromo-3-fluorophenyl)piperidine-1-carboxylate (200 mg, 0.558 mmol) and bis(pinacolato)diboron (213 mg, 0.839 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate as a brown solid. The compound was used directly in the next step without further purification.

Yield 200 mg (crude). $^1$H NMR not run. m/z: [ESI$^+$]350 (M+H-56)$^+$.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)piperidine-1-carboxylate Compound tert-butyl 3-(3-fluoro-4-(7-((3-(4-fluoropiperidin-1-yl)propyl)carbamoyl)benzo[d]imidazo[2,1-b]thiazol-2-yl)phenyl)piperidine-1-carboxylate was prepared from 2-bromo-N-(3-(4-fluoropiperidin-1-yl)propyl)benzo[d]imidazo[2,1-b]thiazole-7-carboxamide (200 mg, 0.455 mmol) and tert-butyl 3-(3-fluoro-4-(4,4,5,5-tetramethyl-1,3,2-dioxaborolan-2-yl)phenyl)piperidine-1-carboxylate (280 mg, crude) at 90° C., following a similar procedure to that described for the synthesis of tert-butyl 4-(4-bromo-3-fluorophenyl)-3,6-dihydropyridine-1(2H)-carboxylate and was isolated as a yellow solid.

Yield 70 mg (24%). $^1$H NMR (400 MHz, DMSO) δ 8.69 (d, J=3.6 Hz, 1H), 8.62 (t, J=5.6 Hz, 1H), 8.50 (d, J=1.6 Hz, 1H), 8.27 (d, J=8.4 Hz, 1H), 8.14-8.06 (m, 1H), 8.02 (dd, J=1.6, 8.4 Hz, 1H), 7.31-7.26 (m, 1H), 7.24 (dd, J=1.6, 8.0 Hz, 1H), 4.80-4.57 (m, 1H), 4.03-3.89 (m, 2H), 2.89-2.75 (m, 1H), 2.75-2.64 (m, 1H), 2.42-2.24 (m, 4H), 2.00-1.78 (m, 4H), 1.78-1.62 (m, 9H), 1.53-1.36 (m, 2H), 1.43 (s, 9H). m/z: [ESI$^+$]638 (M+H)$^+$.

Synthesis of tert-butyl 2-(3-fluoro-4-(7-((3-(4-fluoropiperidin-1-yl)propyl)carbamoyl)benzo[d]imidazo[2,1-b]thiazol-2-yl)phenyl)piperidine-1-carboxylate Scheme 71.

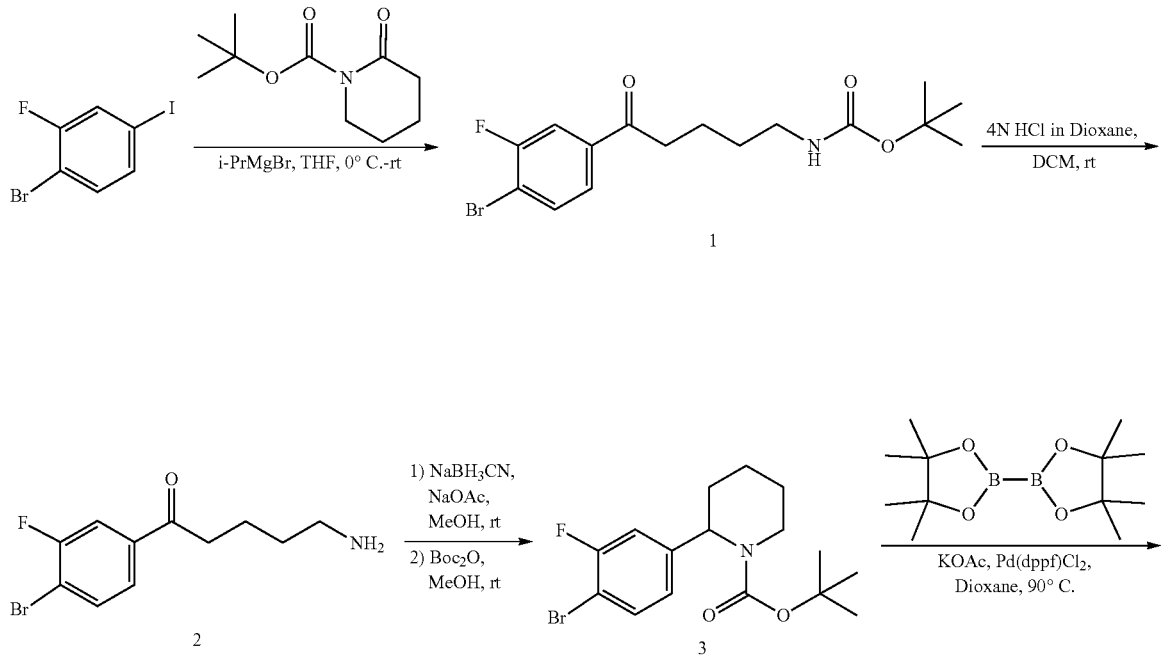

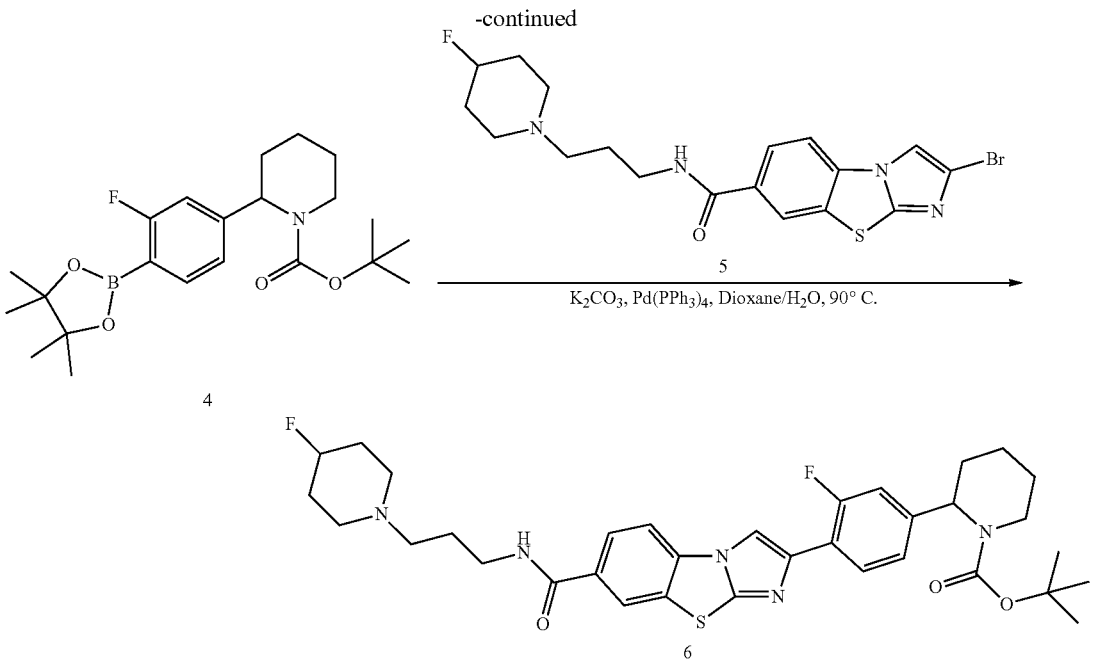

Synthesis of tert-butyl (5-(4-bromo-3-fluorophenyl)-5-oxopentyl)carbamate

Compound tert-butyl (5-(4-bromo-3-fluorophenyl)-5-oxopentyl)carbamate was prepared from 1-bromo-2-fluoro-4-iodobenzene (10.00 g, 33.23 mmol) and tert-butyl 2-oxopiperidine-1-carboxylate (8.00 g, 40.15 mmol), following a similar procedure to that described for the synthesis of tert-butyl (4-(4-bromo-3-fluorophenyl)-4-oxobutyl)carbamate and was isolated as a white solid.

Yield 5.90 g (47%). $^1$H NMR (400 MHz, CDCl$_3$) δ 7.73-7.70 (m, 1H), 7.70-7.66 (m, 1H), 7.65-7.61 (m, 1H), 3.67-3.60 (m, 2H), 3.01-2.94 (m, 2H), 1.79-1.66 (m, 4H), 1.53 (s, 9H). NH proton not observed. m/z: [ESI$^+$]318, 320 (M+H-56)$^+$.

Synthesis of 5-amino-1-(4-bromo-3-fluorophenyl)pentan-1-one hydrochloride

Compound 5-amino-1-(4-bromo-3-fluorophenyl)pentan-1-one hydrochloride was prepared from tert-butyl (5-(4-bromo-3-fluorophenyl)-5-oxopentyl)carbamate (2.70 g, 7.21 mmol), following a similar procedure to that described for the synthesis of 4-amino-1-(4-bromo-3-fluorophenyl)butan-1-one hydrochloride and was isolated as a white solid.

Yield 2.00 g (89%). $^1$H NMR (400 MHz, DMSO) δ 8.09-8.01 (m, 1H), 7.95-7.88 (m, 1H), 7.83 (br s, 3H), 7.79-7.73 (m, 1H), 3.80-3.69 (m, 1H), 3.26-3.18 (m, 1H), 3.14-3.05 (m, 1H), 2.89-2.77 (m, 1H), 1.91-1.83 (m, 2H), 1.72-1.56 (m, 2H). m/z: [ESI$^+$]274, 276 (M+H)$^+$.

Synthesis of tert-butyl 2-(4-bromo-3-fluorophenyl)piperidine-1-carboxylate

Compound tert-butyl 2-(4-bromo-3-fluorophenyl)piperidine-1-carboxylate was prepared from 5-amino-1-(4-bromo-3-fluorophenyl)pentan-1-one hydrochloride (2.20 g, 7.08 mmol), following a similar procedure to that described for the synthesis of tert-butyl 2-(4-bromo-3-fluorophenyl)pyrrolidine-1-carboxylate and was isolated as a light yellow oil.

Yield 2.46 g (97%). $^1$H NMR (300 MHz, CDCl$_3$) δ 7.57-7.48 (m, 1H), 7.05-6.97 (m, 1H), 6.94-6.88 (m, 1H), 5.39-5.33 (m, 1H), 4.12-4.00 (m, 1H), 2.83-2.67 (m, 1H), 2.29-2.16 (m, 1H), 2.00-1.83 (m, 1H), 1.72-1.25 (m, 4H), 1.49 (s, 9H). m/z: [ESI$^+$]302, 304 (M+H-56)$^+$.

Synthesis of tert-butyl 2-(3-fluoro-4-(4,4,5,5-tetramethyl-1,3,2-dioxaborolan-2-yl)phenyl)piperidine-1-carboxylate Compound tert-butyl 2-(3-fluoro-4-(4,4,5,5-tetramethyl-1,3,2-dioxaborolan-2-yl)phenyl)piperidine-1-carboxylate was prepared from tert-butyl 2-(4-bromo-3-fluorophenyl)piperidine-1-carboxylate (400 mg, 1.117 mmol) and bis(pinacolato)diboron (425 mg, 1.674 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate as a brown solid. The compound was used directly in the next step without further purification.

Yield 400 mg (crude). $^1$H NMR not run. m/z: [ESI$^+$]350 (M+H-56)$^+$.

Synthesis of tert-butyl 2-(3-fluoro-4-(7-((3-(4-fluoropiperidin-1-yl)propyl)carbamoyl)benzo[d]imidazo[2,1-b]thiazol-2-yl)phenyl)piperidine-1-carboxylate Compound tert-butyl 2-(3-fluoro-4-(7-((3-(4-fluoropiperidin-1-yl)propyl)carbamoyl)benzo[d]imidazo[2,1-b]thiazol-2-yl)phenyl)piperidine-1-carboxylate was prepared from 2-bromo-N-(3-(4-fluoropiperidin-1-yl)propyl)benzo[d]imidazo[2,1-b]thiazole-7-carboxamide (300 mg, 0.683 mmol) and tert-butyl 2-(3-fluoro-4-(4,4,5,5-tetramethyl-1,3,2-dioxaborolan-2-yl)phenyl)piperidine-1-carboxylate (400 mg, crude) at 90° C., following a similar procedure to that described for the synthesis of tert-butyl 4-(4-bromo-3-fluorophenyl)-3,6-dihydropyridine-1(2H)-carboxylate and was isolated as a white solid.

Yield 70 mg (16%). ¹H NMR (300 MHz, CDCl₃) δ 8.45-8.38 (m, 1H), 8.30-8.25 (m, 1H), 8.25-8.20 (m, 1H), 8.20-8.17 (m, 1H), 7.96-7.87 (m, 1H), 7.74-7.66 (m, 1H), 7.18-7.10 (m, 1H), 7.09-6.97 (m, 1H), 5.49-5.42 (m, 1H), 4.90-4.63 (m, 1H), 4.20-4.04 (m, 1H), 3.71-3.59 (m, 2H), 2.91-2.77 (m, 1H), 2.76-2.58 (m, 3H), 2.58-2.42 (m, 2H), 2.36-2.26 (m, 1H), 2.00-1.81 (m, 7H), 1.72-1.53 (m, 5H), 1.51 (s, 9H). m/z: [ESI⁺]638 (M+H)⁺.
Synthesis of tert-butyl 4-(3-fluoro-4-(7-((3-(4-fluoropiperidin-1-yl)propyl)carbamoyl)benzo[d]imidazo[2,1-b]thiazol-2-yl)phenyl)-4-hydroxypiperidine-1-carboxylate
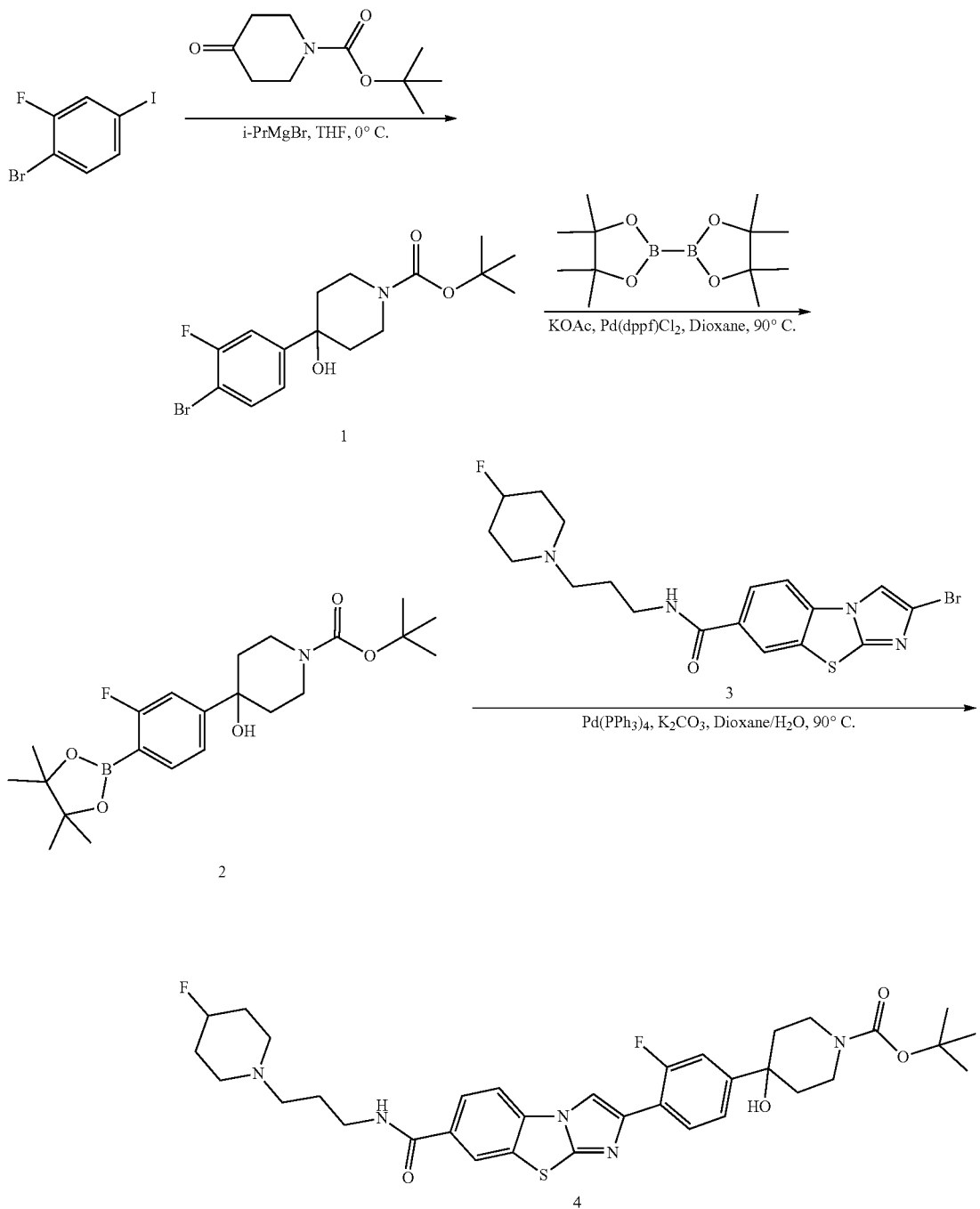

Synthesis of tert-butyl 4-(4-bromo-3-fluorophenyl)-4-hydroxypiperidine-1-carboxylate Compound tert-butyl 4-(4-bromo-3-fluorophenyl)-4-hydroxypiperidine-1-carboxylate was prepared from 1-bromo-2-fluoro-4-iodobenzene (4.53 g, 15.05 mmol) and tert-butyl 4-oxopiperidine-1-carboxylate (3.00 g, 15.06 mmol), following a similar procedure to that described for the synthesis of tert-butyl (4-(4-bromo-3-fluorophenyl)-4-oxobutyl)carbamate and was isolated as a colorless oil.

Yield 3.51 g (62%). $^1$H NMR (400 MHz, CDCl$_3$) δ 7.55 (dd, J=7.2, 8.4 Hz, 1H), 7.30 (dd, J=2.0 10.4 Hz, 1H), 7.14 (dd, J=2.0, 8.4 Hz, 1H), 4.12-4.03 (m, 2H), 3.26-3.16 (m, 2H), 2.02-1.90 (m, 2H), 1.75-1.66 (m, 2H), 1.51 (s, 9H). OH proton not observed. m/z: [ESI-]372, 374 (M−H)$^−$.

Synthesis of tert-butyl 4-(3-fluoro-4-(4,4,5,5-tetramethyl-1,3,2-dioxaborolan-2-yl)phenyl)-4-hydroxypiperidine-1-carboxylate Compound tert-butyl 4-(3-fluoro-4-(4,4,5,5-tetramethyl-1,3,2-dioxaborolan-2-yl)phenyl)-4-hydroxypiperidine-1-carboxylate was prepared from tert-butyl 4-(4-bromo-3-fluorophenyl)-4-hydroxypiperidine-1-carboxylate (300 mg, 0.802 mmol) and bis(pinacolato)diboron (300 mg, 1.181 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid. The compound was used directly in the next step without further purification.

Yield 340 mg (crude). $^1$H NMR not run. m/z: [ESI]420 (M−H)$^−$.

Synthesis of tert-butyl 4-(3-fluoro-4-(7-((3-(4-fluoropiperidin-1-yl)propyl)carbamoyl)benzo[d]imidazo[2,1-b]thiazol-2-yl)phenyl)-4-hydroxypiperidine-1-carboxylate Compound tert-butyl 4-(3-fluoro-4-(7-((3-(4-fluoropiperidin-1-yl)propyl)carbamoyl)benzo[d]imidazo[2,1-b]thiazol-2-yl)phenyl)-4-hydroxypiperidine-1-carboxylate was prepared from 2-bromo-N-(3-(4-fluoropiperidin-1-yl)propyl)benzo[d]imidazo[2,1-b]thiazole-7-carboxamide (300 mg, 0.683 mmol) and tert-butyl 4-(3-fluoro-4-(4,4,5,5-tetramethyl-1,3,2-dioxaborolan-2-yl)phenyl)-4-hydroxypiperidine-1-carboxylate (400 mg, crude) at 90° C., following a similar procedure to that described for the synthesis of tert-butyl 4-(4-bromo-3-fluorophenyl)-3,6-dihydropyridine-1(2H)-carboxylate and was isolated as a grey solid.

Yield 120 mg (27%). $^1$H NMR (300 MHz, CDCl$_3$) δ 8.37-8.31 (m, 1H), 8.31-8.28 (m, 1H), 8.18-8.11 (m, 1H), 8.11-8.07 (m, 1H), 8.01-7.96 (m, 1H), 7.68-7.61 (m, 1H), 7.33-7.30 (m, 1H), 7.26-7.24 (m, 1H), 5.02-4.76 (m, 1H), 4.16-4.00 (m, 2H), 3.71-3.60 (m, 2H), 3.37-3.21 (m, 2H), 3.06-2.81 (m, 7H), 2.40-1.94 (m, 8H), 1.85-1.74 (m, 2H), 1.52 (s, 9H). m/z: [ESI$^+$]654 (M+H)$^+$.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)-3-hydroxypyrrolidine-1-carboxylate Scheme 73.

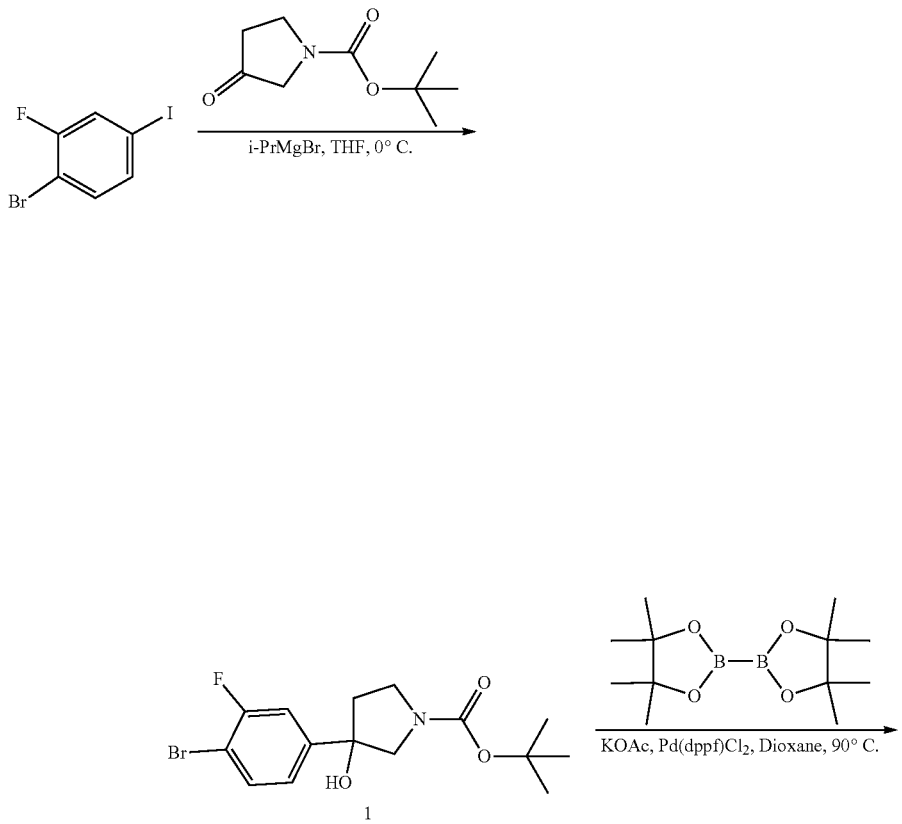

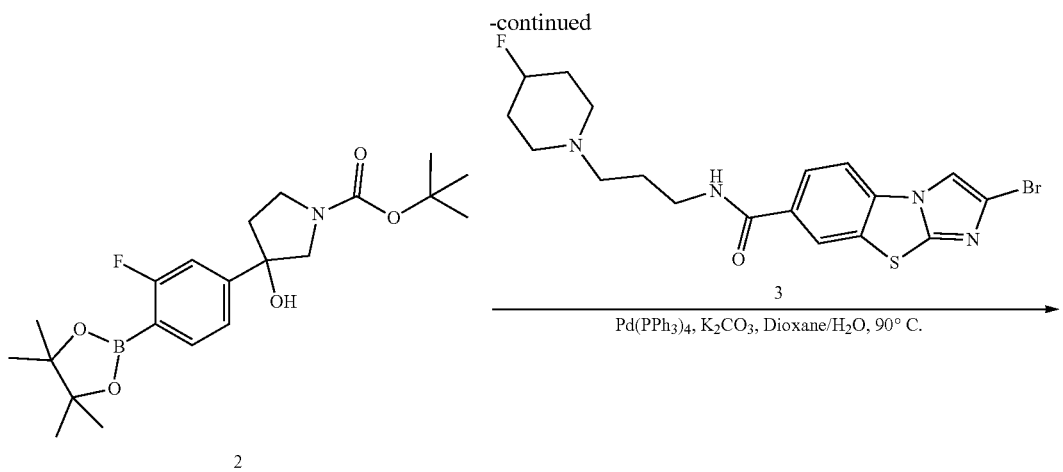

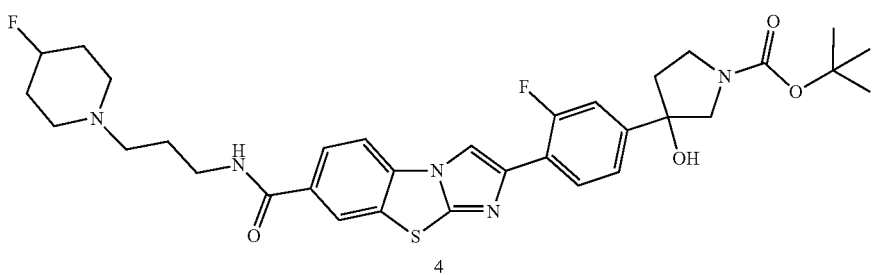

Synthesis of tert-butyl 3-(4-bromo-3-fluorophenyl)-3-hydroxypyrrolidine-1-carboxylate Compound tert-butyl 3-(4-bromo-3-fluorophenyl)-3-hydroxypyrrolidine-1-carboxylate was prepared from 1-bromo-2-fluoro-4-iodobenzene (15.50 g, 51.51 mmol) and tert-butyl 3-oxopyrrolidine-1-carboxylate (10.00 g, 53.99 mmol), following a similar procedure to that described for the synthesis of tert-butyl (4-(4-bromo-3-fluorophenyl)-4-oxobutyl)carbamate and was isolated as a yellow oil. Yield 7.76 g (42%). $^1$H NMR (300 MHz, CDCl$_3$) δ 7.57 (dd, J=7.2, 8.4 Hz, 1H), 7.32 (dd, J=2.1, 9.9 Hz, 1H), 7.16 (dd, J=2.1, 8.4 Hz, 1H), 3.73-3.56 (m, 4H), 2.36-2.22 (m, 1H), 2.22-2.10 (m, 1H), 1.50 (s, 9H). OH proton not observed. m/z: [ESI$^-$]358, 360 (M–H)$^-$.

Synthesis of tert-butyl 3-(3-fluoro-4-(4,4,5,5-tetramethyl-1,3,2-dioxaborolan-2-yl)phenyl)-3-hydroxypyrrolidine-1-carboxylate Compound tert-butyl 3-(3-fluoro-4-(4,4,5,5-tetramethyl-1,3,2-dioxaborolan-2-yl)phenyl)-3-hydroxypyrrolidine-1-carboxylate was prepared from tert-butyl 3-(4-bromo-3-fluorophenyl)-3-hydroxypyrrolidine-1-carboxylate (300 mg, 0.833 mmol) and bis(pinacolato)diboron (330 mg, 1.300 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid. The compound was used directly in the next step without further purification.

Yield 350 mg (crude). $^1$H NMR not run. m/z: [ESI$^+$]430 (M+Na)$^+$.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)-3-hydroxypyrrolidine-1-carboxylate Compound tert-butyl 3-(3-fluoro-4-(7-((3-(4-fluoropiperidin-1-yl)propyl)carbamoyl)benzo[d]imidazo[2,1-b]thiazol-2-yl)phenyl)-3-hydroxypyrrolidine-1-carboxylate was prepared from 2-bromo-N-(3-(4-fluoropiperidin-1-yl)propyl)benzo[d]imidazo[2,1-b]thiazole-7-carboxamide (250 mg, 0.569 mmol) and tert-butyl 3-(3-fluoro-4-(4,4,5,5-tetramethyl-1,3,2-dioxaborolan-2-yl)phenyl)-3-hydroxypyrrolidine-1-carboxylate (350 mg, crude) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 160 mg (44%). $^1$H NMR (300 MHz, CDCl$_3$) δ 8.51-8.45 (m, 1H), 8.45-8.35 (m, 1H), 8.35-8.26 (m, 1H), 8.16-7.96 (m, 3H), 7.64-7.53 (m, 1H), 7.30-7.20 (m, 1H), 5.05-4.80 (m, 1H), 3.79-3.58 (m, 6H), 3.26-3.14 (m, 2H), 3.08-2.89 (m, 4H), 2.42-2.03 (m, 8H), 1.51 (s, 9H). OH proton not observed. m/z: [ESI$^+$]640 (M+H)$^+$.

Synthesis of 2-(2-fluoro-4-(1-((2-(trimethylsilyl)
ethoxy)methyl)-1H-1,2,4-triazol-3-yl)phenyl)-N-(3-
(4-fluoropiperidin-1-yl)propyl)benzo[d]imidazo[2,1-
b]thiazole-7-carboxamide

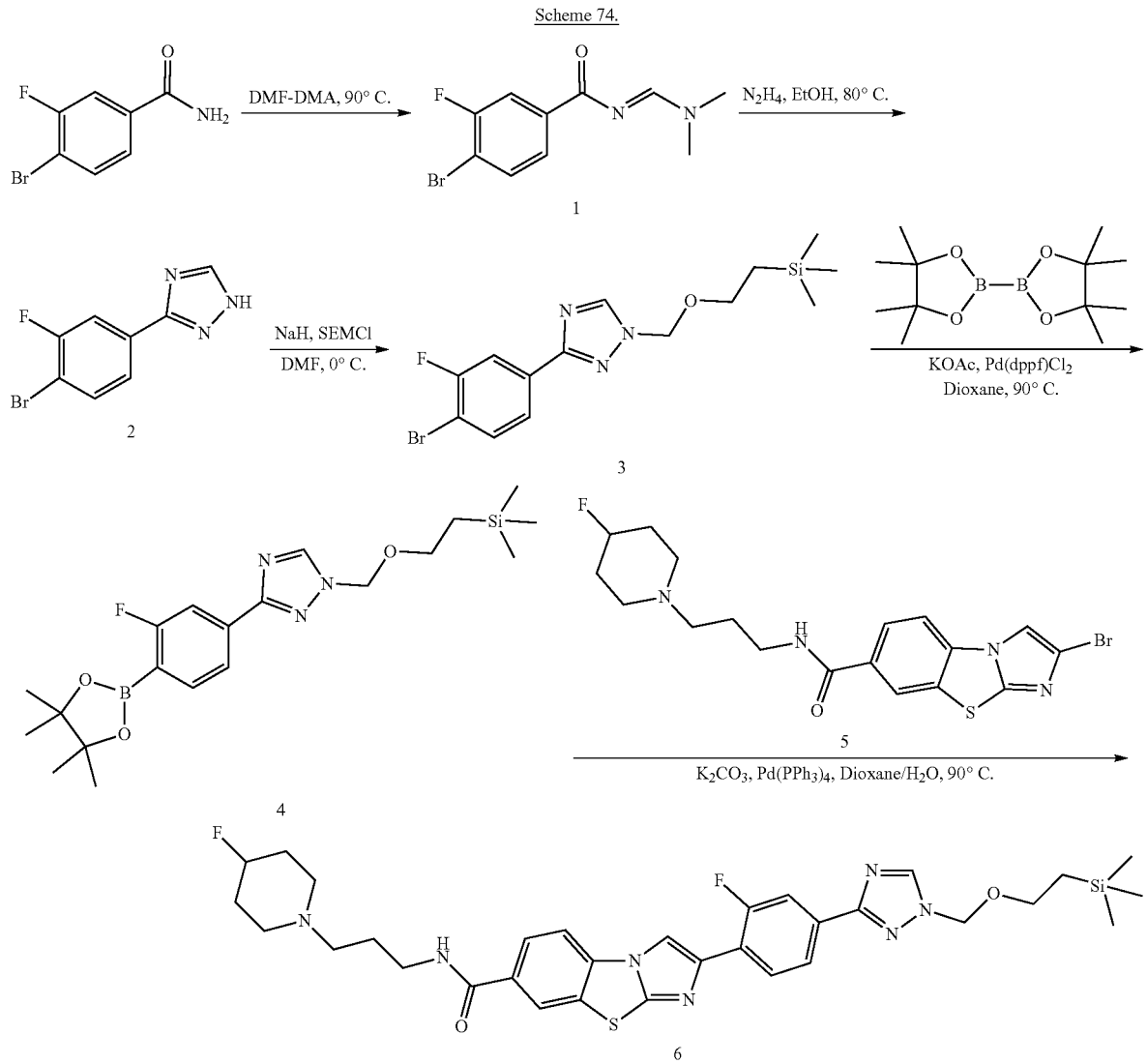

Scheme 74.

Synthesis of (E)-4-bromo-N-((dimethylamino)methylene)-3-fluorobenzamide

A solution of 4-bromo-3-fluorobenzamide (2.00 g, 9.17 mmol) in N,N-dimethylformamide dimethyl acetal (40 mL) was stirred for 2 h at 90° C. The mixture was cooled to room temperature and concentrated under reduced pressure. The residue was purified by silica gel column chromatography (eluted with 50% ethyl acetate in petroleum ether) to afford (E)-4-bromo-N-((dimethylamino)methylene)-3-fluorobenzamide as a white solid.

Yield 2.20 g (88%). $^1$H NMR (400 MHz, CDCl$_3$) δ 8.65 (s, 1H), 8.03 (dd, J=2.0, 9.6 Hz, 1H), 7.94 (dd, J=2.0, 8.4 Hz, 1H), 7.60 (dd, J=6.8, 8.4 Hz, 1H), 3.23 (s, 3H), 3.22 (s, 3H). m/z: [ESI$^+$]273, 275 (M+H)$^+$.

Synthesis of
3-(4-bromo-3-fluorophenyl)-1H-1,2,4-triazole

A mixture of (E)-4-bromo-N-((dimethylamino)methylene)-3-fluorobenzamide (2.00 g, 7.32 mmol) and hydrazine hydrate (80%, 0.80 g, 12.78 mmol) in ethanol (40 mL) was stirred for 2 h at 80° C. The reaction mixture was cooled to room temperature and concentrated under reduced pressure. The residue was purified by silica gel column chromatography (eluted with 20% ethyl acetate in petroleum ether) to afford 3-(4-bromo-3-fluorophenyl)-1H-1,2,4-triazole as a white solid.

Yield 0.60 g (34%). $^1$H NMR (400 MHz, CD$_3$OD) δ 8.47 (s, 1H), 7.84 (dd, J=2.0, 9.6 Hz, 1H), 7.77 (dd, J=2.0, 8.4 Hz, 1H), 7.71 (dd, J=6.8, 8.4 Hz, 1H). m/z: [ESI$^+$]242, 244 (M+H)$^+$.

Synthesis of 3-(4-bromo-3-fluorophenyl)-1-((2-(trimethylsilyl)ethoxy)methyl)-1H-1,2,4-triazole Sodium hydride (60% dispersion in mineral oil, 149 mg, 3.725 mmol) was added to a stirred solution of 3-(4-bromo-3-fluorophenyl)-1H-1,2,4-triazole (600 mg, 2.479 mmol) in N,N-dimethylformamide (6 mL), as a single portion at 0° C. The reaction mixture was stirred for 30 min. The reaction mixture was treated with (2-(chloromethoxy)ethyl)trimethylsilane (838 mg, 5.026 mmol). The reaction was warmed to room temperature and stirred for an additional 2 h. The reaction was quenched by the addition of saturated aqueous ammonium chloride (30 mL). The resulting mixture was extracted with ethyl acetate (3×30 mL). The combined organic layers were dried over anhydrous sodium sulfate and filtered. The filtrate was concentrated under reduced pressure. The residue was purified by reverse phase flash chromatography using the following conditions; Column: WelFlash™ C18-I, 20-40 μm, 330 g; Eluent A: water (plus 10 mmol/L ammonium bicarbonate); Eluent B: acetonitrile; Gradient: 30%-50% B in 25 min; Flow rate: 80 mL/min; UV Detector: 220/254 nm. The desired fractions were collected at 42% B and concentrated under reduced pressure to afford to 3-(4-bromo-3-fluorophenyl)-1-((2-(trimethylsilyl)ethoxy)methyl)-1H-1,2,4-triazole as a white solid.

Yield 300 mg (33%). $^1$H NMR (400 MHz, CDCl$_3$) δ 8.27 (s, 1H), 7.92-7.88 (m, 1H), 7.83-7.80 (m, 1H), 7.65-7.61 (m, 1H), 4.91 (s, 2H), 3.74-3.66 (m, 2H), 1.00-0.93 (m, 2H), 0.01 (s, 9H). m/z: [ESI$^+$]372, 374 (M+H)$^+$.

Synthesis of 3-(3-fluoro-4-(4,4,5,5-tetramethyl-1,3,2-dioxaborolan-2-yl)phenyl)-1-((2-(trimethylsilyl)ethoxy)methyl)-1H-1,2,4-triazole Compound 3-(3-fluoro-4-(4,4,5,5-tetramethyl-1,3,2-dioxaborolan-2-yl)phenyl)-1-((2-(trimethylsilyl)ethoxy)methyl)-1H-1,2,4-triazole was prepared from 3-(4-bromo-3-fluorophenyl)-1-((2-(trimethylsilyl)ethoxy)methyl)-1H-1,2,4-triazole (300 mg, 0.806 mmol) and bis(pinacolato)diboron (240 mg, 0.945 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid. The compound was used directly in the next step without further purification.

Yield 320 mg (crude). $^1$H NMR not run. m/z: [ESI$^+$]420 (M+H)$^+$.

Synthesis of 2-(2-fluoro-4-(1-((2-(trimethylsilyl)ethoxy)methyl)-1H-1,2,4-triazol-3-yl)phenyl)-N-(3-(4-fluoropiperidin-1-yl)propyl)benzo[d]imidazo[2,1-b]thiazole-7-carboxamide Compound 2-(2-fluoro-4-(1-((2-(trimethylsilyl)ethoxy)methyl)-1H-1,2,4-triazol-3-yl)phenyl)-N-(3-(4-fluoropiperidin-1-yl)propyl)benzo[d]imidazo[2,1-b]thiazole-7-carboxamide was prepared from 2-bromo-N-(3-(4-fluoropiperidin-1-yl)propyl)benzo[d]imidazo[2,1-b]thiazole-7-carboxamide (311 mg, 0.708 mmol) and 3-(3-fluoro-4-(4,4,5,5-tetramethyl-1,3,2-dioxaborolan-2-yl)phenyl)-1-((2-(trimethylsilyl)ethoxy)methyl)-1H-1,2,4-triazole (320 mg, crude) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 160 mg (35%). $^1$H NMR (400 MHz, DMSO) δ 8.49-8.36 (m, 1H), 8.36-8.20 (m, 4H), 8.06-8.01 (m, 1H), 7.99-7.88 (m, 2H), 7.73-7.67 (m, 1H), 5.56 (s, 2H), 4.84-4.63 (m, 1H), 3.77-3.69 (m, 2H), 3.67-3.58 (m, 2H), 2.81-2.44 (m, 6H), 2.06-1.78 (m, 6H), 1.04-0.91 (m, 2H), 0.01 (s, 9H). m/z: [ESI$^+$]652 (M+H)$^+$.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)morpholine-4-carboxylate Scheme 75.

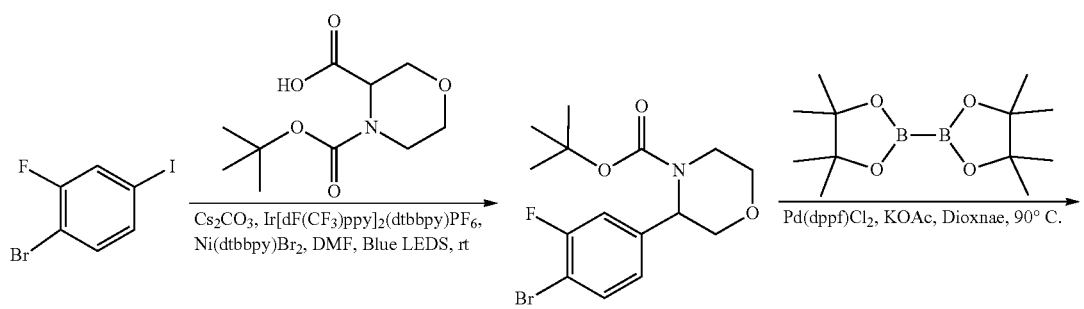

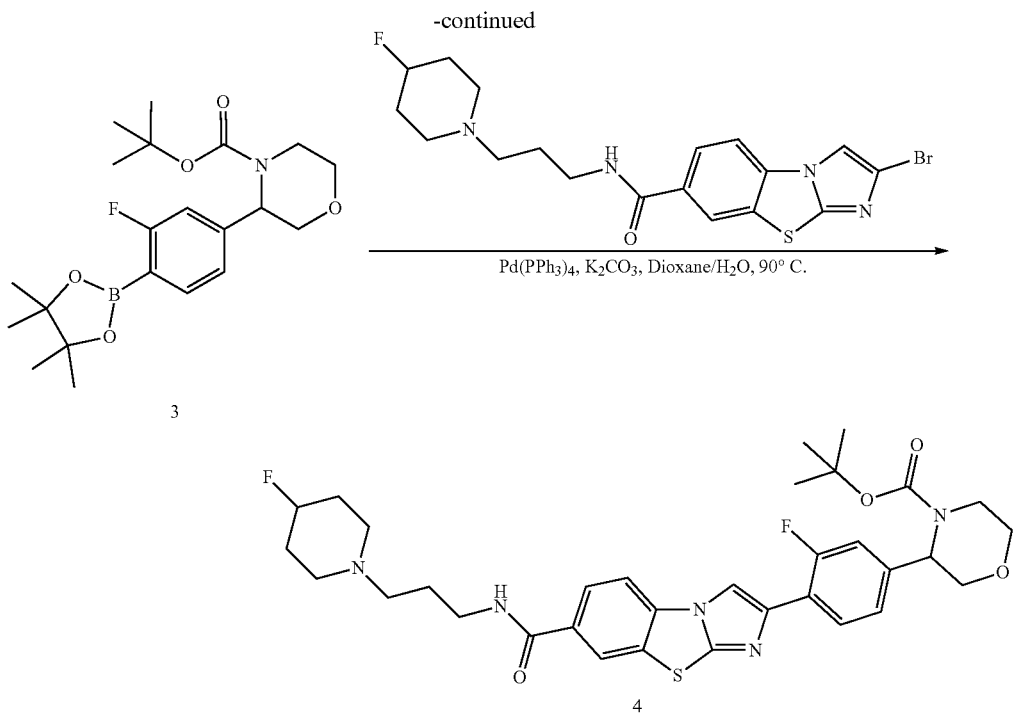

Synthesis of tert-butyl 3-(4-bromo-3-fluorophenyl)morpholine-4-carboxylate

A mixture of 1-bromo-2-fluoro-4-iodobenzene (1.00 g, 3.32 mmol), 4-(tert-butoxycarbonyl)morpholine-3-carboxylic acid (1.00 g, 4.32 mmol), cesium carbonate (2.10 g, 6.45 mmol), (4,4'-di-tert-butyl-2,2'-bipyridine)bis[3,5-difluoro-2-[5-trifluoromethyl-2-pyridinyl-κN]phenyl-κC]iridium(I) hexafluorophosphate (Ir[dF(CF$_3$)ppy]$_2$(dtbbpy)PF$_6$) (20 mg, 0.018 mmol) and (SP-4-2)-[4,4'-bis(1,1-dimethylethyl)-2,2'-bipyridine-κN1,κN1']dibromo-nickel (Ni(dtbbpy)Br$_2$) (250 mg, 0.513 mmol) in N,N-dimethylformamide (20 mL) was stirred for 4 h at room temperature under a nitrogen atmosphere with irradiation by Blue LED light. The reaction mixture was diluted with water (200 mL) and extracted with ethyl acetate (3×200 mL). The combined organic layers were washed with brine (100 mL) and dried over anhydrous sodium sulfate. After filtration, the filtrate was concentrated under reduced pressure. The residue was purified by silica gel column chromatography (eluted with 0-10% ethyl acetate in petroleum ether) to afford tert-butyl 3-(4-bromo-3-fluorophenyl)morpholine-4-carboxylate as a colorless oil.

Yield 320 mg (27%). $^1$H NMR (400 MHz, CDCl$_3$) δ 7.51 (t, J=7.6 Hz, 1H), 7.31-7.27 (m, 1H), 7.19-7.10 (m, 1H), 5.10-4.94 (m, 1H), 4.33-4.22 (m, 1H), 3.93-3.85 (m, 2H), 3.85-3.75 (m, 1H), 3.62-3.53 (m, 1H), 3.12-3.02 (m, 1H), 1.48 (s, 9H). m/z: [ESI$^+$]304, 306 (M+H-56)$^+$.

Synthesis of tert-butyl 3-(3-fluoro-4-(4,4,5,5-tetramethyl-1,3,2-dioxaborolan-2-yl)phenyl)morpholine-4-carboxylate Compound tert-butyl 3-(3-fluoro-4-(4,4,5,5-tetramethyl-1,3,2-dioxaborolan-2-yl)phenyl)morpholine-4-carboxylate was prepared from tert-butyl 3-(4-bromo-3-fluorophenyl)morpholine-4-carboxylate (470 mg, 1.305 mmol) and bis(pinacolato)diboron (500 mg, 1.969 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid. The compound was used directly in the next step without further purification.

Yield 450 mg (crude). $^1$H NMR not run. m/z: [ESI$^+$]352 (M+H-56)$^+$.

Synthesis of tert-butyl 3-(3-fluoro-4-(7-((3-(4-fluoropiperidin-1-yl)propyl)carbamoyl)benzo[d]imidazo[2,1-b]thiazol-2-yl)phenyl)morpholine-4-carboxylate Compound tert-butyl 3-(3-fluoro-4-(7-((3-(4-fluoropiperidin-1-yl)propyl)carbamoyl)benzo[d]imidazo[2,1-b]thiazol-2-yl)phenyl)morpholine-4-carboxylate was prepared from 2-bromo-N-(3-(4-fluoropiperidin-1-yl)propyl)benzo[d]imidazo[2,1-b]thiazole-7-carboxamide (260 mg, 0.592 mmol) and tert-butyl 3-(3-fluoro-4-(4,4,5,5-tetramethyl-1,3,2-dioxaborolan-2-yl)phenyl)morpholine-4-carboxylate (300 mg, crude) at 90° C., following a similar procedure to that described for the synthesis of tert-butyl 4-(4-bromo-3-fluorophenyl)-3,6-dihydropyridine-1(2H)-carboxylate and was isolated as an off-white solid.

Yield 30 mg (8%). $^1$H NMR (400 MHz, DMSO) δ 8.73 (d, J=3.6 Hz, 1H), 8.61 (t, J=5.2 Hz, 1H), 8.50 (s, 1H), 8.28 (d, J=8.4 Hz, 1H), 8.19-8.11 (m, 1H), 8.02 (d, J=8.4 Hz, 1H), 7.33-7.26 (m, 2H), 5.07-4.98 (m, 1H), 4.77-4.58 (m, 1H), 4.36-4.27 (m, 1H), 3.91-3.70 (m, 3H), 3.55-3.46 (m, 1H), 3.43-3.25 (m, 4H), 3.16-3.04 (m, 1H), 2.42-2.24 (m, 4H), 1.94-1.78 (m, 2H), 1.78-1.63 (m, 4H), 1.43 (s, 9H). m/z: [ESI$^+$]640 (M+H)$^+$.

Synthesis of tert-butyl 3-(3-fluoro-4-(7-((1-methylpiperidin-4-yl)carbamoyl)benzo[d]imidazo[2,1-b]thiazol-2-yl)phenyl)morpholine-4-carboxylate Compound tert-butyl 3-(3-fluoro-4-(7-((1-methylpiperidin-4-yl)carbamoyl)benzo[d]imidazo[2,1-b]thiazol-2-yl)

phenyl)morpholine-4-carboxylate was prepared from 2-bromo-N-(1-methylpiperidin-4-yl)benzo[d]imidazo[2,1-b]thiazole-7-carboxamide (180 mg, 0.458 mmol) and tert-butyl 3-(3-fluoro-4-(4,4,5,5-tetramethyl-1,3,2-dioxaborolan-2-yl)phenyl)morpholine-4-carboxylate (200 mg, crude) at 90° C., following a similar procedure to that described for the synthesis of tert-butyl 4-(4-bromo-3-fluorophenyl)-3,6-dihydropyridine-1(2H)-carboxylate and was isolated as a yellow solid.

Yield 95 mg (35%). $^1$H NMR (400 MHz, DMSO) δ 8.75 (d, J=3.6 Hz, 1H), 8.71-8.64 (m, 1H), 8.55 (d, J=5.6 Hz, 1H), 8.33-8.25 (m, 1H), 8.18-8.04 (m, 2H), 7.33-7.24 (m, 2H), 5.07-4.98 (m, 1H), 4.36-4.27 (m, 1H), 4.13-4.01 (m, 1H), 3.90-3.75 (m, 4H), 3.55-3.40 (m, 2H), 3.36-3.26 (m, 1H), 3.16-3.02 (m, 2H), 2.75 (s, 3H), 2.09-1.98 (m, 2H), 1.98-1.82 (m, 2H), 1.42 (s, 9H). m/z: [ESI$^+$]594 (M+H)$^+$.

Synthesis of tert-butyl 2-(3-fluoro-4-(7-((1-methylpiperidin-4-yl)carbamoyl)benzo[d]imidazo[2,1-b]thiazol-2-yl)phenyl)morpholine-4-carboxylate

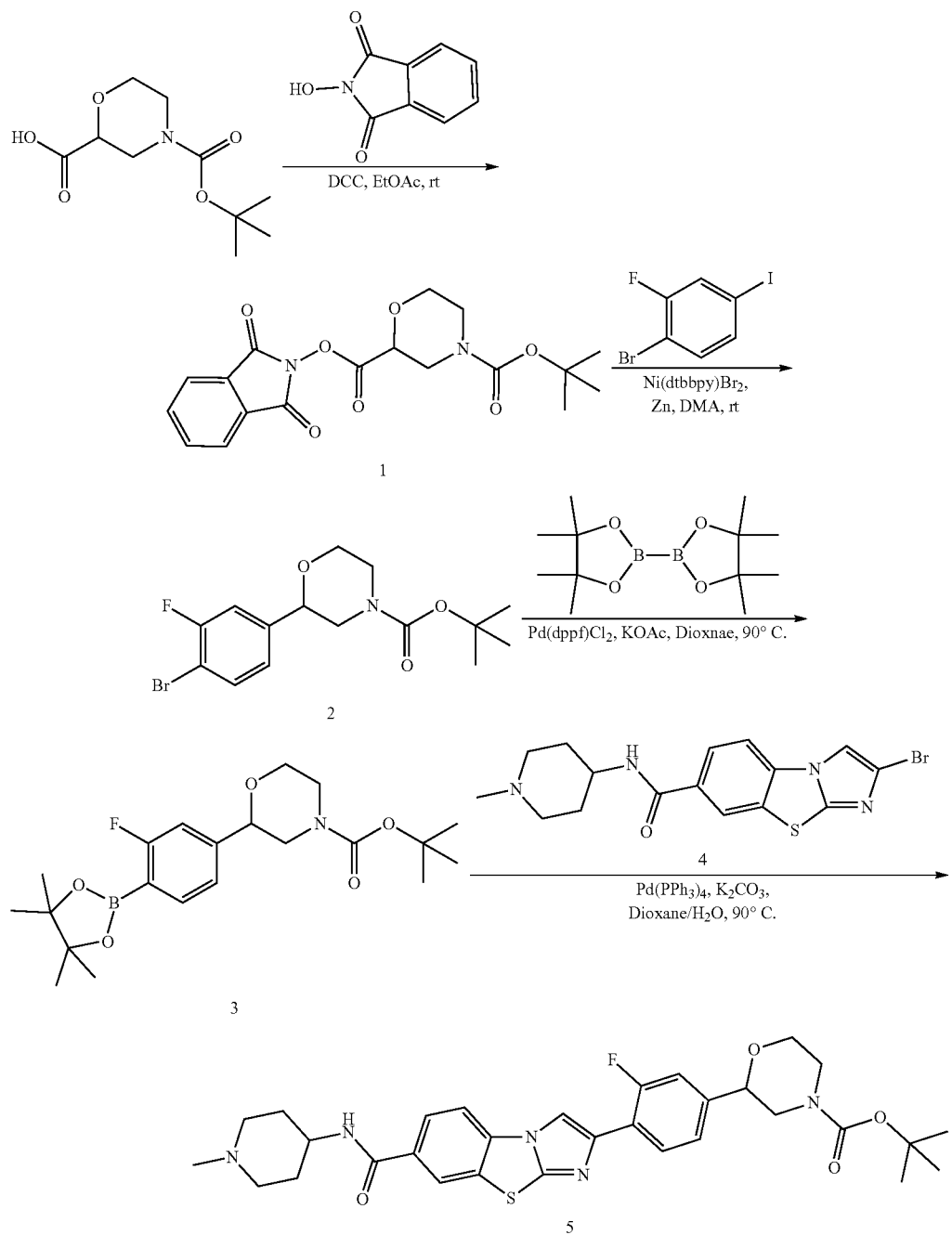

Synthesis of 4-(tert-butyl)₂-(1,3-dioxoisoindolin-2-yl) morpholine-2,4-dicarboxylate A mixture of 4-(tert-butoxycarbonyl)morpholine-2-carboxylic acid (5.00 g, 21.62 mmol), N-hydroxyphthalimide (3.53 g, 21.64 mmol) and dicyclohexylcarbodiimide (4.46 g, 21.62 mmol) in ethyl acetate (100 mL) was stirred for 2 h at room temperature under a nitrogen atmosphere. The reaction was quenched with saturated aqueous sodium bicarbonate (100 mL) and extracted with ethyl acetate (3×100 mL). The combined organic layers were washed with brine (2×100 mL) and dried over anhydrous sodium sulfate. After filtration, the filtrate was concentrated under reduced pressure to afford 4-tert-butyl 2-(1,3-dioxoisoindol-2-yl) morpholine-2,4-dicarboxylate as a brown solid.

Yield 3.86 g (47%). $^1$H NMR (400 MHz, CDCl$_3$) δ 7.94-7.91 (m, 2H), 7.85-7.82 (m, 2H), 4.60-4.52 (m, 1H), 4.17-4.01 (m, 2H), 3.80-3.66 (m, 1H), 3.49-3.41 (m, 1H), 3.34-3.25 (m, 1H), 3.16-3.06 (m, 1H), 1.51 (s, 9H). m/z: [ESI$^+$]321 (M+H-56)$^+$.

Synthesis of tert-butyl 2-(4-bromo-3-fluorophenyl)morpholine-4-carboxylate

To a stirred mixture of 4-tert-butyl 2-(1,3-dioxoisoindol-2-yl) morpholine-2,4-dicarboxylate (3.86 g, 10.256 mmol) and 1-bromo-2-fluoro-4-iodobenzene (3.70 g, 12.307 mmol) in N,N-dimethylacetamide (50 mL), were sequentially added (SP-4-2)-[4,4'-bis(1,1-dimethylethyl)-2,2'-bipyridine-κN1,κN1']dibromo-nickel (Ni(dtbbpy)Br$_2$) (1.00 g, 2.051 mmol) and zinc powder (1.68 g, 25.640 mmol) as single portions at room temperature under a nitrogen atmosphere. The resulting mixture was stirred for 16 h. The reaction mixture was filtered. The filtrate was concentrated to dryness and the residue purified by reverse phase flash chromatography using the following conditions; Column, Spherical C18, 20-40 μm, 330; Mobile Phase A: water (plus 10 mmol/L ammonium bicarbonate); Mobile Phase B; acetonitrile; Flow rate: 80 mL/min; Gradient: 45%-65% B in 20 min; UV Detector: 254 nm. The fractions containing desired product were collected at 54% B and concentrated under reduced pressure to afford tert-butyl 2-(4-bromo-3-fluorophenyl)morpholine-4-carboxylate as a white solid.

Yield 1.77 g (48%). $^1$H NMR (400 MHz, CDCl$_3$) δ 7.60-7.52 (m, 1H), 7.24-7.17 (m, 1H), 7.11-7.02 (m, 1H), 4.45-4.36 (m, 1H), 4.18-3.88 (m, 3H), 3.76-3.64 (m, 1H), 3.11-2.99 (m, 1H), 2.84-2.69 (m, 1H), 1.51 (s, 9H). m/z: [ESI$^+$]304, 306 (M+H-56)$^+$.

Synthesis of tert-butyl 2-(3-fluoro-4-(4,4,5,5-tetramethyl-1,3,2-dioxaborolan-2-yl)phenyl)morpholine-4-carboxylate Compound tert-butyl 2-(3-fluoro-4-(4,4,5,5-tetramethyl-1,3,2-dioxaborolan-2-yl)phenyl)morpholine-4-carboxylate was prepared from tert-butyl 2-(4-bromo-3-fluorophenyl)morpholine-4-carboxylate (200 mg, 0.555 mmol) and bis(pinacolato)diboron (282 mg, 1.110 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid. The compound was used directly in the next step without further purification.

Yield 220 mg (crude). $^1$H NMR not run. m/z: [ESI$^+$]352 (M+H-56)$^+$.

Synthesis of tert-butyl 2-(3-fluoro-4-(7-((1-methylpiperidin-4-yl)carbamoyl)benzo[d]imidazo[2,1-b]thiazol-2-yl)phenyl)morpholine-4-carboxylate Compound tert-butyl 2-(3-fluoro-4-(7-((1-methylpiperidin-4-yl)carbamoyl)benzo[d]imidazo[2,1-b]thiazol-2-yl)phenyl)morpholine-4-carboxylate was prepared from 2-bromo-N-(1-methylpiperidin-4-yl)benzo[d]imidazo[2,1-b]thiazole-7-carboxamide (200 mg, 0.509 mmol) and tert-butyl 2-(3-fluoro-4-(4,4,5,5-tetramethyl-1,3,2-dioxaborolan-2-yl)phenyl)morpholine-4-carboxylate (220 mg, crude) at 90° C., following a similar procedure to that described for the synthesis of tert-butyl 4-(4-bromo-3-fluorophenyl)-3,6-dihydropyridine-1(2H)-carboxylate and was isolated as an off-white solid.

Yield 130 mg (43%). $^1$H NMR (400 MHz, CDCl$_3$) δ 8.24-8.20 (m, 1H), 7.71-7.69 (m, 2H), 7.58-7.54 (m, 1H), 7.50-7.48 (m, 1H), 7.36-7.34 (m, 1H), 7.27-7.22 (m, 2H), 4.53-4.44 (m, 1H), 4.16-3.89 (m, 4H), 3.77-3.66 (m, 1H), 3.16-2.78 (m, 4H), 2.42 (s, 3H), 2.37-2.25 (m, 2H), 2.19-2.08 (m, 2H), 1.85-1.70 (m, 2H), 1.52 (s, 9H). m/z: [ESI$^+$] 594 (M+H)$^+$.

Synthesis of tert-butyl 4,4-difluoro-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate Scheme 77.

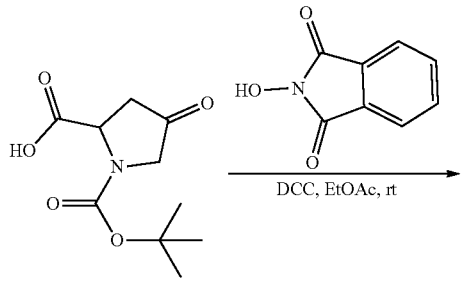

DCC, EtOAc, rt

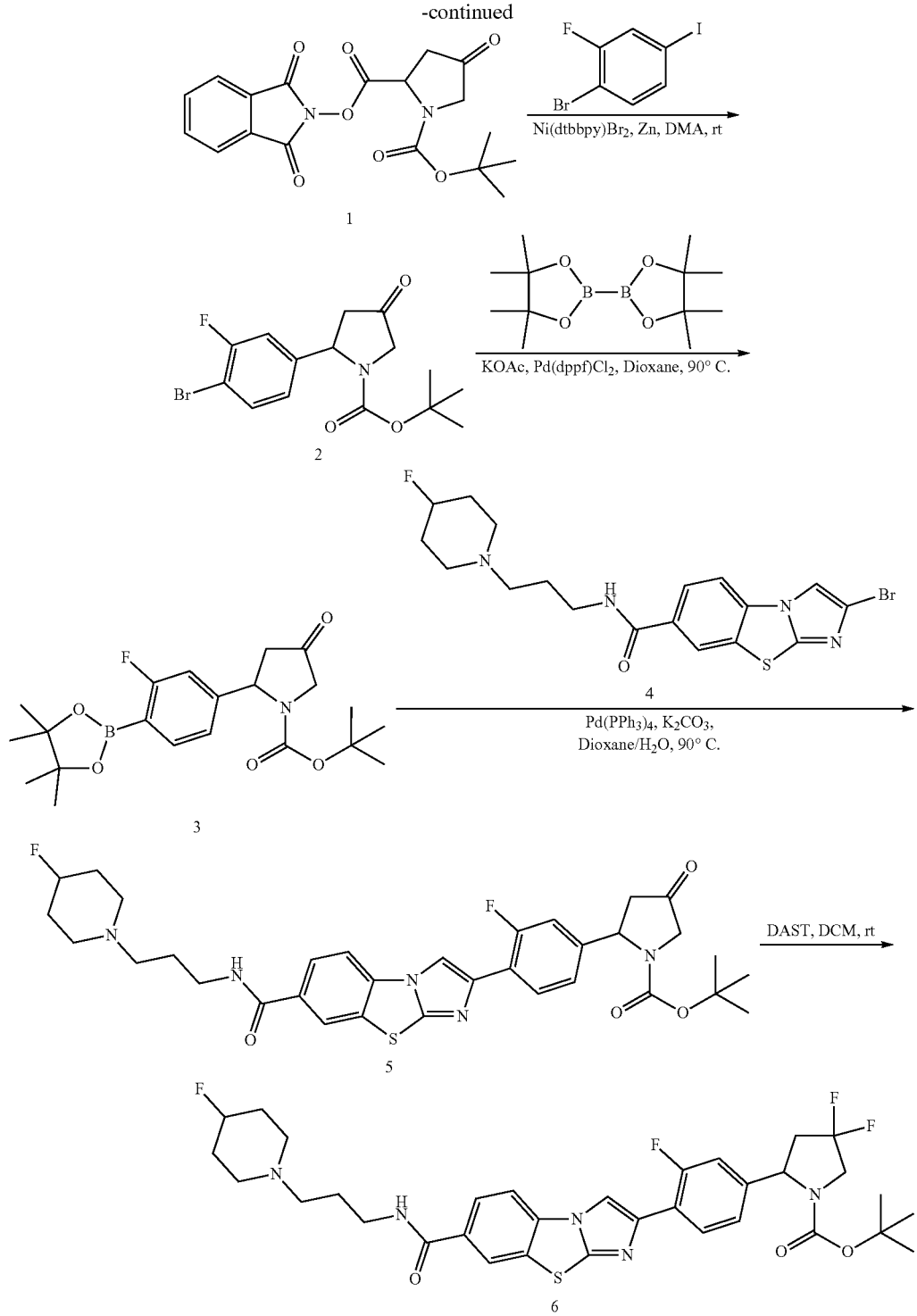

Synthesis of 1-(tert-butyl)$_2$-(1,3-dioxoisoindolin-2-yl) 4-oxopyrrolidine-1,2-dicarboxylate Compound 1-(tert-butyl)$_2$-(1,3-dioxoisoindolin-2-yl) 4-oxopyrrolidine-1,2-dicarboxylate was prepared from 1-(tert-butoxycarbonyl)-4-oxopyrrolidine-2-carboxylic acid (5.00 g, 21.81 mmol) and N-hydroxyphthalimide (3.56 g, 21.82 mmol), following a similar procedure to that described for the synthesis of 4-tert-butyl 2-(1,3-dioxoisoindol-2-yl) morpholine-2,4-dicarboxylate and was isolated as a white solid.

Yield 6.00 g (73%). $^1$H NMR (400 MHz, CDCl$_3$) δ 7.97-7.88 (m, 2H), 7.87-7.77 (m, 2H), 5.24-5.05 (m, 1H), 4.03-3.92 (m, 2H), 3.28-3.06 (m, 1H), 3.06-2.95 (m, 1H), 1.58 (s, 9H). m/z: [ESI$^+$]397 (M+Na)$^+$.

Synthesis of tert-butyl 2-(4-bromo-3-fluorophenyl)-4-oxopyrrolidine-1-carboxylate Compound tert-butyl 2-(4-bromo-3-fluorophenyl)-4-oxopyrrolidine-1-carboxylate was prepared from 1-bromo-2-fluoro-4-iodobenzene (7.40 g, 24.59 mmol) and 1-(tert-butyl)$_2$-(1,3-dioxoisoindolin-2-yl) 4-oxopyrrolidine-1,2-dicarboxylate (10.00 g, 26.71 mmol) following a similar procedure to that described for the synthesis of tert-butyl 2-(4-bromo-3-fluorophenyl)morpholine-4-carboxylate and was isolated as a yellow oil.

Yield 1.28 g (15%). $^1$H NMR (300 MHz, CDCl$_3$) δ 7.55 (dd, J=7.2, 8.1 Hz, 1H), 6.99 (dd, J=2.1, 9.3 Hz, 1H), 6.89 (dd, J=2.1, 8.1 Hz, 1H), 5.35 (dd, J=3.0, 10.2 Hz, 1H), 4.11 (d, J=19.5 Hz, 1H), 3.89 (d, J=19.5 Hz, 1H), 3.16 (dd, J=10.2, 18.6 Hz, 1H), 2.54 (dd, J=3.0, 18.6 Hz, 1H), 1.42 (s, 9H). m/z: [ESI$^+$]302, 304 (M+H-56)$^+$.

Synthesis of tert-butyl 2-(3-fluoro-4-(4,4,5,5-tetramethyl-1,3,2-dioxaborolan-2-yl)phenyl)-4-oxopyrrolidine-1-carboxylate Compound tert-butyl 2-(3-fluoro-4-(4,4,5,5-tetramethyl-1,3,2-dioxaborolan-2-yl)phenyl)-4-oxopyrrolidine-1-carboxylate was prepared from tert-butyl 2-(4-bromo-3-fluorophenyl)-4-oxopyrrolidine-1-carboxylate (590 mg, 1.647 mmol) and bis(pinacolato)diboron (630 mg, 2.481 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid. The compound was used directly in the next step without further purification.

Yield 600 mg (crude). $^1$H NMR not run. m/z: [ESI$^+$]350 (M+H-56)$^+$.

Synthesis of tert-butyl 2-(3-fluoro-4-(7-((3-(4-fluoropiperidin-1-yl)propyl)carbamoyl)benzo[d]imidazo[2,1-b]thiazol-2-yl)phenyl)-4-oxopyrrolidine-1-carboxylate Compound tert-butyl 2-(3-fluoro-4-(7-((3-(4-fluoropiperidin-1-yl)propyl)carbamoyl)benzo[d]imidazo[2,1-b]thiazol-2-yl)phenyl)-4-oxopyrrolidine-1-carboxylate was prepared from 2-bromo-N-(3-(4-fluoropiperidin-1-yl)propyl)benzo[d]imidazo[2,1-b]thiazole-7-carboxamide (550 mg, 1.252 mmol) and tert-butyl 2-(3-fluoro-4-(4,4,5,5-tetramethyl-1,3,2-dioxaborolan-2-yl)phenyl)-4-oxopyrrolidine-1-carboxylate (560 mg, crude) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 390 mg (49%). $^1$H NMR (300 MHz, CDCl$_3$) δ 8.39 (br s, 1H), 8.36-8.33 (m, 1H), 8.27-8.15 (m, 2H), 8.04-7.99 (m, 1H), 7.73-7.67 (m, 1H), 7.13-7.06 (m, 1H), 7.04-6.98 (m, 1H), 5.49-5.35 (m, 1H), 4.97-4.70 (m, 1H), 4.13 (d, J=19.5 Hz, 1H), 3.95 (d, J=19.5 Hz, 1H), 3.70-3.57 (m, 2H), 3.28-3.12 (m, 1H), 2.89-2.73 (m, 6H), 2.71-2.56 (m, 1H), 2.11-1.93 (m, 6H), 1.42 (s, 9H). m/z: [ESI$^+$]638 (M+H)$^+$.

Synthesis of tert-butyl 4,4-difluoro-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate Diethylaminosulfur trifluoride (50 mg, 0.310 mmol) was added dropwise to a stirred solution of tert-butyl 2-(3-fluoro-4-(7-((3-(4-fluoropiperidin-1-yl)propyl)carbamoyl)benzo[d]imidazo[2,1-b]thiazol-2-yl)phenyl)-4-oxopyrrolidine-1-carboxylate (100 mg, 0.157 mmol) in dichloromethane (2 mL) at room temperature. The reaction solution was stirred for 3 h. The reaction solution was purified directly by Prep-TLC (eluted with 9% methanol in dichloromethane) to afford tert-butyl 4,4-difluoro-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate as a white solid.

Yield 35 mg (34%). $^1$H NMR not run. m/z: [ESI$^+$]660 (M+H)$^+$.

Synthesis of tert-butyl (cis)-2-(4-(7-carbamoylbenzo[d]imidazo[2,1-b]thiazol-2-yl)-3-fluorophenyl)-4-hydroxypyrrolidine-1-carboxylate Scheme 78.

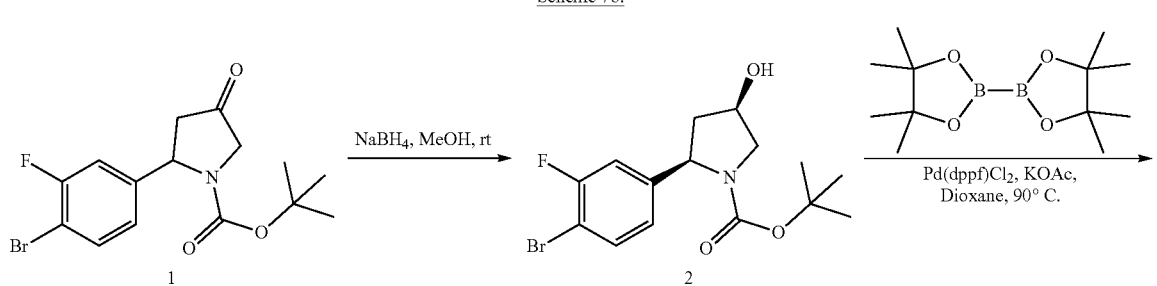

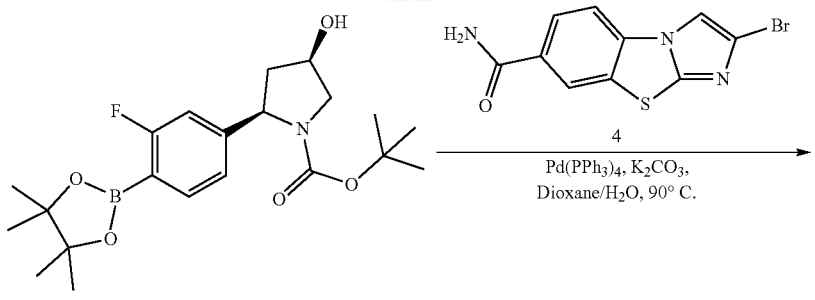

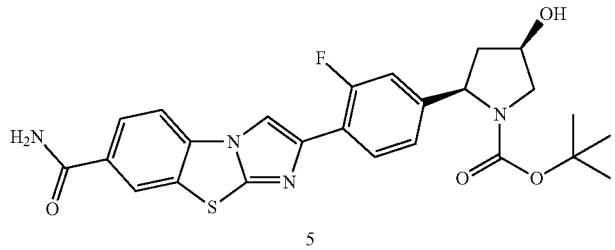

Synthesis of tert-butyl (cis)-2-(4-bromo-3-fluorophenyl)-4-hydroxypyrrolidine-1-carboxylate Sodium borohydride (1.06 g, 28.02 mmol) was added portionwise over 1 min to a stirred solution of tert-butyl 2-(4-bromo-3-fluorophenyl)-4-oxopyrrolidine-1-carboxylate (5.00 g, 13.96 mmol) in methanol (50 mL), at 0° C. under a nitrogen atmosphere. The reaction mixture was stirred for 2 h at room temperature. The reaction was quenched by the addition of acetone (20 mL). The resulting mixture was concentrated under reduced pressure. The residue was purified by silica gel column chromatography (eluted with 12% ethyl acetate in petroleum ether) to afford tert-butyl (cis)-2-(4-bromo-3-fluorophenyl)-4-hydroxypyrrolidine-1-carboxylate as a colorless oil.

Yield 2.50 g (50%). $^1$H NMR (400 MHz, CDCl$_3$) δ 7.49 (dd, J=7.2, 8.4 Hz, 1H), 7.11 (dd, J=2.0, 9.6 Hz, 1H), 6.99 (dd, J=2.0, 8.4 Hz, 1H), 5.01-4.75 (m, 1H), 4.56-4.45 (m, 1H), 3.94-3.76 (m, 1H), 3.65-3.53 (m, 1H), 2.65-2.54 (m, 1H), 2.01-1.92 (m, 1H), 1.48-1.21 (m, 9H). OH proton not observed. m/z: [ESI$^+$]304, 306 (M+H-56)$^+$.

Synthesis of tert-butyl (cis)-2-(3-fluoro-4-(4,4,5,5-tetramethyl-1,3,2-dioxaborolan-2-yl)phenyl)-4-hydroxypyrrolidine-1-carboxylate Compound tert-butyl (cis)-2-(3-fluoro-4-(4,4,5,5-tetramethyl-1,3,2-dioxaborolan-2-yl)phenyl)-4-hydroxypyrrolidine-1-carboxylate was prepared from tert-butyl (cis)-2-(4-bromo-3-fluorophenyl)-4-hydroxypyrrolidine-1-carboxylate (900 mg, 2.498 mmol) and bis(pinacolato)diboron (950 mg, 3.741 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a yellow solid. The compound was used directly in the next step without further purification.

Yield 750 mg (crude). $^1$H NMR not run. m/z: [ESI$^+$]352 (M+H-56)$^+$.

Synthesis of tert-butyl (cis)-2-(3-fluoro-4-(7-((1-methylpiperidin-4-yl)carbamoyl)benzo[d]imidazo[2,1-b]thiazol-2-yl)phenyl)-4-hydroxypyrrolidine-1-carboxylate Compound tert-butyl (cis)-2-(3-fluoro-4-(7-((1-methylpiperidin-4-yl)carbamoyl)benzo[d]imidazo[2,1-b]thiazol-2-yl)phenyl)-4-hydroxypyrrolidine-1-carboxylate was prepared from 2-bromo-N-(1-methylpiperidin-4-yl)benzo[d]imidazo[2,1-b]thiazole-7-carboxamide (150 mg, 0.381 mmol) and tert-butyl (cis)-2-(3-fluoro-4-(4,4,5,5-tetramethyl-1,3,2-dioxaborolan-2-yl)phenyl)-4-hydroxypyrrolidine-1-carboxylate (200 mg, crude) at 90° C., following a similar procedure to that described for the synthesis of tert-butyl 4-(4-bromo-3-fluorophenyl)-3,6-dihydropyridine-1(2H)-carboxylate and was isolated as a yellow solid.

Yield 130 mg (57%). $^1$H NMR (400 MHz, DMSO) δ 8.70 (s, 1H), 8.50 (s, 1H), 8.39 (d, J=7.6 Hz, 1H), 8.30-8.23 (m, 1H), 8.13-7.99 (m, 2H), 7.30-7.15 (m, 2H), 5.13-4.93 (m, 1H), 4.83-4.68 (m, 1H), 4.35-4.24 (m, 1H), 3.85-3.63 (m, 2H), 3.43-3.31 (m, 1H), 2.87-2.77 (m, 2H), 2.60-2.50 (m, 1H), 2.21 (s, 3H), 2.07-1.94 (m, 2H), 1.83-1.72 (m, 2H), 1.69-1.54 (m, 2H), 1.41-1.08 (m, 9H). OH proton not observed. m/z: [ESI$^+$]594 (M+H)$^+$.

Synthesis of tert-butyl (cis)-2-(3-fluoro-4-(7-((tetrahydro-2H-pyran-4-yl)carbamoyl)benzo[d]imidazo[2,1-b]thiazol-2-yl)phenyl)-4-hydroxypyrrolidine-1-carboxylate Compound tert-butyl (cis)-2-(3-fluoro-4-(7-((tetrahydro-2H-pyran-4-yl)carbamoyl)benzo[d]imidazo[2,1-b]thiazol-2-yl)phenyl)-4-hydroxypyrrolidine-1-carboxylate was prepared from 2-bromo-N-(tetrahydro-2H-pyran-4-yl)benzo[d]imidazo[2,1-b]thiazole-7-carboxamide (150 mg, 0.394 mmol) and tert-butyl (cis)-2-(3-fluoro-4-(4,4,5,5-tetramethyl-1,3,2-dioxaborolan-2-yl)phenyl)-4-hydroxypyrrolidine-1-carboxylate (200 mg, crude) at 90° C., following a similar procedure to that described for the synthesis of tert-butyl 4-(4-bromo-3-fluorophenyl)-3,6-dihydropyridine-1(2H)-carboxylate and was isolated as a yellow solid.

Yield 130 mg (57%). ¹HNMR (400 MHz, DMSO) δ 8.70 (d, J=3.6 Hz, 1H), 8.53-8.50 (m, 1H), 8.48-8.43 (m, 1H), 8.30-8.25 (m, 1H), 8.10-7.99 (m, 2H), 7.28-7.14 (m, 2H), 5.12-4.93 (m, 1H), 4.87-4.70 (m, 1H), 4.34-4.24 (m, 1H), 4.13-3.97 (m, 1H), 3.97-3.86 (m, 2H), 3.74-3.65 (m, 1H), 3.47-3.25 (m, 3H), 2.61-2.51 (m, 1H), 1.85-1.71 (m, 3H), 1.67-1.52 (m, 2H), 1.43-1.07 (m, 9H). m/z: [ESI⁺]581 (M+H)⁺.

Synthesis of tert-butyl (cis)-2-(3-fluoro-4-(7-((3-(4-fluoropiperidin-1-yl)propyl)carbamoyl)benzo[d]imidazo[2,1-b]thiazol-2-yl)phenyl)-4-methoxypyrrolidine-1-carboxylate above solution was added iodomethane (296 mg, 2.085 mmol) dropwise. The reaction solution was warmed to room temperature and stirred for an additional 1 h. The reaction was quenched with water (2 mL) at 0° C. The resulting mixture was concentrated under reduced pressure. The residue was purified by reverse phase flash chromatography using the following conditions; Column, Spherical C18, 20-40 μm, 330 g; Mobile Phase A: water (plus 10 mmol/L ammonium bicarbonate); Mobile Phase B; acetonitrile; Flow rate: 80 mL/min; Gradient: 45%-65% B in 20 min; UV Detector: 254 nm. The fractions containing desired product were collected at 54% B and concentrated under reduced pressure to afford tert-butyl (cis)-2-(4-bromo-3-fluorophenyl)-4-methoxypyrrolidine-1-carboxylate as a brown oil.

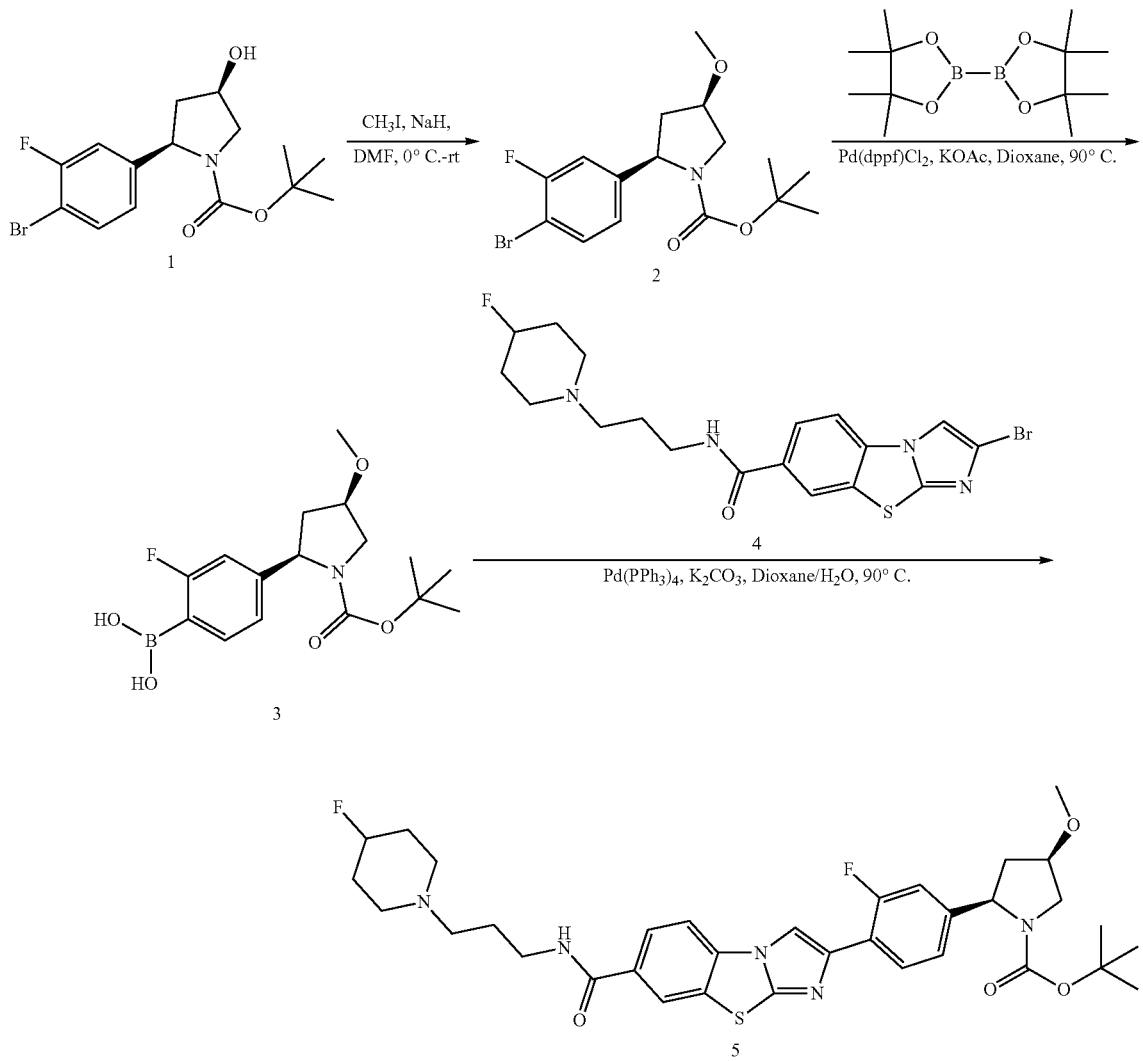

Scheme 79.

Synthesis of tert-butyl (cis)-2-(4-bromo-3-fluorophenyl)-4-methoxypyrrolidine-1-carboxylate A mixture of tert-butyl (cis)-2-(4-bromo-3-fluorophenyl)-4-hydroxypyrrolidine-1-carboxylate (500 mg, 1.388 mmol) and sodium hydride (60% dispersion in mineral oil, 125 mg, 3.125 mmol) in N,N-dimethylformamide (10 mL) was stirred for 1 h at 0° C. under a nitrogen atmosphere. To the Yield 360 mg (69%). ¹H NMR (400 MHz, CDCl₃) δ 7.46 (dd, J=7.2, 8.4 Hz, 1H), 7.08 (dd, J=2.0, 9.6 Hz, 1H), 6.95 (dd, J=2.0, 8.4 Hz, 1H), 4.92-4.69 (m, 1H), 4.03-3.95 (m, 1H), 3.87-3.71 (m, 1H), 3.70-3.56 (m, 1H), 3.25 (s, 3H), 2.60-2.41 (m, 1H), 2.07-1.95 (m, 1H), 1.49-1.20 (m, 9H). m/z: [ESI⁺]318, 320 (M+H-56)⁺.

Synthesis of (4-((cis)-1-(tert-butoxycarbonyl)-4-methoxypyrrolidin-2-yl)-2-fluorophenyl)boronic acid Compound (4-((cis)-1-(tert-butoxycarbonyl)-4-methoxypyrrolidin-2-yl)-2-fluorophenyl)boronic acid was prepared from tert-butyl (cis)-2-(4-bromo-3-fluorophenyl)-4-methoxypyrrolidine-1-carboxylate (340 mg, 0.908 mmol) and bis(pinacolato)diboron (950 mg, 3.741 mmol) following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated after reverse phase flash chromatography using the following conditions; Column, Spherical C18, 20-40 µm, 330 g; Mobile Phase A: water (plus 10 mmol/L ammonium bicarbonate); Mobile Phase B; acetonitrile; Flow rate: 80 mL/min; Gradient: 45%-65% B in 20 min; UV Detector: 254 nm. The fractions containing desired product were collected at 54% B and concentrated under reduced pressure to afford the desired product as a brown solid.

Yield 200 mg (65%). $^1$H NMR (300 MHz, CDCl$_3$) δ 7.79-7.71 (m, 1H), 7.15-7.07 (m, 1H), 7.02-6.95 (m, 1H), 4.98 (br s, 2H), 4.88-4.71 (m, 1H), 4.07-3.93 (m, 1H), 3.93-3.75 (m, 1H), 3.70-3.56 (m, 1H), 3.25 (s, 3H), 2.62-2.45 (m, 1H), 2.09-1.96 (m, 1H), 1.46-1.21 (m, 9H). m/z: [ESI$^+$]284 (M+H-56)$^+$.

Synthesis of tert-butyl (cis)-2-(3-fluoro-4-(7-((3-(4-fluoropiperidin-1-yl)propyl)carbamoyl)benzo[d]imidazo[2,1-b]thiazol-2-yl)phenyl)-4-methoxypyrrolidine-1-carboxylate tert-butyl (cis)-2-(3-fluoro-4-(7-((3-(4-fluoropiperidin-1-yl)propyl)carbamoyl)benzo[d]imidazo[2,1-b]thiazol-2-yl)phenyl)-4-methoxypyrrolidine-1-carboxylate was prepared from 2-bromo-N-(3-(4-fluoropiperidin-1-yl)propyl)benzo[d]imidazo[2,1-b]thiazole-7-carboxamide (130 mg, 0.296 mmol) and (4-((cis)-1-(tert-butoxycarbonyl)-4-methoxypyrrolidin-2-yl)-2-fluorophenyl)boronic acid (100 mg, 0.295 mmol) at 90° C., following a similar procedure to that described for the synthesis of tert-butyl 4-(4-bromo-3-fluorophenyl)-3,6-dihydropyridine-1(2H)-carboxylate and was isolated as a yellow solid.

Yield 90 mg (47%). $^1$H NMR (400 MHz, CDCl$_3$) δ 8.51-8.38 (m, 1H), 8.31-8.23 (m, 1H), 8.22-8.13 (m, 2H), 7.96-7.85 (m, 1H), 7.74-7.66 (m, 1H), 7.19-7.08 (m, 2H), 5.01-4.63 (m, 2H), 4.07-3.97 (m, 1H), 3.94-3.79 (m, 1H), 3.73-3.56 (m, 3H), 3.29 (s, 3H), 2.76-2.40 (m, 7H), 2.12-1.78 (m, 7H), 1.51-1.20 (m, 9H). m/z: [ESI$^+$]654 (M+H)$^+$.

Synthesis of tert-butyl (cis)-2-(3-fluoro-4-(7-((1-methylpiperidin-4-yl)carbamoyl)benzo[d]imidazo[2,1-b]thiazol-2-yl)phenyl)-4-methoxypyrrolidine-1-carboxylate Compound tert-butyl (cis)-2-(3-fluoro-4-(7-((1-methylpiperidin-4-yl)carbamoyl)benzo[d]imidazo[2,1-b]thiazol-2-yl)phenyl)-4-methoxypyrrolidine-1-carboxylate was prepared from 2-bromo-N-(1-methylpiperidin-4-yl)benzo[d]imidazo[2,1-b]thiazole-7-carboxamide (116 mg, 0.295 mmol) and (4-((cis)-1-(tert-butoxycarbonyl)-4-methoxypyrrolidin-2-yl)-2-fluorophenyl)boronic acid (100 mg, 0.295 mmol) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 130 mg (73%). $^1$H NMR (400 MHz, DMSO) δ 8.69 (d, J=3.6 Hz, 1H), 8.53-8.46 (m, 1H), 8.40-8.34 (m, 1H), 8.28-8.22 (m, 1H), 8.10-7.98 (m, 2H), 7.22-7.13 (m, 2H), 4.91-4.74 (m, 1H), 4.07-3.97 (m, 1H), 3.84-3.67 (m, 2H), 3.55-3.46 (m, 1H), 3.32 (s, 3H), 3.22-3.07 (m, 2H), 2.84-2.74 (m, 2H), 2.19 (s, 3H), 2.03-1.87 (m, 2H), 1.85-1.75 (m, 2H), 1.69-1.53 (m, 2H), 1.46-1.09 (m, 9H). m/z: [ESI$^+$]608 (M+H)$^+$.

Synthesis of tert-butyl 2-(3-fluoro-4-(7-((3-(4-fluoropiperidin-1-yl)propyl)carbamoyl)benzo[d]imidazo[2,1-b]thiazol-2-yl)phenyl)-4-hydroxypyrrolidine-1-carboxylate Compound tert-butyl 2-(3-fluoro-4-(7-((3-(4-fluoropiperidin-1-yl)propyl)carbamoyl)benzo[d]imidazo[2,1-b]thiazol-2-yl)phenyl)-4-hydroxypyrrolidine-1-carboxylate was prepared from tert-butyl 2-(3-fluoro-4-(7-((3-(4-fluoropiperidin-1-yl)propyl)carbamoyl)benzo[d]imidazo[2,1-b]thiazol-2-yl)phenyl)-4-oxopyrrolidine-1-carboxylate (100 mg, 0.157 mmol) and sodium borohydride (15 mg, 0.397 mmol), following a similar procedure to that described for the synthesis of tert-butyl (cis)-2-(4-bromo-3-fluorophenyl)-4-hydroxypyrrolidine-1-carboxylate and was isolated as a yellow solid.

Yield 76 mg (76%). $^1$H NMR (300 MHz, CDCl$_3$) δ 8.53-8.42 (m, 1H), 8.39-8.27 (m, 1H), 8.21-8.12 (m, 2H), 8.07-7.96 (m, 1H), 7.73-7.65 (m, 1H), 7.22-7.07 (m, 2H), 5.02-4.72 (m, 2H), 4.59-4.47 (m, 1H), 3.98-3.81 (m, 1H), 3.73-3.56 (m, 3H), 2.97-2.71 (m, 6H), 2.71-2.59 (m, 1H), 2.15-1.92 (m, 8H), 1.48-1.25 (m, 9H). m/z: [ESI$^+$]640 (M+H)$^+$.

Synthesis of tert-butyl (trans)-2-(3-fluoro-4-(7-((1-methylpiperidin-4-yl)carbamoyl)benzo[d]imidazo[2,1-b]thiazol-2-yl)phenyl)-4-hydroxypyrrolidine-1-carboxylate Scheme 80.

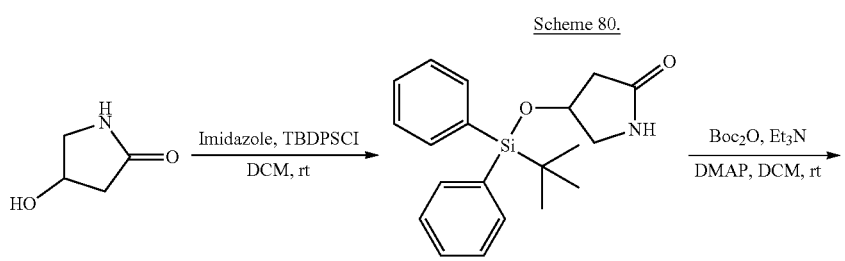

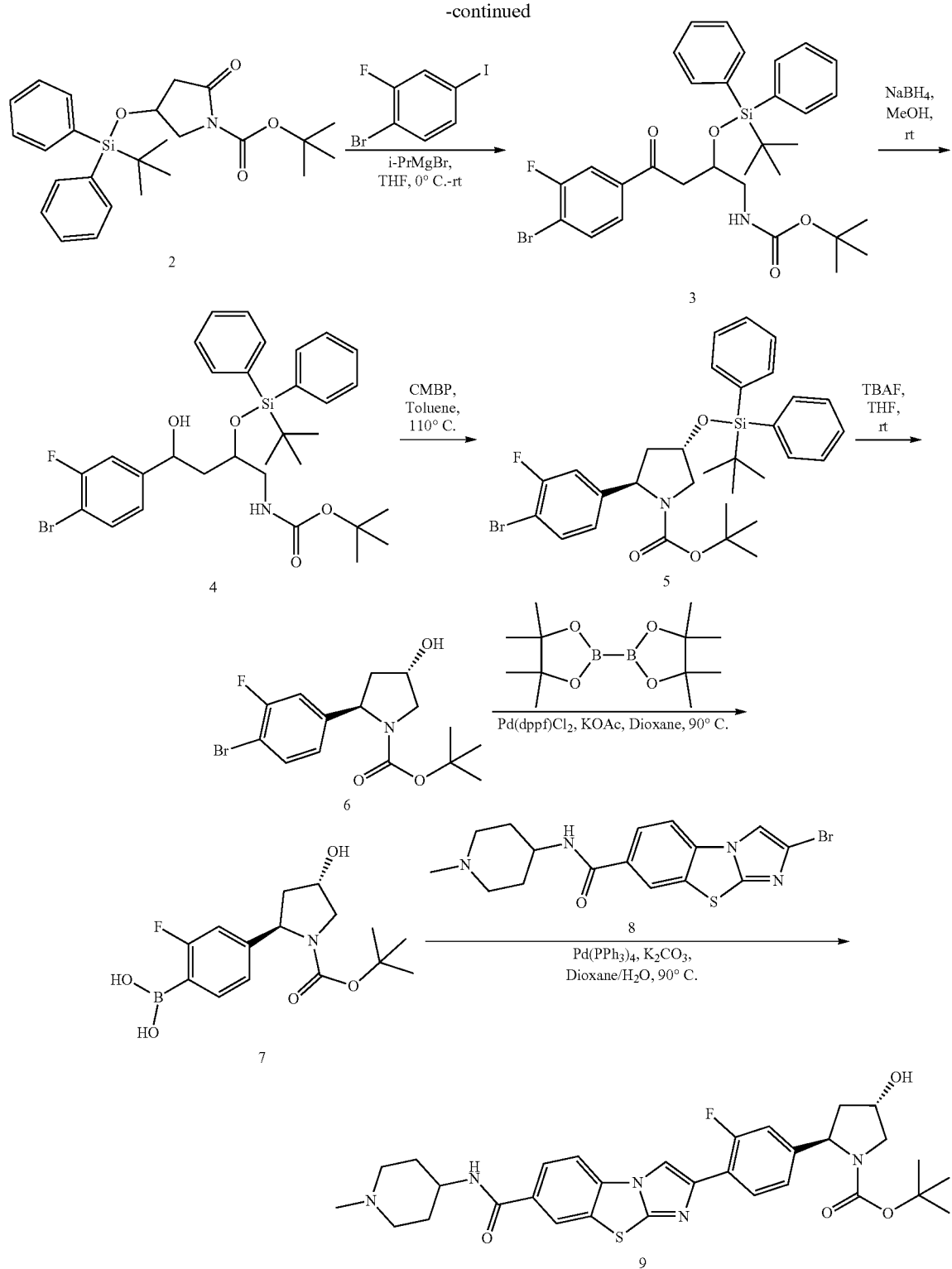

Synthesis of
4-((tert-butyldiphenylsilyl)oxy)pyrrolidin-2-one

To a stirred solution of 4-hydroxypyrrolidin-2-one (15.00 g, 148.35 mmol) in dichloromethane (200 mL) were sequentially added imidazole (15.00 g, 220.33 mmol) and tert-butylchlorodiphenylsilane (53.00 g, 192.83 mmol) as single portions at 0° C. under a nitrogen atmosphere. The reaction solution was stirred for 2 h at room temperature. The resulting mixture was diluted with water (400 mL) and extracted with dichloromethane (2×200 mL). The combined organic layers were washed with water (200 mL) and dried over anhydrous sodium sulfate. After filtration, the filtrate was concentrated under reduced pressure. The residue was purified by silica gel column chromatography (eluted with 30% ethyl acetate in petroleum ether) to afford 4-((tert-butyldiphenylsilyl)oxy)pyrrolidin-2-one as a white solid.

Yield 38.00 g (75%). $^1$H NMR (400 MHz, CDCl$_3$) δ 7.69-7.60 (m, 4H), 7.50-7.38 (m, 6H), 5.99 (br s, 1H), 4.62-4.50 (m, 1H), 3.44-3.36 (m, 1H), 3.36-3.27 (m, 1H), 2.47-2.34 (m, 2H), 1.09 (s, 9H). m/z: [ESI$^+$]340 (M+H)$^+$.

Synthesis of tert-butyl 4-((tert-butyldiphenylsilyl) oxy)-2-oxopyrrolidine-1-carboxylate To a stirred solution of 4-((tert-butyldiphenylsilyl)oxy) pyrrolidin-2-one (20.00 g, 58.91 mmol) and N,N-diisopropylethylamine (15.00 g, 116.05 mmol) in dichloromethane (400 mL) were sequentially added 4-dimethylaminopyridine (0.70 g, 5.73 mmol) and di-tert-butyl dicarbonate (20.00 g, 91.64 mmol) as single portions at room temperature under a nitrogen atmosphere. The reaction solution was stirred for 16 h. The reaction mixture was concentrated under reduced pressure. The residue was purified by silica gel column chromatography (eluted with 30% ethyl acetate in petroleum ether) to afford tert-butyl 4-((tert-butyldiphenylsilyl)oxy)-2-oxopyrrolidine-1-carboxylate as a colorless oil.

Yield 25.00 g (97%). $^1$H NMR (300 MHz, CDCl$_3$) δ 7.68-7.61 (m, 4H), 7.51-7.38 (m, 6H), 4.43-4.34 (m, 1H), 3.73-3.66 (m, 2H), 2.58-2.52 (m, 2H), 1.54 (s, 9H), 1.08 (s, 9H). m/z: [ESI$^+$]384 (M+H-56)$^+$.

Synthesis of tert-butyl (4-(4-bromo-3-fluorophenyl)-2-((tert-butyldiphenylsilyl)oxy)-4-oxobutyl)carbamate Compound tert-butyl (4-(4-bromo-3-fluorophenyl)-2-((tert-butyldiphenylsilyl)oxy)-4-oxobutyl)carbamate was prepared from 1-bromo-2-fluoro-4-iodobenzene (13.00 g, 43.20 mmol) and tert-butyl 4-((tert-butyldiphenylsilyl)oxy)-2-oxopyrrolidine-1-carboxylate (25.00 g, 56.87 mmol), following a similar procedure to that described for the synthesis of tert-butyl (4-(4-bromo-3-fluorophenyl)-4-oxobutyl)carbamate and was isolated as a colorless oil.

Yield 11.00 g (41%). $^1$H NMR (400 MHz, DMSO) δ 7.84-7.79 (m, 1H), 7.67-7.62 (m, 1H), 7.62-7.49 (m, 4H), 7.47-7.29 (m, 7H), 6.83-6.77 (m, 1H), 4.43-4.34 (m, 1H), 3.22-3.02 (m, 4H), 1.32 (s, 9H), 0.93 (s, 9H). m/z: [ESI$^+$] 636, 638 (M+Na)$^+$.

Synthesis of tert-butyl (4-(4-bromo-3-fluorophenyl)-2-((tert-butyldiphenylsilyl)oxy)-4-hydroxybutyl) carbamate Sodium borohydride (1.85 g, 48.90 mmol) was added portionwise over 5 min to a stirred solution of tert-butyl (4-(4-bromo-3-fluorophenyl)-2-((tert-butyldiphenylsilyl) oxy)-4-oxobutyl)carbamate (20.00 g, 32.54 mmol) in methanol (200 mL) at 0° C. The reaction mixture was warmed to room temperature and stirred for 2 h. The reaction was quenched by the addition of acetone (20 mL). The resulting solution was concentrated under reduced pressure. The residue was purified by silica gel column chromatography (eluted with 9% ethyl acetate in petroleum ether) to afford tert-butyl (4-(4-bromo-3-fluorophenyl)-2-((tert-butyldiphenylsilyl)oxy)-4-hydroxybutyl)carbamate as a colorless oil.

Yield 17.00 g (85%). $^1$H NMR (400 MHz, CDCl$_3$) δ 7.75-7.70 (m, 1H), 7.70-7.62 (m, 4H), 7.52-7.37 (m, 6H), 7.02-6.95 (m, 1H), 6.86-6.80 (m, 1H), 4.90-4.82 (m, 1H), 4.78-4.69 (m, 1H), 4.06-4.00 (m, 1H), 3.42-3.32 (m, 2H), 3.29-3.19 (m, 1H), 1.92-1.75 (m, 2H), 1.44 (s, 9H), 1.10 (s, 9H). m/z: [ESI$^+$]616, 618 (M+1)$^+$.

Synthesis of tert-butyl (trans)-2-(4-bromo-3-fluorophenyl)-4-((tert-butyldiphenylsilyl)oxy)pyrrolidine-1-carboxylate To a stirred solution of tert-butyl (4-(4-bromo-3-fluorophenyl)-2-((tert-butyldiphenylsilyl)oxy)-4-hydroxybutyl) carbamate (30.00 g, 48.65 mmol) in toluene (300 mL), was added cyanomethylenetributylphosphorane (25.00 g, 103.58 mmol) dropwise over 5 min, at room temperature, under a nitrogen atmosphere. The resulting solution was stirred for 16 h at 110° C. The reaction solution was cooled to room temperature and concentrated under reduced pressure. The residue was purified by silica gel column chromatography (eluted with 5% ethyl acetate in petroleum ether) to afford tert-butyl (trans)-2-(4-bromo-3-fluorophenyl)-4-((tert-butyldiphenylsilyl)oxy)pyrrolidine-1-carboxylate as a colorless oil.

Yield 17.00 g (58%). $^1$H NMR (400 MHz, DMSO) δ 7.69-7.63 (m, 1H), 7.56-7.33 (m, 10H), 7.30-7.18 (m, 1H), 7.13-7.05 (m, 1H), 4.91-4.75 (m, 1H), 4.42-4.33 (m, 1H), 3.63-3.50 (m, 1H), 3.50-3.39 (m, 1H), 2.50-2.35 (m, 1H), 1.93-1.83 (m, 1H), 1.40-1.13 (m, 9H), 0.87 (s, 9H). m/z: [ESI$^+$]598, 600 (M+1)$^+$.

Synthesis of tert-butyl (trans)-2-(4-bromo-3-fluorophenyl)-4-hydroxypyrrolidine-1-carboxylate Tetrabutylammonium fluoride (8.74 g, 33.43 mmol) was added portionwise over 2 min to a stirred solution of tert-butyl (trans)-2-(4-bromo-3-fluorophenyl)-4-((tert-butyldiphenylsilyl)oxy)pyrrolidine-1-carboxylate (10.00 g, 16.70 mmol) in tetrahydrofuran (100 mL) at room temperature. The resulting mixture was stirred for 2 h. The reaction mixture was concentrated under reduced pressure. The residue was purified by silica gel column chromatography (eluted with 15% ethyl acetate in petroleum ether) to afford tert-butyl (trans)-2-(4-bromo-3-fluorophenyl)-4-hydroxypyrrolidine-1-carboxylate as a white solid.

Yield 3.00 g (50%). $^1$H NMR (400 MHz, CDCl$_3$) δ 7.74-7.63 (m, 1H), 7.10-7.02 (m, 1H), 7.00-6.95 (m, 1H), 5.05-4.78 (m, 1H), 4.54-4.41 (m, 1H), 3.95-3.81 (m, 1H), 3.64-3.55 (m, 1H), 2.66-2.54 (m, 1H), 2.03-1.93 (m, 1H), 1.41-1.22 (m, 9H). OH proton not observed. m/z: [ESI$^+$]304, 306 (M+1-56)$^+$.

Synthesis of (4-((trans)-1-(tert-butoxycarbonyl)-4-hydroxypyrrolidin-2-yl)-2-fluorophenyl)boronic acid Compound (4-((trans)-1-(tert-butoxycarbonyl)-4-hydroxypyrrolidin-2-yl)-2-fluorophenyl)boronic acid was prepared from tert-butyl (trans)-2-(4-bromo-3-fluorophenyl)-4-hydroxypyrrolidine-1-carboxylate (200 mg, 0.555 mmol) and bis(pinacolato)diboron (210 mg, 0.827 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as an off-white solid.

Yield 130 mg (72%). $^1$H NMR (400 MHz, DMSO) δ 7.62-7.54 (m, 1H), 7.09-7.02 (m, 1H), 7.02-6.95 (m, 1H), 5.09-4.97 (m, 1H), 4.86-4.73 (m, 1H), 4.33-4.19 (m, 1H), 3.67-3.53 (m, 1H), 3.51-3.41 (m, 1H), 2.29-2.18 (m, 1H), 1.82-1.68 (m, 1H), 1.31-1.09 (m, 9H). Two OH protons of boronic acid not observed. m/z: [ESI+]270 (M+1-56)+.

Synthesis of tert-butyl (trans)-2-(3-fluoro-4-(7-((1-methylpiperidin-4-yl)carbamoyl)benzo[d]imidazo[2,1-b]thiazol-2-yl)phenyl)-4-hydroxypyrrolidine-1-carboxylate Compound tert-butyl (trans)-2-(3-fluoro-4-(7-((1-methylpiperidin-4-yl)carbamoyl)benzo[d]imidazo[2,1-b]thiazol-2-yl)phenyl)-4-hydroxypyrrolidine-1-carboxylate was prepared from 2-bromo-N-(1-methylpiperidin-4-yl)benzo[d]imidazo[2,1-b]thiazole-7-carboxamide (100 mg, 0.254 mmol) and (4-((trans)-1-(tert-butoxycarbonyl)-4-hydroxypyrrolidin-2-yl)-2-fluorophenyl)boronic acid (120 mg, 0.369 mmol) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 100 mg (66%). $^1$H NMR (400 MHz, DMSO) δ 8.75-8.70 (m, 1H), 8.50 (d, J=1.6 Hz, 1H), 8.38 (d, J=7.6 Hz, 1H), 8.26 (d, J=8.4 Hz, 1H), 8.13-8.06 (m, 1H), 8.03 (dd, J=1.6, 8.4 Hz, 1H), 7.27-7.16 (m, 2H), 5.04-4.69 (m, 1H), 4.03-3.84 (m, 1H), 3.84-3.65 (m, 3H), 3.55-3.42 (m, 1H), 2.87-2.61 (m, 4H), 2.17 (s, 3H), 2.04-1.87 (m, 2H), 1.86-1.69 (m, 2H), 1.69-1.52 (m, 2H), 1.43-1.12 (m, 9H). m/z: [ESI+]594 (M+1)+.

Synthesis of tert-butyl 2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate Synthesis of tert-butyl (R)-2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate Synthesis of tert-butyl (S)-2-(3-fluoro-4-(7-((3-(4-fluoropiperidin-1-yl)propyl)carbamoyl)imidazo[2,1':2,3]thiazolo[4,5-c]pyridin-2-yl)phenyl)pyrrolidine-1-carboxylate Scheme 81.

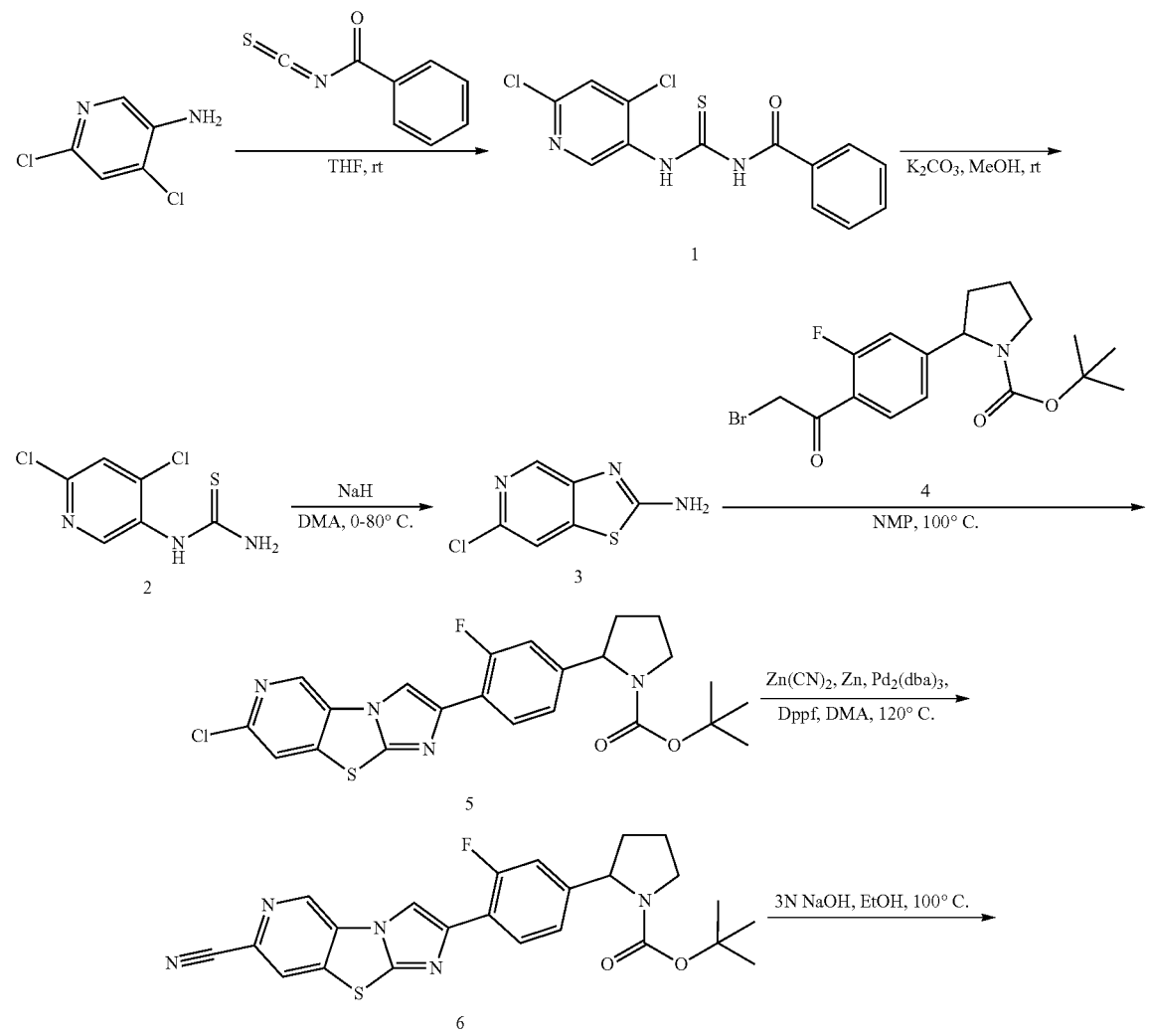

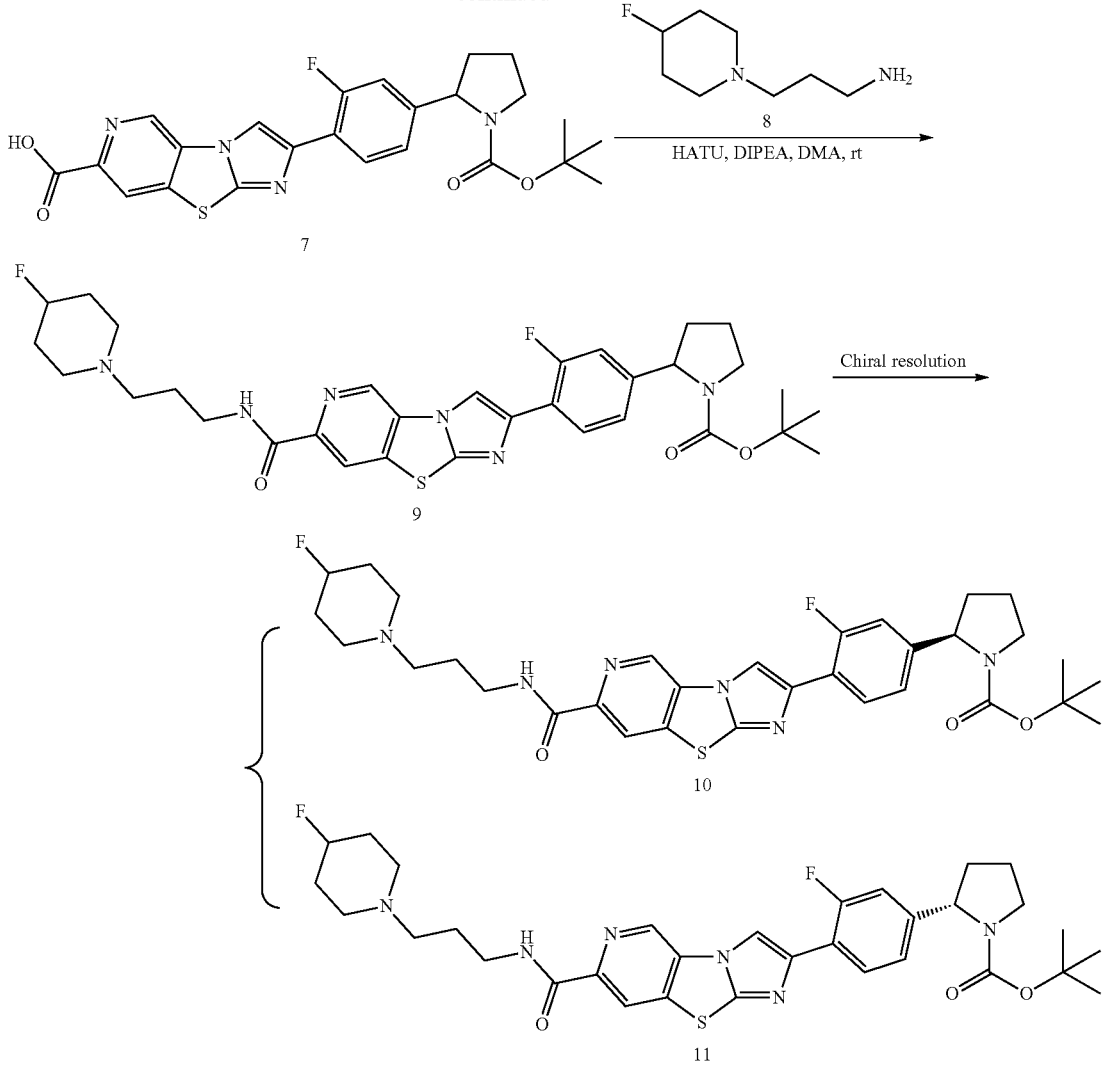

Synthesis of N-((4,6-dichloropyridin-3-yl)carbamothioyl)benzamide

To a stirred solution of 4,6-dichloropyridin-3-amine (3.00 g, 18.40 mmol) in tetrahydrofuran (30 mL), was added benzoyl isothiocyanate (4.51 g, 27.64 mmol) dropwise at 0° C. The resulting solution was stirred for 16 h at room temperature under a nitrogen atmosphere. The product was precipitated by the addition of petroleum ether (100 mL). After filtration, the filter cake was washed with petroleum ether (3×10 mL) and oven dried to afford N-((4,6-dichloropyridin-3-yl)carbamothioyl)benzamide as a yellow solid.

Yield 5.75 g (96%). $^1$H NMR (300 MHz, DMSO) δ 12.40 (br s, 1H), 12.01 (br s, 1H), 8.76 (s, 1H), 8.06-8.02 (m, 1H), 8.02-7.96 (m, 2H), 7.78-7.65 (m, 1H), 7.59-7.54 (m, 2H). m/z: [ESI$^+$]326, 328 (M+H)$^+$.

Synthesis of 1-(4,6-dichloropyridin-3-yl)thiourea

To a stirred solution of N-((4,6-dichloropyridin-3-yl)carbamothioyl)benzamide (16.40 g, 50.28 mmol) in methanol (200 mL) was added potassium carbonate (6.95 g, 50.29 mmol) portionwise at 0° C. The resulting mixture was warmed to room temperature and stirred for 16 h under a nitrogen atmosphere. The reaction mixture was diluted with water (200 mL). The precipitated solids were collected by filtration and washed with water (3×50 mL). The resulting solid was oven dried to afford 1-(4,6-dichloropyridin-3-yl)thiourea as a white solid.

Yield 10.23 g (92%). $^1$H NMR (400 MHz, DMSO) δ 9.48 (br s, 1H), 8.55 (s, 1H), 8.15 (br s, 1H), 7.86 (s, 1H), 7.50 (br s, 1H). m/z: [ESI$^+$]222, 224 (M+H)$^+$.

Synthesis of 6-chlorothiazolo[4,5-c]pyridin-2-amine

To a stirred solution of 1-(4,6-dichloropyridin-3-yl)thiourea (3.00 g, 13.51 mmol) in N,N-dimethylacetamide (30 mL), was added sodium hydride (60% dispersion in mineral oil, 0.97 g, 24.25 mmol) portionwise at 0° C., under a nitrogen atmosphere. The resulting mixture was warmed to room temperature and stirred for 15 min then stirred for additional 3 h at 80° C. The reaction mixture was cooled to 0° C. and quenched with saturated aqueous ammonium chloride (30 mL). The precipitated solids were filtered. The filter cake was washed with water (3×5 mL) and oven dried to afford 6-chlorothiazolo[4,5-c]pyridin-2-amine as a grey solid.

Yield 2.30 g (92%). ¹H NMR (400 MHz, DMSO) δ 8.33 (s, 1H), 7.93 (br s, 2H), 7.88 (s, 1H). m/z: [ESI⁺]186, 188 (M+H)⁺.

Synthesis of tert-butyl 2-(4-(7-chloroimidazo[2',1':2,3]thiazolo[4,5-c]pyridin-2-yl)-3-fluorophenyl)pyrrolidine-1-carboxylate Compound tert-butyl 2-(4-(7-chloroimidazo[2',1':2,3]thiazolo[4,5-c]pyridin-2-yl)-3-fluorophenyl)pyrrolidine-1-carboxylate was prepared from 6-chlorothiazolo[4,5-c]pyridin-2-amine (2.00 g, 10.77 mmol) and tert-butyl 2-(4-(2-bromoacetyl)-3-fluorophenyl)pyrrolidine-1-carboxylate (4.16 g, 10.77 mmol) in 1-methylpyrrolidin-2-one, following a similar procedure to that described for the synthesis of ethyl 2-(4-(1-(tert-butoxycarbonyl)pyrrolidin-2-yl)-2-fluorophenyl)benzo[d]imidazo[2,1-b]thiazole-7-carboxylate and was isolated as a yellow solid.

Yield 1.80 g (35%). ¹H NMR (400 MHz, CDCl₃) δ 8.75 (s, 1H), 8.26-8.07 (m, 2H), 7.74 (s, 1H), 7.13-7.04 (m, 1H), 7.04-6.94 (m, 1H), 5.05-4.75 (m, 1H), 3.73-3.47 (m, 2H), 2.45-2.24 (m, 1H), 2.00-1.80 (m, 3H), 1.53-1.22 (m, 9H). m/z: [ESI⁺]473, 475 (M+H)⁺.

Synthesis of tert-butyl 2-(4-(7-cyanoimidazo[2',1':2,3]thiazolo[4,5-c]pyridin-2-yl)-3-fluorophenyl)pyrrolidine-1-carboxylate To a stirred mixture of tert-butyl 2-(4-(7-chloroimidazo[2',1':2,3]thiazolo[4,5-c]pyridin-2-yl)-3-fluorophenyl)pyrrolidine-1-carboxylate (500 mg, 1.057 mmol) and zinc cyanide (250 mg, 2.129 mmol) in N,N-dimethylacetamide (10 mL), were sequentially added zinc powder (35 mg, 0.535 mmol), tris(dibenzylideneacetone)dipalladium (100 mg, 0.109 mmol) and 1,1'-bis(diphenylphosphino)ferrocene (60 mg, 0.108 mmol) as single portions at room temperature, under a nitrogen atmosphere. The reaction mixture was stirred for 16 h at 120° C. The mixture was cooled to room temperature and filtered. The filter cake was washed with ethyl acetate (3×10 mL). The combined filtrates were diluted with brine (100 mL) and extracted with ethyl acetate (2×50 mL). The combined organic layers were washed with brine (100 mL) and dried over anhydrous sodium sulfate. After filtration, the filtrate was concentrated under reduced pressure. The residue was purified by silica gel column chromatography (eluted with 0-20% ethyl acetate in petroleum ether) to afford tert-butyl 2-(4-(7-cyanoimidazo[2',1':2,3]thiazolo[4,5-c]pyridin-2-yl)-3-fluorophenyl)pyrrolidine-1-carboxylate as a yellow solid.

Yield 440 mg (90%). ¹H NMR (400 MHz, DMSO) δ 9.59-9.53 (m, 1H), 8.88-8.78 (m, 2H), 8.14-8.03 (m, 1H), 7.21-7.08 (m, 2H), 4.91-4.69 (m, 1H), 3.62-3.43 (m, 1H), 2.43-2.22 (m, 1H), 1.94-1.70 (m, 3H), 1.43-1.10 (m, 9H). m/z: [ESI⁺]464 (M+H)⁺.

Synthesis of 2-(4-(1-(tert-butoxycarbonyl)pyrrolidin-2-yl)-2-fluorophenyl)imidazo[2',7':2,3]thiazolo[4,5-c]pyridine-7-carboxylic acid A solution of tert-butyl 2-(4-(7-cyanoimidazo[2',1':2,3]thiazolo[4,5-c]pyridin-2-yl)-3-fluorophenyl)pyrrolidine-1-carboxylate (200 mg, 0.431 mmol) in 3 N aqueous sodium hydroxide/ethanol (1:1, 4 mL) was stirred for 8 h at 100° C. The solution was cooled to room temperature and acidified to pH 4 with 2 N hydrochloric acid. The precipitated solids were collected by filtration, washed with water (2×5 mL) and oven dried to afford 2-(4-(1-(tert-butoxycarbonyl)pyrrolidin-2-yl)-2-fluorophenyl)imidazo[2',1':2,3]thiazolo[4,5-c]pyridine-7-carboxylic acid as a yellow solid.

Yield 140 mg (67%). ¹H NMR (300 MHz, DMSO) δ 9.51-9.41 (m, 1H), 8.85-8.77 (m, 2H), 8.15-8.00 (m, 1H), 7.21-7.08 (m, 2H), 4.88-4.68 (m, 1H), 3.74-3.47 (m, 2H), 2.41-2.24 (m, 1H), 1.96-1.70 (m, 3H), 1.41-1.11 (m, 9H). OH proton not observed. m/z: [ESI⁺]483 (M+H)⁺.

Synthesis of tert-butyl 2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate Compound tert-butyl 2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate was prepared from 2-(4-(1-(tert-butoxycarbonyl)pyrrolidin-2-yl)-2-fluorophenyl)imidazo[2',1':2,3]thiazolo[4,5-c]pyridine-7-carboxylic acid (100 mg, 0.207 mmol) and 3-(4-fluoropiperidin-1-yl)propan-1-amine (50 mg, 0.312 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a light brown solid.

Yield 80 mg (62%). ¹H NMR (300 MHz, CDCl₃) δ 9.37-9.24 (m, 1H), 8.87 (s, 1H), 8.67 (s, 1H), 8.33-8.25 (m, 1H), 8.22-8.11 (m, 1H), 7.16-7.07 (m, 1H), 7.07-6.96 (m, 1H), 5.04-4.64 (m, 2H), 3.76-3.55 (m, 4H), 2.86-2.66 (m, 2H), 2.66-2.53 (m, 2H), 2.50-2.29 (m, 3H), 2.16-1.79 (m, 9H), 1.53-1.22 (m, 9H). m/z: [ESI⁺]625 (M+H)⁺.

Synthesis of tert-butyl (R)-2-(3-fluoro-4-(7-((3-(4-fluoropiperidin-1-yl)propyl)carbamoyl)imidazo[2',7':2,3]thiazolo[4,5-c]pyridin-2-yl)phenyl)pyrrolidine-1-carboxylate and tert-butyl (S)-2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate Tert-butyl 2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate (500 mg, 0.800 mmol) was separated by Prep-CHIRAL-HPLC using the following conditions; Column: CHIRALPAK IG, 2×25 cm, 5 μm; Mobile Phase A: hexane (plus 0.5% 2 N ammonia-methanol), Mobile Phase B: ethanol:dichloromethane=1:1; Flow rate: 20 mL/min; Gradient: 35% B in 17 min; UV Detector: 220/254 nm. The faster eluting peak at 10.80 min was collected and concentrated under reduced pressure to afford tert-butyl (R)-2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate as a yellow solid.

Yield 130 mg (26%). ¹H NMR (300 MHz, CDCl₃) δ 9.37-9.24 (m, 1H), 8.87 (s, 1H), 8.67 (s, 1H), 8.33-8.25 (m, 1H), 8.22-8.11 (m, 1H), 7.16-7.07 (m, 1H), 7.07-6.96 (m, 1H), 5.04-4.64 (m, 2H), 3.76-3.55 (m, 4H), 2.86-2.66 (m, 2H), 2.66-2.53 (m, 2H), 2.50-2.29 (m, 3H), 2.16-1.79 (m, 9H), 1.53-1.22 (m, 9H). m/z: [ESI⁺]625 (M+H)⁺. $[\alpha]^{25}_D$=+68° (c=1 mg/mL, methanol).

The slower eluting peak at 14.19 min was collected and concentrated under reduced pressure to afford tert-butyl (S)-2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate as a yellow solid.

Yield 150 mg (30%). $^1$H NMR (300 MHz, CDCl$_3$) δ 9.37-9.24 (m, 1H), 8.87 (s, 1H), 8.67 (s, 1H), 8.33-8.25 (m, 1H), 8.22-8.11 (m, 1H), 7.16-7.07 (m, 1H), 7.07-6.96 (m, 1H), 5.04-4.64 (m, 2H), 3.76-3.55 (m, 4H), 2.86-2.66 (m, 2H), 2.66-2.53 (m, 2H), 2.50-2.29 (m, 3H), 2.16-1.79 (m, 9H), 1.53-1.22 (m, 9H). m/z: [ESI$^+$]625 (M+H)$^+$. $[α]^{25}_D$= −72° (c=1 mg/mL, methanol).

Synthesis of tert-butyl 2-(4-(7-carbamoylimidazo[2,1':2,3]thiazolo[4,5-c]pyridin-2-yl)-3-fluorophenyl)pyrrolidine-1-carboxylate Compound tert-butyl 2-(4-(7-carbamoylimidazo[2',1':2,3]thiazolo[4,5-c]pyridin-2-yl)-3-fluorophenyl)pyrrolidine-1-carboxylate was prepared from 2-(4-(1-(tert-butoxycarbonyl)pyrrolidin-2-yl)-2-fluorophenyl)imidazo[2,1':2,3]thiazolo[4,5-c]pyridine-7-carboxylic acid (90 mg, 0.187 mmol) and ammonium bicarbonate (30 mg, 0.379 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a yellow solid.

Yield 80 mg (89%). $^1$H NMR (400 MHz, DMSO) δ 9.43 (s, 1H), 8.86-8.80 (m, 2H), 8.28-8.20 (m, 1H), 8.15-8.05 (m, 1H), 7.74-7.68 (m, 1H), 7.20-7.10 (m, 2H), 4.90-4.70 (m, 1H), 3.62-3.42 (m, 2H), 2.39-2.24 (m, 1H), 1.93-1.73 (m, 3H), 1.42-1.13 (m, 9H). m/z: [ESI$^+$]482 (M+H)$^+$.

Synthesis of tert-butyl 2-(3-fluoro-4-(7-(methylcarbamoyl)imidazo[2',1':2,3]thiazolo[4,5-c]pyridin-2-yl)phenyl)pyrrolidine-1-carboxylate Compound tert-butyl 2-(3-fluoro-4-(7-(methylcarbamoyl)imidazo[2',1':2,3]thiazolo[4,5-c]pyridin-2-yl)phenyl)pyrrolidine-1-carboxylate was prepared from 2-(4-(1-(tert-butoxycarbonyl)pyrrolidin-2-yl)-2-fluorophenyl)imidazo[2',1':2,3]thiazolo[4,5-c]pyridine-7-carboxylic acid (90 mg, 0.187 mmol) and methanamine hydrochloride (25 mg, 0.370 mmol), following a similar procedure to that described for the synthesis of tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate and was isolated as a light yellow solid.

Yield 80 mg (87%). $^1$H NMR (400 MHz, DMSO) δ 9.39 (s, 1H), 8.88 (q, J=4.8 Hz, 1H), 8.79 (d, J=3.6 Hz, 1H), 8.77 (s, 1H), 8.11-8.03 (m, 1H), 7.16-7.06 (m, 2H), 4.87-4.67 (m, 1H), 3.62-3.42 (m, 2H), 2.86 (d, J=4.8 Hz, 3H), 2.39-2.19 (m, 1H), 1.91-1.68 (m, 3H), 1.40-1.08 (m, 9H). m/z: [ESI$^+$] 496 (M+H)$^+$.

Example 6

Synthetic Details of Additional Compounds of the Invention (Final Compounds)
Final Compounds

Synthesis of 2-(2-fluoro-4-(pyrrolidin-2-yl)phenyl)-N-(tetrahydro-2H-pyran-4-yl)benzo[d]imidazo[2,1-b]thiazole-7-carboxamide (Compound 510)

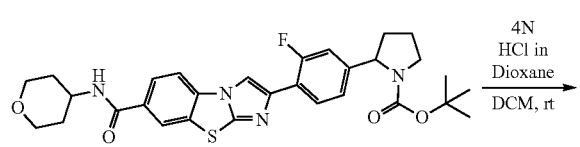

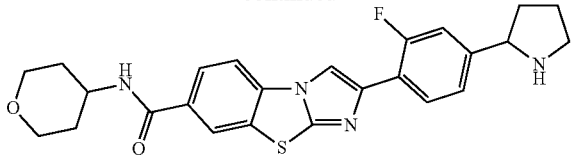

To a solution of tert-butyl 2-(3-fluoro-4-(7-((tetrahydro-2H-pyran-4-yl)carbamoyl)benzo[d]imidazo[2,1-b]thiazol-2-yl)phenyl)pyrrolidine-1-carboxylate (150 mg, 0.266 mmol) in dichloromethane (3 mL), was added a solution of hydrochloride in 1,4-dioxane (4 N, 3 mL) dropwise, at room temperature, under a nitrogen atmosphere. The resulting mixture was stirred for 30 min. The reaction mixture was concentrated under reduced pressure. The residue was purified by Prep-HPLC using the following conditions; Column: Xselect CSH OBD Column 30×150 mm, 5 µm; Mobile Phase A: water (plus 0.05% hydrochloric acid), Mobile Phase B: acetonitrile; Flow rate: 60 mL/min; Gradient: 10%-20% B in 10 min; UV Detector: 254/220 nm. The fractions containing desired product were collected, concentrated under reduced pressure and lyophilized to afford 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride as an off-white solid.

Yield 32 mg (24%). $^1$H NMR (400 MHz, DMSO) δ 10.38 (br s, 1H), 9.24 (br s, 1H), 8.80 (d, J=3.6 Hz, 1H), 8.55 (d, J=1.6 Hz, 1H), 8.51 (d, J=7.6 Hz, 1H), 8.30 (d, J=8.4 Hz, 1H), 8.22-8.17 (m, 1H), 8.07 (dd, J=1.6, 8.4 Hz, 1H), 7.68-7.59 (m, 1H), 7.54-7.43 (m, 1H), 4.67-4.53 (m, 1H), 4.10-3.97 (m, 1H), 3.95-3.84 (m, 2H), 3.47-3.34 (m, 3H), 3.34-3.20 (m, 1H), 2.45-2.37 (m, 1H), 2.19-1.95 (m, 3H), 1.86-1.75 (m, 2H), 1.69-1.55 (m, 2H). $^{19}$F NMR (376 MHz, DMSO) δ−112.75. m/z: [ESI$^+$]465 (M+H)$^+$. (C$_{25}$H$_{26}$ClFN$_4$O$_2$S).

Synthesis of (R)-2-(2-fluoro-4-(pyrrolidin-2-yl)phenyl)-N-(1-methylpiperidin-4-yl)benzo[d]imidazo[2,1-b]thiazole-7-carboxamide (Compound 503R)

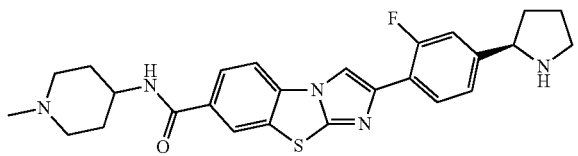 [SMILES: CN1CCC(NC(=O)c2ccc3c(c2)sc2nc(-c4ccc([C@H]5CCCN5)cc4F)cn23)CC1]

Compound (R)-2-(2-fluoro-4-(pyrrolidin-2-yl)phenyl)-N-(1-methylpiperidin-4-yl)benzo[d]imidazo[2,1-b]thiazole-7-carboxamide dihydrochloride was prepared from tert-butyl (R)-2-(3-fluoro-4-(7-((1-methylpiperidin-4-yl)carbamoyl)benzo[d]imidazo[2,1-b]thiazol-2-yl)phenyl)pyrrolidine-1-carboxylate (150 mg, 0.260 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 100 mg (70%). $^1$H NMR (400 MHz, DMSO) δ 10.76 (br s, 1H), 10.31 (br s, 1H), 9.20 (br s, 1H), 8.84-8.79 (m, 1H), 8.78-8.74 (m, 1H), 8.67-8.56 (m, 1H), 8.32-8.29 (m, 1H), 8.23-8.17 (m, 1H), 8.15-8.08 (m, 1H), 7.68-7.58 (m, 1H), 7.51-7.44 (m, 1H), 4.64-4.50 (m, 1H), 4.23-3.97 (m, 1H), 3.50-3.22 (m, 4H), 3.16-2.99 (m, 2H), 2.79-2.68

(m, 3H), 2.46-2.35 (m, 1H), 2.18-1.90 (m, 7H). $^{19}$F NMR (376 MHz, DMSO) δ–112.75. m/z: [ESI$^+$]478 (M+H)$^+$. ($C_{26}H_{30}Cl_2FN_5OS$). $[α]^{25}_D$=+8 (c=1 mg/mL, methanol).

Synthesis of (S)-2-(2-fluoro-4-(pyrrolidin-2-yl)phenyl)-N-(1-methylpiperidin-4-yl)benzo[d]imidazo[2,1-b]thiazole-7-carboxamide (Compound 503S)

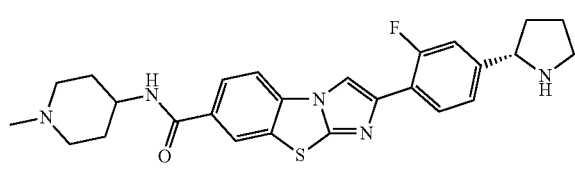

Compound (S)-2-(2-fluoro-4-(pyrrolidin-2-yl)phenyl)-N-(1-methylpiperidin-4-yl)benzo[d]imidazo[2,1-b]thiazole-7-carboxamide dihydrochloride was prepared from tert-butyl (S)-2-(3-fluoro-4-(7-((1-methylpiperidin-4-yl)carbamoyl)benzo[d]imidazo[2,1-b]thiazol-2-yl)phenyl)pyrrolidine-1-carboxylate (250 mg, 0.433 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 88 mg (37%). $^1$H NMR (400 MHz, DMSO) δ 10.76 (br s, 1H), 10.31 (br s, 1H), 9.20 (br s, 1H), 8.84-8.79 (m, 1H), 8.78-8.74 (m, 1H), 8.67-8.56 (m, 1H), 8.32-8.29 (m, 1H), 8.23-8.17 (m, 1H), 8.15-8.08 (m, 1H), 7.68-7.58 (m, 1H), 7.51-7.44 (m, 1H), 4.64-4.50 (m, 1H), 4.23-3.97 (m, 1H), 3.50-3.22 (m, 4H), 3.16-2.99 (m, 2H), 2.79-2.68 (m, 3H), 2.46-2.35 (m, 1H), 2.18-1.90 (m, 7H). $^{19}$F NMR (376 MHz, DMSO) δ–112.75. m/z: [ESI$^+$]478 (M+H)$^+$. ($C_{26}H_{30}Cl_2FN_5OS$). $[α]^{25}_D$=–2° (c=1 mg/mL, methanol).

Synthesis of 2-(2-fluoro-4-(pyrrolidin-2-yl)phenyl)-N-(1-methylpiperidin-4-yl)benzo[d]imidazo[2,1-b]thiazole-7-carboxamide (Compound 500)

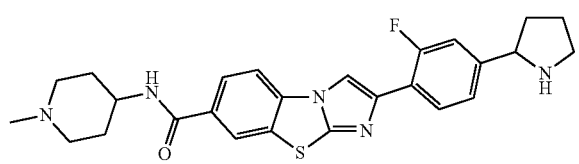 [SMILES: CN1CCC(NC(=O)c2ccc3c(c2)sc2nc(-c4ccc(C5CCCN5)cc4F)cn23)CC1]

Compound 2-(2-fluoro-4-(pyrrolidin-2-yl)phenyl)-N-(1-methylpiperidin-4-yl)benzo[d]imidazo[2,1-b]thiazole-7-carboxamide dihydrochloride was prepared from tert-butyl 2-(3-fluoro-4-(7-((1-methylpiperidin-4-yl)carbamoyl)benzo[d]imidazo[2,1-b]thiazol-2-yl)phenyl)pyrrolidine-1-carboxylate (100 mg, 0.173 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 13 mg (14%). $^1$H NMR (400 MHz, DMSO) δ 10.65 (br s, 1H), 10.28 (br s, 1H), 9.17 (br s, 1H), 8.86-8.79 (m, 1H), 8.79-8.71 (m, 1H), 8.63-8.52 (m, 1H), 8.35-8.29 (m, 1H), 8.24-8.16 (m, 1H), 8.13-8.07 (m, 1H), 7.67-7.57 (m, 1H), 7.53-7.42 (m, 1H), 4.64-4.54 (m, 1H), 4.10-4.00 (m, 1H), 3.49-3.21 (m, 4H), 3.15-3.01 (m, 2H), 2.82-2.66 (m, 3H), 2.45-2.34 (m, 1H), 2.19-1.87 (m, 7H). $^{19}$F NMR (376 MHz, DMSO) δ–112.75. m/z: [ESI$^+$]478 (M+H)$^+$. ($C_{26}H_{30}Cl_2FN_5OS$).

Synthesis of 2-(2-fluoro-4-(pyrrolidin-2-yl)phenyl)benzo[d]imidazo[2,1-b]thiazole-7-carboxamide (Compound 492)

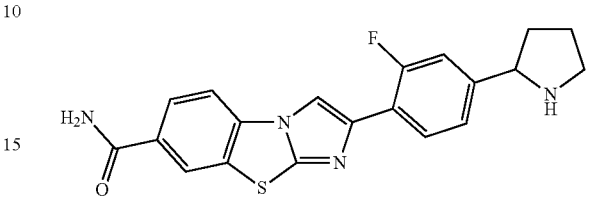

Compound 2-(2-fluoro-4-(pyrrolidin-2-yl)phenyl)benzo[d]imidazo[2,1-b]thiazole-7-carboxamide hydrochloride was prepared from tert-butyl 2-(4-(7-carbamoylbenzo[d]imidazo[2,1-b]thiazol-2-yl)-3-fluorophenyl)pyrrolidine-1-carboxylate (100 mg, 0.208 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 10 mg (12%). $^1$H NMR (400 MHz, DMSO) δ 10.42 (br s, 1H), 9.27 (br s, 1H), 8.80 (d, J=3.6 Hz, 1H), 8.56 (d, J=1.6 Hz, 1H), 8.29 (d, J=8.4 Hz, 1H), 8.22-8.16 (m, 1H), 8.14 (br s, 1H), 8.09 (dd, J=1.6, 8.4 Hz, 1H), 7.67-7.61 (m, 1H), 7.53 (br s, 1H), 7.51-7.46 (m, 1H), 4.65-4.52 (m, 1H), 3.47-3.20 (m, 2H), 2.46-2.36 (m, 1H), 2.23-1.96 (m, 3H). $^{19}$F NMR (376 MHz, DMSO) δ–112.67. m/z: [ESI$^+$]381 (M+H)$^+$. ($C_{20}H_{18}ClFN_4OS$).

Synthesis of 2-(2-fluoro-4-(pyrrolidin-2-yl)phenyl)-N-methylbenzo[d]imidazo[2,1-b]thiazole-7-carboxamide (Compound 498)

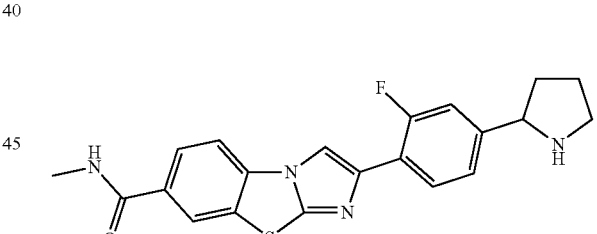

Compound 2-(2-fluoro-4-(pyrrolidin-2-yl)phenyl)-N-methylbenzo[d]imidazo[2,1-b]thiazole-7-carboxamide hydrochloride was prepared from tert-butyl 2-(3-fluoro-4-(7-(methylcarbamoyl)benzo[d]imidazo[2,1-b]thiazol-2-yl)phenyl)pyrrolidine-1-carboxylate (50 mg, 0.101 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 25 mg (58%). $^1$H NMR (400 MHz, DMSO) δ 9.79 (br s, 1H), 8.92 (br s, 1H), 8.78 (d, J=3.6 Hz, 1H), 8.59 (d, J=4.8 Hz, 1H), 8.51 (d, J=1.6 Hz, 1H), 8.29 (d, J=8.4 Hz, 1H), 8.25-8.20 (m, 1H), 8.03 (dd, J=1.6, 8.4 Hz, 1H), 7.60-7.55 (m, 1H), 7.48-7.43 (m, 1H), 4.68-4.56 (m, 1H), 3.43-3.27 (m, 2H), 2.84 (d, J=4.8 Hz, 3H), 2.48-2.35 (m, 1H), 2.18-2.05 (m, 3H). $^{19}$F NMR (376 MHz, DMSO) δ–112.74. m/z: [ESI$^+$]395 (M+H)$^+$. ($C_{21}H_{20}ClFN_4OS$).

Synthesis of 2-(2-fluoro-4-(pyrrolidin-2-yl)phenyl)-N—((S)-1-methylpiperidin-3-yl)benzo[d]imidazo[2,1-b]thiazole-7-carboxamide (Compound 491S)

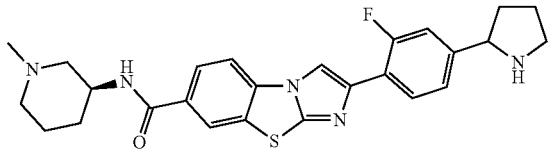 [SMILES: CN1CCC[C@H](NC(=O)c2ccc3c(c2)sc2nc(-c4ccc(C5CCCN5)cc4F)cn23)C1]

Compound 2-(2-fluoro-4-(pyrrolidin-2-yl)phenyl)-N—((S)-1-methylpiperidin-3-yl)benzo[d]imidazo[2,1-b]thiazole-7-carboxamide dihydrochloride was prepared from tert-butyl 2-(3-fluoro-4-(7-(((S)-1-methylpiperidin-3-yl)carbamoyl)benzo[d]imidazo[2,1-b]thiazol-2-yl)phenyl)pyrrolidine-1-carboxylate (200 mg, 0.346 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 50 mg (26%). $^1$H NMR (400 MHz, DMSO) δ 10.91 (br s, 1H), 10.29 (br s, 1H), 9.14 (br s, 1H), 8.88-8.75 (m, 2H), 8.58 (s, 1H), 8.41-8.26 (m, 1H), 8.25-8.13 (m, 1H), 8.13-8.03 (m, 1H), 7.68-7.58 (m, 1H), 7.52-7.42 (m, 1H), 4.65-4.55 (m, 1H), 4.22-4.16 (m, 1H), 3.56-3.44 (m, 1H), 3.44-3.21 (m, 3H), 3.05-2.71 (m, 5H), 2.45-2.36 (m, 1H), 2.22-1.52 (m, 7H). $^{19}$F NMR (376 MHz, DMSO) δ−112.72. m/z: [ESI$^+$]478 (M+H)$^+$. ($C_{26}H_{30}Cl_2FN_5OS$).

Synthesis of 2-(2-fluoro-4-(pyrrolidin-2-yl)phenyl)-N—((R)-1-methylpiperidin-3-yl)benzo[d]imidazo[2,1-b]thiazole-7-carboxamide (Compound 491R)

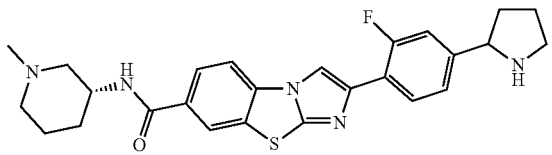 [SMILES: CN1CCC[C@@H](NC(=O)c2ccc3c(c2)sc2nc(-c4ccc(C5CCCN5)cc4F)cn23)C1]

Compound 2-(2-fluoro-4-(pyrrolidin-2-yl)phenyl)-N—((R)-1-methylpiperidin-3-yl)benzo[d]imidazo[2,1-b]thiazole-7-carboxamide dihydrochloride was prepared from tert-butyl 2-(3-fluoro-4-(7-(((R)-1-methylpiperidin-3-yl)carbamoyl)benzo[d]imidazo[2,1-b]thiazol-2-yl)phenyl)pyrrolidine-1-carboxylate (200 mg, 0.346 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 40 mg (21%). $^1$H NMR (400 MHz, DMSO) δ 10.91 (br s, 1H), 10.29 (br s, 1H), 9.14 (br s, 1H), 8.88-8.75 (m, 2H), 8.58 (s, 1H), 8.41-8.26 (m, 1H), 8.25-8.13 (m, 1H), 8.13-8.03 (m, 1H), 7.68-7.58 (m, 1H), 7.52-7.42 (m, 1H), 4.65-4.55 (m, 1H), 4.22-4.16 (m, 1H), 3.56-3.44 (m, 1H), 3.44-3.21 (m, 3H), 3.05-2.71 (m, 5H), 2.45-2.36 (m, 1H), 2.22-1.52 (m, 7H). $^{19}$F NMR (376 MHz, DMSO) δ−112.72. m/z: [ESI$^+$]478 (M+H)$^+$. ($C_{26}H_{30}Cl_2FN_5OS$).

Synthesis of 2-(2-fluoro-4-(pyrrolidin-2-yl)phenyl)-N-(tetrahydro-2H-pyran-3-yl)benzo[d]imidazo[2,1-b]thiazole-7-carboxamide (Compound 525)

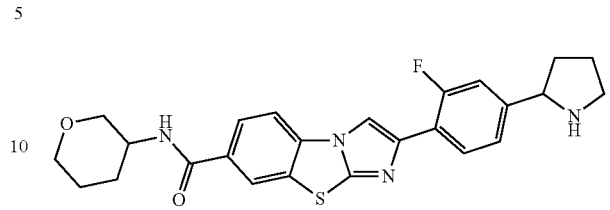

Compound 2-(2-fluoro-4-(pyrrolidin-2-yl)phenyl)-N-(tetrahydro-2H-pyran-3-yl)benzo[d]imidazo[2,1-b]thiazole-7-carboxamide hydrochloride was prepared from tert-butyl 2-(3-fluoro-4-(7-((tetrahydro-2H-pyran-3-yl)carbamoyl)benzo[d]imidazo[2,1-b]thiazol-2-yl)phenyl)pyrrolidine-1-carboxylate (137 mg, 0.243 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 51 mg (42%). $^1$H NMR (400 MHz, DMSO) δ 10.21 (br s, 1H), 9.12 (br s, 1H), 8.79 (d, J=3.6 Hz, 1H), 8.53 (q, J=1.6 Hz, 1H), 8.44-8.35 (m, 1H), 8.29 (d, J=8.4 Hz, 1H), 8.24-8.15 (m, 1H), 8.05 (dd, J=1.6, 8.4 Hz, 1H), 7.68-7.52 (m, 1H), 7.50-7.41 (m, 1H), 4.67-4.54 (m, 1H), 4.01-3.88 (m, 1H), 3.86-3.73 (m, 2H), 3.46-3.24 (m, 3H), 3.24-3.15 (m, 1H), 2.46-2.36 (m, 1H), 2.19-1.89 (m, 4H), 1.78-1.67 (m, 1H), 1.67-1.53 (m, 2H). $^{19}$F NMR (376 MHz, DMSO) δ−112.77. m/z: [ESI$^+$]465 (M+H)$^+$. ($C_{25}H_{26}ClFN_4O_2S$).

Synthesis of 2-(2,3-difluoro-4-(pyrrolidin-2-yl)phenyl)-N-(3-(4-fluoropiperidin-1-yl)propyl)benzo[d]imidazo[2,1-b]thiazole-7-carboxamide (Compound 476)

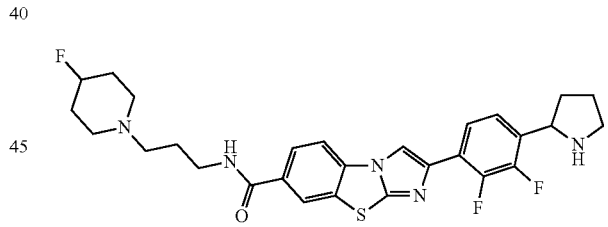

Compound 2-(2,3-difluoro-4-(pyrrolidin-2-yl)phenyl)-N-(3-(4-fluoropiperidin-1-yl)propyl)benzo[d]imidazo[2,1-b]thiazole-7-carboxamide dihydrochloride was prepared from tert-butyl 2-(2,3-difluoro-4-(7-((3-(4-fluoropiperidin-1-yl)propyl)carbamoyl)benzo[d]imidazo[2,1-b]thiazol-2-yl)phenyl)pyrrolidine-1-carboxylate (100 mg, 0.156 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a light yellow solid.

Yield 60 mg (63%). $^1$H NMR (400 MHz, DMSO) δ 10.60 (br s, 1H), 10.03 (br s, 1H), 9.23 (br s, 1H), 8.92-8.85 (m, 2H), 8.58 (s, 1H), 8.32 (d, J=8.4 Hz, 1H), 8.10 (d, J=8.4 Hz, 1H), 8.06-7.97 (m, 1H), 7.61-7.51 (m, 1H), 5.10-4.71 (m, 2H), 3.46-3.28 (m, 6H), 3.21-2.94 (m, 4H), 2.47-2.36 (m, 1H), 2.27-1.91 (m, 9H). $^{19}$F NMR (376 MHz, DMSO) δ−139.77, −139.82, −140.58, −140.63. Aliphatic $^{19}$F not observed. m/z: [ESI$^+$]542 (M+H)$^+$. ($C_{28}H_{32}Cl_2F_3NMOS$).

Synthesis of 2-(3-fluoro-4-(pyrrolidin-2-yl)phenyl)-N-(3-(4-fluoropiperidin-1-yl)propyl)benzo[d]imidazo[2,1-b]thiazole-7-carboxamide (Compound 484)

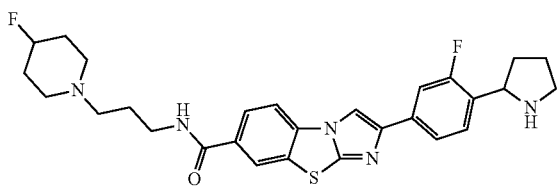 [SMILES: O=C(NCCCN1CCC(F)CC1)c1ccc2c(c1)sc1nc(-c3ccc(C4CCCN4)c(F)c3)cn12]

Compound 2-(3-fluoro-4-(pyrrolidin-2-yl)phenyl)-N-(3-(4-fluoropiperidin-1-yl)propyl)benzo[d]imidazo[2,1-b]thiazole-7-carboxamide dihydrochloride was prepared from tert-butyl 2-(2-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (70 mg, 0.112 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 7 mg (10%). $^1$H NMR (400 MHz, DMSO) δ 8.90 (br s, 1H), 8.64 (br s, 1H), 8.49 (br s, 1H), 8.34-8.21 (m, 2H), 8.08-7.98 (m, 2H), 7.76-7.61 (m, 2H), 4.78-4.52 (m, 2H), 3.35-3.28 (m, 2H), 3.26-3.07 (m, 2H), 2.62-2.53 (m, 2H), 2.44-2.23 (m, 6H), 2.06-1.79 (m, 5H), 1.79-1.64 (m, 4H). NH proton of amide not observed. $^{19}$F NMR (376 MHz, DMSO) δ−116.66. Aliphatic $^{19}$F not observed. m/z: [ESI$^+$] 524 (M+H)$^+$. (C$_{26}$H$_{33}$Cl$_2$F$_2$N$_5$OS).

Synthesis of 2-(4-(1-aminocyclopropyl)-2-fluorophenyl)-N-(3-(4-fluoropiperidin-1-yl)propyl)benzo[d]imidazo[2,1-b]thiazole-7-carboxamide (Compound 474)

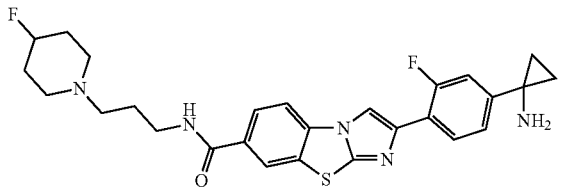 [SMILES: NC1(c2ccc(-c3cn4c(n3)sc3cc(C(=O)NCCCN5CCC(F)CC5)ccc34)c(F)c2)CC1]

Compound 2-(4-(1-aminocyclopropyl)-2-fluorophenyl)-N-(3-(4-fluoropiperidin-1-yl)propyl)benzo[d]imidazo[2,1-b]thiazole-7-carboxamide dihydrochloride was prepared from tert-butyl (1-(3-fluoro-4-(7-((3-(4-fluoropiperidin-1-yl)propyl)carbamoyl)benzo[d]imidazo[2,1-b]thiazol-2-yl)phenyl)cyclopropyl)carbamate (30 mg, 0.049 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 25 mg (87%). $^1$H NMR (400 MHz, DMSO) δ 10.69 (br s, 1H), 9.13-8.73 (m, 5H), 8.56 (s, 1H), 8.37-8.24 (m, 1H), 8.24-8.13 (m, 1H), 8.13-8.02 (m, 1H), 7.49-7.31 (m, 2H), 5.11-4.70 (m, 1H), 3.45-3.31 (m, 4H), 3.23-2.96 (m, 4H), 2.28-1.91 (m, 6H), 1.50-1.36 (m, 2H), 1.36-1.28 (m, 2H). $^{19}$F NMR (376 MHz, DMSO) δ−113.03. Aliphatic $^{19}$F not observed. m/z: [ESI$^+$] 510 (M+H)$^+$. (C$_{27}$H$_{31}$Cl$_2$F$_2$N$_5$OS).

Synthesis of N-(2-(2-fluoro-4-(pyrrolidin-2-yl)phenyl)benzo[d]imidazo[2,1-b]thiazol-7-yl)acetamide (Compound 548)

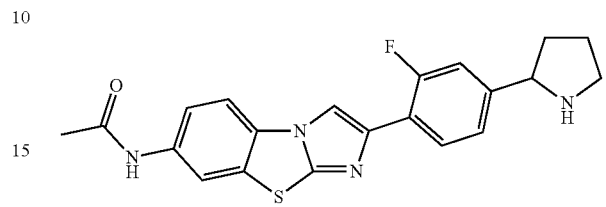

Compound N-(2-(2-fluoro-4-(pyrrolidin-2-yl)phenyl)benzo[d]imidazo[2,1-b]thiazol-7-yl)acetamide hydrochloride was prepared from tert-butyl 2-(4-(7-acetamidobenzo[d]imidazo[2,1-b]thiazol-2-yl)-3-fluorophenyl)pyrrolidine-1-carboxylate (220 mg, 0.445 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a light yellow solid.

Yield 80 mg (42%). $^1$H NMR (400 MHz, DMSO) δ 10.35 (br s, 1H), 10.13 (br s, 1H), 9.08 (br s, 1H), 8.66 (d, J=3.6 Hz, 1H), 8.34 (d, J=2.0 Hz, 1H), 8.23-8.15 (m, 1H), 8.12 (d, J=8.8 Hz, 1H), 7.65 (dd, J=2.0, 8.8 Hz, 1H), 7.59 (d, J=12.4 Hz, 1H), 7.46 (dd, J=1.6, 8.0 Hz, 1H), 4.65-4.55 (m, 1H), 3.44-3.24 (m, 2H), 2.45-2.35 (m, 1H), 2.18-1.99 (m, 6H). $^{19}$F NMR (376 MHz, DMSO) δ−112.95. m/z: [ESI$^+$]395 (M+H)$^+$. (C$_{21}$H$_{20}$ClFN$_4$OS).

Synthesis of 2-(2-fluoro-4-(pyrrolidin-3-yl)phenyl)-N-(3-(4-fluoropiperidin-1-yl)propyl)benzo[d]imidazo[2,1-b]thiazole-7-carboxamide (Compound 479)

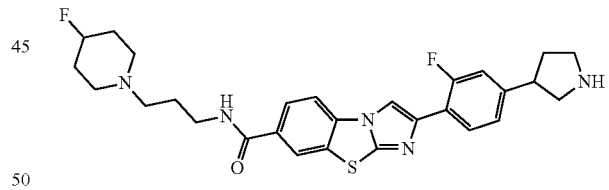

Compound 2-(2-fluoro-4-(pyrrolidin-3-yl)phenyl)-N-(3-(4-fluoropiperidin-1-yl)propyl)benzo[d]imidazo[2,1-b]thiazole-7-carboxamide dihydrochloride was prepared from tert-butyl 3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (100 mg, 0.160 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid. Yield 34 mg (41%). $^1$H NMR (400 MHz, DMSO) δ 10.41 (br s, 1H), 9.25 (br s, 2H), 8.84 (t, J=5.6 Hz, 1H), 8.73 (d, J=3.6 Hz, 1H), 8.55 (s, 1H), 8.30 (d, J=8.4 Hz, 1H), 8.16-8.10 (m, 1H), 8.07 (d, J=8.4 Hz, 1H), 7.41 (d, J=12.8 Hz, 1H), 7.31 (dd, J=1.6, 8.0 Hz, 1H), 5.11-4.68 (m, 1H), 3.70-3.47 (m, 3H), 3.47-3.33 (m, 4H), 3.33-2.96 (m, 6H), 2.46-2.35 (m, 1H), 2.30-

1.93 (m, 7H). $^{19}$F NMR (376 MHz, DMSO) δ –113.23, –175.87, –186.75. m/z: [ESI$^+$]524 (M+H)$^+$. (C$_{28}$H$_{33}$Cl$_2$F$_2$N$_5$OS).

Synthesis of (R)-2-(2-fluoro-4-(pyrrolidin-3-yl)phenyl)-N-(3-(4-fluoropiperidin-1-yl)propyl)benzo[d]imidazo[2,1-b]thiazole-7-carboxamide (Compound 434R)

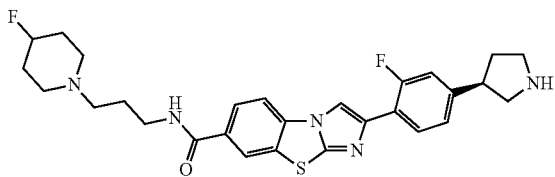 [SMILES: O=C(NCCCN1CCC(F)CC1)c1ccc2c(c1)sc1nc(-c3ccc([C@H]4CCNC4)cc3F)cn12]

Compound (R)-2-(2-fluoro-4-(pyrrolidin-3-yl)phenyl)-N-(3-(4-fluoropiperidin-1-yl)propyl)benzo[d]imidazo[2,1-b]thiazole-7-carboxamide dihydrochloride was prepared from tert-butyl (R)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (30 mg, 0.048 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 10 mg (35%). $^1$H NMR (400 MHz, DMSO) δ 10.41 (br s, 1H), 9.25 (br s, 2H), 8.84 (t, J=5.6 Hz, 1H), 8.73 (d, J=3.6 Hz, 1H), 8.55 (s, 1H), 8.30 (d, J=8.4 Hz, 1H), 8.16-8.10 (m, 1H), 8.07 (d, J=8.4 Hz, 1H), 7.41 (d, J=12.8 Hz, 1H), 7.31 (dd, J=1.6, 8.0 Hz, 1H), 5.11-4.68 (m, 1H), 3.70-3.47 (m, 3H), 3.47-3.33 (m, 4H), 3.33-2.96 (m, 6H), 2.46-2.35 (m, 1H), 2.30-1.93 (m, 7H). $^{19}$F NMR (376 MHz, DMSO) δ –113.23, –175.87, –186.75. m/z: [ESI$^+$]524 (M+H)$^+$. (C$_{28}$H$_{33}$Cl$_2$F$_2$N$_5$OS). [α]$^{25}_D$=+2° (c=1 mg/mL, methanol).

Synthesis of (S)-2-(2-fluoro-4-(pyrrolidin-3-yl)phenyl)-N-(3-(4-fluoropiperidin-1-yl)propyl)benzo[d]imidazo[2,1-b]thiazole-7-carboxamide (Compound 434S)

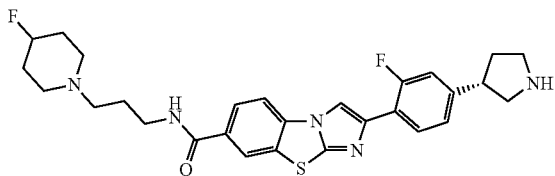 [SMILES: O=C(NCCCN1CCC(F)CC1)c1ccc2c(c1)sc1nc(-c3ccc([C@@H]4CCNC4)cc3F)cn12]

Compound (S)-2-(2-fluoro-4-(pyrrolidin-3-yl)phenyl)-N-(3-(4-fluoropiperidin-1-yl)propyl)benzo[d]imidazo[2,1-b]thiazole-7-carboxamide dihydrochloride was prepared from tert-butyl (S)-3-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (30 mg, 0.048 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 11 mg (38%) $^1$H NMR (400 MHz, DMSO) δ 10.41 (br s, 1H), 9.25 (br s, 2H), 8.84 (t, J=5.6 Hz, 1H), 8.73 (d, J=3.6 Hz, 1H), 8.55 (s, 1H), 8.30 (d, J=8.4 Hz, 1H), 8.16-8.10 (m, 1H), 8.07 (d, J=8.4 Hz, 1H), 7.41 (d, J=12.8 Hz, 1H), 7.31 (dd, J=1.6, 8.0 Hz, 1H), 5.11-4.68 (m, 1H), 3.70-3.47 (m, 3H), 3.47-3.33 (m, 4H), 3.33-2.96 (m, 6H), 2.46-2.35 (m, 1H), 2.30-1.93 (m, 7H). $^{19}$F NMR (376 MHz, DMSO) δ –113.23, –175.87, –186.75. m/z: [ESI$^+$]524 (M+H)$^+$. (C$_{28}$H$_{33}$Cl$_2$F$_2$N$_5$OS). [α]$^{25}_D$=–2° (c=1 mg/mL, methanol).

Synthesis of 2-(2-fluoro-4-(pyrrolidin-3-yl)phenyl)benzo[d]imidazo[2,1-b]thiazole-7-carboxamide (Compound 511)

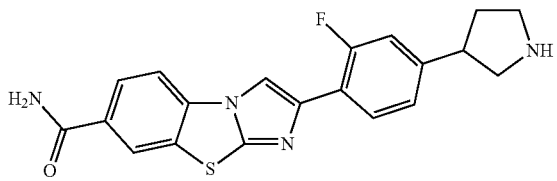 [SMILES: NC(=O)c1ccc2c(c1)sc1nc(-c3ccc(C4CCNC4)cc3F)cn12]

Compound 2-(2-fluoro-4-(pyrrolidin-3-yl)phenyl)benzo[d]imidazo[2,1-b]thiazole-7-carboxamide hydrochloride was prepared from tert-butyl 3-(4-(7-carbamoylbenzo[d]imidazo[2,1-b]thiazol-2-yl)-3-fluorophenyl)pyrrolidine-1-carboxylate (80 mg, 0.166 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 11 mg (16%). $^1$H NMR (400 MHz, DMSO) δ 9.65 (br s, 2H), 8.74 (d, J=3.6 Hz, 1H), 8.59-8.52 (m, 1H), 8.28 (d, J=8.4 Hz, 1H), 8.21-8.03 (m, 3H), 7.54 (br s, 1H), 7.42 (d, J=12.4 Hz, 1H), 7.31 (d, J=8.0 Hz, 1H), 3.70-3.58 (m, 1H), 3.58-3.47 (m, 1H), 3.45-3.37 (m, 1H), 3.29-3.07 (m, 2H), 2.40-2.33 (m, 1H), 2.07-1.92 (m, 1H). $^{19}$F NMR (376 MHz, DMSO) δ –113.09. m/z: [ESI$^+$]381 (M+H)$^+$. (C$_{20}$H$_{18}$ClFN$_4$OS).

Synthesis of 2-(2-fluoro-4-(pyrrolidin-3-yl)phenyl)-N-methylbenzo[d]imidazo[2,1-b]thiazole-7-carboxamide (Compound 504)

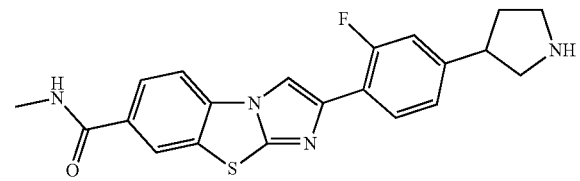 [SMILES: CNC(=O)c1ccc2c(c1)sc1nc(-c3ccc(C4CCNC4)cc3F)cn12]

Compound 2-(2-fluoro-4-(pyrrolidin-3-yl)phenyl)-N-methylbenzo[d]imidazo[2,1-b]thiazole-7-carboxamide hydrochloride was prepared from tert-butyl 3-(3-fluoro-4-(7-(methylcarbamoyl)benzo[d]imidazo[2,1-b]thiazol-2-yl)phenyl)pyrrolidine-1-carboxylate (120 mg, 0.243 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 8 mg (8%). $^1$H NMR (400 MHz, DMSO) δ 9.44 (br s, 2H), 8.72 (d, J=3.6 Hz, 1H), 8.64 (q, J=4.4 Hz, 1H), 8.51

(d, J=1.6 Hz, 1H), 8.28 (d, J=8.4 Hz, 1H), 8.16-8.07 (m, 1H), 8.02 (dd, J=1.6, 8.4 Hz, 1H), 7.41 (dd, J=1.6, 12.4 Hz, 1H), 7.30 (d, J=8.0 Hz, 1H), 3.65-3.47 (m, 2H), 3.46-3.35 (m, 1H), 3.29-3.17 (m, 1H), 3.17-3.06 (m, 1H), 2.83 (d, J=4.4 Hz, 3H), 2.45-2.34 (m, 1H), 2.07-1.92 (m, 1H). $^{19}$F NMR (376 MHz, DMSO) δ–113.20. m/z: [ESI$^+$]395 (M+H)$^+$. (C$_{21}$H$_{20}$ClFN$_4$OS).

Synthesis of 2-(2-fluoro-4-(piperidin-4-yl)phenyl)-N-(tetrahydro-2H-pyran-4-yl)benzo[d]imidazo[2,1-b]thiazole-7-carboxamide (Compound 529)

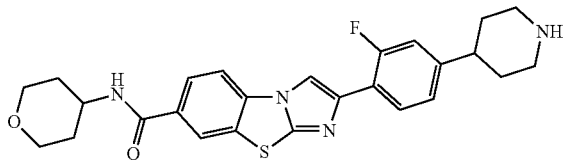 [SMILES: O=C(NC1CCOCC1)c1ccc2c(c1)sc1nc(-c3ccc(C4CCNCC4)cc3F)cn12]

Compound 2-(2-fluoro-4-(piperidin-4-yl)phenyl)-N-(tetrahydro-2H-pyran-4-yl)benzo[d]imidazo[2,1-b]thiazole-7-carboxamide hydrochloride was prepared from tert-butyl 4-(3-fluoro-4-(7-((tetrahydro-2H-pyran-4-yl)carbamoyl)benzo[d]imidazo[2,1-b]thiazol-2-yl)phenyl)piperidine-1-carboxylate (100 mg, 0.173 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 28 mg (31%). $^1$H NMR (400 MHz, DMSO) δ 9.06 (br s, 2H), 8.70 (d, J=3.6 Hz, 1H), 8.55-8.46 (m, 2H), 8.30-8.24 (m, 1H), 8.16-8.07 (m, 1H), 8.07-8.01 (m, 1H), 7.25-7.14 (m, 2H), 4.10-3.98 (m, 1H), 3.94-3.86 (m, 2H), 3.46-3.31 (m, 4H), 3.06-2.84 (m, 3H), 2.06-1.84 (m, 4H), 1.83-1.75 (m, 2H), 1.69-1.53 (m, 2H). $^{19}$F NMR (376 MHz, DMSO) δ–113.30, –113.31. m/z: [ESI$^+$]479 (M+H)$^+$. (C$_{26}$H$_{28}$ClFN$_4$O$_2$S).

Synthesis of 2-(2-fluoro-4-(piperidin-4-yl)phenyl)-N-(3-(4-fluoropiperidin-1-yl)propyl)benzo[d]imidazo[2,1-b]thiazole-7-carboxamide (Compound 508)

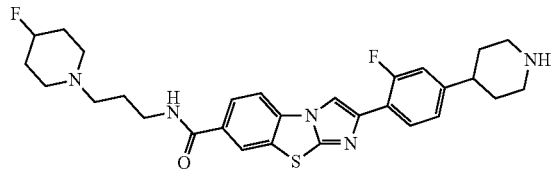 [SMILES: O=C(NCCCN1CCC(F)CC1)c1ccc2c(c1)sc1nc(-c3ccc(C4CCNCC4)cc3F)cn12]

Compound 2-(2-fluoro-4-(piperidin-4-yl)phenyl)-N-(3-(4-fluoropiperidin-1-yl)propyl)benzo[d]imidazo[2,1-b]thiazole-7-carboxamide dihydrochloride was prepared from tert-butyl 4-(3-fluoro-4-(7-((3-(4-fluoropiperidin-1-yl)propyl)carbamoyl)benzo[d]imidazo[2,1-b]thiazol-2-yl)phenyl)piperidine-1-carboxylate (300 mg, 0.470 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 120 mg (42%). $^1$H NMR (400 MHz, DMSO) δ 10.99 (br s, 1H), 9.21 (br s, 2H), 8.96 (q, J=5.6 Hz, 1H), 8.74 (d, J=3.6 Hz, 1H), 8.61-8.56 (m, 1H), 8.34-8.27 (m, 1H), 8.15-8.07 (m, 2H), 7.25-7.15 (m, 2H), 5.02-4.72 (m, 1H), 3.56-3.47 (m, 1H), 3.47-3.30 (m, 5H), 3.23-2.86 (m, 7H), 2.37-1.85 (m, 10H). $^{19}$F NMR (376 MHz, DMSO) δ–113.18, –175.47, –186.62. m/z: [ESI$^+$]538 (M+H)$^+$. (C$_{29}$H$_{35}$Cl$_2$F$_2$N$_5$OS).

Synthesis of 2-(2-fluoro-4-(piperidin-3-yl)phenyl)-N-(3-(4-fluoropiperidin-1-yl)propyl)benzo[d]imidazo[2,1-b]thiazole-7-carboxamide (Compound 513)

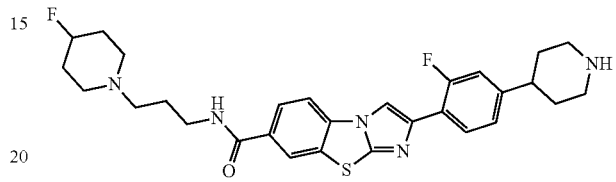

Compound 2-(2-fluoro-4-(piperidin-3-yl)phenyl)-N-(3-(4-fluoropiperidin-1-yl)propyl)benzo[d]imidazo[2,1-b]thiazole-7-carboxamide dihydrochloride was prepared from tert-butyl 3-(3-fluoro-4-(7-((3-(4-fluoropiperidin-1-yl)propyl)carbamoyl)benzo[d]imidazo[2,1-b]thiazol-2-yl)phenyl)piperidine-1-carboxylate (70 mg, 0.110 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 19 mg (28%). 1H NMR (400 MHz, DMSO) δ 10.79 (br s, 1H), 9.31 (br s, 1H), 9.07 (br s, 1H), 8.89 (t, J=5.4 Hz, 1H), 8.73 (d, J=3.6 Hz, 1H), 8.57 (s, 1H), 8.29 (d, J=8.4 Hz, 1H), 8.13 (d, J=8.0 Hz, 1H), 8.09 (d, J=9.2 Hz, 1H), 7.34 (d, J=12.4 Hz, 1H), 7.25 (d, J=8.0 Hz, 1H), 5.10-4.68 (m, 1H), 3.59-3.47 (m, 1H), 3.45-3.24 (m, 5H), 3.21-2.95 (m, 6H), 2.95-2.82 (m, 1H), 2.32-1.67 (m, 10H). $^{19}$F NMR (376 MHz, DMSO) δ–113.16, –175.59, –186.63. m/z: [ESI$^+$]538 (M+H)$^+$. (C29H35Cl2F2N5OS).

Synthesis of 2-(2-fluoro-4-(piperidin-2-yl)phenyl)-N-(3-(4-fluoropiperidin-1-yl)propyl)benzo[d]imidazo[2,1-b]thiazole-7-carboxamide e (Compound 480)

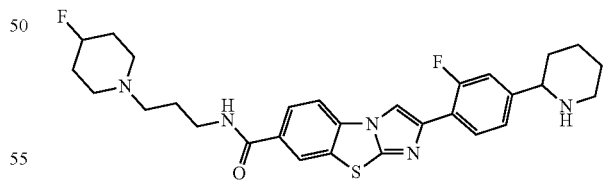

Compound 2-(2-fluoro-4-(piperidin-2-yl)phenyl)-N-(3-(4-fluoropiperidin-1-yl)propyl)benzo[d]imidazo[2,1-b]thiazole-7-carboxamide dihydrochloride was prepared from tert-butyl 2-(3-fluoro-4-(7-((3-(4-fluoropiperidin-1-yl)propyl)carbamoyl)benzo[d]imidazo[2,1-b]thiazol-2-yl)phenyl)piperidine-1-carboxylate (70 mg, 0.110 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 47 mg (70%). ¹H NMR (400 MHz, DMSO) δ 10.68 (br s, 1H), 9.49 (br s, 1H), 9.30 (br s, 1H), 8.87 (s, 1H), 8.78 (d, J=3.6 Hz, 1H), 8.57 (s, 1H), 8.30 (d, J=8.4 Hz, 1H), 8.24-8.16 (m, 1H), 8.09 (d, J=8.4 Hz, 1H), 7.71-7.61 (m, 1H), 7.54-7.47 (m, 1H), 5.09-4.73 (m, 1H), 4.34-4.24 (m, 1H), 3.57-3.47 (m, 1H), 3.44-3.31 (m, 4H), 3.22-2.98 (m, 5H), 2.29-1.73 (m, 11H), 1.73-1.58 (m, 1H). ¹⁹F NMR (376 MHz, DMSO) δ–112.68, –175.63, –186.63. m/z: [ESI⁺]538 (M+H)⁺. (C$_{29}$H$_{35}$Cl$_2$F$_2$NOS).

Synthesis of 2-(2-fluoro-4-(4-hydroxypiperidin-4-yl) phenyl)-N-(3-(4-fluoropiperidin-1-yl)propyl)benzo [d]imidazo[2,1-b]thiazole-7-carboxamide e (Compound 512)

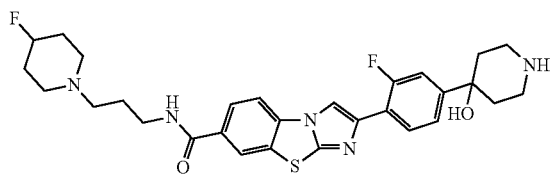 [SMILES: O=C(NCCCN1CCC(F)CC1)c1ccc2c(c1)sc1nc(-c3ccc(C4(O)CCNCC4)cc3F)cn12]

Compound 2-(2-fluoro-4-(4-hydroxypiperidin-4-yl)phenyl)-N-(3-(4-fluoropiperidin-1-yl)propyl)benzo[d]imidazo[2,1-b]thiazole-7-carboxamide dihydrochloride was prepared from tert-butyl 4-(3-fluoro-4-(7-((3-(4-fluoropiperidin-1-yl)propyl)carbamoyl)benzo[d]imidazo[2,1-b]thiazol-2-yl)phenyl)-4-hydroxypiperidine-1-carboxylate (120 mg, 0.184 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 38 mg (33 mg). ¹H NMR (400 MHz, DMSO) δ 10.69 (br s, 1H), 9.07 (br s, 1H), 8.98-8.84 (m, 2H), 8.74 (d, J=3.6 Hz, 1H), 8.56 (s, 1H), 8.30 (d, J=8.4 Hz, 1H), 8.21-8.13 (m, 1H), 8.08 (d, J=8.4 Hz, 1H), 7.46-7.32 (m, 2H), 5.12-4.76 (m, 1H), 3.59-3.48 (m, 1H), 3.48-3.31 (m, 3H), 3.31-2.96 (m, 8H), 2.38-1.94 (m, 8H), 1.90-1.70 (m, 2H). OH proton not observed. ¹⁹F NMR (376 MHz, DMSO) δ–113.27, –175.55, –186.65. m/z: [ESI⁺]554 (M+H)⁺. (C$_{29}$H$_{35}$Cl$_2$F$_2$N$_5$O$_2$S).

Synthesis of 2-(2-fluoro-4-(3-hydroxypyrrolidin-3-yl)phenyl)-N-(3-(4-fluoropiperidin-1-yl)propyl) benzo[d]imidazo[2,1-b]thiazole-7-carboxamide (Compound 516)

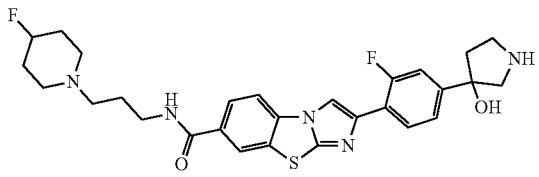 [SMILES: O=C(NCCCN1CCC(F)CC1)c1ccc2c(c1)sc1nc(-c3ccc(C4(O)CCNC4)cc3F)cn12]

Compound 2-(2-fluoro-4-(3-hydroxypyrrolidin-3-yl)phenyl)-N-(3-(4-fluoropiperidin-1-yl)propyl)benzo[d]imidazo[2,1-b]thiazole-7-carboxamide dihydrochloride was prepared from tert-butyl 3-(3-fluoro-4-(7-((3-(4-fluoropiperidin-1-yl)propyl)carbamoyl)benzo[d]imidazo[2,1-b]thiazol-2-yl)phenyl)-3-hydroxypyrrolidine-1-carboxylate (160 mg, 0.250 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 99 mg (65%). ¹H NMR (400 MHz, DMSO) δ 10.85 (br s, 1H), 9.77 (br s, 1H), 9.43 (br s, 1H), 8.90 (t, J=5.6 Hz, 1H), 8.77 (d, J=3.6 Hz, 1H), 8.57 (d, J=1.6 Hz, 1H), 8.30 (d, J=8.4 Hz, 1H), 8.21-8.14 (m, 1H), 8.09 (dd, J=1.6, 8.4 Hz, 1H), 7.53 (dd, J=1.6, 12.8 Hz, 1H), 7.49 (dd, J=1.6, 8.0 Hz, 1H), 5.12-4.70 (m, 1H), 3.57-3.32 (m, 8H), 3.20-2.96 (m, 4H), 2.40-1.94 (m, 8H). OH proton not observed. ¹⁹F NMR (376 MHz, DMSO) δ–113.27, –175.65, –186.65. m/z: [ESI⁺]540 (M+H)⁺. (C$_{28}$H$_{33}$Cl$_2$F$_2$N$_5$O$_2$S).

Synthesis of 2-(2-fluoro-4-(morpholin-3-yl)phenyl)-N-(3-(4-fluoropiperidin-1-yl)propyl)benzo[d]imidazo[2,1-b]thiazole-7-carboxamide (Compound 481)

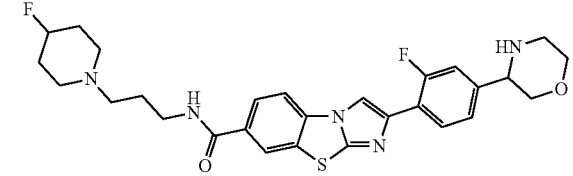 [SMILES: O=C(NCCCN1CCC(F)CC1)c1ccc2c(c1)sc1nc(-c3ccc(C4COCCN4)cc3F)cn12]

Compound 2-(2-fluoro-4-(morpholin-3-yl)phenyl)-N-(3-(4-fluoropiperidin-1-yl)propyl)benzo[d]imidazo[2,1-b]thiazole-7-carboxamide dihydrochloride was prepared from tert-butyl 3-(3-fluoro-4-(7-((3-(4-fluoropiperidin-1-yl)propyl)carbamoyl)benzo[d]imidazo[2,1-b]thiazol-2-yl)phenyl)morpholine-4-carboxylate (20 mg, 0.031 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 5 mg (26%). ¹H NMR (400 MHz, DMSO) δ 10.83 (br s, 1H), 10.33 (br s, 1H), 10.00 (br s, 1H), 8.88 (br s, 1H), 8.79 (d, J=3.6 Hz, 1H), 8.57 (s, 1H), 8.31 (d, J=8.4 Hz, 1H), 8.25-8.16 (m, 1H), 8.09 (d, J=8.4 Hz, 1H), 7.77 (d, J=12.4 Hz, 1H), 7.58 (d, J=8.3 Hz, 1H), 5.13-4.71 (m, 1H), 4.63-4.50 (m, 1H), 4.12-3.95 (m, 3H), 3.50-3.31 (m, 8H), 3.21-2.97 (m, 3H), 2.35-1.94 (m, 6H). ¹⁹F NMR (376 MHz, DMSO) δ–112.51. Aliphatic ¹⁹F not observed. m/z: [ESI⁺] 540 (M+H)⁺. (C$_{28}$H$_{33}$Cl$_2$F$_2$N$_5$O$_2$S).

Synthesis of 2-(2-fluoro-4-(morpholin-3-yl)phenyl)-N-(1-methylpiperidin-4-yl)benzo[d]imidazo[2,1-b] thiazole-7-carboxamide (Compound 517)

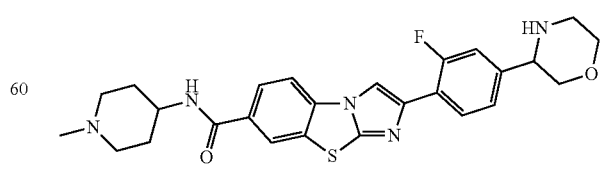

Compound 2-(2-fluoro-4-(morpholin-3-yl)phenyl)-N-(1-methylpiperidin-4-yl)benzo[d]imidazo[2,1-b]thiazole-7-carboxamide dihydrochloride was prepared from tert-butyl 3-(3-fluoro-4-(7-((1-methylpiperidin-4-yl)carbamoyl)benzo[d]imidazo[2,1-b]thiazol-2-yl)phenyl)morpholine-4-carboxylate (90 mg, 0.152 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 40 mg (47%). $^1$H NMR (400 MHz, DMSO) δ 10.65 (br s, 1H), 10.26 (br s, 1H), 9.95 (br s, 1H), 8.80 (d, J=3.6 Hz, 1H), 8.73 (d, J=7.2 Hz, 1H), 8.57 (s, 1H), 8.30 (d, J=8.4 Hz, 1H), 8.26-8.17 (m, 1H), 8.10 (d, J=8.4 Hz, 1H), 7.76 (d, J=12.4 Hz, 1H), 7.57 (d, J=8.0 Hz, 1H), 4.60-4.48 (m, 1H), 3.94-3.82 (m, 4H), 3.50-3.16 (m, 5H), 3.17-2.99 (m, 2H), 2.73 (s, 3H), 2.10-1.87 (m, 4H). $^{19}$F NMR (376 MHz, DMSO) δ−112.51. m/z: [ESI$^+$]494 (M+H)$^+$. ($C_{26}H_{30}Cl_2FN_5O_2S$).

Synthesis of 2-(2-fluoro-4-(1H-1,2,4-triazol-3-yl)phenyl)-N-(3-(4-fluoropiperidin-1-yl)propyl)benzo[d]imidazo[2,1-b]thiazole-7-carboxamide (Compound 483)

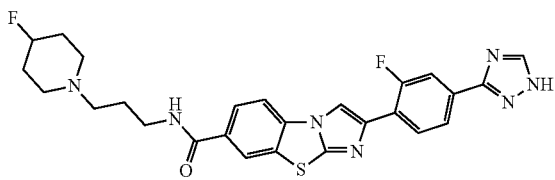 [SMILES: O=C(NCCCN1CCC(F)CC1)c1ccc2c(c1)sc1nc(-c3ccc(-c4nc[nH]n4)cc3F)cn12]

Compound 2-(2-fluoro-4-(1H-1,2,4-triazol-3-yl)phenyl)-N-(3-(4-fluoropiperidin-1-yl)propyl)benzo[d]imidazo[2,1-b]thiazole-7-carboxamide hydrochloride was prepared from 2-(2-fluoro-4-(1-((2-(trimethylsilyl)ethoxy)methyl)-1H-1,2,4-triazol-3-yl)phenyl)-N-(3-(4-fluoropiperidin-1-yl)propyl)benzo[d]imidazo[2,1-b]thiazole-7-carboxamide (160 mg, 0.245 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 23 mg (17%). $^1$H NMR (400 MHz, DMSO) δ 10.67 (br s, 1H), 8.91-8.85 (m, 1H), 8.82 (d, J=3.6 Hz, 1H), 8.61 (s, 1H), 8.57 (d, J=1.6 Hz, 1H), 8.32 (d, J=8.4 Hz, 1H), 8.30-8.24 (m, 1H), 8.09 (dd, J=1.6, 8.4 Hz, 1H), 7.99 (dd, J=1.6, 8.0 Hz, 1H), 7.92 (dd, J=1.6, 12.4 Hz, 1H), 5.11-4.69 (m, 1H), 3.57-3.49 (m, 1H), 3.46-3.36 (m, 3H), 3.23-2.95 (m, 4H), 2.30-1.96 (m, 6H). NH proton of triazole not observed. $^{19}$F NMR (376 MHz, DMSO) δ−112.88, −175.67, −186.64. m/z: [ESI$^+$]522 (M+H)$^+$. ($C_{26}H_{26}ClF_2N_7OS$).

Synthesis of 2-(2-fluoro-4-(morpholin-2-yl)phenyl)-N-(1-methylpiperidin-4-yl)benzo[d]imidazo[2,1-b]thiazole-7-carboxamide (Compound 519)

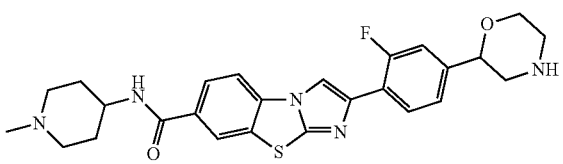 [SMILES: CN1CCC(NC(=O)c2ccc3c(c2)sc2nc(-c4ccc(C5CNCCO5)cc4F)cn23)CC1]

Compound 2-(2-fluoro-4-(morpholin-2-yl)phenyl)-N-(1-methylpiperidin-4-yl)benzo[d]imidazo[2,1-b]thiazole-7-carboxamide dihydrochloride was prepared from tert-butyl 2-(3-fluoro-4-(7-((1-methylpiperidin-4-yl)carbamoyl)benzo[d]imidazo[2,1-b]thiazol-2-yl)phenyl)morpholine-4-carboxylate (90 mg, 0.152 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 17 mg (19%). $^1$H NMR (400 MHz, DMSO) δ 10.77 (br s, 1H), 9.72 (br s, 2H), 8.81-8.73 (m, 2H), 8.57 (d, J=1.6 Hz, 1H), 8.29 (d, J=8.4 Hz, 1H), 8.20-8.13 (m, 1H), 8.09 (dd, J=1.6, 8.4 Hz, 1H), 7.46-7.31 (m, 2H), 4.93-4.82 (m, 1H), 4.24-3.93 (m, 3H), 3.55-3.21 (m, 4H), 3.21-2.98 (m, 4H), 2.72 (s, 3H), 2.11-1.89 (m, 4H). $^{19}$F NMR (376 MHz, DMSO) δ−112.98. m/z: [ESI$^+$]494 (M+H)$^+$. ($C_{26}H_{30}Cl_2FN_5O_2S$).

Synthesis of 2-(2-fluoro-4-(4-oxopyrrolidin-2-yl)phenyl)-N-(3-(4-fluoropiperidin-1-yl)propyl)benzo[d]imidazo[2,1-b]thiazole-7-carboxamide (Compound 507)

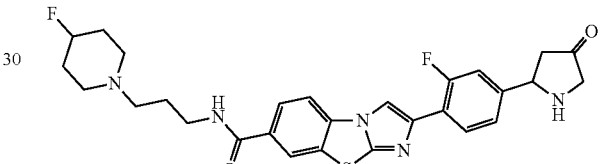

Compound 2-(2-fluoro-4-(4-oxopyrrolidin-2-yl)phenyl)-N-(3-(4-fluoropiperidin-1-yl)propyl)benzo[d]imidazo[2,1-b]thiazole-7-carboxamide dihydrochloride was prepared from tert-butyl 2-(3-fluoro-4-(7-((3-(4-fluoropiperidin-1-yl)propyl)carbamoyl)benzo[d]imidazo[2,1-b]thiazol-2-yl)phenyl)-4-oxopyrrolidine-1-carboxylate (100 mg, 0.157 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 18 mg (19%). $^1$H NMR (400 MHz, DMSO) δ 11.27 (br s, 1H), 10.94 (br s, 1H), 10.17 (br s, 1H), 9.02-8.90 (m, 1H), 8.83 (d, J=3.6 Hz, 1H), 8.59 (s, 1H), 8.32 (d, J=8.4 Hz, 1H), 8.28-8.18 (m, 1H), 8.10 (d, J=8.4 Hz, 1H), 7.80 (d, J=12.4 Hz, 1H), 7.58 (d, J=8.0 Hz, 1H), 5.25-5.12 (m, 1H), 5.12-4.71 (m, 1H), 3.66-3.47 (m, 3H), 3.46-3.32 (m, 3H), 3.27-2.95 (m, 6H), 2.36-1.98 (m, 6H). $^{19}$F NMR (376 MHz, DMSO) δ−112.39, −175.49, −186.63. m/z: [ESI$^+$]538 (M+H)$^+$. ($C_{28}H_{31}Cl_2F_2N_5O_2S$).

Synthesis of 2-(2-fluoro-4-(4-hydroxypyrrolidin-2-yl)phenyl)-N-(3-(4-fluoropiperidin-1-yl)propyl)benzo[d]imidazo[2,1-b]thiazole-7-carboxamide (Compound 493)

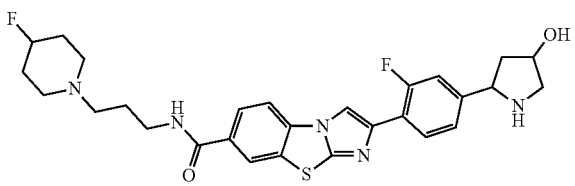 [SMILES: O=C(NCCCN1CCC(F)CC1)c1ccc2c(c1)sc1nc(-c3ccc(C4CC(O)CN4)cc3F)cn12]

Compound 2-(2-fluoro-4-(4-hydroxypyrrolidin-2-yl)phenyl)-N-(3-(4-fluoropiperidin-1-yl)propyl)benzo[d]imidazo[2,1-b]thiazole-7-carboxamide dihydrochloride was prepared from tert-butyl 2-(3-fluoro-4-(7-((3-(4-fluoropiperidin-1-yl)propyl)carbamoyl)benzo[d]imidazo[2,1-b]thiazol-2-yl)phenyl)-4-hydroxypyrrolidine-1-carboxylate (60 mg, 0.094 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a grey solid.

Yield 47 mg (82%). $^1$H NMR (400 MHz, DMSO) δ 10.68 (br s, 1H), 10.34 (br s, 1H), 9.18 (br s, 1H), 8.95-8.84 (m, 1H), 8.81 (d, J=3.6 Hz, 1H), 8.57 (d, J=1.6 Hz, 1H), 8.31 (d, J=8.4 Hz, 1H), 8.24-8.16 (m, 1H), 8.09 (dd, J=1.6, 8.4 Hz, 1H), 7.66-7.54 (m, 1H), 7.51-7.44 (m, 1H), 5.12-4.80 (m, 1H), 4.77-4.66 (m, 1H), 4.62-4.52 (m, 1H), 3.56-3.47 (m, 1H), 3.47-3.26 (m, 3H), 3.24-2.97 (m, 6H), 2.76-2.64 (m, 1H), 2.28-1.93 (m, 7H). OH proton not observed. $^{19}$F NMR (376 MHz, DMSO) δ –112.76, –175.67, –186.66. m/z: [ESI$^+$]540 (M+H)$^+$. ($C_{28}H_{33}Cl_2F_2N_5O_2S$).

Synthesis of 2-(2-fluoro-4-((2S,4S)-4-hydroxypyrrolidin-2-yl)phenyl)-N-(1-methylpiperidin-4-yl)benzo[d]imidazo[2,1-b]thiazole-7-carboxamide (Compound 522S)

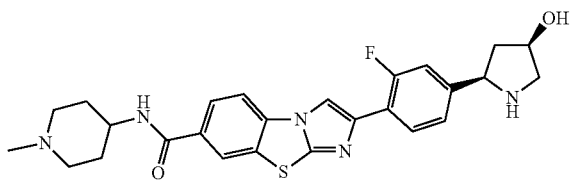 [SMILES: CN1CCC(NC(=O)c2ccc3c(c2)sc2nc(-c4ccc([C@H]5C[C@@H](O)CN5)cc4F)cn23)CC1]

Compound 2-(2-fluoro-4-((cis)-4-hydroxypyrrolidin-2-yl)phenyl)-N-(1-methylpiperidin-4-yl)benzo[d]imidazo[2,1-b]thiazole-7-carboxamide dihydrochloride was prepared from tert-butyl (cis)-2-(3-fluoro-4-(7-((1-methylpiperidin-4-yl)carbamoyl)benzo[d]imidazo[2,1-b]thiazol-2-yl)phenyl)-4-hydroxypyrrolidine-1-carboxylate (130 mg, 0.219 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 49 mg (40%). $^1$H NMR (400 MHz, DMSO) δ 10.78 (br s, 1H), 10.48 (br s, 1H), 9.21 (br s, 1H), 8.82 (d, J=3.6 Hz, 1H), 8.75 (d, J=7.6 Hz, 1H), 8.57 (d, J=1.6 Hz, 1H), 8.30 (d, J=8.4 Hz, 1H), 8.25-8.16 (m, 1H), 8.10 (dd, J=1.6, 8.4 Hz, 1H), 7.67-7.56 (m, 1H), 7.51-7.45 (m, 1H), 4.76-4.64 (m, 1H), 4.57-4.52 (m, 1H), 4.12-3.97 (m, 1H), 3.50-3.24 (m, 3H), 3.24-3.01 (m, 3H), 2.79-2.63 (m, 4H), 2.10-1.91 (m, 5H). OH proton not observed. $^{19}$F NMR (376 MHz, DMSO) δ–112.76. m/z: [ESI$^+$]494 (M+H)$^+$. ($C_{26}H_{30}Cl_2FN_5O_2S$).

Synthesis of 2-(2-fluoro-4-((cis)-4-hydroxypyrrolidin-2-yl)phenyl)-N-(tetrahydro-2H-pyran-4-yl)benzo[d]imidazo[2,1-b]thiazole-7-carboxamide (Compound 533)

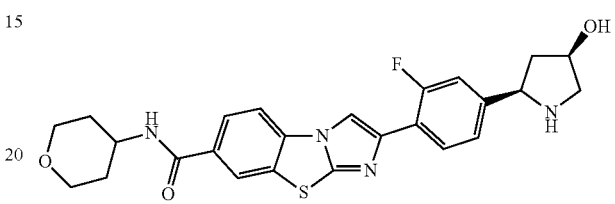

Compound 2-(2-fluoro-4-((cis)-4-hydroxypyrrolidin-2-yl)phenyl)-N-(tetrahydro-2H-pyran-4-yl)benzo[d]imidazo[2,1-b]thiazole-7-carboxamide hydrochloride was prepared from tert-butyl (cis)-2-(3-fluoro-4-(7-((tetrahydro-2H-pyran-4-yl)carbamoyl)benzo[d]imidazo[2,1-b]thiazol-2-yl)phenyl)-4-hydroxypyrrolidine-1-carboxylate (110 mg, 0.189 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 73 mg (75%). $^1$H NMR (400 MHz, DMSO) δ 10.24 (br s, 1H), 9.13 (br s, 1H), 8.80 (d, J=3.6 Hz, 1H), 8.53 (d, J=1.6 Hz, 1H), 8.48 (d, J=7.6 Hz, 1H), 8.30 (d, J=8.4 Hz, 1H), 8.24-8.17 (m, 1H), 8.06 (dd, J=1.6, 8.4 Hz, 1H), 7.59 (d, J=12.4 Hz, 1H), 7.47 (dd, J=1.6, 8.0 Hz, 1H), 4.76-4.63 (m, 1H), 4.60-4.49 (m, 1H), 4.10-3.96 (m, 1H), 3.95-3.84 (m, 2H), 3.47-3.23 (m, 3H), 3.23-3.12 (m, 1H), 2.75-2.63 (m, 1H), 2.54-2.37 (m, 1H), 2.09-1.97 (m, 1H), 1.84-1.73 (m, 2H), 1.68-1.55 (m, 2H). $^{19}$F NMR (376 MHz, DMSO) δ–112.76. m/z: [ESI$^+$]481 (M+H)$^+$. ($C_{25}H_{26}ClFN_4O_3S$).

Synthesis of 2-(2-fluoro-4-((cis)-4-methoxypyrrolidin-2-yl)phenyl)-N-(1-methylpiperidin-4-yl)benzo[d]imidazo[2,1-b]thiazole-7-carboxamide (Compound 532)

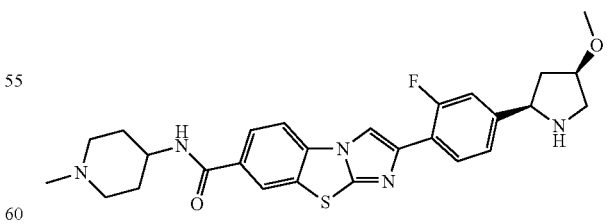

Compound 2-(2-fluoro-4-((cis)-4-methoxypyrrolidin-2-yl)phenyl)-N-(1-methylpiperidin-4-yl)benzo[d]imidazo[2,1-b]thiazole-7-carboxamide dihydrochloride was prepared from tert-butyl (cis)-2-(3-fluoro-4-(7-((1-methylpiperidin-4-yl)carbamoyl)benzo[d]imidazo[2,1-b]thiazol-2-yl)phenyl)-4-methoxypyrrolidine-1-carboxylate (90 mg, 0.148 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 15 mg (17%). $^1$H NMR (400 MHz, DMSO) δ 10.85 (br s, 2H), 9.35 (br s, 1H), 8.82-8.71 (m, 2H), 8.57 (d, J=1.6 Hz, 1H), 8.30 (d, J=8.4 Hz, 1H), 8.24-8.13 (m, 1H), 8.10 (dd, J=1.6, 8.4 Hz, 1H), 7.63-7.55 (m, 1H), 7.51-7.42 (m, 1H), 4.77-4.64 (m, 1H), 4.29-4.17 (m, 1H), 4.13-3.98 (m, 1H), 3.48-3.23 (m, 7H), 3.16-3.02 (m, 2H), 2.84-2.62 (m, 4H), 2.16-1.90 (m, 5H). $^{19}$F NMR (376 MHz, DMSO) δ−112.71. m/z: [ESI$^+$]508 (M+H)$^+$. ($C_{27}H_{32}Cl_2FN_5O_2S$).

Synthesis of 2-(2-fluoro-4-((2S,4R)-4-hydroxypyrrolidin-2-yl)phenyl)-N-(1-methylpiperidin-4-yl)benzo[d]imidazo[2,1-b]thiazole-7-carboxamide (Compound 522R)

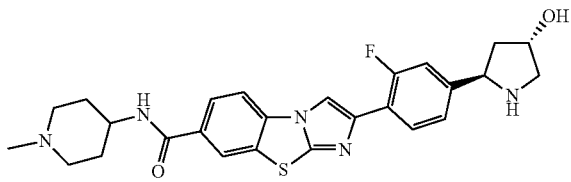 [SMILES: CN1CCC(NC(=O)c2ccc3c(c2)sc2nc(-c4ccc([C@H]5C[C@H](O)CN5)cc4F)cn23)CC1]

Compound 2-(2-fluoro-4-((trans)-4-hydroxypyrrolidin-2-yl)phenyl)-N-(1-methylpiperidin-4-yl)benzo[d]imidazo[2,1-b]thiazole-7-carboxamide dihydrochloride was prepared from tert-butyl (trans)-2-(3-fluoro-4-(7-((1-methylpiperidin-4-yl)carbamoyl)benzo[d]imidazo[2,1-b]thiazol-2-yl)phenyl)-4-hydroxypyrrolidine-1-carboxylate (100 mg, 0.168 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 46 mg (48%). $^1$H NMR (400 MHz, DMSO) δ 10.98 (br s, 1H), 10.57 (br s, 1H), 9.38 (br s, 1H), 8.84-8.76 (m, 2H), 8.58 (d, J=1.6 Hz, 1H), 8.38-8.27 (m, 1H), 8.22-8.16 (m, 1H), 8.11 (dd, J=1.6, 8.4 Hz, 1H), 7.67 (dd, J=1.6, 12.4 Hz, 1H), 7.51 (dd, J=1.6, 8.0 Hz, 1H), 4.89-4.77 (m, 1H), 4.61-4.51 (m, 1H), 4.25-3.99 (m, 1H), 3.67-3.54 (m, 1H), 3.47-3.23 (m, 2H), 3.19-3.02 (m, 3H), 2.79-2.68 (m, 3H), 2.35-2.20 (m, 2H), 2.08-1.96 (m, 4H). OH proton not observed. $^{19}$F NMR (376 MHz, DMSO) δ−112.70. m/z: [ESI$^+$]494 (M+H)$^+$. ($C_{26}H_{30}Cl_2FN_5O_2S$).

Synthesis of 2-(2-fluoro-4-(pyrrolidin-2-yl)phenyl)-N-(3-(4-fluoropiperidin-1-yl)propyl)imidazo[2',7':2,3]thiazolo[4,5-c]pyridine-7-carboxamide (Compound 501)

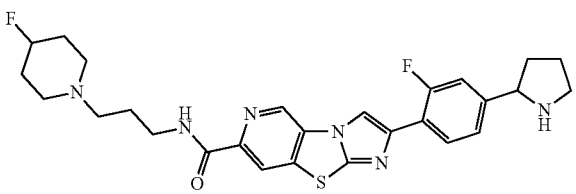

Compound 2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide dihydrochloride was prepared from tert-butyl 2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate (100 mg, 0.160 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 58 mg (61%). $^1$H NMR (400 MHz, DMSO) δ 10.80 (br s, 1H), 10.35 (br s, 1H), 9.50 (s, 1H), 9.22 (br s, 1H), 9.14 (t, J=6.4 Hz, 1H), 8.95 (d, J=3.6 Hz, 1H), 8.86 (s, 1H), 8.27-8.16 (m, 1H), 7.71-7.60 (m, 1H), 7.53-7.46 (m, 1H), 5.09-4.69 (m, 1H), 4.67-4.54 (m, 1H), 3.57-3.24 (m, 6H), 3.19-2.95 (m, 4H), 2.47-2.38 (m, 1H), 2.31-1.96 (m, 9H). $^{19}$F NMR (376 MHz, DMSO) δ−112.83, −175.58, −186.65. m/z: [ESI$^+$]525 (M+H)$^+$. ($C_{27}H_{32}Cl_2F_2N_6OS$).

Synthesis of (R)-2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide (Compound 509

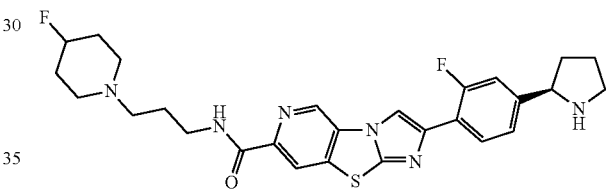

Compound (R)-2-(2-fluoro-4-(pyrrolidin-2-yl)phenyl)-N-(3-(4-fluoropiperidin-1-yl)propyl)imidazo[2,1':2,3]thiazolo[4,5-c]pyridine-7-carboxamide dihydrochloride was prepared from tert-butyl (R)-2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate (130 mg, 0.208 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 103 mg (83%). $^1$H NMR (400 MHz, DMSO) δ 10.80 (br s, 1H), 10.35 (br s, 1H), 9.50 (s, 1H), 9.22 (br s, 1H), 9.14 (t, J=6.4 Hz, 1H), 8.95 (d, J=3.6 Hz, 1H), 8.86 (s, 1H), 8.27-8.16 (m, 1H), 7.71-7.60 (m, 1H), 7.53-7.46 (m, 1H), 5.09-4.69 (m, 1H), 4.67-4.54 (m, 1H), 3.57-3.24 (m, 6H), 3.19-2.95 (m, 4H), 2.47-2.38 (m, 1H), 2.31-1.96 (m, 9H). $^{19}$F NMR (376 MHz, DMSO) δ−112.83, −175.58, −186.65. m/z: [ESI$^+$]525 (M+H)$^+$. ($C_{27}H_{32}Cl_2F_2N_6OS$). $[α]^{25}_D$=+6° (c=1 mg/mL, methanol).

Synthesis of (S)-2-(2-fluoro-4-(pyrrolidin-2-yl)phenyl)-N-(3-(4-fluoropiperidin-1-yl)propyl)imidazo[2',7':2,3]thiazolo[4,5-c]pyridine-7-carboxamide (Compound 5099)

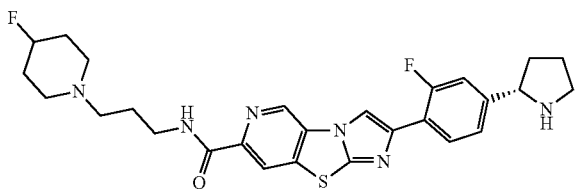 [SMILES: O=C(NCCCN1CCC(F)CC1)c1cc2sc3nc(-c4ccc([C@@H]5CCCN5)cc4F)cn3c2cn1]

Compound (S)-2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide dihydrochloride was prepared from tert-butyl (S)-2-(3-fluoro-4-(7-((3-(4-fluoropiperidin-1-yl)propyl)carbamoyl)imidazo[2',1':2,3]thiazolo[4,5-c]pyridin-2-yl)phenyl)pyrrolidine-1-carboxylate (150 mg, 0.240 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 129 mg (90%). $^1$H NMR (400 MHz, DMSO) δ 10.80 (br s, 1H), 10.35 (br s, 1H), 9.50 (s, 1H), 9.22 (br s, 1H), 9.14 (t, J=6.4 Hz, 1H), 8.95 (d, J=3.6 Hz, 1H), 8.86 (s, 1H), 8.27-8.16 (m, 1H), 7.71-7.60 (m, 1H), 7.53-7.46 (m, 1H), 5.09-4.69 (m, 1H), 4.67-4.54 (m, 1H), 3.57-3.24 (m, 6H), 3.19-2.95 (m, 4H), 2.47-2.38 (m, 1H), 2.31-1.96 (m, 9H). $^{19}$F NMR (376 MHz, DMSO) δ−112.83, −175.58, −186.65. m/z: [ESI$^+$]525 (M+H)$^+$. ($C_{27}H_{32}Cl_2F_2N_6OS$). $[α]^{25}_D=-2°$ (c=1 mg/mL, methanol).

Synthesis of 2-(2-fluoro-4-(pyrrolidin-2-yl)phenyl)imidazo[2',7':2,3]thiazolo[4,5-c]pyridine-7-carboxamide (Compound 514)

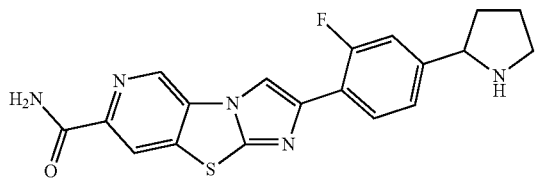 [SMILES: NC(=O)c1cc2sc3nc(-c4ccc(C5CCCN5)cc4F)cn3c2cn1]

Compound 2-(2-fluoro-4-(pyrrolidin-2-yl)phenyl)imidazo[2',1':2,3]thiazolo[4,5-c]pyridine-7-carboxamide hydrochloride was prepared from tert-butyl 2-(4-(7-carbamoylimidazo[2',1':2,3]thiazolo[4,5-c]pyridin-2-yl)-3-fluorophenyl)pyrrolidine-1-carboxylate (90 mg, 0.187 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 41 mg (53%). $^1$H NMR (400 MHz, DMSO) δ 10.29 (br s, 1H), 9.46 (s, 1H), 9.17 (br s, 1H), 8.93 (d, J=3.6 Hz, 1H), 8.83 (s, 1H), 8.26 (br s, 1H), 8.24-8.16 (m, 1H), 7.74 (br s, 1H), 7.68-7.59 (m, 1H), 7.51-7.44 (m, 1H), 4.67-4.54 (m, 1H), 3.48-3.24 (m, 2H), 2.45-2.37 (m, 1H), 2.18-1.99 (m, 3H). $^{19}$F NMR (376 MHz, DMSO) δ−112.77. m/z: [ESI$^+$]382 (M+H)$^+$. ($C_{19}H_{17}ClFN_5OS$).

Synthesis of 2-(2-fluoro-4-(pyrrolidin-2-yl)phenyl)-N-methylimidazo[2',1':2,3]thiazolo[4,5-c]pyridine-7-carboxamide (Compound 515)

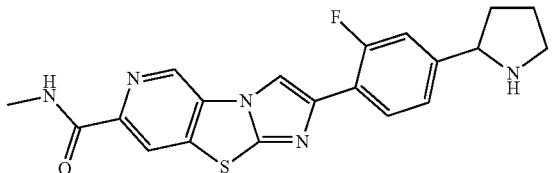

Compound 2-(2-fluoro-4-(pyrrolidin-2-yl)phenyl)-N-methylimidazo[2',1':2,3]thiazolo[4,5-c]pyridine-7-carboxamide hydrochloride was prepared from tert-butyl 2-(3-fluoro-4-(7-(methylcarbamoyl)imidazo[2',1':2,3]thiazolo[4,5-c]pyridin-2-yl)phenyl)pyrrolidine-1-carboxylate (90 mg, 0.182 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a yellow solid.

Yield 48 mg (61%). $^1$H NMR (400 MHz, DMSO) δ 10.09 (br s, 1H), 9.47 (s, 1H), 9.08 (br s, 1H), 8.93 (d, J=3.6 Hz, 1H), 8.90 (q, J=4.8 Hz, 1H), 8.84 (s, 1H), 8.28-8.16 (m, 1H), 7.68-7.56 (m, 1H), 7.53-7.41 (m, 1H), 4.66-4.53 (m, 1H), 3.47-3.24 (m, 2H), 2.87 (d, J=4.8 Hz, 3H), 2.47-2.36 (m, 1H), 2.20-1.96 (m, 3H). $^{19}$F NMR (376 MHz, DMSO) δ−113.99. m/z: [ESI$^+$]396 (M+H)$^+$. ($C_{20}H_{19}ClFN_5OS$).

Synthesis of 2-(2-fluoro-4-(pyrrolidin-3-yl)phenyl)-N-(1-methylpiperidin-4-yl)benzo[d]imidazo[2,1-b]thiazole-7-carboxamide (Compound 505)

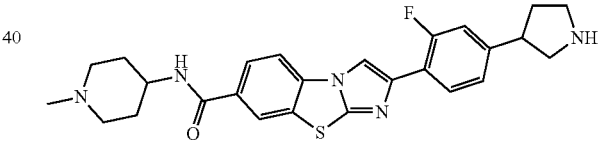

Compound 2-(2-fluoro-4-(pyrrolidin-3-yl)phenyl)-N-(1-methylpiperidin-4-yl)benzo[d]imidazo[2,1-b]thiazole-7-carboxamide diformate was prepared from tert-butyl 3-(3-fluoro-4-(7-((1-methylpiperidin-4-yl)carbamoyl)benzo[d]imidazo[2,1-b]thiazol-2-yl)phenyl)pyrrolidine-1-carboxylate (150 mg, 0.260 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride, and was purified by reverse phase flash chromatography using the following conditions; Column: Xselect CSH OBD Column 30×150 mm, 5 μm; Mobile Phase A: water (plus 0.1% formic acid), Mobile Phase B: acetonitrile; Flow rate: 60 mL/min; Gradient: 3%-5% B in 10 min; UV Detector: 254 nm/220 nm nm. The desired peak was concentrated and lyophilized to give the title compound as a light yellow solid.

Yield 19 mg (13%). $^1$H NMR (400 MHz, DMSO) δ 8.72 (d, J=3.6 Hz, 1H), 8.51 (s, 1H), 8.43 (d, J=7.6 Hz, 1H), 8.34 (s, 2H, HCO of formic acid), 8.27 (d, J=8.4 Hz, 1H), 8.15-8.07 (m, 1H), 8.04 (d, J=8.4 Hz, 1H), 7.38 (d, J=12.8 Hz, 1H), 7.28 (d, J=8.0 Hz, 1H), 3.85-3.73 (m, 1H), 3.64-

3.54 (m, 1H), 3.53-3.42 (m, 1H), 3.42-3.32 (m, 1H), 3.25-3.14 (m, 1H), 3.14-3.05 (m, 1H), 2.90-2.79 (m, 2H), 2.42-2.29 (m, 1H), 2.22 (s, 3H), 2.12-2.02 (m, 2H), 2.02-1.90 (m, 1H), 1.87-1.76 (m, 2H), 1.71-1.56 (m, 2H). two OH of formic acid and NH of pyrrolidine not observed. $^{19}$F NMR (376 MHz, DMSO) δ−113.34. m/z: [ESI$^+$]478 (M+H)$^+$. ($C_{28}H_{32}FN_5O_5S$).

Synthesis of 2-(4-(4,4-difluoropyrrolidin-2-yl)-2-fluorophenyl)-N-(3-(4-fluoropiperidin-1-yl)propyl)benzo[d]imidazo[2,1-b]thiazole-7-carboxamide (Compound 490)

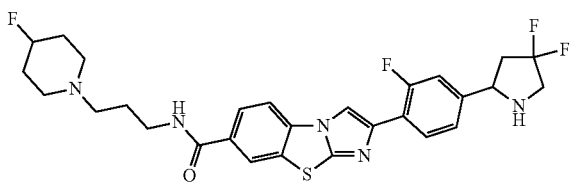 [SMILES: O=C(NCCCN1CCC(F)CC1)c1ccc2c(c1)sc1nc(-c3ccc(C4CC(F)(F)CN4)cc3F)cn12]

Compound 2-(4-(4,4-difluoropyrrolidin-2-yl)-2-fluorophenyl)-N-(3-(4-fluoropiperidin-1-yl)propyl)benzo[d]imidazo[2,1-b]thiazole-7-carboxamide was prepared from tert-butyl 4,4-difluoro-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (35 mg, 0.053 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride, and was purified by Prep-HPLC using the following conditions; Column: XBridge Prep OBD C18 Column, 30×150 mm, 5 μm; Mobile Phase A: water (10 mmol/L ammonium bicarbonate), Mobile Phase B: acetonitrile; Flow rate: 60 mL/min; Gradient: 35%-45% B in 20 min; UV Detector: 254/220 nm. The desired peak was concentrated and lyophilized to give the title compound as a white solid.

Yield 4 mg (13%). $^1$H NMR (400 MHz, DMSO) δ 8.71 (d, J=3.6 Hz, 1H), 8.61 (t, J=5.6 Hz, 1H), 8.49 (d, J=1.6 Hz, 1H), 8.27 (d, J=8.4 Hz, 1H), 8.15-8.08 (m, 1H), 8.02 (dd, J=1.6, 8.4 Hz, 1H), 7.42-7.32 (m, 2H). 4.77-4.56 (m, 1H), 4.40-4.32 (m, 1H), 3.38-3.26 (m, 3H), 3.25-3.11 (m, 1H), 2.77-2.62 (m, 1H), 2.51-2.43 (m, 3H), 2.38-2.27 (m, 4H), 2.20-2.05 (m, 1H), 1.91-1.65 (m, 6H). $^{19}$F NMR (376 MHz, DMSO) δ (−93.41, −94.01, −94.19, −94.78), −113.63. Piperidine $^{19}$F not observed. m/z: [ESI$^+$]560 (M+H)$^+$. ($C_{28}H_{29}F_4N_5OS$).

Synthesis of 2-(2-fluoro-4-((cis)-4-methoxypyrrolidin-2-yl)phenyl)-N-(3-(4-fluoropiperidin-1-yl)propyl)benzo[d]imidazo[2,1-b]thiazole-7-carboxamide (Compound 523)

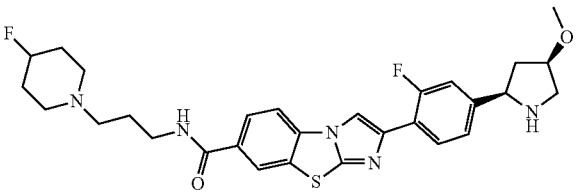 [SMILES: CO[C@H]1CN[C@@H](c2ccc(-c3cn4c(n3)sc3cc(C(=O)NCCCN5CCC(F)CC5)ccc34)c(F)c2)C1]

Compound 2-(2-fluoro-4-((cis)-4-methoxypyrrolidin-2-yl)phenyl)-N-(3-(4-fluoropiperidin-1-yl)propyl)benzo[d]imidazo[2,1-b]thiazole-7-carboxamide was prepared from tert-butyl (cis)-2-(3-fluoro-4-(7-((3-(4-fluoropiperidin-1-yl)propyl)carbamoyl)benzo[d]imidazo[2,1-b]thiazol-2-yl)phenyl)-4-methoxypyrrolidine-1-carboxylate (90 mg, 0.138 mmol), following a similar procedure to that described for the synthesis of 2-(4-(4,4-difluoropyrrolidin-2-yl)-2-fluorophenyl)-N-(3-(4-fluoropiperidin-1-yl)propyl)benzo[d]imidazo[2,1-b]thiazole-7-carboxamide and was isolated as a white solid.

Yield 15 mg (20%). $^1$H NMR (400 MHz, DMSO) δ 8.72 (d, J=3.6 Hz, 1H), 8.63 (t, J=5.6 Hz, 1H), 8.50 (d, J=1.6 Hz, 1H), 8.27 (d, J=8.4 Hz, 1H), 8.17-8.07 (m, 1H), 8.01 (dd, J=1.6, 8.4 Hz, 1H), 7.42-7.30 (m, 2H), 4.78-4.57 (m, 1H), 4.30-4.22 (m, 1H), 4.08-4.00 (m, 1H), 3.32-3.29 (m, 2H), 3.24 (s, 3H), 3.17-3.02 (m, 2H), 2.62-2.52 (m, 2H), 2.42-2.25 (m, 5H), 1.93-1.78 (m, 2H), 1.76-1.63 (m, 5H). NH proton of pyrrolidine not observed. $^{19}$F NMR (376 MHz, DMSO) δ−113.53. Aliphatic $^{19}$F not observed. m/z: [ESI$^+$] 554 (M+H)$^+$. ($C_{29}H_{33}F_2N_5O_2S$).

Synthesis of 2-(2-fluoro-4-(pyrrolidin-2-yl)phenyl)-N-(1-methylazetidin-3-yl)benzo[d]imidazo[2,1-b]thiazole-7-carboxamide (Compound 506)

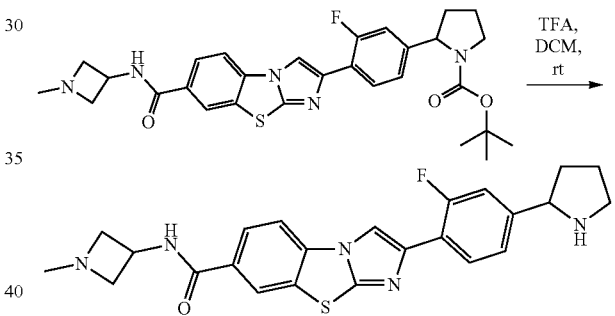

A solution of tert-butyl 2-(3-fluoro-4-(7-((1-methylazetidin-3-yl)carbamoyl)benzo[d]imidazo[2,1-b]thiazol-2-yl)phenyl)pyrrolidine-1-carboxylate (80 mg, 0.146 mmol) in 2,2,2-trifluoroacetic acid/dichloromethane (4:1, 2.5 mL) was stirred for 30 min at room temperature. The reaction solution was concentrated under reduced pressure. The residue was purified by Prep-HPLC using the following conditions; Column: XBridge Prep OBD C18 Column, 30×150 mm, 5 μm; Mobile Phase A: water (plus 10 mmol/L ammonium bicarbonate), Mobile Phase B: acetonitrile; Flow rate: 60 mL/min mL/min; Gradient: 12%-22% B in 7.8 min; UV Detector: 254 nm/220 nm nm. The fractions containing desired product were collected, concentrated under reduced pressure and lyophilized to afford 2-(2-fluoro-4-(pyrrolidin-2-yl)phenyl)-N-(1-methylazetidin-3-yl)benzo[d]imidazo[2,1-b]thiazole-7-carboxamide as a white solid.

Yield 25 mg (38%). $^1$H NMR (400 MHz, DMSO) δ 8.94-8.86 (m, 1H), 8.68 (d, J=3.6 Hz, 1H), 8.54-8.46 (m, 1H), 8.31-8.23 (m, 1H), 8.12-7.99 (m, 2H), 7.35-7.25 (m, 2H), 4.54-4.41 (m, 1H), 4.15-4.06 (m, 1H), 3.62-3.54 (m, 2H), 3.06-2.96 (m, 3H), 2.95-2.87 (m, 1H), 2.27 (s, 3H), 2.21-2.10 (m, 1H), 1.86-1.67 (m, 2H), 1.58-1.44 (m, 1H). Pyrrolidine NH proton not observed. $^{19}$F NMR (376 MHz, DMSO) δ−114.03. m/z: [ESI$^+$]450 (M+H)$^+$. ($C_{24}H_{24}FN_5OS$).

Synthesis of (S)-2-(2-fluoro-4-(5-oxopyrrolidin-2-yl)phenyl)-N-(3-(4-fluoropiperidin-1-yl)propyl)benzo[d]imidazo[2,1-b]thiazole-7-carboxamide
(Compound 432S)

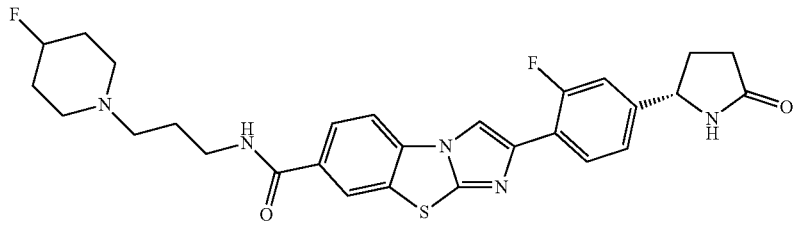 [SMILES: O=C1CC[C@@H](c2ccc(-c3cn4c(n3)sc3cc(C(=O)NCCCN5CCC(F)CC5)ccc34)c(F)c2)N1]

A solution of (S)-2-(2-fluoro-4-(5-oxopyrrolidin-2-yl)phenyl)benzo[d]imidazo[2,1-b]thiazole-7-carboxylic acid (140 mg, 0.354 mmol) in N,N-dimethylacetamide (5 mL), was treated with O-(7-azabenzotriazol-1-yl)-N,N,N',N'-tetramethyluronium hexafluorophosphate (HATU) (202 mg, 0.531 mmol) for 10 min, at room temperature, under a nitrogen atmosphere. 3-(4-fluoropiperidin-1-yl)propan-1-amine (68 mg, 0.424 mmol) and N,N-diisopropylethylamine (137 mg, 1.060 mmol) were added portionwise. The resulting mixture was stirred for 2 h. The reaction mixture was purified directly by reverse phase column chromatography using the following conditions; Column: C18 Column 40 g; Mobile Phase A: water (plus 10 mmol/L ammonium bicarbonate), Mobile Phase B: acetonitrile; Flow rate: 35 mL/min; Gradient: 20%-40% B in 25 min; UV Detector: 254/215 nm. The fractions containing the desired product were collected at 27% B, concentrated under reduced pressure and lyophilized to afford (S)-2-(2-fluoro-4-(5-oxopyrrolidin-2-yl)phenyl)-N-(3-(4-fluoropiperidin-1-yl)propyl)benzo[d]imidazo[2,1-b]thiazole-7-carboxamide as a white solid.

Yield 14 mg (7%). $^1$H NMR (400 MHz, DMSO) δ 8.72 (d, J=3.6 Hz, 1H), 8.61 (t, J=5.6 Hz, 1H), 8.49 (d, J=1.6 Hz, 1H), 8.27 (d, J=8.4 Hz, 1H), 8.20-8.10 (m, 2H), 8.07-7.98 (m, 1H), 7.32-7.21 (m, 2H), 4.79-4.55 (m, 2H), 3.39-3.32 (m, 2H), 2.59-2.52 (m, 3H), 2.41-2.33 (m, 2H), 2.33-2.22 (m, 4H), 1.93-1.77 (m, 3H), 1.77-1.62 (m, 4H). $^{19}$F NMR (376 MHz, DMSO) δ−113.26. Aliphatic $^{19}$F not observed. m/z: [ESI$^+$]538 (M+H)$^+$. ($C_{28}H_{29}F_2N_5O_2S$)

Synthesis of (R)-2-(2-fluoro-4-(5-oxopyrrolidin-2-yl)phenyl)-N-(3-(4-fluoropiperidin-1-yl)propyl)benzo[d]imidazo[2,1-b]thiazole-7-carboxamide
(Compound 432R)

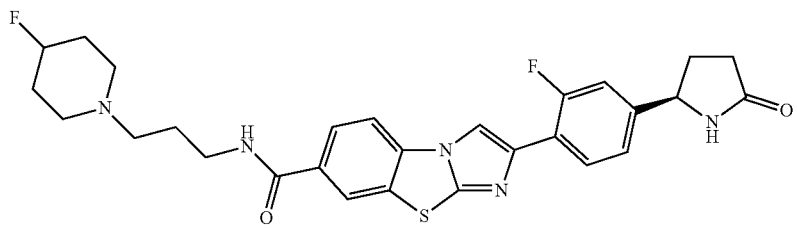 [SMILES: O=C1CC[C@H](c2ccc(-c3cn4c(n3)sc3cc(C(=O)NCCCN5CCC(F)CC5)ccc34)c(F)c2)N1]

Compound (R)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide was prepared from (R)-2-(2-fluoro-4-(5-oxopyrrolidin-2-yl)phenyl)benzo[d]imidazo[2,1-b]thiazole-7-carboxylic acid (100 mg, 0.253 mmol) and 3-(4-fluoropiperidin-1-yl)propan-1-amine (61 mg, 0.381 mmol), following a similar procedure to that described for the synthesis of (S)-2-(2-fluoro-4-(5-oxopyrrolidin-2-yl)phenyl)-N-(3-(4-fluoropiperidin-1-yl)propyl)benzo[d]imidazo[2,1-b]thiazole-7-carboxamide and was isolated as a white solid.

Yield 12 mg (9%). $^1$H NMR (400 MHz, DMSO) δ 8.72 (d, J=3.6 Hz, 1H), 8.61 (t, J=5.6 Hz, 1H), 8.49 (d, J=1.6 Hz, 1H), 8.27 (d, J=8.4 Hz, 1H), 8.20-8.10 (m, 2H), 8.07-7.98 (m, 1H), 7.32-7.21 (m, 2H), 4.79-4.55 (m, 2H), 3.39-3.32 (m, 2H), 2.59-2.52 (m, 3H), 2.41-2.33 (m, 2H), 2.33-2.22 (m, 4H), 1.93-1.77 (m, 3H), 1.77-1.62 (m, 4H). $^{19}$F NMR (376 MHz, DMSO) δ–113.26. Aliphatic $^{19}$F not observed. m/z: [ESI$^+$]538 (M+H)$^+$. (C$_{28}$H$_{29}$F$_2$N$_5$O$_2$S)

Example 7

Synthetic Details of Additional Compounds of the Invention (Schemes 82-85)
Intermediate Preparations Synthesis of tert-butyl 4-fluoro-4-(3-fluoro-4-(7-((1-methylpiperidin-4-yl)carbamoyl)benzo[d]imidazo[2,1-b]thiazol-2-yl)phenyl)piperidine-1-carboxylate Scheme 82.

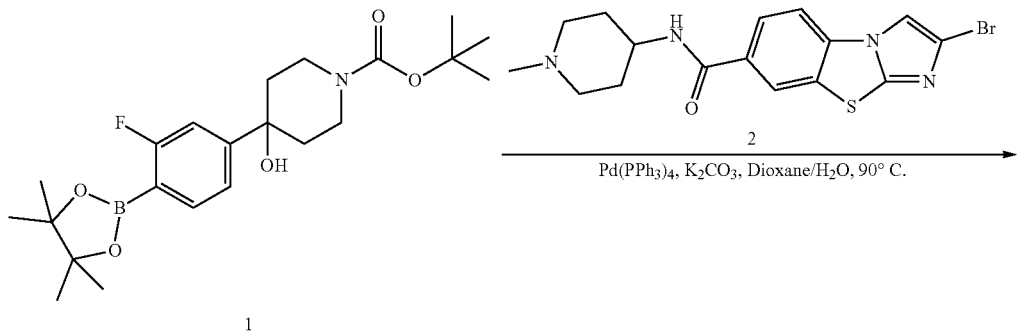

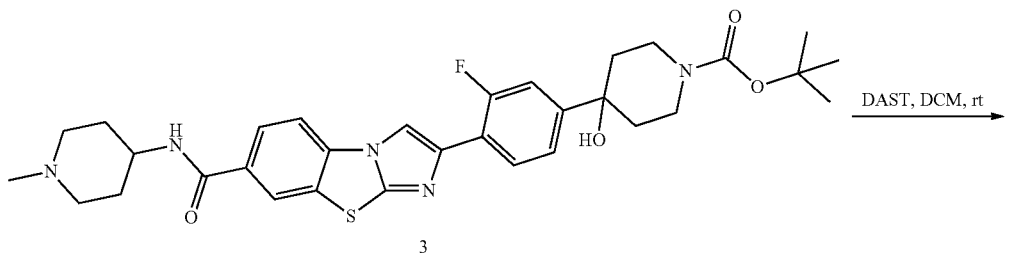

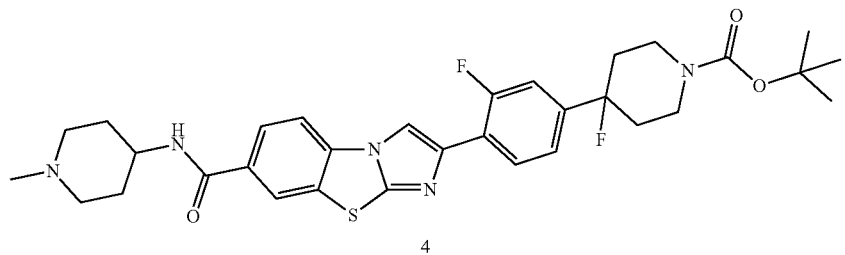

Synthesis of tert-butyl 4-(3-fluoro-4-(7-((1-methylpiperidin-4-yl)carbamoyl)benzo[d]imidazo[2,1-b]thiazol-2-yl)phenyl)-4-hydroxypiperidine-1-carboxylate (3, Scheme 82)

Compound tert-butyl 4-(3-fluoro-4-(7-((1-methylpiperidin-4-yl)carbamoyl)benzo[d]imidazo[2,1-b]thiazol-2-yl)phenyl)-4-hydroxypiperidine-1-carboxylate was prepared from 2-bromo-N-(1-methylpiperidin-4-yl)benzo[d]imidazo[2,1-b]thiazole-7-carboxamide (300 mg, 0.763 mmol) and tert-butyl 4-(3-fluoro-4-(4,4,5,5-tetramethyl-1,3,2-dioxaborolan-2-yl)phenyl)-4-hydroxypiperidine-1-carboxylate (400 mg, crude) at 90° C., following a similar procedure to that described for the synthesis of tert-butyl 4-(4-bromo-3-fluorophenyl)-3,6-dihydropyridine-1(2H)-carboxylate and was isolated as a yellow solid.

Yield 260 mg (56%). 1H NMR (300 MHz, CDCl$_3$) δ 8.48-8.40 (m, 1H), 8.28-8.18 (m, 1H), 8.17-8.06 (m, 2H), 7.95-7.84 (m, 1H), 7.71-7.60 (m, 1H), 7.26-7.16 (m, 2H), 4.41-4.25 (m, 1H), 4.25-4.08 (m, 2H), 3.59-3.48 (m, 2H), 3.27-3.12 (m, 2H), 3.00-2.86 (m, 2H), 2.81 (s, 3H), 2.50-2.32 (m, 2H), 2.32-2.17 (m, 2H), 2.14-1.90 (m, 4H), 1.53 (s, 9H). OH proton not observed. m/z: [ESI$^+$]608 (M+H)$^+$.

Synthesis of tert-butyl 4-fluoro-4-(3-fluoro-4-(7-((1-methylpiperidin-4-yl)carbamoyl)benzo[d]imidazo[2,1-b]thiazol-2-yl)phenyl)piperidine-1-carboxylate (4, Scheme 82)

To a stirred solution of tert-butyl 4-(3-fluoro-4-(7-((1-methylpiperidin-4-yl)carbamoyl)benzo[d]imidazo[2,1-b]thiazol-2-yl)phenyl)-4-hydroxypiperidine-1-carboxylate (160 mg, 0.263 mmol) in dichloromethane (5 mL), was added diethylaminosulfur trifluoride (90 mg, 0.558 mmol) dropwise, at 0° C., under a nitrogen atmosphere. The reaction solution was stirred for 1 h at room temperature. The reaction was quenched by addition of 1 N aqueous sodium bicarbonate solution (1 mL). After separation, the organic phase was purified directly by Prep-TLC (dichloromethane/methanol=10:1) to afford the crude product. Further purification was carried out by PREP-ACHIRAL-SFC using the following conditions; Column: GreenSep Naphthyl, 3×25 cm, 5 μm; Mobile Phase A: carbon dioxide, Mobile Phase B: methanol (plus 0.1% 2 M ammonia-methanol); Flow rate: 75 mL/min; Gradient: isocratic 40% B; Column Temperature (° C.): 35; Back Pressure (bar): 100; UV Detector: 254 nm. The fractions containing the desired product were collected and concentrated under reduced pressure, to afford tert-butyl 4-fluoro-4-(3-fluoro-4-(7-((1-methylpiperidin-4-yl)carbamoyl)benzo[d]imidazo[2,1-b]thiazol-2-yl)phenyl)piperidine-1-carboxylate as a white solid.

Yield 40 mg (25%). $^1$H NMR (300 MHz, DMSO) δ 8.75 (d, J=3.6 Hz, 1H), 8.50 (d, J=1.5 Hz, 1H), 8.39 (d, J=7.5 Hz, 1H), 8.28 (d, J=8.4 Hz, 1H), 8.21-8.12 (m, 1H), 8.04 (dd, J=1.5, 8.4 Hz, 1H), 7.47-7.35 (m, 2H), 4.07-3.94 (m, 2H), 3.84-3.67 (m, 1H), 3.14-2.99 (m, 2H), 2.84-2.70 (m, 2H), 2.17 (s, 3H), 2.16-2.05 (m, 1H), 2.02-1.87 (m, 5H), 1.86-1.73 (m, 2H), 1.68-1.51 (m, 2H), 1.44 (s, 9H). m/z: [ESI$^+$] 610 (M+H)$^+$.

Synthesis of tert-butyl 3-(3-fluoro-4-(7-((tetrahydro-2H-pyran-4-yl)carbamoyl)benzo[d]imidazo[2,1-b]thiazol-2-yl)phenyl)morpholine-4-carboxylate Compound tert-butyl 3-(3-fluoro-4-(7-((tetrahydro-2H-pyran-4-yl)carbamoyl)benzo[d]imidazo[2,1-b]thiazol-2-yl)phenyl)morpholine-4-carboxylate was prepared from 2-bromo-N-(tetrahydro-2H-pyran-4-yl)benzo[d]imidazo[2,1-b]thiazole-7-carboxamide (200 mg, 0.526 mmol) and tert-butyl 3-(3-fluoro-4-(4,4,5,5-tetramethyl-1,3,2-dioxaborolan-2-yl)phenyl)morpholine-4-carboxylate (250 mg, crude) at 90° C., following a similar procedure to that described for the synthesis of tert-butyl 4-(4-bromo-3-fluorophenyl)-3,6-dihydropyridine-1(2H)-carboxylate and was isolated as a light yellow solid.

Yield 260 mg (85%). $^1$H NMR (300 MHz, DMSO) δ 8.78-8.69 (m, 1H), 8.55-8.41 (m, 2H), 8.33-8.22 (m, 1H), 8.20-8.09 (m, 1H), 8.09-7.98 (m, 1H), 7.35-7.23 (m, 2H), 5.07-4.95 (m, 1H), 4.36-4.24 (m, 1H), 4.14-3.66 (m, 7H), 3.57-3.35 (m, 2H), 3.20-2.99 (m, 1H), 1.85-1.72 (m, 2H), 1.69-1.51 (m, 2H), 1.42 (s, 9H). m/z. [ESI$^+$]581 (M+H)$^+$.

Synthesis of tert-butyl 4-(3-fluoro-4-(7-((3-(4-fluoropiperidin-1-yl)propyl)carbamoyl)benzo[d]imidazo[2,1-b]thiazol-2-yl)phenyl)-2,2-dimethyloxazolidine-3-carboxylate Scheme 83.

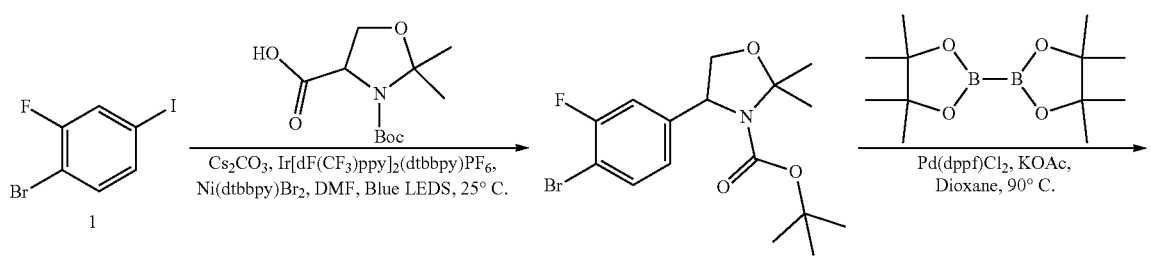

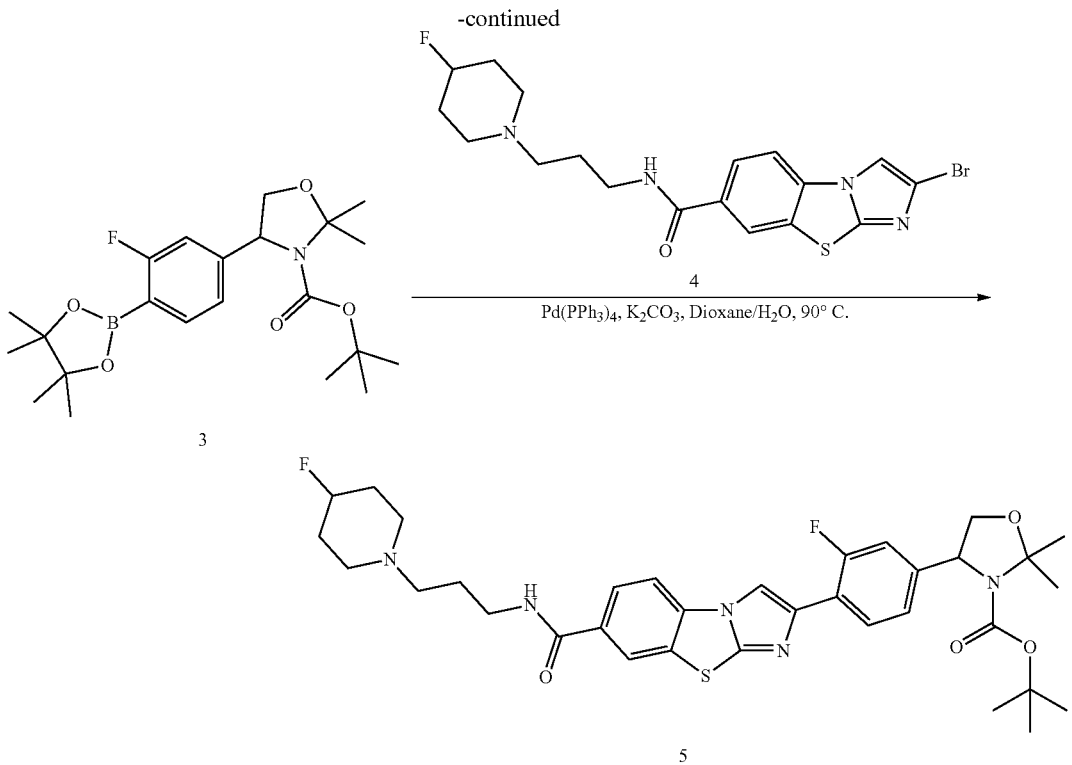

Synthesis of tert-butyl 4-(4-bromo-3-fluorophenyl)-2,2-dimethyloxazolidine-3-carboxylate (2, Scheme 83)

Compound tert-butyl 4-(4-bromo-3-fluorophenyl)-2,2-dimethyloxazolidine-3-carboxylate was prepared from 1-bromo-2-fluoro-4-iodobenzene (2.00 g, 6.65 mmol) and 3-(tert-butoxycarbonyl)-2,2-dimethyloxazolidine-4-carboxylic acid (2.00 g, 8.15 mmol), following a similar procedure to that described for the synthesis of tert-butyl 3-(4-bromo-3-fluorophenyl)morpholine-4-carboxylate and was isolated as a yellow oil.

Yield 0.50 g (20%). $^1$H NMR (300 MHz, CDCl$_3$) δ 7.56-7.47 (m, 1H), 7.18-7.07 (m, 1H), 7.06-6.97 (m, 1H), 4.96-4.73 (m, 1H), 4.34-4.26 (m, 1H), 3.90-3.82 (m, 1H), 1.76 (s, 3H), 1.61 (s, 3H), 1.50-1.25 (m, 9H). m/z: [ESI$^+$] 318, 320 (M+H-56)$^+$.

Synthesis of tert-butyl 4-(3-fluoro-4-(4,4,5,5-tetramethyl-1,3,2-dioxaborolan-2-yl)phenyl)-2,2-dimethyloxazolidine-3-carboxylate (3, Scheme 83)

Compound tert-butyl 4-(3-fluoro-4-(4,4,5,5-tetramethyl-1,3,2-dioxaborolan-2-yl)phenyl)-2,2-dimethyloxazolidine-3-carboxylate was prepared from tert-butyl 4-(4-bromo-3-fluorophenyl)-2,2-dimethyloxazolidine-3-carboxylate (500 mg, 1.336 mmol) and bis(pinacolato)diboron (500 mg, 1.969 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid. The compound was used directly in the next step without further purification.

Yield 500 mg (crude). $^1$H NMR not run. m/z: [ESI$^+$]366 (M+H-56)$^+$.

Synthesis of tert-butyl 4-(3-fluoro-4-(7-((3-(4-fluoropiperidin-1-yl)propyl)carbamoyl)benzo[d]imidazo[2,1-b]thiazol-2-yl)phenyl)-2,2-dimethyloxazolidine-3-carboxylate (5, Scheme 83)

Compound tert-butyl 4-(3-fluoro-4-(7-((3-(4-fluoropiperidin-1-yl)propyl)carbamoyl)benzo[d]imidazo[2,1-b]thiazol-2-yl)phenyl)-2,2-dimethyloxazolidine-3-carboxylate was prepared from 2-bromo-N-(3-(4-fluoropiperidin-1-yl)propyl)benzo[d]imidazo[2,1-b]thiazole-7-carboxamide (300 mg, 0.683 mmol) and tert-butyl 4-(3-fluoro-4-(4,4,5,5-tetramethyl-1,3,2-dioxaborolan-2-yl)phenyl)-2,2-dimethyloxazolidine-3-carboxylate (500 mg, crude) at 90° C., following a similar procedure to that described for the synthesis of tert-butyl 4-(4-bromo-3-fluorophenyl)-3,6-dihydropyridine-1(2H)-carboxylate and was isolated as a white solid.

Yield 200 mg (45%). $^1$H NMR (400 MHz, CDCl$_3$) δ 8.46 (s, 1H), 8.27 (s, 1H), 8.24-8.15 (m, 2H), 7.92 (d, J=8.4 Hz, 1H), 7.70 (d, J=8.4 Hz, 1H), 7.25-7.10 (m, 2H), 5.02-4.66 (m, 2H), 4.38-4.28 (m, 1H), 3.99-3.88 (m, 1H), 3.68-3.60 (m, 2H), 2.78-2.45 (m, 6H), 2.06-1.73 (m, 6H), 1.83 (s, 3H), 1.64 (s, 3H), 1.52-1.24 (m, 9H). m/z: [ESI$^+$]654 (M+H)$^+$.

Synthesis of tert-butyl 2-(3-fluoro-4-(7-((tetrahydro-2H-pyran-4-yl)carbamoyl)benzo[d]imidazo[2,1-b]thiazol-2-yl)phenyl)morpholine-4-carboxylate Compound tert-butyl 2-(3-fluoro-4-(7-((tetrahydro-2H-pyran-4-yl)carbamoyl)benzo[d]imidazo[2,1-b]thiazol-2-yl)phenyl)morpholine-4-carboxylate was prepared from 2-bromo-N-(tetrahydro-2H-pyran-4-yl)benzo[d]imidazo[2,1-b]thiazole-7-carboxamide (206 mg, 0.542 mmol) and tert-butyl 2-(3-fluoro-4-(4,4,5,5-tetramethyl-1,3,2-dioxaborolan-2-yl)phenyl)morpholine-4-carboxylate (250 mg, crude) at 90° C., following a similar procedure to that described for the synthesis of tert-butyl 4-(4-bromo-3-fluorophenyl)-3,6-dihydropyridine-1(2H)-carboxylate and was isolated as an off-white solid.

Yield 161 mg (51%). ¹H NMR not run. m/z: [ESI⁺]581 (M+H)⁺.

Synthesis of tert-butyl 2-(3-fluoro-4-(7-((tetrahydro-2H-pyran-4-yl)carbamoyl)benzo[d]imidazo[2,1-b]thiazol-2-yl)phenyl)-4-oxopyrrolidine-1-carboxylate Compound tert-butyl 2-(3-fluoro-4-(7-((tetrahydro-2H-pyran-4-yl)carbamoyl)benzo[d]imidazo[2,1-b]thiazol-2-yl)phenyl)-4-oxopyrrolidine-1-carboxylate was prepared from 2-bromo-N-(tetrahydro-2H-pyran-4-yl)benzo[d]imidazo[2,1-b]thiazole-7-carboxamide (280 mg, 0.736 mmol) and tert-butyl 2-(3-fluoro-4-(4,4,5,5-tetramethyl-1,3,2-dioxaborolan-2-yl)phenyl)-4-oxopyrrolidine-1-carboxylate (380 mg, crude) at 90° C., following a similar procedure to that described for the synthesis of tert-butyl 4-(4-bromo-3-fluorophenyl)-3,6-dihydropyridine-1(2H)-carboxylate and was isolated as a yellow solid.

Yield 60 mg (14%). ¹H NMR (300 MHz, CDCl₃) δ 8.26-8.14 (m, 3H), 7.87 (d, J=8.4 Hz, 1H), 7.69 (d, J=8.4 Hz, 1H), 7.09 (d, J=7.8 Hz, 1H), 7.00 (d, J=12.0 Hz, 1H), 6.18-6.10 (m, 1H), 5.51-5.33 (m, 1H), 4.35-4.20 (m, 1H), 4.19-3.90 (m, 4H), 3.66-3.51 (m, 2H), 3.27-3.12 (m, 1H), 2.70-2.56 (m, 1H), 2.12-2.02 (m, 2H), 1.73-1.54 (m, 2H), 1.43 (s, 9H). m/z: [ESI⁺]579 (M+H)⁺.

Synthesis of tert-butyl 4-(difluoromethyl)-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate

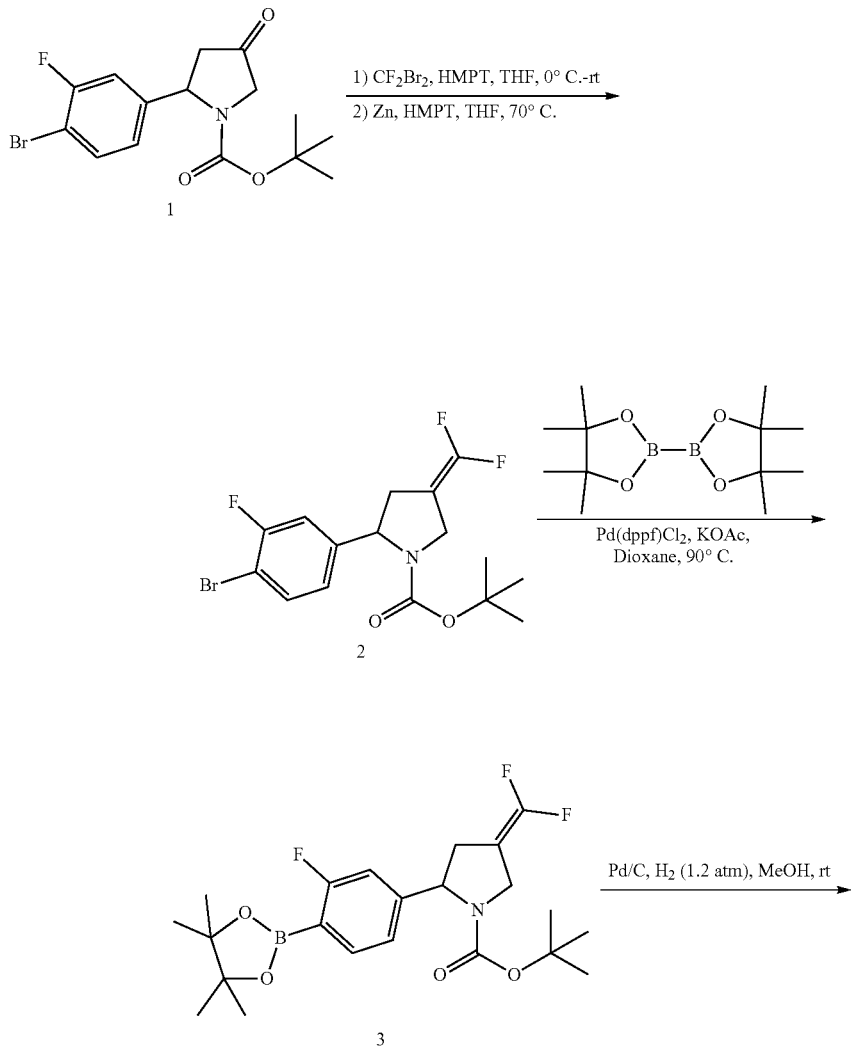

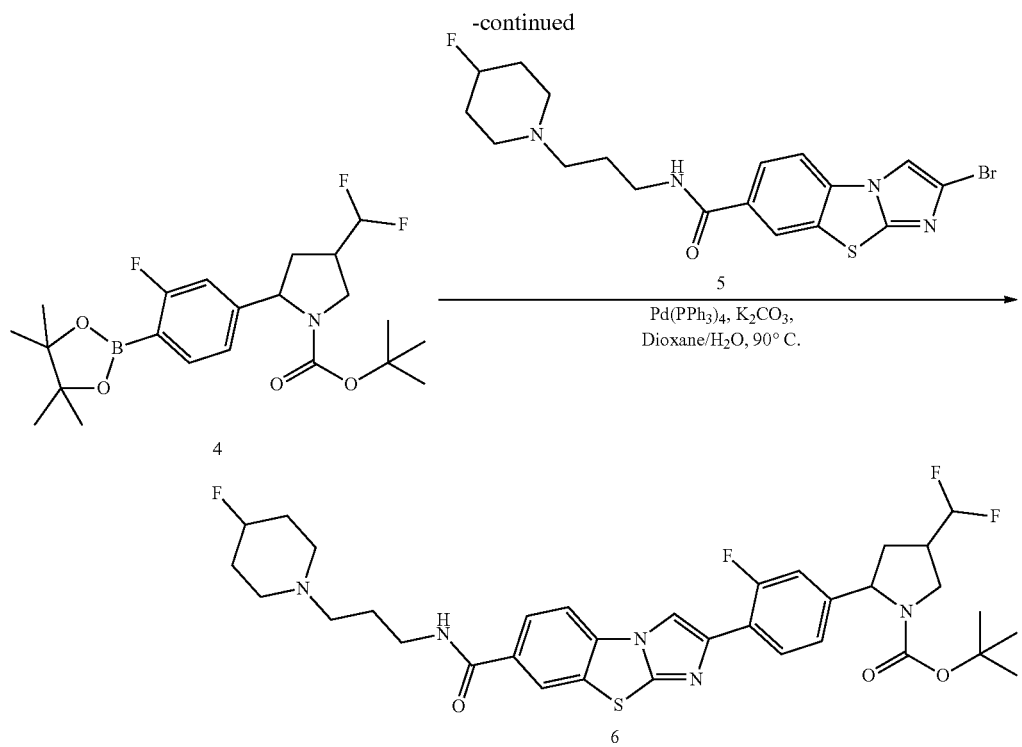

Synthesis of tert-butyl 2-(4-bromo-3-fluorophenyl)-4-(difluoromethylene)pyrrolidine-1-carboxylate (2, Scheme 84)

To a stirred solution of tert-butyl 2-(4-bromo-3-fluorophenyl)-4-oxopyrrolidine-1-carboxylate (1.50 g, 4.19 mmol) in tetrahydrofuran (45 mL), were sequentially added hexamethylphosphorous triamide (HMPT) (2.90 g, 17.77 mmol) and dibromodifluoromethane (3.74 g, 17.82 mmol), dropwise at 0° C. The reaction mixture was stirred for 1 h at room temperature. To the above mixture were added additional hexamethylphosphorous triamide (HMPT) (0.17 g, 1.04 mmol) and zinc powder (1.17 g, 17.90 mmol) at room temperature. The resulting mixture was stirred for an additional 3 h at 70° C. The mixture was cooled to room temperature and diluted with water (100 mL) and ethyl acetate (100 mL) to give a precipitate. After filtration, the filter cake was washed with ethyl acetate (3×20 mL). The combined filtrate mixture was extracted with ethyl acetate (2×400 mL). The combined organic phase was washed sequentially with saturated aqueous copper sulfate (400 mL), water (400 mL) and brine (400 mL) then dried over sodium sulfate. After filtration, the filtrate was concentrated under reduced pressure. The residue was purified by silica gel column chromatography (eluted with 16% ethyl acetate in petroleum ether) to afford tert-butyl 2-(4-bromo-3-fluorophenyl)-4-(difluoromethylene)pyrrolidine-1-carboxylate as a yellow oil.

Yield 0.29 g (18%). $^1$H NMR (300 MHz, CDCl$_3$) δ 7.56-7.47 (m, 1H), 7.00-6.90 (m, 1H), 6.90-6.82 (m, 1H), 5.14-4.87 (m, 1H), 4.31-4.16 (m, 2H), 3.15-2.96 (m, 1H), 2.56-2.44 (m, 1H), 1.50-1.21 (m, 9H). m/z: [ESI$^+$]336, 338 (M+H-56)$^+$.

Synthesis of tert-butyl 4-(difluoromethylene)-2-(3-fluoro-4-(4,4,5,5-tetramethyl-1,3,2-dioxaborolan-2-yl)phenyl)pyrrolidine-1-carboxylate (3, Scheme 84)

Compound tert-butyl 4-(difluoromethylene)-2-(3-fluoro-4-(4,4,5,5-tetramethyl-1,3,2-dioxaborolan-2-yl)phenyl)pyrrolidine-1-carboxylate was prepared from tert-butyl 2-(4-bromo-3-fluorophenyl)-4-(difluoromethylene)pyrrolidine-1-carboxylate (0.50 g, 1.27 mmol) and bis(pinacolato)diboron (0.36 g, 1.42 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a yellow oil.

Yield 0.35 g (63%). $^1$H NMR (400 MHz, CDCl$_3$) δ 7.76-7.66 (m, 1H), 6.99-6.91 (m, 1H), 6.88-6.80 (m, 1H), 5.19-4.92 (m, 1H), 4.30-4.18 (m, 2H), 3.15-2.96 (m, 1H), 2.57-2.47 (m, 1H), 1.55-1.37 (m, 9H), 1.29 (s, 12H). m/z: [ESI$^+$]384 (M+H-56)$^+$.

Synthesis of tert-butyl 4-(difluoromethyl)-2-(3-fluoro-4-(4,4,5,5-tetramethyl-1,3,2-dioxaborolan-2-yl)phenyl)pyrrolidine-1-carboxylate (4, Scheme 84)

10% palladium on activated carbon (300 mg) was added as a single portion to a solution of tert-butyl 4-(difluoromethylene)-2-(3-fluoro-4-(4,4,5,5-tetramethyl-1,3,2-dioxaborolan-2-yl)phenyl)pyrrolidine-1-carboxylate (0.35 g, 0.797 mmol) in methanol (5 mL), under a nitrogen atmosphere. The mixture was stirred at room temperature for 4 h under a hydrogen atmosphere (1.2 atm.). Upon completion the reaction mixture was filtered through a Celite pad. The filtrate was concentrated under reduced pressure to afford tert-butyl 4-(difluoromethyl)-2-(3-fluoro-4-(4,4,5,5-tetramethyl-1,3,2-dioxaborolan-2-yl)phenyl)pyrrolidine-1-carboxylate as a yellow oil.

Yield 0.28 g (80%). $^1$H NMR (300 MHz, CDCl$_3$) δ 7.76-7.67 (m, 1H), 7.03-6.95 (m, 1H), 6.94-6.85 (m, 1H), 5.71 (dd, J=5.4, 56.1 Hz, 1H), 4.89-4.75 (m, 1H), 4.06-3.91 (m, 1H), 3.56-3.44 (m, 1H), 2.83-2.63 (m, 1H), 2.63-2.47 (m, 1H), 1.92-1.77 (m, 1H), 1.38 (s, 9H), 1.27 (s, 12H). m/z: [ESI$^+$]386 (M+H-56)$^+$.

Synthesis of tert-butyl 4-(difluoromethyl)-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (6, Scheme 84)

Compound tert-butyl 4-(difluoromethyl)-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate was prepared from 2-bromo-N-(3-(4-fluoropiperidin-1-yl)propyl)benzo[d]imidazo[2,1-b]thiazole-7-carboxamide (160 mg, 0.364 mmol) and tert-butyl 4-(difluoromethyl)-2-(3-fluoro-4-(4,4,5,5-tetramethyl-1,3,2-dioxaborolan-2-yl)phenyl)pyrrolidine-1-carboxylate (170 mg, 0.385 mmol) at 90° C. following a similar procedure to that described for the synthesis of tert-butyl 4-(4-bromo-3-fluorophenyl)-3,6-dihydropyridine-1(2H)-carboxylate and was isolated as a white solid.

Yield 110 mg (45%). $^1$H NMR (300 MHz, CDCl$_3$) δ 8.42-8.35 (m, 1H), 8.27 (s, 1H), 8.25-8.16 (m, 2H), 7.93 (d, J=8.4 Hz, 1H), 7.70 (d, J=8.4 Hz, 1H), 7.15-7.08 (m, 1H), 7.08-6.95 (m, 1H), 5.78 (dd, J=5.4, 56.1 Hz, 1H), 4.91-4.63 (m, 2H), 4.07-3.93 (m, 1H), 3.70-3.59 (m, 2H), 3.58-3.50 (m, 1H), 2.82-2.51 (m, 8H), 2.05-1.80 (m, 7H), 1.26 (s, 9H). m/z: [ESI$^+$]674 (M+H)$^+$.

Synthesis of 2-(2-fluoro-4-(2-(tetrahydro-2H-pyran-2-yl)isoxazolidin-5-yl)phenyl)-N-(3-(4-fluoropiperidin-1-yl)propyl)benzo[d]imidazo[2,1-b]thiazole-7-carboxamide

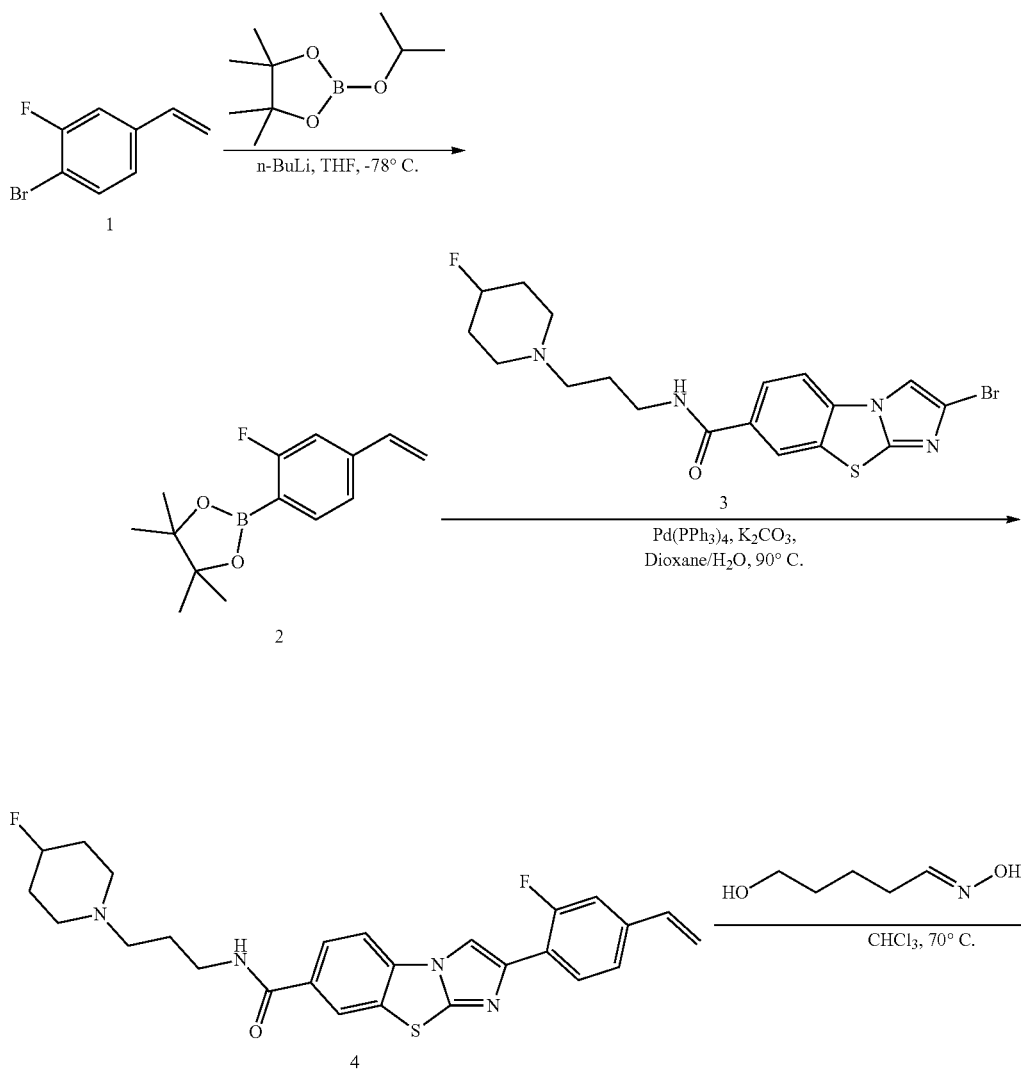

Scheme 85.

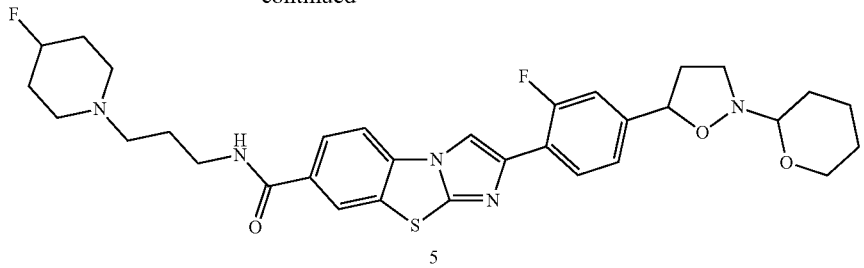

Synthesis of 2-(2-fluoro-4-vinylphenyl)-4,4,5,5-tetramethyl-1,3,2-dioxaborolane (2, Scheme 85)

n-Butyllithium (2.5 N in hexane, 6.17 mL, 15.43 mmol) was added dropwise to a stirred solution of 1-bromo-4-ethenyl-2-fluorobenzene (3.10 g, 15.42 mmol) in tetrahydrofuran (3 mL), at −78° C. under a nitrogen atmosphere. The solution was held at this temperature and stirred for 1 h. The reaction solution was treated with 2-isopropoxy-4,4,5,5-tetramethyl-1,3,2-dioxaborolane (3.16 g, 16.98 mmol), which was added dropwise. The reaction solution was warmed to room temperature slowly and stirred for an additional 1 h. The reaction was quenched by the addition of water (50 mL). The resulting mixture was extracted with ethyl acetate (3×100 mL). The combined organic layers were washed with brine (100 mL) and dried over anhydrous sodium sulfate. After filtration, the filtrate was concentrated under reduced pressure to afford 2-(2-fluoro-4-vinylphenyl)-4,4,5,5-tetramethyl-1,3,2-dioxaborolane as a light yellow oil. The crude product was used directly in the next step without further purification.

Yield 4.00 g (crude). $^1$H NMR not run. m/z: [ESI$^+$]249 (M+H)$^+$.

Synthesis of 2-(2-fluoro-4-vinylphenyl)-N-(3-(4-fluoropiperidin-1-yl)propyl)benzo[d]imidazo[2,1-b]thiazole-7-carboxamide (4, Scheme 85)

Compound 2-(2-fluoro-4-vinylphenyl)-N-(3-(4-fluoropiperidin-1-yl)propyl)benzo[d]imidazo[2,1-b]thiazole-7-carboxamide was prepared from 2-bromo-N-(3-(4-fluoropiperidin-1-yl)propyl)benzo[d]imidazo[2,1-b]thiazole-7-carboxamide (0.80 g, 1.82 mmol) and 2-(2-fluoro-4-vinylphenyl)-4,4,5,5-tetramethyl-1,3,2-dioxaborolane (500 mg, crude) at 90° C., following a similar procedure to that described for the synthesis of tert-butyl 4-(4-bromo-3-fluorophenyl)-3,6-dihydropyridine-1(2H)-carboxylate and was isolated as a light yellow solid.

Yield 0.47 g (54%). $^1$H NMR (400 MHz, DMSO) δ 8.73 (d, J=3.6 Hz, 1H), 8.61 (t, J=5.6 Hz, 1H), 8.49 (d, J=1.6 Hz, 1H), 8.28 (d, J=8.4 Hz, 1H), 8.16-8.07 (m, 1H), 8.01 (dd, J=1.6, 8.4 Hz, 1H), 7.54-7.47 (m, 1H), 7.47-7.40 (m, 1H), 6.77 (dd, J=10.8, 17.6 Hz, 1H), 5.97 (d, J=17.6 Hz, 1H), 5.37 (d, J=10.8 Hz, 1H), 4.77-4.56 (m, 1H), 3.38-3.28 (m, 2H), 2.59-2.49 (m, 2H), 2.40-2.23 (m, 4H), 1.94-1.76 (m, 2H), 1.76-1.60 (m, 4H). m/z: [ESI$^+$]481 (M+H)$^+$.

Synthesis of 2-(2-fluoro-4-(2-(tetrahydro-2H-pyran-2-yl)isoxazolidin-5-yl)phenyl)-N-(3-(4-fluoropiperidin-1-yl)propyl)benzo[d]imidazo[2,1-b]thiazole-7-carboxamide (5, Scheme 85)

To a stirred solution of 2-(2-fluoro-4-vinylphenyl)-N-(3-(4-fluoropiperidin-1-yl)propyl)benzo[d]imidazo[2,1-b]thiazole-7-carboxamide (150 mg, 0.312 mmol) and (E)-5-hydroxypentanal oxime (55 mg, 0.469 mmol) in chloroform (2 mL), was added paraformaldehyde (56 mg, 0.622 mmol) as a single portion at room temperature. The reaction mixture was stirred for 36 h at 70° C. under a nitrogen atmosphere. The mixture was cooled to room temperature and concentrated under reduced pressure. The residue was purified by Prep-TLC (dichloromethane/methanol=10:1) to afford 2-(2-fluoro-4-(2-(tetrahydro-2H-pyran-2-yl)isoxazolidin-5-yl)phenyl)-N-(3-(4-fluoropiperidin-1-yl)propyl)benzo[d]imidazo[2,1-b]thiazole-7-carboxamide as a white solid.

Yield 180 mg (95%). $^1$H NMR (400 MHz, DMSO) δ 8.71 (d, J=3.6 Hz, 1H), 8.62 (t, J=5.6 Hz, 1H), 8.49 (s, 1H), 8.27 (d, J=8.4 Hz, 1H), 8.17-8.07 (m, 1H), 8.01 (d, J=8.4 Hz, 1H), 7.37-7.25 (m, 2H), 5.16-4.99 (m, 1H), 4.77-4.57 (m, 1H), 4.40-4.24 (m, 1H), 4.02-3.91 (m, 1H), 3.47-3.25 (m, 4H), 2.58-2.46 (m, 4H), 2.41-2.17 (m, 4H), 2.12-1.97 (m, 1H), 1.96-1.78 (m, 2H), 1.77-1.63 (m, 5H), 1.49-1.36 (m, 5H). m/z: [ESI$^+$]610 (M+H)$^+$.

Synthesis of tert-butyl 4-(3-fluoro-4-(7-((1-methylpiperidin-4-yl)carbamoyl)benzo[d]imidazo[2,1-b]thiazol-2-yl)phenyl)piperazine-1-carboxylate Scheme 86.

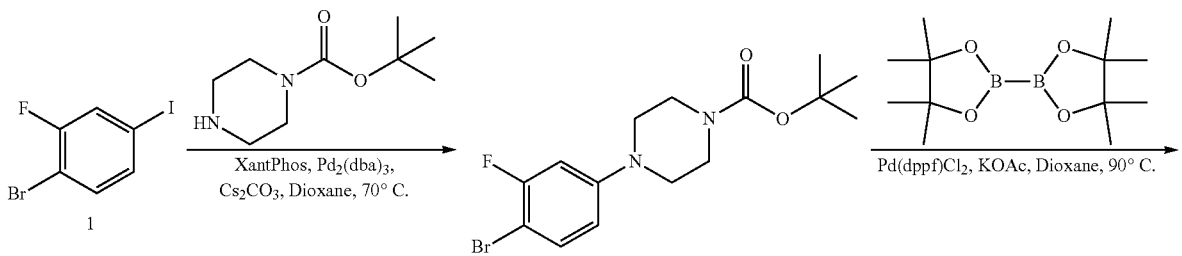

489                                                                                           490

-continued

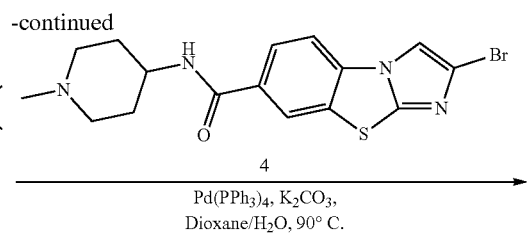

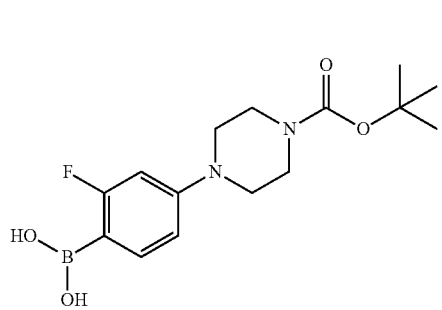

3

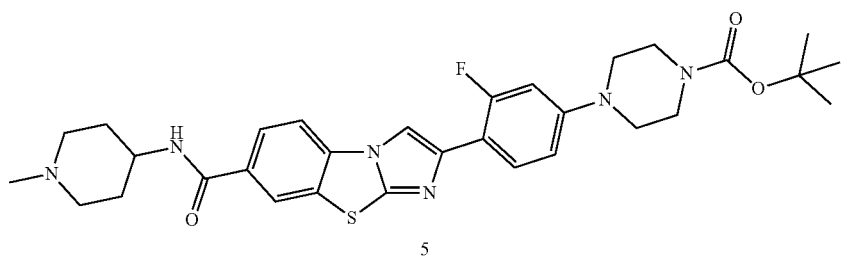

5

Synthesis of tert-butyl 4-(4-bromo-3-fluorophenyl)piperazine-1-carboxylate (2, Scheme 86)

A mixture of 1-bromo-2-fluoro-4-iodobenzene (5.00 g, 16.62 mmol), tris(dibenzylideneacetone)dipalladium (1.50 g, 1.64 mmol), 4,5-bis(diphenylphosphino)-9,9-dimethylxanthene (1.00 g, 1.73 mmol), cesium carbonate (11.00 g, 33.76 mmol) and tert-butyl piperazine-1-carboxylate (4.00 g, 21.48 mmol) in dioxane (80 mL), was stirred for 16 h at 70° C. under a nitrogen atmosphere. The mixture was cooled to room temperature and purified directly by reverse phase flash chromatography using the following conditions; Column, $C_{18}$ silica gel; Mobile phase A: acetonitrile: Mobile phase B: water (plus 50 mmol/L ammonium bicarbonate): Gradient: 50%-60% B in 10 min; UV Detector: 254 nm. The fractions containing desired product at 56% B were collected and concentrated under reduced pressure to afford tert-butyl 4-(4-bromo-3-fluorophenyl)piperazine-1-carboxylate as a light yellow solid.

Yield 3.50 g (59%). $^1$H NMR (400 MHz, DMSO) δ 7.47-7.43 (m, 1H), 6.95 (dd, J=2.8, 12.8 Hz, 1H), 6.75 (dd, J=2.8, 9.2 Hz, 1H), 3.43 (dd, J=4.0, 6.6 Hz, 4H), 3.16 (dd, J=4.0, 6.4 Hz, 4H), 1.42 (s, 9H). m/z: [ESI$^+$]359, 361 (M+H)$^+$.

Synthesis of (4-(4-(tert-butoxycarbonyl)piperazin-1-yl)-2-fluorophenyl)boronic acid (3, Scheme 86)

Compound (4-(4-(tert-butoxycarbonyl)piperazin-1-yl)-2-fluorophenyl)boronic acid was prepared from tert-butyl 4-(4-bromo-3-fluorophenyl)piperazine-1-carboxylate (150 mg, 0.418 mmol) and bis(pinacolato)diboron (120 mg, 0.473 mmol), following a similar procedure to that described for the synthesis of tert-butyl 4-(3-fluoro-4-(4,4,5,5-tetramethyl-1,3,2-dioxaborolan-2-yl)phenyl)piperidine-1-carboxylate and was isolated as a brown solid.

Yield 150 mg (crude). $^1$H NMR not run. m/z: [ESI$^+$]325 (M+H)$^+$.

Synthesis of tert-butyl 4-(3-fluoro-4-(7-((1-methylpiperidin-4-yl)carbamoyl)benzo[d]imidazo[2,1-b]thiazol-2-yl)phenyl)piperazine-1-carboxylate (5, Scheme 86)

Compound tert-butyl 4-(3-fluoro-4-(7-((1-methylpiperidin-4-yl)carbamoyl)benzo[d]imidazo[2,1-b]thiazol-2-yl)phenyl)piperazine-1-carboxylate was prepared from 2-bromo-N-(1-methylpiperidin-4-yl)benzo[d]imidazo[2,1-b]thiazole-7-carboxamide (150 mg, 0.381 mmol) and (4-(4-(tert-butoxycarbonyl)piperazin-1-yl)-2-fluorophenyl)boronic acid (150 mg, crude) at 90° C., following a similar procedure to that described for the synthesis of tert-butyl 4-(4-bromo-3-fluorophenyl)-3,6-dihydropyridine-1(2H)-carboxylate and was isolated as a light brown solid.

Yield 120 mg (53%). $^1$H NMR (300 MHz, DMSO) δ 8.54 (d, J=3.6 Hz, 1H), 8.51-8.46 (m, 1H), 8.41-8.34 (m, 1H), 8.24-8.19 (m, 1H), 8.05-7.98 (m, 1H), 7.98-7.92 (m, 1H), 6.95-6.90 (m, 1H), 6.88 (s, 1H), 3.81-3.69 (m, 1H), 3.50-3.43 (m, 5H), 3.26-3.19 (m, 4H), 2.84-2.74 (m, 2H), 2.18 (s, 3H), 2.02-1.90 (m, 2H), 1.85-1.74 (m, 2H), 1.67-1.53 (m, 1H), 1.43 (s, 9H). m/z: [ESI$^+$]593 (M+H)$^+$.

Synthesis of tert-butyl (trans)-2-(3-fluoro-4-(7-((tetrahydro-2H-pyran-4-yl)carbamoyl)benzo[d]imidazo[2,1-b]thiazol-2-yl)phenyl)-4-hydroxypyrrolidine-1-carboxylate Compound tert-butyl (trans)-2-(3-fluoro-4-(7-((tetrahydro-2H-pyran-4-yl)carbamoyl)benzo[d]imidazo[2,1-b]thiazol-2-yl)phenyl)-4-hydroxypyrrolidine-1-carboxylate was prepared from 2-bromo-N-(tetrahydro-2H-pyran-4-yl)benzo[d]imidazo[2,1-b]thiazole-7-carboxamide (90 mg, 0.237 mmol) and (4-((trans)-1-(tert-butoxycarbonyl)-4-hydroxypyrrolidin-2-yl)-2-fluorophenyl)boronic acid (120 mg, 0.369 mmol) at 90° C., following a similar procedure to that described for the synthesis of tert-butyl 4-(4-bromo-3-fluorophenyl)-3,6-dihydropyridine-1(2H)-carboxylate and was isolated as a brown solid.

Yield 50 mg (36%). $^1$H NMR (300 MHz, DMSO) δ 8.69 (d, J=3.6 Hz, 1H), 8.50 (d, J=1.5 Hz, 1H), 8.43 (d, J=7.5 Hz, 1H), 8.26 (d, J=8.4 Hz, 1H), 8.14-7.97 (m, 2H), 7.25-7.10

(m, 2H), 5.04 (d, J=3.3 Hz, 1H), 4.91-4.74 (m, 1H), 4.34-4.23 (m, 1H), 4.11-3.97 (m, 1H), 3.95-3.85 (m, 2H), 3.70-3.58 (m, 1H), 3.54-3.35 (m, 3H), 2.34-2.20 (m, 1H), 1.95-1.73 (m, 3H), 1.70-1.52 (m, 2H), 1.40-1.09 (m, 9H). m/z: [ESI$^+$]581 (M+1)$^+$.

Synthesis of tert-butyl (trans)-2-(3-fluoro-4-(7-(methylcarbamoyl)benzo[d]imidazo[2,1-b]thiazol-2-yl)phenyl)-4-hydroxypyrrolidine-1-carboxylate Compound tert-butyl (trans)-2-(3-fluoro-4-(7-(methylcarbamoyl)benzo[d]imidazo[2,1-b]thiazol-2-yl)phenyl)-4-hydroxypyrrolidine-1-carboxylate was prepared from 2-bromo-N-methylbenzo[d]imidazo[2,1-b]thiazole-7-carboxamide (80 mg, 0.258 mmol) and (4-((trans)-1-(tert-butoxycarbonyl)-4-hydroxypyrrolidin-2-yl)-2-fluorophenyl)boronic acid (130 mg, 0.400 mmol) at 90° C., following a similar procedure to that described for the synthesis of tert-butyl 4-(4-bromo-3-fluorophenyl)-3,6-dihydropyridine-1(2H)-carboxylate and was isolated as a white solid.

Yield 60 mg (46%). $^1$H NMR (400 MHz, DMSO) δ 8.69 (d, J=3.6 Hz, 1H), 8.57 (q, J=4.4 Hz, 1H), 8.49 (d, J=1.6 Hz, 1H), 8.26 (d, J=8.4 Hz, 1H), 8.12-8.05 (m, 1H), 8.01 (dd, J=1.6, 8.4 Hz, 1H), 7.25-7.09 (m, 2H), 5.05 (d, J=3.2 Hz, 1H), 4.91-4.74 (m, 1H), 4.33-4.21 (m, 1H), 3.68-3.58 (m, 1H), 3.52-3.43 (m, 1H), 2.83 (d, J=4.4 Hz, 3H), 2.33-2.21 (m, 1H), 1.92-1.78 (m, 1H), 1.40-1.09 (m, 9H). m/z: [ESI$^+$] 511 (M+1)$^+$.

Final Compounds

Synthesis of 2-(2-fluoro-4-(morpholin-3-yl)phenyl)-N-(tetrahydro-2H-pyran-4-yl)benzo[d]imidazo[2,1-b]thiazole-7-carboxamide (Compound 534)

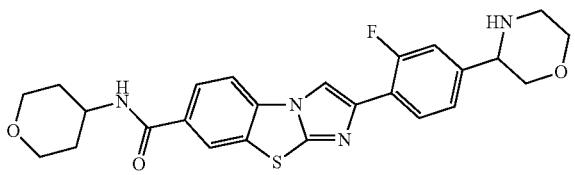 [SMILES: O=C(NC1CCOCC1)c1ccc2c(c1)sc1nc(-c3ccc(C4COCCN4)cc3F)cn12]

Compound 2-(2-fluoro-4-(morpholin-3-yl)phenyl)-N-(tetrahydro-2H-pyran-4-yl)benzo[d]imidazo[2,1-b]thiazole-7-carboxamide hydrochloride was prepared from tert-butyl 3-(3-fluoro-4-(7-((tetrahydro-2H-pyran-4-yl)carbamoyl)benzo[d]imidazo[2,1-b]thiazol-2-yl)phenyl)morpholine-4-carboxylate (260 mg, 0.448 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 78 mg (34%). $^1$H NMR (400 MHz, DMSO) δ 10.30 (br s, 1H), 9.97 (br s, 1H), 8.81 (d, J=3.6 Hz, 1H), 8.54 (s, 1H), 8.50 (d, J=7.6 Hz, 1H), 8.30 (d, J=8.4 Hz, 1H), 8.24-8.17 (m, 1H), 8.07 (dd, J=1.6, 8.4 Hz, 1H), 7.77 (d, J=12.4 Hz, 1H), 7.57 (d, J=8.0 Hz, 1H), 4.60-4.48 (m, 1H), 4.10-3.96 (m, 4H), 3.96-3.82 (m, 3H), 3.47-3.36 (m, 2H), 3.36-3.21 (m, 2H), 1.86-1.74 (m, 2H), 1.69-1.53 (m, 2H). $^{19}$F NMR (376 MHz, DMSO) δ−112.48. m/z: [ESI$^+$]481 (M+H)$^+$. (C$_{25}$H$_{26}$ClFN$_4$O$_3$S).

Synthesis of 2-(2-fluoro-4-(morpholin-2-yl)phenyl)-N-(tetrahydro-2H-pyran-4-yl)benzo[d]imidazo[2,1-b]thiazole-7-carboxamide (Compound 535)

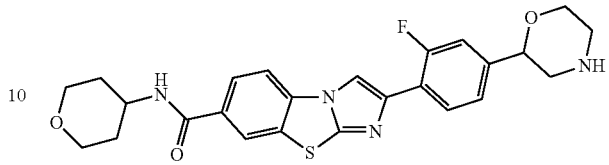

Compound 2-(2-fluoro-4-(morpholin-2-yl)phenyl)-N-(tetrahydro-2H-pyran-4-yl)benzo[d]imidazo[2,1-b]thiazole-7-carboxamide hydrochloride was prepared from tert-butyl 2-(3-fluoro-4-(7-((tetrahydro-2H-pyran-4-yl)carbamoyl)benzo[d]imidazo[2,1-b]thiazol-2-yl)phenyl)morpholine-4-carboxylate (130 mg, 0.224 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 38 mg (33%). $^1$H NMR (400 MHz, DMSO) δ 9.86 (br s, 2H), 8.78 (d, J=3.6 Hz, 1H), 8.65-8.48 (m, 2H), 8.29 (d, J=8.4 Hz, 1H), 8.23-8.12 (m, 1H), 8.12-8.01 (m, 1H), 7.45-7.29 (m, 2H), 4.94-4.82 (m, 1H), 4.20-4.10 (m, 1H), 4.10-3.94 (m, 2H), 3.94-3.80 (m, 2H), 3.55-3.45 (m, 1H), 3.45-3.33 (m, 2H), 3.30-3.20 (m, 1H), 3.17-2.94 (m, 2H), 1.84-1.70 (m, 2H), 1.70-1.53 (m, 2H). $^{19}$F NMR (376 MHz, DMSO) δ−112.96. m/z: [ESI$^+$]481 (M+H)$^+$. (C$_{25}$H$_{26}$ClFN$_4$O$_3$S).

Synthesis of 2-(2-fluoro-4-(4-fluoropiperidin-4-yl)phenyl)-N-(1-methylpiperidin-4-yl)benzo[d]imidazo[2,1-b]thiazole-7-carboxamide (Compound 536)

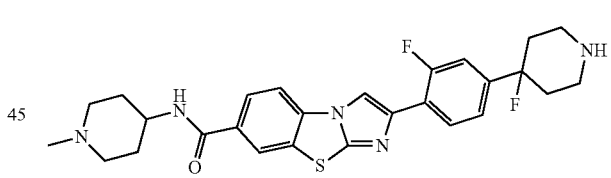

Compound 2-(2-fluoro-4-(4-fluoropiperidin-4-yl)phenyl)-N-(1-methylpiperidin-4-yl)benzo[d]imidazo[2,1-b]thiazole-7-carboxamide dihydrochloride was prepared from tert-butyl 4-fluoro-4-(3-fluoro-4-(7-((1-methylpiperidin-4-yl)carbamoyl)benzo[d]imidazo[2,1-b]thiazol-2-yl)phenyl)piperidine-1-carboxylate (40 mg, 0.066 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 12 mg (31%). $^1$H NMR (400 MHz, DMSO) δ 10.66 (br s, 1H), 9.45 (br s, 1H), 9.14 (br s, 1H), 8.80 (d, J=3.6 Hz, 1H), 8.73 (d, J=7.6 Hz, 1H), 8.56 (s, 1H), 8.36-8.27 (m, 1H), 8.25-8.17 (m, 1H), 8.13-8.05 (m, 1H), 7.40-7.32 (m, 2H), 4.12-3.98 (m, 1H), 3.51-3.26 (m, 4H), 3.23-3.01 (m, 4H), 2.72 (s, 3H), 2.61-2.38 (m, 2H), 2.24-2.11 (m, 2H), 2.09-1.89 (m, 4H). $^{19}$F NMR (376 MHz, DMSO) δ−112.50, −156.09. m/z: [ESI$^+$]510 (M+H)$^+$. (C$_{27}$H$_{31}$Cl$_2$F$_2$N$_5$OS).

Synthesis of 2-(2-fluoro-4-(4-oxopyrrolidin-2-yl)phenyl)-N-(tetrahydro-2H-pyran-4-yl)benzo[d]imidazo[2,1-b]thiazole-7-carboxamide (Compound 537)

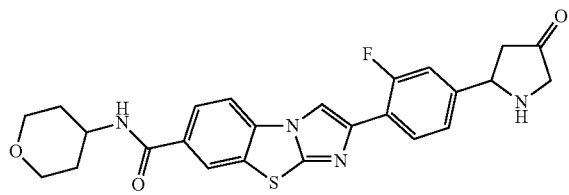 [SMILES: O=C1CNC(c2ccc(-c3cn4c(n3)sc3cc(C(=O)NC5CCOCC5)ccc34)c(F)c2)C1]

Compound 2-(2-fluoro-4-(4-oxopyrrolidin-2-yl)phenyl)-N-(tetrahydro-2H-pyran-4-yl)benzo[d]imidazo[2,1-b]thiazole-7-carboxamide hydrochloride was prepared from tert-butyl 2-(3-fluoro-4-(7-((tetrahydro-2H-pyran-4-yl)carbamoyl)benzo[d]imidazo[2,1-b]thiazol-2-yl)phenyl)-4-oxopyrrolidine-1-carboxylate (60 mg, 0.104 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 37 mg (69%). $^1$H NMR (400 MHz, DMSO) δ 10.93 (br s, 1H), 9.81 (br s, 1H), 8.82 (d, J=3.6 Hz, 1H), 8.53 (d, J=1.6 Hz, 1H), 8.49 (d, J=7.6 Hz, 1H), 8.30 (d, J=8.4 Hz, 1H), 8.27-8.20 (m, 1H), 8.06 (dd, J=1.6, 8.4 Hz, 1H), 7.74 (dd, J=1.6, 12.4 Hz, 1H), 7.56 (dd, J=1.6, 8.0 Hz, 1H), 5.23-5.10 (m, 1H), 4.10-3.97 (m, 1H), 3.96-3.87 (m, 2H), 3.87-3.78 (m, 2H), 3.47-3.33 (m, 2H), 3.10-2.97 (m, 2H), 1.85-1.74 (m, 2H), 1.68-1.53 (m, 2H). $^{19}$F NMR (376 MHz, DMSO) δ−112.48. m/z: [ESI$^+$]479 (M+H)$^+$. ($C_{25}H_{24}ClFN_4O_3S$).

Synthesis of 2-(2-fluoro-4-((trans)-4-hydroxypyrrolidin-2-yl)phenyl)-N-(tetrahydro-2H-pyran-4-yl)benzo[d]imidazo[2,1-b]thiazole-7-carboxamide (Compound 538)

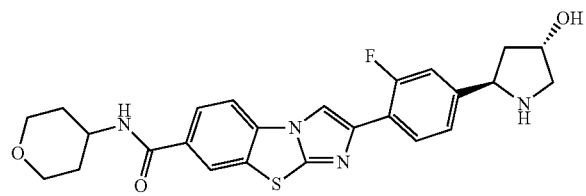 [SMILES: O=C(NC1CCOCC1)c1ccc2c(c1)sc1nc(-c3ccc([C@H]4C[C@H](O)CN4)cc3F)cn12]

Compound 2-(2-fluoro-4-((trans)-4-hydroxypyrrolidin-2-yl)phenyl)-N-(tetrahydro-2H-pyran-4-yl)benzo[d]imidazo[2,1-b]thiazole-7-carboxamide hydrochloride was prepared from tert-butyl (trans)-2-(3-fluoro-4-(7-((tetrahydro-2H-pyran-4-yl)carbamoyl)benzo[d]imidazo[2,1-b]thiazol-2-yl)phenyl)-4-hydroxypyrrolidine-1-carboxylate (50 mg, 0.086 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 7 mg (16%). $^1$H NMR (400 MHz, DMSO) δ 10.54 (br s, 1H), 9.37 (br s, 1H), 8.80 (d, J=3.6 Hz, 1H), 8.59-8.51 (m, 2H), 8.30 (d, J=8.4 Hz, 1H), 8.22-8.13 (m, 1H), 8.07 (d, J=8.4 Hz, 1H), 7.66 (d, J=12.4 Hz, 1H), 7.50 (d, J=8.4 Hz, 1H), 4.91-4.76 (m, 1H), 4.60-4.51 (m, 1H), 4.11-3.96 (m, 1H), 3.96-3.83 (m, 2H), 3.67-3.52 (m, 1H), 3.46-3.31 (m, 2H), 3.22-3.06 (m, 1H), 2.36-2.19 (m, 2H), 1.86-1.70 (m, 2H), 1.70-1.55 (m, 2H). OH proton not observed. $^{19}$F NMR (376 MHz, DMSO) δ−112.67. m/z: [ESI$^+$]481 (M+H)$^+$. ($C_{25}H_{26}ClFN_4O_3S$).

Synthesis of 2-(2-fluoro-4-((trans)-4-hydroxypyrrolidin-2-yl)phenyl)-N-methylbenzo[d]imidazo[2,1-b]thiazole-7-carboxamide (Compound 544)

Compound 2-(2-fluoro-4-((trans)-4-hydroxypyrrolidin-2-yl)phenyl)-N-methylbenzo[d]imidazo[2,1-b]thiazole-7-carboxamide hydrochloride was prepared from tert-butyl (trans)-2-(3-fluoro-4-(7-(methylcarbamoyl)benzo[d]imidazo[2,1-b]thiazol-2-yl)phenyl)-4-hydroxypyrrolidine-1-carboxylate (60 mg, 0.118 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 21 mg (40%). $^1$H NMR (400 MHz, DMSO) δ 10.17 (br s, 1H), 9.07 (br s, 1H), 8.79 (d, J=3.6 Hz, 1H), 8.62 (q, J=4.4 Hz, 1H), 8.51 (d, J=1.6 Hz, 1H), 8.29 (d, J=8.4 Hz, 1H), 8.24-8.15 (m, 1H), 8.03 (dd, J=1.6, 8.4 Hz, 1H), 7.65-7.56 (m, 1H), 7.52-7.45 (m, 1H), 4.89-4.78 (m, 1H), 4.59-4.53 (m, 1H), 3.65-3.55 (m, 1H), 3.20-3.09 (m, 1H), 2.83 (d, J=4.4 Hz, 3H), 2.36-2.21 (m, 2H). OH proton not observed. $^{19}$F NMR (376 MHz, DMSO) δ−112.71. m/z: [ESI$^+$]411 (M+H)$^+$. ($C_{21}H_{20}ClFN_4O_2S$).

Synthesis of 2-(4-(4-(difluoromethyl)pyrrolidin-2-yl)-2-fluorophenyl)-N-(3-(4-fluoropiperidin-1-yl)propyl)benzo[d]imidazo[2,1-b]thiazole-7-carboxamide (Compound 542)

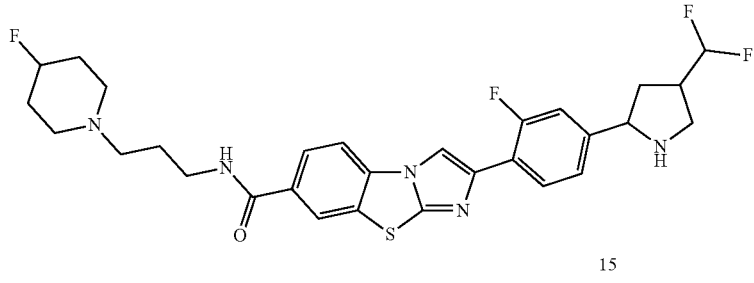

Compound 2-(4-(4-(difluoromethyl)pyrrolidin-2-yl)-2-fluorophenyl)-N-(3-(4-fluoropiperidin-1-yl)propyl)benzo[d]imidazo[2,1-b]thiazole-7-carboxamide dihydrochloride was prepared from tert-butyl 4-(difluoromethyl)-2-(3-fluoro-4-(7-((3-(4-fluoropiperidin-1-yl)propyl)carbamoyl)benzo[d]imidazo[2,1-b]thiazol-2-yl)phenyl)pyrrolidine-1-carboxylate (110 mg, 0.163 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as a white solid.

Yield 63 mg (60%). $^1$H NMR (400 MHz, DMSO) δ 10.39 (br s, 2H), 9.51 (br s, 1H), 8.93-8.82 (m, 1H), 8.81 (d, J=3.6 Hz, 1H), 8.56 (s, 1H), 8.31 (d, J=8.4 Hz, 1H), 8.25-8.19 (m, 1H), 8.07 (d, J=8.4 Hz, 1H), 7.70-7.62 (m, 1H), 7.53-7.48 (m, 1H), 6.49-6.10 (m, 1H), 5.11-4.79 (m, 1H), 4.79-4.65 (m, 1H), 3.56-3.45 (m, 2H), 3.44-3.31 (m, 4H), 3.28-2.89 (m, 5H), 2.65-2.53 (m, 1H), 2.27-1.93 (m, 7H). $^{19}$F NMR (377 MHz, DMSO) δ −112.65, (−118.50, −119.25, −119.77, −119.81, −120.51, −120.56, −121.61), −175.58, −186.63. m/z: [ESI$^+$]574 (M+H)$^+$. ($C_{29}H_{33}Cl_2F_4NOS$). The ratio of two diastereomers is approximately 4:1.

Synthesis of 2-(2-fluoro-4-(piperazin-1-yl)phenyl)-N-(1-methylpiperidin-4-yl)benzo[d]imidazo[2,1-b]thiazole-7-carboxamide (Compound 547)

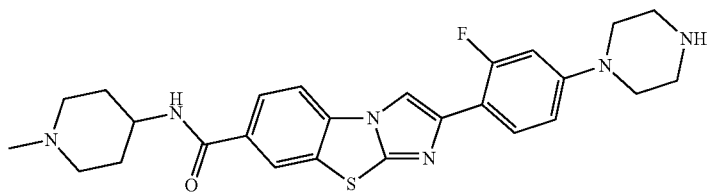 [SMILES: CN1CCC(NC(=O)c2ccc3c(c2)sc2nc(-c4ccc(N5CCNCC5)cc4F)cn23)CC1]

Compound 2-(2-fluoro-4-(piperazin-1-yl)phenyl)-N-(1-methylpiperidin-4-yl)benzo[d]imidazo[2,1-b]thiazole-7-carboxamide dihydrochloride was prepared from tert-butyl 4-(3-fluoro-4-(7-((1-methylpiperidin-4-yl)carbamoyl)benzo[d]imidazo[2,1-b]thiazol-2-yl)phenyl)piperazine-1-carboxylate (120 mg, 0.202 mmol), following a similar procedure to that described for the synthesis of 2-(2-fluoro-4-(pyrrolidin-2-yl)phenyl)-N-(tetrahydro-2H-pyran-4-yl)benzo[d]imidazo[2,1-b]thiazole-7-carboxamide hydrochloride and was isolated as an off-white solid.

Yield 31 mg (27%). $^1$H NMR (400 MHz, DMSO) δ 10.65 (br s, 1H), 9.42 (br s, 2H), 8.75 (d, J=7.6 Hz, 1H), 8.60 (d, J=3.6 Hz, 1H), 8.56 (s, 1H), 8.25 (d, J=8.4 Hz, 1H), 8.08 (d, J=8.4 Hz, 1H), 8.02-7.89 (m, 1H), 7.02-6.87 (m, 2H), 4.13-3.96 (m, 1H), 3.56-3.34 (m, 6H), 3.27-3.14 (m, 4H), 3.14-3.02 (m, 2H), 2.72 (s, 3H), 2.10-1.87 (m, 4H). $^{19}$F NMR (376 MHz, DMSO) δ −111.84. m/z: [ESI$^+$]493 (M+H)$^+$. ($C_{26}H_{31}Cl_2FN_6OS$).

Synthesis of 2-(4-(1-amino-2-hydroxyethyl)-2-fluorophenyl)-N-(3-(4-fluoropiperidin-1-yl)propyl)benzo[d]imidazo[2,1-b]thiazole-7-carboxamide (Compound 539)

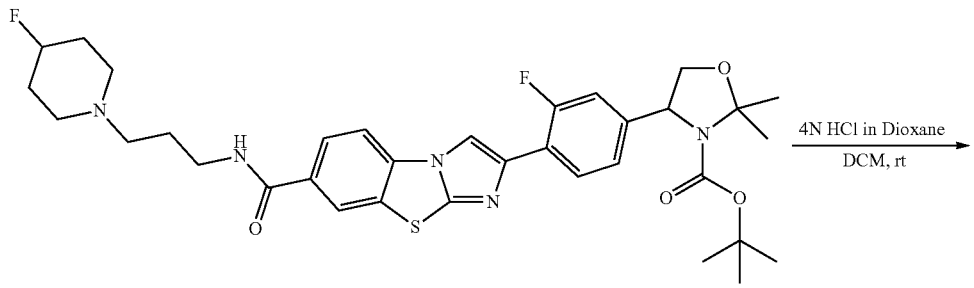

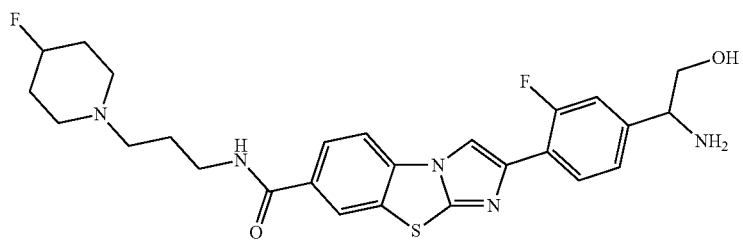

To a stirred solution of tert-butyl 4-(3-fluoro-4-(7-((3-(4-fluoropiperidin-1-yl)propyl)carbamoyl)benzo[d]imidazo[2,1-b]thiazol-2-yl)phenyl)-2,2-dimethyloxazolidine-3-carboxylate (200 mg, 0.306 mmol) in dichloromethane (3 mL) was added 4 N hydrochloride in 1,4-dioxane (3 mL) dropwise at room temperature. The reaction solution was stirred for 2 h at room temperature. Upon completion, the resulting mixture was concentrated under reduced pressure. The residue was dissolved in water (1 mL) and the pH was adjusted to 8 using saturated aqueous sodium bicarbonate. The resulting mixture was purified by Prep-HPLC using the following conditions Column: XBridge Prep OBD C18 Column (19× 250 mm); Mobile Phase A: water (plus 0.1% formic acid), Mobile Phase B: acetonitrile; Flow rate: 60 mL/min; Gradient: 20%-40% B in 20 min; UV Detector: 254/220 nm. The fractions contained desired product at 35% B were collected, concentrated under reduced pressure and lyophilized to afford 2-(4-(1-amino-2-hydroxyethyl)-2-fluorophenyl)-N-(3-(4-fluoropiperidin-1-yl)propyl)benzo[d]imidazo[2,1-b]thiazole-7-carboxamide diformate as an off-white solid.

Yield 20 mg (12%). $^1$H NMR (400 MHz, DMSO) δ 8.71 (d, J=3.6 Hz, 1H), 8.64 (t, J=5.6 Hz, 1H), 8.50 (d, J=1.6 Hz, 1H), 8.31-8.24 (m, 3H), 8.14-8.07 (m, 1H), 8.01 (dd, J=1.6, 8.4 Hz, 1H), 7.39 (d, J=12.8 Hz, 1H), 7.32 (d, J=8.4 Hz, 1H), 4.76-4.57 (m, 1H), 4.09-4.02 (m, 1H), 3.60-3.53 (m, 1H), 3.53-3.41 (m, 1H), 3.34-3.26 (m, 2H), 2.60-2.50 (m, 2H), 2.39-2.32 (m, 2H), 2.32-2.23 (m, 2H), 1.92-1.77 (m, 2H), 1.75-1.65 (m, 4H). All the OH protons and NH$_2$ protons not observed. Two $^{19}$F not observed. m/z: [ESI$^+$]514 (M+H)$^+$. (C$_{28}$H$_{33}$F$_2$N$_5$O$_6$S).

Synthesis of 2-(2-fluoro-4-(isoxazolidin-5-yl)phenyl)-N-(3-(4-fluoropiperidin-1-yl)propyl)benzo[d]imidazo[2,1-b]thiazole-7-carboxamide (Compound 543)

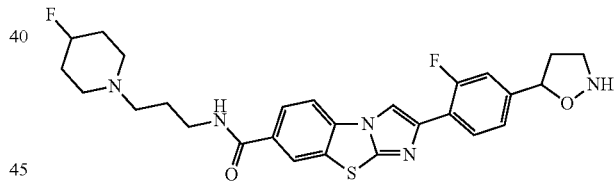

Compound 2-(2-fluoro-4-(isoxazolidin-5-yl)phenyl)-N-(3-(4-fluoropiperidin-1-yl)propyl)benzo[d]imidazo[2,1-b]thiazole-7-carboxamide was prepared from 2-(2-fluoro-4-(2-(tetrahydro-2H-pyran-2-yl)isoxazolidin-5-yl)phenyl)-N-(3-(4-fluoropiperidin-1-yl)propyl)benzo[d]imidazo[2,1-b]thiazole-7-carboxamide (160 mg, 0.262 mmol), following a similar procedure to that described for the synthesis of 2-(4-(4,4-difluoropyrrolidin-2-yl)-2-fluorophenyl)-N-(3-(4-fluoropiperidin-1-yl)propyl)benzo[d]imidazo[2,1-b]thiazole-7-carboxamide and was isolated as a white solid.

Yield 8 mg (6%). $^1$H NMR (400 MHz, DMSO) δ 8.72 (d, J=3.6 Hz, 1H), 8.62 (d, J=5.6 Hz, 1H), 8.49 (d, J=1.6 Hz, 1H), 8.27 (d, J=8.4 Hz, 1H), 8.15-8.08 (m, 1H), 8.01 (dd, J=1.6, 8.4 Hz, 1H), 7.38-7.25 (m, 2H), 6.59-6.42 (m, 1H), 4.96-4.78 (m, 1H), 4.77-4.55 (m, 1H), 3.37-3.26 (m, 3H), 3.17-2.90 (m, 1H), 2.65-2.49 (m, 3H), 2.39-2.20 (m, 4H), 2.08-1.96 (m, 1H), 1.93-1.76 (m, 2H), 1.76-1.62 (m, 4H). $^{19}$F NMR (376 MHz, DMSO) δ−113.44. Aliphatic $^{19}$F not observed. m/z: [ESI$^+$]526 (M+H)$^+$. (C$_{27}$H$_{29}$F$_2$N$_5$O$_2$S).

Synthesis of (S)-2-(2-fluoro-4-(pyrrolidin-2-yl)phenyl)-N-(3-(4-fluoropiperidin-1-yl)propyl)-9-methyl-9H-benzo[d]imidazo[1,2-a]imidazole-7-carboxamide

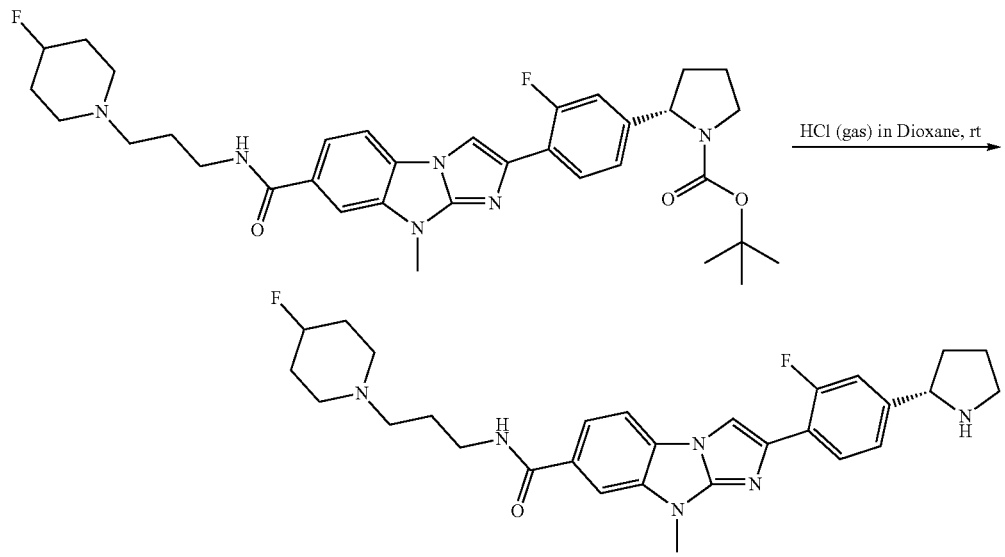

A solution of tert-butyl (S)-2-(3-fluoro-4-(7-((3-(4-fluoropiperidin-1l-yl)propyl)carbamoyl)-9-methyl-9H-benzo[d]imidazo[1,2-a]imidazol-2-yl)phenyl)pyrrolidine-1-carboxylate (200 mg, 0.322 mmol) in HCl/1,4-dioxane (4 N, 3 mL) was stirred for 2 h at room temperature under a nitrogen atmosphere. The reaction mixture was concentrated under reduced pressure. The solid was washed with dichloromethane (3×2 mL), diethyl ether (3×2 mL) and dried in a vacuum oven to afford (S)-2-(2-fluoro-4-(pyrrolidin-2-yl)phenyl)-N-(3-(4-fluoropiperidin-1-yl)propyl)-9-methyl-9H-benzo[d]imidazo[1,2-a]imidazole-7-carboxamide dihydrochloride as a brown solid.

Yield 85 mg (44%). $^1$H NMR (400 MHz, DMSO) δ 10.92 (br s, 1H), 10.39 (br s, 1H), 9.32 (brs, 1H), 8.97 (s, 1H), 8.55-8.46 (m, 1H), 8.40-8.29 (m, 2H), 8.14 (t, J=6.8 Hz, 1H), 7.97-7.90 (m, 1H), 7.73-7.64 (m, 1H), 7.54 (d, J=8.4 Hz, 1H), 5.12-4.71 (m, 1H), 4.66-4.55 (m, 1H), 4.10-3.97 (m, 3H), 3.57-3.47 (m, 1H), 3.45-3.39 (m, 4H), 3.35-3.24 (m, 1H), 3.22-2.97 (m, 4H), 2.47-2.37 (m, 1H), 2.35-1.96 (m, 9H). $^{19}$F NMR (376 MHz, DMSO) δ−111.83, −175.55, −186.58. m/z: [ESI$^+$]521 (M+H)$^+$. ($C_{29}H_{36}Cl_2F_2N_6O$).

Synthesis of (S)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide dihydrochloride (Compound 464S)

Compound (S)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide dihydrochloride was prepared from tert-butyl (S)-2-(3-fluoro-4-(7-((3-(4-fluoropiperidin-1-yl)propyl)carbamoyl)-3-methylbenzo[d]imidazo[2,1-b]thiazol-2-yl)phenyl)pyrrolidine-1-carboxylate (46 mg, 0.072 mmol) following a similar procedure to that described for the synthesis of (S)-2-(2-fluoro-4-(pyrrolidin-2-yl)phenyl)-N-(3-(4-fluoropiperidin-1-yl)propyl)-9-methyl-9H-benzo[d]imidazo[1,2-a]imidazole-7-carboxamide dihydrochloride, and was isolated as a light yellow solid.

Yield 33 mg (75%). $^1$H NMR (400 MHz, DMSO) δ 10.87 (br s, 1H), 10.36 (br s, 1H), 9.23 (br s, 1H), 8.93 (d, J=7.2 Hz, 1H), 8.64-8.52 (m, 1H), 8.13 (d, J=8.4 Hz, 1H), 8.07 (dd, J=2.0, 8.8 Hz, 1H), 7.74-7.67 (m, 1H), 7.67-7.58 (m, 1H), 7.53-7.48 (m, 1H), 5.10-4.72 (m, 1H), 4.70-4.58 (m, 1H), 3.59-3.47 (m, 1H), 3.46-3.35 (m, 4H), 3.35-3.24 (m, 1H), 3.22-2.96 (m, 4H), 2.72 (d, J=2.0 Hz, 3H), 2.47-2.39 (m, 1H), 2.33-1.96 (m, 9H). $^{19}$F NMR (376 MHz, DMSO) δ−113.52, −175.60, −186.61. m/z: [ESI$^+$]538 (M+H)$^+$. ($C_{29}H_{35}Cl_2F_2N_5OS$).

Synthesis of (R)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide dihydrochloride (Compound 464R)

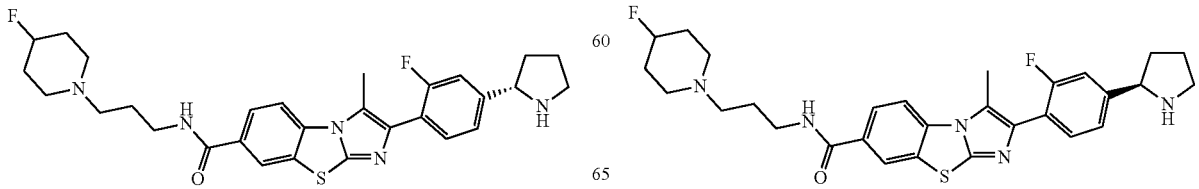

Compound (R)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide dihydrochloride was prepared from tert-butyl (R)-2-(3-fluoro-4-(7-((3-(4-fluoropiperidin-1-yl)propyl)carbamoyl)-3-methylbenzo[d]imidazo[2,1-b]thiazol-2-yl)phenyl)pyrrolidine-1-carboxylate (38 mg, 0.060 mmol) following a similar procedure to that described for the synthesis of (S)-2-(2-fluoro-4-(pyrrolidin-2-yl)phenyl)-N-(3-(4-fluoropiperidin-1-yl)propyl)-9-methyl-9H-benzo[d]imidazo[1,2-a]imidazole-7-carboxamide dihydrochloride, and was isolated as a light yellow solid.

Yield 26 mg (71%). $^1$H NMR (400 MHz, DMSO) δ 10.73 (br s, 1H), 10.22 (br s, 1H), 9.15 (br s, 1H), 8.93 (d, J=7.2 Hz, 1H), 8.64-8.52 (m, 1H), 8.13 (d, J=8.4 Hz, 1H), 8.07 (dd, J=2.0, 8.8 Hz, 1H), 7.74-7.67 (m, 1H), 7.67-7.58 (m, 1H), 7.53-7.48 (m, 1H), 5.10-4.72 (m, 1H), 4.70-4.58 (m, 1H), 3.59-3.47 (m, 1H), 3.46-3.35 (m, 4H), 3.35-3.24 (m, 1H), 3.22-2.96 (m, 4H), 2.72 (d, J=2.0 Hz, 3H), 2.47-2.39 (m, 1H), 2.33-1.96 (m, 9H). $^{19}$F NMR (376 MHz, DMSO) δ−113.52, −175.60, −186.61. m/z: [ESI$^+$]538 (M+H)$^+$. ($C_{29}H_{35}Cl_2F_2N_5OS$).

Synthesis of 2-(6-fluoro-1,2,3,4-tetrahydroisoquinolin-7-yl)-N-(3-(4-fluoropiperidin-1-yl)propyl)benzo[d]imidazo[2,1-b]thiazole-7-carboxamide dihydrochloride (Compound 600)

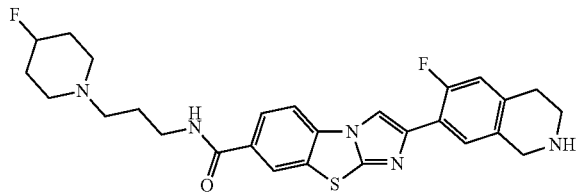 [SMILES: O=C(NCCCN1CCC(F)CC1)c1ccc2c(c1)sc1nc(-c3cc4c(cc3F)CCNC4)cn12]

Compound 2-(6-fluoro-1,2,3,4-tetrahydroisoquinolin-7-yl)-N-(3-(4-fluoropiperidin-1-yl)propyl)benzo[d]imidazo[2,1-b]thiazole-7-carboxamide dihydrochloride was prepared from tert-butyl 6-fluoro-7-(7-((3-(4-fluoropiperidin-1-yl)propyl)carbamoyl)benzo[d]imidazo[2,1-b]thiazol-2-yl)-3,4-dihydroisoquinoline-2(1H)-carboxylate (580 mg, 0.951 mmol) following a similar procedure to that described for the synthesis of (S)-2-(2-fluoro-4-(pyrrolidin-2-yl)phenyl)-N-(3-(4-fluoropiperidin-1-yl)propyl)-9-methyl-9H-benzo[d]imidazo[1,2-a]imidazole-7-carboxamide dihydrochloride, and was isolated as a pink solid.

Yield 168 mg (30%). $^1$H NMR (400 MHz, DMSO) δ 10.79 (br s, 1H), 9.60 (br s, 2H), 8.94-8.87 (m, 1H), 8.74 (d, J=3.6 Hz, 1H), 8.57 (s, 1H), 8.29 (d, J=8.4 Hz, 1H), 8.09 (dd, J=1.6, 8.4 Hz, 1H), 8.02 (d, J=7.6 Hz, 1H), 7.26 (d, J=12.0 Hz, 1H), 5.10-4.71 (m, 1H), 4.38-4.28 (m, 2H), 3.56-3.47 (m, 1H), 3.45-3.33 (m, 5H), 3.21-2.94 (m, 6H), 2.31-1.94 (m, 6H). $^{19}$F NMR (376 MHz, DMSO) δ−115.67, −175.53, −186.62. m/z: [ESI$^+$]510 (M+H)$^+$. ($C_{27}H_{31}Cl_2F_2N_5OS$).

Synthesis of 2-(6-fluoroindolin-5-yl)-N-(3-(4-fluoropiperidin-1-yl)propyl)benzo[d]imidazo[2,1-b]thiazole-7-carboxamide (Compound 602)

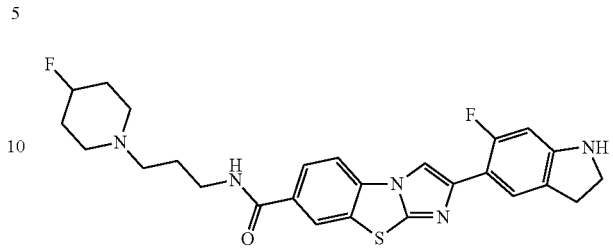

A mixture of tert-butyl 6-fluoro-5-(7-((3-(4-fluoropiperidin-1-yl)propyl)carbamoyl)benzo[d]imidazo[2,1-b]thiazol-2-yl)indoline-1-carboxylate (80 mg, 0.134 mmol) in a solution of hydrochloride (gas) in 1,4-dioxane (4 N, 2 mL) and dichloromethane (2 mL) was stirred for 3 h at room temperature under a nitrogen atmosphere. The resulting mixture was concentrated under reduced pressure. The residue was basified to pH 7 with an aqueous solution of saturated sodium bicarbonate. The resulting mixture was concentrated under reduced pressure. The residue was purified by reverse phase flash column chromatography with the following conditions; column, C18 silica gel, 20-40 um, 120 g; Mobile phase A: water (10 mmol/L ammonium bicarbonate); Mobile phase B: acetonitrile; Gradient: 30%-50% B in 25 min; Flow rate: 60 mL/min; Detector, UV 254 nm. The fractions containing desired product were collected at 45% B and concentrated under reduced pressure to afford 2-(6-fluoroindolin-5-yl)-N-(3-(4-fluoropiperidin-1-yl)propyl)benzo[d]imidazo[2,1-b]thiazole-7-carboxamide as a white solid.

Yield 8 mg (12%). $^1$H NMR (400 MHz, DMSO) δ 8.58 (t, J=5.6 Hz, 1H), 8.46 (d, J=1.6 Hz, 1H), 8.38 (d, J=3.6 Hz, 1H), 8.18 (d, J=8.4 Hz, 1H), 7.99 (dd, J=1.6, 8.4 Hz, 1H), 7.74 (d, J=7.6 Hz, 1H), 6.35 (d, J=12.4 Hz, 1H), 5.95 (s, 1H), 4.76-4.57 (m, 1H), 3.56-3.49 (m, 2H), 3.33-3.32 (m, 2H), 2.96 (t, J=8.4 Hz, 2H), 2.59-2.51 (m, 2H), 2.36 (t, J=7.2 Hz, 2H), 2.32-2.24 (m, 2H), 1.93-1.77 (m, 2H), 1.76-1.63 (m, 4H). $^{19}$F NMR (376 MHz, DMSO) δ−115.61, Aliphatic $^{19}$F signal not observed. m/z: [ESI$^+$]496 (M+H)$^+$. ($C_{26}H_{27}F_2N_5OS$).

Synthesis of N-(2-(2-fluoro-4-(pyrrolidin-2-yl)phenyl)benzo[d]imidazo[2,1-b]thiazol-7-yl)-1-methylpiperidine-4-carboxamide dihydrochloride (Compound 593)

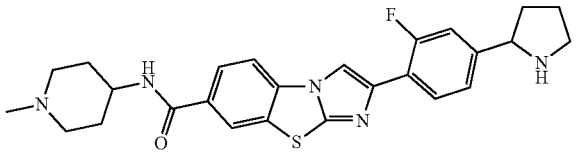

Compound N-(2-(2-fluoro-4-(pyrrolidin-2-yl)phenyl)benzo[d]imidazo[2,1-b]thiazol-7-yl)-1-methylpiperidine-4-carboxamide dihydrochloride was prepared from tert-butyl 2-(3-fluoro-4-(7-(1-methylpiperidine-4-carboxamido)benzo[d]imidazo[2,1-b]thiazol-2-yl)phenyl)pyrrolidine-1-carboxylate (100 mg, 0.173 mmol) following a similar procedure to that described for the synthesis of (S)-2-(2-fluoro- 4-(pyrrolidin-2-yl)phenyl)-N-(3-(4-fluoropiperidin-1-yl) propyl)-9-methyl-9H-benzo[d]imidazo[1,2-a]imidazole-7-carboxamide dihydrochloride and was isolated as a white solid.

Yield 13 mg (14%). 1H NMR (400 MHz, DMSO) δ 10.70 (br s, 1H), 10.48 (br s, 1H), 10.30 (br s, 1H), 9.19 (br s, 1H), 8.67 (d, J 3.6 Hz, 1H), 8.41-8.34 (m, 1H), 8.21-8.16 (m, 1H), 8.15-8.12 (m, 1H), 7.77-7.70 (m, 1H), 7.64-7.57 (m, 1H), 7.51-7.44 (m, 1H), 4.66-4.53 (m, 1H), 3.50-3.42 (m, 2H), 3.42-3.34 (m, 1H), 3.33-3.24 (m, 1H), 3.04-2.93 (m, 2H), 2.78-2.66 (m, 4H), 2.45-2.36 (m, 1H), 2.20-1.91 (m, 7H). $^{19}$F NMR (376 MHz, DMSO) δ−112.94. m/z: [ESI$^+$]478 (M+H)$^+$. ($C_{26}H_{30}Cl_2FN_5OS$).

Synthesis of N-(2-(2-fluoro-4-(pyrrolidin-2-yl)phenyl)benzo[d]imidazo[2,1-b]thiazol-7-yl)tetrahydro-2H-pyran-4-carboxamide hydrochloride (Compound 594)

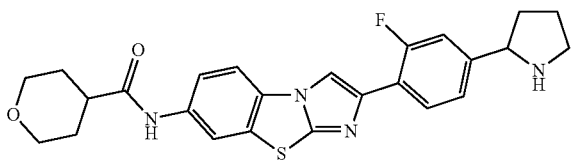 [SMILES: O=C(Nc1ccc2c(c1)sc1nc(-c3ccc(C4CCCN4)cc3F)cn12)C1CCOCC1]

Compound N-(2-(2-fluoro-4-(pyrrolidin-2-yl)phenyl)benzo[d]imidazo[2,1-b]thiazol-7-yl)tetrahydro-2H-pyran-4-carboxamide hydrochloride was prepared from tert-butyl 2-(3-fluoro-4-(7-(tetrahydro-2H-pyran-4-carboxamido) benzo[d]imidazo[2,1-b]thiazol-2-yl)phenyl)pyrrolidine-1-carboxylate (100 mg, 0.177 mmol) following a similar procedure to that described for the synthesis of (S)-2-(2-fluoro-4-(pyrrolidin-2-yl)phenyl)-N-(3-(4-fluoropiperidin-1-yl)propyl)-9-methyl-9H-benzo[d]imidazo[1,2-a]imidazole-7-carboxamide dihydrochloride and was isolated as an off-white solid.

Yield 85 mg (95%). $^1$H NMR (400 MHz, DMSO) δ 10.29 (br s, 1H), 10.02 (br s, 1H), 9.01 (br s, 1H), 8.66 (d, J 3.6 Hz, 1H), 8.41-8.32 (m, 1H), 8.23-8.16 (m, 1H), 8.16-8.07 (m, 1H), 7.74-7.65 (m, 1H), 7.61-7.54 (m, 1H), 7.50-7.41 (m, 1H), 4.67-4.56 (m, 1H), 3.99-3.86 (m, 2H), 3.46-3.25 (m, 4H), 2.74-2.58 (m, 1H), 2.46-2.35 (m, 1H), 2.18-1.97 (m, 3H), 1.80-1.61 (m, 4H). $^{19}$F NMR (376 MHz, DMSO) δ−112.96. m/z: [ESI$^+$]465 (M+H)$^+$. ($C_{25}H_{26}ClFN_4O_2S$).

Example 8

Biological Activity of Compounds of the Invention

The biological activity results of compounds of the invention are summarized in Table 2.

TABLE 2

Cellular −LogEC$_{50}$ values of compounds of the invention in the immunofluorescence assay.

| Compound No. | Myc Efficacy (−LogEC$_{50}$) |
|---|---|
| 100 | ++ |
| 101 | +++ |
| 102 | + |
| 103 | +++ |
| 104 | + |
| 105 | + |
| 106 | + |
| 107 | ++ |
| 108 | ++ |
| 109 | ++ |
| 110 | − |
| 111 | ++ |
| 112 | + |
| 114 | ++ |
| 115 | + |
| 116 | ++ |
| 117 | + |
| 118 | +++ |
| 119 | ++ |
| 122 | + |
| 123 | ++ |
| 124 | ++ |
| 125 | ++ |
| 126 | ++ |
| 127 | + |
| 129 | ++ |
| 130 | ++ |
| 131 | ++ |
| 132 | ++ |
| 133 | ++ |
| 134 | + |
| 135 | + |
| 136 | ++ |
| 137 | ++ |
| 138 | ++ |
| 139 | + |
| 140 | ++ |
| 141 | + |
| 142 | ++ |
| 143 | ++ |
| 144 | + |
| 145 | ++ |
| 149 | ++ |
| 150 | + |
| 151 | + |
| 152 | ++ |
| 153 | + |
| 154 | + |
| 155 | ++ |
| 156 | ++ |
| 157 | ++ |
| 158 | ++ |
| 159 | + |
| 160 | + |
| 161 | +++ |
| 162 | − |
| 163 | +++ |
| 164 | +++ |
| 165 | + |
| 166 | +++ |
| 167 | + |
| 168 | ++ |
| 169 | ++ |
| 170 | ++ |
| 171 | ++ |
| 172 | − |
| 173 | ++ |
| 174 | +++ |
| 175 | − |
| 176 | − |
| 177 | + |
| 178 | + |
| 179 | + |
| 180 | + |
| 181 | ++ |
| 182 | − |
| 183 | + |
| 184 | + |
| 185 | ++ |
| 186 | + |

TABLE 2-continued

Cellular $-LogEC_{50}$ values of compounds of the invention in the immunofluorescence assay.

| Compound No. | Myc Efficacy ($-LogEC_{50}$) |
|---|---|
| 187 | − |
| 188 | + |
| 189 | − |
| 190 | + |
| 191 | + |
| 192 | − |
| 193 | + |
| 194 | + |
| 195 | − |
| 196 | + |
| 197 | + |
| 198 | + |
| 199 | + |
| 200 | + |
| 201 | + |
| 202 | − |
| 203 | + |
| 204 | + |
| 205 | + |
| 206 | − |
| 207 | ++ |
| 208 | + |
| 209 | + |
| 210 | + |
| 211 | − |
| 212 | + |
| 213 | + |
| 214 | + |
| 215 | − |
| 216 | + |
| 217 | + |
| 218 | ++ |
| 219 | + |
| 220 | + |
| 221 | + |
| 222 | + |
| 223 | − |
| 224 | − |
| 225 | + |
| 226 | − |
| 227 | ++ |
| 228 | + |
| 229 | + |
| 230 | + |
| 231 | − |
| 232 | − |
| 233 | − |
| 234 | + |
| 235 | + |
| 236 | − |
| 237 | − |
| 238 | − |
| 239 | + |
| 240 | + |
| 241 | + |
| 242 | + |
| 243 | + |
| 244 | − |
| 245 | − |
| 246 | + |
| 247 | − |
| 248 | + |
| 249 | − |
| 250 | + |
| 251 | − |
| 252 | + |
| 253 | + |
| 254 | + |
| 255 | − |
| 256 | − |
| 257 | ++ |
| 258 | + |
| 259 | + |
| 260 | − |
| 261 | − |
| 262 | + |
| 263 | − |
| 264 | +++ |
| 265 | + |
| 266 | + |
| 267 | + |
| 268 | + |
| 269 | + |
| 270 | + |
| 271 | + |
| 272 | − |
| 273 | − |
| 274 | + |
| 275 | − |
| 276 | +++ |
| 277 | ++ |
| 278 | − |
| 279 | − |
| 280 | ++ |
| 281 | ++ |
| 282 | + |
| 283 | + |
| 284 | + |
| 285 | + |
| 286 | ++ |
| 287 | + |
| 288 | +++ |
| 289 | +++ |
| 290 | +++ |
| 291 | + |
| 292 | +++ |
| 293 | ++ |
| 294 | ++ |
| 295 | ++ |
| 296 | + |
| 297 | + |
| 298 | +++ |
| 299 | ++ |
| 300 | +++ |
| 301 | + |
| 303 | + |
| 306 | ++ |
| 307 | ++ |
| 308 | + |
| 309 | ++ |
| 310 | + |
| 312 | ++ |
| 314 | + |
| 315 | ++ |
| 317 | + |
| 318 | ++ |
| 319 | ++ |
| 320 | +++ |
| 321 | ++ |
| 322 | + |
| 323 | +++ |
| 324 | ++ |
| 325 | ++ |
| 326 | ++ |
| 327 | + |
| 328 | ++ |
| 329 | + |
| 330 | + |
| 331 | +++ |
| 332 | +++ |
| 333 | + |
| 334 | ++ |
| 348 | ++ |
| 362 | ++ |
| 363 | ++ |
| 364 | ++ |
| 365 | ++ |
| 368 | +++ |

TABLE 2-continued

Cellular $-LogEC_{50}$ values of compounds of the invention in the immunofluorescence assay.

| Compound No. | Myc Efficacy ($-LogEC_{50}$) |
|---|---|
| 369 | +++ |
| 370 | +++ |
| 371 | ++ |
| 372 | ++ |
| 373 | +++ |
| 374 | +++ |
| 375 | +++ |
| 376 | +++ |
| 378 | +++ |
| 379 | +++ |
| 381 | +++ |
| 383 | ++ |
| 384 | ++ |
| 386 | +++ |
| 387 | +++ |
| 388 | ++ |
| 389 | ++ |
| 390 | ++ |
| 392 | +++ |
| 393 | +++ |
| 394 | ++ |
| 395 | ++ |
| 396 | ++ |
| 397 | ++ |
| 398 | ++ |
| 406 | ++ |
| 412 | +++ |
| 413 | +++ |
| 414 | +++ |
| 415 | +++ |
| 416 | +++ |
| 417 | +++ |
| 418 | +++ |
| 419 | +++ |
| 420 | +++ |
| 421 | ++ |
| 422 | +++ |
| 425 | +++ |
| 428S | +++ |
| 428R | ++ |
| 432S | +++ |
| 432R | +++ |
| 434S | +++ |
| 434R | +++ |
| 454 | +++ |
| 464S | +++ |
| 464R | +++ |
| 474 | +++ |
| 475 | ++ |
| 476 | +++ |
| 477 | +++ |
| 478 | + |
| 479 | +++ |
| 480 | +++ |
| 481 | +++ |
| 482 | +++ |
| 483 | +++ |
| 484 | +++ |
| 485 | +++ |
| 486 | ++ |
| 487 | ++ |
| 488 | +++ |
| 489 | ++ |
| 490 | +++ |
| 491R | +++ |
| 491S | +++ |
| 492 | +++ |
| 493 | +++ |
| 495 | +++ |
| 496 | + |
| 497 | +++ |
| 498 | +++ |
| 499 | ++ |
| 500 | +++ |
| 501 | +++ |
| 502 | ++ |
| 503S | +++ |
| 503R | +++ |
| 504 | +++ |
| 505 | +++ |
| 506 | +++ |
| 507 | +++ |
| 508 | +++ |
| 509R | +++ |
| 509S | +++ |
| 510 | +++ |
| 511 | +++ |
| 512 | +++ |
| 513 | +++ |
| 514 | +++ |
| 515 | +++ |
| 516 | +++ |
| 517 | +++ |
| 518 | +++ |
| 519 | +++ |
| 520 | ++ |
| 521 | +++ |
| 522S | +++ |
| 522R | +++ |
| 523 | +++ |
| 524S | ++ |
| 524R | ++ |
| 525 | +++ |
| 526 | ++ |
| 527 | +++ |
| 528 | +++ |
| 529 | +++ |
| 530 | +++ |
| 531 | ++ |
| 532 | +++ |
| 533 | +++ |
| 534 | +++ |
| 535 | +++ |
| 536 | +++ |
| 537 | +++ |
| 538 | +++ |
| 539 | +++ |
| 540 | +++ |
| 541 | +++ |
| 542 | +++ |
| 543 | +++ |
| 544 | +++ |
| 545 | +++ |
| 546 | +++ |
| 547 | +++ |
| 548 | +++ |
| 593 | +++ |
| 594 | +++ |
| 600 | +++ |
| 601 | +++ |
| 602 | +++ |

Activity ($-LogEC_{50}$):
− ≤3
+ >3 and <5
++ ≥5 and <6
+++ ≥6

Figure 1:
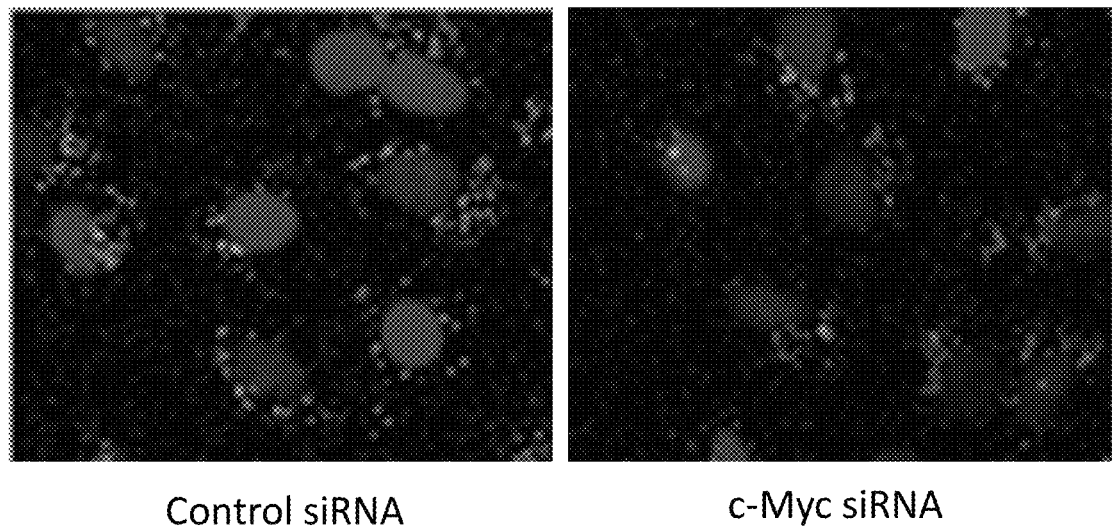
FIG. 1 demonstrates how Protein Synthesis Monitoring (PSM) specifically monitors c-Myc synthesis. The assay system comprises human non-small cell lung carcinoma cell line A549, which is expressing high level of c-Myc. Two tRNAs (di-tRNA) which decode one specific glutamine codon and one specific serine codon were transfected with control RNAi or an RNAi directed to c-Myc. The FRET signal specifically monitors c-Myc translation, as the FRET signal in c-Myc siRNA treated cells was inhibited. In blue, cell nuclei stained with DAPI; in yellow, FRET signals from tRNA pair which decodes glutamine-serine di-codons.

Compounds activity was tested in tumor cell lines expressing c-Myc by using high content image analysis. c-Myc mRNA rate of translation was assays using PSM assay, c-Myc protein levels and intracellular localization were assayed by immunofluorescence using a c-Myc specific antibody and c-Myc mRNA levels and intracellular localization was tested using specific fluorescent probes, as detailed in the Experimental Methods below (Example 10). The di-tRNA translation rate measurement specificity to c-Myc was shown by co-transfecting c-Myc specific siRNA. Transfection of labelled di-tRNA with c-Myc specific siRNA reduced the FRET signal originating from ribosome translating c-Myc, relative to cells transfected with nonrelevant siRNA (FIG. 1).

Figure 2:
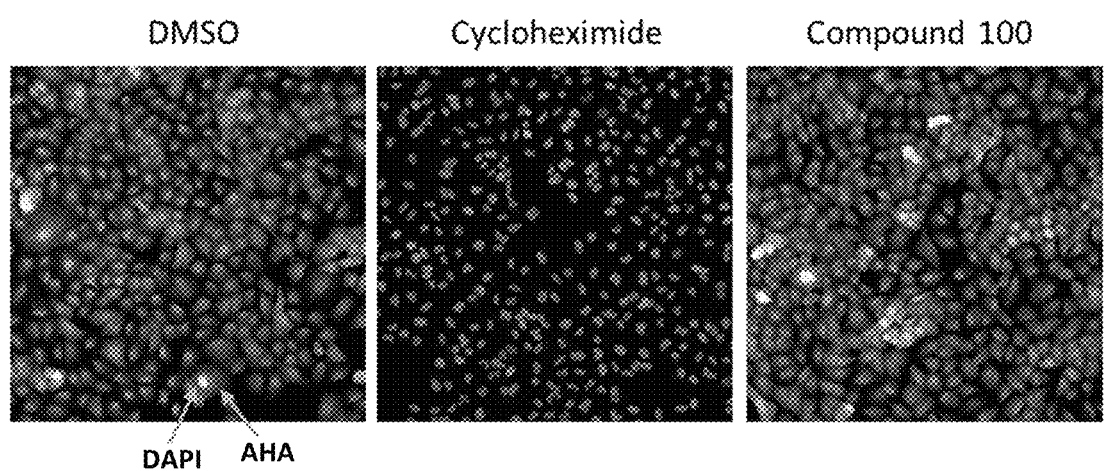
FIG. 2 depicts selective regulation of c-Myc translation. The panel demonstrates metabolic labeling in A549 cells, treated with vehicle, general translation inhibitor cycloheximide or anti-c-Myc compound. Treatment with cycloheximide resulted in total inhibition of global protein synthesis, while treatment with tested compound showed no significant effect. In gray, cell nuclei stained with DAPI; in yellow, L-Azidohomoalanine (AHA) metabolic labeling.

Compounds did not affect global translation. A549 cells were incubated with active compounds and metabolically labelled with fluorescent methionine for a 4 hour pulse (click-chemistry modified methionine). Cells were fixed and newly synthesized proteins detected by using click-chemistry with a fluorescent detector (FIG. 2). Global ribosome inhibitor, cycloheximide (CHX) completely reduced incorporation of modified methionine (FIG. 2, compare middle and left panels). However, a representative compound did not inhibit incorporation of modified methionine, indicating that global translation is not affected by the compounds (FIG. 2, compare right and left panels, respectively).

Figure 3:
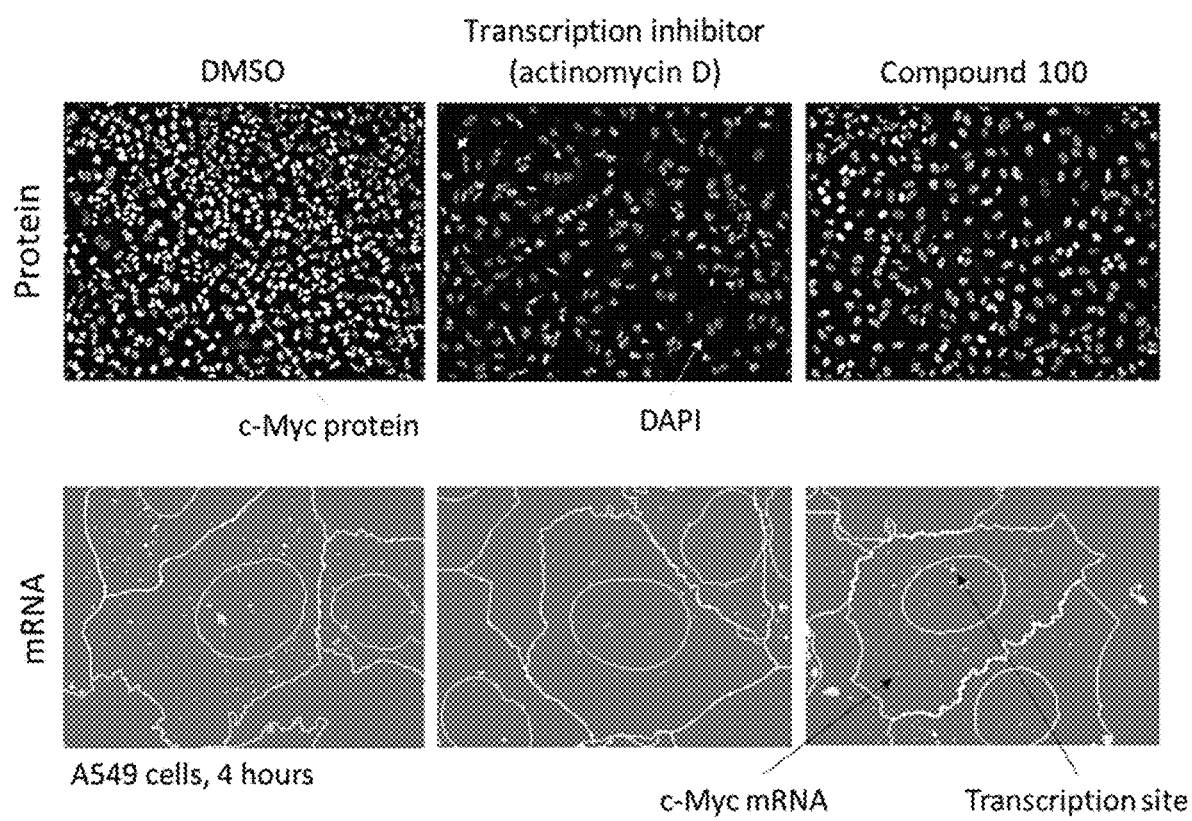
FIG. 3 demonstrates that compounds act at the level of mRNA processing/stability. A549 cells were exposed to vehicle, general transcription inhibitor actinomycin D or anti-c-Myc compound.

Compounds reduced c-Myc protein accumulation in A549 cells without affecting c-Myc transcription. A549 cells were incubated with compounds for 24 hours (FIG. 3, upper panel) and c-Myc protein detected by immunofluorescence. In parallel, A549 cells were incubated with compounds for 4 hours and c-Myc mRNA was visualized by micrscopy using c-Myc mRNA specific fluorescent-tagged probes (FIG. 3, lower panel). Both a general transcription inhibitor, Actinomycin D, and compounds of the invention, reduced c-Myc protein (FIG. 3, upper panel). Actinomycin D inhibited transcription site (FIG. 3, middle lower panel, spots inside the nucleus) and mRNA accumulation in the cytoplasm (FIG. 3, middle lower panel, spots in the cytoplasm). However, compound treated cells did not affect transcription site intensity or number (FIG. 3, right lower panel, spots inside the nucleus are evident), but did affect steady state levels of mRNA in the cytoplasm (FIG. 3, right lower panel, reduction of spots in the cytoplasm relative to DMSO control). This indicates that compounds of the invention affect c-Myc steady state mRNA levels, either by affecting turn over rate of c-Myc mRNA, or by inhibiting its recruitment by ribosomes.

A549 human non-small cell lung carcinoma cells were treated for 24 hours with increasing compound concentration, cells were fixed and stained with a nuclei stain (DAPI) and anti-c-Myc fluorescent antibody. The c-Myc signal was quantified by image analysis, and data was exported and analyzed using TIBCO Spotfire® (TIBCO Corporation). Dose response curves were generated and fitted with logaristic regression to calculate potency ($EC_{50}$ values). Potency values are presented in Table 2 for all compounds and are shown for selected compounds (FIG. 4).

Example 9

In Vivo Activity of Compounds of the Invention
A549 Xenograft Model in Nude Mice.

NMRI nude female mice of 6-8 weeks of age were acclimated after shipping for >4 days. A549 cells, $5 \times 10^6$ in 100 ul Matrigel:PBS (50:50), were subcutaneously injected into flanks of mice. When the tumor size reached 80 to 200 mm³, mice were grouped with similar average tumor size in each group, 10 animals per group. Compounds were dissolved in 10% DMSO, 10% Solutol, 80% water. Compounds were given i.p. for 49 days at 3 mg/kg twice a week. Caliper measurement of tumor size was done twice a week.

Compound 332 inhibited c-Myc-dependent tumor growth in-vivo. FIG. 5 shows the relative tumor volumes of A549 xenografts in NMRI female nude mice after they were treated with compound 332, 3 mg/kg, twice a week, for 49 days. Error bars represent median±SEM, n=10 mice at each time point and analyzed by one-tailed T-TEST in Prism for *p<0.05.

Example 10

Experimental Methods
High Content Screen for the Identification of c-Myc Modulators Compound effect on translation of c-Myc in A549, human non-small cell lung carcinoma cell line, was conducted using specific PSM assay using tRNAgln and tRNAser isoacceptors, as described below. A library of diverse small molecules, 90,000 compounds, was used at a final concentration of 30 µM. Image and data analyses were conducted using Anima's proprietary algorithms. False positive and toxic compounds were eliminated. A total of 3,307 compounds were identified as hits, compounds which increased or decreased the FRET signal generated by ribosomes during c-Myc translation.

Positive hits were re-screened in the specific PSM assay, using tRNAgln and tRNAser. Hits were scored using Anima's proprietary algorithms, and 348 compounds, which selectively inhibited c-Myc synthesis in specific PSM assay, were selected as confirmed hits. These compounds were purchased as powder to confirm activity. Re-purchased hits were tested in the specific PSM assay (tRNAgln-tRNAser) and anti-c-Myc immunofluorescence, and in counter assays to eliminate global translation modulators: (1) bulk tRNA and (2) metabolic labeling using Click-IT™ AHA (L-Azidohomoalanine).

Cell Culture

A549 cells (ATCC® CCL-185™) were maintained in DMEM low glucose medium (Biological Industries, Cat. 01-050-1A), containing 10% fetal bovine serum, 1% L-glutamine and 1% penicillin-streptomycin solution.

SK-N-F1 cells (ATCC® CRL-2142') were maintained in DMEM high glucose medium (Biological Industries, Cat. 01-055-1A), containing 10% fetal bovine serum, 2% L-glutamine, 1% penicillin-streptomycin solution, 1% sodium pyruvate and 1% non-essential amino acids.

Specific tRNA (tRNA isoacceptor) isolation and labeling

The Specific tRNAgln (TTG) and tRNAser (CGA) were Isolated for from Baker's Yeast (Roche) using biotinylated oligos complimentary to sequences encompassing the D-loop and anti-codon. The biotinylated oligos were mixed with total yeast tRNA and heated up to 82° C. for 10 min, followed by addition of TMA buffer (20 mM Tris, pH 7.6, 1.8M tetramethylammonium chloride, 0.2 mM EDTA). The mixture was incubated at 68° C. for 10 min, and annealed by slow cooling to 37° C. tRNA:DNA oligo mixture then was incubated with streptavidin linked agarose beads at room temperature for 30 min while shaking. Unbound tRNA and tRNA:DNA complexes were removed by centrifugation and beads washed with 10 mM Tris-HCl (pH 7.6). The target tRNA was eluted from the resin by incubation at 45° C. or 55° C. for 7 min followed by centrifugation and collection of the supernatant to clean tubes.

The purity of the isolated tRNA isoacceptors was confirmed using fluorescent polarization assay. Purified tRNA was annealed to a complementary oligo tagged at the 3'-end with Cy3. The annealed purified tRNA isoacceptor FP signal was compared to the signal derived from annealing of a tRNA isoacceptor oligo annealed to the same Cy3-oligo. Samples with more than 80% purity were selected for labeling.

The dihydrouridines of the target tRNAs or total yeast tRNA were labeled as described in U.S. Pat. No. 8,785,119. Labeled tRNAs were purified by reverse phase HPLC and eluted with an ethanol gradient.

Protein Synthesis Monitoring (PSM) Assays

Cy3 and Cy5 Labeled tRNA, bulk or specific, were transfected with 0.4 µl HiPerFect (Qiagen) per 384 well. First, HiPerFect was mixed with DMEM and incubated for 5 min; next, 6 nanograms Cy3-labeled tRNAgln and 6 ng Cy5-labled tRNAser (or 9 ng each Cy3 and Cy5-labelled bulk tRNA) were diluted in 1×PBS and then added to the HiPerFect:DMEM cocktail and incubated at room temperature for 10 min. The transfection mixture was dispersed automatically into 384-well black plates. Cells were then seeded at 3,500 cells per well in complete culture medium and incubated at 37° C., 5% $CO_2$. Forty-eight hours after transfection compounds were added at a final concentration of 30 µM. Four hours post-treatment, cells were fixed with 4% paraformaldehyde and images were captured with Operetta microscope (Perkin Elmer) using ×20 high NA objective lens.

Metabolic Labeling Assay

A549 cells were seeded at 3,200 cells per well in complete culture medium. Plates were incubated at 37° C., 5% $CO_2$ overnight. After 48 hours of incubation, the growth medium was aspirated, and cells were washed three times with HBSS. Metabolic labeling medium DMEM (-Cys-Met), containing 10% dialyzed FBS, 10% pencillin-streptomycin and 1% L-glutamine was added to the cells for 30 min. Then medium was replaced by metabolic labeling medium containing 25 µM L-Azidohomoalanine (AHA, ThermoFisher) and tested compounds at a final concentration of 30 µM, and cells were incubated for 4 hours at 37° C., 5% $CO_2$. Cells were washed by HBSS at 37° C. for 15 min before fixing with 4% paraformaldehyde. Cells were washed twice with 3% BSA in PBS before permeabilization with 0.5% Triton X-100 in PBS for 20 min. The AHA staining with Alexa Fluor™ 555 alkyne was performed according to the manufacturer protocol. Images were captured with Operetta microscope (Perkin Elmer) using ×20 high NA objective lens.

c-Myc Immunofluorescence Assay

A549 cells were grown in 384-wells plates (Perkin Elmer, Cat. 6057300) for 48 hours, treated with compounds and then fixed for 20 min in 4% paraformaldehyde. After that permeabilization was done using 0.1% Triton X-100 in PBS for 20 min. Primary anti-c-Myc antibody (Abcam, ab32072) staining was performed for 90 min at room temperature. Cells then were washed twice with PBS and incubated with secondary antibody (Abcam, ab150075) for 90 min at room temperature. Nuclei were stained with DAPI for 10 min and washed twice with PBS.

Cell images were taken with Operetta (Perkin Elmer, USA), a wide-field fluorescence microscope at 20× magnification. After acquisition, the images were transferred to Columbus software (Perkin-Elmer) for image analysis. In Columbus, cells were identified by their nucleus, using the "Find Nuceli" module and cytoplasm was detected based on the secondary antibody channel. Subsequently, the fluorescent signal was enumerated in the identified cell region. Then data was exported to a data analysis and visualization software, Tibco Spotfire, USA.

Fluorescent In Situ Hybridization (FISH) Assay

A549 cells were grown in 384-wells plates (Perkin Elmer, Cat. 6057300) for 48 hours, treated with compounds for 4 hours and then fixed for 20 min in 4% paraformaldehyde. Next day, permeabilization was done for 90 min at 4° C., using 70% ethanol. Then, the cells were incubated for 10 min with 10% formamide in 10% saline-sodium citrate. Fluorescently labeled custome DNA probes that target c-Myc (Cy3, BioSearch Technologies, Cat. SMF-1063-5) and GAPDH (Cy5, BioSearch Technologies, Cat. SMF-2019-1) mRNAs were hybridized overnight at 37° C. in a dark chamber in 10% formamide. The next day, cells were washed twice with 10% formamide for 30 min. Next, nuclei were counterstained with DAPI (SIGMA, Cat. 5MG-D9542) and then cells were washed twice with PBS. FISH experiments were performed according to the probes manufacturer's protocol for adherent cells.

Following RNA FISH experiments, images of cells were taken with Operetta (Perkin Elmer, USA), a wide-field fluorescence microscope at ×63 magnification. After acquisition, the images were transferred to Columbus software for image analysis. In Columbus, cells were identified by their nucleus, using the "Find Nuceli" module, cytoplasm was detected based on the FISH-channel, and single mRNAs in the cytoplasm and transcription sites in the nucleus were detected using "Find Spots" module. Subsequently, fluorescent signals were collected for each channel in the identified regions: nucleus, cytoplasm and spots. Data was exported to a data analysis and visualization software, Tibco Spotfire, USA.

A549 Xenograft Model in Nude Mice.

NMRI nude female mice of 6-8 weeks of age were acclimated after shipping for >4 days. A549 cells, $5 \times 10^6$ in 100 ul Matrigel:PBS (50:50), were subcutaneously injected into flanks of mice. When the tumor size reached 80 to 200 $mm^3$, mice were grouped with similar average tumor size in each group, 10 animals per group. Compounds were dissolved in 10% DMSO, 10% Solutol, 80% water. Compounds were given i.p. for 49 days at 3 mg/kg twice a week. Caliper measurement of tumor size was done twice a week.

What is claimed:

1. A compound represented by the structure of formula I (j):

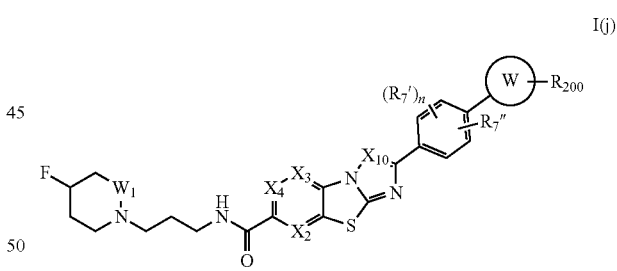

wherein $X_2$, $X_3$, and $X_4$, are each independently nitrogen or CH;

$X_{10}$ is N, CH, C(R), C($CH_2$)OH, C($CH_2$)$_2$OH, C(NH—$CH_2$-cyclopropyl), C($CH_3$), C(cyclopropyl), C(isopropoxy), or C(COOH);

Ring W is a 3-10 membered single, fused, bridged or spiro, saturated, unsaturated or aromatic, carbocyclic or heterocyclic ring, morpholine, tetrahydrofuran, tetrahydropyran, oxetane, pyrrolidine, pyrrolidin-2-one, pyrrolidin-3-one, imidazole, pyrazole, isoxazolidine, piperazine, piperidine, piperidine-2-one, oxadiazole, triazole, 2-oxopyrrolidine, cyclopropyl, 2,2-dimethylpyrrolidine, 4-azaspiro [2.4]heptane, pyrrolidin-3-one-O-methyloxime, 2-oxa-5-azaspiro [3.4]octane, 1,4-dioxa-6-azaspiro [4.4]nonane, 3,3-dimethylmorpholine, 1-methylpiperazine, 4,7-diazaspiro [2.5]octane, bicyclo[1.1.1]pentane, 2,5-diazabicyclo [2.2.1] heptane, piperazine, or piperazine-2-one;

$W_1$ is $CH_2$, C=O, $CH(R_{10})$, or $CHCH_3$;

$R_7'$ and $R_7''$ are each independently H, F, Cl, Br, I, OH, O—$R_{20}$, SH, $R_8$—OH, $R_8$—SH, —$R_8$—O—$R_{10}$, $R_8$-($C_3$-$C_8$ cycloalkyl), $R_8$-(3-8 membered heterocyclic ring), $CF_3$, $CD_3$, $OCD_3$, CN, $NO_2$, —$CH_2CN$, —$R_8CN$, $NH_2$, NHR, $N(R)_2$, $NH(R_{10})$, $N(R_{10})(R_{11})$, $R_8$—$N(R_{10})(R_{11})$, $R_9$-$R_8$—$N(R_{10})(R_{11})$, $B(OH)_2$, —$OC(O)CF_3$, —$OCH_2Ph$, NHC(O)—$R_{10}$, NHCO—N$(R_{10})(R_{11})$, COOH, —C(O)Ph, C(O)O—$R_{10}$, $R_8$—C(O)-$R_{10}$, C(O)H, C(O)-$R_{10}$, $C_1$-$C_5$ linear or branched C(O)-haloalkyl, —C(O)$NH_2$, C(O)NHR, C(O)N($R_{10}$)($R_{11}$), $SO_2R$, $SO_2N(R_{10})(R_{11})$, $CH(CF_3)(NH$—$R_{10})$, $C_1$-$C_5$ linear or branched, substituted or unsubstituted alkyl, isopropyl, methyl, ethyl, $C_1$-$C_5$ linear or branched, substituted or unsubstituted alkenyl, $C_1$-$C_5$ linear or branched, or $C_3$-$C_8$ cyclic haloalkyl, $CHF_2$, $C_1$-$C_5$ linear or branched, or $C_3$-$C_8$ cyclic alkoxy, methoxy, optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, cyclopropyl, cyclohexyl, substituted or unsubstituted 3-8 membered heterocyclic ring, morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine, substituted or unsubstituted aryl, substituted or unsubstituted benzyl;

or $R_7'$ and $R_7''$ are joined to form a 3-8 membered substituted or unsubstituted, saturated, unsaturated or aromatic, carbocyclic or heterocyclic ring, cyclopentyl, cyclohexyl, piperidine, tetrahydrofuran, tetrahydropyran, or pyrrolidine;

$R_{20}$ is represented by the following structure:

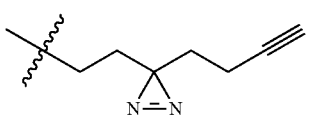 [SMILES: *CCC1(CCC#C)N=N1]

R is H, F, Cl, Br, I, OH, SH, alkoxy, $NH(R_{10})$, NH—$CH_2$-cyclopropyl, $N(R_{10})(R_{11})$, $CF_3$, CN, $NO_2$, COOH, $C_1$-$C_5$ linear or branched, substituted or unsubstituted alkyl, methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$, $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl, $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $R_8$-aryl, $CH_2$-Ph,-$R_8$—O—$R_8$—O—$R_{10}$, $(CH_2)_2$—O—$(CH_2)_2$—O—$CH_3$), —$R_8$—O—$R_{10}$ ($CH_2$—OH, $CH_2$—$CH_2$—OH), —$R_8$-$R_{10}$, $(CH_2)_2$—O—$CH_3$, substituted or unsubstituted aryl, phenyl, substituted or unsubstituted heteroaryl, or pyridine;

$R_{200}$ is H, $R_{20}$, F, Cl, Br, I, OH, SH, alkoxy, $NH_2$, $N(R)_2$, $NH(R_{10})$, $N(R_{10})(R_{11})$, $CF_3$, CN, $NO_2$, $C_1$-$C_5$ linear or branched, substituted or unsubstituted alkyl, methyl, ethyl, $CH_2$—$CH_2$—O—$CH_2$—$CH_2$—O—$CH_3$, $CH_2$—O—$CH_2$—$CH_2$—O—$CH_3$, $C_1$-$C_5$ linear or branched alkoxy, methoxy, $C_1$-$C_5$ linear or branched haloalkyl, $CHF_2$, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $R_8$-aryl, $CH_2$-Ph, —$R_8$—O—$R_8$—O—$R_{10}$, $(CH_2)_2$—O—$(CH_2)_2$—O—$CH_3$, —$R_8$—O—$R_{10}$, —$R_8$-$R_{10}$, $(CH_2)_2$—O—$CH_3$, substituted or unsubstituted aryl, phenyl, substituted or unsubstituted heteroaryl, or pyridine;

or $R_{200}$ and the carbon atom to which it is connected are C=O, C=N—O(R), C=N—O—$CH_3$ or $C(R)_2$, $C(CH_3)_2$, or $CF_2$;

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl, methyl, ethyl, $CH_2$-cyclopropyl, $CH_2$—$CH_2$—O—$CH_3$, $C_1$-$C_5$ substituted or unsubstituted linear or branched haloalky, $CH_2CF_3$, $C_1$-$C_5$ linear or branched alkoxy, O—$CH_3$, $R_{20}$, C(O)R, or S $(O)_2R$;

or $R_{10}$ and $R_{11}$ are joined to form a substituted or unsubstituted 3-8 membered heterocyclic ring, piperazine, or piperidine, n is an integer between 0 and 4;

or its pharmaceutically acceptable salt, stereoisomer, tautomer, hydrate, N-oxide, reverse amide analog, prodrug, isotopic variant, deuterated analog, pharmaceutical product or any combination thereof.

2. The compound of claim 1, wherein

Ring W is a 3-8 membered single saturated heterocyclic ring, morpholine (2 or 3-morpholine), tetrahydrofuran, tetrahydropyran, oxetane, pyrrolidine, isoxazolidine, piperazine, piperidine;

a 3-8 membered single unsaturated heterocyclic ring, pyrrolidin-2-one, pyrrolidin-3-one, imidazole, pyrazole, piperidine-2-one, piperazine-2-one, oxadiazole, triazole, 2-oxopyrrolidine;

a 3-10 membered spiro saturated heterocyclic ring, 4-azaspiro [2.4]heptane, 2-oxa-5-azaspiro [3.4]octane, 1,4-dioxa-6-azaspiro [4.4]nonane, 4,7-diazaspiro [2.5] octane;

a 3-10 membered bridged saturated heterocyclic ring, bicyclo[1.1.1]pentane, 2,5-diazabicyclo [2.2.1]heptane;

or a 3-8 membered single saturated carbocyclic ring (cycloalkyl), cyclopropyl;

$R_{200}$ is H, OH, F, $NH_2$, $C_1$-$C_5$ linear or branched alkoxy, methoxy, CN, $C_1$-$C_5$ linear or branched, substituted or unsubstituted alkyl, methyl, $C_1$-$C_5$ linear or branched haloalkyl, $CHF_2$, or $R_{200}$ and the carbon atom to which it is connected are C=O, C=N—O(R), C=N—O—$CH_3$ $C(R)_2$, $C(CH_3)_2$, or $CF_2$;

$X_2$, and $X_3$ are CH;

$X_4$, is N or CH;

$X_{10}$ is N, CH, $C(CH_2)OH$, $C(CH_2)_2OH$, $C(NH$—$CH_2$-cyclopropyl), $C(CH_3)$, C (cyclopropyl), C(isopropoxy) or C(COOH);

$R_7'$ is H, F, Cl, $CF_3$, $C_1$-$C_5$ linear or branched, substituted or unsubstituted alkyl, methyl, $C_1$-$C_5$ linear or branched, or $C_3$-$C_8$ cyclic alkoxy, methoxy, substituted or unsubstituted $C_3$-$C_8$ cycloalkyl, cyclopropyl or cyclohexyl, or substituted or unsubstituted aryl;

$R_7''$ is H or F;

n is 1 or 2;

or any combination thereof.

3. The compound of claim 1, selected from the group consisting of:

| Compound No. | Compound Name |
|---|---|
| 425 | 2-(2-fluoro-4-(3-hydroxyoxetan-3-yl)phenyl)-N-(3-(4-fluoropiperidin-1-yl)propyl)benzo[d]imidazo[2,1-b]thiazole-7-carboxamide |
| 427S | (S)-N-(3-(4-fluoropiperidin-1-yl)propyl)-2-(4-(pyrrolidin-2-yl)-3-(trifluoromethyl)phenyl)benzo[d]imidazo[2,1-b]thiazole-7-carboxamide |
| 427R | (R)-N-(3-(4-fluoropiperidin-1-yl)propyl)-2-(4-(pyrrolidin-2-yl)-3-(trifluoromethyl)phenyl)benzo[d]imidazo[2,1-b]thiazole-7-carboxamide |
| 428S | (S)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide |
| 428R | (R)-2-(2-fluoro-4-(tetrahydrofuran-2-yl)phenyl)-N-(3-(4-fluoropiperidin-1-yl)propyl)benzo[d]imidazo[2,1-b]thiazole-7-carboxamide |
| 429S | N-(3-(4-fluoro-2-methylpiperidin-1-yl)propyl)-2-(2-fluoro-4-((S)-pyrrolidin-2-yl)phenyl)benzo[d]imidazo[2,1-b]thiazole-7-carboxamide |
| 429R | N-(3-(4-fluoro-2-methylpiperidin-1-yl)propyl)-2-(2-fluoro-4-((R)-pyrrolidin-2-yl)phenyl)benzo[d]imidazo[2,1-b]thiazole-7-carboxamide |
| 430S | N-(3-(4-fluoro-2-oxopiperidin-1-yl)propyl)-2-(2-fluoro-4-((S)-pyrrolidin-2-yl)phenyl)benzo[d]imidazo[2,1-b]thiazole-7-carboxamide |
| 430R | N-(3-(4-fluoro-2-oxopiperidin-1-yl)propyl)-2-(2-fluoro-4-((R)-pyrrolidin-2-yl)phenyl)benzo[d]imidazo[2,1-b]thiazole-7-carboxamide |
| 432S | (S)-2-(2-fluoro-4-(5-oxopyrrolidin-2-yl)phenyl)-N-(3-(4-fluoropiperidin-1-yl)propyl)benzo[d]imidazo[2,1-b]thiazole-7-carboxamide |
| 432R | (R)-2-(2-fluoro-4-(5-oxopyrrolidin-2-yl)phenyl)-N-(3-(4-fluoropiperidin-1-yl)propyl)benzo[d]imidazo[2,1-b]thiazole-7-carboxamide |
| 433S | (S)-2-(2-fluoro-4-(1-methylpyrrolidin-2-yl)phenyl)-N-(3-(4-fluoropiperidin-1-yl)propyl)benzo[d]imidazo[2,1-b]thiazole-7-carboxamide |
| 433R | (R)-2-(2-fluoro-4-(1-methylpyrrolidin-2-yl)phenyl)-N-(3-(4-fluoropiperidin-1-yl)propyl)benzo[d]imidazo[2,1-b]thiazole-7-carboxamide |
| 434S | (S)-2-(2-fluoro-4-(pyrrolidin-3-yl)phenyl)-N-(3-(4-fluoropiperidin-1-yl)propyl)benzo[d]imidazo[2,1-b]thiazole-7-carboxamide |
| 434R | (R)-2-(2-fluoro-4-(pyrrolidin-3-yl)phenyl)-N-(3-(4-fluoropiperidin-1-yl)propyl)benzo[d]imidazo[2,1-b]thiazole-7-carboxamide |
| 435S | (S)-2-(2-fluoro-4-(tetrahydrofuran-3-yl)phenyl)-N-(3-(4-fluoropiperidin-1-yl)propyl)benzo[d]imidazo[2,1-b]thiazole-7-carboxamide |
| 435R | (R)-2-(2-fluoro-4-(tetrahydrofuran-3-yl)phenyl)-N-(3-(4-fluoropiperidin-1-yl)propyl)benzo[d]imidazo[2,1-b]thiazole-7-carboxamide |
| 436S | (S)-2-(2-fluoro-4-(piperidin-2-yl)phenyl)-N-(3-(4-fluoropiperidin-1-yl)propyl)benzo[d]imidazo[2,1-b]thiazole-7-carboxamide |
| 436R | (R)-2-(2-fluoro-4-(piperidin-2-yl)phenyl)-N-(3-(4-fluoropiperidin-1-yl)propyl)benzo[d]imidazo[2,1-b]thiazole-7-carboxamide |
| 440 | 2-(2-fluoro-4-(1-hydroxycyclopropyl)phenyl)-N-(3-(4-fluoropiperidin-1-yl)propyl)benzo[d]imidazo[2,1-b]thiazole-7-carboxamide |
| 442 | (S)-3-((cyclopropylmethyl)amino)-N-(3-(4-fluoropiperidin-1-yl)propyl)-2-(4-(pyrrolidin-2-yl)phenyl)benzo[d]imidazo[2,1-b]thiazole-7-carboxamide |
| 443 | (R)-3-((cyclopropylmethyl)amino)-N-(3-(4-fluoropiperidin-1-yl)propyl)-2-(4-(pyrrolidin-2-yl)phenyl)benzo[d]imidazo[2,1-b]thiazole-7-carboxamide |
| 444 | (S)-3-((cyclopropylmethyl)amino)-2-(2-fluoro-4-(pyrrolidin-2-yl)phenyl)-N-(3-(4-fluoropiperidin-1-yl)propyl)benzo[d]imidazo[2,1-b]thiazole-7-carboxamide |
| 445 | (R)-3-((cyclopropylmethyl)amino)-2-(2-fluoro-4-(pyrrolidin-2-yl)phenyl)-N-(3-(4-fluoropiperidin-1-yl)propyl)benzo[d]imidazo[2,1-b]thiazole-7-carboxamide |
| 446 | N-(3-(4-fluoro-2-oxopiperidin-1-yl)propyl)-2-(2-fluoro-4-((S)-tetrahydrofuran-2-yl)phenyl)benzo[d]imidazo[2,1-b]thiazole-7-carboxamide |
| 447 | N-(3-(4-fluoro-2-oxopiperidin-1-yl)propyl)-2-(2-fluoro-4-((S)-tetrahydrofuran-2-yl)phenyl)benzo[d]imidazo[2,1-b]thiazole-7-carboxamide |
| 448 | N-(3-(4-fluoro-2-oxopiperidin-1-yl)propyl)-2-(2-fluoro-4-((S)-5-oxopyrrolidin-2-yl)phenyl)benzo[d]imidazo[2,1-b]thiazole-7-carboxamide |
| 449 | N-(3-(4-fluoro-2-oxopiperidin-1-yl)propyl)-2-(2-fluoro-4-((R)-5-oxopyrrolidin-2-yl)phenyl)benzo[d]imidazo[2,1-b]thiazole-7-carboxamide |
| 450S | (S)-2-(2,6-difluoro-4-(pyrrolidin-2-yl)phenyl)-N-(3-(4-fluoropiperidin-1-yl)propyl)benzo[d]imidazo[2,1-b]thiazole-7-carboxamide |
| 450R | (R)-2-(2,6-difluoro-4-(pyrrolidin-2-yl)phenyl)-N-(3-(4-fluoropiperidin-1-yl)propyl)benzo[d]imidazo[2,1-b]thiazole-7-carboxamide |
| 451S | (S)-2-(2,6-dimethyl-4-(pyrrolidin-2-yl)phenyl)-N-(3-(4-fluoropiperidin-1-yl)propyl)benzo[d]imidazo[2,1-b]thiazole-7-carboxamide |
| 451R | (R)-2-(2,6-dimethyl-4-(pyrrolidin-2-yl)phenyl)-N-(3-(4-fluoropiperidin-1-yl)propyl)benzo[d]imidazo[2,1-b]thiazole-7-carboxamide |
| 452S | (S)-2-(2-cyclopropyl-4-(pyrrolidin-2-yl)phenyl)-N-(3-(4-fluoropiperidin-1-yl)propyl)benzo[d]imidazo[2,1-b]thiazole-7-carboxamide |
| 452R | (R)-2-(2-cyclopropyl-4-(pyrrolidin-2-yl)phenyl)-N-(3-(4-fluoropiperidin-1-yl)propyl)benzo[d]imidazo[2,1-b]thiazole-7-carboxamide |
| 453S | (S)-2-(2,3-dimethyl-4-(pyrrolidin-2-yl)phenyl)-N-(3-(4-fluoropiperidin-1-yl)propyl)benzo[d]imidazo[2,1-b]thiazole-7-carboxamide |
| 453R | (R)-2-(2,3-dimethyl-4-(pyrrolidin-2-yl)phenyl)-N-(3-(4-fluoropiperidin-1-yl)propyl)benzo[d]imidazo[2,1-b]thiazole-7-carboxamide |
| 462S | (S)-2-(2-fluoro-4-(pyrrolidin-2-yl)phenyl)-N-(3-(4-fluoropiperidin-1-yl)propyl)-3-(hydroxymethyl)benzo[d]imidazo[2,1-b]thiazole-7-carboxamide |
| 462R | (R)-2-(2-fluoro-4-(pyrrolidin-2-yl)phenyl)-N-(3-(4-fluoropiperidin-1-yl)propyl)-3-(hydroxymethyl)benzo[d]imidazo[2,1-b]thiazole-7-carboxamide |
| 463S | (S)-2-(2-fluoro-4-(pyrrolidin-2-yl)phenyl)-N-(3-(4-fluoropiperidin-1-yl)propyl)-3-(2-hydroxyethyl)benzo[d]imidazo[2,1-b]thiazole-7-carboxamide |

-continued

| Compound No. | Compound Name |
|---|---|
| 463R | (R)-2-(2-fluoro-4-(pyrrolidin-2-yl)phenyl)-N-(3-(4-fluoropiperidin-1-yl)propyl)-3-(2-hydroxyethyl)benzo[d]imidazo[2,1-b]thiazole-7-carboxamide |
| 464S | (S)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide |
| 464R | (R)-2-(2-fluoro-4-(pyrrolidin-2-yl)phenyl)-N-(3-(4-fluoropiperidin-1-yl)propyl)-3-methylbenzo[d]imidazo[2,1-b]thiazole-7-carboxamide |
| 465 | (S)-3-cyclopropyl-N-(3-(4-fluoropiperidin-1-yl)propyl)-2-(4-(tetrahydrofuran-2-yl)phenyl)benzo[d]imidazo[2,1-b]thiazole-7-carboxamide |
| 466 | (R)-3-cyclopropyl-N-(3-(4-fluoropiperidin-1-yl)propyl)-2-(4-(tetrahydrofuran-2-yl)phenyl)benzo[d]imidazo[2,1-b]thiazole-7-carboxamide |
| 467 | (S)-3-cyclopropyl-N-(3-(4-fluoropiperidin-1-yl)propyl)-2-(4-(pyrrolidin-2-yl)phenyl)benzo[d]imidazo[2,1-b]thiazole-7-carboxamide |
| 468 | (R)-3-cyclopropyl-N-(3-(4-fluoropiperidin-1-yl)propyl)-2-(4-(pyrrolidin-2-yl)phenyl)benzo[d]imidazo[2,1-b]thiazole-7-carboxamide |
| 469S | (S)-2-(2-fluoro-4-(pyrrolidin-2-yl)phenyl)-N-(3-(4-fluoropiperidin-1-yl)propyl)-3-isopropoxybenzo[d]imidazo[2,1-b]thiazole-7-carboxamide |
| 469R | (R)-2-(2-fluoro-4-(pyrrolidin-2-yl)phenyl)-N-(3-(4-fluoropiperidin-1-yl)propyl)-3-isopropoxybenzo[d]imidazo[2,1-b]thiazole-7-carboxamide |
| 470S | (S)-2-(3-fluoro-5-(pyrrolidin-2-yl)-[1,1'-biphenyl]-2-yl)-N-(3-(4-fluoropiperidin-1-yl)propyl)benzo[d]imidazo[2,1-b]thiazole-7-carboxamide |
| 470R | (R)-2-(3-fluoro-5-(pyrrolidin-2-yl)-[1,1'-biphenyl]-2-yl)-N-(3-(4-fluoropiperidin-1-yl)propyl)benzo[d]imidazo[2,1-b]thiazole-7-carboxamide |
| 471S | (S)-2-(2-cyclohexyl-6-fluoro-4-(pyrrolidin-2-yl)phenyl)-N-(3-(4-fluoropiperidin-1-yl)propyl)benzo[d]imidazo[2,1-b]thiazole-7-carboxamide |
| 471R | (R)-2-(2-cyclohexyl-6-fluoro-4-(pyrrolidin-2-yl)phenyl)-N-(3-(4-fluoropiperidin-1-yl)propyl)benzo[d]imidazo[2,1-b]thiazole-7-carboxamide |
| 472S | (S)-2-(5-cyclopropyl-2-fluoro-4-(pyrrolidin-2-yl)phenyl)-N-(3-(4-fluoropiperidin-1-yl)propyl)benzo[d]imidazo[2,1-b]thiazole-7-carboxamide |
| 472R | (R)-2-(5-cyclopropyl-2-fluoro-4-(pyrrolidin-2-yl)phenyl)-N-(3-(4-fluoropiperidin-1-yl)propyl)benzo[d]imidazo[2,1-b]thiazole-7-carboxamide |
| 473S | (S)-2-(2-fluoro-4-(pyrrolidin-2-yl)phenyl)-7-((3-(4-fluoropiperidin-1-yl)propyl)carbamoyl)benzo[d]imidazo[2,1-b]thiazole-3-carboxylic acid |
| 473R | (R)-2-(2-fluoro-4-(pyrrolidin-2-yl)phenyl)-7-((3-(4-fluoropiperidin-1-yl)propyl)carbamoyl)benzo[d]imidazo[2,1-b]thiazole-3-carboxylic acid |
| 474 | 2-(4-(1-aminocyclopropyl)-2-fluorophenyl)-N-(3-(4-fluoropiperidin-1-yl)propyl)benzo[d]imidazo[2,1-b]thiazole-7-carboxamide |
| 475 | 2-(2-cyclopropyl-6-fluoro-4-(pyrrolidin-2-yl)phenyl)-N-(3-(4-fluoropiperidin-1-yl)propyl)benzo[d]imidazo[2,1-b]thiazole-7-carboxamide |
| 476 | 2-(2,3-difluoro-4-(pyrrolidin-2-yl)phenyl)-N-(3-(4-fluoropiperidin-1-yl)propyl)benzo[d]imidazo[2,1-b]thiazole-7-carboxamide |
| 477 | 2-(2,5-difluoro-4-(pyrrolidin-2-yl)phenyl)-N-(3-(4-fluoropiperidin-1-yl)propyl)benzo[d]imidazo[2,1-b]thiazole-7-carboxamide |
| 479 | 2-(2-fluoro-4-(pyrrolidin-3-yl)phenyl)-N-(3-(4-fluoropiperidin-1-yl)propyl)benzo[d]imidazo[2,1-b]thiazole-7-carboxamide |
| 480 | 2-(2-fluoro-4-(piperidin-2-yl)phenyl)-N-(3-(4-fluoropiperidin-1-yl)propyl)benzo[d]imidazo[2,1-b]thiazole-7-carboxamide |
| 481 | 2-(2-fluoro-4-(morpholin-3-yl)phenyl)-N-(3-(4-fluoropiperidin-1-yl)propyl)benzo[d]imidazo[2,1-b]thiazole-7-carboxamide |
| 482 | 2-(2-fluoro-4-(1H-imidazol-2-yl)phenyl)-N-(3-(4-fluoropiperidin-1-yl)propyl)benzo[d]imidazo[2,1-b]thiazole-7-carboxamide |
| 483 | 2-(2-fluoro-4-(4H-1,2,4-triazol-3-yl)phenyl)-N-(3-(4-fluoropiperidin-1-yl)propyl)benzo[d]imidazo[2,1-b]thiazole-7-carboxamide |
| 484 | 2-(3-fluoro-4-(pyrrolidin-2-yl)phenyl)-N-(3-(4-fluoropiperidin-1-yl)propyl)benzo[d]imidazo[2,1-b]thiazole-7-carboxamide |
| 485 | 2-(3-chloro-5-fluoro-4-(pyrrolidin-2-yl)phenyl)-N-(3-(4-fluoropiperidin-1-yl)propyl)benzo[d]imidazo[2,1-b]thiazole-7-carboxamide |
| 486 | 2-(2-fluoro-4-(6-oxopiperidin-2-yl)phenyl)-N-(3-(4-fluoropiperidin-1-yl)propyl)benzo[d]imidazo[2,1-b]thiazole-7-carboxamide |
| 487 | 2-(2-fluoro-4-(1H-pyrazol-5-yl)phenyl)-N-(3-(4-fluoropiperidin-1-yl)propyl)benzo[d]imidazo[2,1-b]thiazole-7-carboxamide |
| 488 | 2-(2-fluoro-4-(2H-1,2,3-triazol-4-yl)phenyl)-N-(3-(4-fluoropiperidin-1-yl)propyl)benzo[d]imidazo[2,1-b]thiazole-7-carboxamide |
| 489 | 2-(2-fluoro-5-methoxy-4-(pyrrolidin-2-yl)phenyl)-N-(3-(4-fluoropiperidin-1-yl)propyl)benzo[d]imidazo[2,1-b]thiazole-7-carboxamide |
| 490 | 2-(4-(4,4-difluoropyrrolidin-2-yl)-2-fluorophenyl)-N-(3-(4-fluoropiperidin-1-yl)propyl)benzo[d]imidazo[2,1-b]thiazole-7-carboxamide |
| 493 | 2-(2-fluoro-4-(4-hydroxypyrrolidin-2-yl)phenyl)-N-(3-(4-fluoropiperidin-1-yl)propyl)benzo[d]imidazo[2,1-b]thiazole-7-carboxamide |
| 501 | 2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide |
| 507 | 2-(2-fluoro-4-(4-oxopyrrolidin-2-yl)phenyl)-N-(3-(4-fluoropiperidin-1-yl)propyl)benzo[d]imidazo[2,1-b]thiazole-7-carboxamide |
| 508 | 2-(2-fluoro-4-(piperidin-4-yl)phenyl)-N-(3-(4-fluoropiperidin-1-yl)propyl)benzo[d]imidazo[2,1-b]thiazole-7-carboxamide |
| 509R | (R)-2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide |

-continued

| Compound No. | Compound Name |
|---|---|
| 509S | (S)-2-(2-fluoro-4-(pyrrolidin-2-yl)phenyl)-N-(3-(4-fluoropiperidin-1-yl)propyl)imidazo[2',1':2,3]thiazolo[4,5-c]pyridine-7-carboxamide |
| 512 | 2-(2-fluoro-4-(4-hydroxypiperidin-4-yl)phenyl)-N-(3-(4-fluoropiperidin-1-yl)propyl)benzo[d]imidazo[2,1-b]thiazole-7-carboxamide |
| 513 | 2-(2-fluoro-4-(piperidin-3-yl)phenyl)-N-(3-(4-fluoropiperidin-1-yl)propyl)benzo[d]imidazo[2,1-b]thiazole-7-carboxamide |
| 516 | 2-(2-fluoro-4-(3-hydroxypyrrolidin-3-yl)phenyl)-N-(3-(4-fluoropiperidin-1-yl)propyl)benzo[d]imidazo[2,1-b]thiazole-7-carboxamide |
| 523 | 2-(2-fluoro-4-((2S,4S)-4-methoxypyrrolidin-2-yl)phenyl)-N-(3-(4-fluoropiperidin-1-yl)propyl)benzo[d]imidazo[2,1-b]thiazole-7-carboxamide |
| 542 | 2-(4-(4-(difluoromethyl)pyrrolidin-2-yl)-2-fluorophenyl)-N-(3-(4-fluoropiperidin-1-yl)propyl)benzo[d]imidazo[2,1-b]thiazole-7-carboxamide and |
| 543 | 2-(2-fluoro-4-(isoxazolidin-5-yl)phenyl)-N-(3-(4-fluoropiperidin-1-yl)propyl)benzo[d]imidazo[2,1-b]thiazole-7-carboxamide. |

4. A compound represented by the structure of formula I(n):

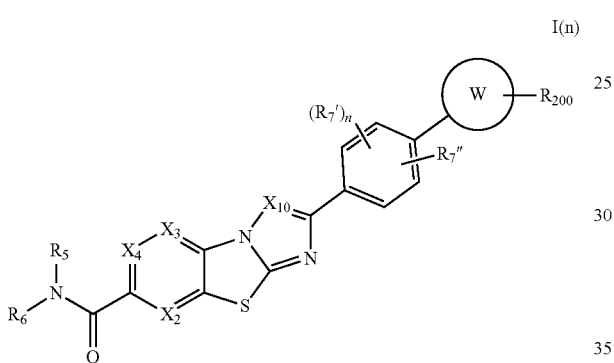

wherein
$X_2$, $X_3$, and $X_4$, are each independently nitrogen or CH;
$X_{10}$ is N, CH, or C(R), C(CH$_2$)OH, C(CH$_2$)$_2$OH, C(NH—CH$_2$-cyclopropyl), C(CH$_3$), C(cyclopropyl), C(iso-propoxy), or C(COOH);
Ring W is a 3-10 membered single, fused, bridged or spiro, saturated, unsaturated or aromatic, carbocyclic or heterocyclic ring, morpholine (2 or 3-morpholine), tetrahydrofuran, tetrahydropyran, oxetane, pyrrolidine, pyrrolidin-2-one, pyrrolidin-3-one, pyrrolidinone, imidazole, pyrazole, isoxazolidine, piperazine, piperidine, piperidine-2-one, oxadiazole, triazole, 2-oxopyrrolidine, cyclopropyl, 4-azaspiro [2.4]heptane, pyrrolidin-3-one-O-methyloxime, 2-oxa-5-azaspiro [3.4]octane, 1,4-dioxa-6-azaspiro [4.4]nonane, 4,7-diazaspiro [2.5] octane, bicyclo[1.1.1]pentane, 2,5-diazabicyclo [2.2.1] heptane, piperazine, or piperazine-2-one;
$R_{200}$ is H, $R_{20}$, F, Cl, Br, I, OH, SH, alkoxy, methoxy, NH$_2$, N(R)$_2$, NH(R$_{10}$), N(R$_{10}$)(R$_{11}$), CF$_3$, CN, NO$_2$, C$_1$-C$_5$ linear or branched, substituted or unsubstituted alkyl, methyl, ethyl, CH$_2$—CH$_2$—O—CH$_2$—CH$_2$—O—CH$_3$, CH$_2$—O—CH$_2$—CH$_2$—O—CH$_3$, C$_1$-C$_5$ linear or branched alkoxy, methoxy, C$_1$-C$_5$ linear or branched haloalkyl, CHF$_2$, CF$_3$, CF$_2$CH$_3$, CH$_2$CF$_3$, CF$_2$CH$_2$CH$_3$, CH$_2$CH$_2$CF$_3$, CF$_2$CH (CH$_3$)$_2$, CF(CH$_3$)—CH (CH$_3$)$_2$, R$_8$-aryl, CH$_2$-Ph, —R$_8$—O—R$_8$—O—R$_{10}$, (CH$_2$)$_2$—O—(CH$_2$)$_2$—O—CH$_3$, -R$_8$—O—R$_{10}$,-R$_8$-R$_{10}$, (CH$_2$)$_2$—O—CH$_3$, substituted or unsubstituted aryl, phenyl, substituted or unsubstituted heteroaryl, or pyridine;
or $R_{200}$ and the carbon atom to which it is connected are C=O, C=N—O(R), C=N—O—CH$_3$ C(R)$_2$, C(CH$_3$)$_2$, or CF$_2$;
$R_5$ is H or C$_1$-C$_5$ linear or branched alkyl or methyl;
$R_6$ is H, C$_1$-C$_5$ linear or branched alkyl, methyl, ethyl, iso-propyl, CD$_3$, or substituted or unsubstituted, saturated or unsaturated, single, fused, bridged or spiro 3-10 membered carbocyclic or heterocyclic ring, piperidine, 1-methylpiperidine (1-methyl-3-piperidine, 1-methyl-4-piperidine), 3-fluoro-1-methylpiperidine, 1-(2,2,2-trifluoroethyl) piperidine, azetidine, 1-methylazetidine (1-methyl-3-azetidine), morpholine, pyrrolidine, pyrrolidinone, quinuclidine, tetrahydropyran (4 or 3-tetrahydropyrane), tetrahydrofurane, azaspiro [3.3] heptane, 8-methyl-8-azabicyclo [3.2.1]octane, dioxane, 1,3-dioxane, imidazole, trifluoromethyl-oxetane, hydroxy-tetrahydrofurane, azepan-2-one, azabicyclohexane, 4,4-difluorocyclohexane, cyclopropyl;
$R_7'$ and $R_7''$ are each independently H, F, Cl, Br, I, OH, O—R$_{20}$, SH, R$_8$—OH, R$_8$—SH, -R$_8$—O—R$_{10}$, R$_8$-(C$_3$-C$_8$ cycloalkyl), R$_8$-(3-8 membered heterocyclic ring), CF$_3$, CD$_3$, OCD$_3$, CN, NO$_2$, —CH$_2$CN, -R$_8$CN, NH$_2$, NHR, N(R)$_2$, NH(R$_{10}$), N(R$_{10}$)(R$_{11}$), R$_8$—N(R$_{10}$)(R$_{11}$), R$_9$-R$_8$—N(R$_{10}$)(R$_{11}$), B(OH)$_2$, —OC(O) CF$_3$, —OCH$_2$Ph, NHC(O)—R$_{10}$, NHCO—N(R$_{10}$)(R$_{11}$), COOH,—C(O)Ph, C(O)O—R$_{10}$, R$_8$—C(O)-R$_{10}$, C(O) H, C(O)-R$_{10}$, C$_1$-C$_5$ linear or branched C(O)-haloalkyl, —C(O) NH$_2$, C(O) NHR, C(O) N(R$_{10}$)(R$_{11}$), SO$_2$R, SO$_2$N(R$_{10}$)(R$_{11}$), CH(CF$_3$)(NH—R$_{10}$), C$_1$-C$_5$ linear or branched, substituted or unsubstituted alkyl, isopropyl, methyl, ethyl, C$_1$-C$_5$ linear or branched, substituted or unsubstituted alkenyl, C$_1$-C$_5$ linear or branched, or C$_3$-C$_8$ cyclic haloalkyl, C$_1$-C$_5$ linear or branched, or C$_3$-C$_8$ cyclic alkoxy, methoxy, optionally wherein at least one methylene group (CH$_2$) in the alkoxy is replaced with an oxygen atom, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl, cyclopropyl, cyclohexyl, substituted or unsubstituted 3-8 membered heterocyclic ring, morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine, substituted or unsubstituted aryl, substituted or unsubstituted benzyl;
or $R_7'$ and $R_7''$ are joined to form a 3-8 membered substituted or unsubstituted, saturated, unsaturated or aromatic, carbocyclic or heterocyclic ring, cyclopentyl, cyclohexyl, piperidine, tetrahydrofuran, tetrahydropyran, or pyrrolidine;

$R_{20}$ is represented by the following structure:

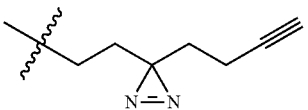 [SMILES: *CCC1(CCC#C)N=N1]

R is H, F, Cl, Br, I, OH, SH, alkoxy, NH($R_{10}$), NH—$CH_2$-cyclopropyl, N($R_{10}$)($R_{11}$), $CF_3$, CN, $NO_2$, COOH, $C_1$-$C_5$ linear or branched, substituted or unsubstituted alkyl, methyl, ethyl, $CH_2$—OH, $CH_2$—$CH_2$—OH, $CH_2$—$CH_2$—O—$CH_2$—$CH_2$—O—$CH_3$, $CH_2$—O—$CH_2$—$CH_2$—O—$CH_3$, $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl, $CHF_2$, $CF_3$, $CF_2CH_3$, $CH_2CF_3$, $CF_2CH_2CH_3$, $CH_2CH_2CF_3$, $CF_2CH$ $(CH_3)_2$, $CF(CH_3)$—$CH(CH_3)_2$, $R_8$-aryl, $CH_2$-Ph, -$R_8$—O—$R_8$—O—$R_{10}$, $(CH_2)_2$—O—$(CH_2)_2$—O—$CH_3$, -$R_8$—O—$R_{10}$, -$R_8$-$R_{10}$, $(CH_2)_2$—O—$CH_3$, substituted or unsubstituted aryl, phenyl, substituted or unsubstituted heteroaryl, or pyridine;

each $R_8$ is independently $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ substituted or unsubstituted linear or branched alkyl, methyl, ethyl, $CH_2$-cyclopropyl, $CH_2$—$CH_2$—O—$CH_3$, $C_1$-$C_5$ substituted or unsubstituted linear or branched haloalky, $CH_2CF_3$, $C_1$-$C_5$ linear or branched alkoxy, O—$CH_3$, $R_{20}$, C(O)R, or S(O)$_2$R;

or $R_{10}$ and $R_{11}$ are joined to form a substituted or unsubstituted 3-8 membered heterocyclic ring, piperazine, or piperidine;

n is an integer between 0 and 4;

or its pharmaceutically acceptable salt, stereoisomer, tautomer, hydrate, N-oxide, reverse amide analog, prodrug, isotopic variant, deuterated analog, pharmaceutical product or any combination thereof.

5. The compound of claim 4, wherein
$X_2$ and $X_3$ are CH;
$X_4$ is CH or nitrogen;
Ring W is a 3-10 membered single, saturated, heterocyclic ring, morpholine, 2 or 3-morpholine, tetrahydrofuran, tetrahydropyran, pyrrolidine, isoxazolidine, piperazine, or piperidine;
3-10 membered single, unsaturated, heterocyclic ring, piperazine-2-one;
3-10 membered spiro, heterocyclic ring, 4-azaspiro [2.4] heptane, 2-oxa-5-azaspiro [3.4]octane, 1,4-dioxa-6-azaspiro [4.4]nonane, 4,7-diazaspiro [2.5]octane;
3-10 membered bridged, heterocyclic ring, bicyclo[1.1.1] pentane, 2,5-diazabicyclo [2.2.1]heptane;
or 3-10 membered single, unsaturated heterocyclic ring, pyrrolidin-2-one, pyrrolidin-3-one, piperazine-2-one, piperidine-2-one, pyrrolidin-3-one-O-methyloxime;

$R_{200}$ is H, OH, CN, $NH_2$, $C_1$-$C_5$ linear or branched, substituted or unsubstituted alkyl, $C_1$-$C_5$ linear or branched alkoxy, methoxy, $C_1$-$C_5$ linear or branched haloalkyl, $CHF_2$; or $R_{200}$ and the carbon atom to which it is connected are C=O, C=N—O(R) (e.g, C=N—O—$CH_3$) or C(R)$_2$, C($CH_3$)$_2$, $CF_2$;

$R_5$ is H or $C_1$-$C_5$ linear or branched alkyl or methyl;

$R_6$ is H, $C_1$-$C_5$ linear or branched, substituted or unsubstituted alkyl, methyl, ethyl, or iso-propyl, $CD_3$, a substituted or unsubstituted saturated single, 3-10 membered heterocyclic ring, piperidine, 1-methylpiperidine, 1-methyl-3-piperidine, 1-methyl-4-piperidine, 3-fluoro-1-methylpiperidine, 1-(2,2,2-trifluoroethyl) piperidine, azetidine, 1-methyl-azetidine, 1-methyl-3-azetidine, morpholine, tetrahydropyran, 4 or 3-tetrahydropyrane, tetrahydrofurane, dioxane, or 1,3-dioxane saturated bridged or spiro 3-10 membered heterocyclic ring, preferably 8-methyl-8-azabicyclo [3.2.1]octane, or substituted or unsubstituted, saturated single, 3-10 membered carbocyclic ring (cycloalkyl), 4,4-difluoro-cyclohexane, cyclopropyl;

$R_7'$ and $R_7''$ are each independently H or F;

or any combination thereof.

6. The compound of claim 4, wherein the carbocyclic or heterocyclic ring as defined in $R_6$ is further substituted with at least one substitution selected from: F, Cl, Br, I, $C_1$-$C_5$ linear or branched alkyl, OH, alkoxy, OMe, amide, C(O) N(R)$_2$, C(O)-alkyl, C(O)-pyrrolidine, C(O)-piperidine, N(R)$_2$, NH($R_{10}$), N($R_{10}$)($R_{11}$), N (CH$_3$)$_2$, NH$_2$, CF$_3$, aryl, phenyl, heteroaryl, substituted or unsubstituted $C_3$-$C_8$ cycloalkyl, cyclobutanol, substituted or unsubstituted 3-8 membered heterocyclic ring, pyran, oxetane, piperidine, pyrazole, triazole, imidazole, $C_1$-$C_5$ linear or branched haloalkyl, $CH_2CF_3$, $CHF_2$, halophenyl, (benzyloxy) phenyl, CN, and $NO_2$.

7. The compound of claim 4, wherein the substituted or unsubstituted ring of $R_6$ is piperidine, 1-methylpiperidine, 1-methyl-3-piperidine, 1-methyl-4-piperidine, 3-fluoro-1-methylpiperidine, 1-(2,2,2-trifluoroethyl) piperidine, azetidine, 1-methyl-azetidine, 1-methyl-3-azetidine, morpholine, tetrahydropyran, 4 or 3-tetrahydropyrane, tetrahydrofurane, dioxane, or 1,3-dioxane, 8-methyl-8-azabicyclo [3.2.1]octane, 4,4-difluorocyclohexane, or cyclopropyl.

8. The compound of claim 4, selected from the group consisting of:

| Compound No. | Compound Name |
|---|---|
| 491R | 2-(2-fluoro-4-(pyrrolidin-2-yl)phenyl)-N-((R)-1-methylpiperidin-3-yl)benzo[d]imidazo[2,1-b]thiazole-7-carboxamide |
| 491S | 2-(2-fluoro-4-(pyrrolidin-2-yl)phenyl)-N-((S)-1-methylpiperidin-3-yl)benzo[d]imidazo[2,1-b]thiazole-7-carboxamide |
| 492 | 2-(2-fluoro-4-(pyrrolidin-2-yl)phenyl)benzo[d]imidazo[2,1-b]thiazole-7-carboxamide |
| 498 | 2-(2-fluoro-4-(pyrrolidin-2-yl)phenyl)-N-methylbenzo[d]imidazo[2,1-b]thiazole-7-carboxamide |
| 499 | 2-(2-fluoro-4-(pyrrolidin-2-yl)phenyl)-N,N-dimethylbenzo[d]imidazo[2,1-b]thiazole-7-carboxamide |

-continued

| Compound No. | Compound Name |
|---|---|
| 500 | 2-(2-fluoro-4-(pyrrolidin-2-yl)phenyl)-N-(1-methylpiperidin-4-yl)benzo[d]imidazo[2,1-b]thiazole-7-carboxamide |
| 503S | (S)-2-(2-fluoro-4-(pyrrolidin-2-yl)phenyl)-N-(1-methylpiperidin-4-yl)benzo[d]imidazo[2,1-b]thiazole-7-carboxamide |
| 503R | (R)-2-(2-fluoro-4-(pyrrolidin-2-yl)phenyl)-N-(1-methylpiperidin-4-yl)benzo[d]imidazo[2,1-b]thiazole-7-carboxamide |
| 504 | 2-(2-fluoro-4-(pyrrolidin-3-yl)phenyl)-N-methylbenzo[d]imidazo[2,1-b]thiazole-7-carboxamide |
| 505 | 2-(2-fluoro-4-(pyrrolidin-3-yl)phenyl)-N-(1-methylpiperidin-4-yl)benzo[d]imidazo[2,1-b]thiazole-7-carboxamide |
| 506 | 2-(2-fluoro-4-(pyrrolidin-2-yl)phenyl)-N-(1-methylazetidin-3-yl)benzo[d]imidazo[2,1-b]thiazole-7-carboxamide |
| 510 | 2-(2-fluoro-4-(pyrrolidin-2-yl)phenyl)-N-(tetrahydro-2H-pyran-4-yl)benzo[d]imidazo[2,1-b]thiazole-7-carboxamide |
| 511 | 2-(2-fluoro-4-(pyrrolidin-3-yl)phenyl)benzo[d]imidazo[2,1-b]thiazole-7-carboxamide |
| 514 | 2-(2-fluoro-4-(pyrrolidin-2-yl)phenyl)imidazo[2',1':2,3]thiazolo[4,5-c]pyridine-7-carboxamide |
| 515 | 2-(2-fluoro-4-(pyrrolidin-2-yl)phenyl)-N-methylimidazo[2',1':2,3]thiazolo[4,5-c]pyridine-7-carboxamide |
| 517 | 2-(2-fluoro-4-(morpholin-3-yl)phenyl)-N-(1-methylpiperidin-4-yl)benzo[d]imidazo[2,1-b]thiazole-7-carboxamide |
| 518 | 2-(2-fluoro-4-((3S,4R)-4-hydroxypyrrolidin-3-yl)phenyl)-N-methylbenzo[d]imidazo[2,1-b]thiazole-7-carboxamide |
| 519 | 2-(2-fluoro-4-(morpholin-2-yl)phenyl)-N-(1-methylpiperidin-4-yl)benzo[d]imidazo[2,1-b]thiazole-7-carboxamide |
| 520 | 2-(2-fluoro-4-((2S,4S)-4-hydroxypyrrolidin-2-yl)phenyl)benzo[d]imidazo[2,1-b]thiazole-7-carboxamide |
| 521 | 2-(2-fluoro-4-((2S,4S)-4-hydroxypyrrolidin-2-yl)phenyl)-N-methylbenzo[d]imidazo[2,1-b]thiazole-7-carboxamide |
| 522S | 2-(2-fluoro-4-((2S,4S)-4-hydroxypyrrolidin-2-yl)phenyl)-N-(1-methylpiperidin-4-yl)benzo[d]imidazo[2,1-b]thiazole-7-carboxamide |
| 522R | 2-(2-fluoro-4-((2S,4R)-4-hydroxypyrrolidin-2-yl)phenyl)-N-(1-methylpiperidin-4-yl)benzo[d]imidazo[2,1-b]thiazole-7-carboxamide |
| 524S | 2-(2-fluoro-4-(pyrrolidin-2-yl)phenyl)-N-((S)-tetrahydrofuran-3-yl)benzo[d]imidazo[2,1-b]thiazole-7-carboxamide |
| 524R | 2-(2-fluoro-4-(pyrrolidin-2-yl)phenyl)-N-((R)-tetrahydrofuran-3-yl)benzo[d]imidazo[2,1-b]thiazole-7-carboxamide |
| 525 | 2-(2-fluoro-4-(pyrrolidin-2-yl)phenyl)-N-(tetrahydro-2H-pyran-3-yl)benzo[d]imidazo[2,1-b]thiazole-7-carboxamide |
| 526 | N-((3S,4R)-3-fluoro-1-methylpiperidin-4-yl)-2-(2-fluoro-4-(pyrrolidin-2-yl)phenyl)benzo[d]imidazo[2,1-b]thiazole-7-carboxamide |
| 527 | 2-(2-fluoro-4-(piperidin-4-yl)phenyl)-N-(1-methylpiperidin-4-yl)benzo[d]imidazo[2,1-b]thiazole-7-carboxamide |
| 528 | 2-(2-fluoro-4-(4-hydroxypiperidin-4-yl)phenyl)-N-(1-methylpiperidin-4-yl)benzo[d]imidazo[2,1-b]thiazole-7-carboxamide |
| 529 | 2-(2-fluoro-4-(piperidin-4-yl)phenyl)-N-(tetrahydro-2H-pyran-4-yl)benzo[d]imidazo[2,1-b]thiazole-7-carboxamide |
| 530 | 2-(2-fluoro-4-(3-hydroxypyrrolidin-3-yl)phenyl)-N-(1-methylpiperidin-4-yl)benzo[d]imidazo[2,1-b]thiazole-7-carboxamide |
| 531 | 2-(2-fluoro-4-(pyrrolidin-2-yl)phenyl)-N-(8-methyl-8-azabicyclo[3.2.1]octan-3-yl)benzo[d]imidazo[2,1-b]thiazole-7-carboxamide |
| 532 | 2-(2-fluoro-4-((2S,4S)-4-methoxypyrrolidin-2-yl)phenyl)-N-(1-methylpiperidin-4-yl)benzo[d]imidazo[2,1-b]thiazole-7-carboxamide |
| 533 | 2-(2-fluoro-4-((2S,4S)-4-hydroxypyrrolidin-2-yl)phenyl)-N-(tetrahydro-2H-pyran-4-yl)benzo[d]imidazo[2,1-b]thiazole-7-carboxamide |
| 534 | 2-(2-fluoro-4-(morpholin-3-yl)phenyl)-N-(tetrahydro-2H-pyran-4-yl)benzo[d]imidazo[2,1-b]thiazole-7-carboxamide |
| 535 | 2-(2-fluoro-4-(morpholin-2-yl)phenyl)-N-(tetrahydro-2H-pyran-4-yl)benzo[d]imidazo[2,1-b]thiazole-7-carboxamide |
| 536 | 2-(2-fluoro-4-(4-fluoropiperidin-4-yl)phenyl)-N-(1-methylpiperidin-4-yl)benzo[d]imidazo[2,1-b]thiazole-7-carboxamide |
| 537 | 2-(2-fluoro-4-(4-oxopyrrolidin-2-yl)phenyl)-N-(tetrahydro-2H-pyran-4-yl)benzo[d]imidazo[2,1-b]thiazole-7-carboxamide |
| 538 | 2-(2-fluoro-4-((2S,4R)-4-hydroxypyrrolidin-2-yl)phenyl)-N-(tetrahydro-2H-pyran-4-yl)benzo[d]imidazo[2,1-b]thiazole-7-carboxamide |
| 540 | 2-(4-(4-(difluoromethyl)pyrrolidin-2-yl)-2-fluorophenyl)benzo[d]imidazo[2,1-b]thiazole-7-carboxamide |
| 541 | 2-(4-(4-cyanopyrrolidin-2-yl)-2-fluorophenyl)-N-(1-methylpiperidin-4-yl)benzo[d]imidazo[2,1-b]thiazole-7-carboxamide |
| 544 | 2-(2-fluoro-4-((2S,4R)-4-hydroxypyrrolidin-2-yl)phenyl)-N-methylbenzo[d]imidazo[2,1-b]thiazole-7-carboxamide |
| 545 | N-(1,3-dioxan-5-yl)-2-(2-fluoro-4-(pyrrolidin-2-yl)phenyl)benzo[d]imidazo[2,1-b]thiazole-7-carboxamide |
| 546 | 2-(2-fluoro-4-(3-hydroxypiperidin-4-yl)phenyl)-N-(1-methylpiperidin-4-yl)benzo[d]imidazo[2,1-b]thiazole-7-carboxamide |

| Compound No. | Compound Name |
|---|---|
| 547 | 2-(2-fluoro-4-(piperazin-1-yl)phenyl)-N-(1-methylpiperidin-4-yl)benzo[d]imidazo[2,1-b]thiazole-7-carboxamide |
| 548 | N-(2-(2-fluoro-4-(pyrrolidin-2-yl)phenyl)benzo[d]imidazo[2,1-b]thiazol-7-yl)acetamide |
| 549R | (R)-2-(2-fluoro-4-(pyrrolidin-2-yl)phenyl)-N-methylimidazo[2',1':2,3]thiazolo[4,5-c]pyridine-7-carboxamide |
| 549S | (S)-2-(2-fluoro-4-(pyrrolidin-2-yl)phenyl)-N-methylimidazo[2',1':2,3]thiazolo[4,5-c]pyridine-7-carboxamide |
| 550 | 2-(4-(5,5-dimethylpyrrolidin-2-yl)-2-fluorophenyl)-N-(tetrahydro-2H-pyran-4-yl)benzo[d]imidazo[2,1-b]thiazole-7-carboxamide |
| 551 | 2-(2-fluoro-4-(4-azaspiro[2.4]heptan-5-yl)phenyl)-N-(tetrahydro-2H-pyran-4-yl)benzo[d]imidazo[2,1-b]thiazole-7-carboxamide |
| 552 | 2-(2-fluoro-4-(pyrrolidin-2-yl)phenyl)-N-(tetrahydro-2H-pyran-4-yl)imidazo[2',1':2,3]thiazolo[4,5-c]pyridine-7-carboxamide |
| 553 | 2-(2-fluoro-4-(morpholin-2-yl)phenyl)-N-(tetrahydro-2H-pyran-4-yl)imidazo[2',1':2,3]thiazolo[4,5-c]pyridine-7-carboxamide |
| 554 | 2-(2-fluoro-4-(4-hydroxypyrrolidin-2-yl)phenyl)-N-(tetrahydro-2H-pyran-4-yl)imidazo[2',1':2,3]thiazolo[4,5-c]pyridine-7-carboxamide |
| 555 | 2-(2-fluoro-4-(4-hydroxypyrrolidin-2-yl)phenyl)-N-methylimidazo[2',1':2,3]thiazolo[4,5-c]pyridine-7-carboxamide |
| 556 | 2-(2-fluoro-4-(4-methoxypyrrolidin-2-yl)phenyl)-N-methylimidazo[2',1':2,3]thiazolo[4,5-c]pyridine-7-carboxamide |
| 557 | 2-(2-fluoro-4-(morpholin-2-yl)phenyl)-N-methylimidazo[2',1':2,3]thiazolo[4,5-c]pyridine-7-carboxamide |
| 566 | 2-(2-fluoro-4-(4-methoxypyrrolidin-2-yl)phenyl)-N-(tetrahydro-2H-pyran-4-yl)benzo[d]imidazo[2,1-b]thiazole-7-carboxamide |
| 567 | 2-(2-fluoro-4-(pyrrolidin-2-yl)phenyl)-N-(methyl-d3)imidazo[2',1':2,3]thiazolo[4,5-c]pyridine-7-carboxamide |
| 568 | (Z)-2-(2-fluoro-4-(4-(methoxyimino)pyrrolidin-2-yl)phenyl)-N-(tetrahydro-2H-pyran-4-yl)benzo[d]imidazo[2,1-b]thiazole-7-carboxamide |
| 569 | 2-(2-fluoro-4-(2-oxa-6-azaspiro[3.4]octan-7-yl)phenyl)-N-methylimidazo[2',1':2,3]thiazolo[4,5-c]pyridine-7-carboxamide |
| 570 | 2-(2-fluoro-4-(2-oxa-6-azaspiro[3.4]octan-7-yl)phenyl)-N-(tetrahydro-2H-pyran-4-yl)benzo[d]imidazo[2,1-b]thiazole-7-carboxamide |
| 571 | 2-(2-fluoro-4-(1,4-dioxa-7-azaspiro[4.4]nonan-8-yl)phenyl)-N-(tetrahydro-2H-pyran-4-yl)benzo[d]imidazo[2,1-b]thiazole-7-carboxamide |
| 572 | N-ethyl-2-(2-fluoro-4-(pyrrolidin-2-yl)phenyl)imidazo[2',1':2,3]thiazolo[4,5-c]pyridine-7-carboxamide |
| 573 | 2-(2-fluoro-4-(pyrrolidin-2-yl)phenyl)-N-(1-(2,2,2-trifluoroethyl)piperidin-4-yl)benzo[d]imidazo[2,1-b]thiazole-7-carboxamide |
| 574 | N-(4,4-difluorocyclohexyl)-2-(2-fluoro-4-(pyrrolidin-2-yl)phenyl)benzo[d]imidazo[2,1-b]thiazole-7-carboxamide |
| 575 | 2-(2-fluoro-4-(pyrrolidin-2-yl)phenyl)-N-isopropylimidazo[2',1':2,3]thiazolo[4,5-c]pyridine-7-carboxamide |
| 576 | N-cyclopropyl-2-(2-fluoro-4-(pyrrolidin-2-yl)phenyl)imidazo[2',1':2,3]thiazolo[4,5-c]pyridine-7-carboxamide |
| 577 | 2-(4-(5,5-dimethylmorpholin-2-yl)-2-fluorophenyl)-N-(tetrahydro-2H-pyran-4-yl)benzo[d]imidazo[2,1-b]thiazole-7-carboxamide |
| 578 | 2-(2-fluoro-4-(1-methylpiperazin-2-yl)phenyl)-N-(tetrahydro-2H-pyran-4-yl)benzo[d]imidazo[2,1-b]thiazole-7-carboxamide |
| 581 | 2-(2-fluoro-4-(4,7-diazaspiro[2.5]octan-7-yl)phenyl)-N-(tetrahydro-2H-pyran-4-yl)benzo[d]imidazo[2,1-b]thiazole-7-carboxamide |
| 582 | 2-(4-(3-aminobicyclo[1.1.1]pentan-1-yl)-2-fluorophenyl)-N-(tetrahydro-2H-pyran-4-yl)benzo[d]imidazo[2,1-b]thiazole-7-carboxamide |
| 583 | 2-(2-fluoro-4-(6-oxopiperazin-2-yl)phenyl)-N-(tetrahydro-2H-pyran-4-yl)benzo[d]imidazo[2,1-b]thiazole-7-carboxamide |
| 584 | 2-(4-(1-aminocyclopropyl)-2-fluorophenyl)-N-(tetrahydro-2H-pyran-4-yl)benzo[d]imidazo[2,1-b]thiazole-7-carboxamide |
| 585 | 2-(4-(1-aminocyclopropyl)-2-fluorophenyl)-N-methylimidazo[2',1':2,3]thiazolo[4,5-c]pyridine-7-carboxamide |
| 586 | 2-(2-fluoro-4-(1-methylpyrrolidin-2-yl)phenyl)-N-(tetrahydro-2H-pyran-4-yl)benzo[d]imidazo[2,1-b]thiazole-7-carboxamide |
| 587 | 2-(6-(pyrrolidin-2-yl)pyridin-3-yl)-N-(tetrahydro-2H-pyran-4-yl)benzo[d]imidazo[2,1-b]thiazole-7-carboxamide |
| 588 | 2-(2-fluoro-4-(piperazin-1-yl)phenyl)-N-(tetrahydro-2H-pyran-4-yl)benzo[d]imidazo[2,1-b]thiazole-7-carboxamide |
| 589 | 2-(2-fluoro-4-(piperazin-1-yl)phenyl)-N-methylimidazo[2',1':2,3]thiazolo[4,5-c]pyridine-7-carboxamide |
| 590 | 2-(2-fluoro-4-(2-oxopiperazin-1-yl)phenyl)-N-(tetrahydro-2H-pyran-4-yl)benzo[d]imidazo[2,1-b]thiazole-7-carboxamide |
| 591 | 2-(4-(2,5-diazabicyclo[2.2.1]heptan-2-yl)-2-fluorophenyl)-N-methylimidazo[2',1':2,3]thiazolo[4,5-c]pyridine-7-carboxamide |
| 592 | 2-(4-(2,5-diazabicyclo[2.2.1]heptan-2-yl)-2-fluorophenyl)-N-(tetrahydro-2H-pyran-4-yl)benzo[d]imidazo[2,1-b]thiazole-7-carboxamide |
| 593 | N-(2-(2-fluoro-4-(pyrrolidin-2-yl)phenyl)benzo[d]imidazo[2,1-b]thiazol-7-yl)-1-methylpiperidine-4-carboxamide and |

| Compound No. | Compound Name |
|---|---|
| 594 | N-(2-(2-fluoro-4-(pyrrolidin-2-yl)phenyl)benzo[d]imidazo[2,1-b]thiazol-7-yl)tetrahydro-2H-pyran-4-carboxamide. |

9. A compound represented by the structure of formula I(o):

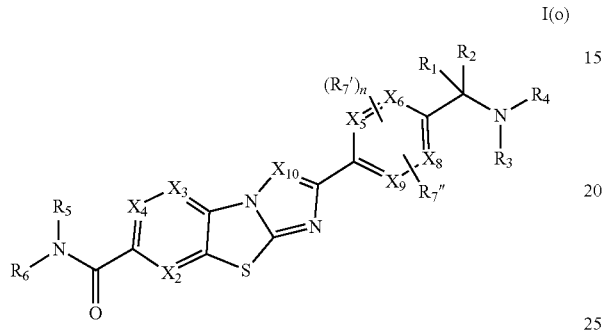

wherein
- $X_2$, $X_3$, and $X_4$ are each independently nitrogen or CH;
- $X_5$, $X_6$, $X_8$ and $X_9$ are each independently nitrogen or carbon atoms;
- $X_{10}$ is N, CH, or C(R), C(CH$_2$)OH, C(CH$_2$)$_2$OH, C(NH—CH$_2$-cyclopropyl), C(CH$_3$), C(cyclopropyl), C(isopropoxy), C(COOH);
- $R_1$ is H, F, Cl, Br, I, OH, SH, or CF$_3$, substituted or unsubstituted $C_1$-$C_5$ alkyl, CH$_2$OH, $C_1$-$C_5$ linear or branched, or $C_3$-$C_8$ cyclic haloalkyl, substituted or unsubstituted $C_1$-$C_5$ linear or branched, or $C_3$-$C_8$ cyclic alkoxy;
- $R_2$ is substituted or unsubstituted $C_1$-$C_5$ alkyl, CH$_2$OH, CH$_2$OCH$_3$, 3-8 membered carbocyclic or heterocyclic ring or, oxetane;
- or $R_1$ and $R_2$ are joined to form a 3-8 membered carbocyclic or heterocyclic ring, cyclopropyl, or oxetane;
- $R_3$ and $R_4$ are each independently H, Me, substituted or unsubstituted $C_1$-$C_5$ alkyl, methoxyethylene, methylaminoethyl, aminoethyl, -$R_8$—O—$R_{10}$, (CH$_2$)$_2$—O—CH$_3$, $R_8$—N($R_{10}$)($R_{11}$), (CH$_2$)$_2$—NH(CH$_3$), substituted or unsubstituted $C_3$-$C_8$ cycloalkyl, cyclopropyl, substituted or unsubstituted 5-7 membered heterocyclic ring, pyrrolidine, methylpyrrolidine, piperidine, or $R_{20}$; or
- $R_3$ and $R_4$ are joined to form a 3-8 membered heterocyclic ring, pyrrolidine, pyrrolidone, 2-oxopyrrolidine, piperidine, morpholine, piperazine, or imidazole;
- $R_5$ is H or $C_1$-$C_5$ linear or branched alkyl;
- $R_6$ is H, $C_1$-$C_5$ linear or branched alkyl, methyl, ethyl, substituted or unsubstituted, saturated or unsaturated, single fused, bridged or spiro 3-10 membered heterocyclic ring, piperidine, 1-methylpiperidine, 3-fluoro-1-methylpiperidine, azetidine, 1-methyl-azetidine, morpholine, pyrrolidine, pyrrolidinone, quinuclidine, tetrahydropyran, tetrahydrofurane, azaspiro [3.3]heptane, 8-methyl-8-azabicyclo [3.2.1]octane, dioxane, 1,3-dioxane, imidazole, trifluoromethyl-oxetane, hydroxy-tetrahydrofurane, azepan-2-one, azabicyclohexane) or (CH$_2$) 3-4-fluoro-piperidine;
- $R_7{}'$ and $R_7{}''$ are each independently H, F, Cl, Br, I, OH, O—$R_{20}$, SH, $R_8$—OH, $R_8$—SH, -$R_8$—O—$R_{10}$, $R_8$-(C$_3$-C$_8$ cycloalkyl), $R_8$-(3-8 membered heterocyclic ring), CF$_3$, CD$_3$, OCD$_3$, CN, NO$_2$, —CH$_2$CN, -$R_8$CN, NH$_2$, NHR, N(R)$_2$, NH($R_{10}$), N($R_{10}$)($R_{11}$), $R_8$—N($R_{10}$)($R_{11}$), $R_9$-$R_8$—N($R_{10}$)($R_{11}$), B(OH)$_2$, —OC(O) CF$_3$, —OCH$_2$Ph, NHC(O)—$R_{10}$, NHCO—N($R_{10}$)($R_{11}$), COOH,—C(O)Ph, C(O)O—$R_{10}$, $R_8$—C(O)-$R_{10}$, C(O) H, C(O)-$R_{10}$, $C_1$-$C_5$ linear or branched C(O)-haloalkyl, —C(O) NH$_2$, C(O) NHR, C(O) N($R_{10}$)($R_{11}$), SO$_2$R, SO$_2$N($R_{10}$)($R_{11}$), CH(CF$_3$)(NH—$R_{10}$), $C_1$-$C_5$ linear or branched, substituted or unsubstituted alkyl, isopropyl, methyl, ethyl, $C_1$-$C_5$ linear or branched, substituted or unsubstituted alkenyl, $C_1$-$C_5$ linear or branched, or $C_3$-$C_8$ cyclic haloalkyl, $C_1$-$C_5$ linear or branched, or $C_3$-$C_8$ cyclic alkoxy, methoxy, optionally wherein at least one methylene group (CH$_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, cyclopropyl, cyclohexyl, substituted or unsubstituted 3-8 membered heterocyclic ring, morpholine, pyran, oxetane, pyrrolidine, 3,3-difluoropyrrolidine, imidazole, pyrazole, triazole, piperazine, piperidine, piperidin-2-one, piperidin-4-ol, dioxazole, 2-oxopyrrolidine, substituted or unsubstituted aryl, substituted or unsubstituted benzyl;
- or $R_7{}'$ and $R_7{}''$ are joined to form a 3-8 membered substituted or unsubstituted, saturated, unsaturated or aromatic, carbocyclic or heterocyclic ring, cyclopentyl, cyclohexyl, piperidine, tetrahydrofuran, tetrahydropyran, or pyrrolidine;
- $R_{20}$ is represented by the following structure:

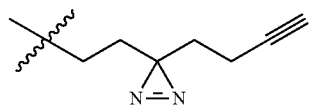 [SMILES: *CCC1(CCC#C)N=N1]

- R is H, F, Cl, Br, I, OH, SH, alkoxy, NH($R_{10}$), NH—CH$_2$-cyclopropyl, N($R_{10}$)($R_{11}$), CF$_3$, CN, NO$_2$, COOH, $C_1$-$C_5$ linear or branched, substituted or unsubstituted alkyl, methyl, ethyl, CH$_2$—OH, CH$_2$—CH$_2$—OH, CH$_2$—CH$_2$—O—CH$_2$—CH$_2$—O—CH$_3$, CH$_2$—O—CH$_2$—CH$_2$—O—CH$_3$, $C_3$-$C_8$ substituted or unsubstituted cycloalkyl, cyclopropyl, $C_1$-$C_5$ linear or branched alkoxy, isopropoxy, $C_1$-$C_5$ linear or branched haloalkyl, CHF$_2$, CF$_3$, CF$_2$CH$_3$, CH$_2$CF$_3$, CF$_2$CH$_2$CH$_3$, CH$_2$CH$_2$CF$_3$, CF$_2$CH (CH$_3$)$_2$, CF(CH$_3$)—CH(CH$_3$)$_2$, $R_8$-aryl, CH$_2$-Ph, -$R_8$—O—$R_8$—O—$R_{10}$ (e.g. (CH$_2$)$_2$—O—(CH$_2$)$_2$—O—CH$_3$), -$R_8$—O—$R_{10}$,-$R_8$-$R_{10}$, (CH$_2$)$_2$—O—CH$_3$, substituted or unsubstituted aryl, phenyl, substituted or unsubstituted heteroaryl, or pyridine;
- each $R_8$ is independently [CH$_2$]$_p$
  - wherein p is between 1 and 10;

R$_9$ is [CH]$_q$, [C]$_q$
wherein q is between 2 and 10;
R$_{10}$ and R$_{11}$ are each independently H, C$_1$-C$_5$ substituted or unsubstituted linear or branched alkyl, methyl, ethyl, CH$_2$-cyclopropyl, CH$_2$—CH$_2$—O—CH$_3$, C$_1$-C$_5$ substituted or unsubstituted linear or branched haloalky, CH$_2$CF$_3$, C$_1$-C$_5$ linear or branched alkoxy, O—CH$_3$, R$_{20}$, C(O)R, or S(O)$_2$R;
or R$_{10}$ and R$_{11}$ are joined to form a substituted or unsubstituted 3-8 membered heterocyclic ring, piperazine, or piperidine,
n is an integer between 0 and 4;
or its pharmaceutically acceptable salt, stereoisomer, tautomer, hydrate, N-oxide, reverse amide analog, prodrug, isotopic variant, deuterated analog, pharmaceutical product or any combination thereof.

10. The compound of claim 9, wherein
R$_1$ is H;
R$_2$ is a substituted C$_1$-C$_5$ alkyl, CH$_2$OH, CH$_2$OCH$_3$, or 3-8 membered heterocyclic ring, or oxetane;
R$_3$ and R$_4$ are each independently H;
R$_5$ is H or C$_1$-C$_5$ linear or branched alkyl;
R$_6$ is C$_1$-C$_5$ linear or branched alkyl, methyl, ethyl, (CH$_2$)$_3$-4-fluoro-piperidine, or tetrahydropyran;
R$_7$' is F;
R$_7$" is H;
n is 1;
or any combination thereof.

11. The compound of claim 9, wherein the compound is selected from the group consisting of:

| Compound No. | Compound Name |
|---|---|
| 539 | 2-(4-(1-amino-2-hydroxyethyl)-2-fluorophenyl)-N-(3-(4-fluoropiperidin-1-yl)propyl)benzo[d]imidazo[2,1-b]thiazole-7-carboxamide |
| 558 | 2-(4-(1-amino-2-hydroxyethyl)-2-fluorophenyl)-N-methylimidazo[2',1':2,3]thiazolo[4,5-c]pyridine-7-carboxamide |
| 559 | 2-(4-(1-amino-2-hydroxyethyl)-2-fluorophenyl)-N-methylbenzo[d]imidazo[2,1-b]thiazole-7-carboxamide |
| 560 | 2-(4-(1-amino-2-hydroxyethyl)-2-fluorophenyl)-N-(tetrahydro-2H-pyran-4-yl)imidazo[2',1':2,3]thiazolo[4,5-c]pyridine-7-carboxamide |
| 561 | 2-(4-(1-amino-2-hydroxyethyl)-2-fluorophenyl)-N-(tetrahydro-2H-pyran-4-yl)benzo[d]imidazo[2,1-b]thiazole-7-carboxamide |
| 562 | 2-(4-(1-amino-2-methoxyethyl)-2-fluorophenyl)-N-methylimidazo[2',1':2,3]thiazolo[4,5-c]pyridine-7-carboxamide |
| 563 | 2-(4-(1-amino-2-methoxyethyl)-2-fluorophenyl)-N-methylbenzo[d]imidazo[2,1-b]thiazole-7-carboxamide |
| 564 | 2-(4-(1-amino-2-methoxyethyl)-2-fluorophenyl)-N-(tetrahydro-2H-pyran-4-yl)imidazo[2',1':2,3]thiazolo[4,5-c]pyridine-7-carboxamide |
| 565 | 2-(4-(1-amino-2-methoxyethyl)-2-fluorophenyl)-N-(tetrahydro-2H-pyran-4-yl)benzo[d]imidazo[2,1-b]thiazole-7-carboxamide |
| 579 | 2-(4-(amino(oxetan-3-yl)methyl)-2-fluorophenyl)-N-(tetrahydro-2H-pyran-4-yl)benzo[d]imidazo[2,1-b]thiazole-7-carboxamide |
| 584 | 2-(4-(1-aminocyclopropyl)-2-fluorophenyl)-N-(tetrahydro-2H-pyran-4-yl)benzo[d]imidazo[2,1-b]thiazole-7-carboxamide and |
| 585 | 2-(4-(1-aminocyclopropyl)-2-fluorophenyl)-N-methylimidazo[2',1':2,3]thiazolo[4,5-c]pyridine-7-carboxamide. |

12. A compound selected from the group consisting of:

| Compound No. | Compound Name |
|---|---|
| 423S | (S)-2-(2-fluoro-4-(pyrrolidin-2-yl)phenyl)-N-(3-(2-oxopiperidin-1-yl)propyl)benzo[d]imidazo[2,1-b]thiazole-7-carboxamide |
| 423R | (R)-2-(2-fluoro-4-(pyrrolidin-2-yl)phenyl)-N-(3-(2-oxopiperidin-1-yl)propyl)benzo[d]imidazo[2,1-b]thiazole-7-carboxamide |
| 424 | N-(3-(4-cyanopiperidin-1-yl)propyl)-2-(2-fluoro-4-(pyrrolidin-2-yl)phenyl)benzo[d]imidazo[2,1-b]thiazole-7-carboxamide |
| 426 | 2-(2-fluoro-4-(pyrrolidin-2-yl)phenyl)-N-(3-(4-(trifluoromethyl)piperidin-1-yl)propyl)benzo[d]imidazo[2,1-b]thiazole-7-carboxamide |
| 431S | N-(3-(6-fluoro-3-azabicyclo[3.1.1]heptan-3-yl)propyl)-2-(2-fluoro-4-((S)-pyrrolidin-2-yl)phenyl)benzo[d]imidazo[2,1-b]thiazole-7-carboxamide |
| 431R | N-(3-(6-fluoro-3-azabicyclo[3.1.1]heptan-3-yl)propyl)-2-(2-fluoro-4-((R)-pyrrolidin-2-yl)phenyl)benzo[d]imidazo[2,1-b]thiazole-7-carboxamide |
| 437S | (S)-2-(2-fluoro-5-(pyrrolidin-2-yl)phenyl)-N-(3-(4-fluoropiperidin-1-yl)propyl)benzo[d]imidazo[2,1-b]thiazole-7-carboxamide |
| 437R | (R)-2-(2-fluoro-5-(pyrrolidin-2-yl)phenyl)-N-(3-(4-fluoropiperidin-1-yl)propyl)benzo[d]imidazo[2,1-b]thiazole-7-carboxamide |
| 438S | (S)-2-(2-fluoro-6-(pyrrolidin-2-yl)phenyl)-N-(3-(4-fluoropiperidin-1-yl)propyl)benzo[d]imidazo[2,1-b]thiazole-7-carboxamide |
| 438R | (R)-2-(2-fluoro-6-(pyrrolidin-2-yl)phenyl)-N-(3-(4-fluoropiperidin-1-yl)propyl)benzo[d]imidazo[2,1-b]thiazole-7-carboxamide |
| 439S | (S)-2-(2-fluoro-3-(pyrrolidin-2-yl)phenyl)-N-(3-(4-fluoropiperidin-1-yl)propyl)benzo[d]imidazo[2,1-b]thiazole-7-carboxamide |

| Compound No. | Compound Name |
|---|---|
| 439R | (R)-2-(2-fluoro-3-(pyrrolidin-2-yl)phenyl)-N-(3-(4-fluoropiperidin-1-yl)propyl)benzo[d]imidazo[2,1-b]thiazole-7-carboxamide |
| 454 | 2-(6-fluoroisoindolin-5-yl)-N-(3-(4-fluoropiperidin-1-yl)propyl)benzo[d]imidazo[2,1-b]thiazole-7-carboxamide |
| 455 | 2-(7-fluoro-1,2,3,4-tetrahydroisoquinolin-6-yl)-N-(3-(4-fluoropiperidin-1-yl)propyl)benzo[d]imidazo[2,1-b]thiazole-7-carboxamide |
| 456 | 2-(6-fluoro-1,3-dihydroisobenzofuran-5-yl)-N-(3-(4-fluoropiperidin-1-yl)propyl)benzo[d]imidazo[2,1-b]thiazole-7-carboxamide |
| 457 | 2-(7-fluoroisochroman-6-yl)-N-(3-(4-fluoropiperidin-1-yl)propyl)benzo[d]imidazo[2,1-b]thiazole-7-carboxamide |
| 458 | 2-(7-fluoroindolin-6-yl)-N-(3-(4-fluoropiperidin-1-yl)propyl)benzo[d]imidazo[2,1-b]thiazole-7-carboxamide |
| 459 | 2-(4-fluoroindolin-5-yl)-N-(3-(4-fluoropiperidin-1-yl)propyl)benzo[d]imidazo[2,1-b]thiazole-7-carboxamide |
| 460S | (S)-2-(2-fluoro-4-(pyrrolidin-2-yl)-5,6,7,8-tetrahydronaphthalen-1-yl)-N-(3-(4-fluoropiperidin-1-yl)propyl)benzo[d]imidazo[2,1-b]thiazole-7-carboxamide |
| 460R | (R)-2-(2-fluoro-4-(pyrrolidin-2-yl)-5,6,7,8-tetrahydronaphthalen-1-yl)-N-(3-(4-fluoropiperidin-1-yl)propyl)benzo[d]imidazo[2,1-b]thiazole-7-carboxamide |
| 461S | (S)-2-(5-fluoro-7-(pyrrolidin-2-yl)-2,3-dihydro-1H-inden-4-yl)-N-(3-(4-fluoropiperidin-1-yl)propyl)benzo[d]imidazo[2,1-b]thiazole-7-carboxamide |
| 461R | (R)-2-(5-fluoro-7-(pyrrolidin-2-yl)-2,3-dihydro-1H-inden-4-yl)-N-(3-(4-fluoropiperidin-1-yl)propyl)benzo[d]imidazo[2,1-b]thiazole-7-carboxamide |
| 478 | methyl 3-fluoro-4-(7-((3-(4-fluoropiperidin-1-yl)propyl)carbamoyl)benzo[d]imidazo[2,1-b]thiazol-2-yl)benzoate |
| 494 | 2-(2-fluoro-4-propionylphenyl)-N-(3-(4-fluoropiperidin-1-yl)propyl)benzo[d]imidazo[2,1-b]thiazole-7-carboxamide |
| 495 | N-(3-(4-fluoropiperidin-1-yl)propyl)-2-(2-methylpyridin-4-yl)benzo[d]imidazo[2,1-b]thiazole-7-carboxamide |
| 496 | 2-(2-methylpyridin-4-yl)-N-(piperidin-4-yl)benzo[d]imidazo[2,1-b]thiazole-7-carboxamide |
| 497 | N-(piperidin-4-yl)-2-(m-tolyl)benzo[4,5]thiazolo[3,2-b][1,2,4]triazole-6-carboxamide |
| 502 | N-(piperidin-4-yl)-2-(m-tolyl)imidazo[2',1':2,3]thiazolo[4,5-c]pyridine-7-carboxamide |
| 580 | N-(3-(4-fluoropiperidin-1-yl)propyl)-2-(pyrrolidin-2-yl)benzo[d]imidazo[2,1-b]thiazole-7-carboxamide |
| 600 | 2-(6-fluoro-1,2,3,4-tetrahydroisoquinolin-7-yl)-N-(3-(4-fluoropiperidin-1-yl)propyl)benzo[d]imidazo[2,1-b]thiazole-7-carboxamide |
| 601 | 2-(5-fluoroindolin-6-yl)-N-(3-(4-fluoropiperidin-1-yl)propyl)benzo[d]imidazo[2,1-b]thiazole-7-carboxamide and |
| 602 | 2-(6-fluoroindolin-5-yl)-N-(3-(4-fluoropiperidin-1-yl)propyl)benzo[d]imidazo[2,1-b]thiazole-7-carboxamide | or its pharmaceutically acceptable salt, stereoisomer, tautomer, hydrate, N-oxide, reverse amide analog, prodrug, isotopic variant, deuterated analog, pharmaceutical product or any combination thereof.

13. The compound according to claim 1, wherein the compound is a c-MYC mRNA translation modulator, a c-MYC mRNA transcription regulator, a c-MYC inhibitor or any combination thereof.

14. A pharmaceutical composition comprising the compound of claim 1 and a pharmaceutically acceptable carrier.

15. A method of treating, suppressing, reducing the severity, reducing the risk of developing or inhibiting cancer in a subject, comprising administering a therapeutically effective amount of a compound according to claim 1 to a subject, thereby treating, suppressing, reducing the severity, reducing the risk of developing or inhibiting cancer in said subject.

16. The method of claim 15,
wherein the cancer is selected from the group consisting of: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer;
wherein the cancer is early cancer, advanced cancer, invasive cancer, metastatic cancer, drug resistant cancer or any combination thereof;
wherein the subject has been previously treated with chemotherapy, immunotherapy, radiotherapy, biological therapy, surgical intervention, or any combination thereof;
wherein the compound is administered in combination with an anti-cancer therapy;
or any combination thereof.

17. The method of claim 16, wherein the anti-cancer therapy is chemotherapy, immunotherapy, radiotherapy, biological therapy, surgical intervention, or any combination thereof.

18. A method of suppressing, reducing or inhibiting tumor growth in a subject, comprising administering a therapeutically effective amount of a compound according to claim 1 to a subject, therby suppressing, reducing or inhibiting tumor growth in said subject.

19. A method of modulating c-MYC mRNA translation, or regulating c-MYC mRNA transcription in a cell, comprising contacting a compound according to claim 1 with a cell, thereby modulating c-MYC mRNA translation, or regulating c-MYC mRNA transcription in said cell.

20. The method of claim 19, wherein said method is carried out
   (a) by regulating c-MYC mRNA splicing (inclusion or exclusion of untranslated region or alternative usage of exons);
   (b) by regulation of c-MYC mRNA modifications;
   (c) by regulation of the interaction of RNA binding protein with c-MYC mRNA thereby changing mRNA localization;
   (d) by regulating c-MYC mRNA localization in the cytoplasm;
   (e) by regulating ribosomes or ribosome accessory factor to c-MYC mRNA;
   (f) by reducing the amount of c-MYC protein in the cell; or any combination thereof.

21. A pharmaceutical composition comprising the compound of claim 4 and a pharmaceutically acceptable carrier.

22. A pharmaceutical composition comprising the compound of claim 9 and a pharmaceutically acceptable carrier.

23. A pharmaceutical composition comprising the compound of claim 12 and a pharmaceutically acceptable carrier.

24. A method of treating, suppressing, reducing the severity, reducing the risk of developing or inhibiting cancer in a subject, or a method of suppressing, reducing or inhibiting tumor growth in a subject, said method comprises administering a therapeutically effective amount of a compound according to claim 5 to a subject, therby treating, suppressing, reducing the severity, reducing the risk of developing or inhibiting cancer, or suppressing, reducing or inhibiting tumor growth in said subject.

25. The method of claim 24,
   wherein the cancer is selected from the group consisting of: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer;
   wherein the cancer is early cancer, advanced cancer, invasive cancer, metastatic cancer, drug resistant cancer or any combination thereof;
   wherein the subject has been previously treated with chemotherapy, immunotherapy, radiotherapy, biological therapy, surgical intervention, or any combination thereof;
   wherein the compound is administered in combination with an anti-cancer therapy;
   or any combination thereof.

26. The method of claim 25, wherein the anti-cancer therapy is chemotherapy, immunotherapy, radiotherapy, biological therapy, surgical intervention, or any combination thereof.

27. A method of modulating c-MYC mRNA translation, or regulating c-MYC mRNA transcription in a cell, comprising contacting a compound according to claim 4 with a cell, thereby modulating c-MYC mRNA translation, or regulating c-MYC mRNA transcription in said cell.

28. The method of claim 27, wherein said method is carried out
   (a) by regulating c-MYC mRNA splicing (inclusion or exclusion of untranslated region or alternative usage of exons);
   (b) by regulation of c-MYC mRNA modifications;
   (c) by regulation of the interaction of RNA binding protein with c-MYC mRNA thereby changing mRNA localization;
   (d) by regulating c-MYC mRNA localization in the cytoplasm;
   (e) by regulating ribosomes or ribosome accessory factor to c-MYC mRNA;
   (f) by reducing the amount of c-MYC protein in the cell; or any combination thereof.

29. A method of treating, suppressing, reducing the severity, reducing the risk of developing or inhibiting cancer in a subject, or a method of suppressing, reducing or inhibiting tumor growth in a subject, said method comprises administering a therapeutically effective amount of a compound according to claim 8 to a subject, therby treating, suppressing, reducing the severity, reducing the risk of developing or inhibiting cancer, or suppressing, reducing or inhibiting tumor growth in said subject.

30. The method of claim 29,
   wherein the cancer is selected from the group consisting of: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer;
   wherein the cancer is early cancer, advanced cancer, invasive cancer, metastatic cancer, drug resistant cancer or any combination thereof;
   wherein the subject has been previously treated with chemotherapy, immunotherapy, radiotherapy, biological therapy, surgical intervention, or any combination thereof;
   wherein the compound is administered in combination with an anti-cancer therapy;
   or any combination thereof.

31. The method of claim 30, wherein the anti-cancer therapy is chemotherapy, immunotherapy, radiotherapy, biological therapy, surgical intervention, or any combination thereof.

32. A method of modulating c-MYC mRNA translation, or regulating c-MYC mRNA transcription in a cell, comprising contacting a compound according to claim 9 with a cell, thereby modulating c-MYC mRNA translation, or regulating c-MYC mRNA transcription in said cell.

33. The method of claim 32, wherein said method is carried out
   (g) by regulating c-MYC mRNA splicing (inclusion or exclusion of untranslated region or alternative usage of exons);
   (h) by regulation of c-MYC mRNA modifications;
   (i) by regulation of the interaction of RNA binding protein with c-MYC mRNA thereby changing mRNA localization;

(j) by regulating c-MYC mRNA localization in the cytoplasm;
(k) by regulating ribosomes or ribosome accessory factor to c-MYC mRNA;
(l) by reducing the amount of c-MYC protein in the cell; or any combination thereof.

34. A method of treating, suppressing, reducing the severity, reducing the risk of developing or inhibiting cancer in a subject, or a method of suppressing, reducing or inhibiting tumor growth in a subject, said method comprises administering a therapeutically effective amount of a compound according to claim 12 to a subject, therby treating, suppressing, reducing the severity, reducing the risk of developing or inhibiting cancer, or suppressing, reducing or inhibiting tumor growth in said subject.

35. The method of claim 34,
wherein the cancer is selected from the group consisting of: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer;
wherein the cancer is early cancer, advanced cancer, invasive cancer, metastatic cancer, drug resistant cancer or any combination thereof;
wherein the subject has been previously treated with chemotherapy, immunotherapy, radiotherapy, biological therapy, surgical intervention, or any combination thereof;
wherein the compound is administered in combination with an anti-cancer therapy;
or any combination thereof.

36. The method of claim 35, wherein the anti-cancer therapy is chemotherapy, immunotherapy, radiotherapy, biological therapy, surgical intervention, or any combination thereof.

37. A method of modulating c-MYC mRNA translation, or regulating c-MYC mRNA transcription in a cell, comprising contacting a compound according to claim 12 with a cell, thereby modulating c-MYC mRNA translation, or regulating c-MYC mRNA transcription in said cell.

38. The method of claim 37, wherein said method is carried out
(a) by regulating c-MYC mRNA splicing (inclusion or exclusion of untranslated region or alternative usage of exons);
(b) by regulation of c-MYC mRNA modifications;
(c) by regulation of the interaction of RNA binding protein with c-MYC mRNA thereby changing mRNA localization;
(d) by regulating c-MYC mRNA localization in the cytoplasm;
(e) by regulating ribosomes or ribosome accessory factor to c-MYC mRNA;
(f) by reducing the amount of c-MYC protein in the cell; or any combination thereof.

\* \* \* \* \*